(12) United States Patent
Chong et al.

(10) Patent No.: US 8,304,419 B2
(45) Date of Patent: Nov. 6, 2012

(54) CHEMICAL COMPOUNDS

(75) Inventors: Pek Yoke Chong, Durham, NC (US); Andrew James Peat, Durham, NC (US); Paul Richard Sebahar, Durham, NC (US); Michael Youngman, Durham, NC (US); Huichang Zhang, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 180 days.

(21) Appl. No.: 12/667,581

(22) PCT Filed: Jun. 5, 2008

(86) PCT No.: PCT/US2008/065865
§ 371 (c)(1),
(2), (4) Date: Jan. 4, 2010

(87) PCT Pub. No.: WO2008/154271
PCT Pub. Date: Dec. 18, 2008

(65) Prior Publication Data
US 2010/0216746 A1    Aug. 26, 2010

Related U.S. Application Data

(60) Provisional application No. 60/942,266, filed on Jun. 6, 2007.

(51) Int. Cl.
*A61K 31/52*      (2006.01)
*A61K 31/4164*    (2006.01)
*A61K 31/40*      (2006.01)
*C07D 473/00*     (2006.01)
*C07D 233/54*     (2006.01)
*C07D 207/30*     (2006.01)

(52) U.S. Cl. .................. 514/263.1; 514/396; 514/427; 544/264; 548/335.1; 548/560

(58) Field of Classification Search ............. 514/263.1, 514/396, 427; 544/264; 548/335.1, 560
See application file for complete search history.

(56) References Cited

U.S. PATENT DOCUMENTS

| 2005/0124683 A1 | 6/2005 | Alegria et al. |
| 2006/0025480 A1 | 2/2006 | Simoneau et al. |
| 2006/0178399 A1 | 8/2006 | Nishizawa et al. |

FOREIGN PATENT DOCUMENTS

| WO | WO 00/40562   | * | 7/2000 |
| WO | WO 03/051846  | * | 6/2003 |
| WO | WO 2005/054176| * | 6/2005 |

OTHER PUBLICATIONS

Notice of Opposition filed May 19, 2011 against Colombian application No. 09.140.797 (co-pending CO equivalent of present case).
GlaxoSmithKline Oct. 7, 2011 Response to Notice of Opposition filed May 19, 2011 against Colombian application No. 09.140.797 (co-pending CO equivalent of present case).
Notice of Opposition by filed Jun. 4, 2009 against Chilean application No. 1631-2008 (co-pending CL equivalent of present case).
GlaxoSmithKline Oct. 6, 2009 Response to Notice of Opposition filed Jun. 4, 2009 against Chilean application No. 1631-2008 (co-pending CL equivalent of present case).

\* cited by examiner

*Primary Examiner* — Joseph K. McKane
*Assistant Examiner* — Samantha Shterengarts
(74) *Attorney, Agent, or Firm* — Barbara J. Carter

(57) ABSTRACT

The present invention relates to compounds that are a non-nucleoside reverse transcriptase inhibitors, and to processes for the preparation and use of the same. Specifically, the present invention includes methods of using such compounds in the treatment of human immunodeficiency virus infection.

17 Claims, No Drawings

CHEMICAL COMPOUNDS

This application is filed pursuant to 35 U.S.C. §371 as a United States National Phase application of International Patent Application Serial No. PCT/US2008/065865 filed Jun. 5, 2008, which claims priority from U.S. Provisional Application No. 60/942,266 filed Jun. 6, 2007, the contents of which are incorporated herein by reference.

FIELD OF THE INVENTION

The present invention relates to compounds that are non-nucleoside reverse transcriptase inhibitors, and the use in the treatment of viral infections, for example, human immunodeficiency virus infections.

BACKGROUND OF THE INVENTION

The human immunodeficiency virus ("HIV") is the causative agent for acquired immunodeficiency syndrome ("AIDS"), a disease characterized by the destruction of the immune system, particularly of CD4+ T-cells, with attendant susceptibility to opportunistic infections, and its precursor AIDS-related complex ("ARC"), a syndrome characterized by symptoms such as persistent generalized lymphadenopathy, fever and weight loss. HIV is a retrovirus; the conversion of its RNA to DNA is accomplished through the action of the enzyme reverse transcriptase. Compounds that inhibit the function of reverse transcriptase inhibit replication of HIV in infected cells. Such compounds are useful in the prevention or treatment of HIV infection in humans.

Non-nucleoside reverse transcriptase inhibitors (NNRTIs), in addition to the nucleoside reverse transcriptase inhibitors (NRTIs), have gained a definitive place in the treatment of HIV-1 infections. NNRTIs interact with a specific site of HIV-1 reverse transcriptase that is closely associated with, but distinct from, the NRTI binding site. NNRTIs, however, are notorious for rapidly eliciting resistance due to mutations of the amino acids surrounding the NNRTI-binding site (E. De Clercq, *Il Famaco* 54, 26-45, 1999). Failure of long-term efficacy of NNRTIs is often associated with the emergence of drug-resistant virus strains (J. Balzarini, *Biochemical Pharmacology*, Vol 58, 1-27, 1999). Moreover, the mutations that appear in the reverse transcriptase enzyme frequently result in a decreased sensitivity to other reverse transcriptase inhibitors, which results in cross-resistance.

WO 02/070470, WO 01/17982, and US 2006/0025480A1 disclosed certain benzophenones as non-nucleoside reverse transcriptase inhibitors. As antiviral use in therapy and prevention of HIV infection continues, the emergence of new resistant strains is expected to increase. There is therefore an ongoing need for new inhibitors of reverse transcriptase, which have different patterns of effectiveness against the various mutants.

SUMMARY OF THE INVENTION

The present invention comprises compounds of formula (I):

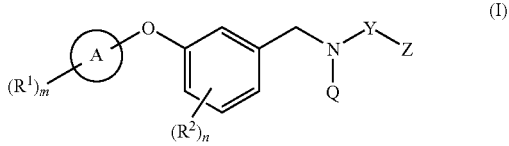

(I)

wherein m is 1, 2, 3 or 4;
n is 1, 2, 3 or 4;
each $R^1$ independently is halogen, —CN, $C_1$-$C_5$ alkyl, $C_2$-$C_5$ alkenyl, $C_2$-$C_6$ alkynyl, $C_3$-$C_7$ cycloalkyl, hydroxyl, $C_1$-$C_8$ alkoxy, —C(O)OR$^5$, —C(O)N(R$^5$)$_2$, —OR$^5$, —R$^3$CN or —N(R$^5$)$_2$;

each $R^2$ independently is halogen, —CN, $C_1$-$C_5$ alkyl, $C_2$-$C_5$ alkenyl, $C_2$-$C_6$ alkynyl, $C_3$-$C_7$ cycloalkyl, hydroxyl, $C_1$-$C_8$ alkoxy, —C(O)OR$^5$, —C(O)N(R$^5$)$_2$, —OR$^5$, —R$^3$CN or —N(R$^5$)$_2$;
A is $C_5$-$C_{12}$ aryl or $C_5$-$C_{12}$ heterocycle;
Q is hydrogen or $C_1$-$C_4$ alkyl;
Y is —C(O)—, —S(O)$_2$—, or —S(O)—;
Z is $C_4$-$C_{12}$ aryl, $C_3$-$C_{14}$ heterocycle, R$^3$Het, or R$^3$Ar, each optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N(R$^5$)C(O)R$^5$, —N(R$^5$)$_2$, —OR$^5$, —C$_3$-C$_{12}$ Het, —C(O)N(R$^5$)$_2$, $C_4$-$C_{12}$ Ar, —SR$^5$, —S(O)$_2$N(R$^5$)$_2$, —OR$^3$HetC(O)R$^5$, —OCF$_3$, —S(O)$_2$R$^5$, —OR$^3$R$^5$, —N(R$^5$)C(O)R$^3$OR$^5$; —N(R$^5$)C(O)R$^3$N(R$^5$)$_2$, —N(R$^5$)C(O)R$^3$R$^5$, —OR$^3$N(R$^5$)$_2$, —R$^3$Het, —R$^3$N(R$^5$)$_2$, —R$^3$N(R$^5$)C(O)R$^5$, —OR$^3$SR$^5$, —C(O)R$^5$, —C(R$^5$)$_3$, —R$^3$C(O)OR$^5$, —R$^3$C(O)N(R$^5$)$_2$, or —N(R$^5$)S(O)$_2$R$^5$; or Z is linked to Q to form a $C_4$-$C_{14}$ heterocycle together with the nitrogen atom and Y group to which they are attached and are optionally substituted with —C(O)OR$^5$ or $C_1$-$C_6$ alkoxy;
each $R^5$ independently is hydrogen, $C_1$-$C_8$ alkyl, $C_3$-$C_7$ cycloalkyl, oxo, $C_3$-$C_{12}$ heterocycle, $C_4$-$C_{12}$ aryl or $C_1$-$C_8$ alkoxy, each optionally substituted with hydroxyl, $C_1$-$C_4$ alkoxy or $C_3$-$C_7$ cycloalkyl;
$R^3$ is $C_2$-$C_6$ alkenylene or $C_1$-$C_4$ alkylene, each optionally substituted with hydroxyl or $C_1$-$C_8$ alkoxy;
Het is $C_3$-$C_{12}$ heterocycle and is optionally substituted with one or more of $C_1$-$C_6$ alkyl, —C(O)N(R$^5$)$_2$, —R$^3$S(O)$_2$R$^5$, or halogen; and
Ar is $C_4$-$C_{12}$ aryl and is optionally substituted with one or more of $C_1$-$C_6$ alkyl or halogen; or pharmaceutically acceptable salts or solvates thereof.

The present invention features a compound of formula (I) wherein m is 2. The present invention features a compound of formula (I) wherein n is 2.

The present invention features a compound of formula (I) wherein Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N(R$^5$)C(O)R$^5$, —N(R$^5$)$_2$, —OR$^5$, —C$_3$-C$_{12}$ Het, —C(O)N(R$^5$)$_2$, $C_4$-$C_{12}$ Ar, —SR$^5$, —S(O)$_2$N(R$^5$)$_2$, —OR$^3$HetC(O)R$^5$, —OCF$_3$, —S(O)$_2$R$^5$, —OR$^3$R$^5$, —N(R$^5$)C(O)R$^3$OR$^5$; —N(R$^5$)C(O)R$^3$N(R$^5$)$_2$, —N(R$^5$)C(O)R$^3$R$^5$, —OR$^3$N(R$^5$)$_2$, —R$^3$Het, —R$^3$N(R$^5$)$_2$, —R$^3$N(R$^5$)C(O)R$^5$, —OR$^3$SR$^5$, —C(O)R$^5$, —C(R$^5$)$_3$, —R$^3$C(O)OR$^5$, —R$^3$C(O)N(R$^5$)$_2$, or —N(R$^5$)S(O)$_2$R$^5$.

The present invention features a compound of formula (I) wherein Y is —C(O)—, Q is hydrogen, and Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N(R$^5$)C(O)R$^5$, —N(R$^5$)$_2$, —OR$^5$, —C$_3$-C$_{12}$ Het, —C(O)N(R$^5$)$_2$, $C_4$-$C_{12}$ Ar, —SR$^5$, —S(O)$_2$N(R$^5$)$_2$, —OR$^3$HetC(O)R$^5$, —OCF$_3$, —S(O)$_2$R$^5$, —OR$^3$R$^5$, —N(R$^5$)C(O)R$^5$, —N(R$^5$)C(O)R$^3$OR$^5$; —N(R$^5$)C(O)R$^3$N(R$^5$)$_2$, —N(R$^5$)C(O)R$^3$R$^5$, —OR$^3$N(R$^5$)$_2$, —R$^3$Het, —R$^3$N(R$^5$)$_2$, —R$^3$NC(O)R$^5$, —OR$^3$SR$^5$, —C(O)R$^5$, —C(R$^5$)$_3$, or —N(R$^5$)S(O)$_2$R$^5$.

The present invention features a compound of formula (I) wherein Y is —C(O)—, Q is $C_1$-$C_8$ alkyl, and Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N(R$^5$)C(O)R$^5$, —N(R$^5$)$_2$, —OR$^5$, —C$_3$-C$_{12}$ Het, —C(O)N(R$^5$)$_2$, $C_4$-$C_{12}$ Ar, —SR$^5$, —S(O)$_2$N(R$^5$)$_2$, —OR$^3$HetC(O)R$^5$, —OCF$_3$, —S(O)$_2$R$^5$, —OR$^3$R$^5$, —N(R$^5$)C(O)R$^3$OR$^5$; —N(R$^5$)C(O)R$^3$N(R$^5$)$_2$, —N(R$^5$)C(O)R$^3$R$^5$, —OR$^3$N(R$^5$)$_2$, —R$^3$Het, —R$^3$N(R$^5$)$_2$, —R³N(R⁵)C(O)R⁵, —OR³SR⁵, —C(O)R⁵, —C(R⁵)₃, —R³C(O)OR⁵, —R³C(O)N(R⁵)₂, or —N(R⁵)S(O)₂R⁵.

The present invention features a compound of formula (I) wherein n is 2 and each R² is halogen. The present invention also features a compound of formula (I) wherein m is 2 and one R¹ is halogen and one R¹ is —CN.

The present invention features a compound of formula (I) wherein m is 2, n is 2, and Z is C₃-C₁₄ heterocycle optionally substituted with one or more of C₁-C₈ alkyl, C₃-C₇ cycloalkyl, C₁-C₈ alkoxy, halogen, oxo, hydroxyl, —CN, —NO₂, —N(R⁵)C(O)R⁵, —N(R⁵)₂, —OR⁵, —C₃-C₁₂ Het, —C(O)N(R⁵)₂, C₄-C₁₂ Ar, —SR⁵, —S(O)₂N(R⁵)₂, —OR³HetC(O)R⁵, —OCF₃, —S(O)₂R⁵, —OR³R⁵, —N(R⁵)C(O)R³OR⁵; —N(R⁵)C(O)R³N(R⁵)₂, —N(R⁵)C(O)R³R⁵, —OR³N(R⁵)₂, —R³Het, —R³N(R⁵)₂, —R³N(R⁵)C(O)R⁵, —OR³SR⁵, —C(O)R⁵, —C(R⁵)₃, —R³C(O)OR⁵, —R³C(O)N(R⁵)₂, or —N(R⁵)S(O)₂R⁵.

The present invention features a compound of formula (I) wherein Z is selected from the group consisting of

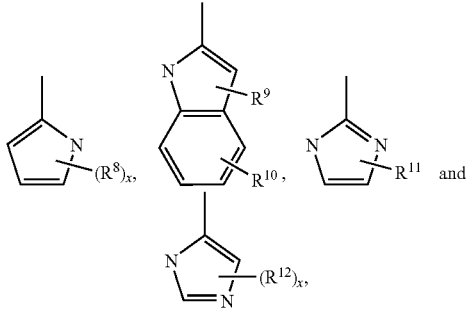

wherein x is 1, 2 or 3;

each R⁸ is independently hydrogen, halogen, N(R¹⁵)₂, OR¹⁵, SR¹⁵, C(O)N(R¹⁵)₂, C(O)OR¹⁵, CF₃, C₁-C₈ alkyl, C₁-C₈ alkoxy, or —CN, wherein each C₁-C₈ alkyl or C₁-C₈ alkoxy is optionally substituted with hydroxyl, C₁-C₄ alkoxy or C₃-C₇ cycloalkyl;

R⁹ is hydrogen or halogen;

R¹⁰ is hydrogen, hydroxyl, C₁-C₈ alkoxy, —N(R¹⁵)C(O)R¹⁵, —N(R¹⁵)C(O)R¹³N(R¹⁵)₂, —N(R¹⁵)₂, or —R¹³N(R¹⁵)C(O)R¹⁵;

R¹³ is C₁-C₆ alkylene;

each R¹⁵ is independently hydrogen, C₁-C₈ alkyl, C₃-C₇ cycloalkyl, C₃-C₁₂ heterocycle, C₄-C₁₂ aryl or C₁-C₈ alkoxy, each optionally substituted with hydroxyl, C₁-C₄ alkoxy or C₃-C₇ cycloalkyl;

R¹¹ is hydrogen or C₁-C₆ alkoxy; and each R¹² is independently hydrogen, halogen, C₁-C₈ alkyl, C₁-C₈ alkoxy, C₃-C₆ cycloalkyl, N(R¹⁵)₂, OR¹⁵, SR¹⁵, C(O)N(R¹⁵)₂, C(O)OR¹⁵, or —N(O)₂, wherein each C₁-C₈ alkyl or C₁-C₈ alkoxy is optionally substituted with hydroxyl, C₁-C₄ alkoxy or C₃-C₇ cycloalkyl.

The present invention also features a compound of formula (II)

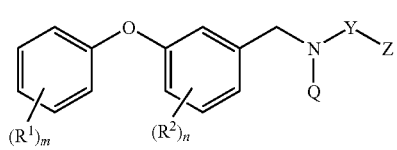

wherein m is 1, 2, 3 or 4;
n is 1, 2, 3 or 4;
each R¹ independently is halogen, —CN, C₁-C₅ alkyl, C₂-C₅ alkenyl, C₂-C₆ alkynyl, C₃-C₇ cycloalkyl, hydroxyl, C₁-C₈ alkoxy, —C(O)OR⁵, —C(O)N(R⁵)₂, —OR⁵, —R³CN, or —N(R⁵)₂;

each R² independently is halogen, —CN, C₁-C₅ alkyl, C₂-C₅ alkenyl, C₂-C₆ alkynyl, C₃-C₇ cycloalkyl, hydroxyl, C₁-C₈ alkoxy, —C(O)OR⁵, —C(O)N(R⁵)₂, —OR⁵, —R³CN or —N(R⁵)₂;

A is C₅-C₁₂ aryl or C₅-C₁₂ heterocycle;
Q is hydrogen or C₁-C₄ alkyl;
Y is —C(O)—, —S(O)₂—, or —S(O)—;
Z is C₄-C₁₂ aryl, C₃-C₁₄ heterocycle, R³Het, or R³Ar, each optionally substituted with one or more of C₁-C₈ alkyl, C₃-C₇ cycloalkyl, C₁-C₈ alkoxy, halogen, oxo, hydroxyl, —CN, —NO₂, —N(R⁵)C(O)R⁵, —N(R⁵)₂, —OR⁵, —C₃-C₁₂ Het, —C(O)N(R⁵)₂, C₄-C₁₂ Ar, —SR⁵, —S(O)₂N(R⁵)₂, —OR³HetC(O)R⁵, —OCF₃, —S(O)₂R⁵, —OR³R⁵, —N(R⁵)C(O)R³OR⁵; —N(R⁵)C(O)R³N(R⁵)₂, —N(R⁵)C(O)R³R⁵, —OR³N(R⁵)₂, —R³Het, —R³N(R⁵)₂, —R³N(R⁵)C(O)R⁵, —OR³SR⁵, —C(O)R⁵, —C(R⁵)₃, —R³C(O)OR⁵, —R³C(O)N(R⁵)₂, or —N(R⁵)S(O)₂R⁵; or Z is linked to Q to form a C₄-C₁₄ heterocycle together with the nitrogen atom and Y group to which they are attached and are optionally substituted with —C(O)OR⁵ or C₁-C₆ alkoxy;

each R⁵ independently is hydrogen, C₁-C₈ alkyl, oxo, C₃-C₁₂ heterocycle, C₄-C₁₂ aryl or C₁-C₈ alkoxy, each optionally substituted with hydroxyl, C₁-C₄ alkoxy or C₃-C₇ cycloalkyl;

R³ is C₂-C₆ alkenylene or C₁-C₄ alkylene, each optionally substituted with hydroxyl or C₁-C₈ alkoxy;

Het is C₃-C₁₂ heterocycle and is optionally substituted with one or more of C₁-C₆ alkyl, —C(O)N(R⁵)R(⁵)₂, —R³S(O)₂R⁵, or halogen; and Ar is C₄-C₁₂ aryl and is optionally substituted with one or more of C₁-C₆ alkyl or halogen; or pharmaceutically acceptable salts or solvates thereof.

Compounds of the present invention include:

N-({4-chloro-3-[(3-chloro-5-cyanophenyl)oxy]phenyl}methyl)-2-methyl-4-(methyloxy)benzamide;

N-({4-chloro-3-[(3-chloro-5-cyanophenyl)oxy]phenyl}methyl)-6-(methyloxy)-1H-indole-3-carboxamide;

4-(aminosulfonyl)-2-chloro-N-({4-chloro-3-[(3-chloro-5-cyanophenyl)oxy]phenyl}methyl)benzamide trifluoroacetate;

3-(aminosulfonyl)-4-chloro-N-({4-chloro-3-[(3-chloro-5-cyanophenyl)oxy]phenyl}methyl)benzamide trifluoroacetate;

N-({4-chloro-3-[(3-chloro-5-cyanophenyl)oxy]phenyl}methyl)-2,4-bis(methyloxy)benzamide;

N-({4-chloro-3-[(3-chloro-5-cyanophenyl)oxy]phenyl}methyl)-6-(methyloxy)-1H-indole-2-carboxamide;

2-chloro-N-({4-chloro-3-[(3-chloro-5-cyanophenyl)oxy]phenyl}methyl)-4-(methylsulfonyl)benzamide;

N-({4-chloro-3-[(3-chloro-5-cyanophenyl)oxy]phenyl}methyl)-5-nitro-1H-indole-2-carboxamide;

N-({4-chloro-3-[(3-chloro-5-cyanophenyl)oxy]phenyl}methyl)-5-(methyloxy)-1H-indole-2-carboxamide;

methyl 4-{[({4-chloro-3-[(3-chloro-5-cyanophenyl)oxy]phenyl}methyl)amino]carbonyl}benzoate;

4-(aminosulfonyl)-2-chloro-N-({4-chloro-3-[(3-chloro-5-cyanophenyl)oxy]-2-fluorophenyl}methyl)benzamide;

methyl 4-{[({4-chloro-3-[(3-chloro-5-cyanophenyl)oxy]-2-fluorophenyl}methyl)amino]carbonyl}benzoate;

2-chloro-N-({4-chloro-3-[(3-chloro-5-cyanophenyl)oxy]-2-fluorophenyl}methyl)-4-(methylsulfonyl)benzamide;

N-({4-chloro-3-[(3-chloro-5-cyanophenyl)oxy]-2-fluorophenyl}methyl)-2-methyl-4-(methyloxy)benzamide;

N-({4-chloro-3-[(3-chloro-5-cyanophenyl)oxy]-2-fluorophenyl}methyl)-6-(methyloxy)-1H-indole-3-carboxamide;
N-({4-chloro-3-[(3-chloro-5-cyanophenyl)oxy]-2-fluorophenyl}methyl)-5-nitro-1H-indole-2-carboxamide;
N-({4-chloro-3-[(3-chloro-5-cyanophenyl)oxy]-2-fluorophenyl}methyl)-5-(methyloxy)-1H-indole-2-carboxamide;
N-({4-chloro-3-[(3-chloro-5-cyanophenyl)oxy]-2-fluorophenyl}methyl)-6-(methyloxy)-1H-indole-2-carboxamide;
N-({4-chloro-3-[(3-chloro-5-cyanophenyl)oxy]-2-fluorophenyl}methyl)-5-{[3-hydroxy-2-(hydroxymethyl)propyl]oxy}-1H-indole-2-carboxamide;
1,1-dimethylethyl (2R)-2-{[(2-{[({4-chloro-3-[(3-chloro-5-cyanophenyl)oxy]-2-fluorophenyl}methyl)amino]carbonyl}-1H-indol-5-yl)oxy]methyl}-4-morpholinecarboxylate;
N-({4-Chloro-3-[(3-chloro-5-cyanophenyl)oxy]-2-fluorophenyl}methyl)-5-{[(2R)-2-morpholinylmethyl]oxy}-1H-indole-2-carboxamide;
N-({4-chloro-3-[(3-chloro-5-cyanophenyl)oxy]-2-fluorophenyl}methyl)-5-{[(2R)-2-morpholinylmethyl]oxy}-1H-indole-2-carboxamide hydrochloride;
N-({4-chloro-3-[(3-chloro-5-cyanophenyl)oxy]-2-fluorophenyl}methyl)-5-hydroxy-1H-indole-2-carboxamide;
N-({4-chloro-3-[(3-chloro-5-cyanophenyl)oxy]-2-fluorophenyl}methyl)-5-[(trifluoromethyl)oxy]-1H-indole-2-carboxamide;
N-({4-chloro-3-[(3-chloro-5-cyanophenyl)oxy]-2-fluorophenyl}methyl)-1H-indole-2-carboxamide;
5-bromo-N-({4-chloro-3-[(3-chloro-5-cyanophenyl)oxy]-2-fluorophenyl}methyl)-1H-indole-2-carboxamide;
5-bromo-N-({4-chloro-3-[(3-chloro-5-cyanophenyl)oxy]-2-fluorophenyl}methyl)-7-methyl-1H-indole-2-carboxamide;
N-({4-chloro-3-[(3-chloro-5-cyanophenyl)oxy]-2-fluorophenyl}methyl)-6-nitro-1H-indole-2-carboxamide;
N-({4-chloro-3-[(3-chloro-5-cyanophenyl)oxy]-2-fluorophenyl}methyl)-7-hydroxy-1H-indole-2-carboxamide;
N-({4-chloro-3-[(3-chloro-5-cyanophenyl)oxy]-2-fluorophenyl}methyl)-5-fluoro-7-(methylsulfonyl)-1H-indole-2-carboxamide;
N-({4-chloro-3-[(3-chloro-5-cyanophenyl)oxy]-2-fluorophenyl}methyl)-4-(methyloxy)-1H-indole-2-carboxamide;
N-({4-chloro-3-[(3-chloro-5-cyanophenyl)oxy]-2-fluorophenyl}methyl)-1H-benzimidazole-2-carboxamide;
N-({4-chloro-3-[(3-chloro-5-cyanophenyl)oxy]-2-fluorophenyl}methyl)-6-hydroxy-1H-indole-2-carboxamide;
N-({4-chloro-3-[(3-chloro-5-cyanophenyl)oxy]-2-fluorophenyl}methyl)-7-nitro-1H-indole-2-carboxamide;
3-chloro-5-[(6-chloro-2-fluoro-3-{[6-(methyloxy)-1-oxo-1,3,4,9-tetrahydro-2H-β-carbolin-2-yl]methyl}phenyl)oxy]benzonitrile;
N-({4-chloro-3-[(3-chloro-5-cyanophenyl)oxy]-2-fluorophenyl}methyl)-3-methyl-1H-indole-2-carboxamide;
5-chloro-N-({4-chloro-3-[(3-chloro-5-cyanophenyl)oxy]-2-fluorophenyl}methyl)-3-methyl-1H-indole-2-carboxamide;
N-({4-chloro-3-[(3-chloro-5-cyanophenyl)oxy]-2-fluorophenyl}methyl)-5-fluoro-1H-indole-2-carboxamide;
N-({4-chloro-3-[(3-chloro-5-cyanophenyl)oxy]-2-fluorophenyl}methyl)-6-(methyloxy)-3-pyridinecarboxamide;
N-({4-chloro-3-[(3-chloro-5-cyanophenyl)oxy]-2-fluorophenyl}methyl)-6-[(phenylmethyl)oxy]-1H-indole-2-carboxamide;
$N^2$-({4-chloro-3-[(3-chloro-5-cyanophenyl)oxy]-2-fluorophenyl}methyl)-7,8-dihydropyrrolo[3,2-e]indole-2,6(3H)-dicarboxamide;
N-({4-chloro-3-[(3-chloro-5-cyanophenyl)oxy]-2-fluorophenyl}methyl)-1-methyl-1H-indole-2-carboxamide;
N-({4-chloro-3-[(3-chloro-5-cyanophenyl)oxy]-2-fluorophenyl}methyl)-5-(methyloxy)-1H-pyrrolo[2,3-c]pyridine-2-carboxamide trifluoroacetate;
N-({4-chloro-3-[(3-chloro-5-cyanophenyl)oxy]-2-fluorophenyl}methyl)-1-benzofuran-2-carboxamide trifluoroacetate;
N-({4-chloro-3-[(3-chloro-5-cyanophenyl)oxy]-2-fluorophenyl}methyl)-3-methyl-1-benzofuran-2-carboxamide trifluoroacetate;
5-chloro-N-({4-chloro-3-[(3-chloro-5-cyanophenyl)oxy]-2-fluorophenyl}methyl)-1-benzofuran-2-carboxamide trifluoroacetate;
N-({4-chloro-3-[(3-chloro-5-cyanophenyl)oxy]-2-fluorophenyl}methyl)-5-nitro-1-benzofuran-2-carboxamide trifluoroacetate;
5-chloro-N-({4-chloro-3-[(3-chloro-5-cyanophenyl)oxy]-2-fluorophenyl}methyl)-1-benzothiophene-2-carboxamide trifluoroacetate;
N-({4-chloro-3-[(3-chloro-5-cyanophenyl)oxy]-2-fluorophenyl}methyl)-3,5-dimethyl-1H-indole-2-carboxamide trifluoroacetate;
3-bromo-N-({4-chloro-3-[(3-chloro-5-cyanophenyl)oxy]-2-fluorophenyl}methyl)-1H-indole-2-carboxamide;
3-bromo-N-({4-chloro-3-[(3-chloro-5-cyanophenyl)oxy]-2-fluorophenyl}methyl)-1H-indole-2-carboxamide trifluoroacetate;
3,6-dichloro-N-({4-chloro-3-[(3-chloro-5-cyanophenyl)oxy]-2-fluorophenyl}methyl)-1H-indole-2-carboxamide trifluoroacetate;
3-(acetylamino)-N-({4-chloro-3-[(3-chloro-5-cyanophenyl)oxy]-2-fluorophenyl}methyl)-5-(methyloxy)-1H-indole-2-carboxamide trifluoroacetate;
N-({4-chloro-3-[(3-chloro-5-cyanophenyl)oxy]-2-fluorophenyl}methyl)-1H-pyrrole-2-carboxamide;
N-({4-chloro-3-[(3-chloro-5-cyanophenyl)oxy]-2-fluorophenyl}methyl)-1H-pyrrole-2-carboxamide trifluoroacetate;
N-({4-chloro-3-[(3-chloro-5-cyanophenyl)oxy]-2-fluorophenyl}methyl)-1H-imidazole-2-carboxamide trifluoroacetate;
N-({4-chloro-3-[(3-chloro-5-cyanophenyl)oxy]-2-fluorophenyl}methyl)-1H-imidazole-2-carboxamide;
3-bromo-N-({4-chloro-3-[(3-chloro-5-cyanophenyl)oxy]-2-fluorophenyl}methyl)-6-hydroxy-1H-indole-2-carboxamide trifluoroacetate;
N-({4-chloro-3-[(3-chloro-5-cyanophenyl)oxy]-2-fluorophenyl}methyl)-3,5-dimethyl-1H-pyrrole-2-carboxamide trifluoroacetate;
N-({4-chloro-3-[(3-chloro-5-cyanophenyl)oxy]-2-fluorophenyl}methyl)-3,5-dimethyl-1H-pyrrole-2-carboxamide;

N-({4-chloro-3-[(3-chloro-5-cyanophenyl)oxy]-2-fluorophenyl}methyl)-1-methyl-1H-imidazole-4-carboxamide trifluoroacetate;

N-({4-chloro-3-[(3-chloro-5-cyanophenyl)oxy]-2-fluorophenyl}methyl)-2-(methylthio)-1-(triphenylmethyl)-1H-imidazole-4-carboxamide trifluoroacetate;

N-({4-chloro-3-[(3-chloro-5-cyanophenyl)oxy]-2-fluorophenyl}methyl)-2-(methylthio)-1H-imidazole-4-carboxamide trifluoroacetate;

N-({4-chloro-3-[(3-chloro-5-cyanophenyl)oxy]-2-fluorophenyl}methyl)-1-methyl-1H-imidazole-5-carboxamide trifluoroacetate;

N-({4-chloro-3-[(3-chloro-5-cyanophenyl)oxy]-2-fluorophenyl}methyl)-4-nitro-1H-imidazole-5-carboxamide trifluoroacetate;

4-bromo-N-({4-chloro-3-[(3-chloro-5-cyanophenyl)oxy]-2-fluorophenyl}methyl)-5-nitro-1H-pyrazole-3-carboxamide trifluoroacetate;

N-({4-chloro-3-[(3-chloro-5-cyanophenyl)oxy]-2-fluorophenyl}methyl)-4-nitro-1H-pyrrole-2-carboxamide trifluoroacetate;

N-({4-chloro-3-[(3-chloro-5-cyanophenyl)oxy]-2-fluorophenyl}methyl)-4-cyano-3,5-dimethyl-1H-pyrrole-2-carboxamide trifluoroacetate;

N-({4-chloro-3-[(3-chloro-5-cyanophenyl)oxy]-2-fluorophenyl}methyl)-1-methyl-1H-imidazole-2-carboxamide trifluoroacetate;

4-bromo-N-({4-chloro-3-[(3-chloro-5-cyanophenyl)oxy]-2-fluorophenyl}methyl)-5-(methyloxy)-1H-indole-2-carboxamide trifluoroacetate;

6-[(acetylamino)methyl]-N-({4-chloro-3-[(3-chloro-5-cyanophenyl)oxy]-2-fluorophenyl}methyl)-1H-indole-2-carboxamide trifluoroacetate;

3-chloro-N-({4-chloro-3-[(3-chloro-5-cyanophenyl)oxy]-2-fluorophenyl}methyl)-1H-indole-2-carboxamide trifluoroacetate;

N-({4-chloro-3-[(3-chloro-5-cyanophenyl)oxy]-2-fluorophenyl}methyl)-4-[(diethylamino)sulfonyl]-1H-pyrrole-2-carboxamide trifluoroacetate;

4-chloro-N-({4-chloro-3-[(3-chloro-5-cyanophenyl)oxy]-2-fluorophenyl}methyl)-2-ethyl-1H-imidazole-5-carboxamide trifluoroacetate;

6-acetyl-N-({4-chloro-3-[(3-chloro-5-cyanophenyl)oxy]-2-fluorophenyl}methyl)-1H-indole-2-carboxamide trifluoroacetate;

N-({4-chloro-3-[(3-chloro-5-cyanophenyl)oxy]-2-fluorophenyl}methyl)-6-cyano-1H-indole-2-carboxamide trifluoroacetate;

5-acetyl-N-({4-chloro-3-[(3-chloro-5-cyanophenyl)oxy]-2-fluorophenyl}methyl)-1H-indole-2-carboxamide trifluoroacetate;

N-({4-chloro-3-[(3-chloro-5-cyanophenyl)oxy]-2-fluorophenyl}methyl)-3-ethyl-5-(methyloxy)-1H-indole-2-carboxamide trifluoroacetate;

N-({4-chloro-3-[(3-chloro-5-cyanophenyl)oxy]-2-fluorophenyl}methyl)-7-(methyloxy)-1H-pyrrolo[2,3-d]pyridazine-2-carboxamide 5-oxide trifluoroacetate;

N-({4-chloro-3-[(3-chloro-5-cyanophenyl)oxy]-2-fluorophenyl}methyl)-1-(triphenylmethyl)-1H-imidazole-4-carboxamide;

N-({4-chloro-3-[(3-chloro-5-cyanophenyl)oxy]-2-fluorophenyl}methyl)-1H-imidazole-4-carboxamide trifluoroacetate;

N-({4-chloro-3-[(3-chloro-5-cyanophenyl)oxy]-2-fluorophenyl}methyl)-2-pyridinecarboxamide;

N-({4-chloro-3-[(3-chloro-5-cyanophenyl)oxy]-2-fluorophenyl}methyl)-2-(methylthio)-3-pyridinecarboxamide trifluoroacetate;

N-({4-chloro-3-[(3-chloro-5-cyanophenyl)oxy]-2-fluorophenyl}methyl)-2-pyrazinecarboxamide trifluoroacetate;

N-({4-chloro-3-[(3-chloro-5-cyanophenyl)oxy]-2-fluorophenyl}methyl)-2-(4-pyridinyl)-1,3-thiazole-4-carboxamide trifluoroacetate;

N-({4-chloro-3-[(3-chloro-5-cyanophenyl)oxy]-2-fluorophenyl}methyl)-4-pyridinecarboxamide trifluoroacetate;

N-({4-chloro-3-[(3-chloro-5-cyanophenyl)oxy]-2-fluorophenyl}methyl)-1,2,3-thiadiazole-4-carboxamide;

N-({4-chloro-3-[(3-chloro-5-cyanophenyl)oxy]-2-fluorophenyl}methyl)-4-methyl-1,2,3-thiadiazole-5-carboxamide;

N-({4-chloro-3-[(3-chloro-5-cyanophenyl)oxy]-2-fluorophenyl}methyl)-4-(methylsulfonyl)benzamide;

N-({4-chloro-3-[(3-chloro-5-cyanophenyl)oxy]-2-fluorophenyl}methyl)-5-isoxazolecarboxamide;

N-({4-chloro-3-[(3-chloro-5-cyanophenyl)oxy]-2-fluorophenyl}methyl)-3-pyridinecarboxamide trifluoroacetate;

N-({4-chloro-3-[(3-chloro-5-cyanophenyl)oxy]-2-fluorophenyl}methyl)-1H-pyrazol e-3-carboxamide;

N-({4-chloro-3-[(3-chloro-5-cyanophenyl)oxy]-2-fluorophenyl}methyl)-5-methyl-2-phenyl-2H-1,2,3-triazole-4-carboxamide trifluoroacetate;

N-({4-chloro-3-[(3-chloro-5-cyanophenyl)oxy]-2-fluorophenyl}methyl)-2-methylimidazo[1,2-a]pyridine-3-carboxamide trifluoroacetate;

N-({4-chloro-3-[(3-chloro-5-cyanophenyl)oxy]-2-fluorophenyl}methyl)-2-(3-pyridinyl)-1,3-thiazole-4-carboxamide trifluoroacetate;

N-({4-chloro-3-[(3-chloro-5-cyanophenyl)oxy]-2-fluorophenyl}methyl)-4-phenyl-1,2,3-thiadiazole-5-carboxamide;

N-({4-chloro-3-[(3-chloro-5-cyanophenyl)oxy]-2-fluorophenyl}methyl)-1H-pyrazole-4-carboxamide trifluoroacetate;

5-chloro-N-({4-chloro-3-[(3-chloro-5-cyanophenyl)oxy]-2-fluorophenyl}methyl)-2-(methylthio)-4-pyrimidinecarboxamide;

N-({4-chloro-3-[(3-chloro-5-cyanophenyl)oxy]-2-fluorophenyl}methyl)-5-{[3-(dimethylamino)propyl]oxy}-1H-indole-2-carboxamide;

N-({4-chloro-3-[(3-chloro-5-cyanophenyl)oxy]-2-fluorophenyl}methyl)-5-{[2-(4-morpholinyl)ethyl]oxy}-1H-indole-2-carboxamide;

N-({4-chloro-3-[(3-chloro-5-cyanophenyl)oxy]-2-fluorophenyl}methyl)-5-{[2-(1-methyl-2-pyrrolidinyl)ethyl]oxy}-1H-indole-2-carboxamide;

N-({4-chloro-3-[(3-chloro-5-cyanophenyl)oxy]-2-fluorophenyl}methyl)-5-{[2-(dimethylamino)ethyl]oxy}-1H-indole-2-carboxamide;

N-({4-chloro-3-[(3-chloro-5-cyanophenyl)oxy]-2-fluorophenyl}methyl)-5-[(3-hydroxybutyl)oxy]-1H-indole-2-carboxamide;

N-({4-chloro-3-[(3-chloro-5-cyanophenyl)oxy]-2-fluorophenyl}methyl)-5-{[(3S)-3,4-dihydroxybutyl]oxy}-1H-indole-2-carboxamide;

N-({4-chloro-3-[(3-chloro-5-cyanophenyl)oxy]-2-fluorophenyl}methyl)-7-methyl-1H-indole-2-carboxamide;

5-chloro-N-({4-chloro-3-[(3-chloro-5-cyanophenyl)oxy]-2-fluorophenyl}methyl)-1H-indole-2-carboxamide;

6-chloro-N-({4-chloro-3-[(3-chloro-5-cyanophenyl)oxy]-2-fluorophenyl}methyl)-1H-indole-2-carboxamide;

5-amino-N-({4-chloro-3-[(3-chloro-5-cyanophenyl)oxy]-2-fluorophenyl}methyl)-1H-indole-2-carboxamide trifluoroacetate;

1,1-dimethylethyl (2-{[({4-chloro-3-[(3-chloro-5-cyanophenyl)oxy]-2-fluorophenyl}methyl)amino]carbonyl}-1H-indol-7-yl)carbamate;

7-amino-N-({4-chloro-3-[(3-chloro-5-cyanophenyl)oxy]-2-fluorophenyl}methyl)-1H-indole-2-carboxamide;

N-({4-chloro-3-[(3-chloro-5-cyanophenyl)oxy]-2-fluorophenyl}methyl)-5-[(4-pyridinylcarbonyl)amino]-1H-indole-2-carboxamide;

N-({4-chloro-3-[(3-chloro-5-cyanophenyl)oxy]-2-fluorophenyl}methyl)-5-[(3-pyridinylcarbonyl)amino]-1H-indole-2-carboxamide;

5-(β-alanylamino)-N-({4-chloro-3-[(3-chloro-5-cyanophenyl)oxy]-2-fluorophenyl}methyl)-1H-indole-2-carboxamide;

1,1-dimethylethyl (2S)-2-{[(2-{[({4-chloro-3-[(3-chloro-5-cyanophenyl)oxy]-2-fluorophenyl}methyl)amino]carbonyl}-1H-indol-5-yl)amino]carbonyl}-1-pyrrolidin ecarboxylate;

N-({4-chloro-3-[(3-chloro-5-cyanophenyl)oxy]-2-fluorophenyl}methyl)-5-(L-prolylamino)-1H-indole-2-carboxamide trifluoroacetate;

N-({4-chloro-3-[(3-chloro-5-cyanophenyl)oxy]-2-fluorophenyl}methyl)-5-[(N-methylglycyl)amino]-1H-indole-2-carboxamide;

N-({4-chloro-3-[(3-chloro-5-cyanophenyl)oxy]-2-fluorophenyl}methyl)-5-(glycylamino)-1H-indole-2-carboxamide trifluoroacetate;

5-(acetylamino)-N-({4-chloro-3-[(3-chloro-5-cyanophenyl)oxy]-2-fluorophenyl}methyl)-1H-indole-2-carboxamide;

6-(acetylamino)-N-({4-chloro-3-[(3-chloro-5-cyanophenyl)oxy]-2-fluorophenyl}methyl)-1H-indole-2-carboxamide;

6-amino-N-({4-chloro-3-[(3-chloro-5-cyanophenyl)oxy]-2-fluorophenyl}methyl)-1H-indole-2-carboxamide trifluoroacetate;

N-({4-chloro-3-[(3-chloro-5-cyanophenyl)oxy]-2-fluorophenyl}methyl)-5-nitro-1H-benzimidazole-2-carboxamide;

5-(acetylamino)-N-({4-chloro-3-[(3-chloro-5-cyanophenyl)oxy]-2-fluorophenyl}methyl)-1H-benzimidazole-2-carboxamide;

N-({4-chloro-3-[(3-chloro-5-cyanophenyl)oxy]-2-fluorophenyl}methyl)-5-(dimethylamino)-1H-indole-2-carboxamide;

5-[bis(cyclopropylmethyl)amino]-N-({4-chloro-3-[(3-chloro-5-cyanophenyl)oxy]-2-fluorophenyl}methyl)-1H-indole-2-carboxamide;

3-chloro-N-({4-chloro-3-[(3-chloro-5-cyanophenyl)oxy]-2-fluorophenyl}methyl)-1H-pyrrole-2-carboxamide;

N-({4-chloro-3-[(3-chloro-5-cyanophenyl)oxy]-2-fluorophenyl}methyl)-N-methyl-1H-pyrrole-2-carboxamide;

N-({4-chloro-3-[(3-chloro-5-cyanophenyl)oxy]-2-fluorophenyl}methyl)-N-methyl-1H-imidazole-2-carboxamide;

4-chloro-N-({4-chloro-3-[(3-chloro-5-cyanophenyl)oxy]-2-fluorophenyl}methyl)-1H-imidazole-5-carboxamide;

4-chloro-N-({4-chloro-3-[(3-chloro-5-cyanophenyl)oxy]-2-fluorophenyl}methyl)-N-methyl-1H-imidazole-5-carboxamide trifluoroacetate;

4-bromo-N-({4-chloro-3-[(3-chloro-5-cyanophenyl)oxy]-2-fluorophenyl}methyl)-1H-imidazole-5-carboxamide trifluoroacetate;

4-bromo-N-({4-chloro-3-[(3-chloro-5-cyanophenyl)oxy]-2-fluorophenyl}methyl)-2-methyl-1H-imidazole-5-carboxamide;

4-chloro-N-({4-chloro-3-[(3-chloro-5-cyanophenyl)oxy]-2-fluorophenyl}methyl)-2-(1-methylethyl)-1H-imidazole-5-carboxamide trifluoroacetate;

4-chloro-N-({4-chloro-3-[(3-chloro-5-cyanophenyl)oxy]-2-fluorophenyl}methyl)-2-cyclopropyl-1H-imidazole-5-carboxamide trifluoroacetate;

4-chloro-N-({4-chloro-3-[(3-chloro-5-cyanophenyl)oxy]-2-fluorophenyl}methyl)-2-methyl-1H-imidazole-5-carboxamide;

4-chloro-N-({4-chloro-3-[(3-chloro-5-cyanophenyl)oxy]-2-fluorophenyl}methyl)-2-ethyl-1H-imidazole-5-carboxamide;

4-chloro-N-({4-chloro-3-[(3-chloro-5-cyanophenyl)oxy]-2-fluorophenyl}methyl)-2-propyl-1H-imidazole-5-carboxamide;

2-butyl-4-chloro-N-({4-chloro-3-[(3-chloro-5-cyanophenyl)oxy]-2-fluorophenyl}methyl)-1H-imidazole-5-carboxamide trifluoroacetate;

3-Bromo-N-({4-chloro-3-[(3-chloro-5-cyanophenyl)oxy]-2-fluorophenyl}methyl)-6-[(2-hydroxyethyl)oxy]-1H-indole-2-carboxamide;

N-({4-chloro-3-[(3-chloro-5-cyanophenyl)oxy]-2-fluorophenyl}methyl)-6-[(2-hydroxyethyl)oxy]-1H-indole-2-carboxamide; and pharmaceutically acceptable derivatives thereof.

Compounds of the invention further include:

N-({4-chloro-3-[(3-chloro-5-cyanophenyl)oxy]-2-fluorophenyl}methyl)-6-hydroxy-1H-indole-2-carboxamide;

3-bromo-N-({4-chloro-3-[(3-chloro-5-cyanophenyl)oxy]-2-fluorophenyl}methyl)-1H-indole-2-carboxamide trifluoroacetate;

N-({4-chloro-3-[(3-chloro-5-cyanophenyl)oxy]-2-fluorophenyl}methyl)-1H-imidazole-2-carboxamide trifluoroacetate;

3-bromo-N-({4-chloro-3-[(3-chloro-5-cyanophenyl)oxy]-2-fluorophenyl}methyl)-6-hydroxy-1H-indole-2-carboxamide trifluoroacetate;

N-({4-chloro-3-[(3-chloro-5-cyanophenyl)oxy]-2-fluorophenyl}methyl)-3,5-dimethyl-1H-pyrrole-2-carboxamide trifluoroacetate;

N-({4-chloro-3-[(3-chloro-5-cyanophenyl)oxy]-2-fluorophenyl}methyl)-3,5-dimethyl-1H-pyrrole-2-carboxamide;

N-({4-chloro-3-[(3-chloro-5-cyanophenyl)oxy]-2-fluorophenyl}methyl)-4-nitro-1H-imidazole-5-carboxamide trifluoroacetate;

N-({4-chloro-3-[(3-chloro-5-cyanophenyl)oxy]-2-fluorophenyl}methyl)-4-cyano-3,5-dimethyl-1H-pyrrole-2-carboxamide trifluoroacetate;

6-[(acetylamino)methyl]-N-({4-chloro-3-[(3-chloro-5-cyanophenyl)oxy]-2-fluorophenyl}methyl)-1H-indole-2-carboxamide trifluoroacetate;

4-chloro-N-({4-chloro-3-[(3-chloro-5-cyanophenyl)oxy]-2-fluorophenyl}methyl)-2-ethyl-1H-imidazole-5-carboxamide trifluoroacetate;

N-({4-chloro-3-[(3-chloro-5-cyanophenyl)oxy]-2-fluorophenyl}methyl)-5-{[(3S)-3,4-dihydroxybutyl]oxy}-1H-indole-2-carboxamide;

3-chloro-N-({4-chloro-3-[(3-chloro-5-cyanophenyl)oxy]-2-fluorophenyl}methyl)-1H-pyrrole-2-carboxamide;

N-({4-chloro-3-[(3-chloro-5-cyanophenyl)oxy]-2-fluorophenyl}methyl)-N-methyl-1H-pyrrole-2-carboxamide;

N-({4-chloro-3-[(3-chloro-5-cyanophenyl)oxy]-2-fluorophenyl}methyl)-N-methyl-1H-imidazole-2-carboxamide;

3-Bromo-N-({4-chloro-3-[(3-chloro-5-cyanophenyl)oxy]-2-fluorophenyl}methyl)-6-[(2-hydroxyethyl)oxy]-1H-indole-2-carboxamide;

N-({4-chloro-3-[(3-chloro-5-cyanophenyl)oxy]-2-fluorophenyl}methyl)-6-[(2-hydroxyethyl)oxy]-1H-indole-2-carboxamide; and pharmaceutically acceptable derivatives thereof.

One aspect of the present invention includes the compounds substantially as hereinbefore defined with reference to any one of the Examples.

One aspect of the present invention includes a pharmaceutical composition comprising one or more compounds of the present invention and a pharmaceutically acceptable carrier.

One aspect of the present invention includes one or more compounds of the present invention for use as an active therapeutic substance.

The present invention features compounds of the present invention for use in medical therapy for example, in the treatment of HIV infections and associated conditions.

The present invention also features the use of compounds of the present invention in the manufacture of a medicament for use in the treatment of viral infections and associated conditions, for example in the treatment of HIV infections and associated conditions.

The present invention features a method for the treatment of viral infections and associated conditions, for example, HIV infections and associated conditions, comprising the administration of compounds of the present invention.

DETAILED DESCRIPTION OF THE INVENTION

Terms are used within their accepted meanings. The following definitions are meant to clarify, but not limit, the terms defined.

As used herein the term "alkyl" alone or in combination with any other term, refers to a straight or branched chain hydrocarbon, containing from one to twelve carbon atoms, unless specified otherwise. Examples of "alkyl" as used herein include, but are not limited to, methyl, ethyl, propyl, isopropyl, isobutyl, n-butyl, tert-butyl, sec-butyl, isopentyl, n-pentyl, n-hexyl, and the like.

As used throughout this specification, the preferred number of atoms, such as carbon atoms, will be represented by, for example, the phrase "$C_x$-$C_y$ alkyl," which refers to an alkyl group, as herein defined, containing the specified number of carbon atoms. Similar terminology will apply for other preferred terms and ranges as well.

As used herein the term "alkenyl" refers to a straight or branched chain aliphatic hydrocarbon containing one or more carbon-to-carbon double bonds. Examples include, but are not limited to, vinyl, allyl, and the like.

As used herein the term "alkynyl" refers to a straight or branched chain aliphatic hydrocarbon containing one or more carbon-to-carbon triple bonds, which may occur at any stable point along the chain. Examples include, but are not limited to, ethynyl, propynyl, butynyl, pentynyl, and the like.

As used herein, the term "alkylene" refers to an optionally substituted straight or branched chain divalent hydrocarbon radical, preferably having from one to ten carbon atoms, unless specified otherwise. Examples of "alkylene" as used herein include, but are not limited to, methylene, ethylene, n-propylene, n-butylene, and the like. Preferred substituent groups include $C_1$-$C_8$ alkyl, hydroxyl or oxo.

As used herein, the term "alkenylene" refers to a straight or branched chain divalent hydrocarbon radical, preferably having from two to ten carbon atoms, unless specified otherwise, containing one or more carbon-to-carbon double bonds. Examples include, but are not limited to, vinylene, allylene or 2-propenylene, and the like.

As used herein, the term "alkynylene" refers to a straight or branched chain divalent hydrocarbon radical, preferably having from two to ten carbon atoms, unless otherwise specified, containing one or more carbon-to-carbon triple bonds. Examples include, but are not limited to, ethynylene and the like.

As used herein, the term "cycloalkyl" refers to an optionally substituted non-aromatic cyclic hydrocarbon ring. Unless otherwise indicated, cycloalkyl is composed of three to eight carbon atoms. Exemplary "cycloalkyl" groups include, but are not limited to, cyclopropyl, cyclobutyl, cyclopentyl, cyclohexyl, and cycloheptyl. As used herein, the term "cycloalkyl" includes an optionally substituted fused polycyclic hydrocarbon saturated ring and aromatic ring system, namely polycyclic hydrocarbons with less than maximum number of non-cumulative double bonds, for example where a saturated hydrocarbon ring (such as a cyclopentyl ring) is fused with an aromatic ring (herein "aryl," such as a benzene ring) to form, for example, groups such as indane. Preferred substituent groups include $C_1$-$C_8$ alkyl, $C_2$-$C_6$ alkenyl, $C_2$-$C_6$ alkynyl, $C_1$-$C_8$ alkoxy, hydroxyl, halogen, $C_1$-$C_8$ haloalkyl, $C_3$-$C_8$ cycloalkyl, $C_3$-$C_8$ cycloalkoxy, cyano, amide, amino, and $C_1$-$C_8$ alkylamino.

As used herein, the term "cycloalkenyl" refers to an optionally substituted non-aromatic cyclic hydrocarbon ring containing one or more carbon-to-carbon double bonds which optionally includes an alkylene linker through which the cycloalkenyl may be attached. Exemplary "cycloalkenyl" groups include, but are not limited to, cyclopropenyl, cyclobutenyl, cyclopentenyl, cyclohexenyl, and cycloheptenyl. Preferred substituent groups include $C_1$-$C_8$ alkyl, $C_2$-$C_6$ alkenyl, $C_2$-$C_6$ alkynyl, $C_1$-$C_8$ alkoxy, hydroxyl, halogen, $C_1$-$C_8$ haloalkyl, $C_3$-$C_8$ cycloalkyl, $C_3$-$C_8$ cycloalkoxy, cyano, amide, amino, and $C_1$-$C_8$ alkylamino.

As used herein, the term "cycloalkylene" refers to a divalent, optionally substituted non-aromatic cyclic hydrocarbon ring. Exemplary "cycloalkylene" groups include, but are not limited to, cyclopropylene, cyclobutylene, cyclopentylene, cyclohexylene, and cycloheptylene. Preferred substituent groups include $C_1$-$C_8$ alkyl, $C_2$-$C_6$ alkenyl, $C_2$-$C_6$ alkynyl, $C_1$-$C_8$ alkoxy, hydroxyl, halogen, $C_1$-$C_8$ haloalkyl, $C_3$-$C_8$ cycloalkyl, $C_3$-$C_8$ cycloalkoxy, cyano, amide, amino, and $C_1$-$C_8$ alkylamino.

As used herein, the term "cycloalkenylene" refers to a divalent optionally substituted non-aromatic cyclic hydrocarbon ring containing one or more carbon-to-carbon double bonds. Exemplary "cycloalkenylene" groups include, but are not limited to, cyclopropenylene, cyclobutenylene, cyclopentenylene, cyclohexenylene, and cycloheptenylene. Preferred substituent groups include $C_1$-$C_8$ alkyl, $C_2$-$C_6$ alkenyl, $C_2$-$C_6$ alkynyl, $C_1$-$C_8$ alkoxy, hydroxyl, halogen, $C_1$-$C_8$ haloalkyl, $C_3$-$C_8$ cycloalkyl, $C_3$-$C_8$ cycloalkoxy, cyano, amide, amino, and $C_1$-$C_8$ alkylamino.

As used herein, the term "heterocycle", "heterocyclic" or "heterocyclyl" refers to an optionally substituted mono- or polycyclic ring system, optionally containing one or more degrees of unsaturation, and also containing one or more heteroatoms. Preferred heteroatoms include N, O, and/or S, including N-oxides, sulfur oxides, and sulfur dioxides. More preferably, the heteroatom is N.

Preferably the heterocyclyl ring is three to twelve-membered, unless otherwise indicated, and is either fully saturated or has one or more degrees of unsaturation. Such rings may be optionally fused to one or more of another "heterocyclic" ring(s), cycloalkyl ring(s) or aryl ring(s). Examples of "heterocyclic" groups include, but are not limited to, tetrahydrofuran, pyran, 1,4-dioxane, 1,3-dioxane, piperidine, piperazine, pyrrolidine, morpholine, tetrahydrothiopyran, aziridine, azetidine and tetrahydrothiophene. Heterocyclic groups include heteroaryl groups. When the heterocyclic ring has substituents, it is understood that the substituents may be attached to any atom in the ring, whether a heteroatom or a carbon atom, provided that a stable chemical structure results. Preferred substituent groups include $C_1$-$C_8$ alkyl, $C_2$-$C_8$ alkenyl, $C_2$-$C_8$ alkynyl, $C_1$-$C_8$ alkoxy, hydroxyl, halogen, $C_1$-$C_8$ haloalkyl, $C_3$-$C_8$ cycloalkyl, $C_3$-$C_8$ cycloalkoxy, cyano, amide, amino, and $C_1$-$C_8$ alkylamino.

As used herein, the term "aryl" refers to an optionally substituted carbocyclic aromatic moiety (such as phenyl or naphthyl) containing the specified number of carbon atoms, preferably 6-14 carbon atoms or 6-10 carbon atoms. The term aryl also refers to optionally substituted ring systems, for example anthracene, phenanthrene, or naphthalene ring systems. Examples of "aryl" groups include, but are not limited to, phenyl, naphthyl, indenyl, azulenyl, fluorenyl, anthracenyl, phenanthrenyl, tetrahydronaphthyl, indanyl, phenathridinyl, and the like. Unless otherwise indicated, the term aryl also includes each possible positional isomer of an aromatic hydrocarbon radical, such as 1-naphthyl, 2-naphthyl, 5-tetrahydronaphthyl, 6-tetrahydronaphthyl, 1 phenanthridinyl, 2-phenanthridinyl, 3-phenanthridinyl, 4-phenanthridinyl, and the like. Preferred substituent groups include $C_1$-$C_8$ alkyl, $C_2$-$C_6$ alkenyl, $C_2$-$C_8$ alkynyl, $C_1$-$C_8$ alkoxy, hydroxyl, halogen, $C_1$-$C_8$ haloalkyl, $C_3$-$C_8$ cycloalkyl, $C_3$-$C_8$ cycloalkoxy, cyano, amide, amino, and $C_1$-$C_8$ alkylamino.

As used herein, the term "heteroaryl" refers to an optionally substituted monocyclic five to seven membered aromatic ring unless otherwise specified, or to an optionally substituted fused bicyclic aromatic ring system comprising two of such aromatic rings. These heteroaryl rings contain one or more nitrogen, sulfur, and/or oxygen atoms, where N-oxides, sulfur oxides, and sulfur dioxides are permissible heteroatom substitutions. Preferably, the heteroatom is N.

Examples of "heteroaryl" groups used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, benzimidizolyl, imidazopyridinyl, pyrazolopyridinyl, and pyrazolopyrimidinyl. Preferred substituent groups include $C_1$-$C_8$ alkyl, $C_2$-$C_6$ alkenyl, $C_2$-$C_6$ alkynyl, $C_1$-$C_8$ alkoxy, hydroxyl, halogen, $C_1$-$C_8$ haloalkyl, $C_3$-$C_8$ cycloalkyl, $C_3$-$C_8$ cycloalkoxy, cyano, amide, amino, and alkylamino.

As used herein the term "halogen" refers to fluorine, chlorine, bromine, or iodine.

As used herein the term "haloalkyl" refers to an alkyl group, as defined herein, which is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, e.g., fluoro, chloro, bromo, and iodo. The term "haloalkyl" should be interpreted to include such substituents as perfluoroalkyl groups and the like.

As used herein the term "alkoxy" refers to a group —OR', where R' is alkyl as defined. Examples of suitable alkoxy radicals include, but are not limited to, methoxy, ethoxy, propoxy, isopropoxy, n-butoxy, isobutoxy, sec-butoxy, tert-butoxy, and the like.

As used herein the term "cycloalkoxy" refers to a group —OR', where R' is cycloalkyl as defined.

As used herein the term "alkoxycarbonyl" refers to groups such as:

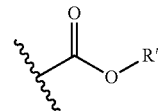

where the R' represents an alkyl group as herein defined.

As used herein the term "aryloxycarbonyl" refers to groups such as:

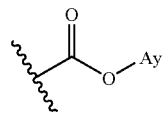

where the Ay represents an aryl group as herein defined.

As used herein the term "nitro" refers to a group —$NO_2$.
As used herein the term "cyano" refers to a group —CN.
As used herein the term "azido" refers to a group —$N_3$.
As used herein the term amino refers to a group —NR'R", where R' and R" independently represent H, alkyl, alkenyl, alkynyl, cycloalkyl, heterocyclyl, aryl, or heteroaryl. Similarly, the term "alkylamino" includes an alkylene linker through which the amino group is attached.

As used herein the term "amide" refers to a group —C(O)NR'R", where R' and R" independently represent H, alkyl, alkenyl, alkynyl, cycloalkyl, heterocyclyl, aryl, or heteroaryl.

As used herein throughout the present specification, the phrase "optionally substituted" or variations thereof denote an optional substitution, including multiple degrees of substitution, with one or more substituent group. The phrase should not be interpreted so as to be imprecise or duplicative of substitution patterns herein described or depicted specifically. Rather, those of ordinary skill in the art will appreciate that the phrase is included to provide for modifications, which are encompassed within the scope of the appended claims.

The compounds of the present invention may crystallize in more than one form, a characteristic known as polymorphism, and such polymorphic forms ("polymorphs") are within the scope of the present invention. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point. Though a crystalline form of compounds of the present invention are generally preferred, the invention also contemplates amorphous forms of the compounds produced by methods known in the art (e.g. spray drying, milling, freeze drying, and so forth).

Certain of the compounds described herein contain one or more chiral centers, or may otherwise be capable of existing as multiple stereoisomers. The scope of the present invention includes mixtures of stereoisomers as well as purified enantiomers or enantiomerically and/or diastereomerically enriched mixtures. Also included within the scope of the invention are the individual isomers of the compounds of the present invention, as well as any wholly or partially equilibrated mixtures thereof. The present invention also includes the individual isomers of the compounds represented by the formulas above as mixtures with isomers thereof in which one or more chiral centers are inverted. The present invention also includes the individual tautomers of the compounds represented by the formulas above. For example, where Z is represented by the formula (III)

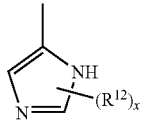
(III)

the tautomer represented by formula (IV):

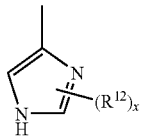
(IV)

is also included within the scope of the present invention.

As used herein, the term "solvate" refers to a complex of variable stoichiometry formed by a solute (in this invention, a compound of the present invention, or a salt or other pharmaceutically acceptable derivative thereof) and a solvent. Such solvents, for the purpose of the invention, should not interfere with the biological activity of the solute. Non-limiting examples of suitable solvents include, but are not limited to water, methanol, ethanol, ethyl acetate, acetone, acetonitrile, trifluoroacetic acid and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "pharmaceutically acceptable derivative" means any pharmaceutically acceptable salt, ester, salt of an ester, ether, amides, or other derivative of a compound of this invention which, upon administration to a recipient, is capable of providing directly or indirectly a compound of this invention or an inhibitorily active metabolite or residue thereof. Particularly favored derivatives and prodrugs are those that increase the bioavailability of the compounds of this invention when such compounds are administered to a mammal, for example, by allowing an orally administered compound to be more readily absorbed into the blood, or which enhance delivery of the parent compound to a biological compartment, for example, the brain or lymphatic system, relative to the parent species.

The present invention features a compound of formula (I)

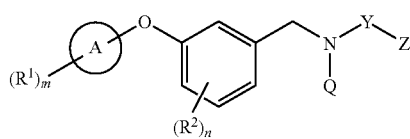
(I)

wherein m is 1, 2, 3 or 4;
n is 1, 2, 3 or 4;
each $R^1$ independently is halogen, —CN, $C_1$-$C_6$ alkyl, $C_2$-$C_6$ alkenyl, $C_2$-$C_6$ alkynyl, $C_3$-$C_7$ cycloalkyl, hydroxyl, $C_1$-$C_8$ alkoxy, —C(O)OR$^5$, —C(O)N(R$^5$)$_2$, —OR$^5$, —R$^3$CN or —N(R$^5$)$_2$;

each $R^2$ independently is halogen, —CN, $C_1$-$C_5$ alkyl, $C_2$-$C_5$ alkenyl, $C_2$-$C_6$ alkynyl, $C_3$-$C_7$ cycloalkyl, hydroxyl, $C_1$-$C_8$ alkoxy, —C(O)OR$^5$, —C(O)N(R$^5$)$_2$, —OR$^5$, —R$^3$CN or —N(R$^5$)$_2$;
A is $C_5$-$C_{12}$ aryl or $C_5$-$C_{12}$ heterocycle;
Q is hydrogen or $C_1$-$C_4$ alkyl;
Y is —C(O)—, —S(O)$_2$—, or —S(O)—;
Z is $C_4$-$C_{12}$ aryl, $C_3$-$C_{14}$ heterocycle, R$^3$Het, or R$^3$Ar, each optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N(R$^5$)C(O)R$^5$, —N(R$^5$)$_2$, —OR$^5$, —$C_3$-$C_{12}$ Het, —C(O)N(R$^5$)$_2$, $C_4$-$C_{12}$ Ar, —SR$^5$, —S(O)$_2$N(R$^5$)$_2$, —OR$^3$HetC(O)R$^5$, —OCF$_3$, —S(O)$_2$R$^5$, —OR$^3$R$^5$, —N(R$^5$)C(O)R$^3$OR$^5$; —N(R$^5$)C(O)R$^3$N(R$^5$)$_2$, —N(R$^5$)C(O)R$^3$R$^5$, —OR$^3$N(R$^5$)$_2$, —R$^3$Het, —R$^3$N(R$^5$)$_2$, —R$^3$N(R$^5$)C(O)R$^5$, —OR$^3$SR$^5$, —C(O)R$^5$, —O(R$^5$)$_3$, —R$^3$C(O)OR$^5$, —R$^3$C(O)N(R$^5$)$_2$, or —N(R$^5$)S(O)$_2$R$^5$; or Z is linked to Q to form a $C_4$-$C_{14}$ heterocycle together with the nitrogen atom and Y group to which they are attached and are optionally substituted with —C(O)OR$^5$ or $C_1$-$C_6$ alkoxy;
each $R^5$ independently is hydrogen, $C_1$-$C_8$ alkyl, oxo, $C_3$-$C_7$ cycloalkyl, $C_3$-$C_{12}$ heterocycle, $C_4$-$C_{12}$ aryl or $C_1$-$C_8$ alkoxy, each optionally substituted with one or more of hydroxyl, $C_1$-$C_8$ alkyl, —C(O)OR$^5$, $C_1$-$C_4$ alkoxy or $C_3$-$C_7$ cycloalkyl;
$R^3$ is $C_2$-$C_6$ alkenylene or $C_1$-$C_4$ alkylene, each optionally substituted with hydroxyl or $C_1$-$C_8$ alkoxy;
Het is $C_3$-$C_{12}$ heterocycle and is optionally substituted with one or more of $C_1$-$C_6$ alkyl, —C(O)NR(⁵)$_2$, —R$^3$S(O)$_2$R$^5$, or halogen; and
Ar is $C_4$-$C_{12}$ aryl and is optionally substituted with one or more of $C_1$-$C_6$ alkyl or halogen; or pharmaceutically acceptable salts or solvates thereof.

The present invention features a compound of formula (I) wherein Z is $C_4$-$C_{12}$ aryl optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N(R$^5$)C(O)R$^5$, —N(R$^5$)$_2$, —OR$^5$, —$C_3$-$C_{12}$ Het, —C(O)N(R$^5$)$_2$, $C_4$-$C_{12}$ Ar, —SR$^5$, —S(O)$_2$N(R$^5$)$_2$, —OR$^3$HetC(O)R$^5$, —OCF$_3$, —S(O)$_2$R$^5$, —OR$^3$R$^5$, —N(R$^5$)C(O)R$^3$OR$^5$; —N(R$^5$)C(O)R$^3$N(R$^5$)$_2$, —N(R$^5$)C(O)R$^3$R$^5$, —OR$^3$N(R$^5$)$_2$, —R$^3$Het, —R$^3$N(R$^5$)$_2$, —R$^3$N(R$^5$)C(O)R$^5$, —OR$^3$SR$^5$, —C(O)R$^5$, —C(R$^5$)$_3$, —R$^3$C(O)OR$^5$, —R$^3$C(O)N(R$^5$)$_2$, or —N(R$^5$)S(O)$_2$R$^5$.

The present invention features a compound of formula (I) wherein Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N(R$^5$)C(O)R$^5$, —N(R$^5$)$_2$, —OR$^5$, —$C_3$-$C_{12}$ Het, —C(O)N(R$^5$)$_2$, $C_4$-$C_{12}$ Ar, —SR$^5$, —S(O)$_2$N(R$^5$)$_2$, —OR$^3$HetC(O)R$^5$, —OCF$_3$, —S(O)$_2$R$^5$, —OR$^3$R$^5$, —N(R$^5$)C(O)R$^3$OR$^5$; —N(R$^5$)C(O)R$^3$N(R$^5$)$_2$, —N(R$^5$)C(O)R$^3$R$^5$, —OR$^3$N(R$^5$)$_2$, —R$^3$Het, —R$^3$N(R$^5$)$_2$, —R$^3$N(R$^5$)C(O)R$^5$, —OR$^3$SR$^5$, —C(O)R$^5$, —C(R$^5$)$_3$, —R$^3$C(O)OR$^5$, —R$^3$C(O)N(R$^5$)$_2$, or —N(R$^5$)S(O)$_2$R$^5$.

The present invention features a compound of formula (I) wherein Y is —C(O)—, Q is hydrogen, and Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N(R$^5$)C(O)R$^5$, —N(R$^5$)$_2$, —OR$^5$, —$C_3$-$C_{12}$ Het, —C(O)N(R$^5$)$_2$, $C_4$-$C_{12}$ Ar, —SR$^5$, —S(O)$_2$N(R$^5$)$_2$, —OR$^3$HetC(O)R$^5$, —OCF$_3$, —S(O)$_2$R$^5$, —OR$^3$R$^5$, —N(R$^5$)C(O)R$^3$OR$^5$; —N(R$^5$)C(O)R$^3$N(R$^5$)$_2$, —N(R$^5$)C(O)R$^3$R$^5$, —OR$^3$N(R$^5$)$_2$, —R$^3$Het, —R$^3$N(R$^5$)$_2$, —R$^3$N(R$^5$)C(O)R$^5$, —OR$^3$SR$^5$, —C(O)R$^5$, —C(R$^5$)$_3$, —R$^3$C(O)OR$^5$, —R$^3$C(O)N(R$^5$)$_2$, or —N(R$^5$)S(O)$_2$R$^5$ The present invention features a compound of formula (I) wherein Y is —C(O)—, Q is $C_1$-$C_8$ alkyl, and Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —$NO_2$, —$N(R^5)C(O)R^5$, —$N(R^5)_2$, —$OR^5$, —$C_3$-$C_{12}$ Het, —$C(O)N(R^5)_2$, $C_4$-$C_{12}$ Ar, —$SR^5$, —$S(O)_2N(R^5)_2$, —$OR^3HetC(O)R^5$, —$OCF_3$, —$S(O)_2R^5$, —$OR^3R^5$, —$N(R^5)C(O)R^3OR^5$, —$N(R^5)C(O)R^3N(R^5)_2$, —$N(R^5)C(O)R^3R^5$, —$OR^3N(R^5)_2$, —$R^3Het$, —$R^3N(R^5)_2$, —$R^3N(R^5)C(O)R^5$, —$OR^3SR^5$, —$C(O)R^5$, —$C(R^5)_3$, —$R^3C(O)OR^5$, —$R^3C(O)N(R^5)_2$, or —$N(R^5)S(O)_2R^5$.

The present invention features a compound of formula (I) wherein Q is methyl and Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —$NO_2$, —$N(R^5)C(O)R^5$, —$N(R^5)_2$, —$OR^5$, —$C_3$-$C_{12}$ Het, —$C(O)N(R^5)_2$, $C_4$-$C_{12}$ Ar, —$SR^5$, —$S(O)_2N(R^5)_2$, —$OR^3HetC(O)R^5$, —$OCF_3$, —$S(O)_2R^5$, —$OR^3R^5$, —$N(R^5)C(O)R^3OR^5$; —$N(R^5)C(O)R^3N(R^5)_2$, —$N(R^5)C(O)R^3R^5$, —$OR^3N(R^5)_2$, —$R^3Het$, —$R^3N(R^5)_2$, —$R^3N(R^5)C(O)R^5$, —$OR^3SR^5$, —$C(O)R^5$, —$C(R^5)_3$, —$R^3C(O)OR^5$, —$R^3C(O)N(R^5)_2$, or —$N(R^5)S(O)_2R^5$.

The present invention features a compound of formula (I) wherein n is 2 and each $R^2$ is halogen. The present invention features a compound of formula (I) wherein m is 2 and each $R^1$ is halogen. The present invention features a compound of formula (I) wherein m is 2 and the first $R^1$ is halogen and the second $R^1$ is —CN. The present invention features a compound of formula (I) wherein m is 2 and each $R^1$ is in the meta position. The present invention features a compound of formula (I) wherein n is 2 and each $R^2$ is in the ortho position to the ether linkage.

The present invention features a compound of formula (I) wherein m is 2, n is 2, and Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —$NO_2$, —$N(R^5)C(O)R^5$, —$N(R^5)_2$, —$OR^5$, —$C_3$-$C_{12}$ Het, —$C(O)N(R^5)_2$, $C_4$-$C_{12}$ Ar, —$SR^5$, —$S(O)_2N(R^5)_2$, —$OR^3HetC(O)R^5$, —$OCF_3$, —$S(O)_2R^5$, —$OR^3R^5$, —$N(R^5)C(O)R^3OR^5$; —$N(R^5)C(O)R^3N(R^5)_2$, —$N(R^5)C(O)R^3R^5$, —$OR^3N(R^5)_2$, —$R^3Het$, —$R^3N(R^5)_2$, —$R^3N(R^5)C(O)R^5$, —$OR^3SR^5$, —$C(O)R^5$, —$C(R^5)_3$, —$R^3C(O)OR^5$, —$R^3C(O)N(R^5)_2$, or —$N(R^5)S(O)_2R^5$.

The present invention features a compound of formula (I) wherein Z is selected from the group consisting of

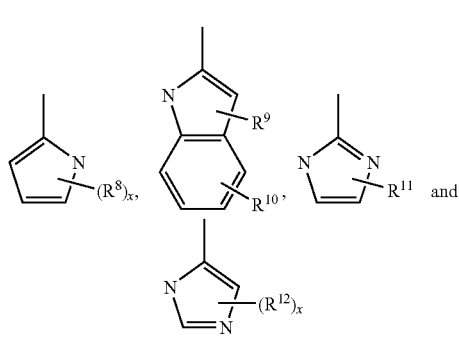

wherein x is 1, 2 or 3;

each $R^8$ is independently hydrogen, halogen, —$N(R^{15})_2$, —$OR^{15}$, —$SR^{15}$, —$C(O)N(R^{15})_2$, —$C(O)OR^{15}$, —$CF_3$, $C_1$-$C_8$ alkyl, $C_1$-$C_8$ alkoxy, or —CN, wherein each $C_1$-$C_8$ alkyl or $C_1$-$C_8$ alkoxy is optionally substituted with hydroxyl, $C_1$-$C_4$ alkoxy or $C_3$-$C_7$ cycloalkyl;

$R^9$ is hydrogen or halogen;

$R^{10}$ is hydrogen, hydroxyl, $C_1$-$C_8$ alkoxy, —$N(R^{15})C(O)R^{15}$, —$N(R^{15})C(O)R^{13}N(R^{15})_2$, —$N(R^{15})_2$, or —$R^{13}N(R^{15})C(O)R^{15}$;

$R^{13}$ is $C_1$-$C_6$ alkylene;

each $R^{15}$ is independently hydrogen, $C_1$-$C_8$ alkyl, $C_3$-$C_7$ cycloalkyl, $C_3$-$C_{12}$ heterocycle, $C_4$-$C_{12}$ aryl or $C_1$-$C_8$ alkoxy, each optionally substituted with hydroxyl, $C_1$-$C_4$ alkoxy or $C_3$-$C_7$ cycloalkyl;

$R^{11}$ is hydrogen or $C_1$-$C_6$ alkoxy; and each $R^{12}$ is independently hydrogen, halogen, $C_1$-$C_8$ alkyl, $C_1$-$C_8$ alkoxy, $C_3$-$C_6$ cycloalkyl, —$N(R^{15})_2$, —$OR^{15}$, —$SR^{15}$, —$C(O)N(R^{15})_2$, —$C(O)OR^{15}$, or —$N(O)_2$, wherein each $C_1$-$C_8$ alkyl or $C_1$-$C_8$ alkoxy is optionally substituted with hydroxyl, $C_1$-$C_4$ alkoxy or $C_3$-$C_7$ cycloalkyl.

The present invention features a compound of formula (I) wherein Y is —C(O)— and Z is selected from the group consisting of

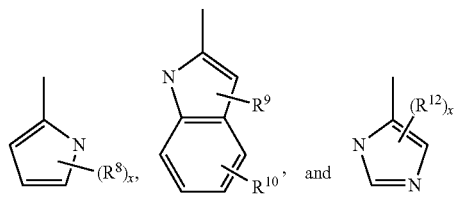

wherein x is 1 or 2;

each $R^8$ is independently hydrogen, halogen, —$N(R^{15})_2$, —$OR^{15}$, —$SR^{15}$, —$C(O)N(R^{15})_2$, —$C(O)OR^{15}$, $C_1$-$C_4$ alkyl, or —CN;

$R^9$ is hydrogen or halogen;

$R^{10}$ is hydrogen, hydroxyl, or $C_1$-$C_6$ alkoxy;

each $R^{12}$ is independently hydrogen, halogen, $C_1$-$C_4$ alkyl, $C_3$-$C_6$ cycloalkyl, —$N(R^{15})_2$, —$OR^{15}$, —$SR^{15}$, —$C(O)N(R^{15})_2$, $C(O)OR^{15}$, or —$N(O)_2$; and each $R^{15}$ is independently hydrogen, $C_1$-$C_8$ alkyl, $C_3$-$C_7$ cycloalkyl, $C_3$-$C_{12}$ heterocycle, $C_4$-$C_{12}$ aryl or $C_1$-$C_8$ alkoxy, each optionally substituted with hydroxyl, $C_1$-$C_4$ alkoxy or $C_3$-$C_7$ cycloalkyl.

The present invention also features a compound of formula (II)

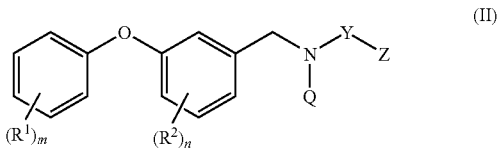

wherein m is 1, 2, 3 or 4;

n is 1, 2, 3 or 4;

each $R^1$ independently is halogen, —CN, $C_1$-$C_5$ alkyl, $C_2$-$C_5$ alkenyl, $C_2$-$C_6$ alkynyl, $C_3$-$C_7$ cycloalkyl, hydroxyl, $C_1$-$C_8$ alkoxy, —$C(O)OR^5$, —$C(O)N(R^5)_2$, —$OR^5$, —$R^3CN$, or —$N(R^5)_2$;

each $R^2$ independently is halogen; —CN, $C_1$-$C_5$ alkyl, $C_2$-$C_5$ alkenyl, $C_2$-$C_6$ alkynyl, $C_3$-$C_7$ cycloalkyl, hydroxyl, $C_1$-$C_8$ alkoxy, —$C(O)OR^5$, —$C(O)N(R^5)_2$, —$OR^5$, —$R^3CN$ or —$N(R^5)_2$;

A is $C_5$-$C_{12}$ aryl or $C_5$-$C_{12}$ heterocycle;

Q is hydrogen or $C_1$-$C_4$ alkyl;

Y is —C(O)—, —$S(O)_2$—, or —S(O)—;

Z is $C_4$-$C_{12}$ aryl, $C_3$-$C_{14}$ heterocycle, $R^3$Het, or $R^3$Ar, each optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N($R^5$)C(O)$R^5$, —N($R^5$)$_2$, —OR$^5$, —C$_3$-C$_{12}$ Het, —C(O)N($R^5$)$_2$, $C_4$-$C_{12}$ Ar, —SR$^5$, —S(O)$_2$N($R^5$)$_2$, —OR$^3$HetC(O)$R^5$, —OCF$_3$, —S(O)$_2$$R^5$, —OR$^3$$R^5$, —N($R^5$)C(O)$R^3$OR$^5$; —N($R^5$)C(O)$R^3$N($R^5$)$_2$, —N($R^5$)C(O)$R^3$$R^5$, —OR$^3$N($R^5$)$_2$, —$R^3$Het, —$R^3$N($R^5$)$_2$, —$R^3$N($R^5$)C(O)$R^5$, —OR$^3$SR$^5$, —C(O)$R^5$, —C($R^5$)$_3$, —$R^3$C(O)OR$^5$, —$R^3$C(O)N($R^5$)$_2$, or —N($R^5$)S(O)$_2$$R^5$; or Z is linked to Q to form a $C_4$-$C_{14}$ heterocycle with the nitrogen atom and Y group to which they are attached and are optionally substituted with —C(O)OR$^5$ or $C_1$-$C_6$ alkoxy;

each $R^5$ independently is hydrogen, $C_1$-$C_8$ alkyl, $C_3$-$C_7$ cycloalkyl, oxo, $C_3$-$C_{12}$ heterocycle, $C_4$-$C_{12}$ aryl or $C_1$-$C_8$ alkoxy, each optionally substituted with hydroxyl, $C_1$-$C_4$ alkoxy or $C_3$-$C_7$ cycloalkyl;

$R^3$ is $C_2$-$C_6$ alkenylene or $C_1$-$C_4$ alkylene, each optionally substituted with hydroxyl or $C_1$-$C_8$ alkoxy;

Het is $C_3$-$C_{12}$ heterocycle and is optionally substituted with one or more of $C_1$-$C_6$ alkyl, C(O)N($R^5$)$_2$, $R^3$S(O)$_2$$R^5$, or halogen; and Ar is $C_4$-$C_{12}$ aryl and is optionally substituted with one or more of $C_1$-$C_6$ alkyl or halogen; or pharmaceutically acceptable salts or solvates thereof.

The present invention features a compound of formula (II) wherein Z is $C_4$-$C_{12}$ aryl optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N($R^5$)C(O)$R^5$, —N($R^5$)$_2$, —OR$^5$, —C$_3$-C$_{12}$ Het, —C(O)N($R^5$)$_2$, $C_4$-$C_{12}$ Ar, —SR$^5$, —S(O)$_2$N($R^5$)$_2$, —OR$^3$HetC(O)$R^5$, —OCF$_3$, —S(O)$_2$$R^5$, —OR$^3$$R^5$, —N($R^5$)C(O)$R^3$OR$^5$; —N($R^5$)C(O)$R^3$N($R^5$)$_2$, —N($R^5$)C(O)$R^3$$R^5$, —OR$^3$N($R^5$)$_2$, —$R^3$Het, —$R^3$N($R^5$)$_2$, —$R^3$N($R^5$)C(O)$R^5$, —OR$^3$SR$^5$, —C(O)$R^5$, —C($R^5$)$_3$, —$R^3$C(O)OR$^5$, —$R^3$C(O)N($R^5$)$_2$, or —N($R^5$)S(O)$_2$$R^5$.

The present invention features a compound of formula (II) wherein Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N($R^5$)C(O)$R^5$, —N($R^5$)$_2$, —OR$^5$, —C$_3$-C$_{12}$ Het, —C(O)N($R^5$)$_2$, $C_4$-$C_{12}$ Ar, —SR$^5$, —S(O)$_2$N($R^5$)$_2$, —OR$^3$HetC(O)$R^5$, —OCF$_3$, —S(O)$_2$$R^5$, —OR$^3$$R^5$, —N($R^5$)C(O)$R^3$OR$^5$; —N($R^5$)C(O)$R^3$N($R^5$)$_2$, —N($R^5$)C(O)$R^3$$R^5$, —OR$^3$N($R^5$)$_2$, —$R^3$Het, —$R^3$N($R^5$)$_2$, —$R^3$N($R^5$)C(O)$R^5$, —OR$^3$SR$^5$, —C(O)$R^5$, —C($R^5$)$_3$, —$R^3$C(O)OR$^5$, —$R^3$C(O)N($R^5$)$_2$, or —N($R^5$)S(O)$_2$$R^5$.

The present invention features a compound of formula (II) wherein Y is —C(O)—, Q is hydrogen, and Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N($R^5$)C(O)$R^5$, —N($R^5$)$_2$, —OR$^5$, —C$_3$-C$_{12}$ Het, —C(O)N($R^5$)$_2$, $C_4$-$C_{12}$ Ar, —SR$^5$, —S(O)$_2$N($R^5$)$_2$, —OR$^3$HetC(O)$R^5$, —OCF$_3$, —S(O)$_2$$R^5$, —OR$^3$$R^5$, —N($R^5$)C(O)$R^3$OR$^5$; —N($R^5$)C(O)$R^3$N($R^5$)$_2$, —N($R^5$)C(O)$R^3$$R^5$, —OR$^3$N($R^5$)$_2$, —$R^3$Het, —$R^3$N($R^5$)$_2$, —$R^3$N($R^5$)C(O)$R^5$, —OR$^3$SR$^5$, —C(O)$R^5$, —C($R^5$)$_3$, —$R^3$C(O)OR$^5$, —$R^3$C(O)N($R^5$)$_2$, or —N($R^5$)S(O)$_2$$R^5$.

The present invention features a compound of formula (II) wherein Y is —C(O)—, Q is $C_1$-$C_8$ alkyl, and Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N($R^5$)C(O)$R^5$, —N($R^5$)$_2$, —OR$^5$, —C$_3$-C$_{12}$ Het, —C(O)N($R^5$)$_2$, $C_4$-$C_{12}$ Ar, —SR$^5$, —S(O)$_2$N($R^5$)$_2$, —OR$^3$HetC(O)$R^5$, —OCF$_3$, —S(O)$_2$$R^5$, —OR$^3$$R^5$, —N($R^5$)C(O)$R^3$OR$^5$; —N($R^5$)C(O)$R^3$N($R^5$)$_2$, —N($R^5$)C(O)$R^3$$R^5$, —OR$^3$N($R^5$)$_2$, —$R^3$Het, —$R^3$N($R^5$)$_2$, —$R^3$N($R^5$)C(O)$R^5$, —OR$^3$SR$^5$, —C(O)$R^5$, —C($R^5$)$_3$, —$R^3$C(O)OR$^5$, —$R^3$C(O)N($R^5$)$_2$, or —N($R^5$)S(O)$_2$$R^5$.

The present invention features a compound of formula (II) wherein Q is methyl and Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N($R^5$)C(O)$R^5$, —N($R^5$)$_2$, —OR$^5$, —C$_3$-C$_{12}$ Het, —C(O)N($R^5$)$_2$, $C_4$-$C_{12}$ Ar, —SR$^5$, —S(O)$_2$N($R^5$)$_2$, —OR$^3$HetC(O)$R^5$, —OCF$_3$, —S(O)$_2$$R^5$, —OR$^3$$R^5$, —N($R^5$)C(O)$R^3$OR$^5$; —N($R^5$)C(O)$R^3$N($R^5$)$_2$, —N($R^5$)C(O)$R^3$$R^5$, —OR$^3$N($R^5$)$_2$, —$R^3$Het, —$R^3$N($R^5$)$_2$, —$R^3$N($R^5$)C(O)$R^5$, —OR$^3$SR$^5$, —C(O)$R^5$, —C($R^5$)$_3$, —$R^3$C(O)OR$^5$, —$R^3$C(O)N($R^5$)$_2$, or —N($R^5$)S(O)$_2$$R^5$.

The present invention features a compound of formula (II) wherein n is 2 and each $R^2$ is halogen. The present invention features a compound of formula (II) wherein m is 2 and each $R^1$ is halogen. The present invention features a compound of formula (II) wherein m is 2 and the first $R^1$ is halogen and the second $R^1$ is —CN. The present invention features a compound of formula (II) wherein m is 2 and each $R^1$ is in the meta position. The present invention features a compound of formula (II) wherein n is 2 and each $R^2$ is in the ortho position to the ether linkage.

The present invention features a compound of formula (II) wherein m is 2, n is 2, and Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N($R^5$)C(O)$R^5$, —N($R^5$)$_2$, —OR$^5$, —C$_3$-C$_{12}$ Het, —C(O)N($R^5$)$_2$, $C_4$-$C_{12}$ Ar, —SR$^5$, —S(O)$_2$N($R^5$)$_2$, —OR$^3$HetC(O)$R^5$, —OCF$_3$, —S(O)$_2$$R^5$, —OR$^3$$R^5$, —N($R^5$) C(O)$R^3$OR$^5$; —N($R^5$)C(O)$R^3$N($R^5$)$_2$, —N($R^5$)C(O)$R^3$$R^5$, —OR$^3$N($R^5$)$_2$, —$R^3$Het, —$R^3$N($R^5$)$_2$, —$R^3$N($R^5$)C(O)$R^5$, OR$^3$SR$^5$, —C(O)$R^5$, —C($R^5$)$_3$, —$R^3$C(O)OR$^5$, —$R^3$C(O)N ($R^5$)$_2$, or —N($R^5$)S(O)$_2$$R^5$.

The present invention features a compound of formula (II)

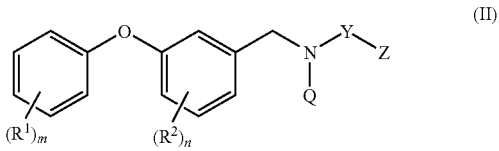

(II)

wherein m is 1, 2, or 3;
n is 1, 2, or 3;
each $R^1$ independently is halogen, —CN, $C_1$-$C_5$ alkyl, $C_2$-$C_5$ alkenyl, $C_2$-$C_6$ alkynyl, $C_3$-$C_7$ cycloalkyl, haloalkyl, hydroxyl, $C_1$-$C_5$ alkoxy, —C(O)OR$^5$, —C(O)N($R^5$)$_2$, —OR$^5$, —$R^3$CN, —$R^3$Het, —$R^3$N($R^5$)$_2$, or —N($R^5$)$_2$;
each $R^2$ independently is halogen; —CN, $C_1$-$C_5$ alkyl, $C_2$-$C_5$ alkenyl, $C_2$-$C_6$ alkynyl, $C_3$-$C_7$ cycloalkyl, haloalkyl, hydroxyl, $C_1$-$C_8$ alkoxy, —C(O)OR$^5$, —C(O)N($R^5$)$_2$, —OR$^5$, —$R^3$CN, —$R^3$N($R^5$)$_2$, or —N($R^5$)$_2$;
Q is hydrogen;
Y is —C(O)—;
Z is $C_4$-$C_{12}$ aryl, $C_3$-$C_{14}$ heterocycle, $R^3$Het, or $R^3$Ar, each optionally substituted with one or more of $C_1$-$C_8$ alkyl, haloalkyl, $C_3$-$C_7$ cycloalkyl, $C_1$-$C_8$ alkoxy, halogen, oxo, hydroxyalkyl, hydroxyl, —CN, —NO$_2$, —N($R^5$)C(O)$R^5$, —N($R^5$)$_2$, —OR$^5$, —C$_3$-C$_{12}$ Het, —C(O)N($R^5$)$_2$, $C_4$-$C_{12}$ Ar, —SR$^5$, —S(O)$_2$N($R^5$)$_2$, —OR$^3$HetC(O)$R^5$, —OCF$_3$, —S(O)$_2$$R^5$, —OR$^3$$R^5$, —N($R^5$)C(O)$R^3$OR$^5$; —N($R^5$)C(O) $R^3$N($R^5$)$_2$, —N($R^5$)C(O)$R^3$$R^5$, —OR$^3$N($R^5$)$_2$, —$R^3$Het, —$R^3$N($R^5$)$_2$, —$R^3$N($R^5$)C(O)$R^5$, —OR$^3$SR$^5$, —C($R^5$)$_3$, —$R^3$C(O)OR$^5$, —$R^3$C(O)N($R^5$)$_2$, or —N($R^5$)S (O)$_2$$R^5$; or Z is linked to Q to form a $C_4$-$C_{14}$ heterocycle together with the nitrogen atom and Y group to which they are attached and are optionally substituted with —C(O)OR$^5$, oxo, or C$_1$-C$_6$ alkoxy;

each R$^5$ independently is hydrogen, C$_1$-C$_8$ alkyl, haloalkyl, C$_3$-C$_7$ cycloalkyl, oxo, C$_3$-C$_{12}$ heterocycle, C$_4$-C$_{12}$ aryl or C$_1$-C$_8$ alkoxy, each optionally substituted with hydroxyl, C$_1$-C$_4$ alkoxy or C$_3$-C$_7$ cycloalkyl;

R$^3$ is C$_2$-C$_{10}$ alkynylene, C$_2$-C$_6$ alkenylene or C$_1$-C$_4$ alkylene, each optionally substituted with hydroxyl, halogen or C$_1$-C$_8$ alkoxy;

Het is C$_3$-C$_{12}$ heterocycle and is optionally substituted with one or more of C$_1$-C$_6$ alkyl, C(O)N(R$^5$)$_2$, R$^3$S(O)$_2$R$^5$, or halogen; and Ar is C$_4$-C$_{12}$ aryl and is optionally substituted with one or more of C$_1$-C$_6$ alkyl or halogen; or a pharmaceutically acceptable salt thereof.

The present invention features a compound of formula (II) wherein m is 2, n is 2, each R$^1$ independently is halogen, —CN, C$_1$-C$_5$ alkyl, C$_2$-C$_5$ alkenyl, C$_2$-C$_6$ alkynyl, C$_3$-C$_7$ cycloalkyl, haloalkyl, hydroxyl, C$_1$-C$_8$ alkoxy, —OR$^5$, —R$^3$CN, —R$^3$N(R$^5$)$_2$, or —N(R$^5$)$_2$;

each R$^2$ independently is halogen; —CN, C$_1$-C$_6$ alkyl, C$_2$-C$_6$ alkenyl, C$_2$-C$_6$ alkynyl, C$_3$-C$_7$ cycloalkyl, haloalkyl, hydroxyl, C$_1$-C$_8$ alkoxy; —R$^3$N(R$^5$)$_2$, or —N(R$^5$)$_2$;

Z is C$_3$-C$_{14}$ heterocycle optionally substituted with one or more of C$_1$-C$_8$ alkyl, haloalkyl, C$_3$-C$_7$ cycloalkyl, C$_1$-C$_8$ alkoxy, halogen, oxo, hydroxyl, —CN, —NO$_2$, —N(R$^5$)$_2$, —OR$^5$, —C(O)N(R$^5$)$_2$, C$_4$-C$_{12}$ Ar, —SR$^5$, —S(O)$_2$N(R$^5$)$_2$, —OCF$_3$, —OR$^3$R$^5$, —N(R$^5$)C(O)R$^3$R$^5$, or —C(O)R$^5$;

R$^3$ is C$_2$-C$_6$ alkenylene or C$_1$-C$_4$ alkylene, each optionally substituted with hydroxyl, halogen or C$_1$-C$_8$ alkoxy;

each R$^5$ is independently hydrogen, C$_1$-C$_5$ alkyl, haloalkyl, or C$_1$-C$_8$ alkoxy.

The present invention features a compound of formula (II) wherein Z is selected from the group consisting of

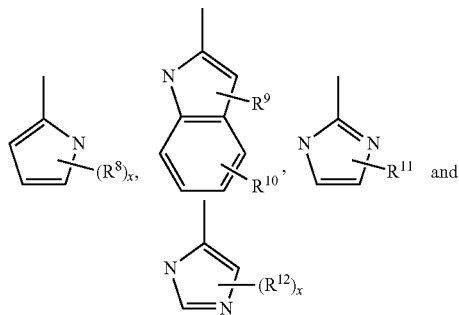

wherein x is 1, 2 or 3;

each R$^8$ is independently hydrogen, halogen, —N(R$^{15}$)$_2$, —OR$^{15}$, —SR$^{15}$, —C(O)N(R$^{15}$)$_2$, —C(O)OR$^{15}$, —CF$_3$, C$_1$-C$_8$ alkyl, C$_1$-C$_8$ alkoxy, or —CN, wherein each C$_1$-C$_8$ alkyl or C$_1$-C$_8$ alkoxy is optionally substituted with hydroxyl, C$_1$-C$_4$ alkoxy or C$_3$-C$_7$ cycloalkyl;

R$^9$ is hydrogen or halogen;

R$^{10}$ is hydrogen, hydroxyl, C$_1$-C$_8$ alkoxy, —N(R$^{15}$)C(O)R$^{15}$, —N(R$^{15}$)C(O)R$^{13}$N(R$^{15}$)$_2$, —N(R$^{15}$)$_2$, or —R$^{13}$N(R$^{15}$)C(O)R$^{15}$;

R$^{13}$ is C$_1$-C$_6$ alkylene;

each R$^{15}$ is independently hydrogen, C$_1$-C$_8$ alkyl, haloalkyl, C$_3$-C$_7$ cycloalkyl, C$_3$-C$_{12}$ heterocycle, C$_4$-C$_{12}$ aryl or C$_1$-C$_8$ alkoxy, each optionally substituted with hydroxyl, C$_1$-C$_4$ alkoxy or C$_3$-C$_7$ cycloalkyl;

R$^{11}$ is hydrogen or C$_1$-C$_6$ alkoxy; and each R$^{12}$ is independently hydrogen, halogen, C$_1$-C$_8$ alkyl, haloalkyl, hydroxyalkyl, C$_1$-C$_8$ alkoxy, C$_3$-C$_6$ cycloalkyl, —N(R$^{15}$)$_2$, —OR$^{15}$, —SR$^{15}$, —S(O)$_2$N(R$^{15}$)$_2$, —S(O)$_2$R$^{15}$, —C(O)N(R$^{15}$)$_2$, —C(O)OR$^{15}$, or —N(O)$_2$, wherein each C$_1$-C$_8$ alkyl or C$_1$-C$_8$ alkoxy is optionally substituted with hydroxyl, C$_1$-C$_4$ alkoxy or C$_3$-C$_7$ cycloalkyl.

The present invention features a compound of formula (II) wherein Y is —C(O)— and Z is selected from the group consisting of

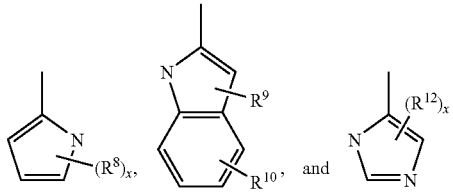

wherein x is 1 or 2;

each R$^8$ is independently hydrogen, halogen, —N(R$^{15}$)$_2$, —OR$^{15}$, —SR$^{15}$, —C(O)N(R$^{15}$)$_2$, —C(O)OR$^{15}$, C$_1$-C$_4$ alkyl, or —CN;

R$^9$ is hydrogen or halogen;

R$^{10}$ is hydrogen, hydroxyl, or C$_1$-C$_6$ alkoxy;

each R$^{12}$ is independently hydrogen, halogen, C$_1$-C$_4$ alkyl, haloalkyl, hydroxyalkyl, C$_3$-C$_6$ cycloalkyl, —N(R$^{15}$)$_2$, —OR$^{15}$, —SR$^{15}$, —S(O)$_2$NR$^{15}$, —S(O)$_2$R$^{15}$, —C(O)N(R$^{15}$)$_2$, —C(O)OR$^{15}$, or —N(O)$_2$; and each R$^{15}$ is independently hydrogen, C$_1$-C$_8$ alkyl, C$_3$-C$_7$ cycloalkyl, C$_3$-C$_{12}$ heterocycle, C$_4$-C$_{12}$ aryl or C$_1$-C$_8$ alkoxy, each optionally substituted with hydroxyl, C$_1$-C$_4$ alkoxy or C$_3$-C$_7$ cycloalkyl.

The present invention features a compound selected from the group consisting of:
3-chloro-N-({4-chloro-3-[(3-chloro-5-cyanophenyl)oxy]-2-fluorophenyl}methyl)-1H-pyrrole-2-carboxamide;
4-chloro-N-({4-chloro-3-[(3-chloro-5-cyanophenyl)oxy]-2-fluorophenyl}methyl)-1H-imidazole-5-carboxamide;
4-bromo-N-({4-chloro-3-[(3-chloro-5-cyanophenyl)oxy]-2-fluorophenyl}methyl)-1H-imidazole-5-carboxamide;
4-chloro-N-({4-chloro-3-[(3-cyano-5-ethenylphenyl)oxy]-2-fluorophenyl}methyl)-1H-imidazole-5-carboxamide;
4-chloro-N-({4-chloro-3-[(2,5-dichloro-3-cyanophenyl)oxy]-2-fluorophenyl}methyl)-1H-imidazole-5-carboxamide;
4-chloro-N-({4-chloro-3-[(3-cyano-5-methylphenyl)oxy]-2-fluorophenyl}methyl)-1H-imidazole-5-carboxamide;
4-bromo-N-({4-chloro-3-[(3-cyano-5-methylphenyl)oxy]-2-fluorophenyl}methyl)-2-methyl-1H-imidazole-5-carboxamide;
4-chloro-N-({4-chloro-3-[(3-cyano-5-ethylphenyl)oxy]-2-fluorophenyl}methyl)-1H-imidazole-5-carboxamide;
4-bromo-N-({4-chloro-3-[(3-cyano-5-ethylphenyl)oxy]-2-fluorophenyl}methyl)-2-methyl-1H-imidazole-5-carboxamide;
N-({3-[(3-bromo-5-cyanophenyl)oxy]-4-chloro-2-fluorophenyl}methyl)-4-chloro-1H-imidazole-5-carboxamide;
4-chloro-N-({4-chloro-3-[(3-cyano-5-propylphenyl)oxy]-2-fluorophenyl}methyl)-1H-imidazole-5-carboxamide;
4-chloro-N-({4-chloro-3-[(3-cyano-5-cyclopropylphenyl)oxy]-2-fluorophenyl}methyl)-1H-imidazole-5-carboxamide;
4-chloro-N-[(4-chloro-3-{[3-cyano-5-(2-propen-1-yl)phenyl]oxy}-2-fluorophenyl)methyl]-1H-imidazole-5-carboxamide;

4-chloro-N-[(4-chloro-3-{[3-cyano-5-(cyclopropylmethyl) phenyl]oxy}-2-fluorophenyl)methyl]-1H-imidazole-5-carboxamide;

4-chloro-N-[(4-chloro-3-{[3-cyano-5-(1-methylethenyl) phenyl]oxy}-2-fluorophenyl)methyl]-1H-imidazole-5-carboxamide;

4-chloro-N-[(4-chloro-3-{[3-cyano-5-(1-methylethyl)phenyl]oxy}-2-fluorophenyl)methyl]-1H-imidazole-5-carboxamide;

3-bromo-N-({4-chloro-3-[(3-chloro-5-cyanophenyl)oxy]-2-fluorophenyl}methyl)-1H-pyrrole-2-carboxamide;

2-amino-4-chloro-N-({4-chloro-3-[(3-chloro-5-cyanophenyl)oxy]-2-fluorophenyl}methyl)-1H-imidazole-5-carboxamide;

2-amino-4-chloro-N-({4-chloro-3-[(3-chloro-5-cyanophenyl)oxy]-2-fluorophenyl}methyl)-1H-imidazole-5-carboxamide;

N-({4-bromo-3-[(3-chloro-5-cyanophenyl)oxy]-2-fluorophenyl}methyl)-4-chloro-2-methyl-1H-imidazole-5-carboxamide;

N-({4-bromo-3-[(3-chloro-5-cyanophenyl)oxy]-2-fluorophenyl}methyl)-4-chloro-2-methyl-1H-imidazole-5-carboxamide;

4-bromo-N-({4-bromo-3-[(3-chloro-5-cyanophenyl)oxy]-2-fluorophenyl}methyl)-2-methyl-1H-imidazole-5-carboxamide;

4-bromo-N-({4,5-dibromo-3-[(3-chloro-5-cyanophenyl)oxy]-2-fluorophenyl}methyl)-2-methyl-1H-imidazole-5-carboxamide;

2-amino-4-bromo-N-({4-chloro-3-[(3-chloro-5-cyanophenyl)oxy]-2-fluorophenyl}methyl)-1H-imidazole-5-carboxamide;

2-amino-4-bromo-N-({4-chloro-3-[(3-chloro-5-cyanophenyl)oxy]-2-fluorophenyl}methyl)-1H-imidazole-5-carboxamide;

2-amino-4-bromo-N-({4-bromo-3-[(3-chloro-5-cyanophenyl)oxy]-2-fluorophenyl}methyl)-1H-imidazole-5-carboxamide;

2-amino-N-({4-bromo-3-[(3-chloro-5-cyanophenyl)oxy]-2-fluorophenyl}methyl)-4-chloro-1H-imidazole-5-carboxamide;

2-amino-N-({4-bromo-3-[(3-cyano-5-methylphenyl)oxy]-2-fluorophenyl}methyl)-4-chloro-1H-imidazole-5-carboxamide;

N-({4-bromo-3-[(3-chloro-5-cyanophenyl)oxy]-2-fluorophenyl}methyl)-4-chloro-2-(hydroxymethyl)-1H-imidazole-5-carboxamide;

4-chloro-N-[(4-chloro-3-{[3-cyano-5-(2-propen-1-yl)phenyl]oxy}-2-fluorophenyl)methyl]-2-methyl-1H-imidazole-5-carboxamide;

4-chloro-N-({3-[(3-chloro-5-cyanophenyl)oxy]-4-ethyl-2-fluorophenyl}methyl)-2-methyl-1H-imidazole-5-carboxamide;

4-chloro-N-({3-[(3-chloro-5-cyanophenyl)oxy]-4-ethyl-2-fluorophenyl}methyl)-1H-imidazole-5-carboxamide;

2-amino-4-chloro-N-({3-[(3-chloro-5-cyanophenyl)oxy]-4-ethyl-2-fluorophenyl}methyl)-1H-imidazole-5-carboxamide;

4-chloro-N-{[3-[(3-chloro-5-cyanophenyl)oxy]-4-(difluoromethyl)-2-fluorophenyl]methyl}-1H-imidazole-5-carboxamide;

2-amino-4-chloro-N-{[3-[(3-chloro-5-cyanophenyl)oxy]-4-(difluoromethyl)-2-fluorophenyl]methyl}-1H-imidazole-5-carboxamide;

4-Chloro-N-({3-[(3-chloro-5-cyanophenyl)oxy]-4-ethenyl-2-fluorophenyl}methyl)-2-methyl-1H-imidazole-5-carboxamide;

4-Chloro-N-({3-[(3-chloro-5-cyanophenyl)oxy]-4-cyclopropyl-2-fluorophenyl}methyl)-2-methyl-1H-imidazole-5-carboxamide;

4-Chloro-N-({4-chloro-3-[(4-cyano-6-methyl-2-pyridinyl)oxy]-2-fluorophenyl}methyl)-2-methyl-1H-imidazole-5-carboxamide;

4-Chloro-N-({4-chloro-3-[(4-cyano-6-ethenyl-2-pyridinyl)oxy]-2-fluorophenyl}methyl)-2-methyl-1H-imidazole-5-carboxamide;

4-Chloro-N-({4-chloro-3-[(4-cyano-6-cyclopropyl-2-pyridinyl)oxy]-2-fluorophenyl}methyl)-2-methyl-1H-imidazole-5-carboxamide;

4-Chloro-N-({4-chloro-3-[(4-cyano-6-ethyl-2-pyridinyl)oxy]-2-fluorophenyl}methyl)-2-methyl-1H-imidazole-5-carboxamide;

4-bromo-N-[(4-chloro-3-{[3-cyano-5-(trifluoromethyl)phenyl]oxy}-2-fluorophenyl)methyl]-1H-imidazole-5-carboxamide;

4-chloro-N-({4-chloro-3-[(3-chloro-5-ethylphenyl)oxy]-2-fluorophenyl}methyl)-1H-imidazole-5-carboxamide;

4-chloro-N-{[4-chloro-3-({3-chloro-5-[(E)-2-cyanoethenyl]phenyl}oxy)-2-fluorophenyl]methyl}-1H-imidazole-5-carboxamide;

4-chloro-N-({4-chloro-3-[(3-chloro-5-ethynylphenyl)oxy]-2-fluorophenyl}methyl)-1H-imidazole-5-carboxamide;

N-({3-[(3-bromo-5-cyanophenyl)oxy]-4-chloro-2-fluorophenyl}methyl)-4-chloro-2-methyl-1H-imidazole-5-carboxamide;

4-chloro-N-[(4-chloro-3-{[3-cyano-5-(difluoromethyl)phenyl]oxy}-2-fluorophenyl)methyl]-2-methyl-1H-imidazole-5-carboxamide;

4-chloro-N-({4-chloro-3-[(3-chloro-5-cyanophenyl)oxy]-5-cyano-2-fluorophenyl}methyl)-2-methyl-1H-imidazole-5-carboxamide;

4-chloro-N-({4-chloro-3-[(3-chloro-5-methylphenyl)oxy]-2-fluorophenyl}methyl)-2-methyl-1H-imidazole-5-carboxamide;

4-chloro-N-({4-chloro-3-[(2,5-dichloro-3-cyanophenyl)oxy]-2-fluorophenyl}methyl)-2-methyl-1H-imidazole-5-carboxamide;

2-amino-4-chloro-N-({4-chloro-3-[(3-cyano-5-cyclopropylphenyl)oxy]-2-fluorophenyl}methyl)-1H-imidazole-5-carboxamide;

4-chloro-N-({4-chloro-3-[(3-cyano-5-cyclopropylphenyl)oxy]-2-fluorophenyl}methyl)-2-methyl-1H-imidazole-5-carboxamide;

4-chloro-N-[(4-chloro-3-{[3-cyano-5-(difluoromethyl)phenyl]oxy}-2-fluorophenyl)methyl]-1H-imidazole-5-carboxamide;

4-chloro-N-({4-chloro-3-[(3-cyano-5-ethynylphenyl)oxy]-2-fluorophenyl}methyl)-1H-imidazole-5-carboxamide;

4-chloro-N-{[4-chloro-3-({3-cyano-5-[(dimethylamino)methyl]phenyl}oxy)-2-fluorophenyl]methyl}-1H-imidazole-5-carboxamide;

4-chloro-N-[(4-chloro-3-{[3-cyano-5-(1-propyn-1-yl)phenyl]oxy}-2-fluorophenyl)methyl]-1H-imidazole-5-carboxamide;

4-chloro-N-{[4-chloro-3-({3-chloro-5-[(3R)-3-hydroxy-1-butyn-1-yl]phenyl}oxy)-2-fluorophenyl]methyl}-1H-imidazole-5-carboxamide;

2-amino-4-chloro-N-[(4-chloro-3-{[3-cyano-5-(difluoromethyl)phenyl]oxy}-2-fluorophenyl)methyl]-1H-imidazole-5-carboxamide;

4-bromo-N-({4-chloro-3-[(3-chloro-5-cyanophenyl)oxy]-2-fluorophenyl}methyl)-1H-imidazole-5-carboxamide;

4-chloro-N-({4-chloro-3-[(3-chloro-5-cyanophenyl)oxy]-2-fluorophenyl}methyl)-2-(ethylamino)-1H-imidazole-5-carboxamide;

4-chloro-N-({4-chloro-3-[(3-chloro-5-cyanophenyl)oxy]-2-fluorophenyl}methyl)-2-(methylamino)-1H-imidazole-5-carboxamide;

2-amino-4-chloro-N-[(4-chloro-3-{[3-cyano-5-(methyloxy)phenyl]oxy}-2-fluorophenyl)methyl]-1H-imidazole-5-carboxamide;

3-({6-chloro-2-fluoro-3-[(6-oxo-6,7-dihydro-1H-purin-1-yl)methyl]phenyl}oxy)-5-(2-propen-1-yl)benzonitrile;

4-bromo-N-[(4-chloro-3-{[3-cyano-5-(difluoromethyl)phenyl]oxy}-2-fluorophenyl)methyl]-1H-imidazole-5-carboxamide;

4-bromo-N-({4-bromo-3-[(3-chloro-5-cyanophenyl)oxy]-2-fluorophenyl}methyl)-1H-imidazole-5-carboxamide;

and pharmaceutically acceptable salts thereof.

Compounds of the present invention may exist in unsolvated forms as well as solvated forms, including hydrated forms. Solvated forms and unsolvated forms are encompassed within the scope of the present invention. Compounds of the present invention may exist in a mixture of forms and/or solvates or as a mixture of amorphous material and one or more forms and/or solvates. In general, all physical forms are intended to be within the scope of the present invention. Forms may be distinguished by various physical characteristics known in the art such as x-ray diffraction patterns, solubility, and melting point.

Other compounds of this invention may be prepared by one skilled in the art following the teachings of the specification coupled with knowledge in the art using reagents that are readily synthesized or commercially available.

Salts of the compounds of the present invention may be made by methods known to a person skilled in the art. For example, treatment of a compound of the present invention with an appropriate base or acid in an appropriate solvent will yield the corresponding salt.

Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trifluoroacetate, trimethylammonium, and valerate salts. Other salts, which are not pharmaceutically acceptable, may be useful in the preparation of compounds of this invention and these should be considered to form a further aspect of the invention.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethane-sulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Other compounds of this invention may be prepared by one skilled in the art following the teachings of the specification coupled with knowledge in the art using reagents that are readily synthesized or commercially available.

Any reference to any of the above compounds also includes a reference to a pharmaceutically acceptable salt thereof.

Esters of the compounds of the present invention are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$ alkyl, or $C_{1-4}$ alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or tri phosphate esters. The phosphate esters may be further esterified by, for example, a $C_{1-20}$ alcohol or reactive derivative thereof, or by a 2,3-di ($C_{6-24}$)acyl glycerol.

In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group.

Ethers of the compounds of the present invention include, but are not limited to methyl, ethyl, butyl and the like.

As used herein, the term "effective amount" means that amount of a drug or pharmaceutical agent that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The term "modulators" as used herein is intended to encompass antagonist, agonist, inverse agonist, partial agonist or partial antagonist, inhibitors and activators.

As used herein, the term "treatment" refers to alleviating the specified condition, eliminating or reducing the symptoms of the condition, slowing or eliminating the progression of the condition and preventing or delaying the initial occurrence of the condition in a subject, or reoccurrence of the condition in a previously afflicted subject.

The present invention features compounds according to the invention for use in medical therapy, for example for the treatment (including prophylaxis) of a viral infection, for example an HIV infection and associated conditions. Compounds of the present invention are useful as inhibitors of both wild tipe and mutant variants of HIV reverse transcriptase. The compounds according to the invention are especially useful for the treatment of AIDS and related clinical conditions such as AIDS related complex (ARC), progressive generalized lymphadenopathy (PGL), Kaposi's sarcoma, thromobocytopenic purpura, AIDS-related neurological conditions such as AIDS dementia complex, multiple sclerosis or tropical paraperesis, anti-HIV antibody-positive and HIV-positive conditions, including such conditions in asymptomatic patients.

The present invention further provides a method for the treatment of a clinical condition in a patient, for example, a mammal including a human which clinical condition includes those which have been discussed hereinbefore, which comprises treating said patient with a pharmaceutically effective amount of a compound according to the invention. The present invention also includes a method for the treatment (including prophylaxis) of any of the aforementioned diseases or conditions.

According to another aspect, the present invention provides a method for the treatment or prevention of the symptoms or effects of a viral infection in an infected patient, for example, a mammal including a human, which comprises administering to said patient a pharmaceutically effective amount of a compound according to the invention. According to one aspect of the invention, the viral infection is a retroviral infection, in particular an HIV infection.

The present invention further includes the use of a compound according to the invention in the manufacture of a medicament for administration to a subject for the treatment of a viral infection, in particular and HIV infection.

The compounds according to the invention may also be used in adjuvant therapy in the treatment of HIV infections or HIV-associated symptoms or effects, for example Kaposi's sarcoma. Reference herein to treatment extends to prophylaxis as well as the treatment of established conditions, disorders and infections, symptoms thereof, and associated clinical conditions. The above compounds according to the invention and their pharmaceutically acceptable derivatives may be employed in combination with other therapeutic agents for the treatment of the above infections or conditions. Combination therapies according to the present invention comprise the administration of a compound of the present invention or a pharmaceutically acceptable derivative thereof and another pharmaceutically active agent. The active ingredient(s) and pharmaceutically active agents may be administered simultaneously (i.e., concurrently) in either the same or different pharmaceutical compositions or sequentially in any order. The amounts of the active ingredient(s) and pharmaceutically active agent(s) and the relative timings of administration will be selected in order to achieve the desired combined therapeutic effect.

For use in therapy, therapeutically effective amounts of a compound of the present invention, as well as salts, solvates, or other pharmaceutically acceptable derivatives thereof, may be administered as the raw chemical. Additionally, the active ingredient may be presented as a pharmaceutical composition.

Accordingly, the invention further provides pharmaceutical compositions that include effective amounts of compounds of the present invention and salts, solvates, or other pharmaceutically acceptable derivatives thereof, and one or more pharmaceutically acceptable carriers, diluents, or excipients. The compounds of the present invention and salts, solvates, or other pharmaceutically acceptable derivatives thereof, are as herein described. The carrier(s), diluent(s) or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a compound of the present invention or salts, solvates, or other pharmaceutically acceptable derivatives thereof, with one or more pharmaceutically acceptable carriers, diluents or excipients.

A therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. Regardless, an effective amount of a compound of the present invention for the treatment of humans suffering from frailty, generally, should be in the range of 0.1 to 100 mg/kg body weight of recipient (mammal) per day. More usually the effective amount should be in the range of 0.1 to 10 mg/kg body weight per day. Thus, for a 70 kg adult mammal one example of an actual amount per day would usually be from 7 to 700 mg. This amount may be given in a single dose per day or in a number (such as two, three, four, five, or more) of sub-doses per day such that the total daily dose is the same. An effective amount of a salt, solvate, or other pharmaceutically acceptable derivative thereof, may be determined as a proportion of the effective amount of the compound of the present invention per se. Similar dosages should be appropriate for treatment of the other conditions referred to herein.

Pharmaceutical formulations may be presented in unit dose forms containing a predetermined amount of active ingredient per unit dose. Such a unit may contain, as a non-limiting example, 0.5 mg to 1 g of a compound of the formula (I), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). By way of example, and not meant to limit the invention, with regard to certain conditions and disorders for which the compounds of the present invention are believed useful certain routes will be preferable to others.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention and salts, solvates, or other pharmaceutically acceptable derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of the present invention and salts, solvates, or other pharmaceutically acceptable derivatives thereof may also be delivered by the use of monoclonal antibodies as individual carriers to which the compound molecules are coupled.

The compounds may also be coupled with soluble polymers as targetable drug carriers. Such polymers can include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

The present invention features compounds according to the invention for use in medical therapy particularly for the treatment of viral infections such as an HIV infection. Compounds according to the invention have been shown to be active against HIV infections, although these compounds may be active against HBV infections as well.

Compounds according to the invention are particularly suited to the treatment of HIV infections and associated conditions. Reference herein to treatment extends to treatment of established infections, symptoms, and associated clinical conditions such as AIDS related complex (ARC), Kaposi's sarcoma, and AIDS dementia.

The present invention provides a method of treatment of HIV mutant viruses that exhibit NNRTI drug resistance by administering a therapeutically effective amount of a compound of the present invention or a pharmaceutically acceptable derivative thereof to a mammal, in particular a human. In particular, the compounds of the present invention may be used to treat wild-type HIV-1 as well as several resistant mutants, for example, K103N, V106A, or Y181C.

The present invention provides a method for the treatment of the symptoms or effects of a viral infection in an infected animal, for example, a mammal including a human, which comprises treating said animal with a therapeutically effective amount of a compound according to the invention. According to a particular embodiment of this aspect of the invention, the viral infection is a retroviral infection, in particular an HIV infection. A further aspect of the invention includes a method for the treatment of the symptoms or effects of an HBV infection.

The compounds of the present invention may also be used in adjuvant therapy in the treatment of HIV infections or HIV-associated symptoms or effects, for example Kaposi's sarcoma.

The compounds of the present invention and their salts, solvates, or other pharmaceutically acceptable derivatives thereof, may be employed alone or in combination with other therapeutic agents. The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

The present invention may be used in combination with one or more agents useful in the prevention or treatment of HIV. Examples of such agents include:

Nucleotide reverse transcriptase inhibitors such as zidovudine, didanosine, lamivudine, zalcitabine, abacavir, stavidine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, TMC-278, TMC-125, etravirine, and similar agents;

Protease inhibitors such as saquinavir, ritonavir, indinavir, nelfinavir, amprenavir, fosamprenavir, brecanavir, raltegravir, atazanavir, tipranavir, palinavir, lasinavir, and similar agents;

Entry inhibitors such as enfuvirtide (T-20), T-1249, PRO-542, PRO-140, TNX-355, BMS-806, 5-Helix and similar agents;

Integrase inhibitors such as L-870,810 and similar agents;

Budding inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

The scope of combinations of compounds of this invention with HIV agents is not limited to those mentioned above, but includes in principle any combination with any pharmaceutical composition useful for the treatment of HIV. As noted, in such combinations the compounds of the present invention and other HIV agents may be administered separately or in conjunction. In addition, one agent may be prior to, concurrent to, or subsequent to the administration of other agent(s).

The compounds of the present invention may be used in the treatment of a variety of disorders and conditions and, as such, the compounds of the present invention may be used in combination with a variety of other suitable therapeutic agents useful in the treatment (including prophylaxis) of those disorders or conditions.

It should be understood that in addition to the ingredients particularly mentioned above, the pharmaceutical compositions of this invention may include other agents conventional in the art having regard to the type of pharmaceutical composition in question, for example, those suitable for oral administration may include such further agents as sweeteners, thickeners, and flavoring agents.

The compounds of the present invention may be prepared according to the following reaction schemes and examples, or modifications thereof using readily available starting materials, reagents and conventional synthesis procedures. In these reactions, it is also possible to make use of variants which are known to those of ordinary skill in the art.

In all of the examples described below, protecting groups for sensitive or reactive groups are employed where necessary in accordance with general principles of synthetic chemistry. Protecting groups are manipulated according to standard methods of organic synthesis. These groups are removed at a convenient stage of the compound synthesis using methods that are readily apparent to those skilled in the art. The selection of processes as well as the reaction conditions and order of their execution shall be consistent with the preparation of compounds of the present invention.

Those skilled in the art will recognize if a stereocenter exists in compounds of the present invention. Accordingly, the scope of the present invention includes all possible stereoisomers and includes not only racemic compounds but the individual enantiomers as well. When a compound is desired as a single enantiomer, such may be obtained by stereospecific synthesis, by resolution of the final product or any convenient intermediate, or by chiral chromatographic methods as are known in the art. Resolution of the final product, an intermediate, or a starting material may be affected by any suitable method known in the art.

EXPERIMENTAL SECTION

Abbreviations

As used herein the symbols and conventions used in these processes, schemes and examples are consistent with those used in the contemporary scientific literature, for example, the Journal of the American Chemical Society or the Journal of Biological Chemistry. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
Hz (Hertz); MHz (megahertz);
mol (moles); mmol (millimoles);
RT (room temperature); h (hours);
min (minutes); TLC (thin layer chromatography);
mp (melting point); RP (reverse phase);
$T_r$ (retention time); TFA (trifluoroacetic acid);
TEA (triethylamine); THF (tetrahydrofuran);
TFAA (trifluoroacetic anhydride); $CD_3OD$ (deuterated methanol);
$CDCl_3$ (deuterated chloroform); DMSO (dimethylsulfoxide);
$SiO_2$ (silica); atm (atmosphere);
EtOAc (ethyl acetate); $CHCl_3$ (chloroform);
HCl (hydrochloric acid); Ac (acetyl);
DMF (N,N-dimethylformamide); Me (methyl);
$Cs_2CO_3$ (cesium carbonate); EtOH (ethanol);
Et (ethyl); tBu (tert-butyl);
MeOH (methanol); p-TsOH (p-toluenesulfonic acid);
NBS (N-bromosuccinimide) NMP (1-methyl-2-pyrrolidinone);
AIBN (2,2'-Azobisisobutyronitrile) EDC (ethylcarbodiimide hydrochloride)
DMAP (4-Dimethylaminopyridine) NCS (N-chlorosuccinimide)
DCM (dichloromethane) DBU (1,8-diazabicyclo [5.4.0]undec-7-ene
MP-TsOH (polystyrene resin bound equivalent of p-TsOH from Argonaut Technologies).
HATU (1-[Bis(dimethylamino)methylene]-1H-1,2,3-triazolo-[4,5-b]pyidinium 3-oxide, hexafluorophosphate)
DIPEA (N,N-diisopropylethylamine)
PS-triphenylphosphine (polystyrene resin bound equivalent of triphenylphosphine) $(Boc)_2O$ (di-tert-butyl carbonate)
TBDMS-Cl (tert-butyldimethylsilyl chloride)
PS-DMAP (Polymer-supported dimethylaminopyridine)

Unless otherwise indicated, all temperatures are expressed in ° C. (degrees Centigrade). All reactions conducted at room temperature unless otherwise noted.

$^1$H-NMR spectra were recorded on a Varian UnityINOVA 400 MHz spectrometer, a Varian Mercury VX 400 MHz spectrometer, or a Varian UnityINOVA 500 MHz spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or br (broad). Mass spectra were obtained on Waters Corporation ZQ, ZMD, Quattro Micro or SQD mass spectrometers from Waters Corporation, Milford, Mass. using either Atmospheric Chemical Ionization (APCI) or Electrospray Ionization (ESI).

Unless otherwise indicated, analytical thin layer chromatography was used to verify the purity of intermediate(s) which could not be isolated or which were too unstable for full characterization as well as to follow the progress of reaction(s).

Absolute configuration of compounds may be assigned by Ab Initio Vibrational Circular Dichroism (VCD) Spectroscopy. Experimental VCD spectra may be acquired in $CDCl_3$ using a Bomem Chiral® VCD spectrometer operating between 2000 and 800 $cm^{-1}$. The Gaussian 98 Suite of computational programs may be used to calculate model VCD spectrums. Stereochemical assignments may be made by comparing this experimental spectrum to the VCD spectrum calculated for a model structure with (R)- or (S)-configuration Compounds of formula (I) may be made by the reactions shown below in Scheme 1. For example, an appropriately substituted benzylic amine can be coupled with a carboxylic acid in the presence of a coupling reagent such as HATU to afford the desired amide product (Y is C(O)). The benzylic amine can also be coupled with an acid chloride in presence of a weak base to afford the amide product. In addition, an appropriately substituted carboxamide can couple with a benzyl bromide to produce the desired amide product.

For compounds wherein Y is $SO_2$, an appropriately substituted benzylic amine can be coupled with a sulfonyl chloride in the presence of a weak base to afford the sulfonamide product.

Scheme 1:

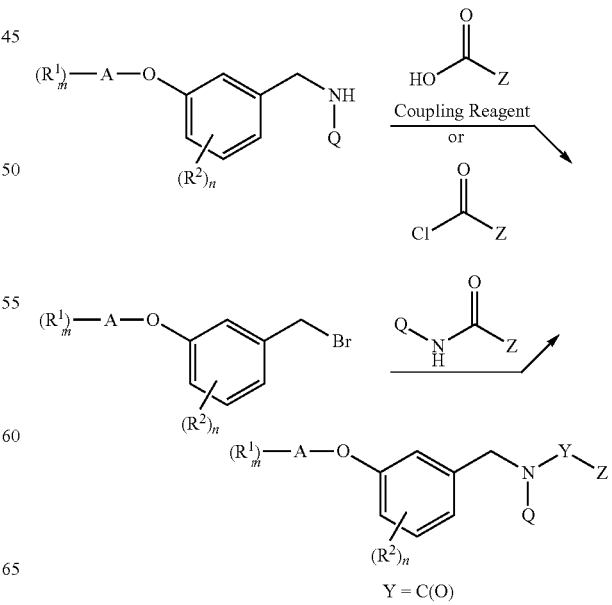

-continued

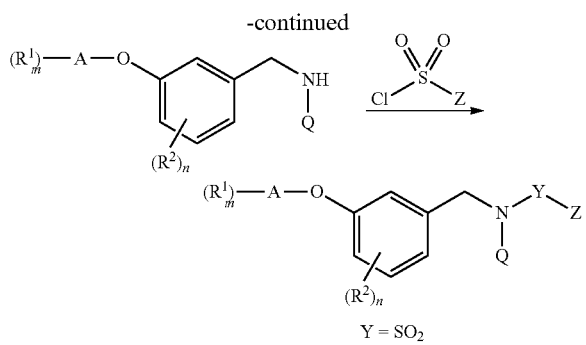

Y = SO$_2$

Example 1

3-{[5-(aminomethyl)-2-chlorophenyl]oxy}-5-chlorobenzonitrile (Intermediate)

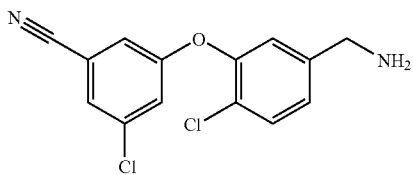

Step A: 2-chloro-5-methylphenyl methyl ether

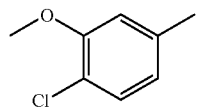

2-Chloro-5-methylphenol (5.0 g, 35.0 mmol) was dissolved in 50% CH$_2$Cl$_2$/methanol (100 mL) and trimethylsilyl diazomethane (2.0 M in hexanes, 25 mL) was added dropwise until a persistent yellow color was observed. The solution was stirred overnight. The solvent was evaporated and the crude product was purified by column chromatography (hexane/EtOAc) to afford the title compound (3.0 g, 55%) as an oil. $^1$H NMR (400 MHz, DMSO-d$_6$): δ ppm 7.25 (d, 1H), 6.95 (d, 1H), 6.74 (dt, 1H), 3.81 (s, 3H), 2.28 (s, 3H).

Step A (alternate procedure): 2-chloro-5-methylphenyl methyl ether

Sodium hydride (60% dispersion, 3.0 g, 77 mmol) was added in three portions to a solution of 2-chloro-5-methylphenol (10.0 g, 70.1 mmol) in DMF (100 mL) at 0° C. under nitrogen. Methyl iodide (5.0 mL, 77 mmol) was added and the solution was warmed to RT. After 1 h, 10% aqueous citric acid (200 mL) and EtOAc (1.0 L) were added. The layers were separated and the aqeuos layer was extracted with EtOAc. The organic layer was washed with saturated NaHCO$_3$ and brine, dried over Na$_2$SO$_4$, filtered and evaporated. Purification was accomplished by column chromatography (hexane/EtOAc) to afford the title compound (12 g, 100%).

Step B: 2-{[4-chloro-3-(methyloxy)phenyl]methyl}-1H-isoindole-1,3(2H)-dione

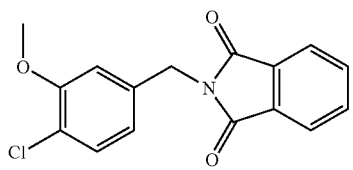

To a solution of 2-chloro-5-methylphenyl methyl ether (12.0 g, 76 mmol) dissolved in CCl$_4$ (200 mL) was added NBS (215.0 g, 83.6 mmol) and AIBN (0.63 g, 3.8 mmol). The reaction mixture was placed in an oil bath at 85° C. and stirred for 2-4 h. The reaction was cooled to RT, filtered and the solid washed with CCl$_4$. The filtrate was evaporated and the resulting solid was dissolved in DMF (200 mL) then potassium phthalimide (35.0 g, 192 mmol) was added. The reaction mixture was placed in an oil bath at 60° C. and stirred for 2 h. The reaction mixture was cooled to RT then 10% citric acid (200 mL) was added and the mixture was extracted with EtOAc (3×200 mL). The organic extracts were combined, washed with water (50 mL) and brine (50 mL), dried over Na$_2$SO$_4$, filtered and evaporated. Purification was accomplished by column chromatography (hexane/EtOAc) to afford the title compound (15.0 g, 65%) as a white solid. $^1$H NMR (400 MHz, DMSO-d$_6$): δ ppm 7.78-7.88 (m, 4H), 7.30 (d, 1H), 7.09 (d, 1H), 6.81 (dd, 1H), 4.72 (s, 2H), 3.80 (s, 3H). MS: m/z 324.0 (M+23).

Step C: 2-[(4-chloro-3-hydroxyphenyl)methyl]-1H-isoindole-1,3(2H)-dione

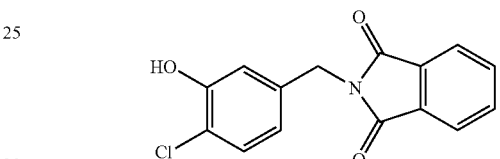

2-{[4-Chloro-3-(methyloxy)phenyl]methyl}-1H-isoindole-1,3(2H)-dione (7.0 g, 23 mmol) was dissolved in CH$_2$Cl$_2$ (25 mL) and cooled to 0° C. Boron tribromide (1.0 M solution, 46 mL) was added slowly then the solution was warmed to RT and stirred for 4 h. The reaction was cooled to 0° C. and ice water (100 mL) and EtOAc (200 mL) were added. The aqueous layer was separated and extracted with EtOAc (2×200 mL). The organic extracts were combined, dried over Na$_2$SO$_4$, filtered, evaporated and triturated with hexanes to afford the title compound (6.5 g, 97%) as a tan solid. $^1$H NMR (400 MHz, DMSO-d$_6$): δ ppm 10.15 (s, 1H), 7.87 (d, 2H), 7.87 (ddd, 2H), 7.25 (d, 1H), 6.88 (d, 1H), 6.74 (dd, 1H), 4.66 (s, 2H). MS: m/z 286.0 (M−1).

Step C (Alternate Procedure): 2-({[(4-chloro-3-hydroxyphenyl)methyl]amino}carbonyl)benzoic acid

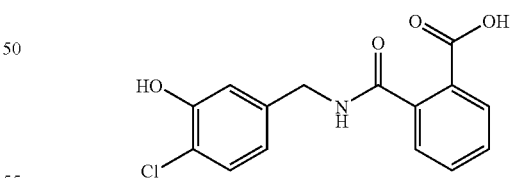

2-{[4-Chloro-3-(methyloxy)phenyl]methyl}-1H-isoindole-1,3(2H)-dione (7.0 g, 23 mmol) was dissolved in CH$_2$Cl$_2$ (25 mL) and cooled to 0° C. Boron tribromide (1.0 M sol., 46 mL) was added slowly then the solution was warmed to RT and stirred for 4 h. The reaction was cooled to 0° C. and ice water (100 mL) and EtOAc (200 mL) were added. The aqueous layer was separated and extracted with EtOAc (2×200 mL). The organic extracts were combined, dried over Na$_2$SO$_4$, filtered and evaporated. The solid was dissolved in EtOAc and washed with 1N NaOH. The aqueous layers were combined, acidified with 10% citric acid and extracted with EtOAc. The organic extracts were combined, dried over Na$_2$SO$_4$, filtered and evaporated to afford the title compound (3.0 g, 42%) as a tan solid. $^1$H NMR (400 MHz, DMSO-d$_6$): δ ppm 12.87 (br. s., 1H), 10.06 (s, 1H), 8.82 (t, 1H), 7.74 (d, 1H), 7.56 (dd, 1H), 7.47-7.54 (m, 1H), 7.45 (d, 1H), 7.23 (d, 1H), 6.94 (d, 1H), 6.80 (dd, 1H), 4.30 (d, 2H). MS: m/z 306.2 (M+1).

Step D: 3-chloro-5-({2-chloro-5-[(1,3-dioxo-1,3-dihydro-2H-isoindol-2-yl)methyl]phenyl}oxy)benzonitrile

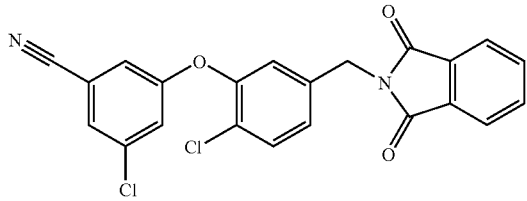

2-[(4-Chloro-3-hydroxyphenyl)methyl]-1H-isoindole-1,3 (2H)-dione (0.50 g, 2.3 mmol), 3-chloro-5-fluorobenzonitrile (0.54 g, 3.5 mmol), K$_2$CO$_3$ (1.0 g, 7.0 mmol) and NMP (5.0 mL) were added to a round bottom flask. The reaction mixture was placed in an oil bath at 110° C. and stirred overnight. The reaction mixture was cooled to RT and aqueous 10% citric acid (25 mL) and EtOAc (25 mL) were added. Additional aqueous 10% citric acid was added until pH ~4-5, the layers were separated and the aqueous layer was extracted with EtOAc (2×25 mL). The organic extracts were combined, dried over Na$_2$SO$_4$, filtered and evaporated. Purification was accomplished by column chromatography (hexane/EtOAc) to afford the title compound (0.47 g, 81%) as a solid. $^1$H NMR (400 MHz, DMSO-d$_6$): δ ppm 7.81-7.92 (m, 4H), 7.79 (d, 1H), 7.58 (d, 1H), 7.44 (d, 1H), 7.37 (d, 1H), 7.29 (d, 1H), 7.23 (dd, 1H), 4.77 (s, 2H). MS: m/z 444.9 (M+23).

Step D (Alternate Procedure): 3-chloro-5-({2-chloro-5-[(1,3-dioxo-1,3-dihydro-2H-isoindol-2-yl)methyl]phenyl}oxy)benzonitrile

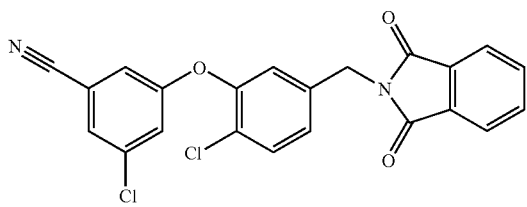

3-Chloro-5-({2-chloro-5-[(1,3-dioxo-1,3-dihydro-2H-isoindol-2-yl)methyl]phenyl}oxy)benzonitrile was prepared in a in a similar manner as described herein from 2-({[(4-chloro-3-hydroxyphenyl)methyl]amino}carbonyl)benzoic acid (3.0 g, 10.4 mmol), 3-chloro-5-fluorobenzonitrile (2.5 g, 15.6 mmol), K$_2$CO$_3$ (4.3 g, 31.0 mmol) and NMP (25.0 mL). Purification was accomplished by column chromatography (hexane/EtOAc) to afford the title compound (1.0 g, 24%) as a solid.

Step E: 3-{[5-(aminomethyl)-2-chlorophenyl]oxy}-5-chlorobenzonitrile

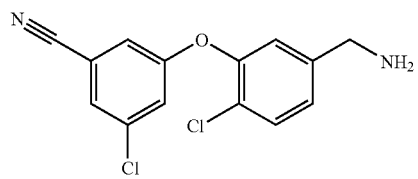

3-Chloro-5-({2-chloro-5-[(1,3-dioxo-1,3-dihydro-2H-isoindol-2-yl)methyl]phenyl}oxy)benzonitrile (1.0 g, 2.3 mmol) was dissolved in methanol (25 mL) and hydrazine monohydrate (0.3 mL, 5.9 mmol) was added. The reaction was stirred for 4 h. Additional hydrazine monohydrate (0.3 mL, 5.9 mmol) was added and stirred overnight. The solvent was evaporated and the crude product was purified by column chromatography (hexane/EtOAc) to afford the title compound (0.5 g, 72%) as a white solid. $^1$H NMR (400 MHz, DMSO-d$_6$): δ ppm 7.77 (t, 1H), 7.53 (d, 1H), 7.40 (dd, 1H), 7.32 (t, 1H), 7.19-7.29 (m, 2H), 3.68 (s, 2H), 1.89 (br. s., 2H). MS: m/z 292.9 (M+1).

Step E (Alternate Procedure): 3-{[5-(aminomethyl)-2-chlorophenyl]oxy}-5-chlorobenzonitrile 3-chloro-5-({2-chloro-5-[(1,3-dioxo-1,3-dihydro-2H-isoindol-2-yl)methyl]phenyl}oxy)benzonitrile (0.40 g, 0.94 mmol) and hydrazine monohydrate (0.11 mL, 2.3 mmol) dissolved in methanol (10 mL). The reaction was stirred at 60° C. for 1.5 h. The solvent was evaporated and the crude product was purified by column chromatography (hexane/EtOAc) to afford the title compound (0.26 g, 94%) as a solid.

Coupling of a Substituted Benzyl Amine with a Carboxylic Acid:

Example 2

N-({4-chloro-3-[(3-chloro-5-cyanophenyl)oxy]phenyl}methyl)-2-methyl-4-(methyloxy)benzamide

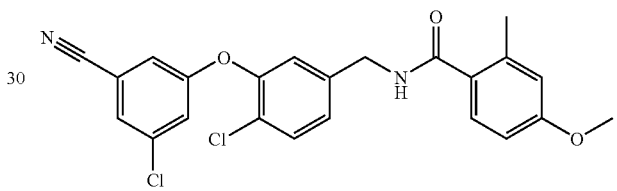

3-{[5-(Aminomethyl)-2-chlorophenyl]oxy}-5-chlorobenzonitrile (0.15 g, 0.51 mmol), 2-methyl-4-(methyloxy)benzoic acid (0.6 g, 0.25 mmol), HATU (0.21 g, 0.56 mmol) and DIPEA (0.11 mL, 0.60 mmol) were dissolved in acetonitrile (3 mL) and DMF (1 mL) then stirred overnight. EtOAc (25 mL) and saturated NaHCO$_3$ (10 mL) were added. The layers were separated and the aqueous layer was extracted with EtOAc (2×10 mL). The organic extracts were combined, dried over Na$_2$SO$_4$, filtered and evaporated. Purification was accomplished by Reverse-Phase HPLC (water/acetonitrile with 0.1% TFA) to afford the title compound (0.05 g, 19%) as a white solid. $^1$H NMR (400 MHz, DMSO-d$_5$): δ ppm 8.63 (s, 1H), 7.82 (d, 1H), 7.59 (d, 1H), 7.46 (dd, 1H), 7.39 (d, 1H), 7.26 (t, 2H), 7.16 (d, 1H), 6.73-6.78 (m, 2H), 4.38 (d, 2H), 3.73 (s, 3H), 2.25 (s, 3H). MS: m/z 441.0 (M+1).

Example 3

N-({4-chloro-3-[(3-chloro-5-cyanophenyl)oxy]phenyl}methyl)-6-(methyloxy)-1H-indole-3-carboxamide

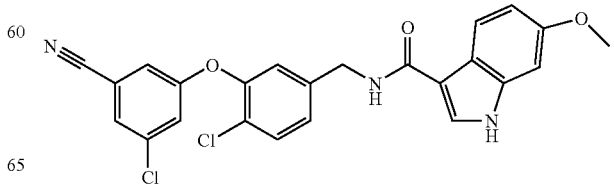

N-({4-Chloro-3-[(3-chloro-5-cyanophenyl)oxy]phenyl}methyl)-6-(methyloxy)-1H-indole-3-carboxamide was prepared in a similar manner as described herein from 3-{[5-(aminomethyl)-2-chlorophenyl]oxy}-5-chlorobenzonitrile (0.05 g, 0.17 mmol), 6-(methyloxy)-1H-indole-3-carboxylic acid, (0.035 g, 0.18 mmol), HATU (0.1 g, 0.25 mmol), DIPEA (0.05 mL, 0.25 mmol), acetonitrile (3 mL) and DMF (1 mL). The crude material was purified by Reverse-Phase HPLC (water/acetonitrile with 0.1% TFA). The desired fractions were neutralized and extracted with EtOAc. The organic extracts were combined, dried over Na₂SO₄, filtered and evaporated to afford the title compound (0.06 g, 75%) as a white solid. $^1$H NMR (400 MHz, DMSO-d$_6$): δ ppm 11.33 (br. s., 1H), 8.39 (s, 1H), 7.93 (d, 1H), 7.86 (d, 1H), 7.77 (d, 1H), 7.58 (d, 1H), 7.43 (dd, 1H), 7.34 (t, 1H), 7.27 (dd, 1H), 7.22 (d, 1H), 6.88 (d, 1H), 6.71 (dd, 1H), 4.43 (d, 2H), 3.74 (s, 3H). MS: m/z 466.0 (M+1).

Example 4

4-(aminosulfonyl)-2-chloro-N-({4-chloro-3-[(3-chloro-5-cyanophenyl)oxy]phenyl}methyl)benzamide trifluoroacetate

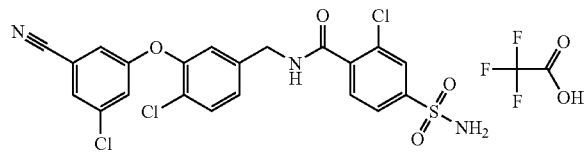

3-{[5-(Aminomethyl)-2-chlorophenyl]oxy}-5-chlorobenzonitrile (0.05 g, 0.17 mmol), 4-(aminosulfonyl)-2-chlorobenzoic acid (0.6 g, 0.25 mmol) (prepared as described in WO2004054581 and incorporated by reference herein as it relates to such preparation), HATU (0.1 g, 0.25 mmol) and DIPEA (0.05 mL, 0.25 mmol) were dissolved in DMF (3 mL) and stirred overnight. Purification was accomplished by Reverse-Phase HPLC (water/acetonitrile with 0.1% TFA) to afford the title compound (0.03 g, 34%) as a white solid. $^1$H NMR (400 MHz, DMSO-d$_6$): δ ppm 9.06-9.18 (m, 1H), 7.84 (d, 2H), 7.78 (d, 1H), 7.62 (dd, 2H), 7.58 (s, 2H), 7.48 (s, 1H), 7.41 (t, 1H), 7.31 (d, 1H), 7.23 (d, 1H), 4.46 (d, 2H). MS: m/z 509.9 (M+1).

Example 5

3-(aminosulfonyl)-4-chloro-N-({4-chloro-3-[(3-chloro-5-cyanophenyl)oxy]phenyl}methyl)benzamide trifluoroacetate

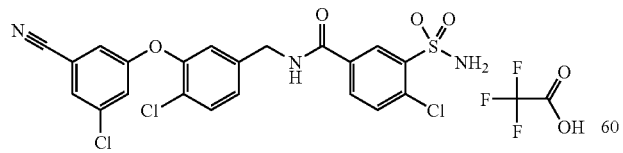

3-(Aminosulfonyl)-4-chloro-N-({4-chloro-3-[(3-chloro-5-cyanophenyl)oxy]phenyl}methyl)benzamide trifluoroacetate was prepared in a similar manner as described herein from 3-{[5-(aminomethyl)-2-chlorophenyl]oxy}-5-chlorobenzonitrile (0.05 g, 0.17 mmol), 3-(aminosulfonyl)-4-chlorobenzoic acid (0.6 g, 0.25 mmol), HATU (0.1 g, 0.25 mmol), DIPEA (0.05 mL, 0.25 mmol) and DMF (3 mL). Purification was accomplished by Reverse-Phase HPLC (water/acetonitrile with 0.1% TFA) to afford the title compound (0.06 g, 68%) as a white solid. $^1$H NMR (400 MHz, DMSO-d$_6$): δ ppm 9.33 (t, 1H), 8.46 (d, 1H), 8.04 (dd, 1H), 7.80 (s, 1H), 7.75 (d, 1H), 7.69 (s, 2H), 7.60 (d, 1H), 7.45 (s, 1H), 7.36 (t, 1H), 7.27 (d, 2H), 4.48 (d, 2H). MS: m/z 509.9 (M+1).

Coupling of a Substituted Benzyl Amine with an Acid Chloride:

Example 6

N-({4-chloro-3-[(3-chloro-5-cyanophenyl)oxy]phenyl}methyl)-2,4-bis(methyloxy)benzamide

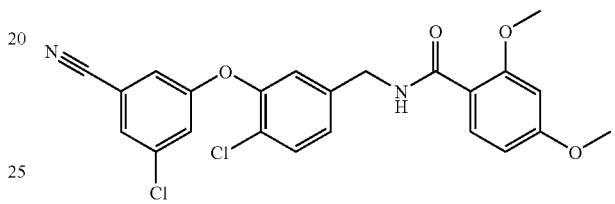

3-{[5-(Aminomethyl)-2-chlorophenyl]oxy}-5-chlorobenzonitrile (0.05 g, 0.17 mmol), 2,4-bis(methyloxy)benzoyl chloride (0.046 g, 0.25 mmol) and DIPEA (0.05 mL, 0.25 mmol) were dissolved in acetonitrile (3 mL) and stirred overnight. The solvent was evaporated. Purification was accomplished by Reverse-Phase HPLC (water/acetonitrile with 0.1% TFA). The desired fractions were lyophilized then EtOAc (25 mL) and saturated NaHCO₃ (10 mL) were added. The layers were separated and the aqueous layer extracted with EtOAc (2×10 mL). The organic extracts were combined, dried over Na₂SO₄, filtered and evaporated to afford the title compound (0.045 g, 57%) as a white solid. $^1$H NMR (400 MHz, DMSO-d$_6$): δ ppm 8.57 (t, 1H), 7.79 (s, 1H), 7.67-7.77 (m, 1H), 7.58 (d, 1H), 7.44 (s, 1H), 7.36 (s, 1H), 7.22-7.26 (m, 1H), 7.12-7.22 (m, 1H), 6.59 (d, 1H), 6.62 (s, 1H), 4.46 (d, 2H), 3.83 (s, 3H), 3.80 (s, 3H). MS: m/z 457.0 (M+1).

One-Pot Hydrolysis of a Carboxylic Ester to the Corresponding Acid and Subsequent Coupling with a Substituted Benzyl Amine:

Example 7

N-({4-chloro-3-[(3-chloro-5-cyanophenyl)oxy]phenyl}methyl)-6-(methyloxy)-1H-indole-2-carboxamide

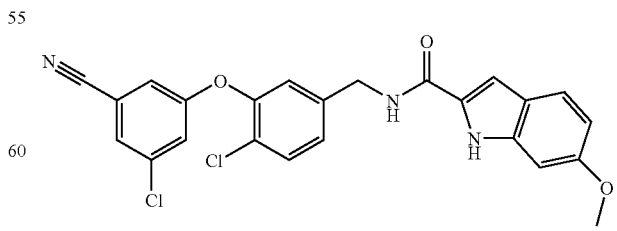

Methyl 6-(methyloxy)-1H-indole-2-carboxylate (0.025 g, 0.13 mmol) was dissolved in THF:methanol:water/1:1:1 (3 mL) and lithium hydroxide (0.01 g, 0.38 mmol) was added.

The reaction was stirred for 1 h, at which time another portion of lithium hydroxide (0.01 g, 0.38 mmol) was added. The reaction was stirred for 1 h, acidified with 10% aqueous citric acid to pH 4-5 and extracted with EtOAc (3×5 mL). The organic extracts were combined, dried over Na$_2$SO$_4$, filtered and evaporated. To the crude intermediate was added 3-{[5-(aminomethyl)-2-chlorophenyl]oxy}-5-chlorobenzonitrile (0.025 g, 0.085 mmol), DIPEA (0.025 mL, 0.13 mmol) and DMF (1 mL) and then stirred overnight. Purification was accomplished by Reverse-Phase HPLC (water/acetonitrile with 0.1% TFA). The desired fractions were neutralized and extracted with EtOAc. The combined organics were dried over Na$_2$SO$_4$, filtered and evaporated to afford the title compound (0.015 g, 26%) as a tan solid. $^1$H NMR (400 MHz, DMSO-d$_6$): δ ppm 11.38 (d, 1H), 8.88-8.93 (m, 1H), 7.77 (d, 1H), 7.59 (d, 1H), 7.42-7.48 (m, 2H), 7.35 (d, 1H), 7.26 (dd, 1H), 7.23 (d, 1H), 7.04 (d, 1H), 6.84 (d, 1H), 6.66 (dd, 1H), 4.47 (d, 2H), 3.73 (s, 3H). MS: m/z 466.2 (M+1).

Example 8

2-chloro-N-({4-chloro-3-[(3-chloro-5-cyanophenyl)oxy]phenyl}methyl)-4-(methylsulfonyl)benzamide

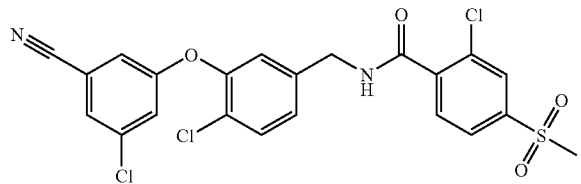

2-Chloro-N-({4-chloro-3-[(3-chloro-5-cyanophenyl)oxy]phenyl}methyl)-4-(methylsulfonyl)benzamide was prepared in a similar manner as described herein from 3-{[5-(aminomethyl)-2-chlorophenyl]oxy}-5-chlorobenzonitrile (0.025 g, 0.085 mmol), 2-chloro-4-(methylsulfonyl)benzoic acid, (0.03 g, 0.13 mmol), HATU (0.05 g, 0.13 mmol), DIPEA (0.025 mL, 0.13 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.030 g, 69%) as a white solid. $^1$H NMR (400 MHz, DMSO-d$_6$): δ ppm 9.20 (t, 1H), 8.02 (d, 1H), 7.92 (dd, 1H), 7.83 (d, 1H), 7.69 (d, 1H), 7.62 (d, 1H), 7.48 (d, 1H), 7.41 (t, 1H), 7.31 (dd, 1H), 7.23 (d, 1H), 4.46 (d, 2H), 3.30 (s, 3H). MS: m/z 508.9 (M+1).

Example 9

N-({4-chloro-3-[(3-chloro-5-cyanophenyl)oxy]phenyl}methyl)-5-nitro-1H-indole-2-carboxamide

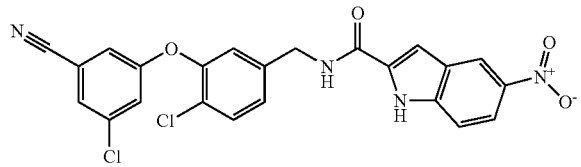

N-({4-Chloro-3-[(3-chloro-5-cyanophenyl)oxy]phenyl}methyl)-5-nitro-1H-indole-2-carboxamide was prepared in a similar manner as described herein from 3-{[5-(aminomethyl)-2-chlorophenyl]oxy}-5-chlorobenzonitrile (0.025 g, 0.085 mmol), 5-nitro-1H-indole-2-carboxylic acid, (0.025 g, 0.13 mmol), HATU (0.05 g, 0.13 mmol), DIPEA (0.025 mL, 0.13 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.015 g, 36%) as a white solid. $^1$H NMR (400 MHz, DMSO-d$_6$): δ ppm 12.36 (s, 1H), 9.34 (t, 1H), 8.67 (d, 1H), 8.04 (dd, 1H), 7.76 (t, 1H), 7.60 (d, 1H), 7.55 (d, 1H), 7.43 (dd, 1H), 7.41 (s, 1H), 7.35 (t, 1H), 7.28 (dd, 1H), 7.25 (d, 1H), 4.50 (d, 2H). MS: m/z 481.0 (M+1).

Example 10

N-({4-chloro-3-[(3-chloro-5-cyanophenyl)oxy]phenyl}methyl)-5-(methyloxy)-1H-indole-2-carboxamide

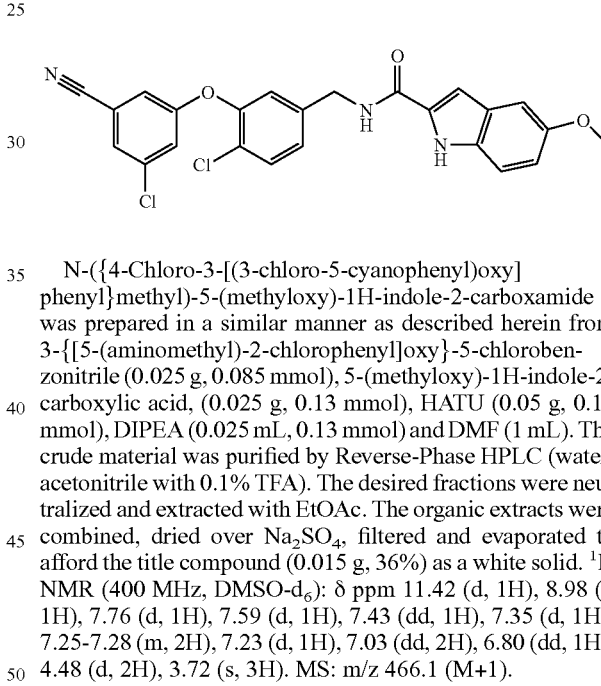

N-({4-Chloro-3-[(3-chloro-5-cyanophenyl)oxy]phenyl}methyl)-5-(methyloxy)-1H-indole-2-carboxamide was prepared in a similar manner as described herein from 3-{[5-(aminomethyl)-2-chlorophenyl]oxy}-5-chlorobenzonitrile (0.025 g, 0.085 mmol), 5-(methyloxy)-1H-indole-2-carboxylic acid, (0.025 g, 0.13 mmol), HATU (0.05 g, 0.13 mmol), DIPEA (0.025 mL, 0.13 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.015 g, 36%) as a white solid. $^1$H NMR (400 MHz, DMSO-d$_6$): δ ppm 11.42 (d, 1H), 8.98 (t, 1H), 7.76 (d, 1H), 7.59 (d, 1H), 7.43 (dd, 1H), 7.35 (d, 1H), 7.25-7.28 (m, 2H), 7.23 (d, 1H), 7.03 (dd, 2H), 6.80 (dd, 1H), 4.48 (d, 2H), 3.72 (s, 3H). MS: m/z 466.1 (M+1).

Example 11

Methyl 4-{[({4-chloro-3-[(3-chloro-5-cyanophenyl)oxy]phenyl}methyl)amino]carbonyl}benzoate

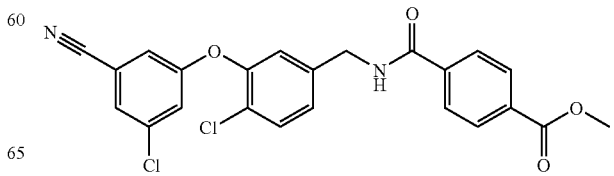

Methyl 4-{[({4-chloro-3-[(3-chloro-5-cyanophenyl)oxy]phenyl}methyl)amino]carbonyl}benzoate was prepared in a similar manner as described herein from 3-{[5-(aminomethyl)-2-chlorophenyl]oxy}-5-chlorobenzonitrile (0.05 g, 0.17 mmol), methyl 4-(chlorocarbonyl)benzoate (0.05 g, 0.25 mmol) and DIPEA (0.05 mL, 0.25 mmol). The crude material was purified by Reverse-Phase HPLC (water/acetonitrile with 0.1% TFA). The desired fractions were lyophilized, neutralized and extracted with EtOAc. The organic extracts were combined, dried over $Na_2SO_4$, filtered and evaporated to afford the title compound (0.035 g, 45%) as a white solid. $^1$H NMR (400 MHz, DMSO-$d_6$): δ ppm 9.22 (s, 1H), 7.98-8.06 (m, 2H), 7.92-7.98 (m, 2H), 7.80 (s, 1H), 7.60 (d, 1H), 7.45 (s, 1H), 7.38 (t, 1H), 7.25 (s, 1H), 7.23 (d, 1H), 4.47 (d, 2H), 3.86 (s, 3H). MS: m/z 455.0 (M+1).

Example 12

3-chloro-5-[(2,3-difluoro-6-nitrophenyl)oxy]benzonitrile (Intermediate)

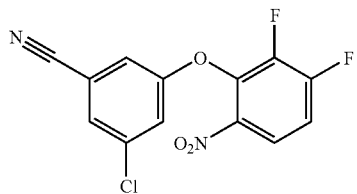

Step A: 3-chloro-5-(methyloxy)benzonitrile

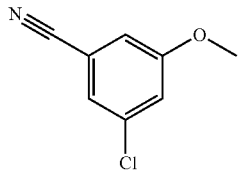

3,5-Dichlorobenzonitrile (52.93 g, 307.7 mmol) was dissolved in anhydrous DMF (300 mL) and cooled to 0° C. in an ice bath. Sodium methoxide (18.28 g, 338.5 mmol) was added as a solid and the mixture was allowed to warm to RT and stirred overnight. The reaction mixture was poured into a mixture of 10% HCl and ice. The solid that formed was filtered, washed with water, and dried overnight. The solid was dissolved in EtOAc and DCM and filtered to remove insoluble material. The solution was washed with water, dried over $MgSO_4$, filtered and evaporated to afford the title compound (46.48 g, 90%) as a solid. $^1$H NMR (400 MHz, CDCl$_3$): δ ppm 7.20 (t, 1H), 7.10 (t, 1H), 7.03 (dd, 1H), 3.82 (s, 3H).

Step B: 3-chloro-5-hydroxybenzonitrile

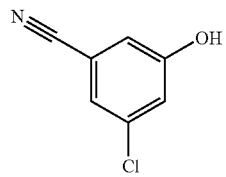

3-Chloro-5-(methyloxy)benzonitrile (46.48 g, 277 mmol) and anhydrous LiI (60.77 g, 454.4 mmol) were suspended in anhydrous 2,4,6-collidine (200 mL) under nitrogen and heated to 185° C. for 8 h. The reaction mixture was cooled to RT and solidified upon standing. The solid was broken-up and added to a mixture of 10% HCl and ice. The solution was extracted with EtOAc (3×200 mL), dried over $MgSO_4$ and evaporated. The solid was triturated in hexanes and EtOAc to afford an off-white solid and a second crop of product was obtained from the filtrate. The combined material was dried under vacuum to afford the title compound (32.40 g, 76%) as a solid. $^1$H NMR (400 MHz, DMSO-$d_6$): δ ppm 10.69 (s, 1H), 7.37 (t, 1H), 7.09-7.13 (m, 2H). MS: m/z 152.1 (M−1).

Step B (alternate procedure): 3-chloro-5-hydroxybenzonitrile

To a stirred solution of LiCl (84 g, 1980 mmol) in DMF (500 mL) was added 3-chloro-5-(methyloxy)benzonitrile (167 g, 1000 mmol). The reaction mixture was heated to 180° C. for 12 h. The reaction mixture was poured into ice (300 g) and EtOAc was added. The organic layer was separated, dried over $MgSO_4$ and evaporated to dryness. The solid was recrystallized from EtOAc and petroleum ether (1:5) to afford the title compound (130 g, 67%) as a solid.

Step C: 3-chloro-5-[(2,3-difluoro-6-nitrophenyl)oxy]benzonitrile

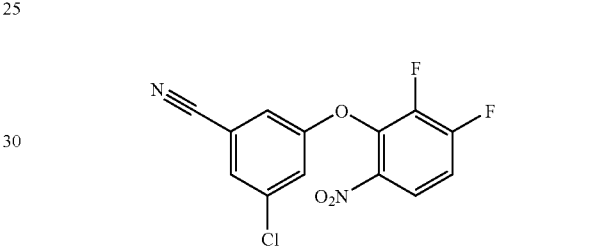

3-Chloro-5-hydroxybenzonitrile (20.0 g, 130 mmol) was dissolved in anhydrous THF (500 mL) and cooled to 0° C. Sodium hydride (60% dispersion in oil, 4.81 g, 125 mmol) was added and stirred for 30 minutes. 2,3,4-Trifluoronitrobenzene (23.06 g, 130 mmol) was added and the reaction was allowed to warm to RT. Stirring was continued until TLC showed no remaining starting material. The reaction mixture was poured into a mixture of 10% HCl and ice. Ethyl acetate was added and the organic layer was separated, dried over $MgSO_4$, filtered and evaporated. The resulting oil was triturated with hexanes and $Et_2O$ to afford a solid. The washing were collected, evaporated and triturated with hexanes. The materials were combined to afford the title compound (30 g, 74%) as a solid. $^1$H NMR (400 MHz, CDCl$_3$): δ ppm 7.98 (ddd, 1H), 7.43 (t, 1H), 7.34 (ddd, 1H), 7.21 (t, 1H), 7.08 (dd, 1H).

Example 13

3-{[3-(aminomethyl)-6-chloro-2-fluorophenyl]oxy}-5-chlorobenzonitrile

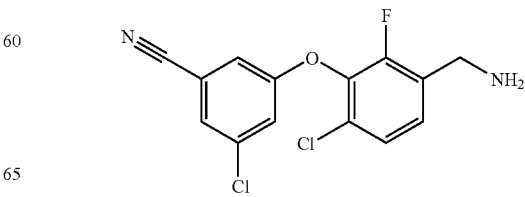

Step A: bis(1,1-dimethylethyl) {3-[(3-chloro-5-cyanophenyl)oxy]-2-fluoro-4-nitrophenyl}propanedioate

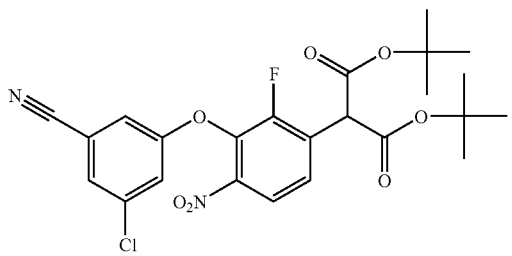

Sodium hydride (60% dispersion in oil, 2.16 g, 54.1 mmol) was added to anhydrous THF (50 mL) and cooled to 0° C. under nitrogen. Di-tert-butyl malonate (4.65 g, 24.8 mmol) was added dropwise and the reaction mixture was stirred 15 min and allowed to warm to RT. The reaction was cooled to 0° C. and 3-chloro-5-[(2,3-difluoro-6-nitrophenyl)oxy]benzonitrile (7.0 g, 22.5 mmol) was added dropwise in a minimal amount of THF. The reaction was allowed to warm to RT and stirred for 3 h then 10% aqueous citric acid (50 ml) and EtOAc (50 mL) were added. The layers were separated and the aqueous layer was extracted with EtOAc (2×50 mL). The organic extracts were combined, washed with brine, dried over $Na_2SO_4$, filtered and evaporated to afford the title compound as an oil. $^1$H NMR (400 MHz, DMSO-$d_6$): δ ppm 8.13 (dd, 1H), 7.84 (d, 1H), 7.65 (dd, 1H), 7.59-7.61 (m, 1H), 7.56-7.59 (m, 1H), 5.10 (s, 1H), 1.40 (s, 18H). MS: m/z 507.2 (M+1).

Step B: {3-[(3-chloro-5-cyanophenyl)oxy]-2-fluoro-4-nitrophenyl}acetic acid

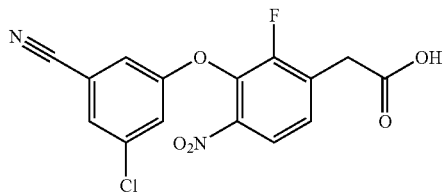

The crude bis(1,1-dimethylethyl) {3-[(3-chloro-5-cyanophenyl)oxy]-2-fluoro-4-nitrophenyl}propanedioate was dissolved in $CH_2Cl_2$ (25 mL) and TFA (25 mL) and heated to reflux for 2 h. The reaction mixture was cooled to RT and evaporated. Water (50 mL) and EtOAc (50 mL) were added, the layers were separated and the aqueous layer extracted with EtOAc (3×50 mL). The organic extracts were combined, dried over $Na_2SO_4$, filtered and evaporated to give the title compound as an oil. $^1$H NMR (400 MHz, DMSO-$d_6$): δ ppm 8.03 (d, 1H), 7.81 (s, 1H), 7.50-7.62 (m, 3H), 3.84 (s, 2H). MS: m/z 349.1 (M−1).

Step C: 3-chloro-5-[(2-fluoro-3-methyl-6-nitrophenyl)oxy]benzonitrile

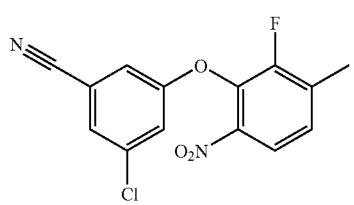

The crude {3-[(3-chloro-5-cyanophenyl)oxy]-2-fluoro-4-nitrophenyl}acetic acid was dissolved in $CH_3CN$ (50 mL) and $Cu_2O$ (0.65 g, 4.5 mmol) was added. A condenser was attached and the heterogeneous mixture was heated to reflux for 2 h. The reaction mixture was cooled to RT, filtered through Celite and the solvent evaporated. Purification was accomplished by column chromatography (hexane/EtOAc) to afford the title compound (6.0 g, 87%), which solidified upon standing. $^1$H NMR (400 MHz, DMSO-$d_6$): δ ppm 7.98 (dd, 1H), 7.81 (d, 1H), 7.60 (d, 2H), 7.52 (t, 1H), 2.37 (d, 3H).

Step D: 3-[(6-amino-2-fluoro-3-methylphenyl)oxy]-5-chlorobenzonitrile

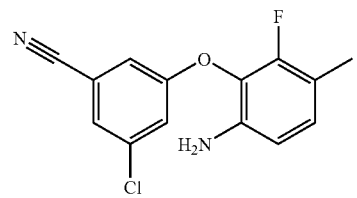

Sodium hydrosulfite (10.2 g, 58.7 mmol) dissolved in water (66 ml) was added dropwise to a vigorously stirred solution of 3-chloro-5-[(2-fluoro-3-methyl-6-nitrophenyl)oxy]benzonitrile (3.0 g, 9.78 mmol) dissolved in THF (33 mL). The reaction was stirred for 1 h then EtOAc (100 mL) was added and the layers were separated. The aqueous layer was extracted with EtOAc (2×50 mL). The organic extracts were combined, dried over $Na_2SO_4$, filtered and evaporated to afford the title compound (2.5 g, 92%) as a solid. $^1$H NMR (400 MHz, DMSO-$d_6$): δ ppm 7.68 (d, 1H), 7.26 (dd, 1H), 7.16 (t, 1H), 6.85 (t, 1H), 6.51 (dd, 1H), 5.17 (d, 2H), 2.06 (d, 3H) MS: m/z 277.2 (M+1).

Step E: 3-chloro-5-[(6-chloro-2-fluoro-3-methylphenyl)oxy]benzonitrile

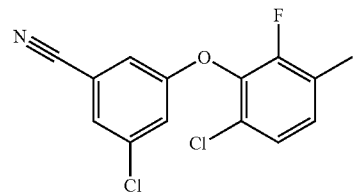

To an oven dried flask was added $CuCl_2$ (2.5 g, 18.0 mmol). The flask was placed under high vacuum, flushed with nitrogen and acetonitrile (10 ml) was added. t-Butyl nitrite (2.7 mL, 22.5 mmol) was added dropwise. The stirred solution was placed in a an oil bath at 50° C. under gentle stream of nitrogen and 3-[(6-amino-2-fluoro-3-methylphenyl)oxy]-5-chlorobenzonitrile dissolved in acetonitrile (15 mL) was added dropwise. The reaction was stirred for 0.5 h, cooled to RT and poured into ice cold, aqueous HCl (0.5 N, 100 mL). EtOAc (100 mL) was added and the layers were separated. The aqueous layer was extracted with EtOAc (2×100 mL). The organic extracts were combined, dried over $Na_2SO_4$, filtered and evaporated. Purification was accomplished by column chromatography (hexane/EtOAc) to afford the title compound (1.8 g, 67%) as a solid. $^1$H NMR (400 MHz, DMSO-$d_6$): δ ppm 7.79 (s, 1H), 7.48 (s, 1H), 7.44 (t, 1H), 7.41 (d, 1H), 7.31 (t, 1H), 2.27 (d, 3H).

Step F: 3-{[3-(bromomethyl)-6-chloro-2-fluorophenyl]oxy}-5-chlorobenzonitrile

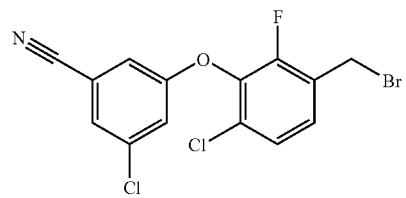

3-Chloro-5-[(6-chloro-2-fluoro-3-methylphenyl)oxy]benzonitrile (1.8 g, 6.1 mmol) was dissolved in $CCl_4$ (200 mL). NBS (1.2 g, 6.7 mmol) and AIBN (0.63 g, 3.8 mmol) were added and the reaction mixture was placed in oil bath at 85° C. and stirred for 4 h. The reaction was monitored by TLC and more AIBN and NBS were added as necessary. The reaction was cooled, filtered and the solid washed with CCl₄. The solvent was evaporated. Purification was accomplished by column chromatography (hexane/EtOAc eluent) to afford the title compound (1.8 g, 79%) as a solid. ¹H NMR (400 MHz, DMSO-d₆): δ ppm 7.81 (s, 1H), 7.49-7.59 (m, 3H), 7.47 (d, 1H), 4.73 (s, 2H). GC-MS, 372.9 (M).

Step G: 3-{[3-(aminomethyl)-6-chloro-2-fluorophenyl]oxy}-5-chlorobenzonitrile

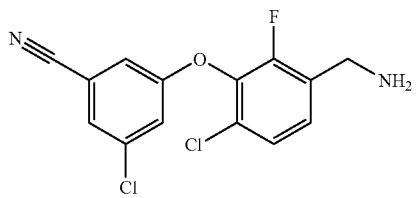

3-{[3-(Bromomethyl)-6-chloro-2-fluorophenyl]oxy}-5-chlorobenzonitrile (1.0 g, 2.6 mmol) was dissolved in CH₂Cl₂ (5 mL) and added dropwise to ammonia in methanol (7N, 25 mL). The reaction mixture was stirred for 2 h then the solvent was evaporated. The resulting oil was purified by column chromatography (CH₂Cl₂/MeOH) to afford the title compound (0.7 g, 84%). ¹H NMR (400 MHz, DMSO-d₆): δ ppm 7.79 (s, 2H), 7.45-7.56 (m, 4H), 7.42 (t, 1H), 3.75 (s, 2H). MS: m/z 311.1 (M+1).

Alternatively, 3-{[3-(aminomethyl)-6-chloro-2-fluorophenyl]oxy}-5-chlorobenzonitrile was prepared via the following two-step process:

Step H: 3-chloro-5-({6-chloro-3-[(1,3-dioxo-1,3-dihydro-2H-isoindol-2-yl)methyl]-2-fluorophenyl}oxy)benzonitrile

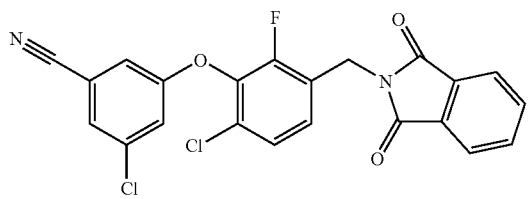

3-{[3-(Bromomethyl)-6-chloro-2-fluorophenyl]oxy}-5-chlorobenzonitrile (1.8 g, 4.8 mmol) was dissolved in DMF (50 mL) and potassium phthalimide (2.25 g, 12.0 mmol) was added. The reaction mixture was placed in an oil bath at 60° C. and stirred for 2-3 h. The reaction mixture was cooled to RT and the solvent was evaporated. Purification was accomplished by column chromatography (CH₂Cl₂/MeOH) to afford the title compound (1.9 g, 90%). ¹H NMR (400 MHz, DMSO-d₆): δ ppm 7.70-7.98 (m, 6H), 7.39-7.49 (m, 2H), 7.35 (dd, 1H), 4.81 (s, 2H). MS: m/z 463.2 (M+23).

Step I: 3-{[3-(aminomethyl)-6-chloro-2-fluorophenyl]oxy}-5-chlorobenzonitrile

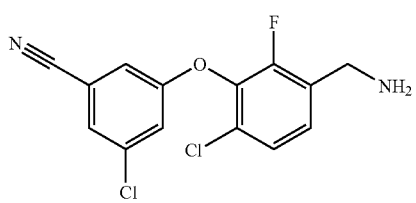

3-Chloro-5-({6-chloro-3-[(1,3-dioxo-1,3-dihydro-2H-isoindol-2-yl)methyl]-2-fluorophenyl}oxy)benzonitrile (1.9 g, 4.3 mmol) was dissolved in MeOH (50 mL) and hydrazine monohydrate (0.63 mL, 12.9 mmol) was added. The reaction mixture was placed in an oil bath at 60° C. and stirred for 2 h. Another portion of hydrazine monohydrate (0.63 mL, 12.9 mmol) was added and the reaction was stirred for 1 h. Purification was accomplished by column chromatography (CH₂Cl₂/MeOH) to afford the title compound (11 g, 82%).

Example 14

4-(aminosulfonyl)-2-chloro-N-({4-chloro-3-[(3-chloro-5-cyanophenyl)oxy]-2-fluorophenyl}methyl)benzamide

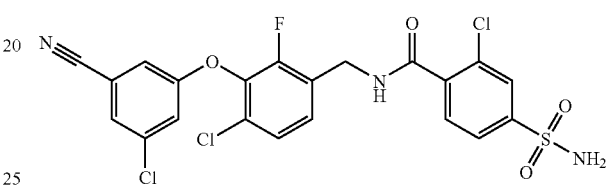

3-{[3-Aminomethyl)-6-chloro-2-fluorophenyl]oxy}-5-chlorobenzonitrile (0.030 g, 0.096 mmol), 4-(aminosulfonyl)-2-chlorobenzoic acid (0.034 g, 0.145 mmol) (prepared as described in WO2004054581), HATU (0.055 g, 0.145 mmol) and DIPEA (0.025 mL, 0.145 mmol) were dissolved in DMF (2 mL) and stirred overnight. Purification was accomplished by Reverse-Phase HPLC (water/acetonitrile with 0.1% TFA). The desired fractions were neutralized with saturated NaHCO₃ and extracted with EtOAc (3×5 mL). The organic extracts were combined, dried over Na₂SO₄, filtered and evaporated to afford the title compound (0.025 g, 49%) as a white solid. ¹H NMR (400 MHz, DMSO-d₆): δ ppm 9.17 (t, 1H), 7.86 (d, 1H), 7.80 (d, 2H), 7.64 (d, 1H), 7.58 (br. s., 2H), 7.48-7.55 (m, 2H), 7.39-7.47 (m, 2H), 4.50 (d, 2H). MS: m/z 528.1 (M+1).

Example 15

Methyl 4-{[({4-chloro-3-[(3-chloro-5-cyanophenyl)oxy]-2-fluorophenyl}methyl)amino]carbonyl}benzoate

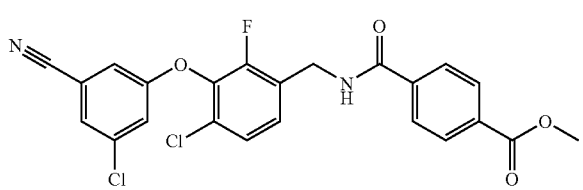

Methyl 4-{[({4-chloro-3-[(3-chloro-5-cyanophenyl)oxy]-2-fluorophenyl}methyl)amino]carbonyl}benzoate was prepared in a similar manner as described herein from 3-{[3-aminomethyl)-6-chloro-2-fluorophenyl]oxy}-5-chlorobenzonitrile (0.030 g, 0.096 mmol), methyl 4-(chlorocarbonyl)benzoate (0.030 g, 0.151 mmol), DIPEA (0.025 mL, 0.145 mmol) and CH₃CN (2 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.02 g, 44%) as a white solid. $^1$H NMR (400 MHz, DMSO-d$_6$): δ ppm 9.23 (t, 1H), 7.94-8.07 (m, 4H), 7.80 (s, 1H), 7.42-7.52 (m, 3H), 7.38 (t, 1H), 4.53 (d, 2H), 3.86 (s, 3H). MS: m/z 473.2 (M+1).

Example 16

2-chloro-N-({4-chloro-3-[(3-chloro-5-cyanophenyl) oxy]-2-fluorophenyl}methyl)-4-(methylsulfonyl) benzamide

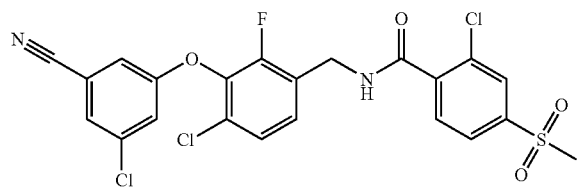

2-Chloro-N-({4-chloro-3-[(3-chloro-5-cyanophenyl) oxy]-2-fluorophenyl}methyl)-4-(methylsulfonyl)benzamide was prepared in a similar manner as described herein from 3-{[3-aminomethyl)-6-chloro-2-fluorophenyl]oxy}-5-chlorobenzonitrile (0.030 g, 0.096 mmol), 2-chloro-4-(methylsulfonyl)benzoic acid (0.034 g, 0.145 mmol), HATU (0.055 g, 0.145 mmol), DIPEA (0.025 mL, 0.145 mmol) and DMF (2 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.028 g, 55%) as a white solid. $^1$H NMR (400 MHz, DMSO-d$_6$): δ ppm 9.21 (br. s., 1H), 8.03 (s, 1H), 7.92 (d, 1H), 7.81 (s, 1H), 7.71 (d, 1H), 7.37-7.59 (m, 4H), 4.51 (d, 2H), 3.30 (br. s., 3H). MS: m/z 527.1 (M+1).

Example 17

N-({4-chloro-3-[(3-chloro-5-cyanophenyl)oxy]-2-fluorophenyl}methyl)-2-methyl-4-(methyloxy)benzamide

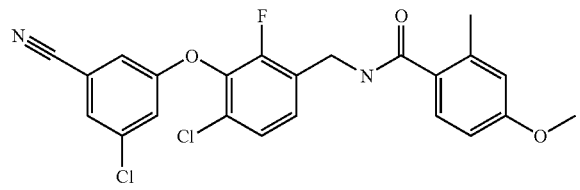

N-({4-Chloro-3-[(3-chloro-5-cyanophenyl)oxy]-2-fluorophenyl}methyl)-2-methyl-4-(methyloxy)benzamide was prepared in a similar manner as described herein from 3-{[3-aminomethyl)-6-chloro-2-fluorophenyl]oxy}-5-chlorobenzonitrile (0.030 g, 0.096 mmol), 2-methyl-4-(methyloxy)benzoic acid (0.025 g, 0.145 mmol), HATU (0.055 g, 0.145 mmol), DIPEA (0.025 mL, 0.145 mmol) and DMF (2 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.032 g, 72%) as a white solid. $^1$H NMR (400 MHz, DMSO-d$_6$): δ ppm 8.66 (t, 1H), 7.80 (s, 1H), 7.47-7.54 (m, 2H), 7.44 (s, 1H), 7.38 (t, 1H), 7.34 (d, 1H), 6.70-6.83 (m, 2H), 4.44 (d, 2H), 3.74 (s, 3H), 2.30 (s, 3H). MS: m/z 459.2 (M+1).

Example 18

N-({4-chloro-3-[(3-chloro-5-cyanophenyl)oxy]-2-fluorophenyl}methyl)-6-(methyloxy)-1H-indole-3-carboxamide

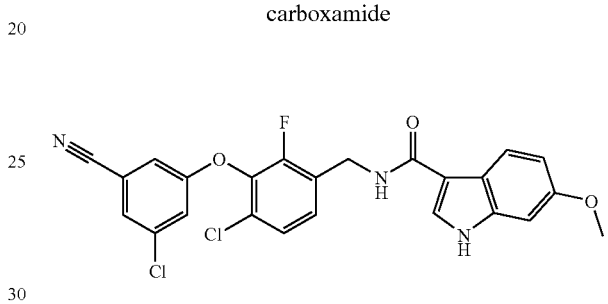

N-({4-Chloro-3-[(3-chloro-5-cyanophenyl)oxy]-2-fluorophenyl}methyl)-6-(methyloxy)-1H-indole-3-carboxamide was prepared in a similar manner as described herein from 3-{[3-aminomethyl)-6-chloro-2-fluorophenyl]oxy}-5-chlorobenzonitrile (0.030 g, 0.096 mmol), 6-(methyloxy)-1H-indole-3-carboxylic acid (0.025 g, 0.131 mmol), HATU (0.055 g, 0.145 mmol), DIPEA (0.025 mL, 0.145 mmol) and DMF (2 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.010 g, 21%) as a yellow solid. $^1$H NMR (400 MHz, DMSO-d$_5$): δ ppm 11.39 (br. s., 1H), 8.43 (s, 1H), 7.92 (d, 2H), 7.80 (s, 1H), 7.34-7.54 (m, 4H), 6.89 (d, 1H), 6.72 (dd, 1H), 4.48 (d, 2H), 3.74 (s, 3H). MS: m/z 484.1 (M+1).

Example 19

N-({4-chloro-3-[(3-chloro-5-cyanophenyl)oxy]-2-fluorophenyl}methyl)-5-nitro-1H-indole-2-carboxamide

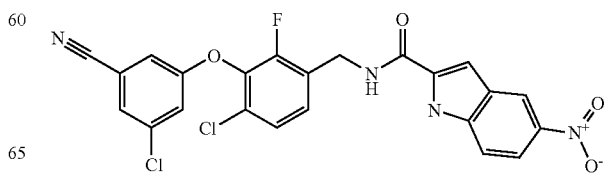

N-({4-Chloro-3-[(3-chloro-5-cyanophenyl)oxy]-2-fluorophenyl}methyl)-5-nitro-1H-indole-2-carboxamide was prepared in a similar manner as described herein from 3-{[3-aminomethyl)-6-chloro-2-fluorophenyl]oxy}-5-chlorobenzonitrile (0.15 g, 0.48 mmol), 5-nitro-1H-indole-2-carboxylic acid (0.12 g, 0.58 mmol), HATU (0.23 g, 0.60 mmol), DIPEA (0.10 mL, 0.60 mmol) and DMF (2 mL). The crude material was purified by Reverse-Phase HPLC (water/acetonitrile with 0.1% TFA). The desired fractions were neutralized and extracted with EtOAc. The organic extracts were combined, dried over $Na_2SO_4$, filtered and evaporated to afford the title compound (0.18 g, 75%) as a tan solid. $^1$H NMR (400 MHz, DMSO-$d_6$): δ ppm 12.38 (s, 1H), 9.29 (t, 1H), 8.71 (d, 1H), 8.07 (dd, 1H), 7.81 (s, 1H), 7.47-7.58 (m, 4H), 7.45 (d, 1H), 7.41 (t, 1H), 4.58 (d, 2H). MS: m/z 499.2 (M+1).

Example 20

N-({4-chloro-3-[(3-chloro-5-cyanophenyl)oxy]-2-fluorophenyl}methyl)-5-(methyloxy)-1H-indole-2-carboxamide

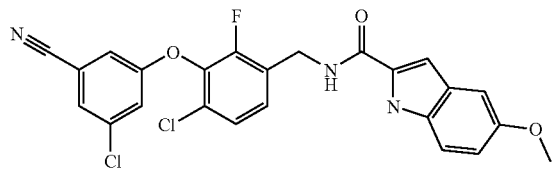

N-({4-Chloro-3-[(3-chloro-5-cyanophenyl)oxy]-2-fluorophenyl}methyl)-5-(methyloxy)-1H-indole-2-carboxamide was prepared in a similar manner as described herein from 3-{[3-aminomethyl)-6-chloro-2-fluorophenyl]oxy}-5-chlorobenzonitrile (0.030 g, 0.096 mmol), 5-(methyloxy)-1H-indole-2-carboxylic acid (0.025 g, 0.131 mmol), HATU (0.055 g, 0.145 mmol), DIPEA (0.025 mL, 0.145 mmol) and DMF (2 mL). The crude material was purified by Reverse-Phase HPLC (water/acetonitrile with 0.1% TFA). The desired fractions were neutralized and extracted with EtOAc. The organic extracts were combined, dried over $Na_2SO_4$, filtered and evaporated to afford the title compound (0.010 g, 21%) as a tan solid. $^1$H NMR (400 MHz, DMSO-$d_6$): δ ppm 11.45 (br. s., 1H), 8.98 (t, 1H), 7.81 (s, 1H), 7.46-7.53 (m, 3H), 7.39 (t, 1H), 7.30 (d, 1H), 7.07 (s, 2H), 6.82 (dd, 1H), 4.55 (d, 2H), 3.74 (s, 3H). MS: m/z 484.1 (M+1).

Example 21

N-({4-chloro-3-[(3-chloro-5-cyanophenyl)oxy]-2-fluorophenyl}methyl)-6-(methyloxy)-1H-indole-2-carboxamide

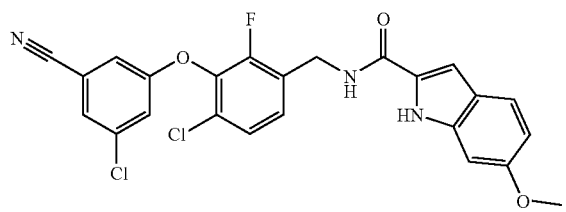

Methyl 6-(methyloxy)-1H-indole-2-carboxylate (0.025 g, 0.131 mmol) was dissolved in THF:MeOH:water (1:1:1, 3.0 mL) then powdered lithium hydroxide (0.02 g, 0.76 mmol) was added and the reaction mixture was stirred for 2 h. The solution was acidified to pH 4-5 with 10% aqueous citric acid and extracted with EtOAc (3×5 mL). The organic extracts were combined, dried over $Na_2SO_4$, filtered, evaporated and placed under high vacuum for 1 h. 3-{[3-Aminomethyl)-6-chloro-2-fluorophenyl]oxy}-5-chlorobenzonitrile (0.030 g, 0.096 mmol), HATU (0.055 g, 0.145 mmol), DIPEA (0.025 mL, 0.145 mmol) and DMF (2 mL) were added and the reaction mixture was stirred overnight. Purification was accomplished by Reverse-Phase HPLC (water/acetonitrile with 0.1% TFA). The desired fractions were neutralized with saturated $NaHCO_3$ and extracted with EtOAc (3×5 mL). The organic extracts were combined dried over $Na_2SO_4$, filtered and evaporated to afford the title compound (0.030 g, 64%) as a white solid. $^1$H NMR (400 MHz, DMSO-$d_6$): δ ppm 11.40 (br. s., 1H), 8.91 (t, 1H), 7.77 (d, 1H), 7.42-7.54 (m, 4H), 7.36 (d, 1H), 7.07 (t, 1H), 6.83 (d, 1H), 6.65 (dd, 1H), 4.51 (d, 2H), 3.70-3.75 (m, 3H). MS: m/z 506.1 (M+23).

Example 22

N-({4-chloro-3-[(3-chloro-5-cyanophenyl)oxy]-2-fluorophenyl}methyl)-5-{[3-hydroxy-2-(hydroxymethyl)propyl]oxy}-1H-indole-2-carboxamide

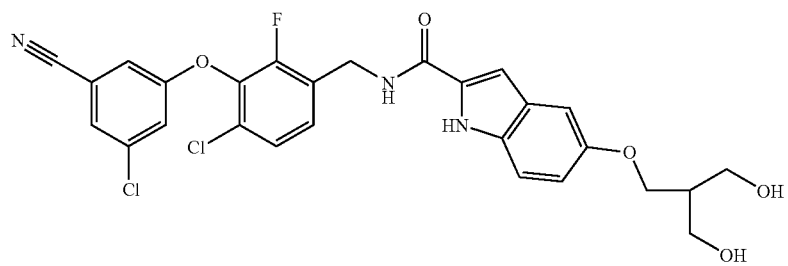

Step A: methyl 5-hydroxy-1H-indole-2-carboxylate

5-Hydroxy-1H-indole-2-carboxylic acid (0.50 g, 2.82 mmol) was dissolved in MeOH:CH$_2$Cl$_2$ (1:1, 15 mL), trimethylsilyl diazomethane (2.0 M in hexanes, ~5.0 mL) was added dropwise until a persistent yellow color formed and the reaction mixture was stirred for 0.5 h. To the solution was added acetic acid (0.5 mL) and the solvent was evaporated. Purification was accomplished by column chromatography (CH$_2$Cl$_2$: MeOH) to afford the title compound (0.55 g, 99%) as a solid. $^1$H NMR (400 MHz, DMSO-d$_6$): δ ppm 11.59 (br. s., 1H), 8.88 (dd, 1H), 7.23 (d, 1H), 6.85-6.96 (m, 2 H), 6.77 (dd, 1H), 3.81 (d, 3H). MS: m/z 192.2 (M+1).

Step B: (2,2-dimethyl-1,3-dioxan-5-yl)methanol

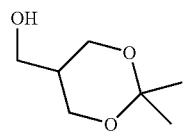

2-(Hydroxymethyl)-1,3-propanediol (1.0 g, 9.4 mmol), 2,2-bis(methyloxy)propane (2.3 mL, 18.8 mmol) and p-toluenesulfonic acid monohydrate (0.09 g, 0.5 mmol) were dissolved in THF and stirred for ~60 h. To the solution was added triethyl amine (1.0 mL) and the solvent was evaporated. Purification was accomplished by column chromatography (CH$_2$Cl$_2$:MeOH) to afford the title compound (0.6 g, 44%) as a oil. $^1$H NMR (400 MHz, DMSO-d$_6$): δ ppm 4.52 (t, 1H), 3.80 (dd, 2H), 3.59 (dd, 2H), 3.36 (dd, 2H), 1.63-1.72 (m, 1H), 1.28 (d, 6H).

Step C: methyl 5-{[(2,2-dimethyl-1,3-dioxan-5-yl)methyl]oxy}-1H-indole-2-carboxylate

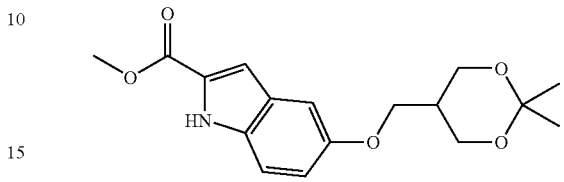

Methyl 5-Hydroxy-1H-indole-2-carboxylate (0.10 g, 0.5 mmol), triphenylphosphine (0.28 g, 1.0 mmol), diethyl azodicarboxylate (0.18 g, 1.0 mmol) and (2,2-dimethyl-1,3-dioxan-5-yl)methanol (0.15 g, 1.0 mmol) were dissolved in CH$_2$Cl$_2$ (5 mL) and the mixture was stirred overnight. The solvent was evaporated. Purification was accomplished by Reverse-Phase HPLC (water/acetonitrile with 0.1% TFA). The desired fractions were neutralized with saturated NaHCO$_3$ and extracted with EtOAc. The organic extracts were combined dried over Na$_2$SO$_4$, filtered and evaporated to afford the title compound (0.15 g, 90%) as a tan solid. $^1$H NMR (400 MHz, DMSO-d$_6$): δ ppm 11.74 (br. s., 1H), 7.29 (d, 1H), 7.09 (d, 1H), 7.01 (d, 1H), 6.88 (dd, 1H), 3.92-4.01 (m, 4H), 3.81 (s, 3H), 3.72 (dd, 2H), 1.97-2.08 (m, 1H), 1.31 (s, 3H), 1.28 (s, 3H). MS: m/z 342.2 (M+23).

Step D: N-({4-chloro-3-[(3-chloro-5-cyanophenyl)oxy]-2-fluorophenyl}methyl)-5-{[3-hydroxy-2-(hydroxymethyl)propyl]oxy}-1H-indole-2-carboxamide

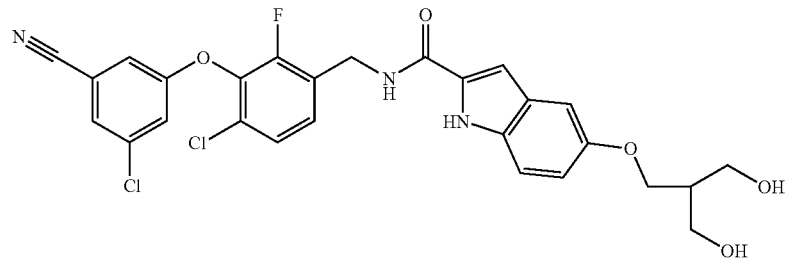

N-({4-Chloro-3-[(3-chloro-5-cyanophenyl)oxy]-2-fluorophenyl}methyl)-5-{[3-hydroxy-2-(hydroxymethyl)propyl]oxy}-1H-indole-2-carboxamide was prepared in a similar fashion as described herein from the hydrolysis of methyl 5-{[(2,2-dimethyl-1,3-dioxan-5-yl)methyl]oxy}-1H-indole-2-carboxylate (0.035 g, 0.11 mmol) and powdered lithium hydroxide (0.015 g, 0.62 mmol) in THF:MeOH:water (1:1:1, 3.0 mL) followed by amide coupling with 3-{[3-aminomethyl)oxy}-6-chloro-2-fluorophenyl]oxy}-5-chlorobenzonitrile (0.025 g, 0.08 mmol), HATU (0.045 g, 0.12 mmol), DIPEA (0.020 mL, 0.12 mmol) and DMF (2 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated and resulted in the deprotection of the acetonide to afford the title compound (0.017 g, 38%) as a tan solid. $^1$H NMR (400 MHz, DMSO-d$_6$): δ ppm 11.45 (s, 1H), 9.00 (t, 1H), 7.79 (s, 1H), 7.46-7.53 (m, 3H), 7.37 (t, 1H), 7.28 (d, 1H), 7.06 (s, 2H), 6.81 (dd, 1H), 4.51 (dt, 4H), 3.93 (d, 2H), 3.51 (t, 4H), 1.95 (dt, 1H). MS: m/z 558.1 (M+1).

Example 23

1,1-dimethylethyl (2R)-2-{[(2-{[({4-chloro-3-[(3-chloro-5-cyanophenyl)oxy]-2-fluorophenyl}methyl)amino]carbonyl}-1H-indol-5-yl)oxy]methyl}-4-morpholinecarboxylate

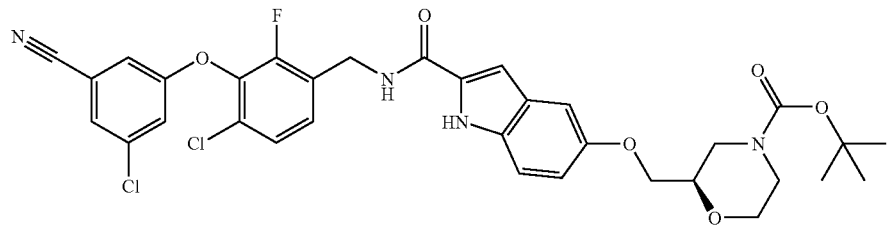

Step A: methyl 5-{[((2R)-4-{[(1,1-dimethylethyl)oxy]carbonyl}-2-morpholinyl)methyl]oxy}-1H-indole-2-carboxylate

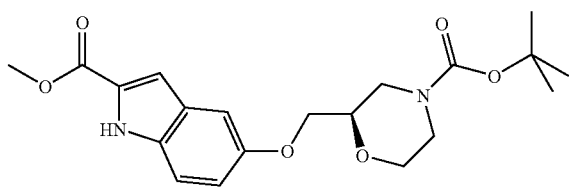

Methyl 5-{[((2R)-4-{[(1,1-dimethylethyl)oxy]carbonyl}-2-morpholinyl)methyl]oxy}-1H-indole-2-carboxylate was prepared in a similar manner as described herein from 5-hydroxy-1H-indole-2-carboxylate (0.10 g, 0.5 mmol), triphenylphosphine (0.28 g, 1.0 mmol), diethyl azodicarboxylate (0.18 g, 1.0 mmol), 1,1-dimethylethyl (2R)-2-(hydroxymethyl)-4-morpholinecarboxylate (0.23 g, 1.0 mmol) and CH$_2$Cl$_2$ (5 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.15 g, 73%) as a white solid. $^1$H NMR (400 MHz, DMSO-d$_6$): δ ppm 11.76 (s, 1H), 7.30 (d, 1H), 7.08 (d, 1H), 7.00 (d, 1H), 6.89 (dd, 1H), 3.94 (d, 2H), 3.81 (s, 3H), 3.78-3.92 (m, 2H), 3.59-3.73 (m, 2H), 3.35-3.46 (m, 1H), 2.76-2.97 (m, 2H), 1.36 (s, 9H)MS: m/z 391.2 (M+1).

Step B: 1,1-dimethylethyl (2R)-2-{[(2-{[({4-chloro-3-[(3-chloro-5-cyanophenyl)oxy]-2-fluorophenyl}methyl)amino]carbonyl}-1H-indol-5-yl)oxy]methyl}-4-morpholinecarboxylate

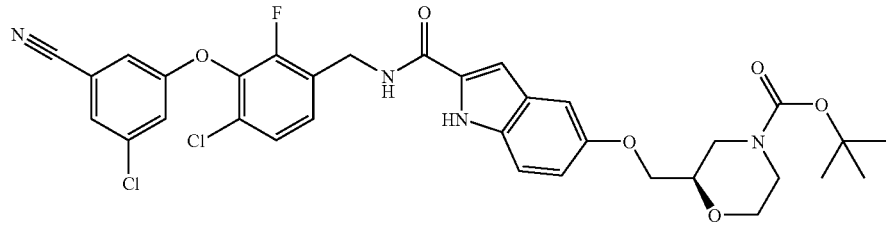

1,1-Dimethylethyl (2R)-2-{[(2-{[({4-chloro-3-[(3-chloro-5-cyanophenyl)oxy]-2-fluorophenyl}methyl)amino]carbonyl}-1H-indol-5-yl)oxy]methyl}-4-morpholinecarboxylate was prepared in a similar fashion as described herein from the hydrolysis of methyl 5-{[((2R)-4-{[(1,1-dimethylethyl)oxy]carbonyl}-2-morpholinyl)methyl]oxy}-1H-indole-2-carboxylate (0.045 g, 0.11 mmol) and powdered lithium hydroxide (0.015 g, 0.62 mmol) in THF:MeOH:water (1:1:1, 3.0 mL) followed by amide coupling with 3-{[3-aminomethyl)-6-chloro-2-fluorophenyl]oxy}-5-chlorobenzonitrile (0.025 g, 0.08 mmol), HATU (0.045 g, 0.12 mmol), DIPEA (0.020 mL, 0.12 mmol) and DMF (2 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.025 g, 46%) as a white solid. $^1$H NMR (400 MHz, DMSO-d$_6$): δ ppm 11.48 (br. s., 1H), 9.00 (t, 1H), 7.81 (d, 1H), 7.44-7.54 (m, 3H), 7.38 (t, 1H), 7.30 (d, 1H), 7.08 (d, 2H), 6.84 (dd, 1H), 4.55 (d, 2H), 3.97 (m, 3H), 3.79-3.87 (m, 1H), 3.69 (d, 2H), 3.37-3.51 (m, 1H), 2.82-2.95 (m, 2H), 1.37-1.41 (m, 9H). MS: m/z 667.1 (M−1).

Example 24

N-({4-Chloro-3-[(3-chloro-5-cyanophenyl)oxy]-2-fluorophenyl}methyl)-5-{[(2R)-2-morpholinylmethyl]oxy}-indole-2-carboxamide

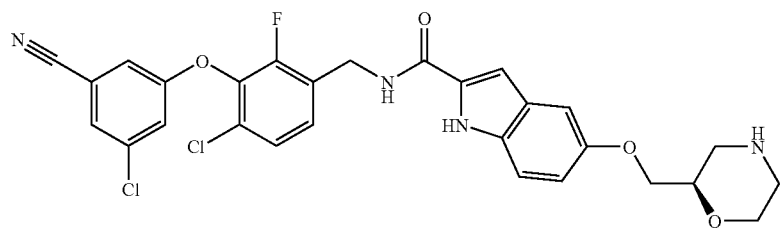

Trifluoroacetic acid (2 mL) and CH$_2$Cl$_2$ (2 mL) were added to 1,1-dimethylethyl (2R)-2-{[(2-{[({4-chloro-3-[(3-chloro-5-cyanophenyl)oxy]-2-fluorophenyl}methyl)amino]carbonyl}-1H-indol-5-yl)oxy]methyl}-4-morpholinecarboxylate (0.02 g, 0.03 mmol) and the mixture was stirred for 1 h. The solvent was evaporated. Purification was accomplished by Reverse-Phase HPLC (water/acetonitrile with 0.1% TFA). The desired fractions were neutralized with saturated NaHCO$_3$ and extracted with EtOAc. The organic extracts were combined dried over Na$_2$SO$_4$, filtered and evaporated to afford the title compound (0.015 g, 88%) as a tan solid. $^1$H NMR (400 MHz, DMSO-d$_6$): δ ppm 11.51 (br. s., 1H), 9.00 (t, 1H), 7.74-7.89 (m, 1H), 7.44-7.56 (m, 3H), 7.33-7.44 (m, 1H), 7.26-7.33 (m, 1H), 7.01-7.13 (m, 2H), 6.72-6.92 (m, 1H), 4.49-4.60 (m, 2H), 3.85-4.02 (m, 4 H), 3.59-3.71 (m, 1H), 3.15-3.24 (m, 1H), 2.98-3.08 (m, 1H), 2.77-2.97 (m, 2 H). MS: m/z 569.1 (M+1).

Example 25

N-({4-chloro-3-[(3-chloro-5-cyanophenyl)oxy]-2-fluorophenyl}methyl)-5-{[(2R)-2-morpholinylmethyl]oxy}-1H-indole-2-carboxamide hydrochloride

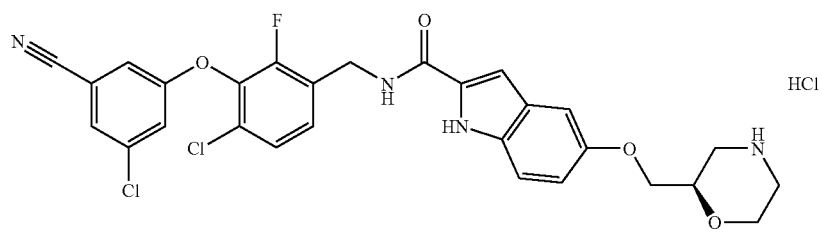

N-({4-Chloro-3-[(3-chloro-5-cyanophenyl)oxy]-2-fluorophenyl}methyl)-5-{[(2R)-2-morpholinylmethyl]oxy}-1H-indole-2-carboxamide (0.01 g, 0.02 mmol) was dissolved in MeOH (1 mL), 1N HCl in ether (2 mL) was added and stirred for 5 min. The solvent was evaporated and the solid recrystallized from MeOH/ether to afford the title compound (0.010 g, 94%) as white solid. $^1$H NMR (400 MHz, DMSO-d$_6$): δ ppm 11.52 (br. s., 1H), 9.23 (br. s., 2H), 9.03 (t, 1H), 7.81 (d, 1H), 7.44-7.54 (m, 3H), 7.40 (t, 1H), 7.31 (d, 1H), 7.09 (dd, 2H), 6.85 (dd, 1H), 4.55 (d, 2H), 4.01-4.10 (m, 4H), 3.73-3.84 (m, 2H), 3.15-3.25 (m, 1H), 2.94-3.05 (m, 2H). MS: m/z 569.1 (M+1).

Example 26

N-({4-chloro-3-[(3-chloro-5-cyanophenyl)oxy]-2-fluorophenyl}methyl)-5-hydroxy-1H-indole-2-carboxamide

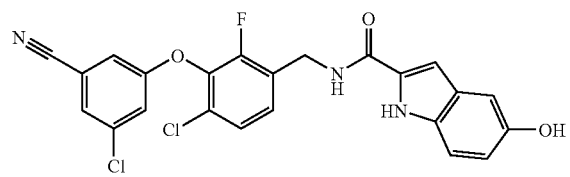

N-({4-Chloro-3-[(3-chloro-5-cyanophenyl)oxy]-2-fluorophenyl}methyl)-5-hydroxy-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 5-hydroxy-1H-indole-2-carboxylic acid (0.020 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.032 g, 85%) as a tan solid. $^1$H NMR (400 MHz, DMSO-d$_6$): δ ppm 11.32 (br. s., 1H), 8.95 (t, 1H), 8.83 (br. s., 1H), 7.82 (s, 1H), 7.44-7.56 (m, 3H), 7.39 (t, 1H), 7.23 (d, 1H), 6.98 (d, 1H), 6.87 (d, 1H), 6.73 (dd, 1H), 4.55 (d, 2H). MS: m/z 470.1 (M+1).

Example 27

N-({4-chloro-3-[(3-chloro-5-cyanophenyl)oxy]-2-fluorophenyl}methyl)-5-[(trifluoromethyl)oxy]-1H-indole-2-carboxamide

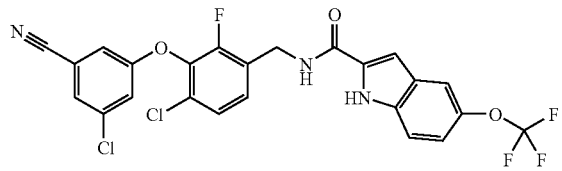

N-({4-Chloro-3-[(3-chloro-5-cyanophenyl)oxy]-2-fluorophenyl}methyl)-5-[(trifluoromethyl)oxy]-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 5-[(trifluoromethyl)oxy]-1H-indole-2-carboxylic acid (0.020 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.047 g, quant) as a white solid. $^1$H NMR (400 MHz, DMSO-d$_6$): δ ppm 11.93 (s, 1H), 9.18 (t, 1H), 7.82 (t, 1H), 7.66 (s, 1H), 7.46-7.57 (m, 4H), 7.41 (t, 1H), 7.25 (d, 1H), 7.18 (d, 1H), 4.58 (d, 2H). MS: m/z 538.1 (M+1).

Example 28

N-({4-chloro-3-[(3-chloro-5-cyanophenyl)oxy]-2-fluorophenyl}methyl)-1H-indole-2-carboxamide

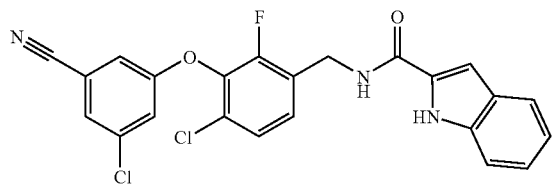

N-({4-Chloro-3-[(3-chloro-5-cyanophenyl)oxy]-2-fluorophenyl}methyl)-1H-indole-2-carboxamide was prepared in a similar manner as described herein from 3-{[3-aminomethyl)-6-chloro-2-fluorophenyl]oxy}-5-chlorobenzonitrile (0.050 g, 0.16 mmol), indole-2-carboxylic acid (0.040 g, 0.24 mmol), HATU (0.090 g, 0.12 mmol), DIPEA (0.020 mL, 0.12 mmol) and DMF (2 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.052 g, 71%) as a white solid. $^1$H NMR (400 MHz, DMSO-d$_6$): δ ppm 11.65 (s, 1H), 9.10 (t, 1H), 7.82 (s, 1H), 7.62 (d, 1H), 7.46-7.59 (m, 3H), 7.34-7.46 (m, 2H), 7.15-7.24 (m, 2H), 7.04 (t, 1H), 4.58 (d, 2H). MS: m/z 454.1 (M+1).

Example 29

5-bromo-N-({4-chloro-3-[(3-chloro-5-cyanophenyl)oxy]-2-fluorophenyl}methyl)-1H-indole-2-carboxamide

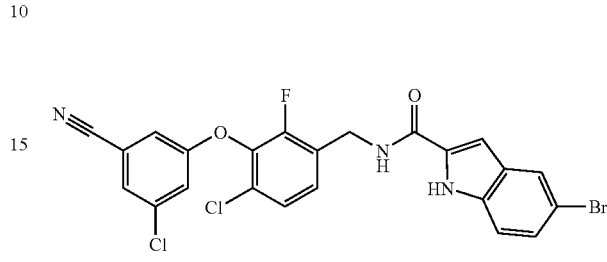

5-Bromo-N-({4-chloro-3-[(3-chloro-5-cyanophenyl)oxy]-2-fluorophenyl}methyl)-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 5-bromo-1H-indole-2-carboxylic acid (0.030 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.014 g, 32%) as a white solid. $^1$H NMR (400 MHz, DMSO-d$_6$): δ 11.88 (br. s., 1H), 9.19 (t, 1H), 7.83 (d, 2H), 7.46-7.56 (m, 3H), 7.36-7.46 (m, 2H), 7.30 (dd, 1H), 7.17 (s, 1H), 4.57 (d, 2H). MS: m/z 532.1, 534.0 (M+1).

Example 30

5-bromo-N-({4-chloro-3-[(3-chloro-5-cyanophenyl)oxy]-2-fluorophenyl}methyl)-7-methyl-1H-indole-2-carboxamide

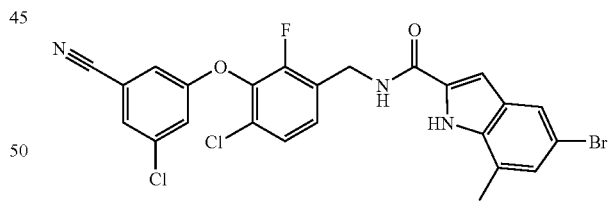

5-Bromo-N-({4-chloro-3-[(3-chloro-5-cyanophenyl)oxy]-2-fluorophenyl}methyl)-7-methyl-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 5-bromo-7-methyl-1H-indole-2-carboxylic acid (0.030 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.027 g, 57%) as a tan solid. $^1$H NMR (400 MHz, DMSO-d$_6$): δ 11.67 (br. s., 1H), 9.11 (t, 1H), 7.79 (t, 1H), 7.64 (d, 1H), 7.43-7.52 (m, 3H), 7.39 (t, 1H), 7.13 (d, 1H), 7.10 (d, 1H), 4.55 (d, 2H), 2.47 (s, 3H). MS: m/z 546.1 (M+1).

Example 31

N-({4-chloro-3-[(3-chloro-5-cyanophenyl)oxy]-2-fluorophenyl}methyl)-6-nitro-1H-indole-2-carboxamide

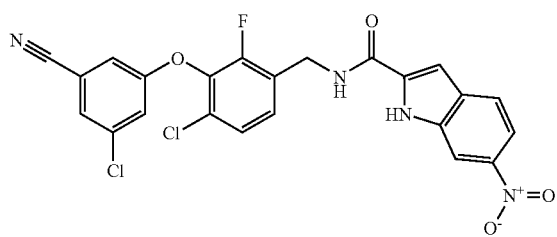

N-({4-Chloro-3-[(3-chloro-5-cyanophenyl)oxy]-2-fluorophenyl}methyl)-6-nitro-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 6-nitro-1H-indole-2-carboxylic acid (0.025 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over $Na_2SO_4$, filtered and evaporated to afford the title compound (0.032 g, 80%) as a yellow solid. $^1$H NMR (400 MHz, DMSO-$d_6$): δ ppm 12.46 (br. s., 1H), 9.38 (t, 1H), 8.34 (d, 1H), 7.79-7.96 (m, 3H), 7.47-7.57 (m, 3H), 7.43 (t, 1H), 7.37 (d, 1H), 4.61 (d, 2H). MS: m/z 499.2 (M+1).

Example 32

N-({4-chloro-3-[(3-chloro-5-cyanophenyl)oxy]-2-fluorophenyl}methyl)-7-hydroxy-1H-indole-2-carboxamide

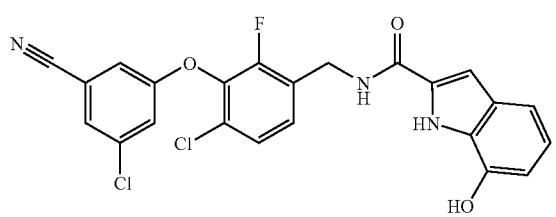

N-({4-Chloro-3-[(3-chloro-5-cyanophenyl)oxy]-2-fluorophenyl}methyl)-7-hydroxy-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 7-hydroxy-1H-indole-2-carboxylic acid (0.020 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over $Na_2SO_4$, filtered and evaporated to afford the title compound (0.025 g, 66%) as a brown solid. $^1$H NMR (400 MHz, DMSO-$d_6$): δ ppm 11.09 (br. s., 1H), 9.49 (br. s., 1H), 9.00 (t, 1H), 7.79 (d, 1H), 7.43-7.54 (m, 3H), 7.39 (t, 1H), 7.00-7.11 (m, 2H), 6.83 (t, 1H), 6.56 (d, 1H), 4.55 (d, 2H). MS: m/z 470.2 (M+1).

Example 33

N-({4-chloro-3-[(3-chloro-5-cyanophenyl)oxy]-2-fluorophenyl}methyl)-5-fluoro-7-(methylsulfonyl)-1H-indole-2-carboxamide

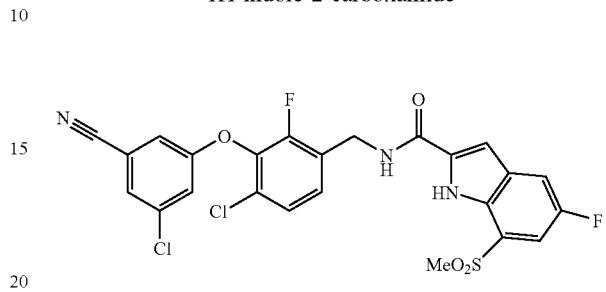

N-({4-chloro-3-[(3-chloro-5-cyanophenyl)oxy]-2-fluorophenyl}methyl)-5-fluoro-7-(methylsulfonyl)-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 5-fluoro-7-(methylsulfonyl)-1H-indole-2-carboxylic acid (0.030 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over $Na_2SO_4$, filtered and evaporated to afford the title compound (0.022 g, 50%) as a white solid. $^1$H NMR (400 MHz, DMSO-$d_6$): δ ppm 10.91 (br. s., 1H), 9.52 (t, 1H), 7.95 (d, 1H), 7.82 (s, 1H), 7.64 (d, 1H), 7.30-7.58 (m, 5H), 4.60 (d, 2H), 2.50 (s, 3H). MS: m/z 550.1 (M+1).

Example 34

N-({4-chloro-3-[(3-chloro-5-cyanophenyl)oxy]-2-fluorophenyl}methyl)-4-(methyloxy)-1H-indole-2-carboxamide

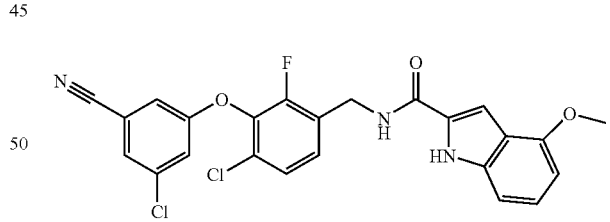

N-({4-Chloro-3-[(3-chloro-5-cyanophenyl)oxy]-2-fluorophenyl}methyl)-4-(methyloxy)-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 4-(methyloxy)-1H-indole-2-carboxylic acid (0.025 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over $Na_2SO_4$, filtered and evaporated to afford the title compound (0.031 g, 80%) as a brown solid. $^1$H NMR (400 MHz, DMSO-$d_6$): δ ppm 11.64

(br. s., 1H), 9.02 (t, 1H), 7.82 (s, 1H), 7.45-7.58 (m, 3H), 7.40 (t, 1H), 7.27 (s, 1H), 7.10 (t, 1H), 7.01 (d, 1H), 6.51 (d, 1H), 4.56 (d, 2H), 3.87 (s, 3H). MS: m/z 484.1 (M+1).

Example 35

N-({4-chloro-3-[(3-chloro-5-cyanophenyl)oxy]-2-fluorophenyl}methyl)-1H-benzimidazole-2-carboxamide

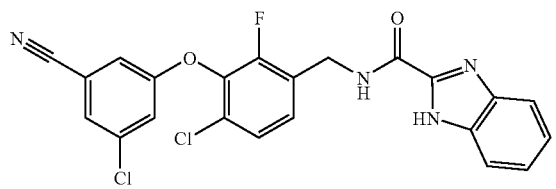

N-({4-Chloro-3-[(3-chloro-5-cyanophenyl)oxy]-2-fluorophenyl}methyl)-1H-benzimidazole-2-carboxamide was prepared in a similar manner as described herein from 3-{[3-aminomethyl)-6-chloro-2-fluorophenyl]oxy}-5-chlorobenzonitrile (0.05 g, 0.16 mmol), 1H-benzimidazole-2-carboxylic acid (0.04 g, 0.24 mmol), HATU (0.09 g, 0.24 mmol), DIPEA (0.04 mL, 0.24 mmol) and DMF (2 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.035 g, 48%) as a white solid. $^1$H NMR (400 MHz, DMSO-d$_6$): δ ppm 9.57 (t, 1H), 7.82 (t, 1H), 7.57-7.72 (m, 2H), 7.54 (d, 1H), 7.47-7.52 (m, 2H), 7.41 (t, 1H), 7.30 (dd, 2H), 4.58 (d, 2H). MS: m/z 455.0 (M+1).

Example 36

N-({4-chloro-3-[(3-chloro-5-cyanophenyl)oxy]-2-fluorophenyl}methyl)-6-hydroxy-1H-indole-2-carboxamide

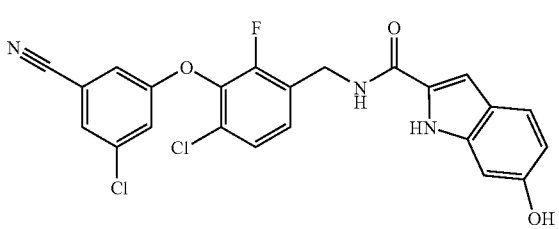

N-({4-chloro-3-[(3-chloro-5-cyanophenyl)oxy]-2-fluorophenyl}methyl)-6-hydroxy-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 6-hydroxy-1H-indole-2-carboxylic acid (0.02 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.021 g, 55%) as a tan solid. $^1$H NMR (400 MHz, DMSO-d$_6$): δ ppm 11.15 (s, 1H), 9.14 (s, 1H), 8.80 (t, 1H), 7.77 (s, 1H), 7.44-7.51 (m, 3H), 7.34 (d, 2H), 7.01 (s, 1H), 6.73 (s, 1H), 6.53 (dd, 1H), 4.50 (d, 2H). MS: m/z 470.1 (M+1).

Example 37

N-({4-chloro-3-[(3-chloro-5-cyanophenyl)oxy]-2-fluorophenyl}methyl)-7-nitro-1H-indole-2-carboxamide

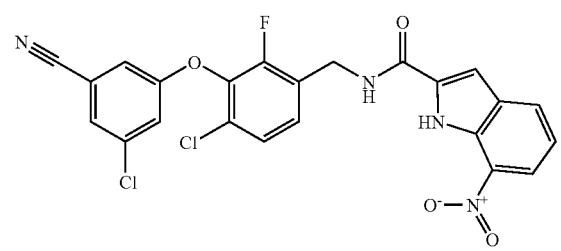

N-({4-Chloro-3-[(3-chloro-5-cyanophenyl)oxy]-2-fluorophenyl}methyl)-7-nitro-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 7-nitro-1H-indole-2-carboxylic acid (0.025 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.008 g, 20%) as a yellow solid. $^1$H NMR (400 MHz, DMSO-d$_6$): δ ppm 11.38 (br. s., 1H), 9.53 (t, 1H), 8.15-8.32 (m, 2H), 7.81 (s, 1H), 7.38-7.57 (m, 5H), 7.33 (t, 1H), 4.60 (d, 2H).

Example 38

3-chloro-5-[(6-chloro-2-fluoro-3-{[6-(methyloxy)-1-oxo-1,3,4,9-tetrahydro-2H-β-carbolin-2-yl]methyl}phenyl)oxy]benzonitrile

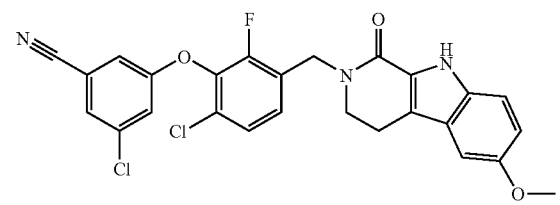

Step A: 1,1-dimethylethyl 6-(methyloxy)-1-oxo-1,2,3,4-tetrahydro-9H-β-carboline-9-carboxylate

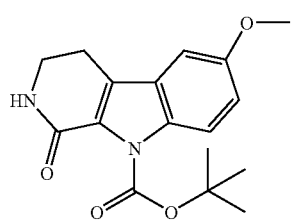

6-(Methyloxy)-2,3,4,9-tetrahydro-1H-β-carbolin-1-one (0.10 g, 0.45 mmol), Boc$_2$O (0.1 g, 0.45 mmol), and DMAP (0.01 g, 0.08 mmol) were dissolved in THF (3.0 mL) and stirred overnight. The solvent was evaporated and the residue was purified by column chromatography (hexane/EtOAc) to afford the title compound (0.075 g, 51%) as a solid. $^1$H NMR (400 MHz, DMSO-d$_6$): δ ppm 7.83 (d, 1H), 7.79 (t, 1H), 7.20 (d, 1H), 7.07 (dd, 1H), 3.81 (s, 3H), 3.41-3.50 (m, 2H), 2.85 (t, 2H), 1.55 (s, 9H).

Step B: 1,1-dimethylethyl 2-({4-chloro-3-[(3-chloro-5-cyanophenyl)oxy]-2-fluorophenyl}methyl)-6-(methyloxy)-1-oxo-1,2,3,4-tetrahydro-9H-β-carboline-9-carboxylate

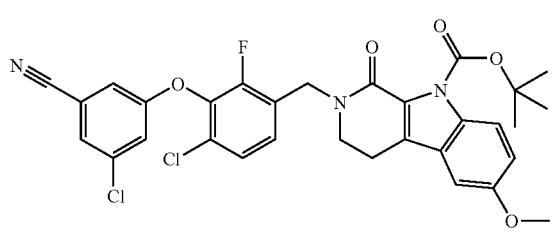

1,1-Dimethylethyl 7-(methyloxy)-1-oxo-1,2,3,4-tetrahydro-9H-β-carboline-9-carboxylate (0.075 g, 0.23 mmol) was dissolved in THF (2 mL) and cooled to 0° C. Sodium hydride (60% dispersion in oil, 0.01 g, 0.25 mmol) was added and the mixture was stirred for 15 min. 3-{[3-(Bromomethyl)-6-chloro-2-fluorophenyl]oxy}-5-chlorobenzonitrile (0.09 g, 0.23 mmol) was added. The reaction mixture was allowed to warm to RT and stirred for 1 h. 10% Aqueous citric acid and EtOAc were added. The layers were separated and the aqueous layer extracted with EtOAc (3×5 mL). The organic extracts were combined, dried over Na$_2$SO$_4$, filtered and evaporated. Purification was accomplished by column chromatography (hexane/EtOAc) to afford the title compound (0.034 g, 24%) as a white solid. $^1$H NMR (400 MHz, DMSO-d$_6$): δ ppm 7.83 (s, 1H), 7.81 (d, 1H), 7.52 (d, 1H), 7.45-7.51 (m, 2H), 7.34 (t, 1H), 7.20 (d, 1H), 7.07 (dd, 1H), 4.79 (s, 2H), 3.79 (s, 3H), 3.71 (t, 2H), 2.94 (t, 2H), 1.48 (s, 9H). MS: m/z 632.2 (M+23).

Step C: 3-chloro-5-[(6-chloro-2-fluoro-3-{[6-(methyloxy)-1-oxo-1,3,4,9-tetrahydro-2H-β-carbolin-2-yl]methyl}phenyl)oxy]benzonitrile

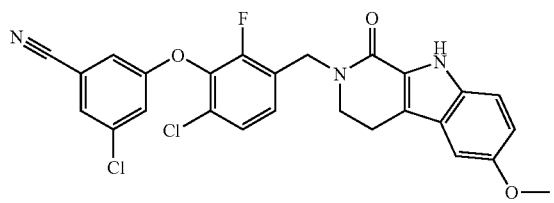

1,1-Dimethylethyl 2-({4-chloro-3-[(3-chloro-5-cyanophenyl)oxy]-2-fluorophenyl}methyl)-6-(methyloxy)-1-oxo-1,2,3,4-tetrahydro-9H-β-carboline-9-carboxylate (0.03 g, 0.05 mmol), was dissolved in CH$_2$Cl$_2$ (1.0 mL) and TFA (1.0 mL) was added dropwise. The reaction mixture was stirred 1 h and the solvent was evaporated. Purification was accomplished by Reverse-Phase HPLC (water/acetonitrile with 0.1% TFA). The desired fractions were neutralized with saturated NaHCO$_3$ and extracted with EtOAc. The organic extracts were combined, dried over Na$_2$SO$_4$, filtered and evaporated to afford the title compound (0.02 g, 80%) as a tan solid. $^1$H NMR (400 MHz, DMSO-d$_6$): δ ppm 11.50 (br. s., 1H), 7.80 (s, 1H), 7.47-7.55 (m, 3H), 7.39 (t, 1H), 7.27 (d, 1H), 7.04 (d, 1H), 6.86 (dd, 1H), 4.76 (s, 2H), 3.75 (s, 3H), 3.66 (t, 2H), 2.97 (t, 2H). MS: m/z 510.2 (M+1).

Example 39

N-({4-chloro-3-[(3-chloro-5-cyanophenyl)oxy]-2-fluorophenyl}methyl)-3-methyl-1H-indole-2-carboxamide

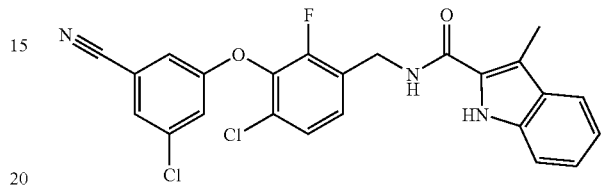

N-({4-Chloro-3-[(3-chloro-5-cyanophenyl)oxy]-2-fluorophenyl}methyl)-3-methyl-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 3-methyl-1H-indole-2-carboxylic acid (0.020 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.015 g, 40%) as a white solid. $^1$H NMR (400 MHz, DMSO-d$_6$): δ ppm 11.28 (br. s., 1H), 8.52 (t, 1H), 7.80 (s, 1H), 7.57 (d, 1H), 7.41-7.53 (m, 4H), 7.35 (d, 1H), 7.18 (t, 1H), 7.01 (t, 1H), 4.55 (d, 2H), 2.5 (s, 3H). MS: m/z 468.0 (M+1).

Example 40

5-chloro-N-({4-chloro-3-[(3-chloro-5-cyanophenyl)oxy]-2-fluorophenyl}methyl)-3-methyl-1H-indole-2-carboxamide

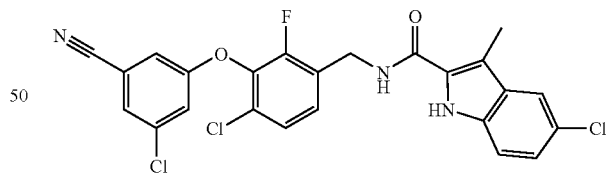

5-Chloro-N-({4-chloro-3-[(3-chloro-5-cyanophenyl)oxy]-2-fluorophenyl}methyl)-3-methyl-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 5-chloro-3-methyl-1H-indole-2-carboxylic acid (0.025 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.015 g, 38%) as a white solid. $^1$H NMR (400 MHz, DMSO-d$_6$): δ ppm 11.51 (br. s., 1H), 8.58 (t, 1H), 7.80 (s, 1H), 7.63 (s, 1H), 7.40-7.52 (m, 5H), 7.18 (d, 1H), 4.55 (d, 2H), 2.44 (s, 3H). MS: m/z 502.0 (M+1).

Example 41

N-({4-chloro-3-[(3-chloro-5-cyanophenyl)oxy]-2-fluorophenyl}methyl)-5-fluoro-1H-indole-2-carboxamide

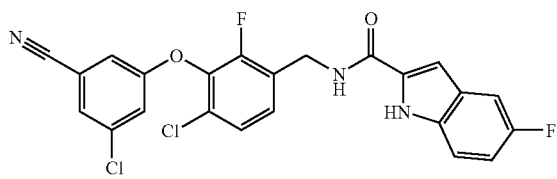

N-({4-Chloro-3-[(3-chloro-5-cyanophenyl)oxy]-2-fluorophenyl}methyl)-5-fluoro-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 5-fluoro-1H-indole-2-carboxylic acid (0.020 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.012 g, 32%) as a white solid. $^1$H NMR (400 MHz, DMSO-d$_6$): δ 11.72 (br. s., 1H), 9.08 (s, 1H), 7.80 (t, 1H), 7.44-7.53 (m, 2H), 7.35-7.41 (m, 4H), 7.14 (d, 1H), 7.02 (td, 1H), 4.55 (d, 2H). MS: m/z 472.0 (M+1).

Example 42

N-({4-chloro-3-[(3-chloro-5-cyanophenyl)oxy]-2-fluorophenyl}methyl)-6-(methyloxy)-3-pyridinecarboxamide

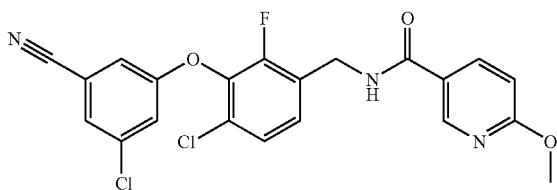

N-({4-Chloro-3-[(3-chloro-5-cyanophenyl)oxy]-2-fluorophenyl}methyl)-6-(methyloxy)-3-pyridinecarboxamide was prepared in a similar manner as described herein from 3-{[3-aminomethyl)-6-chloro-2-fluorophenyl]oxy}-5-chlorobenzonitrile (0.025 g, 0.08 mmol), 6-(methyloxy)-3-pyridinecarboxylic acid (0.020 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.039 g, quant.) as a white solid. $^1$H NMR (400 MHz, DMSO-d$_6$): δ 9.08 (t, 1H), 8.71 (d, 1H), 8.15 (dd, 1H), 7.83 (t, 1H), 7.52 (dd, 1H), 7.45-7.50 (m, 2H), 7.39 (t, 1H), 6.91 (d, 1H), 4.53 (d, 2H), 3.91 (s, 3H). MS: m/z 446.0 (M+1).

Example 43

N-({4-chloro-3-[(3-chloro-5-cyanophenyl)oxy]-2-fluorophenyl}methyl)-6-[(phenylmethyl)oxy]-1H-indole-2-carboxamide

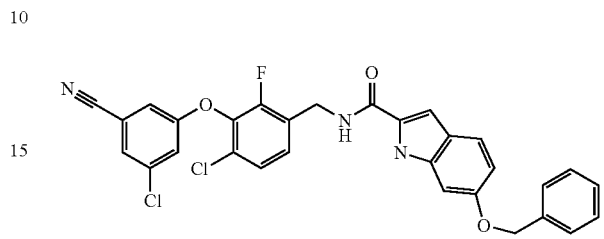

N-({4-chloro-3-[(3-chloro-5-cyanophenyl)oxy]-2-fluorophenyl}methyl)-6-[(phenylmethyl)oxy]-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 6-[(phenylmethyl)oxy]-1H-indole-2-carboxylic acid (0.030 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.029 g, 64%) as a tan solid. 1H NMR (400 MHz, DMSO-d$_6$): δ ppm 11.51 (s, 1H), 9.04 (t, 1H), 7.82 (s, 1H), 7.43-7.58 (m, 5H), 7.39 (t, 3H), 7.33 (d, 2H), 7.19 (d, 1H), 7.09 (d, 1H), 6.92 (dd, 1H), 5.09 (s, 2H), 4.56 (d, 2H). MS: m/z 560.0 (M+1).

Example 44

N$^2$-({4-chloro-3-[(3-chloro-5-cyanophenyl)oxy]-2-fluorophenyl}methyl)-7,8-dihydropyrrolo[3,2-e]indole-2,6(3H)-dicarboxamide

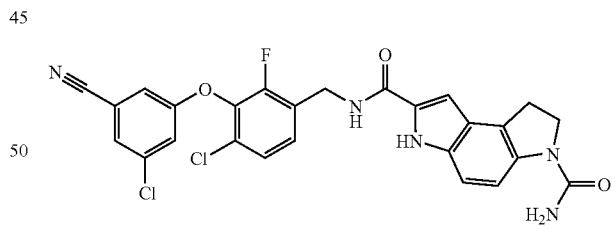

N$^2$-({4-Chloro-3-[(3-chloro-5-cyanophenyl)oxy]-2-fluorophenyl}methyl)-7,8-dihydropyrrolo[3,2-e]indole-2,6(3H)-dicarboxamide was prepared in a similar manner as described herein from 3-{[3-aminomethyl)-6-chloro-2-fluorophenyl]oxy}-5-chlorobenzonitrile (0.025 g, 0.08 mmol), 6-(aminocarbonyl)-3,6,7,8-tetrahydropyrrolo[3,2-e]indole-2-carboxylic acid (0.030 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.020 g, 46%) as a tan solid. $^1$H NMR (400 MHz, DMSO-d$_6$): δ ppm 11.51 (br. s., 1H), 9.02 (t, 1H), 7.93 (d, 1H), 7.82 (t, 1H), 7.47-7.55 (m, 3H), 7.41 (t, 1H), 7.16 (d, 1H), 7.03 (d, 1H), 6.10 (s, 2H), 4.56 (d, 2H), 3.96 (t, 2H), 3.25 (t, 2H). MS: m/z 538.1 (M+1).

Example 45

N-({4-chloro-3-[(3-chloro-5-cyanophenyl)oxy]-2-fluorophenyl}methyl)-1-methyl-1H-indole-2-carboxamide

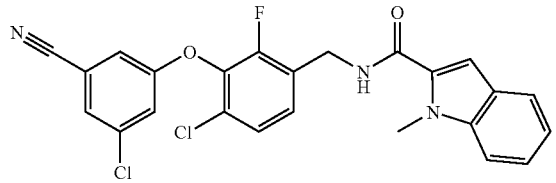

N-({4-Chloro-3-[(3-chloro-5-cyanophenyl)oxy]-2-fluorophenyl}methyl)-1-methyl-1H-indole-2-carboxamide was prepared in a similar manner as described herein from 3-{[3-aminomethyl)-6-chloro-2-fluorophenyl]oxy}-5-chlorobenzonitrile (0.025 g, 0.08 mmol), 1-methyl-1H-indole-2-carboxylic acid (0.030 g, 0.12 mmol), HATU (0.045 g, 0.12 mmol), DIPEA (0.020 mL, 0.12 mmol) and DMF (1 mL). The crude material was purified by Reverse-Phase HPLC (water/acetonitrile with 0.1% TFA). The desired fractions were neutralized and extracted with EtOAc. The organic extracts were combined, dried over Na$_2$SO$_4$, filtered and evaporated to afford the title compound (0.030 g, 80%) as a white solid. $^1$H NMR (400 MHz, DMSO-d$_6$): δ ppm 9.08 (t, 1H), 7.83 (s, 1H), 7.65 (d, 1H), 7.47-7.58 (m, 4H), 7.43 (t, 1H), 7.28 (t, 1H), 7.17 (s, 1H), 7.11 (t, 1H), 4.54 (d, 2H), 3.99 (s, 3H). MS: m/z 468.0 (M+1).

Example 46

N-({4-chloro-3-[(3-chloro-5-cyanophenyl)oxy]-2-fluorophenyl}methyl)-5-(methyloxy)-1H-pyrrolo[2,3-c]pyridine-2-carboxamide trifluoroacetate

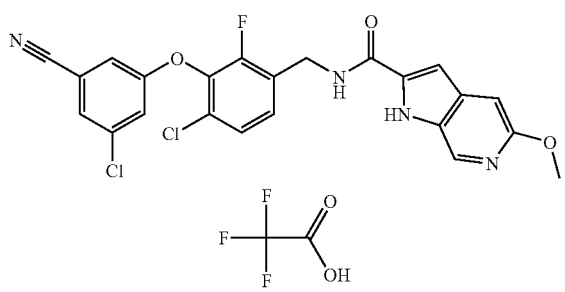

N-({4-Chloro-3-[(3-chloro-5-cyanophenyl)oxy]-2-fluorophenyl}methyl)-5-(methyloxy)-1H-pyrrolo[2,3-c]pyridine-2-carboxamide trifluoroacetate was prepared in a similar manner as described herein from the hydrolysis of ethyl 5-(methyloxy)-1H-pyrrolo[2,3-c]pyridine-2-carboxylate (0.010 g, 0.045 mmol) (prepared as described in J. Org. Chem., 1978, 38, 1824) and powdered lithium hydroxide (0.005 g, 0.22 mmol) in THF:MeOH:water (1:1:1, 1.5 mL) followed by amide coupling with 3-{[3-aminomethyl)-6-chloro-2-fluorophenyl]oxy}-5-chlorobenzonitrile (0.015 g, 0.045 mmol), HATU (0.020 g, 0.054 mmol), DIPEA (0.010 mL, 0.054 mmol) and DMF (1 mL). Purification was accomplished by Reverse-Phase HPLC (water/acetonitrile with 0.1% TFA) to afford the title compound (80% pure, 0.020 g, 73%) as a white solid. 1H NMR (400 MHz, DMSO-d$_6$): δ ppm 12.01 (br. s., 1H), 9.29 (t, 1H), 8.42 (s, 1H), 7.75-7.90 (m, 1H), 7.44-7.53 (m, 3H), 7.39 (t, 1H), 7.09 (d, 2H), 4.56 (d, 2H), 3.85 (s, 3H). MS: m/z 485.0 (M+1).

Example 47

N-({4-chloro-3-[(3-chloro-5-cyanophenyl)oxy]-2-fluorophenyl}methyl)-1-benzofuran-2-carboxamide trifluoroacetate


N-({4-Chloro-3-[(3-chloro-5-cyanophenyl)oxy]-2-fluorophenyl}methyl)-1-benzofuran-2-carboxamide trifluoroacetate was prepared in a similar manner as described herein from 3-{[3-aminomethyl)-6-chloro-2-fluorophenyl]oxy}-5-chlorobenzonitrile (0.025 g, 0.08 mmol), 1-benzofuran-2-carboxylic acid (0.020 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA) to afford the title compound (0.024 g, 65%) as a white solid. $^1$H NMR (400 MHz, DMSO-d$_6$): δ ppm 9.32 (t, 1H), 7.82 (s, 1H), 7.78 (d, 1H), 7.66 (d, 1H), 7.59 (s, 1H), 7.44-7.55 (m, 4H), 7.41 (t, 1H), 7.34 (t, 1H), 4.55 (d, 2H). MS: m/z 455.0 (M+1).

Example 48

N-({4-chloro-3-[(3-chloro-5-cyanophenyl)oxy]-2-fluorophenyl}methyl)-3-methyl-1-benzofuran-2-carboxamide trifluoroacetate

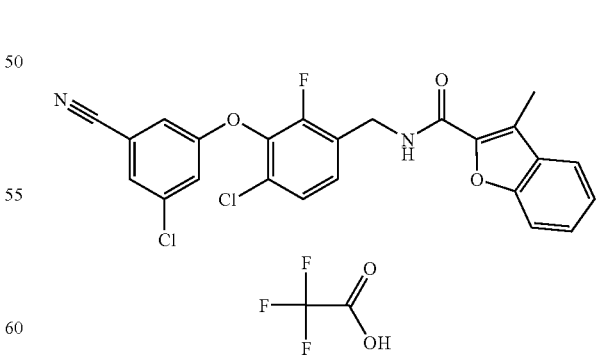

N-({4-Chloro-3-[(3-chloro-5-cyanophenyl)oxy]-2-fluorophenyl}methyl)-3-methyl-1-benzofuran-2-carboxamide trifluoroacetate was prepared in a similar manner as described herein from 3-{[3-aminomethyl)-6-chloro-2-fluorophenyl]oxy}-5-chlorobenzonitrile (0.025 g, 0.08 mmol), 3-methyl-1-benzofuran-2-carboxylic acid (0.020 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA) to afford the title compound (0.020 g, 53%) as a white solid. $^1$H NMR (400 MHz, DMSO-$d_6$): δ ppm 9.14 (t, 1H), 7.80 (t, 1H), 7.73 (d, 1H), 7.55-7.58 (m, 1H), 7.43-7.52 (m, 4H), 7.38 (t, 1H), 7.32 (dd, 1H), 4.50 (d, 2 H), 2.51 (s, 3H). MS: m/z 469.0 (M+1).

Example 49

5-chloro-N-({4-chloro-3-[(3-chloro-5-cyanophenyl)oxy]-2-fluorophenyl}methyl)-1-benzofuran-2-carboxamide trifluoroacetate

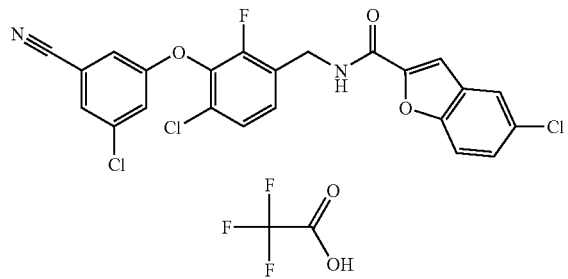

5-Chloro-N-({4-chloro-3-[(3-chloro-5-cyanophenyl)oxy]-2-fluorophenyl}methyl)-1-benzofuran-2-carboxamide trifluoroacetate was prepared in a similar manner as described herein from 3-{[3-aminomethyl)-6-chloro-2-fluorophenyl]oxy}-5-chlorobenzonitrile (0.025 g, 0.08 mmol), 5-chloro-1-benzofuran-2-carboxylic acid (0.025 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA) to afford the title compound (0.025 g, 63%) as a white solid. $^1$H NMR (400 MHz, DMSO-$d_6$): δ ppm 9.36 (t, 1H), 7.86 (d, 1H), 7.80 (t, 1H), 7.68 (d, 1H), 7.55 (s, 1H), 7.43-7.52 (m, 4H), 7.38 (t, 1H), 4.52 (d, 2H). MS: m/z 488.9 (M+1).

Example 50

N-({4-chloro-3-[(3-chloro-5-cyanophenyl)oxy]-2-fluorophenyl}methyl)-5-nitro-1-benzofuran-2-carboxamide trifluoroacetate

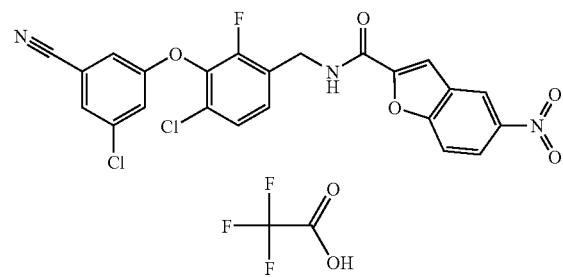

N-({4-Chloro-3-[(3-chloro-5-cyanophenyl)oxy]-2-fluorophenyl}methyl)-5-nitro-1-benzofuran-2-carboxamide trifluoroacetate was prepared in a similar manner as described herein from 3-{[3-aminomethyl)-6-chloro-2-fluorophenyl]oxy}-5-chlorobenzonitrile (0.025 g, 0.08 mmol), 5-nitro-1-benzofuran-2-carboxylic acid (0.025 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA) to afford the title compound (0.018 g, 45%) as a white solid. $^1$H NMR (400 MHz, DMSO-$d_6$): δ ppm 9.49 (t, 1H), 8.77 (d, 1H), 8.31 (dd, 1H), 7.89 (d, 1H), 7.78 (d, 2H), 7.49 (dd, 3H), 7.40 (t, 1H), 4.54 (d, 2H). MS: m/z 500.0 (M+1).

Example 51

5-chloro-N-({4-chloro-3-[(3-chloro-5-cyanophenyl)oxy]-2-fluorophenyl}methyl)-1-benzothiophene-2-carboxamide trifluoroacetate

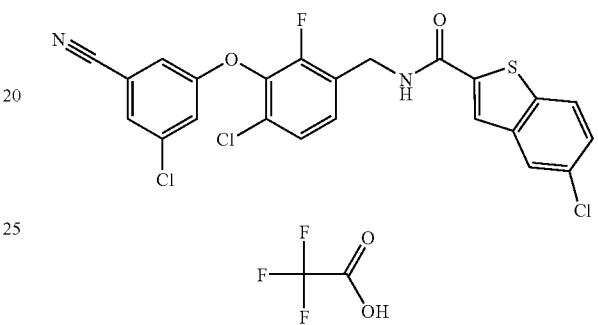

5-Chloro-N-({4-chloro-3-[(3-chloro-5-cyanophenyl)oxy]-2-fluorophenyl}methyl)-1-benzothiophene-2-carboxamide trifluoroacetate was prepared in a similar manner as described herein from 3-{[3-aminomethyl)-6-chloro-2-fluorophenyl]oxy}-5-chlorobenzonitrile (0.025 g, 0.08 mmol), 5-chloro-1-benzothiophene-2-carboxylic acid (0.025 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA) to afford the title compound (0.018 g, 44%) as a white solid. $^1$H NMR (400 MHz, DMSO-$d_6$): δ ppm 9.42 (t, 1H), 8.02-8.15 (m, 3H), 7.83 (s, 1H), 7.52 (d, 5H), 4.56 (d, 2H). MS: m/z 504.9 (M+1).

Example 52

N-({4-chloro-3-[(3-chloro-5-cyanophenyl)oxy]-2-fluorophenyl}methyl)-3,5-dimethyl-1H-indole-2-carboxamide trifluoroacetate

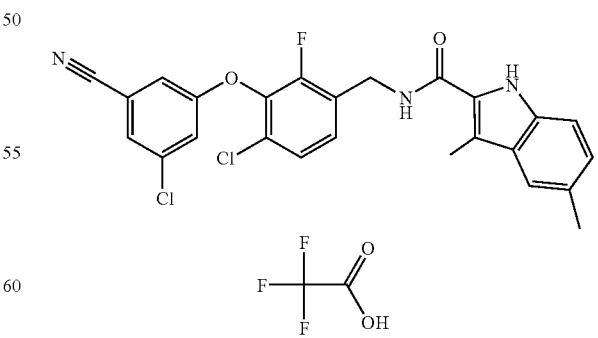

N-({4-Chloro-3-[(3-chloro-5-cyanophenyl)oxy]-2-fluorophenyl}methyl)-3,5-dimethyl-1H-indole-2-carboxamide trifluoroacetate was prepared in a similar manner as described herein from 3-{[3-aminomethyl)-6-chloro-2-fluorophenyl]oxy}-5-chlorobenzonitrile (0.025 g, 0.08 mmol), 3,5-dimethyl-1H-indole-2-carboxylic acid 0.025 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA) to afford the title compound (0.008 g, 20%) as a white solid. ¹H NMR (400 MHz, DMSO-d₆): δ ppm 11.02 (br. s., 1H), 8.36 (t, 1H), 7.80 (s, 1H), 7.48-7.53 (m, 2H), 7.39-7.48 (m, 2H), 7.34 (s, 1H), 7.24 (d, 1H), 7.02 (s, 1H), 4.54 (d, 2H), 2.44 (s, 3H), 2.35 (s, 3H). MS: m/z 482.1 (M+1).

Example 53

3-bromo-N-({4-chloro-3-[(3-chloro-5-cyanophenyl)oxy]-2-fluorophenyl}methyl)-1H-indole-2-carboxamide

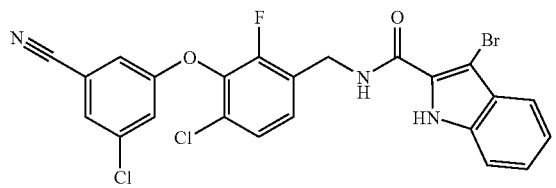

3-Bromo-N-({4-chloro-3-[(3-chloro-5-cyanophenyl)oxy]-2-fluorophenyl}methyl)-1H-indole-2-carboxamide was prepared in a similar manner as described herein from the hydrolysis of ethyl 3-bromo-1H-indole-2-carboxylate (0.025 g, 0.11 mmol) and powdered lithium hydroxide (0.025 g, 0.96 mmol) in THF:MeOH:water (1:1:1, 3.0 mL) followed by amide coupling with 3-{[3-aminomethyl)-6-chloro-2-fluorophenyl]oxy}-5-chlorobenzonitrile (0.050 g, 0.16 mmol), HATU (0.090 g, 0.24 mmol), DIPEA (0.040 mL, 0.24 mmol) and DMF (1 mL). The crude material was purified by Reverse-Phase HPLC (water/acetonitrile with 0.1% TFA). The desired fractions were lyophilized, neutralized and extracted with EtOAc. The organic extracts were combined, dried over Na₂SO₄, filtered and evaporated to afford the title compound (0.017 g, 29%) as a white solid. ¹H NMR (400 MHz, DMSO-d₆): δ ppm 12.0 (br. s., 1H), 8.58 (t, 1H), 7.80 (s, 1H), 7.40-7.58 (m, 6H), 7.30 (m, 1H), 7.18 (m, 1H), 4.62 (m, 2H). MS: m/z 531.9 (M+1).

Example 54

3-bromo-N-({4-chloro-3-[(3-chloro-5-cyanophenyl)oxy]-2-fluorophenyl}methyl)-1H-indole-2-carboxamide trifluoroacetate

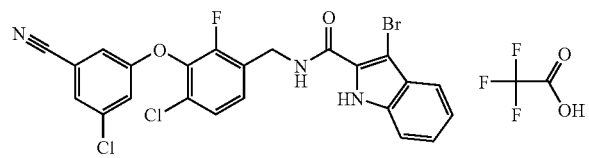

Step A: 3-bromo-1H-indole-2-carboxylic acid

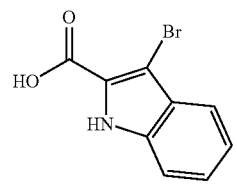

Ethyl 3-bromo-1H-indole-2-carboxylate (0.070 g, 0.30 mmol) and powdered lithium hydroxide (0.073 g, 3.0 mmol) were dissolved in 1:1:1 mixture of THF/MeOH/water (3.0 mL) and the solution was stirred at RT for 4.5 h. The solvent was evaporated. Purification was accomplished by Reverse-Phase HPLC (water/acetonitrile with 0.1% TFA) to afford (0.042 g, 67%) of the title compound as a white solid. ¹H NMR (400 MHz, DMSO-d₆): δ ppm 12.09 (br. s., 1H), 7.50 (d, 1H), 7.43 (d, 1H), 7.30 (t, 1H), 7.15 (t, 1H). MS: m/z 240.1 (M+1).

Step B: 3-bromo-N-({4-chloro-3-[(3-chloro-5-cyanophenyl)oxy]-2-fluorophenyl}methyl)-1H-indole-2-carboxamide trifluoroacetate

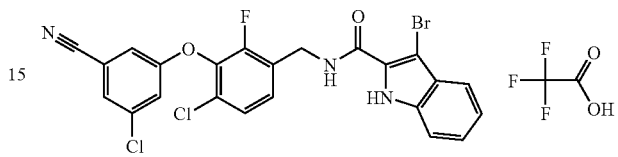

3-Bromo-N-({4-chloro-3-[(3-chloro-5-cyanophenyl)oxy]-2-fluorophenyl}methyl)-1H-indole-2-carboxamide trifluoroacetate was prepared in a similar manner as described herein from 3-{[3-aminomethyl)-6-chloro-2-fluorophenyl]oxy}-5-chlorobenzonitrile (0.065 g, 0.20 mmol), 3-bromo-1H-indole-2-carboxylic acid (0.040 g, 0.16 mmol), HATU (0.080 g, 0.20 mmol), DIPEA (0.040 mL, 0.20 mmol) and DMF (2 mL). Purification was accomplished by Reverse-Phase HPLC (water/acetonitrile with 0.1% TFA). The desired fractions were lyophilized to afford the title compound (0.046 g, 44%) as a white solid. ¹H NMR (400 MHz, DMSO-d₆): δ ppm 12.03 (s, 1H), 8.55 (t, 1H), 7.82 (d, 1H), 7.44-7.55 (m, 6H), 7.30 (t, 1H), 7.18 (t, 1H), 4.63 (d, 2H). MS: m/z 531.9 (M+1).

Step B (alternate procedure): 3-bromo-N-({4-chloro-3-[(3-chloro-5-cyanophenyl)oxy]-2-fluorophenyl}methyl)-1H-indole-2-carboxamide trifluoroacetate Alternatively: 3-bromo-N-({4-chloro-3-[(3-chloro-5-cyanophenyl)oxy]-2-fluorophenyl}methyl)-1H-indole-2-carboxamide trifluoroacetate was prepared in a similar manner as described herein from the hydrolysis of ethyl 3-bromo-1H-indole-2-carboxylate (0.050 g, 0.22 mmol) and powdered lithium hydroxide (0.025 g, 0.96 mmol) in THF:MeOH:water (1:1:1, 1.5 mL) followed by amide coupling with 3-{[3-aminomethyl)-6-chloro-2-fluorophenyl]oxy}-5-chlorobenzonitrile (0.10 g, 0.32 mmol), HATU (0.125 g, 0.32 mmol), DIPEA (0.06 mL, 0.32 mmol) and DMF (1 mL). Purification was accomplished by Reverse-Phase HPLC. The desired fractions were lyophilized to afford the title compound (0.006 g, 11%) as a white solid.

Example 55

3,6-dichloro-N-({4-chloro-3-[(3-chloro-5-cyanophenyl)oxy]-2-fluorophenyl}methyl)-1H-indole-2-carboxamide trifluoroacetate

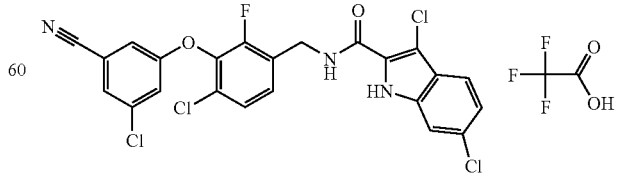

3,6-Dichloro-N-({4-chloro-3-[(3-chloro-5-cyanophenyl)oxy]-2-fluorophenyl}methyl)-1H-indole-2-carboxamide trifluoroacetate was prepared in a similar manner as described herein from the hydrolysis of ethyl 3,6-dichloro-1H-indole-2-carboxylate (0.050 g, 0.19 mmol) and powdered lithium hydroxide (0.025 g, 0.96 mmol) in THF:MeOH:water (1:1:1, 1.5 mL) followed by amide coupling with 3-{[3-aminomethyl)-6-chloro-2-fluorophenyl]oxy}-5-chlorobenzonitrile (0.090 g, 0.29 mmol), HATU (0.110 g, 0.29 mmol), DIPEA (0.050 mL, 0.29 mmol) and DMF (1 mL). Na$_2$SO$_4$, Purification was accomplished by Reverse-Phase HPLC (water/acetonitrile with 0.1% TFA). The desired fractions were lyophilized to afford the title compound (0.003 g, 3%) as a white solid. $^1$H NMR (400 MHz, DMSO-d$_6$): δ ppm 12.09 (br. s., 1H), 8.58 (t, 1H), 7.80 (t, 1H), 7.58 (d, 1H), 7.48-7.53 (m, 2H), 7.46 (d, 2H), 7.41 (t, 1H), 7.18 (dd, 1H), 4.60 (d, 2H). MS: m/z 522.0 (M+1).

Example 56

3-(acetylamino)-N-({4-chloro-3-[(3-chloro-5-cyanophenyl)oxy]-2-fluorophenyl}methyl)-5-(methyloxy)-1H-indole-2-carboxamide trifluoroacetate

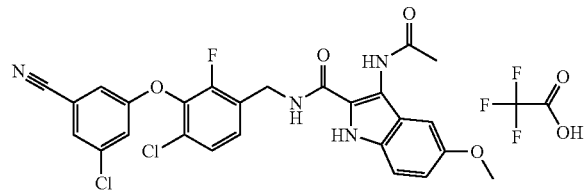

3-(Acetylamino)-N-({4-chloro-3-[(3-chloro-5-cyanophenyl)oxy]-2-fluorophenyl}methyl)-5-(methyloxy)-1H-indole-2-carboxamide trifluoroacetate was prepared in a similar manner as described herein from 3-{[3-aminomethyl)-6-chloro-2-fluorophenyl]oxy}-5-chlorobenzonitrile (0.018 g, 0.058 mmol), 3-(acetylamino)-5-(methyloxy)-1H-indole-2-carboxylic acid (0.024 g, 0.096 mmol), HATU (0.035 g, 0.096 mmol), DIPEA (0.017 mL, 0.096 mmol) and DMF (1 mL). Purification was accomplished by Reverse-Phase HPLC (water/acetonitrile with 0.1% TFA). The desired fractions were lyophilized to afford the title compound (0.006 g, 16%) as a white solid. $^1$H NMR (400 MHz, DMSO-d$_6$): δ ppm 11.34 (br. s., 1H), 9.63 (br. s., 1H), 8.26 (t, 1H), 7.80 (s, 1H), 7.45-7.54 (m, 3H), 7.40 (t, 1H), 7.26 (d, 1H), 6.91 (d, 1H), 6.85 (d, 1H), 4.56 (d, 2H), 3.72 (s, 3H), 2.05 (s, 3H). MS: m/z 541.0 (M+1).

Example 57

N-({4-chloro-3-[(3-chloro-5-cyanophenyl)oxy]-2-fluorophenyl}methyl)-1H-pyrrole-2-carboxamide

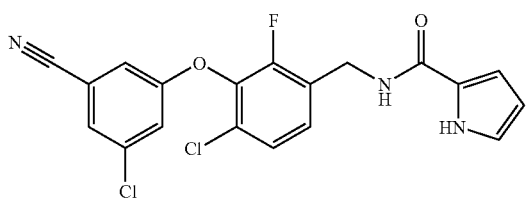

N-({4-chloro-3-[(3-chloro-5-cyanophenyl)oxy]-2-fluorophenyl}methyl)-1H-pyrrole-2-carboxamide was prepared in a similar manner as described herein from 3-{[3-aminomethyl)-6-chloro-2-fluorophenyl]oxy}-5-chlorobenzonitrile (0.025 g, 0.08 mmol), 1H-pyrrole-2-carboxylic acid (0.013 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA). The desired fractions were neutralized with saturated NaHCO$_3$ and extracted with EtOAc (3×5 mL). The organic extracts were combined, dried over Na$_2$SO$_4$, filtered and evaporated to afford the title compound (0.015 g, 46%) as a white solid. $^1$H NMR (400 MHz, DMSO-d$_6$): δ ppm 11.51 (br. s., 1H), 8.57 (t, 1H), 7.82 (s, 1H), 7.43-7.55 (m, 3H), 7.31-7.39 (m, 1H), 6.87 (d, 2H), 6.09 (s, 1H), 4.49 (d, 2H). MS: m/z 404.0 (M+1).

Example 58

N-({4-chloro-3-[(3-chloro-5-cyanophenyl)oxy]-2-fluorophenyl}methyl)-1H-pyrrole-2-carboxamide trifluoroacetate

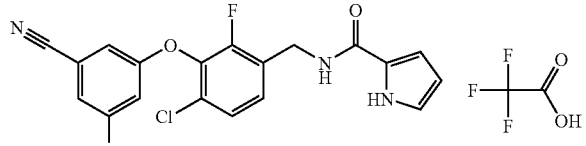

N-({4-Chloro-3-[(3-chloro-5-cyanophenyl)oxy]-2-fluorophenyl}methyl)-1H-pyrrole-2-carboxamide trifluoroacetate was prepared in a similar manner as described herein from 3-{[3-aminomethyl)-6-chloro-2-fluorophenyl]oxy}-5-chlorobenzonitrile (0.018 g, 0.058 mmol), 1H-pyrrole-2-carboxylic acid (0.012 g, 0.096 mmol), HATU (0.035 g, 0.096 mmol), DIPEA (0.017 mL, 0.096 mmol) and DMF (1 mL). Purification was accomplished by Reverse-Phase HPLC (water/acetonitrile with 0.1% TFA) and the desired fractions were lyophilized to afford the title compound (0.0075 g, 25%) as a white solid. $^1$H NMR (400 MHz, DMSO-d$_6$): δ ppm 11.51 (br. s., 1H), 8.56 (t, 1H), 7.83 (t, 1H), 7.50 (m, 3H), 7.35 (t, 1H), 6.86-6.90 (m, 1H), 6.80-6.85 (m, 1H), 5.87-6.17 (m, 1H), 4.49 (d, 2H). MS: m/z 404.0 (M+1).

Example 59

N-({4-chloro-3-[(3-chloro-5-cyanophenyl)oxy]-2-fluorophenyl}methyl)-1H-imidazole-2-carboxamide trifluoroacetate

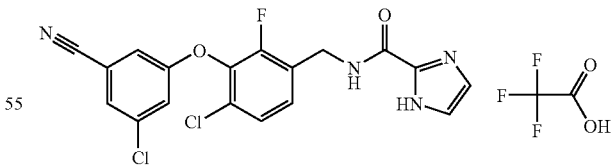

N-({4-Chloro-3-[(3-chloro-5-cyanophenyl)oxy]-2-fluorophenyl}methyl)-1H-imidazole-2-carboxamide trifluoroacetate was prepared in a similar manner as described herein from 3-{[3-aminomethyl)-6-chloro-2-fluorophenyl]oxy}-5-chlorobenzonitrile (0.025 g, 0.08 mmol), 1H-imidazole-2-carboxylic acid (0.015 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA) and the desired fractions were lyophilized to afford the title compound (0.017 g, 60%) as a white solid. ¹H NMR (400 MHz, DMSO-d₆): δ ppm 9.05 (t, 1H), 7.83 (s, 1H), 7.43-7.56 (m, 3H), 7.36 (t, 1H), 7.21 (s, 2H), 4.51 (d, 2H). MS: m/z 404.9 (M+1).

Example 60

N-({4-chloro-3-[(3-chloro-5-cyanophenyl)oxy]-2-fluorophenyl}methyl)-1H-imidazole-2-carboxamide

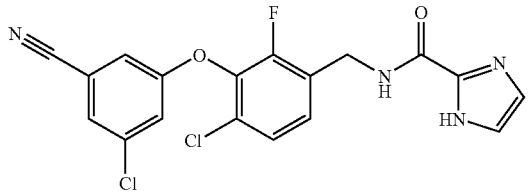

N-({4-Chloro-3-[(3-chloro-5-cyanophenyl)oxy]-2-fluorophenyl}methyl)-1H-imidazole-2-carboxamide was prepared in a similar manner as described herein from 3-{[3-aminomethyl)-6-chloro-2-fluorophenyl]oxy}-5-chlorobenzonitrile (0.025 g, 0.08 mmol), 1H-imidazole-2-carboxylic acid (0.015 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA). The desired fractions were neutralized with saturated NaHCO₃ and extracted with EtOAc (3×5 mL). The organic extracts were combined, dried over Na₂SO₄, filtered and evaporated to afford the title compound (0.020 g, 61%) as a white solid. ¹H NMR (400 MHz, DMSO-d₆): δ ppm 9.01 (s, 1H), 7.79 (s, 1H), 7.42-7.53 (m, 3H), 7.33 (t, 1H), 7.27 (s, 1H), 7.04 (s, 1H), 4.48 (d, 2H). MS: m/z 405.0 (M+1).

Example 61

3-bromo-N-({4-chloro-3-[(3-chloro-5-cyanophenyl)oxy]-2-fluorophenyl}methyl)-6-hydroxy-1H-indole-2-carboxamide trifluoroacetate

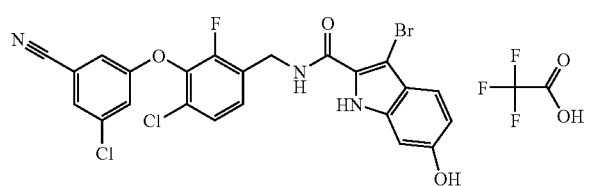

Step A: methyl 3-bromo-6-(methyloxy)-1H-indole-2-carboxylate

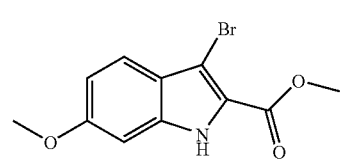

Methyl 6-(methyloxy)-1H-indole-2-carboxylate (0.10 g, 0.49 mmol) was dissolved in DMF (2 mL) then N-bromosuccinimide (0.095 g, 0.53 mmol) added and the reaction stirred for 38 h. The solvent was evaporated and the reaction mixture was purified by column chromatography (hexanes/EtOAc) to afford the title compound (0.075 g, 54%) as a white solid. ¹H NMR (400 MHz, DMSO-d₆): δ 12.08 (s, 1H), 7.41 (d, 1H), 6.82-6.89 (m, 2H), 3.88 (s, 3H), 3.80 (s, 3H). MS: m/z 284.0 (M+1).

Step B: 3-bromo-6-hydroxy-1H-indole-2-carboxylic acid

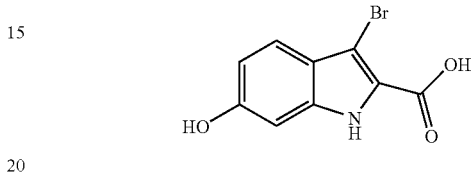

Methyl 3-Bromo-6-(methyloxy)-1H-indole-2-carboxylate (0.075 g, 0.26 mmol) was dissolved in CH₂Cl₂ (5 mL), cooled to 0° C. under nitrogen and BBr₃ (1.0 M in CH₂Cl₂, 1.6 mL, 1.6 mmol) added dropwise. The reaction mixture was allowed to warm to RT and stirred overnight. Ice cold water (1 mL) and EtOAc (5 mL) were added. The layers were separated and the aqueous layer extracted with EtOAc (3×5 mL). The organic extracts were combined, dried over Na₂SO₄, filtered and evaporated. Purification was accomplished by Reverse-Phase HPLC (water/acetonitrile with 0.1% TFA) to afford the title compound (0.005 g, 7%) as a solid. ¹H NMR (400 MHz, DMSO-d₆): δ ppm 13.06 (br. s., 1H), 11.63 (br. s., 1H), 9.55 (s, 1H), 7.30 (d, 1H), 6.78 (d, 1H), 6.70 (dd, 1H). MS: m/z 256.13 (M+1).

Step C: 3-bromo-N-({4-chloro-3-[(3-chloro-5-cyanophenyl)oxy]-2-fluorophenyl}methyl)-6-hydroxy-1H-indole-2-carboxamide trifluoroacetate

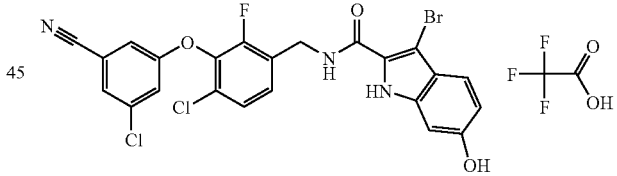

3-Bromo-N-({4-chloro-3-[(3-chloro-5-cyanophenyl)oxy]-2-fluorophenyl}methyl)-6-hydroxy-1H-indole-2-carboxamide trifluoroacetate was prepared in a similar manner as described herein from 3-{[3-aminomethyl)-6-chloro-2-fluorophenyl]oxy}-5-chlorobenzonitrile (0.009 g, 0.029 mmol), 3-bromo-6-hydroxy-1H-indole-2-carboxylic acid (0.005 g, 0.02 mmol), HATU (0.010 g, 0.029 mmol), DIPEA (0.005 mL, 0.029 mmol) and DMF (1 mL). Purification was accomplished by Reverse-Phase HPLC (water/acetonitrile with 0.1% TFA). The desired fractions were lyophilized to afford the title compound (0.009 g, 88%) as a white solid. ¹H NMR (400 MHz, DMSO-d₆): δ ppm 11.57 (s, 1H), 9.47 (br. s., 1H), 8.29 (t, 1H), 7.80 (s, 1H), 7.39-7.51 (m, 4H), 7.25 (d, 1H), 6.76 (d, 1H), 6.68 (dd, 1H), 4.58 (d, 2H). MS: m/z 548.2 (M+1).

Example 62

N-({4-chloro-3-[(3-chloro-5-cyanophenyl)oxy]-2-fluorophenyl}methyl)-3,5-dimethyl-1H-pyrrole-2-carboxamide trifluoroacetate

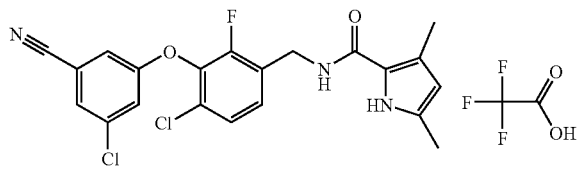

3-{[3-Aminomethyl)-6-chloro-2-fluorophenyl]oxy}-5-chlorobenzonitrile (0.025 g, 0.08 mmol), 3,5-dimethyl-1H-pyrrole-2-carboxylic acid (0.017 g, 0.12 mmol), HATU (0.045 g, 0.12 mmol), DIPEA (0.020 mL, 0.12 mmol) and DMF (1 mL) were added to a flask and the solution was stirred overnight. The solvent was evaporated and the reaction mixture was purified by Reverse-Phase HPLC (water/acetonitrile with 0.1% TFA). The desired fractions were lyophilized to afford the title compound (0.006 g, 17%) as a white solid. $^1$H NMR (400 MHz, DMSO-$d_6$): δ ppm 10.80 (br. s., 1H), 7.83 (s, 1H), 7.68 (t, 1H), 7.46-7.57 (m, 3H), 7.38 (t, 1H), 5.67 (s, 1H), 4.48 (d, 2H), 2.21 (s, 3 H), 2.14 (s, 3H). MS: m/z 432.1 (M+1).

Example 63

N-({4-chloro-3-[(3-chloro-5-cyanophenyl)oxy]-2-fluorophenyl}methyl)-ethyl-1H-pyrrole-2-carboxamide

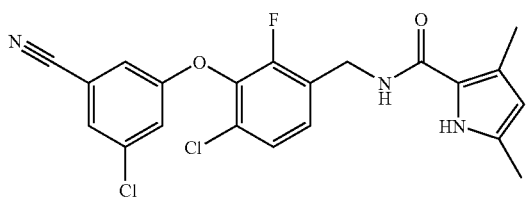

3-{[3-Aminomethyl)-6-chloro-2-fluorophenyl]oxy}-5-chlorobenzonitrile (0.15 g, 0.48 mmol), 3,5-dimethyl-1H-pyrrole-2-carboxylic acid (0.055 g, 0.038 mmol), HATU (0.183 g, 0.48 mmol), DIPEA (0.070 mL, 0.48 mmol) and DMF (5 mL) were added to a flask and the solution was stirred overnight. The solvent was evaporated, saturated NaHCO$_3$ (10 mL) and EtOAc (10 mL) were added. The layers were separated and the aqueous layer was extracted with EtOAc (2×15 mL). The organic extracts were combined, dried over Na$_2$SO$_4$, filtered and evaporated. The reaction mixture was purified by recrystallization from EtOAc to afford the title compound (0.040 g) as a white solid. Purification of the filtrate was accomplished by Reverse-Phase HPLC (water/acetonitrile with 0.1% TFA). The desired fractions were lyophilized to afford N-({4-chloro-3-[(3-chloro-5-cyanophenyl)oxy]-2-fluorophenyl}methyl)-3,5-dimethyl-1H-pyrrole-2-carboxamide trifluoroacetate (0.042 g, 48% combined) as a white solid. $^1$H NMR (400 MHz, DMSO-$d_6$): δ ppm 10.8 (br. s., 1H), 7.82 (t, 1H), 7.67 (t, 1H), 7.43-7.55 (m, 3H), 7.38 (t, 1H), 5.66 (d, 1H), 4.48 (d, 2H), 2.20 (s, 3H), 2.14 (s, 3H). MS: m/z 432.0 (M+1).

Example 64

N-({4-chloro-3-[(3-chloro-5-cyanophenyl)oxy]-2-fluorophenyl}methyl)-1-methyl-1H-imidazole-4-carboxamide trifluoroacetate

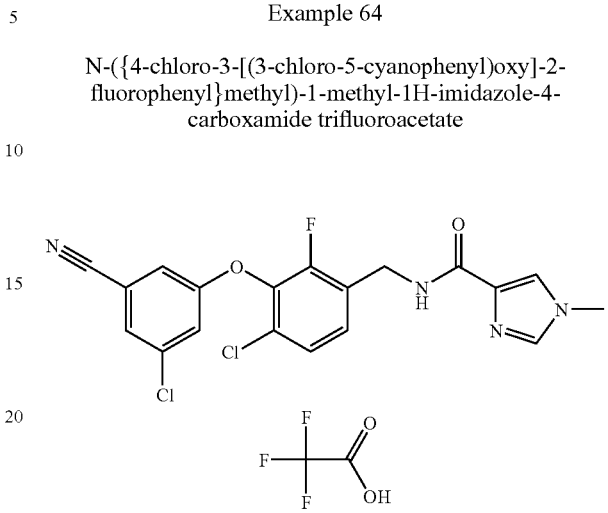

N-({4-Chloro-3-[(3-chloro-5-cyanophenyl)oxy]-2-fluorophenyl}methyl)-1-methyl-1H-imidazole-4-carboxamide trifluoroacetate was prepared in a similar manner as described herein from 3-{[3-aminomethyl)-6-chloro-2-fluorophenyl]oxy}-5-chlorobenzonitrile (0.025 g, 0.08 mmol), 1-methyl-1H-imidazole-4-carboxylic acid (0.015 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA). The desired fractions were lyophilized to afford the title compound (0.030 g, 71%) as a white solid. $^1$H NMR (400 MHz, DMSO-$d_6$): δ ppm 8.90 (t, 1H), 8.29 (s, 1H), 7.84 (d, 2H), 7.45-7.56 (m, 3H), 7.34 (t, 1H), 4.51 (d, 2 H), 3.77 (s, 3H). MS: m/z 419.2 (M+1).

Example 65

N-({4-chloro-3-[(3-chloro-5-cyanophenyl)oxy]-2-fluorophenyl}methyl)-2-(methylthio)-1-(triphenylmethyl)-1H-imidazole-4-carboxamide trifluoroacetate

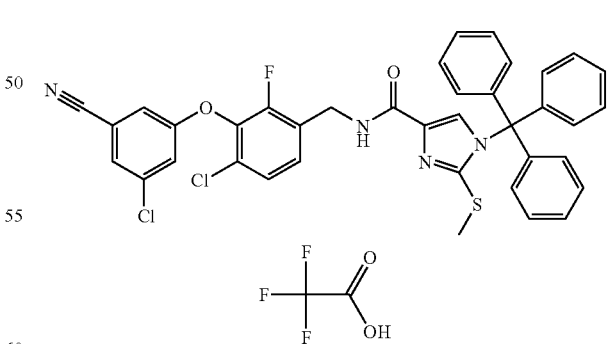

N-({4-Chloro-3-[(3-chloro-5-cyanophenyl)oxy]-2-fluorophenyl}methyl)-2-(methylthio)-1-(triphenylmethyl)-1H-imidazole-4-carboxamide trifluoroacetate was prepared in a similar manner as described herein from 3-{[3-aminomethyl)-6-chloro-2-fluorophenyl]oxy}-5-chlorobenzonitrile (0.025 g, 0.08 mmol), 2-(methylthio)-1-(triphenylmethyl)-

1H-imidazole-4-carboxylic acid (0.050 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA). The desired fractions were lyophilized to afford the title compound (0.035 g, 63%) as a white solid. $^1$H NMR (400 MHz, DMSO-$d_6$): δ ppm 8.60 (t, 1H), 7.79 (s, 1H), 7.70 (s, 1H), 7.42-7.53 (m, 2H), 7.11-7.36 (m, 17H), 4.45 (d, 2H), 2.56 (s, 3H). MS: m/z 449.2 (M−243).

Example 66

N-({4-chloro-3-[(3-chloro-5-cyanophenyl)oxy]-2-fluorophenyl}methyl)-2-(methylthio)-1H-imidazole-4-carboxamide trifluoroacetate

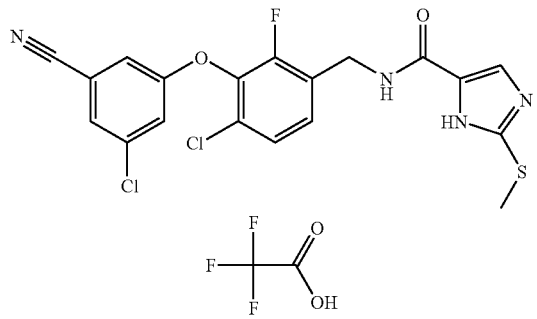

N-({4-chloro-3-[(3-chloro-5-cyanophenyl)oxy]-2-fluorophenyl}methyl)-2-(methylthio)-1-(triphenylmethyl)-1H-imidazole-4-carboxamide trifluoroacetate (0.030 g, 0.04 mmol) was dissolved in CH$_2$Cl$_2$ (2 mL) and trifluoroacetic acid (2 mL) and stirred for 2 h. The solvent was evaporated. Purification was accomplished by Reverse-Phase HPLC (water/acetonitrile with 0.1% TFA). The desired fractions were lyophilized to afford the title compound (0.017 g, 70%) as a white solid. $^1$H NMR (400 MHz, DMSO-$d_6$): δ ppm 8.57 (t, 1H), 7.79 (s, 1H), 7.68 (s, 1H), 7.43-7.52 (m, 3H), 7.30 (t, 1H), 4.45 (d, 2H), 2.55 (s, 3H). MS: m/z 451.0 (M+1).

Example 67

N-({4-chloro-3-[(3-chloro-5-cyanophenyl)oxy]-2-fluorophenyl}methyl)-1-methyl-1H-imidazole-5-carboxamide trifluoroacetate

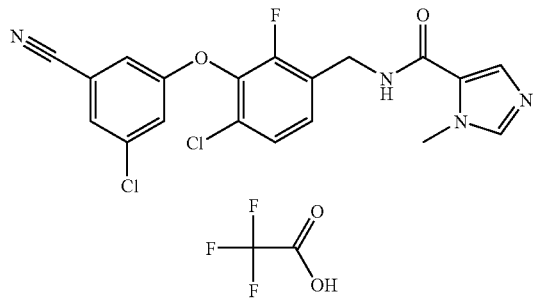

N-({4-Chloro-3-[(3-chloro-5-cyanophenyl)oxy]-2-fluorophenyl}methyl)-1-methyl-1H-imidazole-5-carboxamide trifluoroacetate was prepared in a similar manner as described herein from 3-{[3-aminomethyl)-6-chloro-2-fluo-rophenyl]oxy}-5-chlorobenzonitrile (0.025 g, 0.08 mmol), 1-methyl-1H-imidazole-5-carboxylic acid (0.015 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA). The desired fractions were lyophilized to afford the title compound (0.035 g, 83%) as a white solid. $^1$H NMR (400 MHz, DMSO-$d_6$): δ ppm 9.13 (t, 1H), 8.62 (br. s., 1H), 7.95 (s, 1H), 7.81 (s, 1H), 7.43-7.52 (m, 3H), 7.38 (t, 1H), 4.48 (d, 2H), 3.90 (s, 3H). MS: m/z 419.0 (M+1).

Example 68

N-({4-chloro-3-[(3-chloro-5-cyanophenyl)oxy]-2-fluorophenyl}methyl)-4-nitro-1H-imidazole-5-carboxamide trifluoroacetate

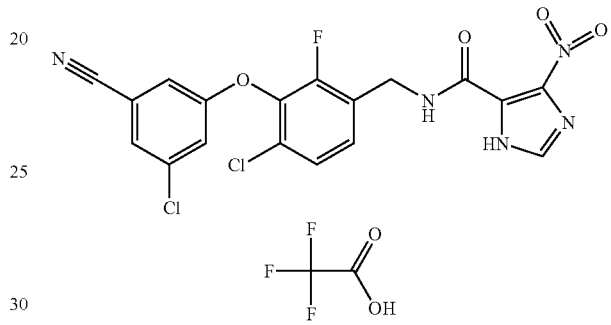

N-({4-Chloro-3-[(3-chloro-5-cyanophenyl)oxy]-2-fluorophenyl}methyl)-4-nitro-1H-imidazole-5-carboxamide trifluoroacetate was prepared in a similar manner as described herein from 3-{[3-aminomethyl)-6-chloro-2-fluorophenyl]oxy}-5-chlorobenzonitrile (0.025 g, 0.08 mmol), 4-nitro-1H-imidazole-5-carboxylic acid (0.019 g, 0.12 mmol), HATU (0.045 g, 0.12 mmol), DIPEA (0.020 mL, 0.12 mmol) and DMF. Purification was accomplished by Reverse-Phase HPLC (water/acetonitrile with 0.1% TFA). The desired fractions were lyophilized to afford the title compound (0.0065 g, 14%) as a white solid. $^1$H NMR (400 MHz, DMSO-$d_6$): δ 9.32 (t, 1H), 7.86 (s, 1H), 7.80 (s, 1H), 7.42-7.53 (m, 4H), 4.54 (d, 2H)). MS: m/z 450.0 (M+1).

Example 69

4-bromo-N-({4-chloro-3-[(3-chloro-5-cyanophenyl)oxy]-2-fluorophenyl}methyl)-5-nitro-1H-pyrazole-3-carboxamide trifluoroacetate

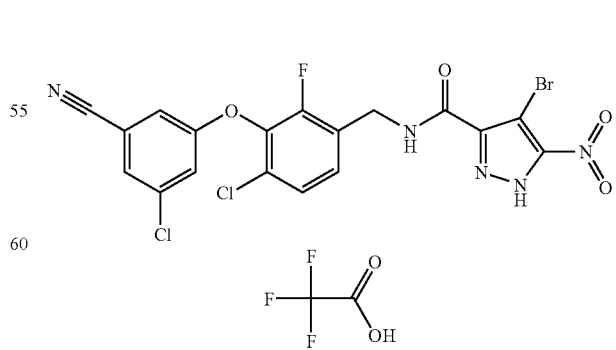

4-Bromo-N-({4-chloro-3-[(3-chloro-5-cyanophenyl)oxy]-2-fluorophenyl}methyl)-5-nitro-1H-pyrazole-3-carboxamide trifluoroacetate was prepared in a similar manner as described herein from 3-{[3-aminomethyl)-6-chloro-2-fluorophenyl]oxy}-5-chlorobenzonitrile (0.025 g, 0.08 mmol), 4-bromo-5-nitro-1H-pyrazole-3-carboxylic acid (0.028 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA). The desired fractions were lyophilized to afford the title compound (0.023 g, 44%) as a white solid. $^1$H NMR (400 MHz, DMSO-$d_6$): δ ppm 9.02 (t, 1H), 7.80 (s, 1H), 7.47-7.55 (m, 2H), 7.37-7.47 (m, 2H), 4.55 (d, 2H). MS: m/z 528.2 (M+1).

Example 70

N-({4-chloro-3-[(3-chloro-5-cyanophenyl)oxy]-2-fluorophenyl}methyl)-4-nitro-1H-pyrrole-2-carboxamide trifluoroacetate

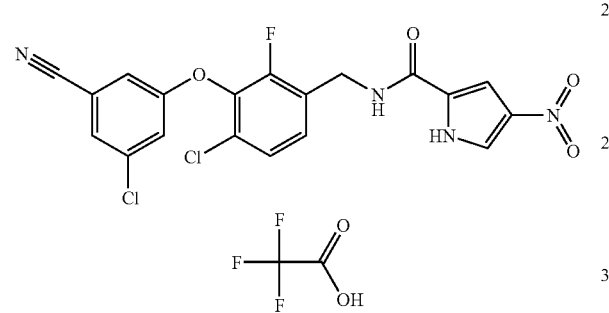

N-({4-Chloro-3-[(3-chloro-5-cyanophenyl)oxy]-2-fluorophenyl}methyl)-4-nitro-1H-pyrrole-2-carboxamide trifluoroacetate was prepared in a similar manner as described herein from 3-{[3-aminomethyl)-6-chloro-2-fluorophenyl]oxy}-5-chlorobenzonitrile (0.025 g, 0.08 mmol), 4-nitro-1H-pyrrole-2-carboxylic acid (0.028 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA). The desired fractions were lyophilized to afford the title compound (0.003 g, 8%) as a tan solid. $^1$H NMR (400 MHz, DMSO-$d_6$): δ 8.99 (t, 1H), 7.94 (dd, 1H), 7.82 (s, 1H), 7.50 (m, 4H), 7.39 (t, 1H), 4.51 (d, 2H). MS: m/z 447.4 (M−1).

Example 71

N-({4-chloro-3-[(3-chloro-5-cyanophenyl)oxy]-2-fluorophenyl}methyl)-4-cyano-3,5-dimethyl-1H-pyrrole-2-carboxamide trifluoroacetate

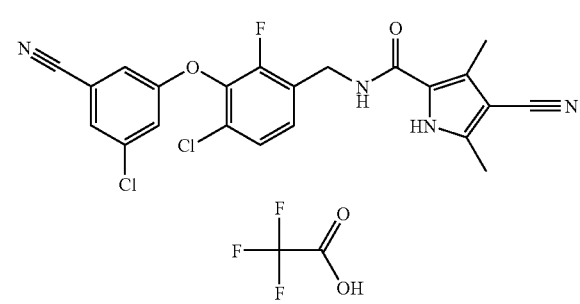

N-({4-Chloro-3-[(3-chloro-5-cyanophenyl)oxy]-2-fluorophenyl}methyl)-4-cyano-3,5-dimethyl-1H-pyrrole-2-carboxamide trifluoroacetate was prepared in a similar manner as described herein from 3-{[3-aminomethyl)-6-chloro-2-fluorophenyl]oxy}-5-chlorobenzonitrile (0.025 g, 0.08 mmol), 4-cyano-3,5-dimethyl-1H-pyrrole-2-carboxylic acid (0.020 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA). The desired fractions were lyophilized to afford the title compound (0.015 g, 41%) as a white solid. $^1$H NMR (400 MHz, DMSO-$d_6$): δ ppm 11.87 (br. s., 1H), 8.07 (t, 1H), 7.83 (s, 1H), 7.47-7.53 (m, 3H), 7.39 (t, 1H), 4.50 (d, 2H), 2.29 (d, 6H). MS: m/z 457.2 (M+1).

Example 72

N-({4-chloro-3-[(3-chloro-5-cyanophenyl)oxy]-2-fluorophenyl}methyl)-1-methyl-1H-imidazole-2-carboxamide trifluoroacetate

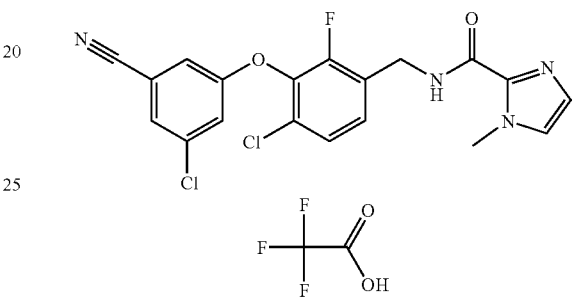

N-({4-Chloro-3-[(3-chloro-5-cyanophenyl)oxy]-2-fluorophenyl}methyl)-1-methyl-1H-imidazole-2-carboxamide trifluoroacetate was prepared in a similar manner as described herein from 3-{[3-aminomethyl)-6-chloro-2-fluorophenyl]oxy}-5-chlorobenzonitrile (0.025 g, 0.08 mmol), 1-methyl-1H-imidazole-2-carboxylic acid (0.015 g, 0.12 mmol), HATU (0.045 g, 0.12 mmol), DIPEA (0.020 mL, 0.12 mmol) and DMF (1 mL). Purification was accomplished by Reverse-Phase HPLC (water/acetonitrile with 0.1% TFA). The desired fractions were lyophilized to afford the title compound (0.028 g, 65%, 80% pure) as a white solid. $^1$H NMR (400 MHz, DMSO-$d_6$): δ ppm 9.05 (t, 1H), 7.79 (s, 1H), 7.61 (d, 1H), 7.43-7.55 (m, 2H), 7.30-7.41 (m, 2H), 7.01 (s, 1H), 4.44 (d, 2H), 3.91 (s, 3H). MS: m/z 419.2 (M+1).

Example 73

4-bromo-N-({4-chloro-3-[(3-chloro-5-cyanophenyl)oxy]-2-fluorophenyl}methyl)-5-(methyloxy)-1H-indole-2-carboxamide trifluoroacetate

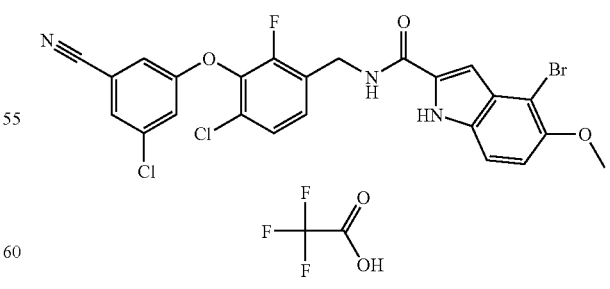

4-Bromo-N-({4-chloro-3-[(3-chloro-5-cyanophenyl)oxy]-2-fluorophenyl}methyl)-5-(methyloxy)-1H-indole-2-carboxamide trifluoroacetate was prepared in a similar manner as described herein from 3-{[3-aminomethyl)-6-chloro-2-fluorophenyl]oxy}-5-chlorobenzonitrile (0.040 g, 0.13 mmol), 4-bromo-5-(methyloxy)-1H-indole-2-carboxylic acid (0.023 g, 0.08 mmol), HATU (0.050 g, 0.13 mmol), DIPEA (0.022 mL, 0.13 mmol) and DMF (1 mL). Purification was accomplished by Reverse-Phase HPLC (water/acetonitrile with 0.1% TFA). The desired fractions were lyophilized to afford the title compound (0.016 g, 33%) as a white solid. $^1$H NMR (400 MHz, DMSO-$d_6$): δ ppm 11.81 (s, 1H), 9.15 (t, 1H), 7.80 (s, 1H), 7.45-7.52 (m, 3H), 7.35-7.41 (m, 2H), 7.02-7.16 (m, 2H), 4.53 (d, 2H), 3.81 (s, 3H). MS: m/z 562.0 (M+1).

Example 74

6-[(acetylamino)methyl]-N-({4-chloro-3-[(3-chloro-5-cyanophenyl)oxy]-2-fluorophenyl}methyl)-1H-indole-2-carboxamide trifluoroacetate

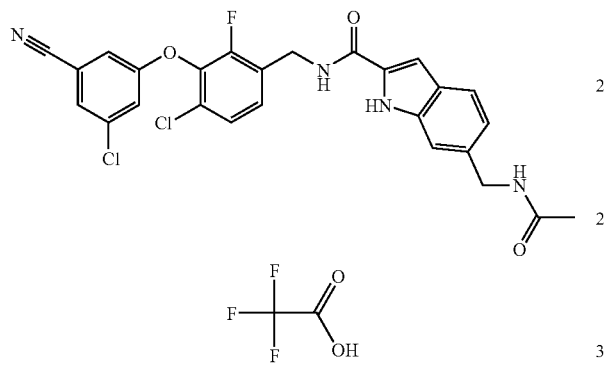

6-[(Acetylamino)methyl]-N-({4-chloro-3-[(3-chloro-5-cyanophenyl)oxy]-2-fluorophenyl}methyl)-1H-indole-2-carboxamide trifluoroacetate was prepared in a similar manner as described herein from 3-{[3-aminomethyl)-6-chloro-2-fluorophenyl]oxy}-5-chlorobenzonitrile (0.046 g, 0.15 mmol), 6-[(acetylamino)methyl]-1H-indole-2-carboxylic acid (0.023 g, 0.10 mmol), HATU (0.056 g, 0.15 mmol), DIPEA (0.026 mL, 0.15 mmol) and DMF (1 mL). Purification was accomplished by Reverse-Phase HPLC (water/acetonitrile with 0.1% TFA). The desired fractions were lyophilized to afford the title compound (0.033 g, 63%) as a white solid. $^1$H NMR (400 MHz, DMSO-$d_6$): δ ppm 11.59 (br. s., 1H), 9.01 (t, 1H), 8.35 (t, 1H), 7.83 (s, 1H), 7.47-7.59 (m, 4H), 7.41 (t, 1H), 7.30 (s, 1H), 7.15 (d, 1H), 6.95 (d, 1H), 4.57 (d, 2 H), 4.31 (d, 2H), 1.86 (s, 3H). MS: m/z 525.1 (M+1).

Example 75

3-chloro-N-({4-chloro-3-[(3-chloro-5-cyanophenyl)oxy]-2-fluorophenyl}methyl)-1H-indole-2-carboxamide trifluoroacetate

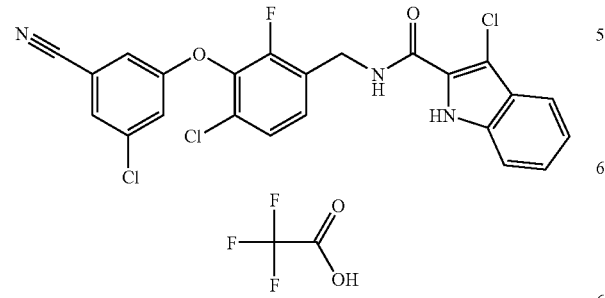

3-Chloro-N-({4-chloro-3-[(3-chloro-5-cyanophenyl)oxy]-2-fluorophenyl}methyl)-1H-indole-2-carboxamide trifluoroacetate was prepared in a similar manner as described herein from 3-{[3-aminomethyl)-6-chloro-2-fluorophenyl]oxy}-5-chlorobenzonitrile (0.057 g, 0.18 mmol), 3-chloro-1H-indole-2-carboxylic acid (0.024 g, 0.18 mmol), HATU (0.070 g, 0.18 mmol), DIPEA (0.032 mL, 0.18 mmol) and DMF (1 mL). Purification was accomplished by Reverse-Phase HPLC (water/acetonitrile with 0.1% TFA). The desired fractions were lyophilized to afford the title compound (0.015 g, 25%) as a white solid. $^1$H NMR (400 MHz, DMSO-$d_6$): δ ppm 11.93 (br. s., 1H), 8.52 (t, 1H), 7.80 (s, 1H), 7.55 (d, 1H), 7.48-7.53 (m, 2H), 7.37-7.48 (m, 3H), 7.28 (t, 1H), 7.15 (t, 1H), 4.61 (d, 2H). MS: m/z 487.9 (M+1).

Example 76

N-({4-chloro-3-[(3-chloro-5-cyanophenyl)oxy]-2-fluorophenyl}methyl)-4-[(diethylamino)sulfonyl]-1H-pyrrole-2-carboxamide trifluoroacetate

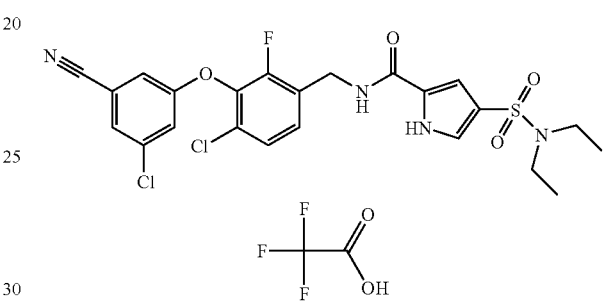

N-({4-Chloro-3-[(3-chloro-5-cyanophenyl)oxy]-2-fluorophenyl}methyl)-4-[(diethylamino)sulfonyl]-pyrrole-2-carboxamide trifluoroacetate was prepared in a similar manner as described herein from 3-{[3-aminomethyl)-6-chloro-2-fluorophenyl]oxy}-5-chlorobenzonitrile (0.050 g, 0.16 mmol), 4-[(diethylamino)sulfonyl]-1H-pyrrole-2-carboxylic acid (0.026 g, 0.11 mmol), HATU (0.060 g, 0.16 mmol), DIPEA (0.028 mL, 0.16 mmol) and DMF (1 mL). Purification was accomplished by Reverse-Phase HPLC (water/acetonitrile with 0.1% TFA). The desired fractions were lyophilized to afford the title compound (0.032 g, 56%) as a white solid. $^1$H NMR (400 MHz, DMSO-$d_6$): δ ppm 12.35 (br. s., 1H), 8.81 (t, 1H), 7.80 (s, 1H), 7.43-7.53 (m, 3H), 7.32 (d, 1H), 7.35 (t, 1H), 7.13 (s, 1H), 4.47 (d, 2 H), 3.02 (q, 4H), 1.04 (t, 6H). MS: m/z 539.1 (M+1).

Example 77

4-chloro-N-({4-chloro-3-[(3-chloro-5-cyanophenyl)oxy]-2-fluorophenyl}methyl)-2-ethyl-1H-imidazole-5-carboxamide trifluoroacetate

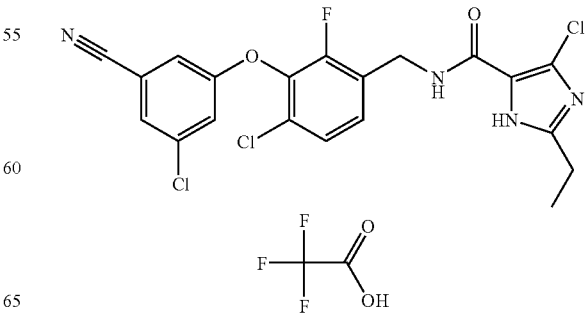

4-Chloro-N-({4-chloro-3-[(3-chloro-5-cyanophenyl)oxy]-2-fluorophenyl}methyl)-2-ethyl-1H-imidazole-5-carboxamide trifluoroacetate was prepared in a similar manner as described herein from 3-{[3-aminomethyl)-6-chloro-2-fluorophenyl]oxy}-5-chlorobenzonitrile (0.066 g, 0.21 mmol), 4-chloro-2-ethyl-1H-imidazole-5-carboxylic acid (0.025 g, 0.14 mmol), HATU (0.060 g, 0.21 mmol), DIPEA (0.040 mL, 0.21 mmol) and DMF (1 mL). Purification was accomplished by Reverse-Phase HPLC (water/acetonitrile with 0.1% TFA). The desired fractions were lyophilized to afford the title compound (0.070 g, 84%) as a white solid. $^1$H NMR (400 MHz, DMSO-$d_6$): δ ppm 8.15 (t, 1H), 7.83 (s, 1H), 7.45-7.53 (m, 3H), 7.36 (t, 1H), 4.53 (d, 2H), 2.60 (q, 2 H), 1.18 (t, 3H). MS: m/z 467.0 (M+1).

Example 78

6-acetyl-N-({4-chloro-3-[(3-chloro-5-cyanophenyl)oxy]-2-fluorophenyl}methyl)-1H-indole-2-carboxamide trifluoroacetate

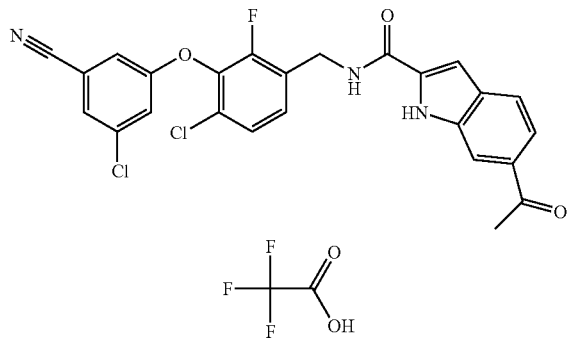

6-Acetyl-N-({4-chloro-3-[(3-chloro-5-cyanophenyl)oxy]-2-fluorophenyl}methyl)-1H-indole-2-carboxamide trifluoroacetate was prepared in a similar manner as described herein from 3-{[3-aminomethyl)-6-chloro-2-fluorophenyl]oxy}-5-chlorobenzonitrile (0.032 g, 0.10 mmol), 6-acetyl-1H-indole-2-carboxylic acid (0.014 g, 0.07 mmol), HATU (0.040 g, 0.10 mmol), DIPEA (0.018 mL, 0.10 mmol) and DMF (1 mL). Purification was accomplished by Reverse-Phase HPLC (water/acetonitrile with 0.1% TFA). The desired fractions were lyophilized to afford the title compound (0.029 g, 85%) as a white solid. $^1$H NMR (400 MHz, DMSO-$d_6$): δ ppm 2.05 (br. s., 1H), 9.18 (t, 1H), 8.03 (s, 1H), 7.80 (s, 1H), 7.56-7.76 (m, 3H), 7.44-7.55 (m, 2H), 7.38 (t, 1H), 7.23 (s, 1H), 4.57 (d, 2H), 2.58 (s, 3H). MS: m/z 496.1 (M+1).

Example 79

N-({4-chloro-3-[(3-chloro-5-cyanophenyl)oxy]-2-fluorophenyl}methyl)-6-cyano-1H-indole-2-carboxamide trifluoroacetate

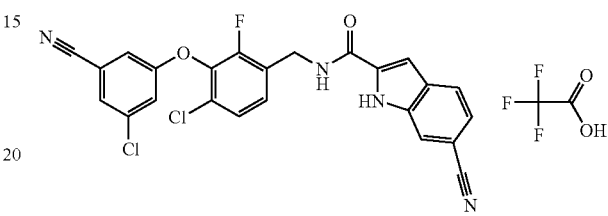

N-({4-Chloro-3-[(3-chloro-5-cyanophenyl)oxy]-2-fluorophenyl}methyl)-6-cyano-1H-indole-2-carboxamide trifluoroacetate was prepared in a similar manner as described herein from 3-{[3-aminomethyl)-6-chloro-2-fluorophenyl]oxy}-5-chlorobenzonitrile (0.032 g, 0.10 mmol), 6-cyano-1H-indole-2-carboxylic acid (0.013 g, 0.07 mmol), HATU (0.040 g, 0.10 mmol), DIPEA (0.019 mL, 0.10 mmol) and DMF (1 mL). Purification was accomplished by Reverse-Phase HPLC (water/acetonitrile with 0.1% TFA). The desired fractions were lyophilized to afford the title compound (0.020 g, 60%) as a white solid. $^1$H NMR (400 MHz, DMSO-$d_6$): δ ppm 12.22 (br. s., 1H), 9.27 (t, 1H), 7.86 (s, 2H), 7.80-7.85 (m, 1H), 7.47-7.58 (m, 3H), 7.35-7.47 (m, 2 H), 7.31 (s, 1H), 4.60 (d, 2H). MS: m/z 478.9 (M+1).

Example 80

5-acetyl-N-({4-chloro-3-[(3-chloro-5-cyanophenyl)oxy]-2-fluorophenyl}methyl)-1H-indole-2-carboxamide trifluoroacetate

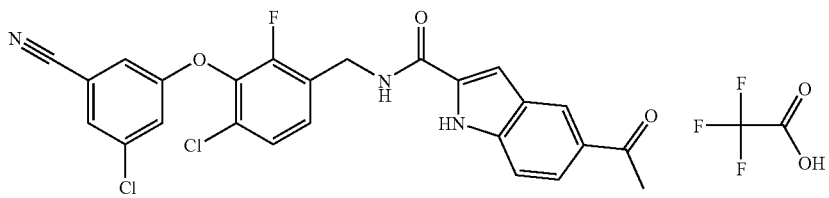

5-Acetyl-N-({4-chloro-3-[(3-chloro-5-cyanophenyl)oxy]-2-fluorophenyl}methyl)-1H-indole-2-carboxamide trifluoroacetate was prepared in a similar manner as described herein from 3-{[3-aminomethyl)-6-chloro-2-fluorophenyl]oxy}-5-chlorobenzonitrile (0.034 g, 0.11 mmol), 5-acetyl-1H-indole-2-carboxylic acid (0.015 g, 0.07 mmol), HATU (0.042 g, 0.11 mmol), DIPEA (0.020 mL, 0.11 mmol) and DMF (1 mL). Purification was accomplished by Reverse-Phase HPLC (water/acetonitrile with 0.1% TFA). The desired fractions were lyophilized to afford the title compound (0.025 g, 68%) as a white solid. $^1$H NMR (400 MHz, DMSO-$d_6$): δ ppm 12.00 (br. s., 1H), 9.16 (t, 1H), 8.36 (s, 1H), 7.75-7.82 (m, 2H), 7.51 (s, 2H), 7.47 (t, 2H), 7.39 (t, 1H), 7.33 (d, 1H), 4.56 (d, 2H), 2.58 (s, 3H). MS: m/z 496.1 (M+1).

Example 81

N-({4-chloro-3-[(3-chloro-5-cyanophenyl)oxy]-2-fluorophenyl}methyl)-3-ethyl-5-(methyloxy)-1H-indole-2-carboxamide trifluoroacetate

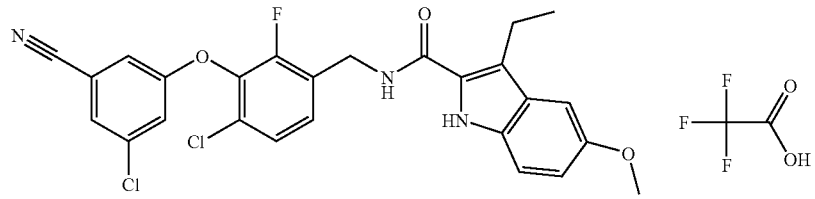

N-({4-Chloro-3-[(3-chloro-5-cyanophenyl)oxy]-2-fluorophenyl}methyl)-3-ethyl-5-(methyloxy)-1H-indole-2-carboxamide trifluoroacetate was prepared in a similar manner as described herein from 3-{[3-aminomethyl)-6-chloro-2-fluorophenyl]oxy}-5-chlorobenzonitrile (0.050 g, 0.17 mmol), 3-ethyl-5-(methyloxy)-1H-indole-2-carboxylic acid (0.025 g, 0.11 mmol), HATU (0.065 g, 0.17 mmol), DIPEA (0.030 mL, 0.17 mmol) and DMF (1 mL). Purification was accomplished by Reverse-Phase HPLC (water/acetonitrile with 0.1% TFA). The desired fractions were lyophilized to afford the title compound (0.023 g, 39%) as a white solid. $^1$H NMR (400 MHz, DMSO-$d_6$): δ ppm 10.99 (br. s., 1H), 8.40 (t, 1H), 7.83 (s, 1H), 7.43-7.55 (m, 4H), 7.29 (d, 1H), 7.05 (d, 1H), 6.86 (dd, 1H), 4.56 (d, 2H), 3.78 (s, 3H), 3.01 (q, 2H), 1.15 (t, 3H). MS: m/z 512.0 (M+1).

Example 82

N-({4-chloro-3-[(3-chloro-5-cyanophenyl)oxy]-2-fluorophenyl}methyl)-7-(methyloxy)-1H-pyrrolo[2,3-d]pyridazine-2-carboxamide 5-oxide trifluoroacetate

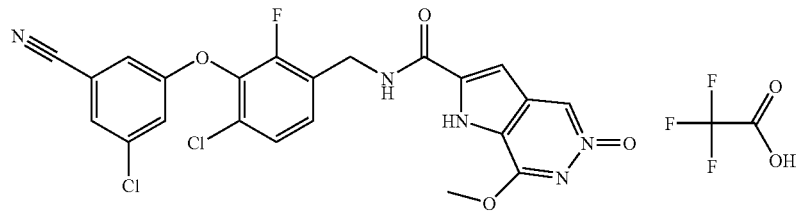

N-({4-Chloro-3-[(3-chloro-5-cyanophenyl)oxy]-2-fluorophenyl}methyl)-7-(methyloxy)-1H-pyrrolo[2,3-d]pyridazine-2-carboxamide 5-oxide trifluoroacetate was prepared in a similar manner as described herein from 3-{[3-aminomethyl)-6-chloro-2-fluorophenyl]oxy}-5-chlorobenzonitrile (0.018 g, 0.058 mmol), 7-(methyloxy)-1H-pyrrolo[2,3-d]pyridazine-2-carboxylic acid 5-oxide (0.018 g, 0.096 mmol), HATU (0.035 g, 0.096 mmol), DIPEA (0.017 mL, 0.096 mmol) and DMF (1 mL). Purification was accomplished by Reverse-Phase HPLC (water/acetonitrile with 0.1% TFA). The desired fractions were lyophilized to afford the title compound (0.003 g, 8%) as a white solid. $^1$H NMR (400 MHz, DMSO-$d_6$): δ ppm 9.34 (t, 1H), 8.66-8.94 (m, 2H), 7.64 (dd, 1H), 7.58 (d, 1H), 7.49-7.55 (m, 2H), 7.42-7.49 (m, 2H), 4.60 (d, 2H), 3.98 (s, 3H). MS: m/z 500.9 (M).

Example 83

N-({4-chloro-3-[(3-chloro-5-cyanophenyl)oxy]-2-fluorophenyl}methyl)-1-(triphenylmethyl)-1H-imidazole-4-carboxamide

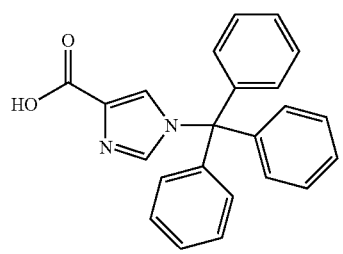

Step A: 1-(Triphenylmethyl)-1H-imidazole-4-carboxylic acid 1-(Triphenylmethyl)-1H-imidazole-4-carboxylic acid was prepared as described in *J. Med. Chem.* 2001, 44, 1268. 1H-Imidazole-4-carboxylic acid (0.50 g, 4.5 mmol) and trityl chloride (1.35 g, 4.9 mmol) were added to a solution of DMF (30 mL) and pyridine (15 mL) and stirred overnight. Water and EtOAc were added. The layers were separated and the aqueous layer extracted with EtOAc (2×50 mL). The organic extracts were combined, washed with water and brine, dried over Na$_2$SO$_4$, filtered and evaporated. The oil was triturated with EtOAc to afford the title compound (1.5 g, 95%) as a white solid. $^1$H NMR (400 MHz, DMSO-d$_6$): δ ppm 12.40 (br. s., 1H), 7.42 (t, 9H), 7.17-7.35 (m, 2H), 7.10 (d, 6H). MS: m/z 111 (M−243).

Step B: N-({4-chloro-3-[(3-chloro-5-cyanophenyl)oxy]-2-fluorophenyl}methyl)-1-(triphenylmethyl)-1H-imidazole-4-carboxamide

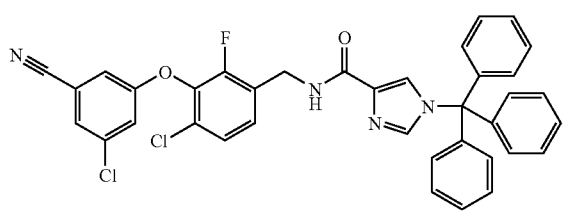

3-{[3-Aminomethyl)-6-chloro-2-fluorophenyl]oxy}-5-chlorobenzonitrile (0.100 g, 0.30 mmol), 1-(triphenylmethyl)-1H-imidazole-4-carboxylic acid (0.140 g, 0.40 mmol), HATU (0.150 g, 0.40 mmol) and DIPEA (0.070 mL, 0.40 mmol) were dissolved in DMF (5 mL) and stirred overnight. The solvent was evaporated. Water and EtOAc were added. The layers were separated and the aqueous layer extracted with EtOAc. The organic extracts were combined, dried over Na$_2$SO$_4$, filtered and evaporated. Purification was accomplished by column chromatography (hexane/EtOAc) to afford the title compound (0.150 g, 72%) as a white solid. $^1$H NMR (400 MHz, DMSO-d$_6$): δ ppm 8.70 (s, 1H), 7.81 (t, 1H), 7.55 (d, 1H), 7.40-7.51 (m, 12H), 7.30-7.36 (m, 2 H), 7.12 (dd, 6H), 4.45 (d, 2H). MS: m/z 649.2 (M+1).

Example 84

N-({4-chloro-3-[(3-chloro-5-cyanophenyl)oxy]-2-fluorophenyl}methyl)-1H-imidazole-4-carboxamide trifluoroacetate

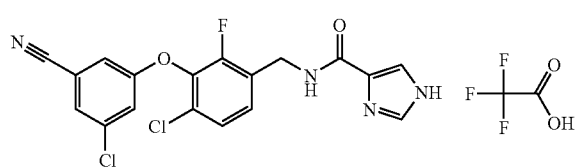

N-({4-Chloro-3-[(3-chloro-5-cyanophenyl)oxy]-2-fluorophenyl}methyl)-1-(triphenylmethyl)-1H-imidazole-4-carboxamide (0.145 g, 0.22 mmol) was dissolved in CH$_2$Cl$_2$ (3 mL) and TFA (3 mL) added. The solution was stirred for 2.5 h. The solvent was evaporated. Purification was accomplished by Reverse-Phase HPLC (water/acetonitrile with 0.1% TFA) to afford the title compound (0.070 g, 60%) as a white solid. $^1$H NMR (400 MHz, DMSO-d$_6$): δ ppm 9.01 (br. s., 1H), 8.53 (br. s., 1H), 7.94 (s, 1H), 7.83 (s, 1H), 7.45-7.54 (m, 4H), 7.38 (t, 1H), 4.54 (d, 2H). MS: m/z 405.0 (M+1).

Example 85

N-({4-chloro-3-[(3-chloro-5-cyanophenyl)oxy]-2-fluorophenyl}methyl)-2

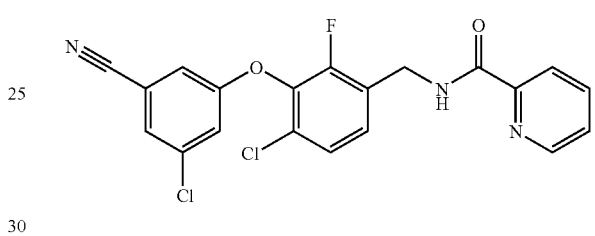

To a solution of 3-{[3-(aminomethyl)-6-chloro-2-fluorophenyl]oxy}-5-chlorobenzonitrile (25.0 mg, 0.080 mmol) and 2-pyridinecarboxylic acid (9.89 mg, 0.080 mmol) in DMF (1 mL) was added HATU (30.6 mg, 0.080 mmol). The reaction mixture was stirred at RT for 1 h. DIPEA (0.014 mL, 0.080 mmol) was added and the solution was stirred overnight. The reaction mixture was diluted to 2 mL with MeOH. Purification was accomplished by Reverse-Phase HPLC (water/acetonitrile with 0.1% TFA) to afford the title compound (0.017 g, 39.0%) as a white solid. $^1$H NMR (400 MHz, Acetone-d$_6$): δ ppm 8.94 (t, 1H), 8.57-8.65 (m, 1H), 8.10-8.18 (m, 1H), 8.00 (td, 1H), 7.63 (t, 1H), 7.58 (ddd, 1H), 7.35-7.49 (m, 4H), 4.73 (d, 2H). LCMS m/z 415.6 (M+1).

Example 86

N-({4-chloro-3-[(3-chloro-5-cyanophenyl)oxy]-2-fluorophenyl}methyl)-2-(methylthio)-3-pyridinecarboxamide trifluoroacetate

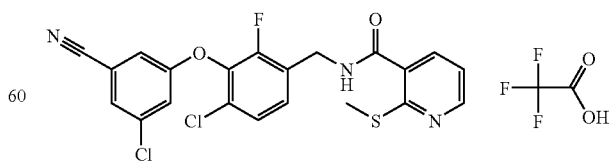

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 2-(methylthio)-3-pyridinecarboxylic acid (13.60 mg, 0.080 mmol) were dissolved in DMF (1 mL). HATU (30.6 mg, 0.080 mmol) was added and the solution was stirred overnight. The reaction mixture was diluted to 2 mL with MeOH. Purification was accomplished by Reverse-Phase HPLC (water/acetonitrile with 0.1% TFA) to afford the title compound (0.021 g, 44%) as a white solid. $^1$H NMR (400 MHz, Acetone-$d_6$): δ ppm 8.51 (dd, 1H), 8.18 (br. s., 1H), 7.84 (dd, 1H), 7.63 (t, 1H), 7.54 (t, 1H), 7.44 (dd, 1H), 7.39-7.41 (m, 1H), 7.37-7.39 (m, 1H), 7.13 (dd, 1H), 4.65 (d, 2H), 2.46 (s, 3H). LCMS m/z 461.9 (M+1).

Example 87

N-({4-chloro-3-[(3-chloro-5-cyanophenyl)oxy]-2-fluorophenyl}methyl)-2-pyrazinecarboxamide trifluoroacetate

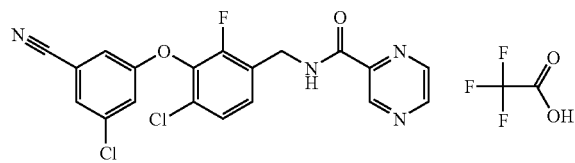

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 2-pyrazinecarboxylic acid (9.97 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.0223 g, 52.2%) as a white solid. $^1$H NMR (400 MHz, Acetone-$d_6$): δ ppm 9.26 (d, 1H), 8.95 (br. s., 1H), 8.83 (d, 1H), 8.64-8.68 (m, 1H), 7.63 (t, 1H), 7.44-7.52 (m, 1H), 7.42 (d, 1H), 7.37-7.41 (m, 2H), 4.75 (d, 2H). LCMS m/z 416.9 (M+1).

Example 88

N-({4-chloro-3-[(3-chloro-5-cyanophenyl)oxy]-2-fluorophenyl}methyl)-2-(4-pyridinyl)-1,3-thiazole-4-carboxamide trifluoroacetate

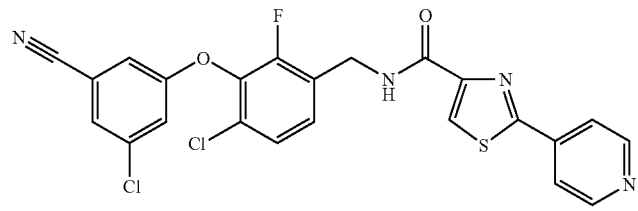

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 2-(4-pyridinyl)-1,3-thiazole-4-carboxylic acid (16.57 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.019 g, 39%) as a white solid. $^1$H NMR (400 MHz, Acetone-$d_6$): δ ppm 9.01 (br. s., 2H), 8.92 (t, 1H), 8.50-8.59 (m, 2H), 8.47 (d, 1H), 7.63 (t, 1H), 7.48 (d, 1H), 7.44 (d, 1H), 7.39-7.42 (m, 1H), 7.37-7.39 (m, 1H), 4.74 (d, 2H). LCMS m/z 499 (M+1).

Example 89

N-({4-chloro-3-[(3-chloro-5-cyanophenyl)oxy]-2-fluorophenyl}methyl)-4-pyridinecarboxamide trifluoroacetate

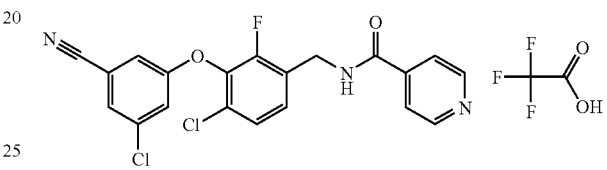

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 4-pyridinecarboxylic acid (9.89 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.011 g, 32%) as a white solid. $^1$H NMR (400 MHz, Acetone-$d_6$): δ ppm 8.95 (d, 2H), 8.83 (br. s., 1H), 8.15 (d, 2H), 7.61-7.67 (m, 1H), 7.49-7.55 (m, 1H), 7.42-7.46 (m, 1H), 7.40 (t, 1H), 7.36-7.39 (m, 1H), 4.73 (d, 2H). LCMS m/z 415.9 (M+1).

Example 90

N-({4-chloro-3-[(3-chloro-5-cyanophenyl)oxy]-2-fluorophenyl}methyl)-1,2,3-thiadiazole-4-carboxamide

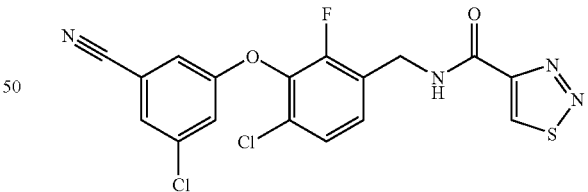

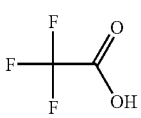

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 1,2,3-thiadiazole-4-carboxylic acid (10.46 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.016 g, 46%) as a white solid. ¹H NMR (400 MHz, Acetone-d₆): δ ppm 9.55 (s, 1H), 8.94 (br. s., 1H), 7.63 (t, 1H), 7.53 (t, 1H), 7.41-7.46 (m, 1H), 7.37-7.41 (m, 2 H), 4.79 (d, 2H). LCMS m/z 422.8 (M+1).

Example 91

N-({4-chloro-3-[(3-chloro-5-cyanophenyl)oxy]-2-fluorophenyl}methyl)-4-methyl-1,2,3-thiadiazole-5-carboxamide

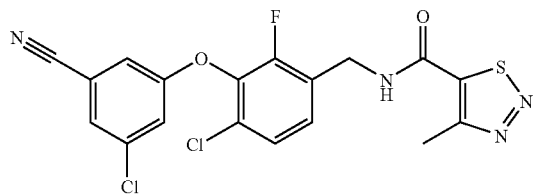

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 4-methyl-1,2,3-thiadiazole-5-carboxylic acid (11.58 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.014 g, 39%) as a white solid. ¹H NMR (400 MHz, Acetone-d₆): δ ppm 8.50 (br. s., 1H), 7.64 (t, 1H), 7.48-7.55 (m, 1H), 7.42-7.46 (m, 1H), 7.36-7.41 (m, 2H), 4.68 (d, 2H), 2.81-2.86 (m, 3H). LCMS m/z 436.8 (M+1).

Example 92

N-({4-chloro-3-[(3-chloro-5-cyanophenyl)oxy]-2-fluorophenyl}methyl)-4-(methylsulfonyl)benzamide

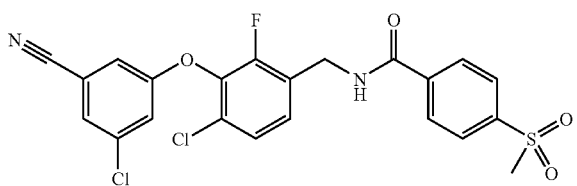

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 4-(methylsulfonyl)benzoic acid (16.09 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.016 g, 39%) as a white solid. ¹H NMR (400 MHz, Acetone-d₆): δ ppm 8.59 (t, 1H), 8.11-8.18 (m, 2H), 8.00-8.07 (m, 2H), 7.63 (t, 1H), 7.47-7.53 (m, 1H), 7.41-7.45 (m, 1H), 7.36-7.41 (m, 2H), 4.70 (d, 2H), 3.16 (s, 3H). LCMS m/z 494.9 (M+1).

Example 93

N-({4-chloro-3-[(3-chloro-5-cyanophenyl)oxy]-2-fluorophenyl}methyl)-5-isoxazolecarboxamide

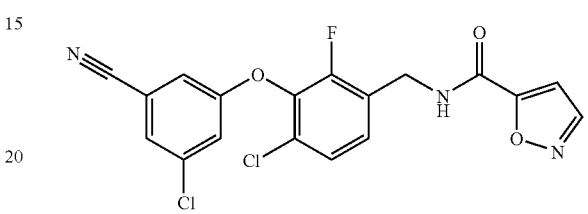

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 5-isoxazolecarboxylic acid (9.09 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.015 g, 46%) as a white solid. ¹H NMR (400 MHz, Acetone-d₆): δ ppm 8.65 (br. s., 1H), 8.57 (d, 1H), 7.63 (t, 1H), 7.46-7.53 (m, 1H), 7.41-7.46 (m, 1H), 7.35-7.41 (m, 2H), 6.99 (d, 1H), 4.69 (d, 2H). LCMS m/z 405.9 (M+1).

Example 94

N-({4-chloro-3-[(3-chloro-5-cyanophenyl)oxy]-2-fluorophenyl}methyl)-3-pyridinecarboxamide trifluoroacetate

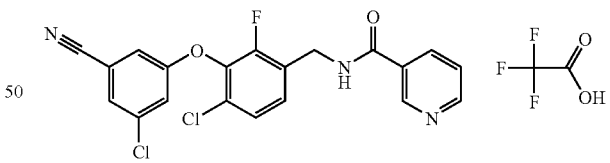

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 3-pyridinecarboxylic acid (9.89 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.022 g, 51%) as a white solid. ¹H NMR (400 MHz, Acetone-d₆): δ ppm 9.23 (br. s., 1H), 8.90 (d, 1H), 8.74 (br. s., 1H), 8.61 (dt, 1H), 7.84 (dd, 1H), 7.63 (t, 1H), 7.53 (t, 1H), 7.40-7.46 (m, 1H), 7.35-7.40 (m, 2H), 4.72 (d, 2H). LCMS m/z 415.9 (M+1).

Example 95

N-({4-chloro-3-[(3-chloro-5-cyanophenyl)oxy]-2-fluorophenyl}methyl)-1H-pyrazole-3-carboxamide

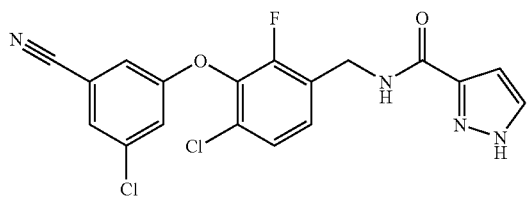

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 1H-pyrazole-3-carboxylic acid (9.01 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.016 g, 50%) as a white solid. $^1$H NMR (400 MHz, Acetone-$d_6$): δ ppm 8.11 (br. s., 1H), 7.79 (d, 1H), 7.62 (t, 1H), 7.36-7.46 (m, 4H), 6.75 (d, 1H), 4.59-4.69 (m, 2 H). LCMS m/z 404.9 (M+1).

Example 96

N-({4-chloro-3-[(3-chloro-5-cyanophenyl)oxy]-2-fluorophenyl}methyl)-5-methyl-2-phenyl-2H-1,2,3-triazole-4-carboxamide trifluoroacetate

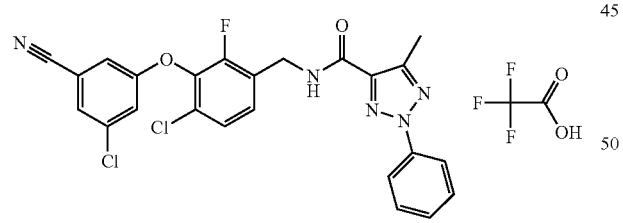

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 5-methyl-2-phenyl-2H-1,2,3-triazole-4-carboxylic acid (16.33 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.021 g, 44%) as a white solid. $^1$H NMR (400 MHz, Acetone-$d_6$): δ ppm 8.53 (t, 1H), 7.99-8.08 (m, 2H), 7.63 (t, 1H), 7.51-7.59 (m, 2 H), 7.49 (d, 1H), 7.42-7.46 (m, 2H), 7.38-7.42 (m, 2H), 4.70 (d, 2H), 2.58 (s, 3 H). LCMS m/z 495.9 (M+1).

Example 97

N-({4-chloro-3-[(3-chloro-5-cyanophenyl)oxy]-2-fluorophenyl}methyl)-2-methylimidazo[1,2-a]pyridine-3-carboxamide trifluoroacetate

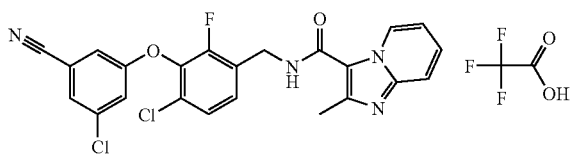

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 2-methylimidazo[1,2-a]pyridine-3-carboxylic acid (14.16 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.007 g, 14%) as a tan solid. $^1$H NMR (400 MHz, Acetone-$d_6$): δ ppm 9.37 (d, 1H), 8.15-8.24 (m, 1H), 8.09 (d, 1H), 7.86-7.95 (m, 1H), 7.63-7.67 (m, 1H), 7.58 (t, 1H), 7.43-7.48 (m, 2H), 7.41 (t, 1H), 7.37-7.39 (m, 1H), 4.78 (d, 2H), 2.82 (s, 3H). LCMS m/z 468.9 (M+1).

Example 98

N-({4-chloro-3-[(3-chloro-5-cyanophenyl)oxy]-2-fluorophenyl}methyl)-2-(3-pyridinyl)-1,3-thiazole-4-carboxamide trifluoroacetate

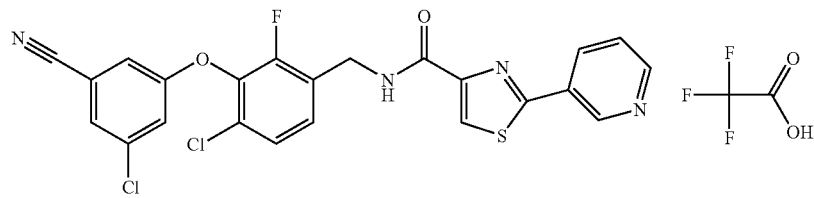

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 2-(3-pyridinyl)-1,3-thiazole-4-carboxylic acid (16.57 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.021 g, 42%) as a white solid. $^1$H NMR (400 MHz, CDCl$_3$): δ ppm 9.40 (br. s., 1H), 8.75-8.86 (m, 1H), 8.58 (d, 1H), 8.34 (s, 1H), 7.89 (t, 1H), 7.81 (dd, 1H), 7.35-7.41 (m, 1H), 7.33 (t, 1H), 7.26-7.31 (m, 1H), 7.16 (t, 1H), 6.99 (s, 1H), 4.75 (d, 2H). LCMS m/z 498.9 (M+1).

Example 99

N-({4-chloro-3-[(3-chloro-5-cyanophenyl)oxy]-2-fluorophenyl}methyl)-4-phenyl-1,2,3-thiadiazole-5-carboxamide

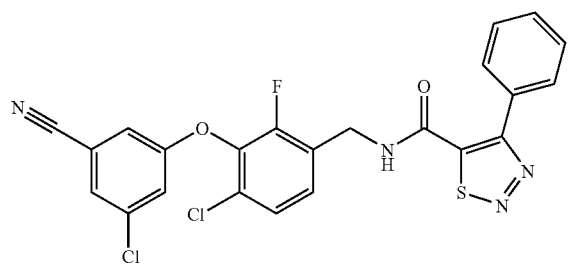

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 4-phenyl-1,2,3-thiadiazole-5-carboxylic acid (16.57 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.015 g, 35%) as a tan solid. $^1$H NMR (400 MHz, Acetone-d$_6$): δ ppm 8.51 (br. s., 1H), 7.80-7.90 (m, 2H), 7.63 (t, 1H), 7.45-7.51 (m, 3H), 7.38-7.45 (m, 2H), 7.33-7.38 (m, 2H), 4.65 (d, 2H). LCMS m/z 498.9 (M+1).

Example 100

N-({4-chloro-3-[(3-chloro-5-cyanophenyl)oxy]-2-fluorophenyl}methyl)-1H-pyrazole-4-carboxamide trifluoroacetate

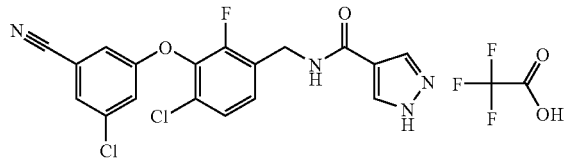

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 1H-pyrazole-4-carboxylic acid (9.01 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.013 g, 31%) as a white solid. $^1$H NMR (400 MHz, Acetone-d$_6$): δ ppm 8.09 (br. s., 2H), 8.00 (br. s., 1H), 7.63 (t, 1H), 7.40-7.48 (m, 2H), 7.36-7.40 (m, 2H), 5.63 (br. s., 1H), 4.60 (d, 2H). LCMS m/z 404.9 (M+1).

Example 101

5-chloro-N-({4-chloro-3-[(3-chloro-5-cyanophenyl)oxy]-2-fluorophenyl}methyl)-2-(methylthio)-4-pyrimidinecarboxamide

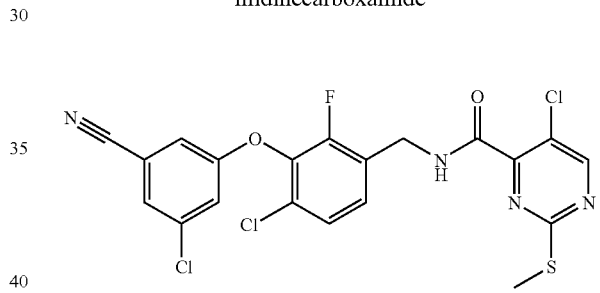

In a 1 dram vial, 3-{[3-(aminomethyl)-6-chloro-2-fluorophenyl]oxy}-5-chlorobenzonitrile (25 mg, 0.080 mmol), DIPEA (0.014 mL, 0.080 mmol) and 5-chloro-2-(methylthio)-4-pyrimidinecarboxylic acid (16.44 mg, 0.080 mmol) were dissolved in DMF (1 mL). HATU was added (30.6 mg, 0.080 mmol) and the solution stirred overnight. The reaction mixture was diluted to 2 mL with MeOH. Purification was accomplished by Reverse-Phase HPLC (water/acetonitrile with 0.1% TFA) to afford the title compound (0.017 g, 38%) as a white solid. $^1$H NMR (400 MHz, Acetone-d$_6$): δ ppm 8.73-8.81 (m, 2H), 7.63 (t, 1H), 7.47-7.54 (m, 1H), 7.42-7.47 (m, 1H), 7.36-7.41 (m, 2H), 4.69 (d, 2H), 2.56 (br. s., 3H). LCMS m/z 496.9 (M+1).

Example 102

N-({4-chloro-3-[(3-chloro-5-cyanophenyl)oxy]-2-fluorophenyl}methyl)-5-{[3-(dimethylamino)propyl]oxy}-1H-indole-2-carboxamide

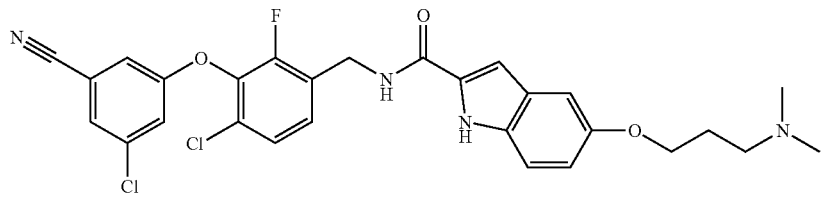

In a 24-well Bohdan block, ethyl 5-hydroxy-1H-indole-2-carboxylate (0.100 g, 0.487 mmol), 3-(dimethylamino)-1-propanol (0.126 g, 1.22 mmol) and PS-triphenylphosphine (406 mg, 1.22 mmol) were dissolved in THF (1 mL). Di-tert-butyl azodicarboxylate (1.22 M in THF, 1 mL) was added and the block shaken overnight. The reactor block was drained into a second Bohdan block and rinsed with THF. 1 N LiOH (1 mL) was added and the reactor block shaken for 6 hours at RT. 1 N HCl (1 mL) was added and the block was drained into a 24-well plate, rinsed with THF and the solvent evaporated. The residue was dissolved in DMF and filtered to remove salts. To the DMF solution was added 3-{[3-(aminomethyl)-6-chloro-2-fluorophenyl]oxy}-5-chlorobenzonitrile (50 mg, 0.161 mmol) followed by HATU (61.1 mg, 0.161 mmol) and DIPEA (30 µL, 0.222 mmol) and the reaction mixture stirred overnight. The resulting solution was diluted to 2 mL with MeOH. Purification was accomplished by Reverse-Phase HPLC (water/acetonitrile with 0.1% TFA) to afford the title compound (0.008 g, 3%) as a glass. $^1$H NMR (400 MHz, CDCl$_3$-d): δ ppm 9.26 (br. s., 1H), 7.30-7.36 (m, 2H), 7.25-7.27 (m, 1H), 7.22-7.24 (m, 1H), 7.13 (t, 1H), 6.95-7.00 (m, 2H), 6.88 (dd, 1H), 6.79 (d, 1H), 6.73-6.78 (m, 1H), 4.69 (d, 2H), 4.01 (t, 2H), 3.68-3.75 (m, 2H), 3.00-3.08 (m, 2H), 2.68 (s, 6H). LCMS m/z 555.2 (M+1).

Example 103

N-({4-chloro-3-[(3-chloro-5-cyanophenyl)oxy]-2-fluorophenyl}methyl)-5-{[2-(4-morpholinyl)ethyl]oxy}-1H-indole-2-carboxamide

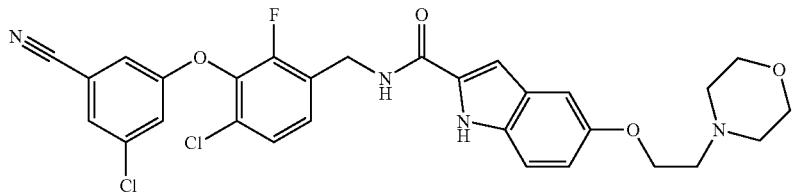

In a 24-well Bohdan block, ethyl 5-hydroxy-1H-indole-2-carboxylate (0.100 g, 0.487 mmol), 2-(4-morpholinyl)ethanol (0.160 g, 1.22 mmol) and PS-triphenylphosphine (406 mg, 1.22 mmol) were dissolved in THF (1 mL). Di-tert-butyl azodicarboxylate (1.22 M in THF, 1 mL) was added and the block shaken overnight. The reactor block was drained into a second Bohdan block and rinsed with THF. 1 N LiOH (1 mL) was added and the reactor block shaken for 6 hours at RT. 1 N HCl (1 mL) was added and the block was drained into a 24-well plate, rinsed with THF and the solvent evaporated. The residue was dissolved in DMF and filtered to remove salts. To the DMF solution was added 3-{[3-(aminomethyl)-6-chloro-2-fluorophenyl]oxy}-5-chlorobenzonitrile (50 mg, 0.161 mmol) followed by HATU (61.1 mg, 0.161 mmol) and DIPEA (30 µL, 0.222 mmol) and the reaction mixture stirred overnight. The resulting solution was diluted to 2 mL with MeOH. Purification was accomplished by Reverse-Phase HPLC (water/acetonitrile with 0.1% TFA) to afford the title compound (0.003 g, 1%) as a glass. $^1$H NMR (400 MHz, CDCl$_3$): δ ppm 9.05-9.11 (m, 1H), 7.35-7.37 (m, 1H), 7.34 (s, 1H), 7.27-7.31 (m, 2H), 7.15-7.18 (m, 1H), 7.05 (d, 1H), 7.02 (dd, 1H), 6.99 (dd, 1H), 6.79 (d, 1H), 6.50-6.57 (m, 1H), 4.73 (d, 2H), 4.13-4.18 (m, 2H), 3.72-3.79 (m, 4H), 2.82-2.90 (m, 2H), 2.60-2.69 (m, 4H). LCMS m/z 583.1 (M+1).

Example 104

N-({4-chloro-3-[(3-chloro-5-cyanophenyl)oxy]-2-fluorophenyl}methyl)-5-{[2-(1-methyl-2-pyrrolidinyl)ethyl]oxy}-1H-indole-2-carboxamide

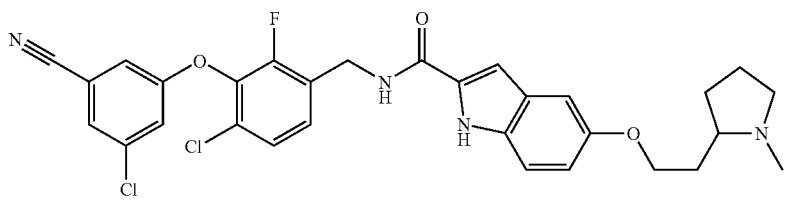

In a 24-well Bohdan block, ethyl 5-hydroxy-1H-indole-2-carboxylate (0.100 g, 0.487 mmol), 2-(1-methyl-2-pyrrolidinyl)ethanol (0.157 g, 1.22 mmol) and PS-triphenylphosphine (406 mg, 1.22 mmol) were dissolved in THF (1 mL). Di-tert-butyl azodicarboxylate (1.22 M in THF, 1 mL) was added and the block shaken overnight. The reactor block was drained into a second Bohdan block and rinsed with THF. 1 N LiOH (1 mL) was added and the reactor block shaken for 6 hours at RT. 1 N HCl (1 mL) was added and the block was drained into a 24-well plate, rinsed with THF and the solvent evaporated. The residue was dissolved in DMF and filtered to remove salts. To the DMF solution was added 3-{[3-(aminomethyl)-6-chloro-2-fluorophenyl]oxy}-5-chlorobenzonitrile (50 mg, 0.161 mmol) followed by HATU (61.1 mg, 0.161 mmol) and DIPEA (30 μL, 0.222 mmol) and the reaction mixture stirred overnight. The resulting solution was diluted to 2 mL with MeOH. Purification was accomplished by Reverse-Phase HPLC (water/acetonitrile with 0.1% TFA) to afford the title compound (0.007 g, 2%) as a glass. $^1$H NMR (400 MHz, CDCl$_3$): δ ppm 9.50 (br. s., 1H), 7.22-7.39 (m, 4H), 7.13-7.18 (m, 1H), 7.05-7.12 (m, 1H), 6.95-7.03 (m, 2H), 6.84-6.91 (m, 2H), 4.66-4.75 (m, 2H), 4.07-4.17 (m, 1H), 3.91-4.00 (m, 1H), 3.27-3.41 (m, 1H), 2.76-2.91 (m, 4H), 2.39-2.51 (m, 1H), 2.24-2.36 (m, 1H), 2.16 (br. s., 2H), 1.91-2.08 (m, 3H). LCMS m/z 581.1 (M+1).

Example 105

N-({4-chloro-3-[(3-chloro-5-cyanophenyl)oxy]-2-fluorophenyl}methyl)-5-{[2-(dimethylamino)ethyl]oxy}-1H-indole-2-carboxamide

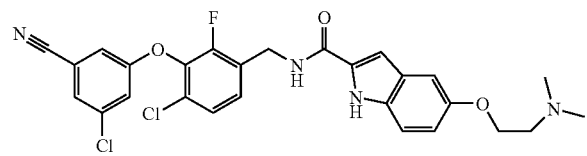

In a 24-well Bohdan block, ethyl 5-hydroxy-1H-indole-2-carboxylate (0.100 g, 0.487 mmol), 2-(dimethylamino)ethanol (0.109 g, 1.22 mmol) and PS-triphenylphosphine (406 mg, 1.22 mmol) were dissolved in THF (1 mL). Di-tert-butyl azodicarboxylate (1.22 M in THF, 1 mL) was added and the block shaken overnight. The reactor block was drained into a second Bohdan block and rinsed with THF. 1 N LiOH (1 mL) was added and the reactor block shaken for 6 hours at RT. 1 N HCl (1 mL) was added and the block was drained into a 24-well plate, rinsed with THF and the solvent evaporated. The residue was dissolved in DMF and filtered to remove salts. To the DMF solution was added 3-{[3-(aminomethyl)-6-chloro-2-fluorophenyl]oxy}-5-chlorobenzonitrile (50 mg, 0.161 mmol) followed by HATU (61.1 mg, 0.161 mmol) and DIPEA (30 μL, 0.222 mmol) and the reaction mixture stirred overnight. The resulting solution was diluted to 2 mL with MeOH. Purification was accomplished by Reverse-Phase HPLC (water/acetonitrile with 0.1% TFA) to afford the title compound (0.008 g, 3%) as a glass. $^1$H NMR (400 MHz, CDCl$_3$): δ ppm 9.28 (s, 1H), 7.31-7.38 (m, 3H), 7.29 (d, 1H), 7.14-7.17 (m, 1H), 7.00-7.04 (m, 2H), 6.96 (dd, 1H), 6.80-6.83 (m, 1H), 6.73 (t, 1H), 4.72 (d, 2H), 4.19 (t, 2H), 3.04 (t, 2H), 2.59 (s, 6H). LCMS m/z 541.1 (M+1).

Example 106

N-({4-chloro-3-[(3-chloro-5-cyanophenyl)oxy]-2-fluorophenyl}methyl)-5-[(3-hydroxybutyl)oxy]-1H-indole-2-carboxamide

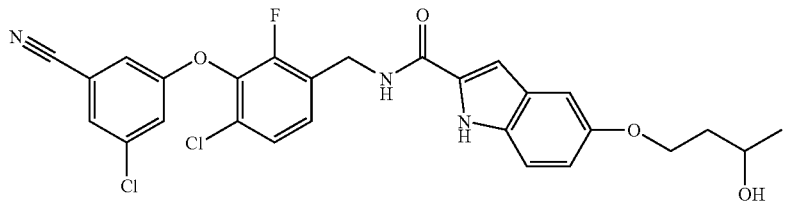

In a 24-well Bohdan block, ethyl 5-hydroxy-1H-indole-2-carboxylate (0.100 g, 0.487 mmol), 1,3-butanediol (0.110 g, 1.22 mmol) and PS-triphenylphosphine (406 mg, 1.22 mmol) were dissolved in THF (1 mL). Di-tert-butyl azodicarboxylate (1.22 M in THF, 1 mL) was added and the block shaken overnight. The reactor block was drained into a second Bohdan block and rinsed with THF. 1 N LiOH (1 mL) was added and the reactor block shaken for 6 hours at RT. 1 N HCl (1 mL) was added and the block was drained into a 24-well plate, rinsed with THF and the solvent evaporated. The residue was dissolved in DMF and filtered to remove salts. To the DMF solution was added 3-{[3-(aminomethyl)-6-chloro-2-fluorophenyl]oxy}-5-chlorobenzonitrile (50 mg, 0.161 mmol) followed by HATU (61.1 mg, 0.161 mmol) and DIPEA (30 μL, 0.222 mmol) and the reaction mixture stirred overnight. The resulting solution was diluted to 2 mL with MeOH. Purification was accomplished by Reverse-Phase HPLC (water/acetonitrile with 0.1% TFA) to afford the title compound (0.016 g, 6%) as a glass. $^1$H NMR (400 MHz, CDCl$_3$): δ ppm 9.42 (br. s., 1H), 7.26-7.38 (m, 4H), 7.16 (t, 1H), 7.05 (d, 1H), 7.00-7.03 (m, 1H), 6.92-6.98 (m, 1H), 6.80 (d, 1H), 6.69 (t, 1H), 4.72 (d, 2H), 4.07-4.24 (m, 3H), 1.89-2.02 (m, 2H), 1.29 (d, 3H). LCMS m/z 540.3 (M−1).

Example 107

N-({4-chloro-3-[(3-chloro-5-cyanophenyl)oxy]-2-fluorophenyl}methyl)-5-{[(3S)-3,4-dihydroxybutyl]oxy}-1H-indole-2-carboxamide

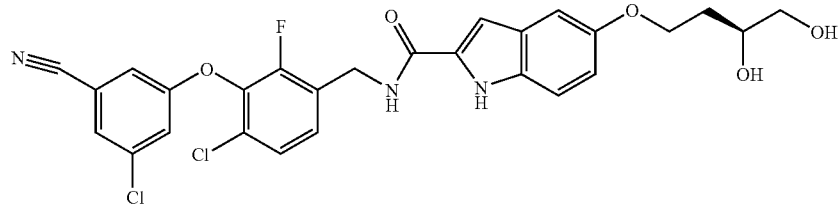

Step A: 1-(1,1-Dimethylethyl)2-ethyl 5-[(phenylmethyl)oxy]-1H-indole-1,2-dicarboxylate

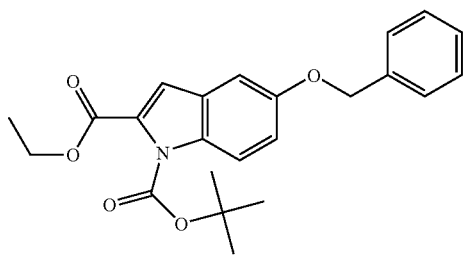

To a solution of ethyl 5-[(phenylmethyl)oxy]-1H-indole-2-carboxylate (24.91 g, 84 mmol) in THF was added PS-DMAP (9.37 g, 16.87 mmol) and BOC$_2$O (23.50 mL, 101 mmol) and the reaction stirred at RT until no ethyl 5-[(phenylmethyl)oxy]-1H-indole-2-carboxylate (24.91 g, 84 mmol) remained. The resin was filtered and the solvent evaporated. Purification was accomplished by column chromatography (0 to 20% EtOAc/Hexanes) to afford the title compound (33.9 g, >99%): as a white solid. $^1$H NMR (400 MHz, DMSO-d$_6$): δ ppm 7.86 (d, 1H), 7.42-7.48 (m, 2H), 7.38 (t, 2 H), 7.28-7.34 (m, 2H), 7.11-7.19 (m, 2H), 5.12 (s, 2H), 4.29 (q, 2H), 1.54 (s, 9H), 1.29 (t, 3H). LCMS m/z 294.6 (M−100).

Step B: 1-(1,1-dimethylethyl)2-ethyl 5-hydroxy-1H-indole-1,2-dicarboxylate

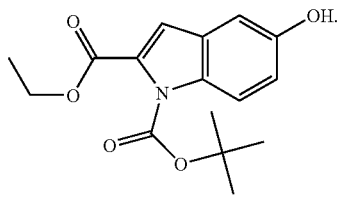

To a solution of 1-(1,1-dimethylethyl)2-ethyl 5-[(phenylmethyl)oxy]-1H-indole-1,2-dicarboxylate (33.92 g, 86 mmol) was added ammonium formate (54.1 g, 858 mmol) and Pd/C (1.00 g, 0.470 mmol). The mixture was stirred until TLC showed the starting material had been consumed. The mixture was filtered through celite and evaporated. The residue was partitioned with DCM and water, washed with brine, dried over MgSO$_4$ and evaporated onto silica gel. Purification was accomplished by column chromatography (0 to 40% EtOAc/Hexanes) to afford the title compound (25.03 g, 96%) as a white solid. $^1$H NMR (400 MHz, DMSO-d$_6$): δ ppm 9.36 (s, 1H), 7.75 (d, 1H), 7.08 (s, 1H), 6.96 (d, 1H), 6.91 (dd, 1H), 4.26 (q, 2H), 1.52 (s, 9H), 1.27 (t, 3H). LCMS m/z 304.8 (M−1).

Step C: 1-(1,1-dimethylethyl)2-ethyl 5-({2-[(4S)-2,2-dimethyl-1,3-dioxolan-4-yl]ethyl}oxy)-1H-indole-1,2-dicarboxylate

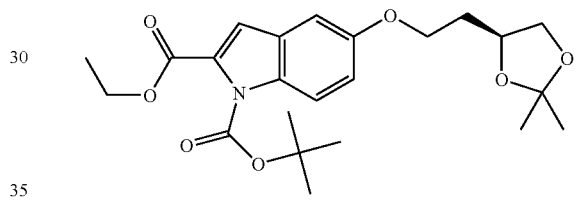

To a solution of 1-(1,1-dimethylethyl)2-ethyl 5-hydroxy-1H-indole-1,2-dicarboxylate (0.50 g, 1.638 mmol) in DCM was added 2-[(4S)-2,2-dimethyl-1,3-dioxolan-4-yl]ethanol (0.287 g, 1.965 mmol), PS-triphenylphosphine (0.546 g, 1.64 mmol) and di-tert-butyl azodicarboxylate (0.377 g, 1.64 mmol). The resulting mixture was stirred at 45° C. overnight. The mixture was poured into water and EtOAc. The organic layer was separated, dried over MgSO$_4$, filtered and evaporated onto silica gel. Purification was accomplished by column chromatography (0 to 50% EtOAc/Hexanes) to afford the title compound (0.167 g, 24%) as an oil. $^1$H NMR (400 MHz, CDCl$_3$): δ ppm 7.94 (d, 1H), 6.96-7.08 (m, 3H), 4.34 (q, 2H), 4.29 (t, 1H), 4.06-4.17 (m, 3H), 3.64 (t, 1H), 1.97-2.10 (m, 2H), 1.59 (s, 9H), 1.40 (s, 3H), 1.32-1.39 (m, 6H)

Step D: 5-({2-[(4S)-2,2-dimethyl-1,3-dioxolan-4-yl]ethyl}oxy)-1-{[(1,1-dimethylethyl)oxy]carbonyl}-1H-indole-2-carboxylic acid

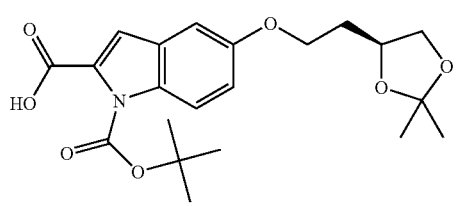

To a solution of 1-(1,1-dimethylethyl)2-ethyl 5-({2-[(4S)-2,2-dimethyl-1,3-dioxolan-4-yl]ethyl}oxy)-1H-indole-1,2-dicarboxylate (167 mg, 0.385 mmol) in MeOH (2 mL) was added 1N LiOH (0.58 mL). A precipitate appeared and THF (2 mL) was added. The solution was stirred until TLC showed the starting material had been consumed. The reaction mixture was quenched with 1N HCl (0.58 mL) and the solvent evaporated. The residue was dissolved in EtOAc and extracted with 1N NaOH. The aqueous layer was acidified with conc. HCl until a precipitate formed and then partitioned with EtOAc. The organic layer was separated, dried over MgSO$_4$ and the solvent evaporated. The crude material was directly with no further purification.

Step E: N-({4-chloro-3-[(3-chloro-5-cyanophenyl)oxy]-2-fluorophenyl}methyl)-5-{[(3S)-3,4-dihydroxybutyl]oxy}-1H-indole-2-carboxamide

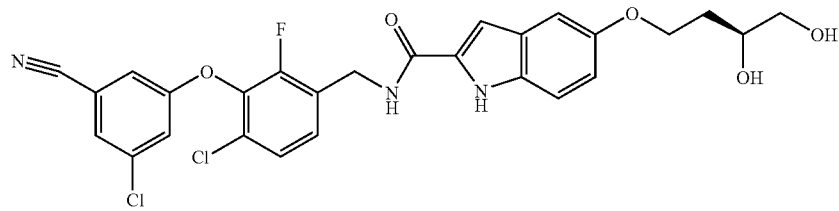

To a solution of 3-{[3-(aminomethyl)-6-chloro-2-fluorophenyl]oxy}-5-chlorobenzonitrile (25.0 mg, 0.080 mmol), 5-({2-[(4S)-2,2-dimethyl-1,3-dioxolan-4-yl]ethyl}oxy)-1H-indole-2-carboxylic acid (24.53 mg, 0.080 mmol) and DIPEA (0.014 mL, 0.080 mmol) in DMF (1 mL) was added HATU (30.6 mg, 0.080 mmol). After 2 h the reaction mixture was poured into EtOAc and water. The organic layer was separated, dried over MgSO$_4$ and the solvent evaporated. The residue was diluted to 2 mL with MeOH. Purification was accomplished by Reverse-Phase HPLC (water/acetonitrile with 0.1% TFA) to afford the title compound (0.019 g, 42%) as a white solid. $^1$H NMR (400 MHz, Acetone-d$_6$): δ ppm 10.67 (br. s., 1H), 8.31 (t, 1H), 7.60 (t, 1H), 7.46 (d, 1H), 7.40-7.42 (m, 1H), 7.38-7.40 (m, 1H), 7.34-7.38 (m, 2H), 7.07 (d, 1H), 7.04 (d, 1H), 6.88 (dd, 1H), 4.67 (d, 2H), 4.04-4.17 (m, 2H), 3.82-3.91 (m, 1H), 3.51-3.58 (m, 1H), 3.43-3.50 (m, 1H), 1.92-2.01 (m, 1H), 1.73-1.84 (m, 1H). LCMS m/z 558.0 (M+1).

Example 108

N-({4-chloro-3-[(3-chloro-5-cyanophenyl)oxy]-2-fluorophenyl}methyl)-7-methyl-1H-indole-2-carboxamide

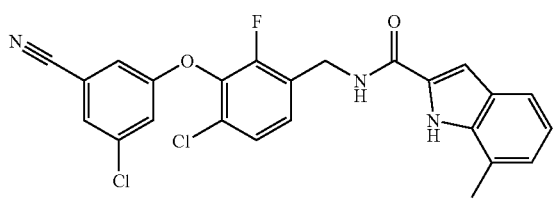

HATU (0.072 g, 0.19 mmol) was added to a solution of 3-{[3-(aminomethyl)-6-chloro-2-fluorophenyl]oxy}-5-chlorobenzonitrile (0.040 g, 0.13 mmol), 7-methyl-1H-indole-2-carboxylic acid (0.033 g, 0.19 mmol) and DIPEA (0.033 mL, 0.19 mmol) in DMF (1 mL). After 1 h, the reaction mixture was diluted with ethyl acetate and water. The organic layer was washed with water and brine, dried over anhydrous sodium sulfate, and concentrated. The residue was purified by column chromatography (hexane/EtOAc) to give a sticky solid, which was triturated with methanol and dried under vacuum to give the title compound (0.035 g, 57%) as a white solid. $^1$H NMR (400 MHz, DMSO-d$_6$): δ ppm 11.38 (s, 1H), 8.99 (t, 1H), 7.81 (s, 1H), 7.26-7.63 (m, 5H), 7.15 (d, 1H), 6.68-7.06 (m, 2H), 4.57 (d, 2H), 2.21-2.69 (s, 3H). MS: m/z 468 (M+1).

Example 109

5-chloro-N-({4-chloro-3-[(3-chloro-5-cyanophenyl)oxy]-2-fluorophenyl}methyl)-1H-indole-2-carboxamide

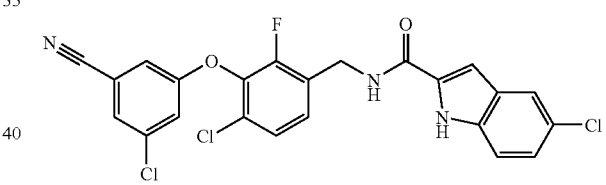

HATU (91 mg, 0.24 mmol) was added to a solution of 3-{[3-(aminomethyl)-6-chloro-2-fluorophenyl]oxy}-5-chlorobenzonitrile (50 mg, 0.16 mmol), 5-chloro-1H-indole-2-carboxylic acid (50 mg, 0.24 mmol) and DIPEA (0.042 ml, 0.24 mmol) in DMF (1.5 mL). After 1 h, the reaction mixture was diluted with ethyl acetate and water. A solid precipitated which was filtered, triturated with methanol and dried under vacuum to give the title compound (0.045 g, 57%) as an off-white solid. $^1$H NMR (400 MHz, DMSO-d$_6$): δ ppm 11.82 (s, 1H), 9.10 (s, 1H), 7.80 (s, 1H), 7.69 (s, 1H), 7.45-7.55 (m, 3H), 7.35-7.44 (m, 2H), 7.11-7.21 (m, 2H), 4.56 (d, 2H). MS: m/z 488 (M+1).

Example 110

6-chloro-N-({4-chloro-3-[(3-chloro-5-cyanophenyl)oxy]-2-fluorophenyl}methyl)-1H-indole-2-carboxamide

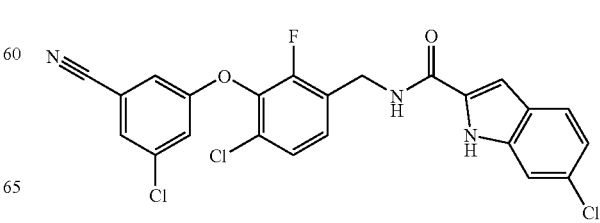

HATU (91 mg, 0.24 mmol) was added to a solution of 3-{[3-(aminomethyl)-6-chloro-2-fluorophenyl]oxy}-5-chlorobenzonitrile (0.050 g, 0.16 mmol), 6-chloro-1H-indole-2-carboxylic acid (0.050 g, 0.24 mmol) and DIPEA (0.042 ml, 0.24 mmol) in DMF (1.5 mL). After 1 h, the reaction mixture was diluted with ethyl acetate and water. The organic layer was separated, dried over sodium sulfate and concentrated. The residue was purified by column chromatography (hexane/EtOAc) to give the title compound (0.033 g, 42%) as a white solid. $^1$H NMR (400 MHz, DMSO-d$_6$): δ ppm 11.76 (s, 1H), 9.09 (t, 1H), 7.81 (s, 1H), 7.64 (d, 1H), 7.45-7.54 (m, 3H), 7.36-7.44 (m, 2H), 7.19 (s, 1H), 7.04 (dd, 1H), 4.56 (d, 2H). MS: m/z 488 (M+1).

Example 111

5-amino-N-({4-chloro-3-[(3-chloro-5-cyanophenyl) oxy]-2-fluorophenyl}methyl)-1H-indole-2-carboxamide trifluoroacetate

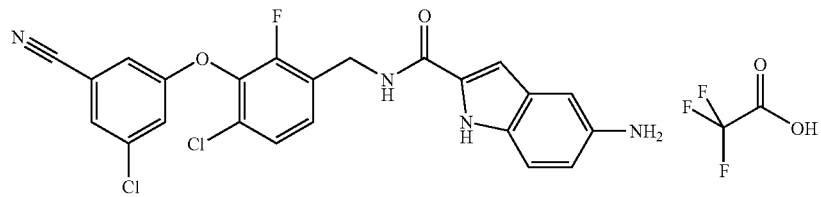

Step A: ethyl 5-amino-1H-indole-2-carboxylate

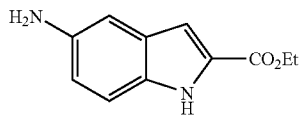

To a suspension of ethyl 5-nitro-1H-indole-2-carboxylate (0.100 g, 0.43 mmol) in 5 mL of absolute ethanol was added 5% palladium on carbon (0.045 g, 0.021 mmol). The mixture was evacuated and flushed with nitrogen, then filled with hydrogen at 50 psi. After 3 h, the reaction mixture was filtered through Celite and the filtrate was evaporated to give the title compound (0.053 g, 60%) as a light brown solid. $^1$H NMR (400 MHz, DMSO-d$_6$): δ ppm 11.33 (s, 1H), 7.10 (d, 1H), 6.78 (d, 1H), 6.58-6.69 (m, 2H), 4.70 (br. s., 2H), 4.25 (q, 2H), 1.27 (t, 3H). MS: m/z 205 (M+1).

Step B: 5-({[(1,1-dimethylethyl)oxy]carbonyl}amino)-1H-indole-2-carboxylic acid

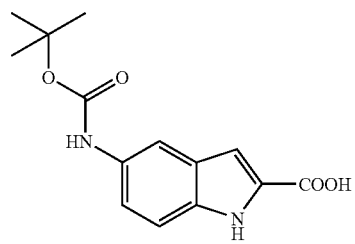

Di-t-butyldicarbonate (0.133 g, 0.61 mmol) was added to a solution of ethyl 5-amino-1H-indole-2-carboxylate (0.050 g, 0.245 mmol) and triethylamine (0.1 ml, 0.73 mmol) in dichloromethane (3 mL). After stirring at RT overnight, the solvent was evaporated to give ethyl 5-({[(1,1-dimethylethyl)oxy]carbonyl}amino)-1H-indole-2-carboxylate (0.149 g) as a light brown solid. The crude product was dissolved in THF:methanol:water/3:1:1 (1.5 mL), and lithium hydroxide (0.059 g, 2.45 mmol) was added. The mixture was stirred at RT overnight. The solvent was evaporated and the residue was dissolved in water, and acidified with 1N aqueous HCl. The resulting suspension was extracted with ethyl acetate. The organic layer was separated, dried over sodium sulfate, filtered and concentrated to give the title compound (0.035 g, 52% over two steps) as an off-white solid. $^1$H NMR (400 MHz, DMSO-d$_5$): δ ppm 11.46 (s, 1H), 9.11 (s, 1H), 7.73 (s, 1H), 7.22-7.29 (m, 1H), 7.15-7.23 (m, 1H), 6.87-6.92 (m, 1H), 1.46 (s, 9H). MS: m/z 275 (M−1).

Step C: 1,1-dimethylethyl (2-{[({4-chloro-3-[(3-chloro-5-cyanophenyl)oxy]-2-fluorophenyl}methyl)amino]carbonyl}-1H-indol-5-yl)carbamate

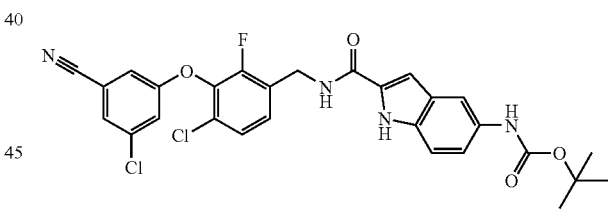

HATU (0.064 g, 0.168 mmol) was added to a solution of 3-{[3-(aminomethyl)-6-chloro-2-fluorophenyl]oxy}-5-chlorobenzonitrile (0.035 g, 0.112 mmol), 5-({[(1,1-dimethylethyl)oxy]carbonyl}amino)-1H-indole-2-carboxylic acid (0.032 g, 0.116 mmol), and DIPEA (0.030 ml, 0.168 mmol) in DMF (1 mL). The mixture was stirred at RT for 1.5 h. Water and EtOAc were added. The organic layer was separated and washed with water and brine, dried over sodium sulfate, and concentrated to give the title compound (0.038 g, 60%) as a colorless oil. $^1$H NMR (400 MHz, CDCl$_3$): δ ppm 9.67 (s, 1H), 7.75 (s, 1H), 7.17-7.37 (m, 4H), 7.14 (t, 1H), 7.08 (dd, 1H), 6.94-7.02 (m, 2H), 6.80 (m, 1H), 6.60 (s, 1H), 4.69 (d, 2H), 1.52 (m, 9H). MS: m/z 569 (M).

Step D: 5-amino-N-({4-chloro-3-[(3-chloro-5-cyanophenyl)oxy]-2-fluorophenyl}methyl)-1H-indole-2-carboxamide trifluoroacetate

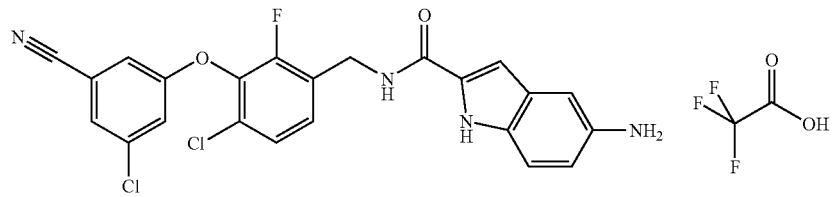

Trifluoroacetic acid (0.5 ml, 6.49 mmol) was added to a suspension of 1,1-dimethylethyl (2-{[({4-chloro-3-[(3-chloro-5-cyanophenyl)oxy]-2-fluorophenyl}methyl)amino]carbonyl}-1H-indol-5-yl)carbamate (0.038 g, 0.066 mmol) in dichloromethane (2 mL). The resulting solution was stirred at RT for 2 h. The solvent was evaporated and the residue was purified by Reverse-Phase HPLC (water/acetonitrile with 0.1% TFA) to give the title compound (0.017 g, 44%) as a white solid. $^1$H NMR (400 MHz, DMSO-d$_6$): δ ppm 11.85 (s, 1H), 9.57 (br. s., 2H), 9.07 (s, 1H), 7.78 (s, 1H), 7.41-7.57 (m, 5H), 7.32-7.41 (m, 1H), 7.17 (s, 1H), 6.99-7.13 (m, 1H), 4.53 (s, 2H). MS: m/z 469 (M+1).

Example 112

1,1-dimethylethyl (2-{[({4-chloro-3-[(3-chloro-5-cyanophenyl)oxy]-2-fluorophenyl}methyl)amino]carbonyl}-1H-indol-7-yl)carbamate

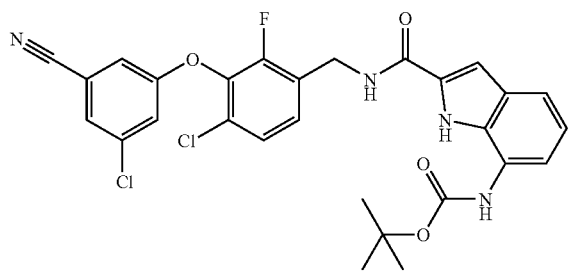

Step A: ethyl 7-amino-1H-indole-2-carboxylate

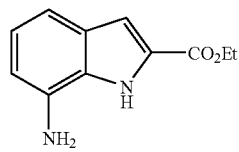

Platinum(IV) oxide (0.024 g, 0.107 mmol) was added to a suspension of ethyl 7-nitro-1H-indole-2-carboxylate (0.10 g, 0.30 mmol) in ethanol (20 mL) in a Fisher-Porter vessel. The mixture was evacuated and flushed with nitrogen three times, flushed with hydrogen (60 psi) and evacuated three times, then filled with hydrogen (60 psi). After 30 min, the reaction mixture was filtered through celite. The filtrate was concentrated and the residue was purified by column chromatography (hexane/EtOAc) to give the title compound (0.324 g, 74%) as a yellow solid. $^1$H NMR (400 MHz, CDCl$_3$): δ ppm 9.60 (s, 1H), 7.22 (d, 1H), 7.19 (d, 1H), 6.94-7.03 (m, 1H), 6.66 (d, 1H), 4.43 (q, 2H), 1.44 (t, 3H). MS: m/z 205 (M+1).

Step B: ethyl 7-({[(1,1-dimethylethyl)oxy]carbonyl}amino)-1H-indole-2-carboxylate

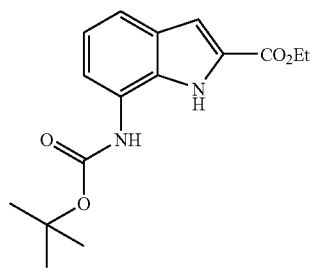

Di-t-butyldicarbonate (0.389 g, 1.78 mmol) was added to a solution of ethyl 7-amino-1H-indole-2-carboxylate (0.303 g, 1.48 mmol) and triethylamine (0.41 mL, 2.97 mmol) in dichloromethane (15 mL). After stirring at RT overnight, the reaction mixture was diluted with dichloromethane and water. The organic layer was separated, dried over sodium sulfate and concentrated. The residue was purified by column chromatography (hexane/EtOAc) to give the title compound (0.271 g, 60%) as a light yellow solid. $^1$H NMR (400 MHz, CDCl$_3$): δ ppm 10.30 (s, 1H), 7.46 (d, 1H), 7.21 (d, 1H), 6.98-7.09 (m, 1H), 6.93 (d, 1H), 6.82 (s, 1H), 4.42 (q, 2H), 1.53-1.58 (m, 9 H), 1.42 (t, 3H). MS: m/z 305 (M+1).

Step C: 7-({[(1,1-dimethylethyl)oxy]carbonyl}amino)-1H-indole-2-carboxylic acid

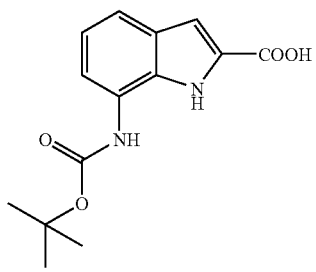

Lithium hydroxide (0.196 g, 8.18 mmol) was added to a solution of ethyl 7-({[(1,1-dimethylethyl)oxy]carbonyl}amino)-1H-indole-2-carboxylate (0.249 g, 0.818 mmol) in THF:MeOH:water/3:1:1 (5 mL). The mixture was stirred at RT overnight. The solvent was evaporated and the residue was dissolved in water, acidified with 6N aqueous HCl, and extracted with ethyl acetate. The organic layer was dried over sodium sulfate and concentrated to give the title compound (0.206 g, 90%) as a white solid. $^1$H NMR (400 MHz, CDCl$_3$) δ ppm 11.36 (s, 1H), 9.29 (s, 1H), 7.28-7.53 (m, 2H), 7.14-7.28 (m, 2H), 6.97-7.13 (m, 1H), 1.41-1.80 (m, 9H). MS m/z 277 (M+1).

Step D: 1,1-dimethylethyl (2-{[({4-chloro-3-[(3-chloro-5-cyanophenyl)oxy]-2-fluorophenyl}methyl)amino]carbonyl}-1H-indol-7-yl)carbamate

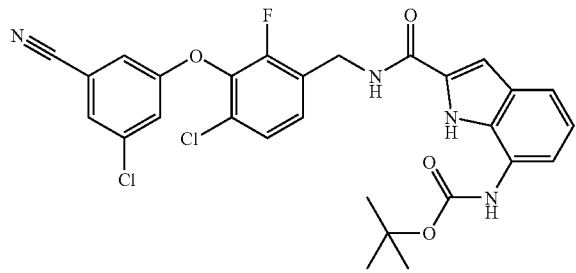

HATU (0.055 g, 0.145 mmol) was added to a solution of 3-{[3-(aminomethyl)-6-chloro-2-fluorophenyl]oxy}-5-chlorobenzonitrile (0.030 g, 0.096 mmol), 7-({[(1,1-dimethylethyl)oxy]carbonyl}amino)-1H-indole-2-carboxylic acid (0.026 g, 0.096 mmol) and DIPEA (0.025 mL, 0.145 mmol) in DMF (1 mL). The mixture was stirred at RT overnight then extracted with water and ethyl acetate. The organic layer was separated, dried over sodium sulfate, and concentrated. The residue was purified by column chromatography (hexane/EtOAc) to give the title compound (0.027 g, 44%) as a white solid. $^1$H NMR (400 MHz, DMSO-d$_6$): δ ppm 11.59 (s, 1H), 9.32 (s, 1H), 9.07 (t, 1H), 7.81 (s, 1H), 7.67-7.77 (m, 1H), 7.44-7.57 (m, 3H), 7.39 (t, 1H), 7.27 (d, 1H), 7.17 (d, 1H), 6.96 (t, 1H), 4.57 (d, 2H), 1.5 (s, 9H). MS: m/z 569 (M).

Example 113

7-amino-N-({4-chloro-3-[(3-chloro-5-cyanophenyl)oxy]-2-fluorophenyl}methyl)-1H-indole-2-carboxamide

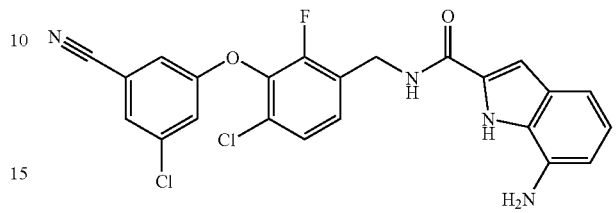

Trifluoroacetic acid (0.028 mL, 0.369 mmol) was added to a solution of 1,1-dimethylethyl (2-{[({4-chloro-3-[(3-chloro-5-cyanophenyl)oxy]-2-fluorophenyl}methyl)amino]carbonyl}-1H-indol-7-yl)carbamate (0.021 g, 0.037 mmol) in dichloromethane. The mixture was stirred at RT overnight. The solvent was evaporated and the residue was purified by Reverse-Phase HPLC (water/acetonitrile with 0.1% TFA) to give the title compound (0.009 g, 45%) as a white solid. $^1$H NMR (400 MHz, DMSO-d$_6$): δ ppm 11.46 (s, 1H), 9.07 (s, 1H), 7.81 (s, 1H), 7.43-7.58 (m, 3H), 7.32-7.43 (m, 1H), 7.09-7.22 (m, 2H), 6.82-6.97 (m, 1H), 6.62-6.75 (m, 1H), 4.58 (s, 2H), 4.20 (br s, 2H). MS: m/z 469 (M+1).

General preparation of amide derivatives of 5-amino-N-({4-chloro-3-[(3-chloro-5-cyanophenyl)oxy]-2-fluorophenyl}methyl)-1H-indole-2-carboxamide Bis(2-oxo-3-oxazolidinyl)phosphinic chloride (0.065 g, 0.257 mmol) was added to a solution of 5-amino-N-({4-chloro-3-[(3-chloro-5-cyanophenyl)oxy]-2-fluorophenyl}methyl)-1H-indole-2-carboxamide trifluoroacetate (0.050 g, 0.086 mmol), carboxylic acid (0.086 mmol) and DIPEA (0.075 mL, 0.429 mmol) in DMF (1 mL). The mixture was stirred at RT for 30 min. The reaction mixture was diluted with ethyl acetate and water. The organic layer was washed with water, dried over sodium sulfate and concentrated. The crude products were purified by column chromatography (hexane:EtOAc), by trituration with methanol or by Reverse-Phase HPLC (water/acetonitrile with 0.1% TFA).

Example 114

N-({4-chloro-3-[(3-chloro-5-cyanophenyl)oxy]-2-fluorophenyl}methyl)-5-[(4-pyridinylcarbonyl)amino]-1H-indole-2-carboxamide

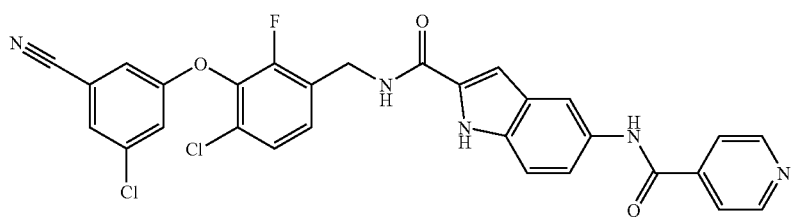

The title compound (0.020 g, 34% yield) was prepared from 5-amino-N-({4-chloro-3-[(3-chloro-5-cyanophenyl)oxy]-2-fluorophenyl}methyl)-1H-indole-2-carboxamide trifluoroacetate (0.060 g, 0.103 mmol), 4-pyridinecarboxylic acid (0.013 g, 0.103 mmol), DIPEA (0.090 ml, 0.514 mmol) and bis(2-oxo-3-oxazolidinyl)phosphinic chloride (0.079 g, 0.309 mmol) in a similar manner as described in the general procedure. $^1$H NMR (400 MHz, DMSO-d$_6$): δ ppm 11.64 (s, 1H), 10.39 (s, 1H), 8.90-9.22 (m, 1H), 8.76 (d, 8.09 (s, 1H), 7.86 (d, 2H), 7.81 (s, 1H), 7.52 (s, 1H), 7.43-7.51 (m, 3H), 7.36-7.43 (m, 2H), 7.16 (d, 1H), 4.56 (d, 2H). MS: m/z 574 (M+1).

Example 115

N-({4-chloro-3-[(3-chloro-5-cyanophenyl)oxy]-2-fluorophenyl}methyl)-5-[(3-pyridinylcarbonyl)amino]-1H-indole-2-carboxamide

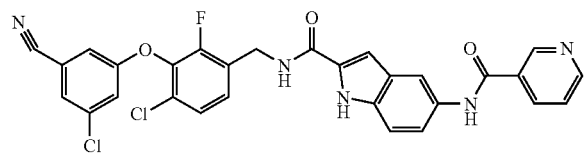

The title compound (0.011 g, 19%) was prepared from 5-amino-N-({4-chloro-3-[(3-chloro-5-cyanophenyl)oxy]-2-fluorophenyl}methyl)-1H-indole-2-carboxamide trifluoroacetate (0.050 g, 0.086 mmol), 3-pyridinecarboxylic acid (0.011 g, 0.086 mmol), DIPEA (0.075 mL, 0.43 mmol) and bis(2-oxo-3-oxazolidinyl)phosphinic chloride (0.065 g, 0.257 mmol) in a similar manner as described in the general procedure. $^1$H NMR (400 MHz, DMSO-d$_6$): δ ppm 11.66 (s, 1H), 10.38 (s, 1H), 9.16 (s, 2H), 8.80 (s, 1H), 8.38 (s, 1H), 8.12 (s, 1H), 7.72-7.97 (m, 1H), 7.32-7.97 (m, 7H), 7.19 (s, 1H), 4.58 (d, 2H). MS: m/z 574 (M+1).

Example 116

5-(β-alanylamino)-N-({4-chloro-3-[(3-chloro-5-cyanophenyl)oxy]-2-fluorophenyl}methyl)-1H-indole-2-carboxamide

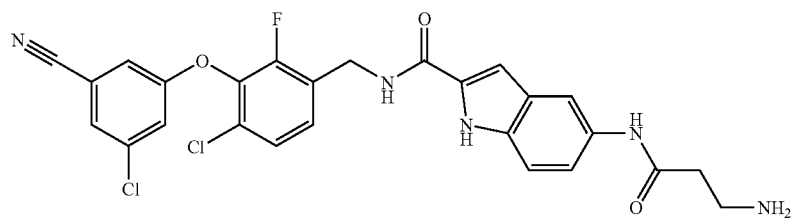

5-Amino-N-({4-chloro-3-[(3-chloro-5-cyanophenyl)oxy]-2-fluorophenyl}methyl)-1H-indole-2-carboxamide trifluoroacetate (0.100 g, 0.213 mmol) was treated with N-{[(1,1-dimethylethyl)oxy]carbonyl}-β-alanine (0.040 g, 0.213 mmol), DIPEA (0.19 mL, 1.07 mmol) and bis(2-oxo-3-oxazolidinyl)phosphinic chloride (0.163 g, 0.639 mmol) in a similar manner as in the general procedure described herein to afford crude 1,1-dimethylethyl {3-[(2-{[({4-chloro-3-[(3-chloro-5-cyanophenyl)oxy]-2-fluorophenyl}methyl)amino]carbonyl}-1H-indol-5-yl)amino]-3-oxopropyl}carbamate as a yellow solid. This crude material (0.027 g, 0.042 mmol) was suspended in dichloromethane (1 mL) and treated with trifluoroacetic acid (0.25 mL, 3.24 mmol) at RT for 1 h. The solvent was evaporated and the residue was purified by Reverse-Phase HPLC (water/acetonitrile with 0.1% TFA) to give the title compound (0.017 g, 62%) as a white solid. $^1$H NMR (400 MHz, DMSO-d$_6$): δ ppm 11.59 (s, 1H), 10.01 (s, 1H), 9.00 (s, 1H), 7.97 (s, 1H), 7.82 (s, 1H), 7.63-7.79 (m, 2H), 7.44-7.57 (m, 2 H), 7.31-7.44 (m, 1H), 7.22-7.31 (m, 1H), 7.11 (s, 1H), 4.57 (s, 2H), 2.94-3.19 (m, 2H), 2.62-2.77 (m, 2H). MS: m/z 540 (M+1).

Example 117

1,1-dimethylethyl (2S)-2-{[(2-{[({4-chloro-3-[(3-chloro-5-cyanophenyl)oxy]-2-fluorophenyl}methyl)amino]carbonyl}-1H-indol-5-yl)amino]carbonyl}-1-pyrrolidinecarboxylate

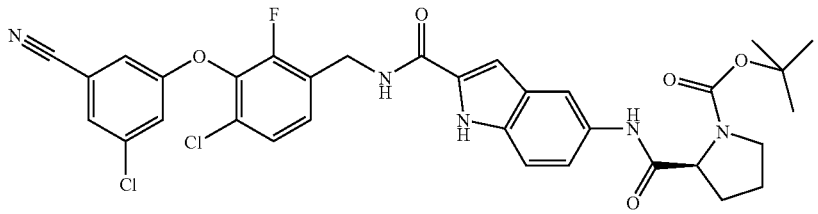

5-amino-N-({4-chloro-3-[(3-chloro-5-cyanophenyl)oxy]-2-fluorophenyl}methyl)-1H-indole-2-carboxamide trifluoroacetate (0.060 g, 0.103 mmol) was treated with 1-{[(1,1-dimethylethyl)oxy]carbonyl}-L-proline (0.022 g, 0.103 mmol), DIPEA (0.090 mL, 0.514 mmol) and bis(2-oxo-3-oxazolidinyl)phosphinic chloride (0.079 g, 0.309 mmol) as in the general procedure described herein. The crude product was purified by silica gel chromatography (hexanes/ethyl acetate) to afford the title compound (0.035 g, 51%) as a white solid. $^1$H NMR (400 MHz, DMSO-d$_6$): δ ppm 11.51 (s, 1H), 9.77 (s, 1H), 8.95 (s, 1H), 7.88-7.98 (m, 1H), 7.77 (s, 1H), 7.44 (s, 3H), 7.33-7.40 (m, 1H), 7.27-7.33 (m, 1H), 7.19-7.26 (m, 1H), 7.07 (s, 1H), 4.52 (s, 2H), 4.15 (m, 1H), 3.24-3.45 (m, 2H), 2.14 (m, 1H), 1.62-1.92 (m, 3H), 1.36 (s, 3H), 1.23 (s, 6 H). MS: m/z 666 (M+1).

Example 118

N-({4-chloro-3-[(3-chloro-5-cyanophenyl)oxy]-2-fluorophenyl}methyl)-5-(L-prolylamino)-1H-indole-2-carboxamide trifluoroacetate

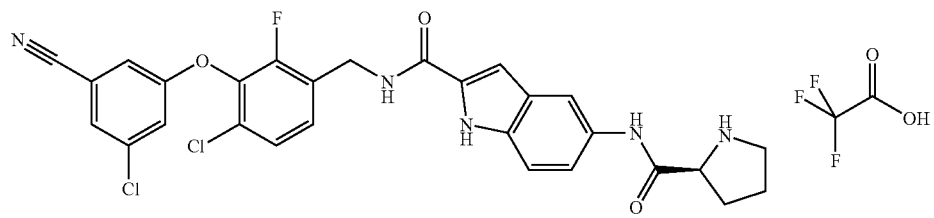

Trifluoroacetic acid (0.25 mL, 3.24 mmol) was added to a suspension of 1,1-dimethylethyl(2S)-2-{[(2-{[({4-chloro-3-[(3-chloro-5-cyanophenyl)oxy]-2-fluorophenyl}methyl)amino}carbonyl]-1H-indol-5-yl)amino]carbonyl}-1-pyrrolidinecarboxylate (0.013 g, 0.020 mmol) in dichloromethane (1 mL). The resulting solution was stirred at RT for 1 h. The solvent was evaporated to give the title compound (0.013 g, 98%) an off-white solid. $^1$H NMR (400 MHz, DMSO-$d_6$): δ ppm 11.67 (s, 1H), 10.38 (s, 1H), 9.24 (s, 1H), 9.02 (s, 1H), 8.66 (s, 1H), 7.95 (s, 1H), 7.81 (s, 1H), 7.46-7.55 (m, 2H), 7.36-7.44 (m, 1H), 7.28 (dd, 1H), 7.15 (d, 1H), 4.57 (s, 2H), 4.30 (m, 1H), 3.28 (m, 2H), 1.75-2.14 (m, 4H). MS: m/z 566 (M).

Example 119

N-({4-chloro-3-[(3-chloro-5-cyanophenyl)oxy]-2-fluorophenyl}methyl)-5-[(N-methylglycyl)amino-1-1H-indole-2-carboxamide

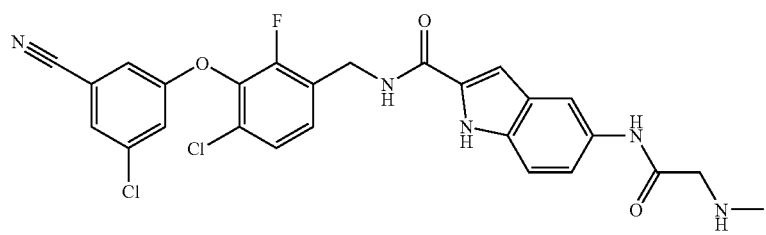

1,1-Dimethylethyl {2-[(2-{[({4-chloro-3-[(3-chloro-5-cyanophenyl)oxy]-2-fluorophenyl}methyl)amino]carbonyl} 1H-indol-5-yl)amino]-2-oxoethyl}methyl-carbamate (0.030 g, 45%) was prepared from 5-amino-N-({4-chloro-3-[(3-chloro-5-cyanophenyl)oxy]-2-fluorophenyl}methyl)-1H-indole-2-carboxamide trifluoroacetate (0.060 g, 0.0103 mmol), N-{[(1,1-dimethylethyl)oxy]carbonyl}-N-methylglycine (0.019 g, 0.103 mmol), DIPEA (0.090 mL, 0.514 mmol) and bis(2-oxo-3-oxazolidinyl)phosphinic chloride (0.079 g, 0.309 mmol) by the general procedure described herein. Purification was accomplished by silica gel chromatography (hexanes/ethyl acetate). A solution of 1,1-dimethylethyl {2-[(2-{[({4-chloro-3-[(3-chloro-5-cyanophenyl)oxy]-2-fluorophenyl}methyl)amino]carbonyl} 1H-indol-5-yl)amino]-2-oxoethyl}methylcarbamate (0.027 g, 0.042 mmol) in dichloromethane (1 mL) was treated with trifluoroacetic acid (0.25 mL, 3.24 mmol) at RT. The solvent was evaporated to give the title compound (0.027 g, 98%) as an off-white solid. $^1$H NMR (400 MHz, DMSO-$d_6$): δ ppm 11.61 (s, 1H), 10.31 (s, 1H), 8.98 (s, 1H), 8.75 (s, 2H), 7.91 (s, 1H), 7.78 (d, 1H), 7.41-7.52 (m, 2H), 7.31-7.40 (m, 2H), 7.23 (d, 1H), 7.11 (s, 1H), 4.53 (d, 2H), 3.87 (s, 2H), 2.60 (s, 3H). MS: m/z 539 (M+1).

Example 120

N-({4-chloro-3-[(3-chloro-5-cyanophenyl)oxy]-2-fluorophenyl}methyl)-5-(glycylamino)-1H-indole-2-carboxamide trifluoroacetate

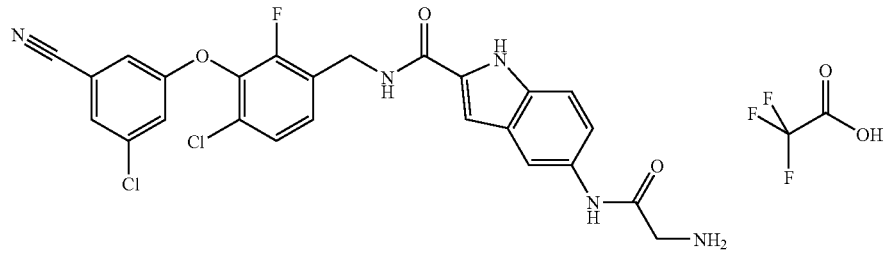

5-amino-N-({4-chloro-3-[(3-chloro-5-cyanophenyl)oxy]-2-fluorophenyl}methyl)-1H-indole-2-carboxamide trifluoroacetate (0.060 g, 0.0103 mmol) was treated with N-{[(1,1-dimethylethyl)oxy]carbonyl}glycine (0.018 g, 0.103 mmol), DIPEA (0.090 mL, 0.514 mmol) and bis(2-oxo-3-oxazolidinyl)phosphinic chloride (0.079 g, 0.309 mmol) in a similar manner as described herein to afford crude 1,1-dimethylethyl {2-[(2-{[({4-chloro-3-[(3-chloro-5-cyanophenyl)oxy]-2-fluorophenyl}methyl)amino]carbonyl}-1H-indol-5-yl)amino]-2-oxoethyl}carbamate (0.031 g) as an off-white solid. This material was treated with trifluoroacetic acid (0.30 mL, 3.89 mmol) in dichloromethane (1 mL) for 1 h. The solvent was evaporated to give the title compound (0.011 g, 40%) as a white solid. $^1$H NMR (400 Hz, DMSO-$d_6$): δ ppm 11.60 (s, 1H), 10.23 (s, 1H), 8.97 (s, 1H), 8.04 (m, 3H), 7.91 (s, 1H), 7.77 (s, 1H), 7.40-7.54 (m, 2H), 7.29-7.40 (m, 2 H), 7.17-7.27 (m, 1H), 7.10 (s, 1H), 4.60 (s, 2H), 3.72 (s, 2H). MS: m/z 526 (M+1).

Example 121

5-(acetylamino)-N-({4-chloro-3-[(3-chloro-5-cyanophenyl)oxy]-2-fluorophenyl}methyl)-1H-indole-2-carboxamide

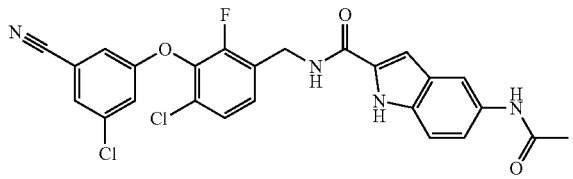

Step A: 1-(1,1-dimethylethyl)2-ethyl 5-nitro-1H-indole-1,2-dicarboxylate

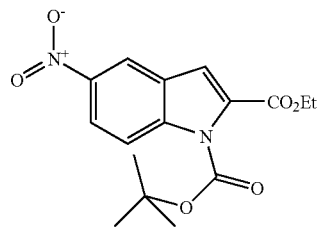

Di-t-butyldicarbonate (1.86 g, 8.55 mmol) and N,N-dimethylaminopyridine (0.52 g, 4.27 mmol) were added to a suspension of ethyl 5-nitro-1H-indole-2-carboxylate (1.00 g, 4.27 mmol) in dichloromethane (30 mL) and THF (8 mL). After stirring at RT for 2 h, 0.2 M HCl in saturated aqueous sodium chloride (80 mL) was added. The mixture was then extracted with dichloromethane. The organic layer was separated, dried over sodium sulfate and concentrated. The residue was purified by column chromatography (hexane/EtOAc) to give the title compound (1.05 g, 74%) as a white solid. $^1$H NMR (400 MHz, CDCl$_3$): δ ppm 8.51 (d, 1H), 8.23-8.29 (m, 1H), 8.10-8.20 (m, 1H), 7.16 (d, 1H), 4.38 (q, 2H), 1.62 (s, 9H), 1.39 (t, 3H). MS: m/z 335 (M+H).

Step B: 1-(1,1-dimethylethyl)2-ethyl 5-amino-1H-indole-1,2-dicarboxylate

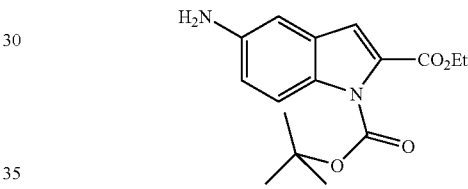

Platinum(IV) oxide (0.0034 g, 0.015 mmol) was added to a suspension of 1-(1,1-dimethylethyl)2-ethyl 5-nitro-1H-indole-1,2-dicarboxylate (0.1 g, 0.299 mmol) in ethanol (4 mL) in a Fisher-Porter vessel. The mixture was evacuated and flushed with nitrogen three times, flushed with hydrogen (60 psi) and evacuated three times, then filled with hydrogen (60 psi). After 45 min, the reaction mixture was filtered through celite. The filtrate was concentrated to give the title compound (91 mg) as a yellow crystalline solid. $^1$H NMR (400 MHz, CDCl$_3$): δ ppm 7.85 (d, 1H), 6.92 (s, 1H), 6.76-6.85 (m, 2H), 4.35 (q, 2H), 3.64 (s, 2H), 1.60 (s, 9H), 1.37 (t, 3H). MS: m/z 305 (M+H).

Step C: 1-(1,1-dimethylethyl)2-ethyl 5-(acetylamino)-1H-indole-1,2-dicarboxylate

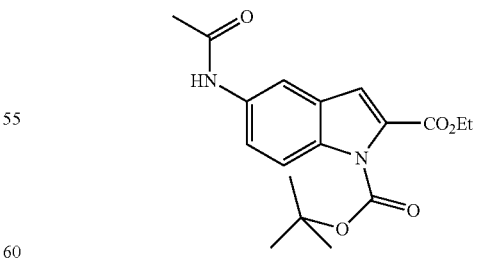

Acetyl chloride (0.019 mL, 0.269 mmol) was added to a solution of 1-(1,1-dimethylethyl)2-ethyl 5-amino-1H-indole-1,2-dicarboxylate (0.082 g, 0.269 mmol) and triethylamine (0.075 mL, 0.539 mmol) in dichloromethane (1.5 mL). After 15 min, the reaction mixture was diluted with dichloromethane and water. The organic layer was separated, dried over sodium sulfate, and concentrated. The residue was purified by column chromatography (hexane/EtOAc) to give the title compound (0.041 g) as a white solid. $^1$H NMR (400 MHz, CDCl$_3$): δ ppm 7.87-7.97 (m, 2H), 7.61 (s, 1H), 7.27 (d, 1H), 6.98 (s, 1H), 4.34 (q, 2H), 2.14 (s, 3H), 1.58 (s, 9H), 1.35 (t, 3H). MS: m/z 347 (M+1).

Step D: 5-(acetylamino)-1H-indole-2-carboxylic acid

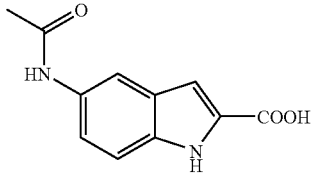

Lithium hydroxide (0.028 g, 1.184 mmol) was added to a solution of 1-(1,1-dimethylethyl)2-ethyl 5-(acetylamino)-1H-indole-1,2-dicarboxylate (0.041 g, 0.118 mmol) in THF:MeOH:water/3:1:1. The reaction mixture was heated at 50° C. for 1 h. The solvent was evaporated. The residue was dissolved in water, acidified with 6N aqueous HCl and extracted with dichloromethane. A solid formed in the aqueous layer which was collected by filtration and dried to give the title compound (0.011 g, 43%) as a white solid. $^1$H NMR (400 MHz, DMSO-d$_6$): δ ppm 12.85 (s, 1H), 11.63 (s, 1H), 9.79 (s, 1H), 7.97 (s, 1H), 7.22-7.38 (m, 2H), 7.01 (s, 1H), 2.01 (s, 3H). MS: m/z 219 (M+1).

Step E: 5-(acetylamino)-N-({4-chloro-3-[(3-chloro-5-cyanophenyl)oxy]-2-fluorophenyl}methyl)-1H-indole-2-carboxamide

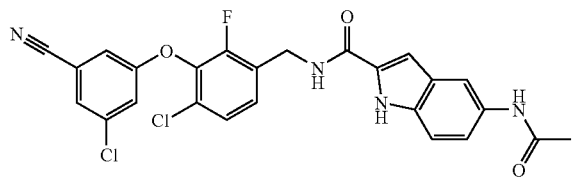

HATU (0.023 g, 0.062 mmol) was added to a solution of 3-{[3-(aminomethyl)-6-chloro-2-fluorophenyl]oxy}-5-chlorobenzonitrile (0.013 g, 0.041 mmol), 5-(acetylamino)-1H-indole-2-carboxylic acid (0.009 g, 0.041 mmol) and DIPEA (0.011 mL, 0.062 mmol) in DMF (0.5 mL). The reaction mixture was stirred at RT overnight and was extracted with ethyl acetate. The organic layer was washed with brine, dried over sodium sulfate and concentrated. The residue was triturated with methanol to give the title compound (0.009 g, 43%) as a white solid. $^1$H NMR (400 MHz, DMSO-d$_6$): δ ppm 11.50 (s, 1H), 9.74 (s, 1H), 8.95 (s, 1H), 7.91 (s, 1H), 7.78 (s, 1H), 7.40-7.49 (m, 3H), 7.32-7.40 (m, 1H), 7.28 (s, 1H), 7.15-7.24 (m, 1H), 7.06 (s, 1H), 4.53 (s, 2H), 1.98 (s, 3H). MS: m/z 511 (M+1).

Example 122

6-(acetylamino)-N-({4-chloro-3-[(3-chloro-5-cyanophenyl)oxy]-2-fluorophenyl}methyl)-1H-indole-2-carboxamide

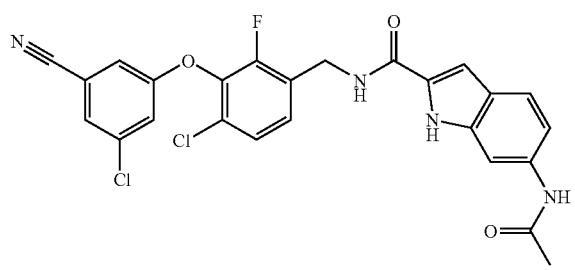

Step A: methyl 6-nitro-1H-indole-2-carboxylate

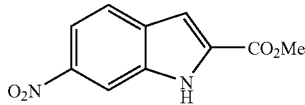

Sulfuric acid (1 mL, 18.76 mmol) was added to a suspension of 6-nitro-1H-indole-2-carboxylic acid (0.5 g, 2.425 mmol) in methanol (5 mL). The mixture was heated to reflux for 2 h. The reaction mixture was cooled to RT, poured into ice/water, neutralized with sodium bicarbonate, and extracted with ethyl acetate. The organic extracts were combined, dried over sodium sulfate, and concentrated to give the title compound (0.433 g, 81%) as a yellow solid. $^1$H NMR (400 MHz, CDCl$_3$): δ ppm 9.31 (s, 1H), 8.41 (s, 1H), 8.05 (dd, 1H), 7.79 (d, 1H), 7.29 (s, 1H), 3.70-4.24 (m, 3H). MS: m/z 221 (M+1).

Step B: 1-(1,1-dimethylethyl)2-methyl 6-nitro-1H-indole-1,2-dicarboxylate

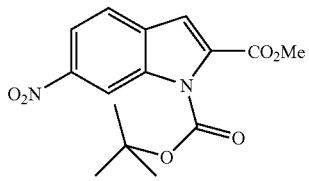

Di-t-butyldicarbonate (0.425 g, 1.948 mmol) and N,N-dimethylaminopyridine (0.238 g, 1.948 mmol) were added to a suspension of methyl 6-nitro-1H-indole-2-carboxylate (0.429 g, 1.948 mmol) in dichloromethane (15 mL). The mixture was stirred at RT for 1 h. The solvent was evaporated and the residue was purified by column chromatography (hexane/EtOAc) to give the title compound (0.455 g, 73%) as an off-white solid. $^1$H NMR (400 MHz, CDCl$_3$): δ ppm 8.87-9.13 (m, 1H), 8.08-8.18 (m, 1H), 7.68 (d, 1H), 7.07 (s, 1H), 3.93 (s, 3H), 1.70 (s, 9H). MS: m/z 321 (M+1).

Step C: 1-(1,1-dimethylethyl)2-methyl 6-amino-1H-indole-1,2-dicarboxylate

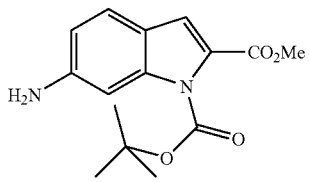

Platinum(IV) oxide (0.016 g, 0.069 mmol) was added to a suspension of 1-(1,1-dimethylethyl)2-methyl 6-nitro-1H-indole-1,2-dicarboxylate (0.443 g, 1.383 mmol) in ethanol (20 mL). The mixture was evacuated and flushed with nitrogen three times, flushed with hydrogen (50 Psi) and evacuated three times, then filled with hydrogen (50 psi). After 1 h, ethyl acetate was added and the mixture was filtered through Celite. The solvent was evaporated to afford the title compound (0.373 g, 93%) as a white solid. $^1$H NMR (400 MHz, CDCl$_3$-d): δ ppm 7.41 (d, 1H), 7.35 (d, 1H), 7.04 (s, 1H), 6.65 (dd, 1H), 3.88 (s, 3H), 1.55 (s, 9H). MS: m/z 291 (M+1).

Step D: 1-(1,1-dimethylethyl)2-methyl 6-(acetylamino)-1H-indole-1,2-dicarboxylate

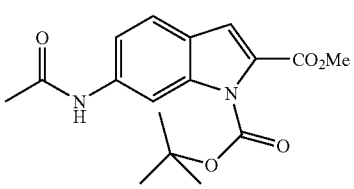

Acetyl chloride (0.027 mL, 0.379 mmol) was added to a solution of 1-(1,1-dimethylethyl)2-methyl 6-amino-1H-indole-1,2-dicarboxylate (0.100 g, 0.344 mmol) and triethylamine (0.096 mL, 0.689 mmol) in dichloromethane (2 mL). After 30 minutes the reaction mixture was diluted wih dichloromethane and water. The organic layer was separated, dried over sodium sulfate and concentrated. The residue was purified by column chromatography (hexane/EtOAc) to give the title compound (0.089 g, 94%) as a white solid. $^1$H NMR (400 MHz, CDCl$_3$): δ ppm 8.33 (s, 1H), 7.52 (d, 1H), 7.41 (d, 1H), 7.33 (s, 1H), 7.07 (s, 1H), 3.91 (s, 3H), 2.21 (s, 3H), 1.60 (s, 9H). MS: m/z 332 (M)

Step E: 6-(acetylamino)-1H-indole-2-carboxylic acid

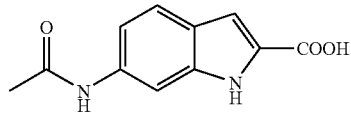

Lithium hydroxide (0.063 g, 2.65 mmol) was added to a solution of 1-(1,1-dimethylethyl)2-methyl 6-(acetylamino)-1H-indole-1,2-dicarboxylate (0.088 g, 0.265 mmol) in THF: methanol:water/3:1:1 (3.5 mL). The mixture was heated at 50° C. for 1 h. The solvent was evaporated. The residue was dissolved in water, acidified with 1N aqueous HCl and extracted with ethyl acetate. The organic layer was dried over sodium sulfate and concentrated to give the title compound (0.033 g, 54%) as a light yellow solid. $^1$H NMR (400 MHz, DMSO-d$_5$): δ ppm 12.72 (s, 1H), 11.57 (s, 1H), 9.92 (s, 1H), 7.99 (s, 1H), 7.50 (d, 1H), 7.07 (dd, 1H), 6.96-7.00 (m, 1H), 2.12 (s, 3H). MS: m/z 219 (M+1).

Step F: 6-(acetylamino)-N-({4-chloro-3-[(3-chloro-5-cyanophenyl)oxy]-2-fluorophenyl}methyl)-1H-indole-2-carboxamide

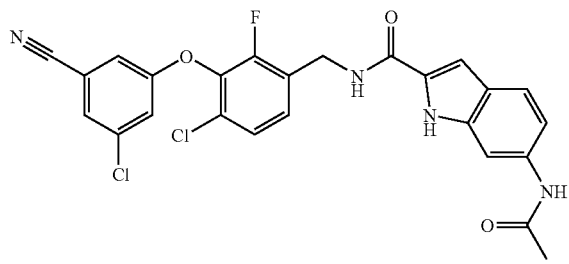

HATU (0.086 g, 0.227 mmol) was added to a solution of 3-{[3-(aminomethyl)-6-chloro-2-fluorophenyl]oxy}-5-chlorobenzonitrile (0.047 g, 0.151 mmol), 6-(acetylamino)-1H-indole-2-carboxylic acid (0.033 g, 0.151 mmol) and DIPEA (0.040 mL, 0.227 mmol) in DMF (1 mL). The mixture was stirred at RT for 2 h. The reaction mixture was diluted with ethyl acetate and water. The organic layer was washed with water and dried over sodium sulfate, and the solvent was evaporated. The resulting oil was triturated with methylene chloride:methanol. The resulting solid was collected by filtration and dried under vacuum to give the title compound (0.024 g, 31%) as an off-white solid. $^1$H NMR (400 MHz, DMSO-d$_6$): δ ppm 11.46 (s, 1H), 9.85 (s, 1H), 9.01 (m, 1H), 7.91 (s, 1H), 7.80 (s, 1H), 7.40-7.53 (m, 4H), 7.35 (t, 1H), 7.11 (m, 2H), 4.51 (d, 2H), 2.00 (s, 3H). MS: m/z 511 (M+1).

Example 123

6-amino-N-({4-chloro-3-[(3-chloro-5-cyanophenyl)oxy]-2-fluorophenyl}methyl)-1H-indole-2-carboxamide trifluoroacetate

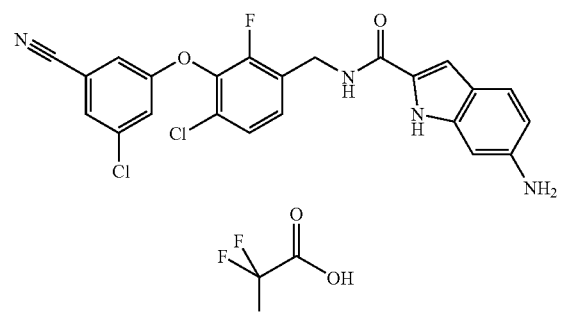

Step A: methyl 6-amino-1H-indole-2-carboxylate

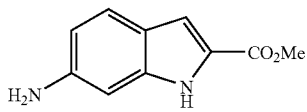

Trifluoroacetic acid (0.5 mL, 6.49 mmol) was added to a solution of 1-(1,1-dimethylethyl)2-methyl 6-amino-1H-indole-1,2-dicarboxylate (0.150 g, 0.517 mmol) in dichloromethane (2 mL). The mixture was stirred at RT for 2 h. The solvent was evaporated to give the title compound (0.175 g, 81%) as a white solid. $^1$H NMR (400 MHz, DMSO-d$_6$): δ ppm 11.86 (s, 1H), 8.89 (br. s., 2H), 7.61 (d, 1H), 7.16 (s, 1H), 7.12 (d, 1H), 6.85 (dd, 1H), 3.84 (s, 3H). MS m/z 191 (M+1)

Step B: methyl 6-({[(1,1-dimethylethyl)oxy]carbonyl}amino)-1H-indole-2-carboxylate

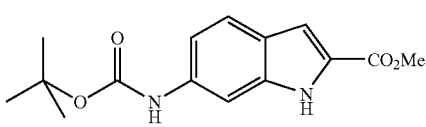

Di-t-butyldicarbonate (0.089 g, 0.406 mmol) and triethylamine (0.170 mL, 1.219 mmol) were added to a solution of methyl 6-amino-1H-indole-2-carboxylate (0.170 g, 0.406 mmol) in dichloromethane (5 mL). The mixture was stirred at RT for 1 h then diluted with dichloromethane and washed with water and brine. The organic layer was separated, dried over sodium sulfate and evaporated to give the title compound (0.134 g, >99%) as a light pink solid. $^1$H NMR (400 MHz, CDCl$_3$): δ ppm 8.75 (s, 1H), 7.81 (s, 1H), 7.55 (d, 1H), 7.15 (d, 1H), 6.83 (dd, 1H), 6.59 (s, 1H), 3.93 (s, 3H), 1.55 (s, 9H). MS: m/z 289 (M−1).

Step C: 6-({[(1,1-dimethylethyl)oxy]carbonyl}amino)-1H-indole-2-carboxylic acid

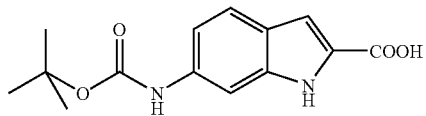

Lithium hydroxide (0.095 g, 3.96 mmol) was added to a solution of methyl 6-({[(1,1-dimethylethyl)oxy]carbonyl}amino)-1H-indole-2-carboxylate (0.115 g, 0.396 mmol) in a 3:1:1 mixture of THF:methanol:water (2 ml). The reaction mixture was stirred at RT overnight. The solvent was evaporated. The residue was dissolved in water and acidified with 1N aqueous HCl. The resulting suspension was extracted with ethyl acetate. The organic layer was separated, dried over sodium sulfate and the solvent was evaporated to give the title compound (0.115 g, >99%) as an off-white solid. $^1$H NMR (400 MHz, DMSO-$d_6$): δ ppm 11.18 (s, 1H), 9.21 (s, 1H), 7.70 (s, 1H), 7.37 (d, 1H), 6.93 (dd, 1H), 6.74 (s, 1H), 1.46 (s, 9H). MS: m/z 275 (M−1).

Step D: 1,1-dimethylethyl (2-{[({4-chloro-3-[(3-chloro-5-cyanophenyl)oxy]-2-fluorophenyl}methyl)amino]carbonyl}-1H-indol-6-yl)carbamate

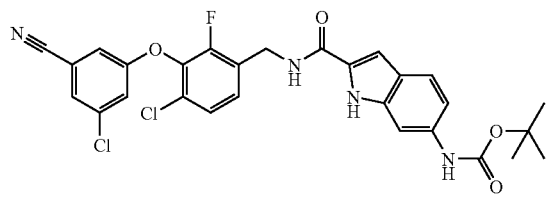

HATU (0.104 g, 0.272 mmol) was added to a solution of 3-{[3-(aminomethyl)-6-chloro-2-fluorophenyl]oxy}-5-chlorobenzonitrile (0.056 g, 0.182 mmol), 6-({[(1,1-dimethylethyl)oxy]carbonyl}amino)-1H-indole-2-carboxylic acid (0.050 g, 0.182 mmol) and DIPEA (0.048 mL, 0.272 mmol) in DMF (1.5 mL). The mixture was stirred at RT for 1.5 h. The reaction mixture was diluted with ethyl acetate and water. The organic layer was washed with water and brine, dried over sodium sulfate, and the solvent was evaporated. The residue was purified by column chromatography (hexane/EtOAc) to give the title compound (0.056 g, 48%) as an off-white solid. $^1$H NMR (400 MHz, CDCl$_3$): δ ppm 9.74 (s, 1H), 7.78 (s, 1H), 7.44 (d, 1H), 7.27-7.37 (m, 2H), 7.21 (dd, 1H), 7.08-7.13 (m, 1H), 6.98 (d, 1H), 6.74-6.86 (m, 3H), 6.63 (s, 1H), 4.66 (d, 2H), 1.50 (s, 9H). MS: m/z 569 (M+1).

Step E: 6-amino-N-({4-chloro-3-[(3-chloro-5-cyanophenyl)oxy]-2-fluorophenyl}methyl)-1H-indole-2-carboxamide trifluoroacetate

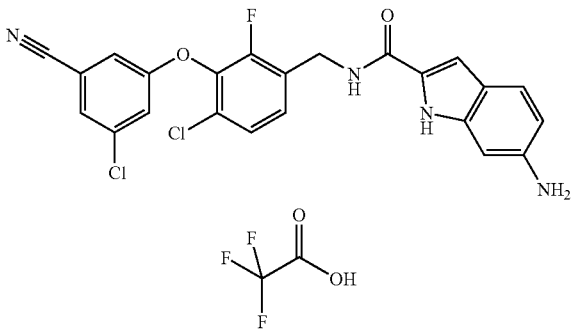

Trifluoroacetic acid (0.5 mL, 6.49 mmol) was added to a solution of 1,1-dimethylethyl (2-{[({4-chloro-3-[(3-chloro-5-cyanophenyl)oxy]-2-fluorophenyl}methyl)amino]carbonyl}-1H-indol-6-yl)carbamate (0.046 g, 0.081 mmol) in dichloromethane (2 mL). The mixture was stirred at RT overnight. The solvent was evaporated and the residue was purified by column chromatography (dichloromethane/methanol) to give the title compound (0.037 g, 74%) as a grey solid. $^1$H NMR (400 MHz, DMSO-$d_6$) δ ppm 11.73 (s, 1H), 9.35 (br. s., 2H), 9.04 (s, 1H), 7.80 (s, 1H), 7.63 (d, 1H), 7.44-7.54 (m, 3H), 7.38 (t, 1H), 7.27 (s, 1H), 7.17 (s, 1H), 6.88 (d, 1H), 4.55 (d, 2H). MS: m/z 548 (M+1).

Example 124

N-({4-chloro-3-[(3-chloro-5-cyanophenyl)oxy]-2-fluorophenyl}methyl)-5-nitro-1H-benzimidazole-2-carboxamide

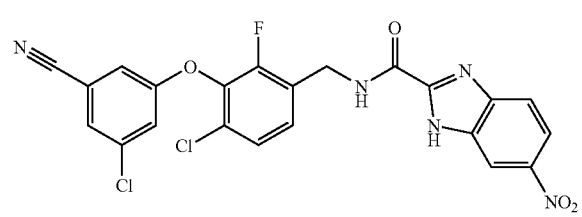

Step A: 5-nitro-1H-benzimidazole-2-carboxylic acid

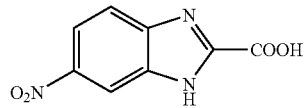

Methyl 2,2,2-trichloroacetimidate (0.73 g, 4.09 mmol) and trifluoroacetic acid (0.63 mL, 8.17 mmol) were added to a suspension of 4-nitrophenylenediamine (0.50 g, 3.27 mmol) in a 2:3 mixture of dichloromethane/diethyl ether (40 mL). After stirring at RT for 3 h, the reaction mixture was filtered. The residue in the filter was washed with a 1:1 mixture of dichloromethane:ether. The filtrates were combined and shaken with 1.5N aqueous sodium hydroxide (40 mL). The organic layer was removed. A 1:1 mixture of methanol/ether (40 mL) was added, and the mixture was stirred at RT overnight. The precipitated yellow solid was collected by filtration, suspended in water and the mixture acidified with 6N aqueous HCl. The precipitate was collected by filtration and dried under vacuum overnight to give the title compound (0.331 g, 49%) as a white solid. $^1$H NMR (400 MHz, DMSO-$d_6$): δ 8.56 (s, 1H), 8.20 (d, 1H), 7.79 (d, 1H). MS: m/z 208 (M+H).

Step B: N-({4-chloro-3-[(3-chloro-5-cyanophenyl)oxy]-2-fluorophenyl}methyl)-5-nitro-1H-benzimidazole-2-carboxamide

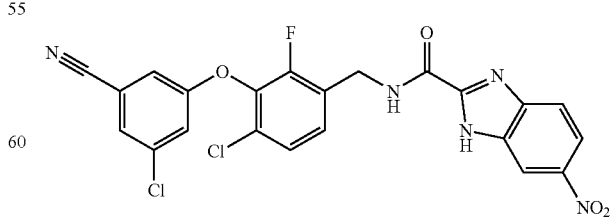

HATU (0.055 g, 0.145 mmol) was added to a solution of 3-{[3-(aminomethyl)-6-chloro-2-fluorophenyl]oxy}-5-chlorobenzonitrile (0.030 g, 0.096 mmol), 5-nitro-1H-benzimidazole-2-carboxylic acid (0.020 g, 0.096 mmol), and DIPEA (0.025 mL, 0.145 mmol) in DMF. After stirring at RT overnight, the reaction mixture was diluted with ethyl acetate and water. The organic layer was separated, dried over sodium sulfate and the solvent was evaporated to give 0.028 g of a yellow oil. The reaction was repeated to give 0.038 g of the same material. The crude products were combined, triturated with methanol, and dried under vacuum to give the title compound (0.012 g, 25% combined) as a white solid. $^1$H NMR (400 MHz, DMSO-d$_6$): δ ppm 9.76 (s, 1H), 8.51 (s, 1H), 8.19 (d, 1H), 7.69-7.88 (m, 2H), 7.44-7.55 (m, 3H), 7.34-7.44 (m, 1H), 4.58 (d, 2H). MS: m/z 499.9 (M+H).

Example 125

5-(acetylamino)-N-({4-chloro-3-[(3-chloro-5-cyanophenyl)oxy]-2-fluorophenyl}methyl)-1H-benzimidazole-2-carboxamide

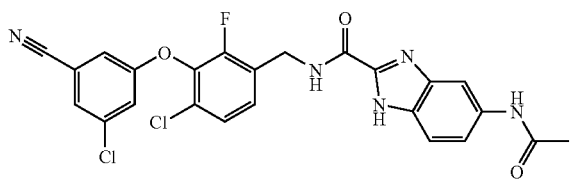

Step A: 1,1-dimethylethyl 5-nitro-1H-benzimidazole-2-carboxylate

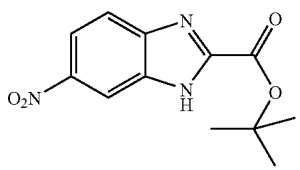

Di-t-butyldicarbonate (2.107 g, 9.66 mmol) and N,N-dimethylaminopyridine (1.180 g, 9.66 mmol) were added to a suspension of 5-nitro-1H-benzimidazole-2-carboxylic acid (1.00 g, 4.83 mmol) which was prepared according to literature procedures (*Heterocycles* 2006, 67, 769) in dichloromethane (20 mL). Vigorous gas evolution was observed. After 2 h, the reaction mixture was filtered. The filtrate was concentrated and the residue was subjected to column chromatography (hexane/EtOAc) to give the title compound (0.149 g) as a white solid. An additional 1 g of material, as a mixture of the desired t-butyl ester and N,N-dimethylaminopyridine was isolated. This material was dissolved in ethyl acetate and washed with 1N aqueous HCl. The organic layer was separated, dried over sodium sulfate and concentrated to give additional title compound (0.359 g, 39% combined). $^1$H NMR (400 MHz, CDCl$_3$): δ ppm 8.72 (s, 1H), 8.30 (dd, 1H), 7.78 (d, 1H), 1.68 (s, 9H). MS: m/z 262 (M-1).

Step B: 1,1-dimethylethyl 5-amino-1H-benzimidazole-2-carboxylate

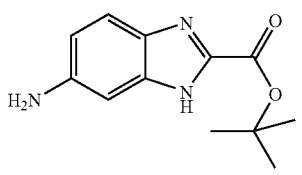

Platinum(IV) oxide (0.020 g, 0.090 mmol) was added to a suspension of 1,1-dimethylethyl 5-nitro-1H-benzimidazole-2-carboxylate (0.472 g, 1.793 mmol) in ethanol (20 mL) in a pressure vessel. The mixture was evacuated and flushed with nitrogen, then evacuated and flushed with hydrogen (50 Psi). After 1 h, the reaction mixture was filtered through Celite. The filtrate was concentrated and the residue was dried under vacuum to give the title compound (0.359 g, 69%) as a yellow solid. $^1$H NMR (400 MHz, CDCl$_3$): δ ppm 10.03 (s, 1H), 7.66 (d, 1H), 6.49-6.90 (m, 2H), 3.77 (br. s., 2H), 1.64 (s, 9H). MS: m/z 234 (M+1).

Step C: 1,1-dimethylethyl 5-(acetylamino)-1H-benzimidazole-2-carboxylate

A suspension of 1,1-dimethylethyl 5-amino-1H-benzimidazole-2-carboxylate (0.147 g, 0.630 mmol) in dichloromethane (5 mL) was cooled in an ice bath. Pyridine (0.076 mL, 0.945 mmol) and acetic anhydride (0.059 mL, 0.630 mmol) were added. The reaction mixture was filtered and the collected solid was washed with dichloromethane and dried under vacuum to give the title compound (0.160 g, 92%) as a white solid. $^1$H NMR (400 MHz, DMSO-d$_6$): δ ppm 13.06 (s, 1H), 10.05 (s, 1H), 8.14 (s, 1H), 7.61 (m, 1H), 7.24 (m, 1H), 2.04 (s, 3H), 1.55 (s, 9H). MS: m/z 276 (M+1).

Step D: 5-(acetylamino)-1H-benzimidazole-2-carboxylic acid

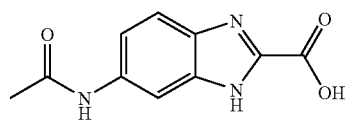

Trifluoroacetic acid (0.5 mL, 6.49 mmol) was added to a suspension of 1,1-dimethylethyl 5-(acetylamino)-1H-benzimidazole-2-carboxylate (0.155 g, 0.563 mmol) in dichloromethane (2 mL). After stirring at RT overnight, the solvent was evaporated to give the title compound (0.166 g, 88%) as a white solid. $^1$H NMR (400 MHz, DMSO-d$_6$): δ ppm 10.17 (s, 1H), 8.19 (d, 1H), 7.61 (d, 1H), 7.40 (dd, 1H), 2.1 (s, 3 H). MS: m/z 218 (M-1).

Step E: 5-(acetylamino)-N-({4-chloro-3-[(3-chloro-5-cyanophenyl)oxy]-2-fluorophenyl}methyl)-1H-benzimidazole-2-carboxamide

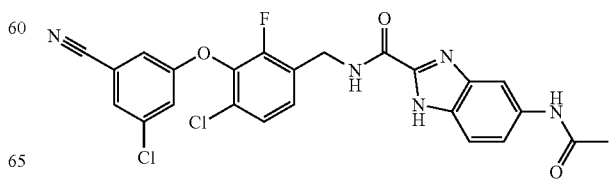

HATU (0.092 g, 0.241 mmol) was added to a solution of 5-(acetylamino)-1H-benzimidazole-2-carboxylic acid (0.035 g, 0.161 mmol), 3-{[3-(aminomethyl)-6-chloro-2-fluorophenyl]oxy}-5-chlorobenzonitrile (0.050 g, 0.161 mmol), and DIPEA (0.031 g, 0.241 mmol) in DMF (1 mL). After stirring at RT overnight, the reaction mixture was diluted with ethyl acetate and water. The organic layer was washed with water, dried over sodium sulfate and concentrated. The crude product was purified by Reverse-Phase HPLC (water/acetonitrile with 0.1% TFA) to give the title compound (0.007 g, 8.5%) as a white solid. $^1$H NMR (400 MHz, DMSO-$d_6$): δ ppm 10.03 (s, 1H), 9.48 (s, 1H), 8.11 (m, 1H), 7.74-7.90 (m, 1H), 7.43-7.67 (m, 4H), 7.35-7.44 (m, 1H), 7.26-7.34 (m, 1H), 4.55 (s, 2H), 2.05 (s, 3H). MS: m/z 512 (M+1).

Example 126

N-({4-chloro-3-[(3-chloro-5-cyanophenyl)oxy]-2-fluorophenyl}methyl)-5-(dimethylamino)-1H-indole-2-carboxamide

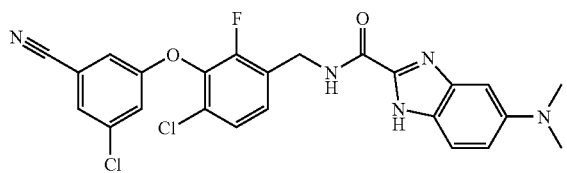

Triethylamine (0.036 mL, 0.257 mmol) was added to a suspension of 5-amino-N-({4-chloro-3-[(3-chloro-5-cyanophenyl)oxy]-2-fluorophenyl}methyl)-1H-indole-2-carboxamide trifluoroacetate (100 mg, 0.171 mmol) in dichloroethane (4 mL). To this suspension was added formaldehyde (37% aqueous solution) (0.019 mL, 0.257 mmol), acetic acid (0.049 mL, 0.857 mmol) and sodium triacetoxyborohydride (145 mg, 0.686 mmol). The mixture was stirred at RT for 1 h. Saturated aqueous sodium bicarbonate was added until the pH ~8-9. The mixture was extracted with ethyl acetate. The organic layer was dried over sodium sulfate and concentrated. The residue was purified by column chromatography (hexane/EtOAc) to give the title compound (0.035 g, 41%) as a light yellow solid. $^1$H NMR (400 MHz, DMSO-$d_6$): δ ppm 11.23 (s, 1H), 8.88 (s, 1H), 7.77 (s, 1H), 7.41-7.58 (m, 3H), 7.30-7.40 (m, 1H), 7.18-7.29 (m, 1H), 6.96 (s, 1H), 6.81 (s, 2H), 4.52 (s, 2H), 2.81 (s, 6H). MS: m/z 497 (M+1).

Example 127

5-[bis(cyclopropylmethyl)amino]-N-({4-chloro-3-[(3-chloro-5-cyanophenyl)oxy]-2-fluorophenyl}methyl)-1H-indole-2-carboxamide

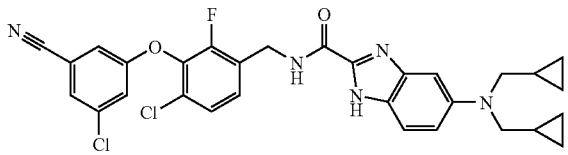

Triethylamine (0.049 mL, 0.355 mmol) was added to a suspension of 5-amino-N-({4-chloro-3-[(3-chloro-5-cy-anophenyl)oxy]-2-fluorophenyl}methyl)-1H-indole-2-carboxamide trifluoroacetate (0.207 g, 0.355 mmol) in dichloroethane (5 mL). To the resulting solution was added cyclopropanecarbaldehyde (0.027 mL, 0.355 mmol) and sodium triacetoxyborohydride (0.188 g, 0.887 mmol). After stirring at RT overnight, the reaction mixture was diluted with ethyl acetate and washed with saturated aqueous sodium bicarbonate. The organic layer was dried over sodium sulfate and concentrated. The residue was purified by column chromatography (dichloromethane/methanol) to give the title compound (0.075 g, 37%) as a yellow solid. $^1$H NMR (400 MHz, DMSO-$d_6$): δ ppm 11.23 (d, 1H), 8.89 (t, 1H), 7.80 (d, 1H), 7.43-7.55 (m, 3H), 7.33-7.41 (m, 1H), 7.24 (d, 1H), 6.86-7.00 (m, 3H), 4.54 (d, 2H), 3.16 (d, 4H), 0.75-1.05 (m, 2H), 0.21-0.57 (m, 4H), −0.05-0.26 (m, 4H). MS: m/z 577 (M+1).

Example 128

3-chloro-N-({4-chloro-3-[(3-chloro-5-cyanophenyl)oxy]-2-fluorophenyl}methyl)-1H-pyrrole-2-carboxamide

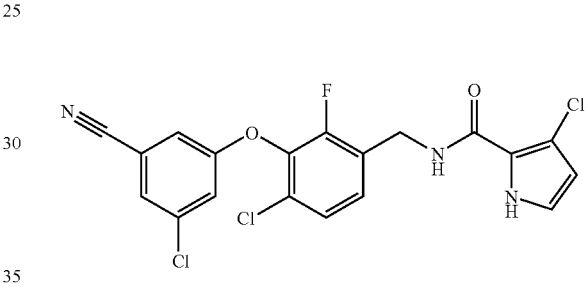

Step A: methyl 3-chloro-1H-pyrrole-2-carboxylate

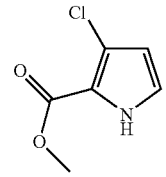

5-Methyl-3,4-dihydro-2H-pyrrole (1.00 g, 12.0 mmol) was dissolved in carbon tetrachloride. To the solution was added NCS (12.85 g, 96 mmol) as a solid and reaction mixture heated to 85° C. and stirred overnight. The mixture was cooled to 0° C. and the precipitate filtered off and the solvent evaporated. The residue was dissolved in methanol and sodium methoxide (3.90 g, 72.2 mmol) was added. The resulting suspension was heated to reflux and stirred for 3 h. The methanol was evaporated and the residue suspended in Et2O. The solid was filtered off and the ether evaporated. The residue was dissolved in DCM and 2M HCl was added. The biphasic solution was stirred until no SM remained. The phases were separated and the organic layer was dried over MgSO$_4$ and evaporated to an orange oil. The crude oil was adsorbed onto silica and run on 40 g of silica with EtOAc and Hexanes to afford the title compound as an orange solid (0.2958 g, 1.854 mmol, 15.41% yield). $^1$H NMR (400 MHz, CDCl$_3$): δ ppm 9.54 (br. s., 1H), 6.80 (s., 1H), 6.17 (s., 1H), 3.83 (s, 3H). MS: m/z 160.0 (M+1).

Step B: 3-chloro-1H-pyrrole-2-carboxylic acid

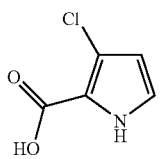

A solution of 1M LiOH (7.415 ml, 7.415 mmole) was added to methyl 3-chloro-1H-pyrrole-2-carboxylate (0.2958 g, 1.854 mmole) dissolved in methanol (4 ml). To the solution was added THF (4 ml) and the resulting mixture was heated to 60° C. for 4 h. The mixture was acidified with 1M HCl and partitioned with EtOAc. The organic phase was dried over MgSO$_4$ and evaporated to afford the title compound (0.2331 g, 86%) as a brownish solid. $^1$H NMR (400 MHz, Acetone-d$_6$): δ ppm 11.01 (br. s., 1H), 7.03 (t, 1H), 6.23 (t, 1H). MS: m/z 146.2 (M+1).

Step C: 3-chloro-N-({4-chloro-3-[(3-chloro-5-cyanophenyl)oxy]-2-fluorophenyl}methyl)-1H-pyrrole-2-carboxamide

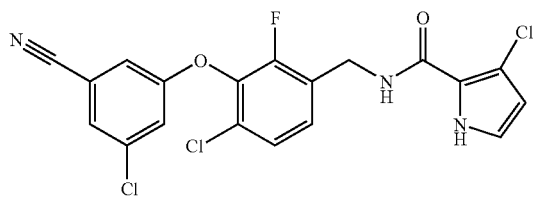

HATU (0.061 g, 0.16 mmole) was added to a DMF (2 ml) solution of 3-{[3-(aminomethyl)-6-chloro-2-fluorophenyl]oxy}-5-chlorobenzonitrile (0.050 g, 0.16 mmole) and 3-chloro-1H-pyrrole-2-carboxylic acid (0.023 g, 0.16 mmole) in DMF. DIPEA (0.021 g, 0.16 mmole) was added and the solution stirred for 2 h. The mixture was partitioned between EtOAc and water. The organic layer was separated and washed with 15% NaHCO3 and dried over MgSO4 and the EtOAc evaporated. The residue was purified on silica with EtOAc and Hexanes to afford the title compound (0.0187 g, 26%) as a white solid. $^1$H NMR (400 MHz, Acetone-d$_6$): δ ppm 10.93 (br. s., 1H), 7.62-7.67 (m, 1H), 7.56-7.62 (m, 1H), 7.37-7.48 (m, 4H), 7.02 (t, 1H), 6.23 (t, 1H), 4.72 (d, 2H). MS: m/z 438.1 (M+1).

Example 129

N-({4-chloro-3-[(3-chloro-5-cyanophenyl)oxy]-2-fluorophenyl}methyl)-N-methyl-1H-pyrrole-2-carboxamide

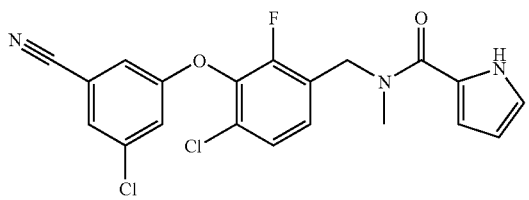

Step A: 3-chloro-5-({6-chloro-2-fluoro-3-[(methylamino)methyl]phenyl}oxy)benzonitrile

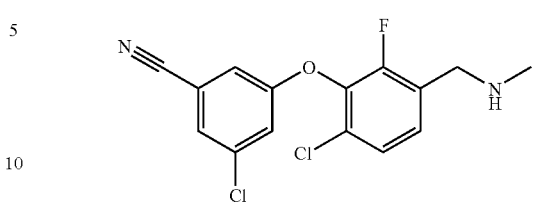

A solution of 3-{[3-(bromomethyl)-6-chloro-2-fluorophenyl]oxy}-5-chlorobenzonitrile (1.04 g, 2.77 mmol) in CH$_2$Cl$_2$ (10 mL) was added dropwise to a 2M solution of MeNH$_2$ (13.9 mL, 27.73 mmol) in THF. The solution turned light yellow and the flask was stoppered and stirred at RT overnight. Ethyl acetate (200 ml) and saturated NaHCO$_3$ solution (150 ml) were added. The organic layer was separated, washed with brine (150 mL), dried over MgSO$_4$, filtered and concentrated to give the title compound (0.81 g, 90%) as a yellow oil. $^1$H NMR (400 MHz, CDCl$_3$) δ ppm 7.30-7.33 (m, 1H), 7.24-7.30 (m, 2H), 7.11-7.14 (m, 1H), 6.98 (dd, 1H), 3.81 (s, 2H), 2.45 (s, 3H).

Step B: N-({4-chloro-3-[(3-chloro-5-cyanophenyl)oxy]-2-fluorophenyl}methyl)-N-methyl-1H-pyrrole-2-carboxamide

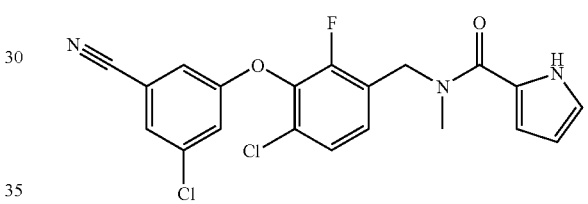

HATU (0.16 g, 0.43 mmol) was added to a solution of 3-chloro-5-({6-chloro-2-fluoro-3-[(methylamino)methyl]phenyl}oxy)benzonitrile (0.10 g, 0.30 mmol) and 1H-pyrrole-2-carboxylic acid (0.05 g, 0.43 mmol) in DMF (3 mL) and the solution was stirred at RT overnight. After 16 h, ethyl acetate (100 ml) and saturated NaHCO$_3$ solution (100 ml) were added. The organic layer was separated, washed with saturated NaHCO$_3$ solution (2×100 ml), brine (150 mL), dried over MgSO$_4$, filtered and concentrated. The crude material was purified by Reverse Phase HPLC to give the title compound (0.042 g, 33%) as a white solid. $^1$H NMR (400 MHz, CDCl$_3$) δ ppm 9.77 (d, 1H), 7.34-7.40 (m, 1H), 7.21-7.33 (m, 3H), 7.17 (t, 1H), 7.01-7.05 (m, 1H), 6.99 (d, 1H), 6.28 (d, 1H), 4.85 (br. s., 2H), 3.33 (br. s., 3H).

Example 130

N-({4-chloro-3-[(3-chloro-5-cyanophenyl)oxy]-2-fluorophenyl}methyl)-N-methyl-1H-imidazole-2-carboxamide

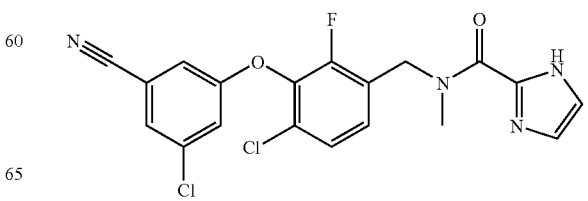

HATU (0.16 g, 0.43 mmol) was added to a solution of 3-chloro-5-({6-chloro-2-fluoro-3-[(methylamino)methyl]phenyl}oxy)benzonitrile (0.10 g, 0.30 mmol) and 1H-imidazole-2-carboxylic acid (0.05 g, 0.43 mmol) in DMF (3 mL) and the solution was stirred at RT overnight. After 16 h, ethyl acetate (100 ml) and saturated NaHCO₃ solution (100 ml) were added. The organic layer was separated, washed with saturated NaHCO₃ solution (2×100 ml), brine (150 mL), dried over MgSO₄, filtered and concentrated. The crude material was purified by Reverse Phase HPLC to give the title compound (0.025 g, 20%) as a white solid. $^1$H NMR (400 MHz, DMSO-d$_6$) δ ppm 7.82 (s, 1H), 7.46-7.57 (m, 3H), 7.27-7.37 (m, 2H), 7.18 (s, 1H), 5.57 (s, 1H), 4.77 (s, 1H), 3.53 (s, 1.5H), 2.98 (s, 1.5H). $^{19}$F NMR (376 MHz, DMSO-d$_6$) δ ppm −75.19 (s, 1F). LCMS m/z 418 (M−1).

Example 131

4-chloro-N-({4-chloro-3-[(3-chloro-5-cyanophenyl)oxy]-2-fluorophenyl}methyl)-1H-imidazole-5-carboxamide

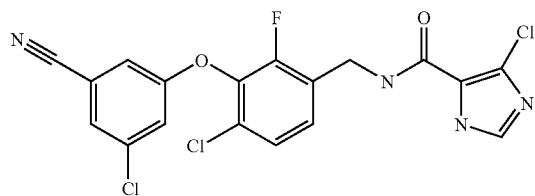

Step A: methyl 4-chloro-1H-imidazole-5-carboxylate

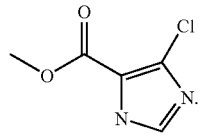

N-chlorosuccinimide (0.318 g, 2.4 mmol) was added to a stirred solution of methyl 1H-imidazole-4-carboxylate (0.300 g, 2.4 mmol) in CH₃CN (16 mL). The reaction mixture was stirred for 12 h in the dark and then concentrated. The white residue was taken up in EtOAc, satd. aqueous Na₂S (10 mL) was added and the solution was stirred for 15 min. The organic layer was isolated, dried (Na₂SO₄), concentrated and the crude product was purified by column chromatography (20-70% EtOAc/hexanes) to afford the title compound (0.061 g, 16%) as a white solid. $^1$H NMR (400 MHz, DMSO-d$_6$) δ ppm 11.05 (br. s., 1H), 7.85 (s, 1H), 3.81 (s, 3H). ES-LCMS: m/z 160.9, 162.9 (M+1).

Step B: 4-chloro-N-({4-chloro-3-[(3-chloro-5-cyanophenyl)oxy]-2-fluorophenyl}methyl)-1H-imidazole-5-carboxamide

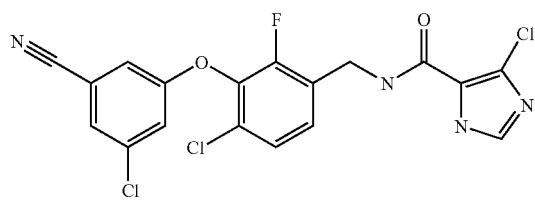

A solution of methyl 4-chloro-1H-imidazole-5-carboxylate (0.061 g, 0.4 mmol) was stirred in a solution of MeOH (2 mL), dioxane (2 mL) and 2N NaOH (1.9 mL, 3.8 mmol) at RT for 4 days. The reaction mixture was then acidified by addition of 1M HCl (20 mL) and extracted with EtOAc. The organic extracts were dried (Na₂SO₄), and the solvent was evaporated to provide 4-chloro-1H-imidazole-5-carboxylic acid (0.0523 g, 94%) as a white solid which was used without further purification. 4-Chloro-N-({4-chloro-3-[(3-chloro-5-cyanophenyl)oxy]-2-fluorophenyl}methyl)-1H-imidazole-5-carboxamide was prepared in a similar manner as described herein from 3-{[3-aminomethyl)-6-chloro-2-fluorophenyl]oxy}-5-chlorobenzonitrile (0.054 g, 0.17 mmol), 4-chloro-1H-imidazole-5-carboxylic acid (0.026 g, 0.17 mmol), HATU (0.086 g, 0.23 mmol), DIPEA (0.039 mL, 0.23 mmol) and DMF (2 mL). Purification was accomplished by Reverse-Phase HPLC (water/acetonitrile with 0.1% TFA) to afford the title compound (0.008 g, 10%) as a white solid. $^1$H NMR (400 MHz, DMSO-d$_6$): δ ppm 13.16 (br. s., 1H), 8.24 (br. s., 1H), 7.82 (s, 1H), 7.78 (s, 1H), 7.45-7.54 (m, 3H), 7.35-7.42 (m, 1H), 4.54 (s, 2H). ES-LCMS: m/z 439.0, 441.0 (M+1).

Example 132

4-chloro-N-({4-chloro-3-[(3-chloro-5-cyanophenyl)oxy]-2-fluorophenyl}methyl)-N-methyl-1'-imidazole-5-carboxamide trifluoroacetate

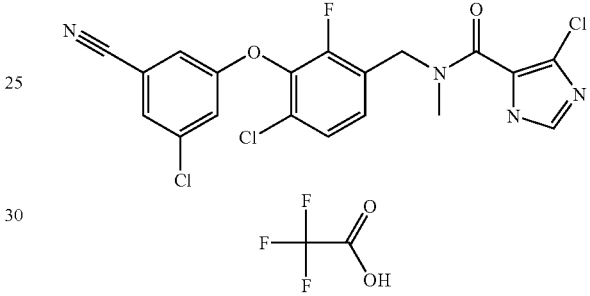

4-Chloro-N-({4-chloro-3-[(3-chloro-5-cyanophenyl)oxy]-2-fluorophenyl}methyl)-N-methyl-1H-imidazole-5-carboxamide trifluoroacetate was prepared in a similar manner as described herein from 3-chloro-5-({6-chloro-2-fluoro-3-[(methylamino)methyl]phenyl}oxy)benzonitrile (0.057 g, 0.17 mmol), 4-chloro-1H-imidazole-5-carboxylic acid (0.026 g, 0.17 mmol), HATU (0.086 g, 0.23 mmol), DIPEA (0.039 mL, 0.23 mmol) and DMF (2 mL). Purification was accomplished by Reverse-Phase HPLC (water/acetonitrile with 0.1% TFA) to afford the title compound (0.005 g, 11%) as a white solid. $^1$H NMR (400 MHz, DMSO-d$_6$) δ ppm 7.82 (s, 1H), 7.77 (s, 1H), 7.44-7.58 (m, 3H), 7.30-7.40 (m, 1H), 4.74 (s, 2H), 3.00 (br. s., 3 H). ES-LCMS: m/z 453.0, 455.0 (M+1).

Example 133

4-bromo-N-({4-chloro-3-[(3-chloro-5-cyanophenyl)oxy]-2-fluorophenyl}methyl)-1H-imidazole-5-carboxamide trifluoroacetate

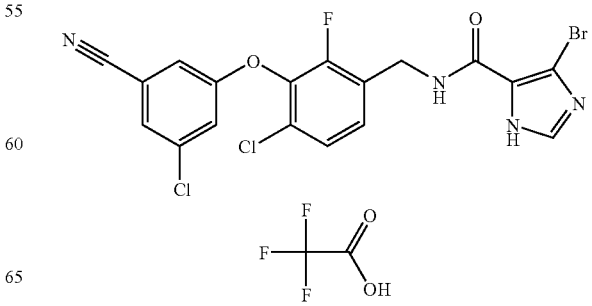

135

Step A: methyl 4-bromo-1H-imidazole-5-carboxylate

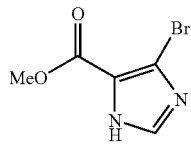

N-bromosuccinimide (0.900 g, 5.0 mmol) was added to a stirred solution of methyl 1H-imidazole-4-carboxylate (0.630 g, 5.0 mmol) in CH$_3$CN (50 mL). The reaction mixture was stirred for 12 h in the dark and then concentrated in the presence of silica gel. The absorbed crude material was purified by column chromatography (20-100% EtOAc/hexanes) to afford the title compound (0.708 g, 70%) as a white solid. $^1$H NMR (400 MHz, DMSO-d$_6$) δ ppm 11.00 (br. s., 1H), 7.81 (s, 1H), 3.81 (s, 3H). ES-LCMS: m/z 204.9, 206.9 (M+1).

Step B: 4-bromo-N-({4-chloro-3-[(3-chloro-5-cyanophenyl)oxy]-2-fluorophenyl}methyl)-1H-imidazole-5-carboxamide trifluoroacetate

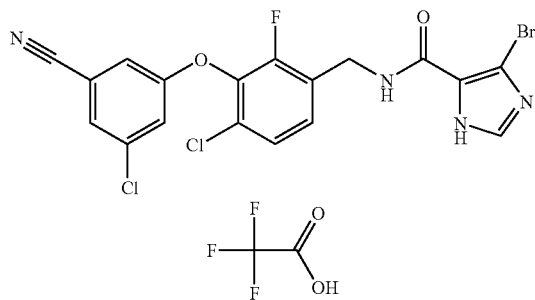

A solution of methyl 4-bromo-1H-imidazole-5-carboxylate (0.708 g, 3.5 mmol) was stirred in a solution of MeOH (20 mL) and 2N NaOH (20 mL, 40 mmol) at 40° C. for 4 h, then additional 2N NaOH (20 mL, 40 mmol) was added and the reaction mixture kept at 40° C. for another hour. The reaction mixture was then acidified by addition of 1M HCl (100 mL) and extracted with EtOAc. The organic extracts were dried (Na$_2$SO$_4$), and the solvent was evaporated to provide crude 4-bromo-1H-imidazole-5-carboxylic acid (0.156 g, 24%) as a white solid which was used without further purification.

4-Bromo-N-({4-chloro-3-[(3-chloro-5-cyanophenyl)oxy]-2-fluorophenyl}methyl)-1H-imidazole-5-carboxamide trifluoroacetate was prepared in a similar manner as described herein from 3-{[3-aminomethyl)-6-chloro-2-fluorophenyl]oxy}-5-chlorobenzonitrile (0.062 g, 0.20 mmol), 4-bromo-1H-imidazole-5-carboxylic acid (0.038 g, 0.20 mmol), HATU (0.091 g, 0.24 mmol), DIPEA (0.042 mL, 0.24 mmol) and DMF (2 mL). Purification was accomplished by Reverse-Phase HPLC (water/acetonitrile with 0.1% TFA) to afford the title compound (0.010 g, 8%) as a white solid. $^1$H NMR (400 MHz, DMSO-d$_6$) δ ppm 8.38 (br. s., 1H), 7.82 (s, 2H), 7.44-7.54 (m, 3H), 7.38 (t, 1H), 4.51 (d, 2H). ES-LCMS: m/z 482.9, 484.9, 486.9 (M+1).

Example 134

4-bromo-N-({4-chloro-3-[(3-chloro-5-cyanophenyl)oxy]-2-fluorophenyl}methyl)-2-methyl-1H-imidazole-5-carboxamide

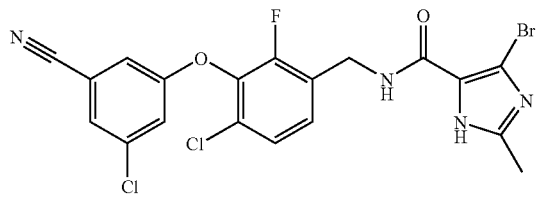

136

Step A: 4-bromo-2-methyl-1H-imidazole-5-carbaldehyde

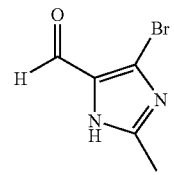

N-bromosuccinimide (0.900 g, 5.0 mmol) was added to a stirred solution of 2-methyl-1H-imidazole-4-carbaldehyde (0.500 g, 5.0 mmol) in CH$_3$CN (50 mL). The reaction mixture was stirred for 3 days in the dark and then concentrated in the presence of silica gel. The absorbed crude material was purified by column chromatography (5-70% EtOAc/hexanes) to afford the title compound (0.334 g, 35%) as a white solid. $^1$H NMR (400 MHz, DMSO-d$_6$): δ ppm 13.34 (br. s., 1H), 9.48 (s, 1H), 2.31 (s, 3H). ES-LCMS: m/z 189.2, 191.2 (M+1).

Step B: 4-bromo-2-methyl-1H-imidazole-5-carboxylic acid

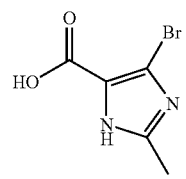

A solution of sodium chlorite (1.6 g, 17.8 mmol) and sodium dihydrogen phosphate monohydrate (1.5 g, 10.6 mmol) in water (3.9 mL) was added to a stirred solution of 4-bromo-2-methyl-1H-imidazole-5-carbaldehyde (0.334 g, 1.8 mmol), 2-methyl-2-butene (11 mL of a 2M solution in THF, 22.0 mmol), and tert-butanol (1.3 mL) in THF (5.5 mL). The reaction mixture was stirred at RT for 6 h. The aqueous phase was separated and extracted with EtOAc (4×10 mL). The combined extracts were dried (Na$_2$SO$_4$), filtered, concentrated and the residue was triturated with diethyl ether to provide the title compound (0.316 g, 87%) as white solid. $^1$H NMR (400 MHz, DMSO-d$_6$) δ ppm 12.91 (br. s., 1H), 2.27 (s, 3H). ES-LCMS: m/z 205.2, 207.3 (M+1).

Step C: 4-bromo-N-({4-chloro-3-[(3-chloro-5-cyanophenyl)oxy]-2-fluorophenyl}methyl)-2-methyl-1H-imidazole-5-carboxamide

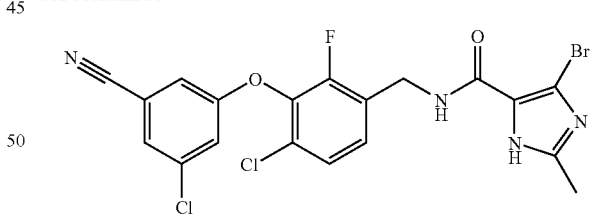

4-Bromo-N-({4-chloro-3-[(3-chloro-5-cyanophenyl)oxy]-2-fluorophenyl}methyl)-2-methyl-1H-imidazole-5-carboxamide was prepared in a similar manner as described herein from 3-{[3-aminomethyl)-6-chloro-2-fluorophenyl]oxy}-5-chlorobenzonitrile (0.062 g, 0.20 mmol), 4-bromo-2-methyl-1H-imidazole-5-carboxylic acid (0.041 g, 0.20 mmol), HATU (0.091 g, 0.24 mmol), DIPEA (0.042 mL, 0.24 mmol) and DMF (2 mL). Purification was accomplished by Reverse-Phase HPLC (water/acetonitrile with 0.1% TFA) to afford the title compound (0.066 g, 69%) as a white solid. $^1$H NMR (400 MHz, DMSO-d$_6$): δ ppm 8.20 (br. s., 1H), 7.80-7.85 (m, 1H), 7.45-7.55 (m, 3H), 7.31-7.41 (m, 1H), 4.50 (d, 2H), 2.27 (s, 3H). ES-LCMS: m/z 496.9, 498.9, 500.9 (M+1).

Example 135

4-chloro-N-({4-chloro-3-[(3-chloro-5-cyanophenyl)oxy]-2-fluorophenyl}methyl)-2-(1-methylethyl)-1H-imidazole-5-carboxamide trifluoroacetate

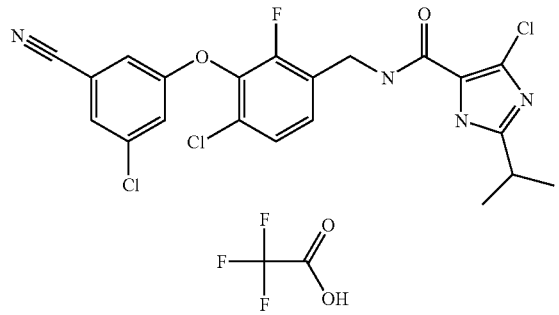

Step A: N-{1-cyano-2-[(phenylmethyl)oxy]ethyl}-2-methylpropanamide

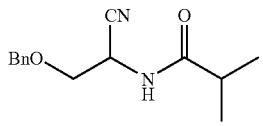

Benzyloxyacetaldehyde (1.5 g, 10.0 mmol) was added dropwise to a stirred solution of sodium cyanide (0.61 g, 12.4 mmol) and ammonium chloride (0.79 g, 14.8 mmol) in 25% ammonium hydroxide (5 mL). The solution was stirred at RT for 48 h, then extracted with $CH_2Cl_2$ (20 mL). The organic extract was washed with brine, dried ($Na_2SO_4$) and filtered. 2-Methylpropanoic acid (0.90 g, 10.2 mmol), EDC (2.85 g, 14.9 mmol) and DMAP (0.305 g, 2.5 mmol) were added to the filtrate and the solution was stirred for 12 h at RT. Water (10 mL) was added and the organic phase was separated and washed with 1N HCl (20 mL), dried ($Na_2SO_4$), filtered and concentrated. The residue was purified by silica gel flash column chromatography (5-50% EtOAc:hexanes) to give the title compound (1.60 g, 65%) as an off-white solid. $^1$H NMR (400 MHz, $CDCl_3$) δ ppm 7.31-7.44 (m, 5H), 6.13 (d, 1H), 5.06-5.13 (m, 1H), 4.64 (ABq, 2H), 3.69 (ABq, 2H), 2.32-2.45 (sept, 1H), 1.17 (t, 6H). ES-LCMS: m/z 247.1 (M+1).

Step B: 4-chloro-2-(1-methylethyl)-5-{[(phenylmethyl)oxy]methyl}-1H-imidazole

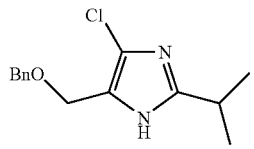

A solution of N-{1-cyano-2-[(phenylmethyl)oxy]ethyl}-2-methylpropanamide (1.60 g, 6.5 mmol), triphenylphosphine (4.2 g, 16.0 mmol), and carbon tetrachloride (1.6 mL, 16.6 mmol) in acetonitrile (65 mL) was heated at 45° C. for 4.5 h. The reaction was concentrated and the residue was stirred in $CH_2Cl_2$ (70 mL) and 0.5 N NaOH (60 mL) for 10 min. The organic layer was isolated, dried ($Na_2SO_4$), filtered, concentrated and the residue was purified by silica gel flash column chromatography (5-50% EtOAc:hexanes) to give the title compound (0.710 g, 41%) as a yellow oil. $^1$H NMR (400 MHz, $CDCl_3$) δ ppm 10.69 (br. s., 1H), 7.28-7.36 (m, 5H), 4.51 (s, 2H), 4.48 (s, 2 H), 2.92 (sept, 1H), 1.24 (d, 6H).

Step C: 4-chloro-2-(1-methylethyl)-1H-imidazole-5-carbaldehyde

A solution of 4-chloro-2-(1-methylethyl)-5-{[(phenylmethyl)oxy]methyl}-1H-imidazole (0.710 g, 2.7 mmol) and methanesulfonic acid (6.8 mL, 105 mmol) in chloroform (14 mL) was stirred at RT for 1 h. The reaction mixture was poured into ice (~50 g) and the solution was neutralized by addition of 5N NaOH until the pH was 10. The solution was extracted with methyl tert-butyl ether (2×40 mL) followed by n-butanol (3×20 mL). The combined n-butanol extracts were concentrated, azeotroped with toluene, and dried in vacuo to provide crude [4-chloro-2-(1-methylethyl)-1H-imidazol-5-yl]methanol as a brown solid. A solution of this solid and manganese dioxide (1.5 g, 17.0 mmol) in $CH_2Cl_2$ (8 mL) and 1,4-dioxane (4 mL) was heated under reflux for 6 h. The reaction mixture was cooled to RT and filtered through celite, and washed thoroughly with $CH_2Cl_2$. The filtrate was concentrated and dried to provide the title compound (0.165 g, 37%) as an off-white solid. $^1$H NMR (400 MHz, $CDCl_3$) δ ppm 11.82 (br. s., 1H), 9.60 (s, 1H), 3.12 (sept, 1H), 1.34 (d, 6H). ES-LCMS: m/z 173.0 (M+1).

Step D: 4-chloro-2-(1-methylethyl)-1H-imidazole-5-carboxylic acid

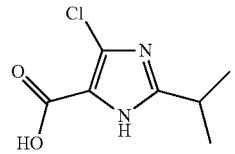

A solution of sodium chlorite (0.92 g, 10.2 mmol) and sodium dihydrogen phosphate monohydrate (0.81 g, 5.9 mmol) in water (2.2 mL) was added to a stirred solution of 4-chloro-2-(1-methylethyl)-1H-imidazole-5-carbaldehyde (0.165 g, 1.0 mmol), 2-methyl-2-butene (6.2 mL of a 2M solution in THF, 12.4 mmol), and tert-butanol (0.8 mL) in THF (3.1 mL). The reaction mixture was stirred at RT for 6 h. The aqueous phase was separated and extracted with EtOAc (4×10 mL). The combined extracts were dried ($Na_2SO_4$), filtered, concentrated and the residue was triturated with diethyl ether to provide the title compound (0.173 g, 92%) as light yellow solid. $^1$H NMR (400 MHz, DMSO-$d_6$) δ ppm 12.99 (br. s., 1H), 12.82 (br. s., 1H), 2.95 (sept, 1H), 1.20 (d, 6H). ES-LCMS: m/z 189.0 (M+1).

Step E: 4-chloro-N-({4-chloro-3-[(3-chloro-5-cyanophenyl)oxy]-2-fluorophenyl}methyl)-2-(1-methylethyl)-1H-imidazole-5-carboxamide trifluoroacetate

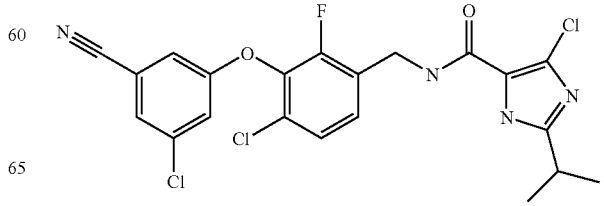

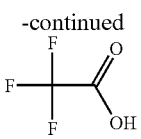

4-chloro-N-({4-chloro-3-[(3-chloro-5-cyanophenyl)oxy]-2-fluorophenyl}methyl)-2-(1-methylethyl)-1H-imidazole-5-carboxamide trifluoroacetate was prepared in a similar manner as described herein from 3-chloro-5-({6-chloro-2-fluoro-3-[(methylamino)methyl]phenyl}oxy)benzonitrile (0.093 g, 0.30 mmol), 4-chloro-2-(1-methylethyl)-1H-imidazole-5-carboxylic acid (0.057 g, 0.30 mmol), HATU (0.137 g, 0.36 mmol), DIPEA (0.063 mL, 0.36 mmol) and DMF (3 mL). Purification was accomplished by Reverse-Phase HPLC (water/acetonitrile with 0.1% TFA) to afford the title compound (0.084 g, 47%) as a white solid. $^1$H NMR (400 MHz, DMSO-$d_5$) δ ppm 8.17 (t, 1H), 7.82 (s, 1H), 7.43-7.53 (m, 3H), 7.37 (t, 1H), 4.53 (d, 2H), 2.95 (sept, 1H), 1.21 (d, 6H). ES-LCMS: m/z 481.0, 483.0 (M+1).

Example 136

4-chloro-N-({4-chloro-3-[(3-chloro-5-cyanophenyl)oxy]-2-fluorophenyl}methyl)-2-cyclopropyl-1H-imidazole-5-carboxamide trifluoroacetate

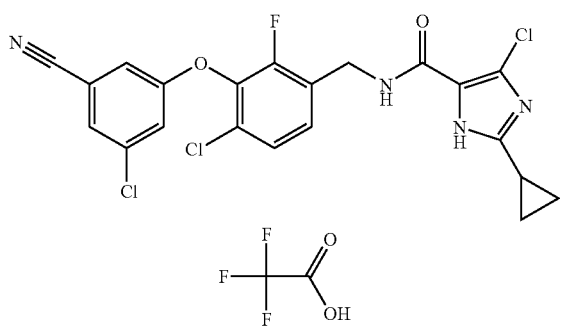

Step A: N-{1-cyano-2-[(phenylmethyl)oxy]ethyl}cyclopropanecarboxamide

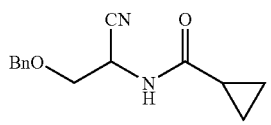

Benzyloxyacetaldehyde (1.5 g, 10.0 mmol) was added dropwise to a stirred solution of sodium cyanide (0.61 g, 12.4 mmol) and ammonium chloride (0.79 g, 14.8 mmol) in 25% ammonium hydroxide (5 mL). The solution was stirred at RT for 48 h, then extracted with CH$_2$Cl$_2$ (20 mL). The organic extract was washed with brine, dried (Na$_2$SO$_4$) and filtered. The filtrate was cooled to 0° C., and pyridine (1.3 mL, 16.1 mmol) was added followed by cyclopropanecarbonyl chloride (1.1 g, 10.1 mmol). The reaction mixture was stirred for 12 h at RT. Water (10 mL) was added and the organic phase was separated and washed with 1N HCl (20 mL), dried (Na$_2$SO$_4$), filtered and concentrated. The residue was purified by silica gel flash column chromatography (5-50% EtOAc:hexanes) to give the title compound (1.84 g, 75%) as a translucent solid. $^1$H NMR (400 MHz, CDCl$_3$) δ ppm 7.31-7.44 (m, 5H), 6.33 (d, 1H), 5.07-5.15 (m, 1H), 4.66 (s, 2H), 3.71 (ABq, 2H), 1.33-1.42 (m, 1H), 0.97-1.09 (m, 2H), 0.79-0.90 (m, 2H). ES-LCMS: m/z 245.1 (M+1).

Step B: 4-chloro-2-cyclopropyl-5-{[(phenylmethyl)oxy]methyl}-1H-imidazole

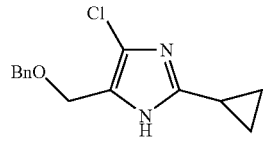

A solution of N-{1-cyano-2-[(phenylmethyl)oxy]ethyl}cyclopropanecarboxamide (1.84 g, 7.5 mmol), triphenylphosphine (4.8 g, 18.3 mmol), and carbon tetrachloride (1.9 mL, 19.7 mmol) in acetonitrile (74 mL) was heated at 45° C. for 6 h. The reaction was concentrated and the residue was stirred in CH$_2$Cl$_2$ (80 mL) and 0.5 N NaOH (70 mL) for 10 min. The organic layer was isolated, dried (Na$_2$SO$_4$), filtered, concentrated and the residue was purified by silica gel flash column chromatography (5-50% EtOAc:hexanes) to give the title compound (1.02 g, 52%) as a yellow oil. $^1$H NMR (400 MHz, CDCl$_3$) δ ppm 10.90 (br. s., 1H), 7.26-7.36 (m, 5H), 4.50 (s, 2H), 4.47 (s, 2H), 1.74-1.84 (m, 1H), 0.81-0.95 (m, 4H).

Step C: 4-chloro-2-cyclopropyl-1H-imidazole-5-carbaldehyde

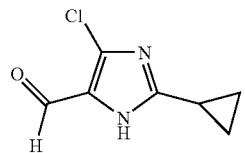

A solution of 4-chloro-2-cyclopropyl-5-{[(phenylmethyl)oxy]methyl}-1H-imidazole (1.02 g, 3.9 mmol) and methanesulfonic acid (9.7 mL, 149 mmol) in chloroform (22 mL) was stirred at RT for 1 h. The reaction mixture was poured into ice (~50 g) and the solution was neutralized by addition of 5N NaOH until the pH was 10. The solution was extracted with methyl tert-butyl ether (2×40 mL) and then with n-butanol (3×20 mL). The combined n-butanol extracts were concentrated, azeotroped with toluene, and dried in vacuo to provide crude (4-chloro-2-cyclopropyl-1H-imidazol-5-yl)methanol as a brown solid. A solution of this solid and manganese dioxide (2.1 g, 24.8 mmol) in CH$_2$Cl$_2$ (12 mL) and 1,4-dioxane (6 mL) was heated under reflux for 6 h. The reaction mixture was cooled to RT, filtered through Celite and washed thoroughly with CH$_2$Cl$_2$. The filtrate was concentrated and dried to provide the title compound (0.282 g, 41%) as a brown solid. $^1$H NMR (400 MHz, CDCl$_3$) δ ppm 11.05 (br. s., 1H), 9.49 (s, 1H), 1.95-2.04 (m, 1H), 1.09-1.17 (m, 2 H), 1.03-1.09 (m, 2H). ES-LCMS: m/z 171.0 (M+1).

Step D: 4-chloro-2-cyclopropyl-1H-imidazole-5-carboxylic acid

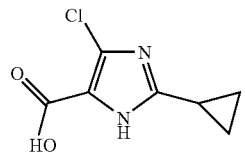

A solution of sodium chlorite (1.5 g, 16.6 mmol) and sodium dihydrogen phosphate monohydrate (1.3 g, 9.4 mmol) in water (3.7 mL) was added to a stirred solution of 4-chloro-2-cyclopropyl-1H-imidazole-5-carbaldehyde (0.282 g, 1.6 mmol), 2-methyl-2-butene (10 mL of a 2M solution in THF, 20.0 mmol), and tert-butanol (1.2 mL) in THF (5.0 mL). The reaction mixture was stirred at RT for 6 h. The aqueous phase was separated and extracted with EtOAc (4×10 mL). The combined extracts were dried ($Na_2SO_4$), filtered, concentrated and the residue was triturated with diethyl ether to provide the title compound (0.285 g, 95%) as light yellow solid. $^1$H NMR (400 MHz, DMSO-$d_6$) δ ppm 12.95 (br. s., 1H), 1.90-2.00 (m, 1H), 0.89-0.98 (m, 2H), 0.82-0.89 (m, 2H). ES-LCMS: m/z 187.0 (M+1).

Step E: 4-chloro-N-({4-chloro-3-[(3-chloro-5-cyanophenyl) oxy]-2-fluorophenyl}methyl)-2-cyclopropyl-1H-imidazole-5-carboxamide trifluoroacetate

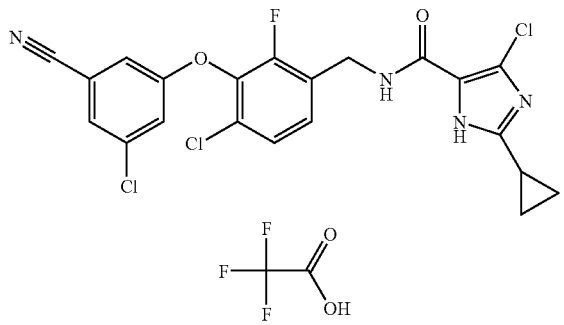

4-chloro-N-({4-chloro-3-[(3-chloro-5-cyanophenyl)oxy]-2-fluorophenyl}methyl)-2-cyclopropyl-1H-imidazole-5-carboxamide trifluoroacetate was prepared in a similar manner as described herein from 3-chloro-5-({6-chloro-2-fluoro-3-[(methylamino)methyl]phenyl}oxy)benzonitrile (0.093 g, 0.30 mmol), 4-chloro-2-cyclopropyl-1H-imidazole-5-carboxylic acid (0.056 g, 0.30 mmol), HATU (0.137 g, 0.36 mmol), DIPEA (0.063 mL, 0.36 mmol) and DMF (3 mL). Purification was accomplished by Reverse-Phase HPLC (water/acetonitrile with 0.1% TFA) to afford the title compound (0.050 g, 28%) as a white solid. $^1$H NMR (400 MHz, DMSO-$d_6$) δ ppm 8.05-8.11 (m, 1H), 7.81-7.83 (m, 1H), 7.44-7.53 (m, 3H), 7.32-7.39 (m, 1H), 4.53 (d, 2H), 1.89-1.99 (m, 1H), 0.91-0.97 (m, 2H), 0.82-0.88 (m, 2H). ES-LCMS: m/z 479.0, 481.0 (M+1).

Example 137

4-chloro-N-({4-chloro-3-[(3-chloro-5-cyanophenyl) oxy]-2-fluorophenyl}methyl)-2-methyl-1H-imidazole-5-carboxamide

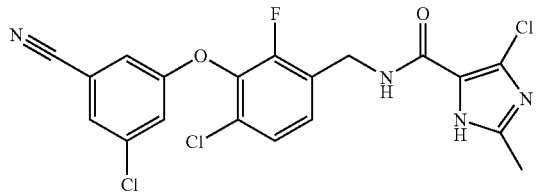

Step A: N-{1-cyano-2-[(phenylmethyl)oxy]ethyl}acetamide

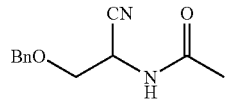

Benzyloxyacetaldehyde (1.5 g, 10.0 mmol) was added dropwise to a stirred solution of sodium cyanide (0.61 g, 12.4 mmol) and ammonium chloride (0.79 g, 14.8 mmol) in 25% ammonium hydroxide (5 mL). The solution was stirred at RT for 48 h, then extracted with $CH_2Cl_2$ (20 mL). The organic extract was washed with brine, dried ($Na_2SO_4$) and filtered. The filtrate was cooled to 0° C., and pyridine (1.3 mL, 16.1 mmol) was added followed by acetyl chloride (1.1 mL, 15.5 mmol). The reaction mixture was stirred for 2 h at 0° C. Water was added (10 mL) and the organic phase was separated and washed with 1 N HCl (20 mL), dried ($Na_2SO_4$), filtered and concentrated. The residue was purified by silica gel flash column chromatography (5-50% EtOAc:hexanes) to give the title compound (1.60 g, 65%) as an off-white solid. $^1$H NMR (400 MHz, $CDCl_3$) δ ppm 7.33-7.44 (m, 5H), 6.14 (br. s., 1H), 5.05-5.12 (m, 1H), 4.65 (ABq, 2H), 3.69 (ABq, 2H), 2.04 (s, 3H).

Step B: 4-chloro-2-methyl-5-{[(phenylmethyl)oxy]methyl}-1H-imidazole

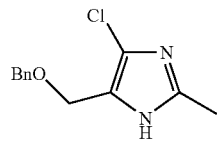

A solution of N-{1-cyano-2-[(phenylmethyl)oxy] ethyl}acetamide (1.64 g, 7.5 mmol), triphenylphosphine (4.9 g, 18.8 mmol), and carbon tetrachloride (1.8 mL, 18.8 mmol) in acetonitrile (75 mL) was heated at 45° C. for 6 h. The reaction was concentrated and the residue was stirred in $CH_2Cl_2$ (80 mL) and 0.5 N NaOH (70 mL) for 15 min. The organic layer was isolated, dried ($Na_2SO_4$), filtered, concentrated and the residue was purified by silica gel flash column chromatography (5-70% EtOAc:hexanes) to give the title compound as a yellow solid, in assumed quantitative yield due to inseparable triphenylphosphine oxide. $^1$H NMR (400 MHz, $CDCl_3$) δ ppm 7.28-7.37 (m, 5H), 4.50 (s, 2H), 4.48 (s, 2H), 2.37 (s, 3H).

Step C: 4-chloro-2-methyl-1H-imidazole-5-carboxylic acid

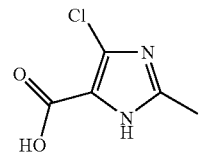

A solution of 4-chloro-2-methyl-5-{[(phenylmethyl)oxy] methyl}-1H-imidazole (1.78 g, 7.5 mmol) and methanesulfonic acid (18.5 mL, 285 mmol) in chloroform (39 mL) was stirred at RT for 1 h. The reaction mixture was poured into ice (~70 g) and the solution was neutralized by addition of 5N NaOH until the pH was 10. The solution was extracted with methyl tert-butyl ether (2×60 mL) and then with n-butanol (3×40 mL). The combined n-butanol extracts were washed with brine, concentrated, and dried in vacuo to provide crude (4-chloro-2-methyl-1H-imidazol-5-yl)methanol as a brown solid. A solution of this solid and manganese dioxide (2.0 g, 23.0 mmol) in $CH_2Cl_2$ (12 mL) and 1,4-dioxane (6 mL) was heated under reflux for 6 h. The reaction mixture was cooled to RT, filtered through Celite, which was washed thoroughly with $CH_2Cl_2$. The filtrate was concentrated and dried to provide crude 4-chloro-2-methyl-1H-imidazole-5-carbaldehyde as a yellow solid (0.308 g, 28%), which was used without further purification.

A solution of sodium chlorite (1.4 g, 15.3 mmol) and sodium dihydrogen phosphate monohydrate (1.2 g, 8.7 mmol) in water (3.3 mL) was added to a stirred solution of 4-chloro-2-methyl-1H-imidazole-5-carbaldehyde (0.308 g, 2.1 mmol), 2-methyl-2-butene (9.3 mL of a 2M solution in THF, 18.6 mmol), and tert-butanol (1.2 mL) in THF (4.7 mL). The reaction mixture was stirred at RT for 6 h. The aqueous phase was separated and extracted with EtOAc (4×10 mL). The combined extracts were dried (Na$_2$SO$_4$), filtered, concentrated and the residue was triturated with diethyl ether to provide the title compound (0.168 g, 50%) as white solid. $^1$H NMR (400 MHz, DMSO-d$_6$) δ ppm 12.98 (br. s., 1H), 12.88, (br. s., 1H), 2.26 (s, 3H). ES-LCMS: m/z 160.9 (M+1).

Step D: 4-chloro-N-({4-chloro-3-[(3-chloro-5-cyanophenyl) oxy]-2-fluorophenyl}methyl)-2-methyl-1H-imidazole-5-carboxamide

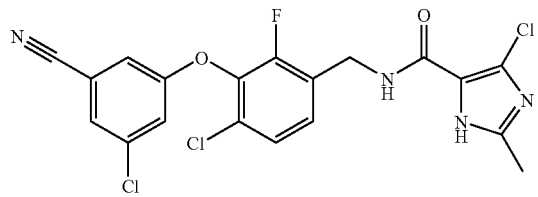

4-chloro-N-({4-chloro-3-[(3-chloro-5-cyanophenyl)oxy]-2-fluorophenyl}methyl)-2-methyl-1H-imidazole-5-carboxamide was prepared in a similar manner as described herein from 3-chloro-5-({6-chloro-2-fluoro-3-[(methylamino)methyl]phenyl}oxy)benzonitrile (0.062 g, 0.20 mmol), 4-chloro-2-methyl-1H-imidazole-5-carboxylic acid (0.032 g, 0.20 mmol), HATU (0.091 g, 0.24 mmol), DIPEA (0.042 mL, 0.24 mmol) and DMF (2 mL). Purification was accomplished by Reverse-Phase HPLC (water/acetonitrile with 0.1% TFA) to afford the title compound (0.051 g, 56%) as a white solid. $^1$H NMR (400 MHz, DMSO-d$_6$) δ ppm 12.77 (br. s., 1H), 8.08 (br. s., 1H), 7.80-7.84 (m, 1H), 7.44-7.53 (m, 3H), 7.36 (t, 1H), 4.49-4.56 (m, 2H), 2.26 (s, 3H). ES-LCMS: m/z 453.0, 454.0 (M+1).

Example 138

4-chloro-N-({4-chloro-3-[(3-chloro-5-cyanophenyl) oxy]-2-fluorophenyl}methyl)-2-ethyl-1H-imidazole-5-carboxamide

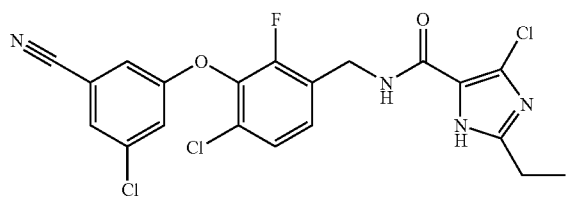

Step A: N-{1-cyano-2-[(phenylmethyl)oxy] ethyl}propanamide

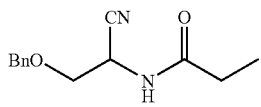

Benzyloxyacetaldehyde (3.0 g, 20.0 mmol) was added dropwise to a stirred solution of sodium cyanide (1.22 g, 24.9 mmol) and ammonium chloride (1.58 g, 29.5 mmol) in 25% ammonium hydroxide (9.6 mL). The solution was stirred at RT for 48 h, then extracted with CH$_2$Cl$_2$ (40 mL). The organic extract was washed with brine, dried (Na$_2$SO$_4$) and filtered. Propionic acid (1.5 g, 20.0 mmol), EDC (5.7 g, 30.0 mmol) and DMAP (610 mg, 5 mmol) were added to the filtrate and the solution was stirred for 12 h at RT. Water was added (20 mL) and the organic phase was separated and washed with 1N HCl (20 mL), dried (Na$_2$SO$_4$), filtered and concentrated. The residue was purified by silica gel flash column chromatography (0-50% EtOAc:hexanes) to give the title compound (3.62 g, 78%) as a yellow oil. $^1$H NMR (400 MHz, CDCl$_3$) δ ppm 7.32-7.43 (m, 5H), 6.09 (br. s., 1H), 5.08-5.13 (m, 1H), 4.59-4.69 (ABq, 2 H), 3.66 (ABq, 2H), 2.25 (qd, 2H), 1.17 (t, 3H). ES-LCMS: m/z 233.0 (M+H).

Step B: 4-chloro-2-ethyl-5-{[(phenylmethyl)oxy]methyl}-1H-imidazole

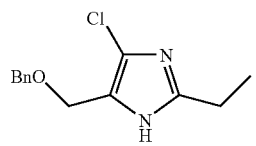

A solution of N-{1-cyano-2-[(phenylmethyl)oxy] ethyl}propanamide (3.62 g, 15.6 mmol), triphenylphosphine (10.2 g, 39.0 mmol), and carbon tetrachloride (3.8 mL, 39.0 mmol) in acetonitrile (150 mL) was heated at 45° C. for 4.5 h. The reaction was concentrated and the residue was stirred in CH$_2$Cl$_2$ (170 mL) and 0.5 N NaOH (150 mL) for 15 min. The organic layer was isolated, dried (Na$_2$SO$_4$), filtered, concentrated and the residue was purified by silica gel flash column chromatography (5-50% EtOAc:hexanes) to give the title compound (2.51 g, 64%) as a light yellow solid. $^1$H NMR (400 MHz, CDCl$_3$) δ ppm 7.29-7.38 (m, 5H), 4.52 (s, 2H), 4.50 (s, 2H), 2.65 (q, 2H), 1.26 (t, 3H). ES-LCMS: m/z 250.6, 252.9 (M+H).

Step C: (4-chloro-2-ethyl-1H-imidazol-5-yl)methanol

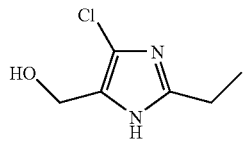

A solution of 4-chloro-2-ethyl-5-{[(phenylmethyl)oxy] methyl}-1H-imidazole (2.51 g, 10.0 mmol) and methanesulfonic acid (25 mL, 385 mmol) in chloroform (56 mL) was stirred at RT for 1 h. The reaction mixture was poured into ice (~100 g) and the solution was neutralized by addition of 5N NaOH until the pH was 10. The solution was extracted with methyl tert-butyl ether (2×100 mL) and then with n-butanol (3×100 mL). The combined n-butanol extracts were concentrated, azeotroped with toluene, and dried in vacuo to provide the title compound in quantitative yield as an off-white solid. $^1$H NMR (400 MHz, DMSO-d$_6$) δ ppm 12.10 (br. s., 1H), 5.10 (br. s., 1H), 4.32 (s, 2H), 2.54 (q, 2H), 1.15 (t, 3H).

Step D: 4-chloro-2-ethyl-1H-imidazole-5-carbaldehyde

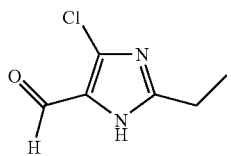

A solution of (4-chloro-2-ethyl-1H-imidazol-5-yl)methanol (1.60 g, 10.0 mmol) and manganese dioxide (5.5 g, 63.3 mmol) in CH$_2$Cl$_2$ (30 mL) and 1,4-dioxane (15 mL) was heated under reflux for 6.5 h. The reaction mixture was cooled to RT, then filtered through Celite, which was washed thoroughly with CH$_2$Cl$_2$. The filtrate was concentrated and dried to provide the title compound (0.763 mg, 48%) as a pale yellow solid. $^1$H NMR (400 MHz, CDCl$_3$) δ ppm 9.66 (s, 1H), 2.84 (q, 2H), 1.38 (t, 3 H).

Step E: 4-chloro-2-ethyl-1H-imidazole-5-carboxylic acid

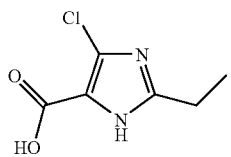

A solution of sodium chlorite (4.41 g, 48.8 mmol) and sodium dihydrogen phosphate monohydrate (3.9 g, 28.3 mmol) in water (11 mL) was added to a stirred solution of 4-chloro-2-ethyl-1H-imidazole-5-carbaldehyde (0.763 g, 4.81 mmol), 2-methyl-2-butene (30 mL of a 2M solution in THF, 60 mmol), and tert-butanol (3.7 mL) in THF (15 mL). The reaction mixture was stirred at RT for 6 h. The aqueous phase was separated and extracted with EtOAc (4×40 mL). The combined extracts were dried (Na$_2$SO$_4$), filtered, concentrated and the residue was triturated with diethyl ether to provide the title compound (0.715 g, 85%) as a white solid. $^1$H NMR (400 MHz, DMSO-d$_6$) δ ppm 12.86 (br. s., 2H), 2.59 (q, 2H), 1.17 (t, 3H). ES-LCMS: m/z 174.9, 176.9 (M+H).

Step F: 4-chloro-N-({4-chloro-3-[(3-chloro-5-cyanophenyl)oxy]-2-fluorophenyl}methyl)-2-ethyl-1H-imidazole-5-carboxamide

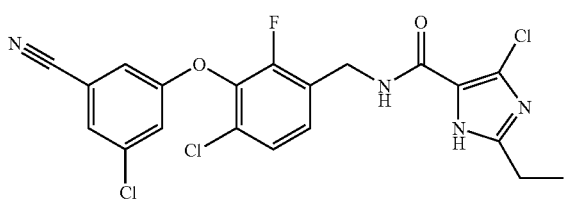

4-chloro-N-({4-chloro-3-[(3-chloro-5-cyanophenyl)oxy]-2-fluorophenyl}methyl)-2-ethyl-1H-imidazole-5-carboxamide was prepared in a similar manner as described herein from 3-chloro-5-({6-chloro-2-fluoro-3-[(methylamino)methyl]phenyl}oxy)benzonitrile (0.713 g, 2.29 mmol), 4-chloro-2-ethyl-1H-imidazole-5-carboxylic acid (0.400 g, 2.29 mmol), HATU (1.133 g, 2.98 mmol), DIPEA (0.520 mL, 2.98 mmol) and DMF (12 mL). Purification was accomplished by silica gel chromatography (0-5% MeOH (2M NH$_3$) in CH$_2$Cl$_2$) to afford the title compound (0.622 g, 58%) as a white solid. $^1$H NMR (400 MHz, DMSO-d$_6$) δ 12.74 (s, 1H), 8.09 (br. s., 1H), 7.81-7.84 (m, 1H), 7.48-7.53 (m, 2H), 7.45-7.47 (m, 1H), 7.33-7.40 (m, 1H), 4.54 (d, 2H), 2.60 (q, 2H), 1.18 (t, 3H). ES-LCMS: m/z 467.0, 469.0 (M+H).

Example 139

4-chloro-N-({4-chloro-3-[(3-chloro-5-cyanophenyl)oxy]-2-fluorophenyl}methyl)-2-propyl-1H-imidazole-5-carboxamide

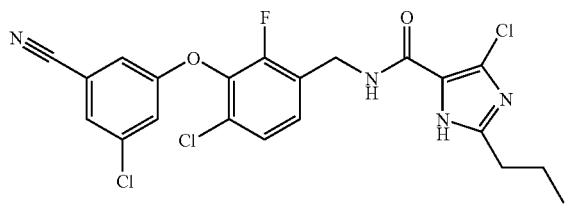

Step A: N-{1-cyano-2-[(phenylmethyl)oxy]ethyl}butanamide

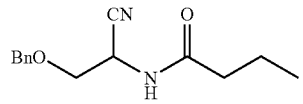

Benzyloxyacetaldehyde (1.5 g, 10.0 mmol) was added dropwise to a stirred solution of sodium cyanide (0.61 g, 12.4 mmol) and ammonium chloride (0.79 g, 14.8 mmol) in 25% ammonium hydroxide (5 mL). The solution was stirred at RT for 48 h, then extracted with CH$_2$Cl$_2$ (20 mL). The organic extract was washed with brine, dried (Na$_2$SO$_4$) and filtered. The filtrate was cooled to 0° C., and pyridine (1.3 mL, 16.1 mmol) was added followed by butyryl chloride (1.56 mL, 15.0 mmol). The reaction mixture was stirred for 2 h at 0° C. Water was added (10 mL) and the organic phase was separated, dried (Na$_2$SO$_4$), filtered and concentrated. The residue was purified by silica gel flash column chromatography (5-35% EtOAc:hexanes) to give the title compound (1.99 g, 81%) as a light yellow oil. $^1$H NMR (400 MHz, CDCl$_3$) δ ppm 7.32-7.43 (m, 5H), 6.09 (d, 1H), 5.08-5.14 (m, 1H), 4.64 (ABq, 2H), 3.71 (ABq, 2H), 2.20 (t, 2H), 1.62-1.73 (m, 2H), 0.96 (t, 3H). ES-LCMS: m/z 247.2 (M+1).

Step B: 4-chloro-5-{[(phenylmethyl)oxy]methyl}-2-propyl-1H-imidazole

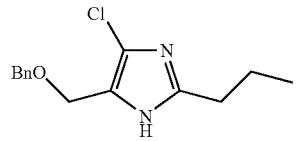

A solution of N-{1-cyano-2-[(phenylmethyl)oxy]ethyl}butanamide (1.60 g, 6.5 mmol), triphenylphosphine (4.3 g, 16.3 mmol), and carbon tetrachloride (1.6 mL, 16.3 mmol) in acetonitrile (65 mL) was heated at 42° C. for 12 h. The reaction was then concentrated and the residue was stirred in CH$_2$Cl$_2$ (70 mL) and 0.5 N NaOH (60 mL) for 15 min. The organic layer was isolated, dried (Na$_2$SO$_4$), filtered, concentrated and the residue was purified by silica gel flash column chromatography (5-40% EtOAc:hexanes) to give the title compound as a light yellow solid, in assumed quantitative yield due to inseparable triphenylphosphine oxide. $^1$H NMR (400 MHz, CDCl$_3$) δ 7.30-7.40 (m, 5H), 4.52 (s, 4H), 2.58-2.68 (m, 2H), 1.68-1.82 (m, 2H), 0.97 (t, 3H).

Step C: (4-chloro-2-propyl-1H-imidazol-5-yl)methanol

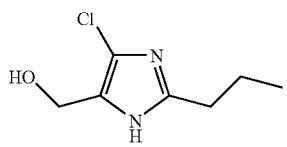

A solution of 4-chloro-5-{[(phenylmethyl)oxy]methyl}-2-propyl-1H-imidazole (1.72 g, 6.5 mmol) and methanesulfonic acid (16 mL, 247 mmol) in chloroform (36 mL) was stirred at RT for 1 h. The reaction mixture was poured into ice (~70 g) and the solution was neutralized by addition of 5N NaOH until the pH was 10. The solution was extracted with methyl tert-butyl ether (2×60 mL) and then with n-butanol (3×40 mL). The combined n-butanol extracts were concentrated, washed with brine, and dried in vacuo to provide the title compound (0.927 g, 82%) as a light yellow solid. $^1$H NMR (400 MHz, DMSO-d$_6$) δ ppm 12.09 (br. s., 1H), 5.10 (br. s., 1H), 4.31 (s, 2H), 2.45-2.51 (m, 2H), 1.60 (sex, 2H), 0.87 (t, 3H).

Step D: 4-chloro-2-propyl-1H-imidazole-5-carbaldehyde

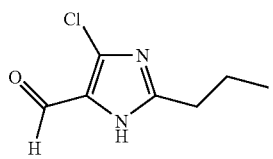

A solution of (4-chloro-2-propyl-1H-imidazol-5-yl)methanol (0.927 g, 5.3 mmol) and manganese dioxide (2 g, 23.0 mmol) in CH$_2$Cl$_2$ (12 mL) and 1,4-dioxane (6 mL) was heated under reflux for 6 h. The reaction mixture was cooled to RT, then filtered through celite, washing thoroughly with CH$_2$Cl$_2$. The filtrate was concentrated and dried to provide the title compound (0.541 g, 59%) as a pale yellow solid. $^1$H NMR (400 MHz, CDCl$_3$) δ ppm 11.61 (br. s., 1H), 9.63 (s, 1H), 2.80 (t, 2H), 1.83 (sex, 2 H), 0.99 (t, 3H). ES-LCMS: m/z 173.0 (M+1).

Step E: 4-chloro-2-propyl-1H-imidazole-5-carboxylic acid

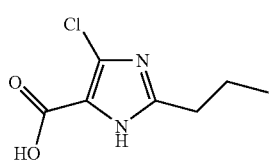

A solution of sodium chlorite (2.9 g, 32.1 mmol) and sodium dihydrogen phosphate monohydrate (2.5 g, 18.1 mmol) in water (7.2 mL) was added to a stirred solution of 4-chloro-2-propyl-1H-imidazole-5-carbaldehyde (0.541 g, 3.1 mmol), 2-methyl-2-butene (19.3 mL of a 2M solution in THF, 38.6 mmol), and tert-butanol (2.3 mL) in THF (10 mL). The reaction mixture was stirred at RT for 6 h. The aqueous phase was separated and extracted with EtOAc (4×40 mL). The combined extracts were dried (Na$_2$SO$_4$), filtered, concentrated and the residue was triturated with diethyl ether to provide the title compound (0.587 g, quant.) as a white solid. $^1$H NMR (400 MHz, DMSO-d$_6$) δ ppm 12.99 (br. s., 1H), 12.88, (br. s., 1H), 2.55 (t, 2H), 1.63 (sex, 2H), 0.86 (t, 3H). ES-LCMS: m/z 189.0 (M+H).

Step F: 4-chloro-N-({4-chloro-3-[(3-chloro-5-cyanophenyl)oxy]-2-fluorophenyl}methyl)-2-propyl-1H-imidazole-5-carboxamide

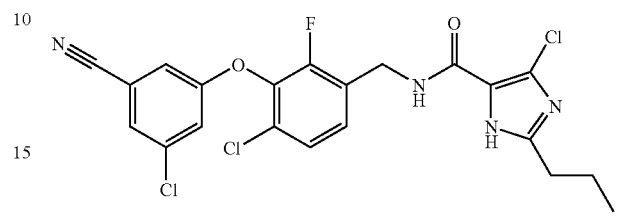

4-chloro-N-({4-chloro-3-[(3-chloro-5-cyanophenyl)oxy]-2-fluorophenyl}methyl)-2-propyl-1H-imidazole-5-carboxamide was prepared in a similar manner as described herein from 3-chloro-5-({6-chloro-2-fluoro-3-[(methylamino)methyl]phenyl}oxy)benzonitrile (0.062 g, 0.20 mmol), 4-chloro-2-propyl-1H-imidazole-5-carboxylic acid (0.038 g, 0.20 mmol), HATU (0.091 g, 0.24 mmol), DIPEA (0.042 mL, 0.24 mmol) and DMF (2 mL). Purification was accomplished by Reverse-Phase HPLC (water/acetonitrile with 0.1% TFA) to afford the title compound (0.062 g, 64%) as a white solid. $^1$H NMR (400 MHz, DMSO-d$_6$) δ ppm 12.73 (br. s., 1H), 8.12 (br. s., 1H), 7.81-7.84 (m, 1H), 7.45-7.52 (m, 3H), 7.37 (t, 1H), 4.53 (d, 2H), 2.55 (t, 2H), 1.64 (sex, 2H), 0.87 (t, 3H). ES-LCMS: m/z 481.0, 483.0 (M+1).

Example 140

2-butyl-4-chloro-N-({4-chloro-3-[(3-chloro-5-cyanophenyl)oxy]-2-fluorophenyl}methyl)-1H-imidazole-5-carboxamide trifluoroacetate

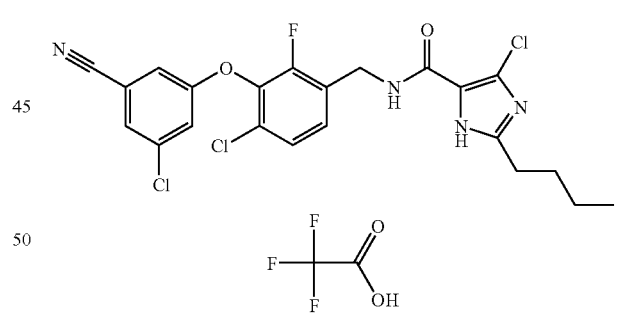

Step A: 2-butyl-4-chloro-1H-imidazole-5-carboxylic acid

A solution of sodium chlorite (2.0 g, 21.6 mmol) and sodium dihydrogen phosphate monohydrate (1.8 g, 12.9 mmol) in water (4.8 mL) was added to a stirred solution of 4-chloro-2-butyl-1H-imidazole-5-carbaldehyde (0.400 g, 2.1 mmol), 2-methyl-2-butene (13.4 mL of a 2M solution in THF, 26.8 mmol), and tert-butanol (1.6 mL) in THF (6.7 mL). The reaction mixture was stirred at RT for 12 h. The aqueous phase was separated and extracted with EtOAc (4×40 mL). The combined extracts were dried ($Na_2SO_4$), filtered, concentrated and the residue was triturated with diethyl ether to provide the title compound (0.411 g, 95%) as a white solid. $^1$H NMR (400 MHz, DMSO-$d_6$) δ ppm 12.99 (br. s., 1H), 12.88, (br. s., 1H), 2.58 (t, 2H), 1.59 (quint, 2H), 1.20-1.31 (sex, 2H), 0.87 (t, 3H). ES-LCMS: m/z 203.1 (M+H).

Step B: 2-butyl-4-chloro-N-({4-chloro-3-[(3-chloro-5-cyanophenyl)oxy]-2-fluorophenyl}methyl)-1H-imidazole-5-carboxamide trifluoroacetate

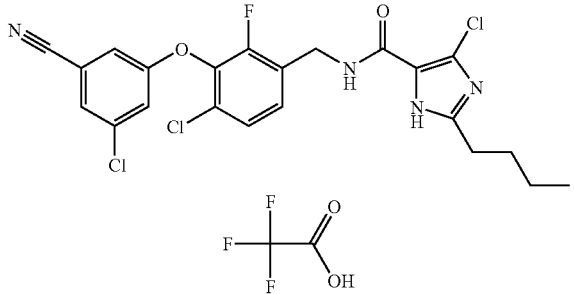

2-butyl-4-chloro-N-({4-chloro-3-[(3-chloro-5-cyanophenyl)oxy]-2-fluorophenyl}methyl)-1H-imidazole-5-carboxamide trifluoroacetate was prepared in a similar manner as described herein from 3-chloro-5-({6-chloro-2-fluoro-3-[(methylamino)methyl]phenyl}oxy)benzonitrile (0.062 g, 0.20 mmol), 2-butyl-4-chloro-1H-imidazole-5-carboxylic acid (0.041 g, 0.20 mmol), HATU (0.091 g, 0.24 mmol), DIPEA (0.042 mL, 0.24 mmol) and DMF (2 mL). Purification was accomplished by Reverse-Phase HPLC (water/acetonitrile with 0.1% TFA) to afford the title compound (0.080 g, 65%) as a white solid. $^1$H NMR (400 MHz, DMSO-$d_6$) δ ppm 8.13 (br. s., 1H), 7.80-7.84 (m, 1H), 7.44-7.53 (m, 3H), 7.33-7.40 (m, 1H), 4.53 (d, 2H), 2.58 (t, 2H), 1.60 (quint, 2H), 1.27 (sex, 2H), 0.87 (t, 3H). ES-LCMS: m/z 495.2, 497.3 (M+1).

Example 141

3-Bromo-N-({4-chloro-3-[(3-chloro-5-cyanophenyl)oxy]-2-fluorophenyl}methyl)-6-[(2-hydroxyethyl)oxy]-1H-indole-2-carboxamide

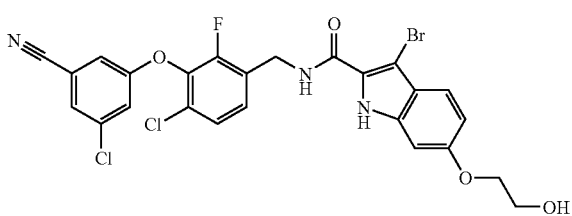

Step A: Methyl 6-hydroxy-1H-indole-2-carboxylate

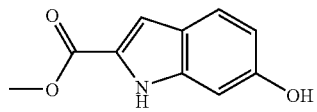

A 2M solution of trimethylsilyldiazomethane in hexanes was added to a solution of 6-hydroxy-1H-indole-2-carboxylic acid (0.500 g, 2.82 mmol) in MeOH until the solution remained yellow in color. The solution was stirred at RT until the starting material was consumed as evident by TLC. The reaction mixture was partitioned between water and EtOAc then the organic layer was separated, dried over $MgSO_4$, filtered and concentrated. Purification was accomplished by column chromatography (EtOAc/hexanes) to afford the title compound (0.464 g, 86% yield). $^1$H NMR (400 MHz, Acetone-$d_6$): δ ppm 10.55 (br. s., 1H), 8.32 (s, 1H), 7.50 (d, 1H), 7.09 (d, 1H), 6.95 (d, 1H), 6.74 (dd, 1H), 3.85 (s, 3H). MS m/z=191.9 (M+1).

Step B: Methyl 6-{[(1,1-dimethylethyl)(dimethyl)silyl]oxy}-1H-indole-2-carboxylate

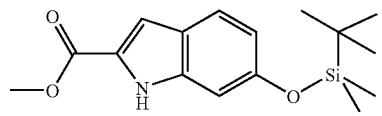

TBDMS-Cl (0.544 g, 3.61 mmol) and DIPEA (0.840 mL, 4.81 mmol) were added to a solution of methyl 6-hydroxy-1H-indole-2-carboxylate (0.460 g, 2.40 mmol) in DCM (10 mL) and THF (5 mL). The resulting solution was stirred overnight at room temperature. The reaction mixture was partitioned between EtOAc and water, the organic layer was separated and washed with saturated $NaHCO_3$, dried over $MgSO_4$, filtered and concentrated. Purification was accomplished by silica gel column chromatography (EtOAc/hexanes) to afford the title compound (0.426 g, 58%). $^1$H NMR (400 MHz, Acetone-$d_6$): δ ppm 10.64 (br. s., 1H), 7.54 (d, 1H), 6.98-7.04 (m, 1H), 6.73 (dd, 1H), 3.86 (s, 3H), 1.00 (s, 9H), 0.22 (s, 6H).

Step B (Alternative procedure): Methyl 6-{[(1,1-dimethylethyl)(dimethyl)silyl]oxy}-1H-indole-2-carboxylate

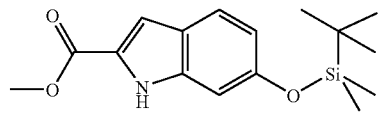

TBDMS-Cl (6.83 g, 45.3 mmol) and DBU (3.41 mL, 22.6 mmol) were added to a solution of methyl 6-hydroxy-1H-indole-2-carboxylate (4.33 g, 22.65 mmol) in THF (100 mL). The reaction mixture was stirred at room temperature for 1 hour. The reaction mixture was partitioned between EtOAc and water and the organic layer was separated, dried over $MgSO_4$, filtered and concentrated. The residue was adsorbed onto silica gel and purification was accomplished by silica gel column chromatography (EtOAc/hexanes) to afford the title compound (4.93 g, 71%). $^1$H NMR (400 MHz, $CDCl_3$): δ ppm 8.82 (br. s., 1H), 7.52 (d, 1H), 7.16 (s, 1H), 6.85 (s, 1H), 6.74 (d, 1H), 3.94 (s, 3H), 1.01 (s, 9H), 0.23 (s, 6H). Ms m/z 306 (M+1).

Step C: Methyl 3-bromo-6-{[(1,1-dimethylethyl)(dimethyl)silyl]oxy}-1H-indole-2-carboxylate

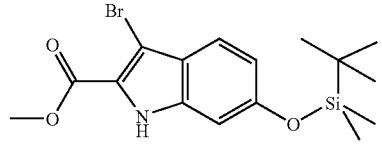

NBS (0.670 g, 3.77 mmol) was added to a solution of methyl 6-{[(1,1-dimethylethyl)(dimethyl)silyl]oxy}-1H-indole-2-carboxylate (1.15 g, 3.77 mmol) in DMF (6 mL) and stirred overnight. The reaction was partitioned between EtOAc and water. The organic layer was separated, dried over MgSO$_4$, filtered and concentrated. The residue was adsorbed onto silica gel and purification was accomplished by silica gel column chromatography (EtOAc/hexanes) to afford the title compound (0.246 g, 17%). $^1$H NMR (400 MHz, CDCl$_3$): δ ppm 9.31 (br. s., 1H), 7.48 (d, 1H), 6.76-6.84 (m, 2H), 3.98 (s, 3H), 0.99 (s, 9H), 0.21 (s, 6H).

Step D: 1-(1,1-Dimethylethyl)2-methyl 3-bromo-6-{[(1,1-dimethylethyl)(dimethyl)silyl]oxy}-1H-indole-1,2-dicarboxylate

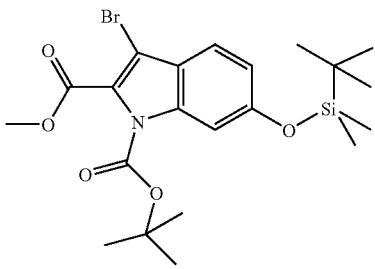

DIPEA (0.224 mL, 1.28 mmol), (Boc)$_2$O (0.157 g, 0.768 mmol) and PS-DMAP (0.043 g, 0.064 mmol) were added to a solution of methyl 3-bromo-6-{[(1,1-dimethylethyl)(dimethyl)silyl]oxy}-1H-indole-2-carboxylate (0.246 g, 0.640 mmol) in THF. The reaction mixture was stirred at 60° C. until starting material was consumed as evident by TLC. The resin was filtered off and the solvent evaporated to afford an oil. The residue was adsorbed onto silica gel and purification was accomplished by silica gel column chromatography (EtOAc/hexanes) to afford the title compound (0.293 g, 94%) as a clear oil. $^1$H NMR (400 MHz, CDCl$_3$): δ ppm 7.57 (s, 1H), 7.40 (d, 1H), 6.86 (d, 1H), 3.95 (d, 3H), 1.60 (s, 9H), 0.99 (s, 9H), 0.22 (d, 6H).

Step E: 1-(1,1-dimethylethyl)2-methyl 3-bromo-6-hydroxy-1H-indole-1,2

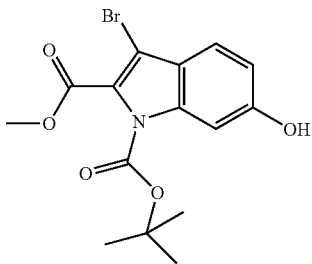

Cesium fluoride (0.455 g, 2.99 mmol) was added to a solution of 1-(1,1-dimethylethyl) 2-methyl 3-bromo-6-{[(1,1-dimethylethyl)(dimethyl)silyl]oxy}-1H-indole-1,2-dicarboxylate (0.290 g, 0.599 mmol) in 5 mL of DMF. The reaction mixture was stirred at room temperature until the starting material was consumed as evident by TLC. The reaction mixture was poured into EtOAc and water and the organic layer was separated, dried over MgSO$_4$, filtered, concentrated and adsorbed onto silica gel. Purification was accomplished by silica gel column chromatography (EtOAc/hexanes) to afford the title compound (0.256 g, 70%) as a white solid. $^1$H NMR (400 MHz, Acetone-d$_6$): δ ppm 8.89 (s, 1H), 7.63 (d, 1H), 7.42 (d, 1 H), 6.98 (dd, 1, H), 3.94 (s, 3H), 1.61 (s, 9H). MS m/z 368 (M−1).

Step F: 1-(1,1-Dimethylethyl)2-methyl 3-bromo-6-[(2-{[(1,1-dimethylethyl)(dimethyl)silyl]oxy}ethyl)oxy]-1H-indole-1,2-dicarboxylate

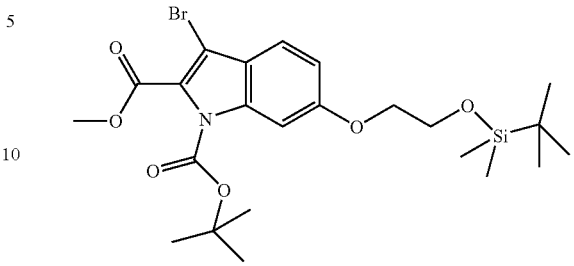

Cesium Carbonate (0.275 g, 0.844 mmol) was added to a solution of 1-(1,1-dimethylethyl)2-methyl 3-bromo-6-hydroxy-1H-indole-1,2-dicarboxylate (0.156 g, 0.422 mmol) and (2-bromoethyl)(1,1-dimethylethyl)dimethylsilane (0.151 g, 0.633 mmol) in DMF. After stirring for 2 h TLC showed clean conversion to product and the reaction mixture was partitioned between EtOAc and water. The organic layer was separated and dried over MgSO$_4$, filtered and concentrated. Purification was accomplished by silica gel column chromatography (EtOAc/hexanes) to afford the title compound (0.145 g, 65%). $^1$H NMR (400 MHz, CDCl$_3$): δ ppm 7.63 (s, 1H), 7.42 (d, 1H), 6.96 (d, 1H), 4.10 (t, 2H), 3.99 (t, 2H), 3.94 (s, 3H), 1.59 (s, 9H), 0.90 (s, 9H), 0.10 (s, 6H).

Step G: 3-Bromo-6-[(2-hydroxyethyl)oxy]-1H-indole-2-carboxylic acid

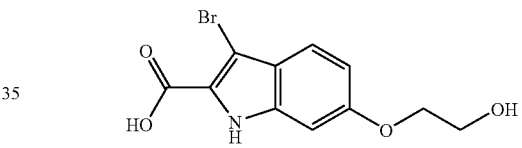

LiOH (1 N, 4 mL, 4 mmol) was added to a solution of 1-(1,1-dimethylethyl)2-methyl 3-bromo-6-[(2-{[(1,1-dimethylethyl)(dimethyl)silyl]oxy}ethyl)oxy]-1H-indole-1,2-dicarboxylate (0.145 g, 0.274 mmol) in THF (4 mL) and Methanol (4 mL). The reaction mixture was stirred overnight at room temperature. The solvents were evaporated and the residue was partitioned between EtOAc and 1 N HCl. The organic layer was separated, dried over MgSO$_4$ and evaporated to give a solid. The solid was triturated with DCM and filtered to afford the title compound (0.081 g, 98%) as a white solid. $^1$H NMR (400 MHz, DMSO-d$_6$): δ ppm 13.06 (br. s., 1H), 11.82 (s, 1H), 7.35 (d, 1H), 6.83 (d, 1H), 6.79 (dd, 1H), 4.84 (t, 1H), 3.95 (t, 2H), 3.70 (q, 2 H). MS m/z 300 (M+1).

Step H: 3-Bromo-N-({4-chloro-3-[(3-chloro-5-cyanophenyl)oxy]-2-fluorophenyl}methyl)-6-[(2-hydroxyethyl)oxy]-1H-indole-2-carboxamide

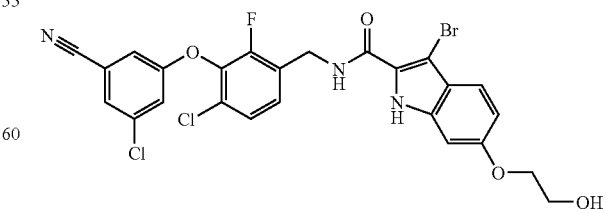

HATU (0.061 g, 0.161 mmol) and DIPEA (0.028 mL, 0.161 mmol) were added to a solution of 3-bromo-6-[(2-hydroxyethyl)oxy]-1H-indole-2-carboxylic acid (0.048 g, 0.161 mmol) and 3-{[3-(aminomethyl)-6-chloro-2-fluorophenyl]oxy}-5-chlorobenzonitrile (0.050 g, 0.161 mmol) in DMF (2 mL). This solution was stirred overnight at room temperature. The mixture was partitioned between water and EtOAc, followed by washing of the organic layer with a 15% solution of Na$_2$CO$_3$. The organic layer was separated and dried over MgSO$_4$. The EtOAc was evaporated to yield a residue which was triturated in acetone to afford the title compound (0.059 g, 59%) as a white solid. $^1$H NMR (400 MHz, DMSO-d$_6$): δ ppm 11.78 (s, 1H), 8.37 (t, 1H), 7.80 (s, 1H), 7.48-7.54 (m, 2H), 7.40-7.47 (m, 2H), 7.35 (d, 1H), 6.87 (s, 1H), 6.82 (d, 1H), 4.86 (t, 1H), 4.59 (d, 2H), 3.97 (t, 2H), 3.72 (q, 2H). MS m/z 592 (M+1).

Example 142

N-({4-chloro-3-[(3-chloro-5-cyanophenyl)oxy]-2-fluorophenyl}methyl)-6-[(2-hydroxyethyl)oxy]-1H-indole-2-carboxamide

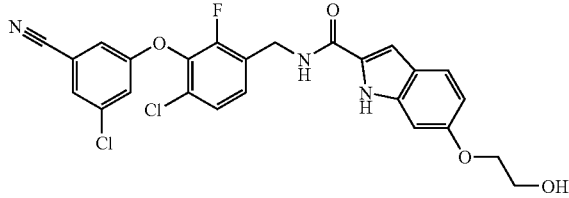

Step A: 1-(1,1-Dimethylethyl)2-methyl 6-{[(1,1-dimethylethyl)(dimethyl)silyl]oxy}-1H-indole-1,2-dicarboxylate

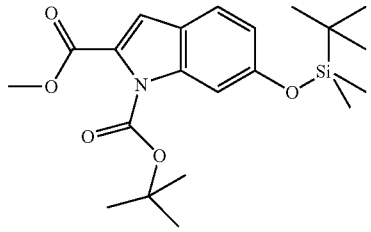

PS-DMAP (0.387 g, 0.697 mmol) and Boc2O (0.342 g, 1.67 mmol) were added to a solution of methyl 6-{[(1,1-dimethylethyl)(dimethyl)silyl]oxy}-1H-indole-2-carboxylate (0.426 g, 1.39 mmol) in THF and the reaction stirred at room temperature. The PS-DMAP resin was filtered off and the resulting solution concentrated. Purification was accomplished by silica gel column chromatography (EtOAc/hexanes) to afford the title compound (0.343 g, 60%) as a clear oil. $^1$H NMR (400 MHz, CDCl$_3$): δ ppm 7.57 (s, 1H), 7.40 (d, 1H), 7.04 (s, 1H), 6.79 (dd, 1H), 3.87 (s, 3H), 1.60 (s, 9H), 0.99 (s, 9H), 0.22 (s, 6H). MS m/z 428 (M+23).

Step B: 1-(1,1-dimethylethyl)2-methyl 6-hydroxy-1H-indole-1,2-dicarboxylate

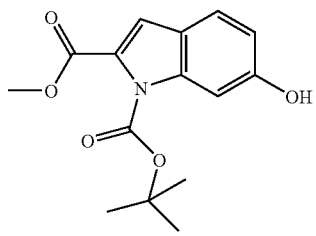

Cesium fluoride (2.76 g, 18.1 mmol) was added to a solution of 1-(1,1-dimethylethyl) 2-methyl 6-{[(1,1-dimethylethyl)(dimethyl)silyl]oxy}-1H-indole-1,2-dicarboxylate (3.68 g, 9.07 mmol) in 20 mL DMF and the reaction was stirred at room temperature until the starting material was consumed as evident by TLC. The reaction was poured into EtOAc and water and the organic layer was separated, dried over MgSO$_4$, filtered and concentrated onto silica. Purification was accomplished by silica gel column chromatography (EtOAc/hexanes) to afford the title compound (2.458 g, 93%) u24780-129-1 as a white solid. $^1$H NMR (400 MHz, CDCl$_3$): δ ppm 7.59 (d, 1H), 7.43 (d, 1H), 7.08 (s, 1H), 6.84 (dd, 1H), 5.92 (br. s., 1H), 3.91 (s, 3H), 1.59 (s, 9H). MS m/z 290 (M-1).

Step C: 1-(1,1-Dimethylethyl)2-methyl 6-[(2-{[(1,1-dimethylethyl)(dimethyl)silyl]oxy}ethyl)oxy]-1H-indole-1,2-dicarboxylate

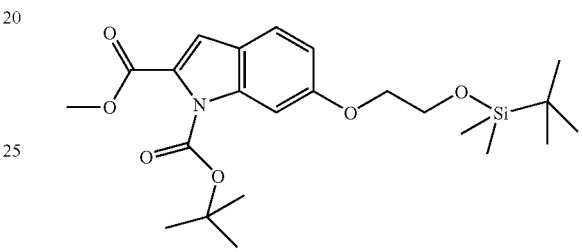

DBU (0.052 mL, 0.34 mmol) was added to a solution of 1-(1,1-dimethylethyl)2-methyl 6-hydroxy-1H-indole-1,2-dicarboxylate (0.100 g, 0.343 mmol) and [(2-bromoethyl)oxy](1,1-dimethylethyl)dimethylsilane (0.082 g, 0.34 mmol) in DMF. The reaction mixture was heated for 1 h at 90° C. The reaction mixture was poured into EtOAc and water, the organic layer was separated, dried over MgSO$_4$ and concentrated onto silica. Purification was accomplished by silica gel column chromatography (EtOAc/hexanes) to afford the title compound (0.129 g, 84%) as an oil. $^1$H NMR (400 MHz, CDCl$_3$): δ ppm 7.61 (s, 1H), 7.44 (d, 1H), 7.06 (s, 1H), 6.89 (d, 1H), 4.10 (t, 2H), 3.99 (t, 2H), 3.88 (s, 3H), 1.60 (s, 9H), 0.90 (s, 9H), 0.10 (s, 6H). MS m/z 350 (M+23).

Step D: 6-[(2-Hydroxyethyl)oxy]-1H-indole-2-carboxylic acid

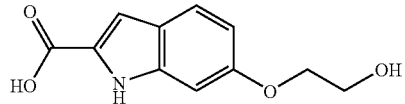

LiOH (1 N, 4 mL) was added to a methanol solution of 1-(1,1-dimethylethyl)2-methyl 6-[(2-{[(1,1-dimethylethyl)(dimethyl)silyl]oxy}ethyl)oxy]-1H-indole-1,2-dicarboxylate (0.129 g, 0.288 mmol). The reaction turned cloudy and THF was added to dissolve the precipitate. The reaction was heated to 70° C. until the starting material was consumed as evident by TLC. The reaction mixture was poured into EtOAc and water and the aqueous layer was separated and acidified with concentrated HCl. The aqueous layer was extracted with EtOAc dried over MgSO$_4$ and concentrated to afford the title compound (0.041 g, 64%). $^1$H NMR (400 MHz, Acetone-d$_6$): δ ppm 10.62 (br. s., 1H), 7.52 (d, 1H), 7.11 (s, 1H), 6.99 (s, 1H), 6.68-6.82 (m, 1H), 4.06 (t, 2H), 3.88 (t, 2H). MS m/z 220 (M-1).

Step E: N-({4-chloro-3-[(3-chloro-5-cyanophenyl)oxy]-2-fluorophenyl}methyl)-6-[(2-hydroxyethyl)oxy]-1H-indole-2-carboxamide

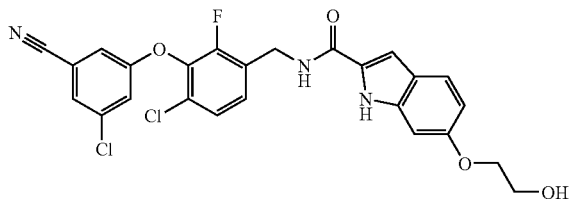

HATU (0.070 g, 0.186 mmol) and DIPEA (0.024 mL, 0.186 mmol) were added to a solution 6-[(2-hydroxyethyl)oxy]-1H-indole-2-carboxylic acid (0.041 g, 0.186 mmol) and 3-{[3-(aminomethyl)-6-chloro-2-fluorophenyl]oxy}-5-chlorobenzonitrile (0.057 g, 0.186 mmol) in DMF. This solution was stirred 2 h at room temperature. The mixture was partitioned between water and EtOAc, the organic layer was separated, washed with a 15% solution of $Na_2CO_3$, dried over $MgSO_4$ and filtered. The EtOAc was evaporated to yield a residue which upon trituration in EtOAc afforded the title compound (0.041 g, 42%) as a white solid. $^1H$ NMR (400 MHz, DMSO-$d_6$): δ ppm 11.38 (s, 1H), 8.88 (t, 1H), 7.80 (s, 1H), 7.43-7.53 (m, 4H), 7.37 (t, 1H), 7.08 (s, 1H), 6.85 (s, 1H), 6.68 (d, 1H), 4.83 (t, 1H), 4.53 (d, 2H), 3.94 (t, 2H), 3.71 (q, 2H). MS m/z 512 (M−1).

Example 143

4-chloro-N-({4-chloro-3-[(3-cyano-5-ethenylphenyl)oxy]-2-fluorophenyl}methyl)-1H-imidazole-5-carboxamide

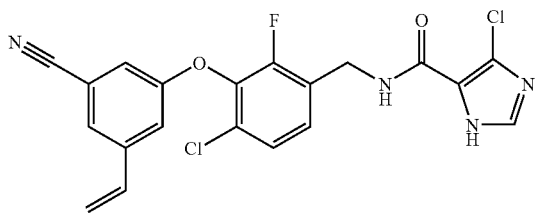

Step A: 3-bromo-5-[(6-chloro-2-fluoro-3-methylphenyl)oxy]benzonitrile 6-chloro-2-fluoro-3-methylphenol (8.03 g, 50.0 mmol) and 18-crown-6 (7.7 g, 29.1 mmol) were dissolved in dry DMSO (100 mL) and treated with 20% potassium t-butoxide in THF (28.1 g, 50.0 mmol) for 15 minutes at room temperature. 3-bromo-5-fluorobenzonitrile (10 g, 50.0 mmol) was added in one portion and the reaction mixture heated at 125° C. for 20 h at which time LC-MS indicated >90% conversion. The reaction mixture was cooled to ambient temperature and water was added to afford the crude product as a black precipitate which was filtered off, washed with water and air dried. The crude product was dissolved in DCM, dried over $MgSO_4$, and filtered through a plug of 45 g silica gel which was eluted with 500 mL DCM. The filtrate was concentrated to an amber oil and crystallized by addition of IPA (100 mL). The precipitate was cooled in an ice bath and filtered to afford 3-bromo-5-[(6-chloro-2-fluoro-3-methylphenyl)oxy]benzonitrile (10.7 g, 31.4 mmol, 62.8% yield) as a tan solid in >90% purity as determined by LCMS. 1H NMR (400 MHz, DMSO-$d_6$) δ ppm 7.91 (s, 1H), 7.56 (s, 1H), 7.53 (s, 1H), 7.28-7.45 (m, 2H), 2.28 (s, 3H).

Step B: 3-bromo-5-{[3-(bromomethyl)-6-chloro-2-fluorophenyl]oxy}benzonitrile 3-bromo-5-[(6-chloro-2-fluoro-3-methylphenyl)oxy]benzonitrile (6.05 g, 17.76 mmol) and NBS (3.16 g, 17.76 mmol) were combined in carbon tetrachloride (100 mL) with a catalytic amount of AIBN (0.146 g, 0.888 mmol) and stirred at reflux for 16 h. The reaction mixture was washed with water, dried over $MgSO_4$, filtered and concentrated to dryness. The residue was purified on silica gel (eluted with 0 to 10% $Et_2O$ in hexanes) to give 3-bromo-5-{[3-(bromomethyl)-6-chloro-2-fluorophenyl]oxy}benzonitrile (4.5 g, 10.73 mmol, 60.4% yield) as a white solid. 1H NMR (400 MHz, DMSO-$d_6$) δ ppm 7.92-7.95 (m, 1H), 7.52-7.61 (m, 4H), 4.75 (s, 2H).

Step C: 3-{[3-(azidomethyl)-6-chloro-2-fluorophenyl]oxy}-5-bromobenzonitrile 3-bromo-5-{[3-(bromomethyl)-6-chloro-2-fluorophenyl]oxy}benzonitrile (2.25 g, 5.36 mmol) and sodium azide (0.349 g, 5.36 mmol) were combined in DMSO (10 mL) and stirred overnight at 25° C. The reaction mixture was diluted with EtOAc, washed 4× with water, dried over $MgSO_4$, filtered and concentrated to dryness to give 3-{[3-(azidomethyl)-6-chloro-2-fluorophenyl]oxy}-5-bromobenzonitrile (2.04 g, 5.35 mmol, 100% yield) as a clear oil. 1H NMR (400 MHz, DMSO-$d_6$) δ ppm 7.93 (t, 1H), 7.48-7.63 (m, 4H), 4.60 (s, 2H).

Step D: 3-{[3-(aminomethyl)-6-chloro-2-fluorophenyl]oxy}-5-bromobenzonitrile

3-{[3-(azidomethyl)-6-chloro-2-fluorophenyl]oxy}-5-bromobenzonitrile (2.04 g, 5.35 mmol) dissolved in THF (30 mL) was treated successively with triphenylphosphine (2.10 g, 8.02 mmol) and water (0.482 g, 26.7 mmol) at 25° C. for 16 h with stirring. The reaction mixture was concentrated to dryness and purified on silica gel (eluted successively with EtOAc (to remove triphylphosphine oxide) followed by a gradient of 100% EtOAc to 10% $CH_3OH/DCM$) to give 3-{[3-(aminomethyl)-6-chloro-2-fluorophenyl]oxy}-5-bromobenzonitrile (1.12 g, 3.15 mmol, 58.9% yield) as a white solid. 1H NMR (400 MHz, DMSO-$d_6$) δ ppm 7.92 (t, 1H), 7.46-7.57 (m, 4H), 3.77 (s, 2H), 1.91 (br. s., 2H). LC-MS ($ES^+$) m/z 354.92, 356.91, 358.88 [M+H].

Step E: 3-{[3-(aminomethyl)-6-chloro-2-fluorophenyl]oxy}-5-ethenylbenzonitrile

3-{[3-(aminomethyl)-6-chloro-2-fluorophenyl]oxy}-5-bromobenzonitrile (0.70 g, 1.969 mmol) was combined with potassium vinyl trifluoroborate (0.396 g, 2.95 mmol), [1,1'-bis(diphenylphosphino)ferrocene]dichloropalladium(II), dichloromethane complex (1:1) (0.058 g, 0.079 mmol) and TEA (0.412 mL, 2.95 mmol) in n-propanol (10 mL) and heated in a microwave reactor at 120° C. for 30 min. The reaction mixture was filtered through Celite™ and concentrated to dryness. The residue was dissolved in DCM, washed with saturated aqueous $NaHCO_3$, dried over $MgSO_4$, filtered and concentrated to dryness. The crude material was purified on silica gel (eluted with 0 to 10% $CH_3OH/DCM$) to give 3-{[3-(aminomethyl)-6-chloro-2-fluorophenyl]oxy}-5-ethenylbenzonitrile (0.52 g, 1.718 mmol, 87% yield) as an orange solid. 1H NMR (400 MHz, DMSO-$d_6$) δ ppm 7.79 (s, 1H), 7.45-7.55 (m, 2H), 7.40 (s, 1H), 7.25 (s, 1H), 6.75 (dd, 1H), 6.04 (d, 1H), 5.43 (d, 1H), 3.77 (s, 2H), 2.05 (br. s., 2H). LC-MS ($ES^+$) m/z 303.32, 305.30 [M+H].

Step F: 2-bromo-4,5-dichloro-1-({[2-(trimethylsilyl)ethyl]oxy}methyl)-1H-imidazole A solution of 2-bromo-4,5-dichloro-1H-imidazole (2.16 g, 10 mmol) in THF (25 mL) was added dropwise to a suspension of NaH (440 mg of a 60% suspension in mineral oil, 11 mmol) in THF (20 mL) at 0° C. The mixture was stirred at RT for 2 h, cooled to 0° C. and {2-[(chloromethyl)oxy]ethyl}(trimethyl)silane (1.9 mL, 11 mmol) was added dropwise. The mixture was stirred at RT overnight. Saturated NaHCO$_3$ was added and the aqueous layer was extracted with CH$_2$Cl$_2$. The organic layer was dried (Na$_2$SO$_4$), filtered, concentrated and purified by silica gel chromatography (0-50% CH$_2$Cl$_2$/hexanes) to give the title compound (3.26 g, 95%) as a white solid. 1H NMR (400 MHz, CHLOROFORM-d) δ ppm 5.26 (2H, s) 3.55-3.61 (2H, m) 0.88-0.94 (2H, m) −0.02 (9H, s). LCMS: m/z 346 (M+1).

Step G: 4-chloro-1-({[2-(trimethylsilyl)ethyl]oxy}methyl)-1H-imidazole-5-carboxylic acid nBuLi (1.27 mL of a 1.57 M solution in hexanes, 2.00 mmol) was added dropwise to a solution of 2-bromo-4,5-dichloro-1-({[2-(trimethylsilyl)ethyl]oxy}methyl)-1H-imidazole (0.69 g, 2.0 mmol) in THF (40 mL) at −78° C. under N$_2$. The reaction mixture was stirred for 20 min and TMSCl (0.25 mL, 2.00 mmol) was added dropwise. The cooling bath was removed and the reaction mixture was allowed to warm to RT. After 4 h at RT, the solution was cooled to −78° C. and nBuLi (1.27 mL of a 1.57 M solution in hexanes, 2.00 mmol) was added dropwise. After 30 min, DMF (1.0 mL, 12.91 mmol) was added and the reaction was stirred at RT for 20 min. Saturated aqueous NH$_4$Cl solution was added to the reaction and extracted with EtOAc. The organic phase was dried (Na$_2$SO$_4$), filtered, and purified by silica gel chromatography (0-30% EtOAc/hexanes) to afford a mixture of two compounds. THF (5 mL) was added followed by tBuOH (1.21 mL) and 2-methyl-butene (9.8 mL of a 2M solution in THF, 19.5 mmol). A solution of NaClO$_2$ (1.4 g, 15.6 mmol) and NaH$_2$PO$_4$.H$_2$O (1.29 g, 9.4 mmol) in water (4 mL) was added and the solution was stirred at RT overnight. The organic layer was separated and the aqueous layer was extracted with ethyl acetate. The organic layer was separated, dried over Na$_2$SO$_4$, filtered and concentrated to give 0.43 g (77%) of the title compound as a pale yellow oil. 1H NMR (400 MHz, DMSO-d$_6$) δ ppm 13.43 (br. s., 1H), 8.10 (s, 1H), 5.60 (s, 2 H), 3.48 (t, 2H), 0.82 (t, 2H), −0.06 (s, 9H).

Step H: 4-chloro-N-({4-chloro-3-[(3-cyano-5-ethenylphenyl)oxy]-2-fluorophenyl}methyl)-1H-imidazole-5-carboxamide 3-{[3-(aminomethyl)-6-chloro-2-fluorophenyl]oxy}-5-ethenylbenzonitrile (0.076 g, 0.251 mmol), 4-chloro-1-({[2-(trimethylsilyl)ethyl]oxy}methyl)-1H-imidazole-5-carboxylic acid (0.069 g, 0.251 mmol) and DIPEA (0.088 mL, 0.502 mmol) were combined in THF (2 mL) and treated with HATU (0.105 g, 0.276 mmol) at 25° C. overnight with stirring. The reaction mixture was concentrated to dryness, dissolved in DCM, washed with water, dried over MgSO$_4$, filtered and concentrated to dryness. The residue was dissolved in DCM (2.5 mL) and treated with TFA (2.5 mL) at 25° C. for 3 days. The reaction mixture was concentrated to dryness and partitioned between EtOAc and saturated aqueous NaHCO$_3$. The organic phase was isolated, dried over MgSO$_4$, filtered and concentrated to dryness. The crude material was purified on an XTerra™ C-18 column eluted with 5 to 90% CH$_3$CN/H$_2$O (0.2% NH$_4$OH buffer). Appropriate fractions were combined, concentrated to dryness, chased twice with ethanol and twice with toluene to remove residual water to give 4-chloro-N-({4-chloro-3-[(3-cyano-5-ethenyl phenyl)oxy]-2-fluorophenyl}methyl)-1H-imidazole-5-carboxamide (0.040 g, 0.093 mmol, 36.9% yield) as a white solid. 1H NMR (400 MHz, DMSO-d$_6$) δ ppm 13.2 (br. s., 1H), 8.31 (br. s., 1H), 7.80 (s, 1H), 7.77 (s, 1H), 7.26-7.53 (m, 4H), 6.75 (dd, 1H), 6.04 (d, 1H), 5.44 (d, 1H), 4.53 (d, 2H). LC-MS (ES$^-$) m/z 429.08, 431.11, 433.00 [M−1]. LC-MS (ES$^+$) m/z 430.97, 432.95, 434.95 [M+H].

Example 144

4-chloro-N-({4-chloro-3-[(2,5-dichloro-3-cyanophenyl)oxy]-2-fluorophenyl}methyl)-1H-imidazole-5-carboxamide

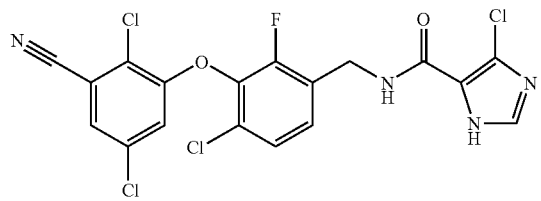

Step A: 2-[(3-bromo-2,5-dichlorophenyl)oxy]-1-chloro-3-fluoro-4-methylbenzene 6-chloro-2-fluoro-3-methylphenol (3.3 g, 20.55 mmol) and 18-crown-6 (1.086 g, 4.11 mmol) were dissolved in dry DMSO (50 mL) and treated with 20% potassium t-butoxide in THF (11.50 g, 20.55 mmol) for 15 minutes at room temperature. 1-bromo-2,5-dichloro-3-fluorobenzene (7.21 g, 29.6 mmol) was added in one portion and the reaction mixture heated at 110° C. for 3 days at which time LC-MS indicated nearly complete consumption of phenol and formation of a major new product. Addition of water to the reaction mixture resulted in a brown gummy oil which was extracted with EtOAc. The organic phase was isolated, washed with brine four times, dried over MgSO$_4$, filtered and concentrated to dryness to give a brown syrup. This material was filtered through a plug of 45 g silica gel which was eluted with 500 mL DCM. The filtrate was concentrated to an amber oil and crystallized from EtOH and a few drops of water. This mixture was cooled in an ice bath, filtered, and the precipitate washed with three portions of cold EtOH to give 2-[(3-bromo-2,5-dichlorophenyl)oxy]-1-chloro-3-fluoro-4-methylbenzene (4.0 g, 10.40 mmol, 50.6% yield) as a cream solid. 1H NMR (400 MHz, DMSO-d$_6$) δ ppm 7.73 (s, 1H), 7.29-7.47 (m, 2H), 6.81 (s, 1H), 2.29 (s, 3H).

Step B: 2,5-dichloro-3-[(6-chloro-2-fluoro-3-methylphenyl)oxy]benzonitrile

2-[(3-bromo-2,5-dichlorophenyl)oxy]-1-chloro-3-fluoro-4-methylbenzene (2.0 g, 5.20 mmol) was combined with dicyanozinc (0.305 g, 2.60 mmol) and tetrakis(triphenylphosphine)palladium(0) (0.601 g, 0.520 mmol) and heated at 120° C. for 60 min in a microwave reactor under an inert atmosphere. The reaction mixture was diluted with EtOAc, washed four times with water, dried over MgSO$_4$, filtered and concentrated to dryness. The residue was purified on 120 g silica eluted successively with 100% hexanes followed by 0 to 10% EtOAc/hexanes to give 2,5-dichloro-3-[(6-chloro-2-fluoro-3-methylphenyl)oxy]benzonitrile (1.01 g, 3.06 mmol, 58.7% yield) as a white solid. 1H NMR (400 MHz, DMSO-d$_6$) δ ppm 8.00 (d, J=2.20 Hz, 1H), 7.31-7.47 (m, 2H), 7.24 (d, J=1.83 Hz, 1H), 2.29 (d, J=1.74 Hz, 3H).

Step C: 3-{[3-(bromomethyl)-6-chloro-2-fluorophenyl]oxy}-2,5-dichlorobenzonitrile 2,5-dichloro-3-[(6-chloro-2-fluoro-3-methylphenyl)oxy]benzonitrile (1.01 g, 3.06 mmol) and NBS (0.544 g, 3.06 mmol) were combined in carbon tetrachloride (30 mL) with a catalytic amount of AIBN (0.025 g, 0.153 mmol) and stirred at reflux for 16 h. The reaction mixture was washed with water, dried over MgSO$_4$, filtered and concentrated to dryness. The residue was purified by chromatography on 80 g silica gel eluted with 0 to 10% Et$_2$O in hexanes to give the 3-{[3-(bromomethyl)-6-chloro-2-fluorophenyl]oxy}-2,5-dichlorobenzonitrile (0.647 g, 1.580 mmol, 51.7% yield) as a white solid. 1H NMR (400 MHz, DMSO-d$_6$) δ ppm 8.03 (d, J=2.20 Hz, 1H), 7.53-7.64 (m, 2H), 7.29 (d, J=1.92 Hz, 1H), 4.75 (s, 2H).

Step D: 3-{[3-(azidomethyl)-6-chloro-2-fluorophenyl]oxy}-2,5-dichlorobenzonitrile 3-{[3-(bromomethyl)-6-chloro-2-fluorophenyl]oxy}-2,5-dichlorobenzonitrile (0.65 g, 1.587 mmol) and sodium azide (0.114 g, 1.746 mmol) were combined in DMSO (7 mL) and stirred overnight at 25° C. Water was added to the reaction mixture to give a white precipitate. The reaction mixture was stirred for 15 min at room temperature, filtered, washed with water, and air dried to give 3-{[3-(azidomethyl)-6-chloro-2-fluorophenyl]oxy}-2,5-dichlorobenzonitrile (0.565 g, 1.521 mmol, 96% yield) as a white solid. 1H NMR (400 MHz, DMSO-d$_6$) δ ppm 8.02 (d, J=2.20 Hz, 1H), 7.50-7.63 (m, 2H), 7.31 (d, J=1.74 Hz, 1H), 4.61 (s, 2H).

Step E: 3-{[3-(aminomethyl)-6-chloro-2-fluorophenyl]oxy}-2,5-dichlorobenzonitrile 3-{[3-(azidomethyl)-6-chloro-2-fluorophenyl]oxy}-2,5-dichlorobenzonitrile (0.565 g, 1.521 mmol) was dissolved in THF (5 mL) and was treated successively with triphenylphosphine (0.598 g, 2.281 mmol) and water (0.137 g, 7.60 mmol) at 25° C. for 3 days with stirring. The reaction mixture was concentrated to dryness and purified on 40 g silica gel eluted successively with EtOAc (to remove triphylphosphine oxide) followed by a gradient of 100% EtOAc to 10% CH$_3$OH/DCM to give the desired product, 3-{[3-(aminomethyl)-6-chloro-2-fluorophenyl]oxy}-2,5-dichlorobenzonitrile (0.487 g, 1.409 mmol, 93% yield), as a white solid. 1H NMR (400 MHz, DMSO-d$_6$) δ ppm 8.00 (d, J=2.20 Hz, 1H), 7.48-7.58 (m, 2H), 7.19 (d, J=1.83 Hz, 1H), 3.77 (s, 2H), 1.94 (br. s., 2H). LC-MS (ES$^+$) m/z 344.89, 346.89, 348.89 [M+H].

Step F: 4-chloro-N-({4-chloro-3-[(2,5-dichloro-3-cyanophenyl)oxy]-2-fluorophenyl}methyl)-1H-imidazole-5-carboxamide 3-{[3-(aminomethyl)-6-chloro-2-fluorophenyl]oxy}-2,5-dichlorobenzonitrile (0.062 g, 0.181 mmol), 4-chloro-1-({[2-(trimethylsilyl)ethyl]oxy}methyl)-1H-imidazole-5-carboxylic acid (0.05 g, 0.181 mmol) and DIPEA (0.063 mL, 0.361 mmol) were combined in THF (2 mL) and treated with HATU (0.076 g, 0.199 mmol) at 25° C. for 6 h with stirring. The reaction mixture was concentrated to dryness, dissolved in DCM, washed with saturated aqueous NaHCO$_3$, dried over MgSO$_4$, filtered and concentrated to dryness. The residue was dissolved in DCM (2.5 mL) and treated with TFA (2.5 mL) at 25° C. for 16 h. The reaction mixture was concentrated to dryness, dissolved in DCM, washed with saturated aqueous NaHCO$_3$, dried over MgSO$_4$, filtered and concentrated to dryness. The resultant solid was recrystallized from boiling EtOH, cooled in an ice bath and filtered to give 4-chloro-N-({4-chloro-3-[(2,5-dichloro-3-cyanophenyl)oxy]-2-fluorophenyl}methyl)-1H-imidazole-5-carboxamide (0.067 g, 0.141 mmol, 78% yield) as a white solid. 1H NMR (400 MHz, DMSO-d$_6$) δ ppm 13.18 (br. s., 1H), 8.27 (s, 1H), 8.02 (d, J=2.06 Hz, 1H), 7.78 (s, 1H), 7.53 (d, J=8.38 Hz, 1H), 7.40 (t, J=7.69 Hz, 1H), 7.25 (d, J=1.65 Hz, 1H), 4.53 (d, 2H).

LC-MS (ES$^-$) m/z 471.01, 473.00, 474.99 [M−1]. LC-MS (ES$^+$) m/z 472.91, 474.92, 476.90 [M+H].

Example 145

4-chloro-N-({4-chloro-3-[(3-cyano-5-methylphenyl)oxy]-2-fluorophenyl}methyl)-1H-imidazole-5-carboxamide

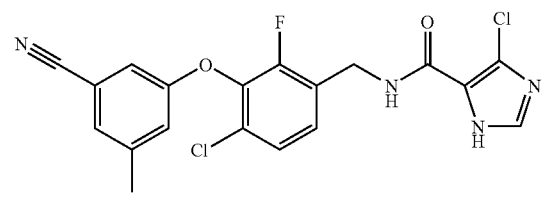

Step A: 3-{[3-(aminomethyl)-6-chloro-2-fluorophenyl]oxy}-5-methylbenzonitrile

3-{[3-(aminomethyl)-6-chloro-2-fluorophenyl]oxy}-5-bromobenzonitrile (0.200 g, 0.562 mmol) and tetrakis(triphenylphosphine)palladium(0) (0.065 g, 0.056 mmol) were combined in THF (4 mL) and treated with dimethylzinc (1 M in heptane) (1.125 mL, 1.125 mmol) with stirring under an inert atmosphere. The reaction mixture was heated to 65° C. and stirred for 1 h. The reaction mixture was concentrated to dryness, partitioned between EtOAc and saturated aqueous NaHCO$_3$, the organic phase was isolated, dried over MgSO$_4$, filtered and concentrated to dryness. The residue was dissolved in CH$_3$OH and gravity filtered through a StratoSpheres™ PL-Thiol MP SPE+ cartridge. The filtrate was cooled in an ice bath and the resultant precipitate filtered off to give 3-{[3-(aminomethyl)-6-chloro-2-fluorophenyl]oxy}-5-methylbenzonitrile (0.023 g, 0.079 mmol, 14.07% yield) as a white solid. The mother liquor was concentrated to dryness and purified on 40 g silica gel eluted successively with EtOAc and 10% CH$_3$OH/DCM to give a second batch of 3-{[3-(aminomethyl)-6-chloro-2-fluorophenyl]oxy}-5-methylbenzonitrile (0.072 g, 0.248 mmol, 44.0% yield) as a white solid. 1H NMR (400 MHz, DMSO-d$_6$) δ ppm 7.45-7.53 (m, 2H), 7.42 (s, 1H), 7.19 (s, 1H), 7.10 (s, 1H), 3.76 (s, 2H), 2.33 (s, 3H), 1.99 (br. s., 2H). LC-MS (ES$^-$) m/z 289.99, 291.15 [M−1]. LC-MS (ES$^+$) m/z 290.98, 293.00 [M+H].

Step B: 4-chloro-N-({4-chloro-3-[(3-cyano-5-methylphenyl)oxy]-2-fluorophenyl}methyl)-1H-imidazole-5-carboxamide 3-{[3-(aminomethyl)-6-chloro-2-fluorophenyl]oxy}-5-methylbenzonitrile (0.053 g, 0.181 mmol), 4-chloro-1-({[2-(trimethylsilyl)ethyl]oxy}methyl)-1H-imidazole-5-carboxylic acid (0.050 g, 0.181 mmol) and DIPEA (0.063 mL, 0.361 mmol) were combined in THF (2 mL) and treated with HATU (0.076 g, 0.199 mmol) at 25° C. overnight with stirring. The reaction mixture was concentrated to dryness, dissolved in DCM, washed with water, dried over MgSO$_4$, filtered and concentrated to dryness. The residue was dissolved in DCM (2.5 mL) and treated with TFA (2.5 mL) at 25° C. for 3 days. The reaction mixture was concentrated to dryness, dissolved in DCM, washed with saturated aqueous NaHCO$_3$, dried over MgSO$_4$, filtered and concentrated to dryness. The resultant solid was recrystallized from boiling IPA, cooled in an ice bath and filtered to give 4-chloro-N-({4-chloro-3-[(3-cyano-5-methylphenyl)oxy]-2-fluorophenyl}methyl)-1H-imidazole-5-carboxamide (0.043 g, 0.103 mmol, 56.8% yield) as a white solid. 1H NMR (400 MHz, DMSO-d$_6$) δ ppm 13.17 (br. s., 1H), 8.25 (m, 1H), 7.78 (s, 1H), 7.50 (m, 1H), 7.44 (s, 1H), 7.36 (t, J=8.03 Hz, 1H), 7.22 (s, 1H), 7.13 (s, 1H), 4.54 (d, J=5.36 Hz, 2H), 2.33 (s, 3H). LC-MS (ES⁻) m/z 417.04, 419.01 [M−1]. LC-MS (ES⁺) m/z 418.79, 420.06 [M+H].

Example 146

4-bromo-N-({4-chloro-3-[(3-cyano-5-methylphenyl)oxy]-2-fluorophenyl}methyl)-2-methyl-1H-imidazole-5-carboxamide

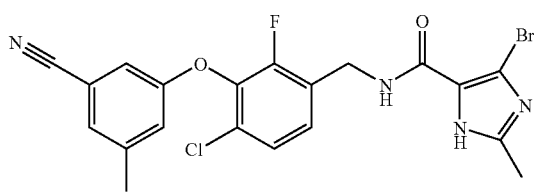

3-{[3-(aminomethyl)-6-chloro-2-fluorophenyl]oxy}-5-methylbenzonitrile (0.046 g, 0.158 mmol), 4-bromo-2-methyl-1H-imidazole-5-carboxylic acid (0.032 g, 0.158 mmol) and DIEA (0.055 mL, 0.316 mmol) were combined in THF (3 mL) and treated with EDC (0.061 g, 0.316 mmol) at 25° C. overnight with stirring. The reaction mixture was concentrated to dryness and partitioned between EtOAc and water. The organic phase was isolated, dried over MgSO₄, filtered and concentrated to dryness. The residue was purified on 40 g silica gel eluted with 0 to 10% CH₃OH/DCM to give 4-bromo-N-({4-chloro-3-[(3-cyano-5-methylphenyl)oxy]-2-fluorophenyl}methyl)-2-methyl-1H-imidazole-5-carboxamide (0.052 g, 0.109 mmol, 68.8% yield) as a white solid. 1H NMR (400 MHz, DMSO-d₆+1 drop D₂O) δ ppm 7.38-7.49 (m, 2H), 7.31 (t, J=7.90 Hz, 1H), 7.15 (m, 1H), 7.11 (s, 1H), 4.47 (s, 2H), 2.31 (s, 3H), 2.24 (s, 3 H). LC-MS (ES⁻) m/z 475.07, 477.03, 479.03 [M−1]. LC-MS (ES⁺) m/z 477.11, 479.09, 481.07 [M+H].

Example 147

4-chloro-N-({4-chloro-3-[(3,5-dicyanophenyl)oxy]-2-fluorophenyl}methyl)-1H-imidazole-5-carboxamide

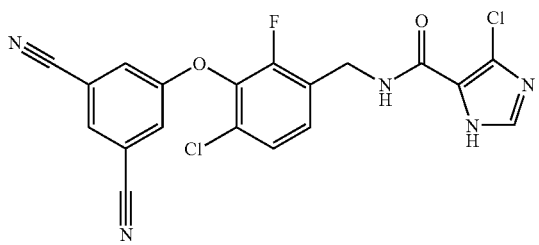

Step A: 5-{[3-(aminomethyl)-6-chloro-2-fluorophenyl]oxy}-1,3-benzenedicarbonitrile 3-{[3-(aminomethyl)-6-chloro-2-fluorophenyl]oxy}-5-bromobenzonitrile (0.355 g, 0.998 mmol) was combined with dicyanozinc (0.100 g, 0.852 mmol) and tetrakis(triphenylphosphine)palladium(0) (0.115 g, 0.100 mmol) in DMF (3 mL) and heated at 120° C. for 25 min in a microwave reactor under an inert atmosphere. The reaction mixture was diluted with EtOAc, washed twice with saturated aqueous NaHCO₃ and twice with water, dried over MgSO₄, filtered and concentrated to dryness. The residue was dissolved in CH₃OH and gravity filtered through a StratoSpheres™ PL-Thiol MP SPE+ cartridge. The filtrate was concentrated to dryness and purified on 40 g silica gel eluted successively with EtOAc and 10% CH₃OH/DCM to give 5-{[3-(aminomethyl)-6-chloro-2-fluorophenyl]oxy}-1,3-benzenedicarbonitrile (0.200 g, 0.663 mmol, 66.4% yield) as a white solid. 1H NMR (400 MHz, DMSO-d₆) δ ppm 8.22 (s, 1H), 7.91 (s, 2H), 7.46-7.57 (m, 2H), 3.77 (s, 2H), 1.90 (br. s., 2H). LC-MS (ES⁺) m/z 302.27, 304.19 [M+H].

Step B: 4-chloro-N-({4-chloro-3-[(3,5-dicyanophenyl)oxy]-2-fluorophenyl}methyl)-1H-imidazole-5-carboxamide 5-{[3-(aminomethyl)-6-chloro-2-fluorophenyl]oxy}-1,3-benzenedicarbonitrile (0.054 g, 0.181 mmol), 4-chloro-1-({[2-(trimethylsilyl)ethyl]oxy}methyl)-1H-imidazole-5-carboxylic acid (0.050 g, 0.181 mmol) and DIPEA (0.063 mL, 0.361 mmol) were combined in THF (2 mL) and treated with HATU (0.076 g, 0.199 mmol) at 25° C. overnight with stirring. The reaction mixture was concentrated to dryness, dissolved in DCM, washed with water, dried over MgSO₄, filtered and concentrated to dryness. The residue was dissolved in DCM (2.5 mL) and treated with TFA (2.5 mL) at 25° C. for 3 days. The reaction mixture was concentrated to dryness, dissolved in DCM, washed with saturated aqueous NaHCO₃, dried over MgSO₄, filtered and concentrated to dryness. The resultant solid was recrystallized from boiling IPA, cooled in an ice bath and filtered to give 4-chloro-N-({4-chloro-3-[(3,5-dicyanophenyl)oxy]-2-fluorophenyl}methyl)-1H-imidazole-5-carboxamide (0.056 g, 0.130 mmol, 72.1% yield) as a white solid. 1H NMR (400 MHz, DMSO-d₆) δ ppm 13.19 (br. s., 1H), 8.20-8.36 (m, 2H), 7.94 (d, J=0.82 Hz, 2H), 7.78 (s, 1H), 7.33-7.55 (m, 2H), 4.54 (d, J=3.43 Hz, 2H). LC-MS (ES⁻) m/z 428.03, 430.02 [M−1]. LC-MS (ES⁺) m/z 430.27, 431.98 [M+H].

Example 148

4-chloro-N-({4-chloro-3-[(3-cyano-5-ethylphenyl)oxy]-2-fluorophenyl}methyl)-1H-imidazole-5-carboxamide

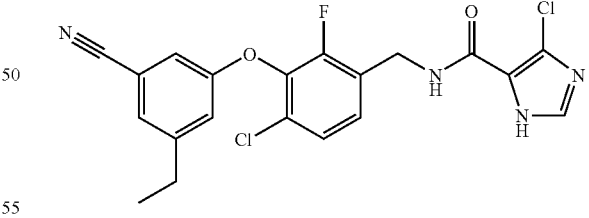

Step A: 3-{[3-(aminomethyl)-6-chloro-2-fluorophenyl]oxy}-5-ethylbenzonitrile

3-{[3-(aminomethyl)-6-chloro-2-fluorophenyl]oxy}-5-bromobenzonitrile (0.400 g, 1.125 mmol) and tetrakis(triphenylphosphine)palladium(0) (0.130 g, 0.112 mmol) were combined in THF (7 mL) and treated with diethylzinc (1 M in heptane) (2.250 mL, 2.250 mmol) with stirring under an inert atmosphere. The reaction mixture was heated to 70° C. and stirred for 2 h. The reaction mixture was concentrated to dryness and partitioned between EtOAc and saturated aqueous NaHCO₃. The organic phase was isolated, dried over MgSO₄, filtered and concentrated to dryness. The residue was purified on 40 g silica gel eluted successively with EtOAc and 10% CH₃OH/DCM to give 3-{[3-(aminomethyl)-6-chloro-2-fluorophenyl]oxy}-5-ethylbenzonitrile (0.213 g, 0.699 mmol, 62.1% yield) as a clear oil. 1H NMR (400 MHz, DMSO-d₆) δ ppm 7.44-7.54 (m, 3H), 7.12-7.20 (m, 2H), 3.76 (s, 2H), 2.64 (q, J=7.60 Hz, 2H), 1.90 (br. s., 2H), 1.15 (t, J=7.55 Hz, 3H). LC-MS (ES⁻) m/z 303.25, 305.16 [M−1]. LC-MS (ES⁺) m/z 305.01, 306.98 [M+H].

Step B: 4-chloro-N-({4-chloro-3-[(3-cyano-5-ethylphenyl) oxy]-2-fluorophenyl}methyl)-1H-imidazole-5-carboxamide 3-{[3-(aminomethyl)-6-chloro-2-fluorophenyl]oxy}-5-ethylbenzonitrile (0.055 g, 0.181 mmol), 4-chloro-1-({[2-(trimethylsilyl)ethyl]oxy}methyl)-1H-imidazole-5-carboxylic acid (0.050 g, 0.181 mmol) and DIPEA (0.063 mL, 0.361 mmol) were combined in THF (2 mL) and treated with HATU (0.076 g, 0.199 mmol) at 25° C. overnight with stirring. The reaction mixture was concentrated to dryness, dissolved in DCM, washed with water, dried over MgSO₄, filtered and concentrated to dryness. The residue was dissolved in DCM (2.5 mL) and treated with TFA (2.5 mL) at 25° C. for 3 days. The reaction mixture was concentrated to dryness, dissolved in DCM, washed with saturated aqueous NaHCO₃, dried over MgSO₄, filtered and concentrated to dryness. The resultant solid was recrystallized from boiling IPA, cooled in an ice bath and filtered to give 4-chloro-N-({4-chloro-3-[(3-cyano-5-ethylphenyl)oxy]-2-fluorophenyl}methyl)-1H-imidazole-5-carboxamide (0.021 g, 0.048 mmol, 26.8% yield) as a white solid. The mother liquor was concentrated to dryness and purified on an XTerra™ C-18 column eluted with 5 to 75% CH₃CN/H₂O (0.2% NH₄OH buffer). Appropriate fractions were combined, concentrated to dryness, chased twice with ethanol and twice with toluene to remove residual water to give additional 4-chloro-N-({4-chloro-3-[(3-cyano-5-ethylphenyl)oxy]-2-fluorophenyl}methyl)-1H-imidazole-5-carboxamide (0.043 g, 0.099 mmol, 54.9% yield) as a white solid. 1H NMR (400 MHz, DMSO-d₆) δ ppm 13.19 (br. s., 1H), 8.30 (br. s., 1H), 7.76 (s, 1H), 7.43-7.54 (m, 2H), 7.29-7.42 (m, 1H), 7.18 (m, 2H), 4.53 (d, J=5.22 Hz, 2H), 2.64 (q, J=7.23 Hz, 2H), 1.15 (t, J=7.48 Hz, 3H). LC-MS (ES⁻) m/z 431.16, 433.15 [M−1]. LC-MS (ES⁺) m/z 433.08, 435.07 [M+H].

Example 149

4-bromo-N-({4-chloro-3-[(3-cyano-5-ethylphenyl) oxy]-2-fluorophenyl}methyl)-2-methyl-1H-imidazole-5-carboxamide

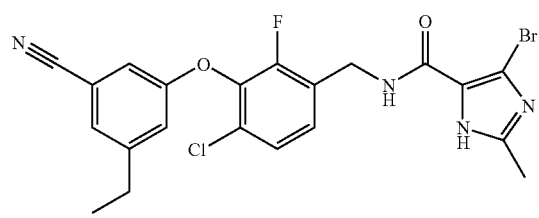

3-{[3-(aminomethyl)-6-chloro-2-fluorophenyl]oxy}-5-ethylbenzonitrile (0.053 g, 0.174 mmol), 4-bromo-2-methyl-1H-imidazole-5-carboxylic acid (0.036 g, 0.174 mmol) and DIEA (0.061 mL, 0.348 mmol) were combined and treated with EDC (0.067 g, 0.348 mmol) at 25° C. overnight with stirring. The reaction mixture was concentrated to dryness and partitioned between EtOAc and water. The organic phase was isolated, dried over MgSO₄, filtered and concentrated to dryness. The residue was purified on 40 g silica gel eluted with 0 to 10% CH₃OH/DCM to give 4-bromo-N-({4-chloro-3-[(3-cyano-5-ethylphenyl)oxy]-2-fluorophenyl}methyl)-2-methyl-1H-imidazole-5-carboxamide (0.054 g, 0.110 mmol, 63.1%) as a white solid. 1H NMR (400 MHz, DMSO-d₆+1 drop D₂O) δ ppm 7.40-7.51 (m, 2H), 7.32 (t, J=7.83 Hz, 1H), 7.14 (d, J=6.73 Hz, 2H), 4.47 (s, 2H), 2.62 (q, J=7.51 Hz, 2H), 2.24 (s, 3H), 1.12 (t, J=7.49 Hz, 3H). LC-MS (ES⁻) m/z 488.97, 490.93, 492.87 [M−1]. LC-MS (ES⁺) m/z 491.10, 493.10, 495.07 [M+H].

Example 150

N-({3-[(3-bromo-5-cyanophenyl)oxy]-4-chloro-2-fluorophenyl}methyl)-4-chloro-1H-imidazole-5-carboxamide

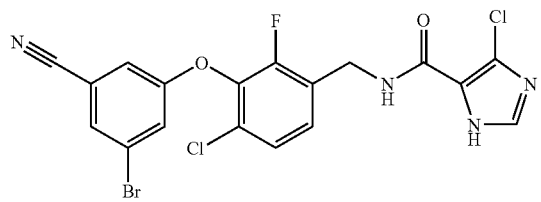

3-{[3-(aminomethyl)-6-chloro-2-fluorophenyl]oxy}-5-bromobenzonitrile (0.193 g, 0.542 mmol), 4-chloro-1-({[2-(trimethylsilyl)ethyl]oxy}methyl)-1H-imidazole-5-carboxylic acid (0.150 g, 0.542 mmol) and DIPEA (0.189 mL, 1.084 mmol) were combined in THF (2 mL) and treated with HATU (0.227 g, 0.596 mmol) at 25° C. overnight with stirring. The reaction mixture was concentrated to dryness, dissolved in DCM, washed with water, dried over MgSO₄, filtered and concentrated to dryness. The residue was dissolved in DCM (2.5 mL) and treated with TFA (2.5 mL) at 25° C. overnight. The reaction mixture was concentrated to dryness, dissolved in DCM, washed with saturated aqueous NaHCO₃, dried over MgSO₄, filtered and concentrated to dryness. The resultant solid was recrystallized from EtOH, cooled in an ice bath and filtered to give N-({3-[(3-bromo-5-cyanophenyl) oxy]-4-chloro-2-fluorophenyl}methyl)-4-chloro-1H-imidazole-5-carboxamide (0.195 g, 0.403 mmol, 74.3% yield) as a white solid. 1H NMR (400 MHz, DMSO-d₆) δ ppm 13.18 (br. s., 1H), 8.26 (s, 1H), 7.93 (s, 1H), 7.78 (s, 1H), 7.46-7.60 (m, 3H), 7.37 (t, J=7.69 Hz, 1H), 4.53 (d, J=2.47 Hz, 2H). LC-MS (ES⁻) m/z 481.04, 483.07 [M−1]. LC-MS (ES⁺) m/z 482.94, 484.92 [M+H].

Example 151

4-chloro-N-({4-chloro-3-[(3-cyano-5-propylphenyl) oxy]-2-fluorophenyl}methyl)-1H-imidazole-5-carboxamide

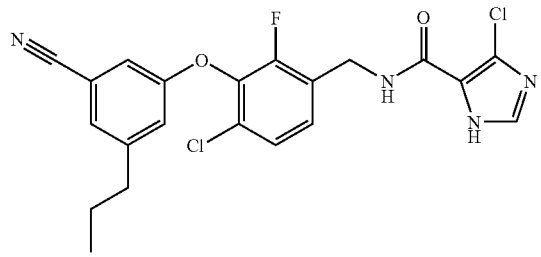

Step A: 3-{[3-(aminomethyl)-6-chloro-2-fluorophenyl]oxy}-5-(1-methylethyl)benzonitrile and 3-{[3-(aminomethyl)-6-chloro-2-fluorophenyl]oxy}-5-propylbenzonitrile (1:6 ratio)

3-{[3-(aminomethyl)-6-chloro-2-fluorophenyl]oxy}-5-bromobenzonitrile (0.400 g, 1.125 mmol) and tetrakis(triphenylphosphine)palladium(0) (0.130 g, 0.112 mmol) were combined in THF (7 mL) and treated with an apparent mixture of diisopropylzinc and di-n-propylzinc (1 M in toluene, Aldrich 568112) (2.250 mL, 2.250 mmol) with stirring under an inert atmosphere. The reaction mixture was heated to 70° C. and stirred for 2 h. The reaction mixture was concentrated to dryness and partitioned between EtOAc and saturated aqueous NaHCO$_3$. The organic phase was isolated, dried over MgSO$_4$, filtered and concentrated to dryness. The residue was purified on 40 g silica gel eluted successively with EtOAc and 10% CH$_3$OH/DCM to give a mixture of 3-{[3-(aminomethyl)-6-chloro-2-fluorophenyl]oxy}-5-(1-methylethyl)benzonitrile and 3-{[3-(aminomethyl)-6-chloro-2-fluorophenyl]oxy}-5-propylbenzonitrile (1:6 ratio) (0.198 g, 0.621 mmol, 55.2% yield) as a clear oil. Diagnostic peaks in the aliphatic region of the NMR are as indicated below and were found to be in a ratio of ~1:6, 3-{[3-(aminomethyl)-6-chloro-2-fluorophenyl]oxy}-5-(1-methylethyl)benzonitrile to 3-{[3-(aminomethyl)-6-chloro-2-fluorophenyl]oxy}-5-propylbenzonitrile. 3-{[3-(aminomethyl)-6-chloro-2-fluorophenyl]oxy}-5-(1-methylethyl)benzonitrile: 1H NMR (400 MHz, DMSO-d$_6$) δ ppm 2.95 (spt, J=6.82 Hz, 1H), 1.19 (d, J=6.87 Hz, 6H). 3-{[3-(aminomethyl)-6-chloro-2-fluorophenyl]oxy}-5-propylbenzonitrile: 1H NMR (400 MHz, DMSO-d$_6$) δ ppm 2.58 (t, J=7.55 Hz, 2H), 1.49-1.63 (m, 2H), 0.85 (t, J=7.33 Hz, 3H). LC-MS (ES$^-$) m/z 317.12, 319.14 [M−1]. LC-MS (ES$^+$) m/z 318.99, 320.99 [M+H].

Step B: 4-chloro-N-({4-chloro-3-[(3-cyano-5-propylphenyl)oxy]-2-fluorophenyl}methyl)-1H-imidazole-5-carboxamide A mixture of 3-{[3-(aminomethyl)-6-chloro-2-fluorophenyl]oxy}-5-(1-methylethyl)benzonitrile and 3-{[3-(aminomethyl)-6-chloro-2-fluorophenyl]oxy}-5-propylbenzonitrile (1:6 ratio, 0.058 g, 0.181 mmol), 4-chloro-1-({[2-(trimethylsilyl)ethyl]oxy}methyl)-1H-imidazole-5-carboxylic acid (0.050 g, 0.181 mmol) and DIPEA (0.063 mL, 0.361 mmol) were combined in THF (2 mL) and treated with HATU (0.076 g, 0.199 mmol) at 25° C. overnight with stirring. The reaction mixture was concentrated to dryness, dissolved in DCM, washed with water, dried over MgSO$_4$, filtered and concentrated to dryness. The residue was dissolved in DCM (2.5 mL) and treated with TFA (2.5 mL) at 25° C. for 3 days. The reaction mixture was concentrated to dryness, dissolved in DCM, washed with saturated aqueous NaHCO$_3$, dried over MgSO$_4$, filtered and concentrated to dryness. The resultant solid was recrystallized from boiling IPA, cooled in an ice bath and filtered to give a mix of isopropyl and n-propyl isomers (0.034 g, 0.076 mmol, 42.1% yield) as a white solid. The mother liquor was concentrated to dryness and purified on an XTerra™ C-18 column eluted with 5 to 75% CH$_3$CN/H$_2$O (0.2% NH$_4$OH buffer). Selected fractions were combined, concentrated to dryness, chased twice with ethanol and twice with toluene to remove residual water to give a mix of isopropyl and n-propyl isomers. Other selected fractions were likewise combined and concentrated to give >90% of the n-propyl isomer, 4-chloro-N-({4-chloro-3-[(3-cyano-5-propylphenyl)oxy]-2-fluorophenyl}methyl)-1H-imidazole-5-carboxamide (0.015 g, 0.034 mmol, 18.56% yield) as a clear glass. 1H NMR (400 MHz, DMSO-d$_6$) δ ppm 13.20 (br. s., 1H), 8.29 (br. s., 1H), 7.78 (s, 1H), 7.09-7.55 (m, 5H), 4.52 (d, J=4.67 Hz, 2H), 2.58 (t, J=7.42 Hz, 2H), 1.49-1.63 (m, 2H), 0.85 (t, J=7.21 Hz, 3H). LC-MS (ES$^-$) m/z 445.13, 447.19 [M−1]. LC-MS (ES$^+$) m/z 447.08, 449.12 [M+H].

Example 152

4-chloro-N-({4-chloro-3-[(3-cyano-5-cyclopropylphenyl)oxy]-2-fluorophenyl}methyl)-1H-imidazole-5-carboxamide

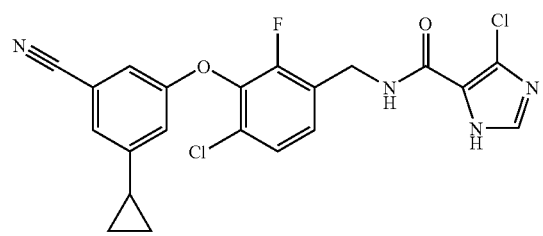

Step A: 4-chloro-N-({4-chloro-3-[(3-cyano-5-ethenylphenyl)oxy]-2-fluorophenyl}methyl)-1-({[2-(trimethylsilyl)ethyl]oxy}methyl)-1H-imidazole-5-carboxamide 3-{[3-(aminomethyl)-6-chloro-2-fluorophenyl]oxy}-5-ethenylbenzonitrile (0.109 g, 0.361 mmol), 4-chloro-1-({[2-(trimethylsilyl)ethyl]oxy}methyl)-1H-imidazole-5-carboxylic acid (0.100 g, 0.361 mmol) and DIPEA (0.126 mL, 0.723 mmol) were combined in THF (3 mL) and treated with HATU (0.151 g, 0.397 mmol) at 25° C. overnight with stirring. The reaction mixture was concentrated to dryness, dissolved in EtOAc, washed with water, dried over MgSO$_4$, filtered and concentrated to dryness. The residue was purified on 40 g silica gel eluted with 20 to 60% EtOAc/hexanes to give 4-chloro-N-({4-chloro-3-[(3-cyano-5-ethenylphenyl)oxy]-2-fluorophenyl}methyl)-1-({[2-(trimethylsilyl)ethyl]oxy}methyl)-1H-imidazole-5-carboxamide (0.16 g, 0.285 mmol, 79% yield) as a clear oil. 1H NMR (400 MHz, DMSO-d$_6$) δ ppm 8.79 (t, J=5.63 Hz, 1H), 8.00 (s, 1H), 7.80 (s, 1H), 7.37-7.54 (m, 3H), 7.25 (s, 1H), 6.75 (dd, J=17.67, 11.08 Hz, 1H), 6.05 (d, J=17.67 Hz, 1H), 5.51 (s, 2H), 5.44 (d, J=10.99 Hz, 1H), 4.50 (d, J=5.59 Hz, 2H), 3.40 (t, J=8.10 Hz, 2H), 0.76 (t, J=8.06 Hz, 2H), −0.07 (s, 9H). LC-MS (ES$^-$) m/z 559.13, 561.19 [M−1]. LC-MS (ES$^+$) m/z 561.14, 563.12 [M+H].

Step B: 4-chloro-N-({4-chloro-3-[(3-cyano-5-cyclopropylphenyl)oxy]-2-fluorophenyl}methyl)-1-({[2-(trimethylsilyl)ethyl]oxy}methyl)-1H-imidazole-5-carboxamide To a mixture of 30% aqueous KOH (30 mL) and diethyl ether (30 mL) was added N-methyl-N-nitrosourea (0.264 g, 2.56 mmol) in one potion with stirring and cooling at 0° C. and the reaction mixture was maintained at this temperature for 20 min. The organic phase was isolated, dried over KOH pellets and added dropwise to a solution of 4-chloro-N-({4-chloro-3-[(3-cyano-5-ethenylphenyl)oxy]-2-fluorophenyl}methyl)-1-({[2-(trimethylsilyl)ethyl]oxy}methyl)-1H-imidazole-5-carboxamide (0.144 g, 0.256 mmol) and palladium(II) acetate (5.8 mg, 0.026 mmol) in diethyl ether (30.0 mL) with stirring and cooling at 0° C. DCM (20 mL) was added to the reaction mixture to achieve complete solution and the reaction mixture was stirred at 0° C. for 1 h at which time LC-MS indicated complete conversion to desired product. Water and a small amount of acetic acid were added to the reaction mixture and stirred vigorously at room temperature for 1 h. The organic phase was isolated, washed with saturated aqueous NaHCO$_3$, dried over MgSO$_4$, filtered and concentrated to dryness. The residue was purified on 40 g silica gel eluted with 20 to 60% EtOAc/hexanes to give 4-chloro-N-({4-chloro-3-[(3-cyano-5-cyclopropylphenyl)oxy]-2-fluorophenyl}methyl)-1-({[2-(trimethylsilyl)ethyl]oxy}methyl)-1H-imidazole-5-carboxamide (0.132 g, 0.230 mmol, 90% yield) as a clear oil. 1H NMR (400 MHz, DMSO-$d_6$) δ ppm 8.79 (t, J=5.68 Hz, 1H), 8.00 (s, 1H), 7.36-7.54 (m, 2H), 7.28 (s, 1H), 7.11 (s, 1H), 7.05 (s, 1H), 5.51 (s, 2H), 4.50 (d, J=5.68 Hz, 2H), 3.40 (t, J=8.10 Hz, 2H), 1.92-2.05 (m, 1H), 0.95-1.05 (m, 2H), 0.71-0.82 (m, 4H), −0.07 (s, 9H). LC-MS (ES⁻) m/z 575.13, 575.05 [M−1]. LC-MS (ES⁺) m/z 575.11, 577.12 [M+H].

Step C: 4-chloro-N-({4-chloro-3-[(3-cyano-5-cyclopropylphenyl)oxy]-2-fluorophenyl}methyl)-1H-imidazole-5-carboxamide 4-chloro-N-({4-chloro-3-[(3-cyano-5-cyclopropylphenyl)oxy]-2-fluorophenyl}methyl)-1-({[2-(trimethylsilyl)ethyl]oxy}methyl)-1H-imidazole-5-carboxamide (0.132 g, 0.230 mmol) was dissolved in DCM (3 mL) and treated with TFA (3 mL) at 25° C. for 3 days. The reaction mixture was concentrated to dryness and partitioned between DCM and saturated aqueous NaHCO₃. The organic phase was isolated, dried over MgSO₄, filtered and concentrated to dryness. The residue was purified on 40 g silica gel eluted with 0 to 10% CH₃OH/DCM to give 4-chloro-N-({4-chloro-3-[(3-cyano-5-cyclopropylphenyl)oxy]-2-fluorophenyl}methyl)-1H-imidazole-5-carboxamide (0.0705 g, 0.158 mmol, 68.8% yield) as a white foam. 1H NMR (400 MHz, DMSO-$d_6$) δ ppm 13.19 (br. s., 1H), 8.26 (br. s., 1H), 7.78 (s, 1H), 7.31-7.55 (m, 2H), 7.27 (br. s., 1H), 7.09 (s, 2H), 4.53 (d, J=1.39 Hz, 2H), 1.91-2.07 (m, 1H), 0.99 (m, 2H), 0.77 (m, 2H). LC-MS (ES⁻) m/z 443.18, 445.11 [M−1]. LC-MS (ES⁺) m/z 445.07, 447.08 [M+H].

Example 153

N-({3-[(5-bromo-2-chloro-3-fluorophenyl)oxy]-4-chloro-2-fluorophenyl}methyl)-4-chloro-1H-imidazole-5-carboxamide

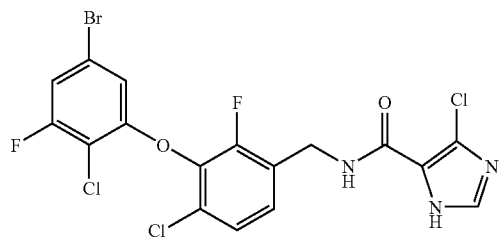

Step A: 2-[(5-bromo-2-chloro-3-fluorophenyl)oxy]-1-chloro-3-fluoro-4-methylbenzene 6-chloro-2-fluoro-3-methylphenol (9.96 g, 62.0 mmol) and 18-crown-6 (4.5 g, 17.03 mmol) were dissolved in dry DMSO (100 mL) and treated with 20% potassium t-butoxide in THF (34.8 g, 62.0 mmol) in THF for 15 minutes at room temperature. 5-bromo-2-chloro-1,3-difluorobenzene (14.11 g, 62.0 mmol) was added in one portion and the reaction mixture heated at 130° C. for 3 days. The reaction mixture was filtered through Celite™, cooled to ambient temperature and water was added to afford the crude product as a black precipitate which was filtered off, washed with water and air dried. The crude product was dissolved in DCM, dried over MgSO₄, and filtered through a plug of 45 g silica gel which was eluted with 500 mL DCM. The filtrate was concentrated to an amber oil and crystallized by addition of EtOH (150 mL). The precipitate was cooled in an ice bath and filtered to afford 2-[(5-bromo-2-chloro-3-fluorophenyl)oxy]-1-chloro-3-fluoro-4-methylbenzene (8.7 g, 23.64 mmol, 38.1% yield) as a white solid. The mother liquor was concentrated to dryness and crystallized from IPA (70 mL) to give a second batch of the desired product (4.55 g, 12.36 mmol, 19.93% yield) as a tan solid. 1H NMR (400 MHz, DMSO-$d_6$) δ ppm 7.61 (dd, J=8.56, 1.97 Hz, 1H), 7.30-7.47 (m, 2H), 6.74 (s, 1H), 2.29 (d, J=1.56 Hz, 3H).

Step B: 2-[(5-bromo-2-chloro-3-fluorophenyl)oxy]-4-(bromomethyl)-1-chloro-3-fluorobenzene 2-[(5-bromo-2-chloro-3-fluorophenyl)oxy]-1-chloro-3-fluoro-4-methylbenzene (13.25 g, 36.0 mmol) and NBS (6.41 g, 36.0 mmol) were combined in carbon tetrachloride (150 mL) with a catalytic amount of AIBN (0.296 g, 1.800 mmol) and stirred at reflux for 16 h. The reaction mixture was washed with water, dried over MgSO₄, filtered and concentrated to dryness. The residue was purified by chromatography on 330 g silica gel eluted with 0 to 10% Et₂O in hexanes to give the desired product, 2-[(5-bromo-2-chloro-3-fluorophenyl)oxy]-4-(bromomethyl)-1-chloro-3-fluorobenzene (10.04 g, 22.47 mmol, 62.4% yield), as a white solid. 1H NMR (400 MHz, DMSO-$d_6$) δ ppm 7.53-7.67 (m, 3H), 6.78 (s, 1H), 4.75 (s, 2H).

Step C: 1-(azidomethyl)-3-[(5-bromo-2-chloro-3-fluorophenyl)oxy]-4-chloro-2-fluorobenzene 2-[(5-bromo-2-chloro-3-fluorophenyl)oxy]-4-(bromomethyl)-1-chloro-3-fluorobenzene (10.04 g, 22.47 mmol) and sodium azide (1.461 g, 22.47 mmol) were combined in DMSO (50 mL) and stirred 3 days at 25° C. The reaction mixture was diluted with EtOAc, washed 4× with water, dried over MgSO₄, filtered and concentrated to dryness to give 1-(azidomethyl)-3-[(5-bromo-2-chloro-3-fluorophenyl)oxy]-4-chloro-2-fluorobenzene (8.3 g, 20.29 mmol, 90% yield) as a clear oil. 1H NMR (400 MHz, DMSO-$d_6$) δ ppm 7.49-7.66 (m, 3H), 6.80 (s, 1H), 4.61 (s, 2H).

Step D: ({3-[(5-bromo-2-chloro-3-fluorophenyl)oxy]-4-chloro-2-fluorophenyl}methyl)amine 1-(azidomethyl)-3-[(5-bromo-2-chloro-3-fluorophenyl)oxy]-4-chloro-2-fluorobenzene (8.3 g, 20.29 mmol) dissolved in THF (100 mL) was treated successively with triphenylphosphine (7.98 g, 30.4 mmol) and water (1.828 g, 101 mmol) at 25° C. for 2 days with stirring. The reaction mixture was concentrated to dryness and purified on 330 g silica gel eluted successively with EtOAc (to remove triphenylphosphine oxide) followed by 0 to 10% CH₃OH/DCM to give ({3-[(5-bromo-2-chloro-3-fluorophenyl)oxy]-4-chloro-2-fluorophenyl}methyl)amine (5.73 g, 14.96 mmol, 73.7% yield) as a white solid. 1H NMR (400 MHz, DMSO-$d_6$) δ ppm 7.48-7.63 (m, 3H), 6.71 (s, 1H), 3.77 (s, 2H), 1.90 (s, 2H). LC-MS (ES⁻) m/z 380.00, 381.97, 384.06 [M−1]. LC-MS (ES⁺) m/z 381.84, 383.83, 385.87 [M+H].

Step E: N-({3-[(5-bromo-2-chloro-3-fluorophenyl)oxy]-4-chloro-2-fluorophenyl}methyl)-4-chloro-1H-imidazole-5-carboxamide ({3-[(5-bromo-2-chloro-3-fluorophenyl)oxy]-4-chloro-2-fluorophenyl}methyl)amine (0.069 g, 0.181 mmol), 4-chloro-1-({[2-(trimethylsilyl)ethyl]oxy}methyl)-1H-imidazole-5-carboxylic acid (0.050 g, 0.181 mmol) and DIPEA (0.063 mL, 0.361 mmol) were combined in THF (2 mL) and treated with HATU (0.076 g, 0.199 mmol) at 25° C. overnight with stirring. The reaction mixture was concentrated to dryness, dissolved in DCM, washed with water, dried over MgSO₄, filtered and concentrated to dryness. The residue was dissolved in DCM (2.5 mL) and treated with TFA (2.5 mL) at 25° C. for 3 days. The reaction mixture was concentrated to dryness, dissolved in DCM, washed with saturated aqueous NaHCO₃, dried over MgSO₄, filtered and concentrated to dryness. The resultant solid was recrystallized from EtOH, cooled in an ice bath and filtered to give N-({3-[(5-bromo-2-chloro-3-fluorophenyl)oxy]-4-chloro-2-fluorophenyl}methyl)-4-chloro-1H-imidazole-5-carboxamide (0.048 g, 0.094 mmol, 51.9% yield) as a white solid. 1H NMR (400 MHz, DMSO-d₆) δ ppm 13.17 (br. s., 1H), 8.27 (br. s., 1H), 7.78 (s, 1H), 7.63 (dd, J=8.52, 1.79 Hz, 1H), 7.53 (d, J=8.52 Hz, 1H), 7.39 (m, 1H), 6.76 (s, 1H), 4.54 (d, 2H). LC-MS (ES⁻) m/z 507.94, 509.95, 511.94 [M−1]. LC-MS (ES⁺) m/z 509.88, 511.87, 513.88 [M+H].

Example 154

4-chloro-N-({4-chloro-3-[(2-chloro-5-cyano-3-fluorophenyl)oxy]-2-fluorophenyl}methyl)-1H-imidazole-5-carboxamide

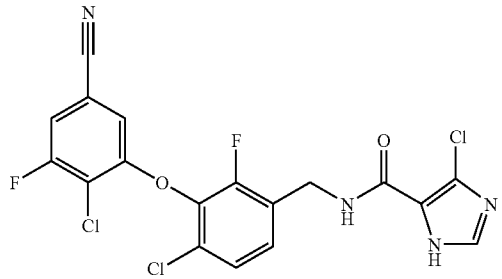

Step A: 3-{[3-(aminomethyl)-6-chloro-2-fluorophenyl]oxy}-4-chloro-5-fluorobenzonitrile ({3-[(5-bromo-2-chloro-3-fluorophenyl)oxy]-4-chloro-2-fluorophenyl}methyl)amine (3.00 g, 7.83 mmol) was combined with dicyanozinc (0.460 g, 3.92 mmol) and tetrakis(triphenylphosphine)palladium(0) (0.453 g, 0.392 mmol) in n-propanol (15 mL) and heated at 120° C. for 25 min in a microwave reactor under an inert atmosphere. DMF (8 mL) was added and the reaction mixture was again heated at 120° C. for 90 min in a microwave reactor at which time LC-MS indicated complete conversion. The reaction mixture was concentrated to remove the n-propanol, diluted with EtOAc, washed four times with saturated aqueous NaHCO₃, dried over MgSO₄, filtered and concentrated to dryness. The residue was purified on 80 g silica gel eluted successively with EtOAc followed by 0 to 10% CH₃OH/DCM to give 3-{[3-(aminomethyl)-6-chloro-2-fluorophenyl]oxy}-4-chloro-5-fluorobenzonitrile (1.16 g, 3.52 mmol, 45.0% yield) as a pale yellow oil which crystallized on standing. 1H NMR (400 MHz, DMSO-d₆) δ ppm 7.92 (dd, J=8.65, 1.51 Hz, 1H), 7.47-7.58 (m, 2H), 7.25 (s, 1H), 3.77 (s, 2H), 1.93 (br. s., 2H). LC-MS (ES⁻) m/z 326.96, 329.05 [M−1]. LC-MS (ES⁺) m/z 329.00, 330.96 [M+H].

Step B: 4-chloro-N-({4-chloro-3-[(2-chloro-5-cyano-3-fluorophenyl)oxy]-2-fluorophenyl}methyl)-1H-imidazole-5-carboxamide 3-{[3-(aminomethyl)-6-chloro-2-fluorophenyl]oxy}-4-chloro-5-fluorobenzonitrile (0.059 g, 0.181 mmol), 4-chloro-1-({[2-(trimethylsilyl)ethyl]oxy}methyl)-1H-imidazole-5-carboxylic acid (0.05 g, 0.181 mmol) and DIPEA (0.063 mL, 0.361 mmol) were combined in THF (2 mL) and treated with HATU (0.076 g, 0.199 mmol) at 25° C. overnight with stirring. The reaction mixture was concentrated to dryness, dissolved in DCM, washed with water, dried over MgSO₄, filtered and concentrated to dryness. The residue was dissolved in DCM (2.5 mL) and treated with TFA (2.5 mL) at 25° C. for 3 days. The reaction mixture was concentrated to dryness, dissolved in DCM, washed with saturated aqueous NaHCO₃, dried over MgSO₄, filtered and concentrated to dryness. The resultant solid was recrystallized from EtOH, cooled in an ice bath and filtered to give 4-chloro-N-({4-chloro-3-[(2-chloro-5-cyano-3-fluorophenyl)oxy]-2-fluorophenyl}methyl)-1H-imidazole-5-carboxamide (0.041 g, 0.090 mmol, 49.6% yield) as a white solid. The mother liquor was concentrated to small volume, diluted with IPA, stirred for 30 minutes, and filtered to give a second batch of 4-chloro-N-({4-chloro-3-[(2-chloro-5-cyano-3-fluorophenyl)oxy]-2-fluorophenyl}methyl)-1H-imidazole-5-carboxamide (0.011 g, 0.024 mmol, 13.31% yield) as a white solid. 1H NMR (400 MHz, DMSO-d₆) δ ppm 13.17 (br. s., 1H), 8.25 (t, J=5.56 Hz, 1H), 7.88-7.99 (m, 1H), 7.78 (s, 1H), 7.37-7.57 (m, 2H), 7.30 (s, 1H), 4.55 (d, J=5.49 Hz, 2H). LC-MS (ES⁻) m/z 455.10, 457.03 [M−1]. LC-MS (ES⁺) m/z 456.99, 459.87 [M+H].

Example 155

4-chloro-N-({4-chloro-3-[(6-chloro-4-cyano-2-pyridinyl)oxy]-2-fluorophenyl}methyl)-1H-imidazole-5-carboxamide

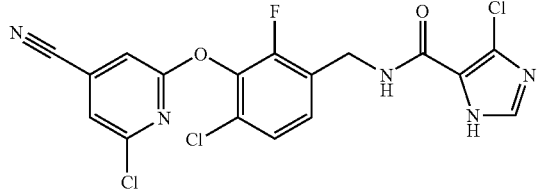

Step A: 2-chloro-6-[(6-chloro-2-fluoro-3-methylphenyl)oxy]-4-pyridinecarbonitrile 6-chloro-2-fluoro-3-methylphenol (4.73 g, 29.5 mmol) and 18-crown-6 (1.558 g, 5.90 mmol) were combined and treated with 20% potassium t-butoxide in THF (16.54 g, 29.5 mmol) in THF at 25° C. and stirred 15 min. 2,6-dichloro-4-pyridinecarbonitrile (5.1 g, 29.5 mmol) was added to the reaction mixture and stirred at ambient temperature for 4 days. A fine white precipitate was filtered off from the reaction mixture and washed with a small amount of DMSO. This material was partitioned between EtOAc and saturated aqueous NaHCO₃, the phases separated, and the aqueous phase extracted twice with EtOAc. The organic phases were combined, dried over MgSO₄, filtered and concentrated to dryness to give 2-chloro-6-[(6-chloro-2-fluoro-3-methylphenyl)oxy]-4-pyridinecarbonitrile (3.88 g, 13.06 mmol, 44.3% yield) as a white solid. The DMSO filtrate was treated with water and saturated aqueous NaHCO₃ to give a purple precipitate that was filtered off, washed with water and air dried. This material was dissolved in DCM, dried over MgSO₄, filtered and concentrated to dryness to give a purple solid. The residue was trituarated with EtOH, cooled in an ice bath, filtered and air dried to give a second batch of the desired product (3.65 g, 12.28 mmol, 41.7% yield) as a white solid. 1H NMR (400 MHz, DMSO-d₆) δ ppm 7.96 (d, J=0.82 Hz, 1H), 7.93 (d, J=0.73 Hz, 1H), 7.28-7.43 (m, 2H), 2.28 (d, J=1.74 Hz, 3H). LC-MS (ES⁺) m/z 296.95, 298.88 [M+H].

Step B: 2-{[3-(bromomethyl)-6-chloro-2-fluorophenyl]oxy}-6-chloro-4-pyridinecarbonitrile 2-chloro-6-[(6-chloro-2-fluoro-3-methylphenyl)oxy]-4-pyridinecarbonitrile (3.65 g, 12.28 mmol) and NBS (2.187 g, 12.28 mmol) were combined in carbon tetrachloride (100 mL) with a catalytic amount of AIBN (0.101 g, 0.614 mmol) and stirred at reflux for 16 h. The reaction mixture was washed with water, dried over MgSO$_4$, filtered and concentrated to dryness. The residue was purified by chromatography on 120 g silica gel eluted with 0% to 10% Et$_2$O in hexanes to give the desired product, 2-{[3-(bromomethyl)-6-chloro-2-fluorophenyl]oxy}-6-chloro-4-pyridinecarbonitrile (2.64 g, 7.02 mmol, 57.2% yield), as a white solid. 1H NMR (400 MHz, DMSO-d$_6$) δ ppm (8.01 (s, 1H), 7.96 (s, 1H), 7.50-7.62 (m, 2H), 4.75 (s, 2H). LC-MS (ES$^+$) m/z 374.98, 377.01, 379.03 [M+H].

Step C: 2-{[3-(azidomethyl)-6-chloro-2-fluorophenyl]oxy}-6-chloro-4-pyridinecarbonitrile 2-{[3-(bromomethyl)-6-chloro-2-fluorophenyl]oxy}-6-chloro-4-pyridinecarbonitrile (2.00 g, 5.32 mmol) and sodium azide (0.346 g, 5.32 mmol) were combined in DMSO (10 mL) and stirred 16 h at 25° C. at which time TLC indicated complete conversion (10% Et$_2$O/hexanes). Water (150 mL) and saturated aqueous NaHCO$_3$ (30 mL) were added and the mixture stirred vigorously for 30 min. The resultant precipitate was filtered off, washed with water, and air dried to give 2-{[3-(azidomethyl)-6-chloro-2-fluorophenyl]oxy}-6-chloro-4-pyridinecarbonitrile (1.76 g, 5.21 mmol, 98% yield) as a white solid. 1H NMR (400 MHz, DMSO-d$_6$) δ ppm 8.01 (d, J=0.73 Hz, 1H), 7.96 (d, J=0.73 Hz, 1H), 7.48-7.60 (m, 2H), 4.60 (s, 2H).

Step D: 2-{[3-(aminomethyl)-6-chloro-2-fluorophenyl]oxy}-6-chloro-4-pyridinecarbonitrile 2-{[3-(azidomethyl)-6-chloro-2-fluorophenyl]oxy}-6-chloro-4-pyridinecarbonitrile (0.402 g, 1.189 mmol) dissolved in THF (10 mL) was treated successively with triphenylphosphine (0.468 g, 1.783 mmol) and water (0.107 mL, 5.94 mmol) at 25° C. for 16 h with stirring. The reaction mixture was concentrated to dryness and purified on 40 g silica gel eluted successively with EtOAc (to remove tripheylphosphine oxide) followed by 0 to 10% CH$_3$OH/DCM to give 2-{[3-(aminomethyl)-6-chloro-2-fluorophenyl]oxy}-6-chloro-4-pyridinecarbonitrile (0.161 g, 0.516 mmol, 43.4% yield) as a white solid. 1H NMR (400 MHz, DMSO-d$_6$) δ ppm 7.96 (s, 1H), 7.93 (s, 1H), 7.44-7.55 (m, 2H), 3.77 (s, 2H), 1.94 (br. s., 2H). LC-MS (ES$^+$) m/z 312.29, 314.28 [M+H].

Step E: 4-chloro-N-({4-chloro-3-[(6-chloro-4-cyano-2-pyridinyl)oxy]-2-fluorophenyl}methyl)-1H-imidazole-5-carboxamide 2-{[3-(aminomethyl)-6-chloro-2-fluorophenyl]oxy}-6-chloro-4-pyridinecarbonitrile (0.056 g, 0.181 mmol), 4-chloro-1-({[2-(trimethylsilyl)ethyl]oxy}methyl)-1H-imidazole-5-carboxylic acid (0.05 g, 0.181 mmol) and DIPEA (0.063 mL, 0.361 mmol) were combined in THF (2 mL) and treated with HATU (0.076 g, 0.199 mmol) at 25° C. for 6 h with stirring. The reaction mixture was concentrated to dryness, dissolved in DCM, washed with saturated aqueous NaHCO$_3$, dried over MgSO$_4$, filtered and concentrated to dryness. The residue was dissolved in DCM (2.5 mL) and treated with TFA (2.5 mL) at 25° C. for 16 h. The reaction mixture was concentrated to dryness, dissolved in DCM, washed with saturated aqueous NaHCO$_3$, dried over MgSO$_4$, filtered and concentrated to dryness. The resultant solid was triturated with boiling IPA, cooled in an ice bath and filtered to give 4-chloro-N-({4-chloro-3-[(6-chloro-4-cyano-2-pyridinyl)oxy]-2-fluorophenyl}methyl)-1H-imidazole-5-carboxamide (0.069 g, 0.157 mmol, 87% yield) as a white solid. 1H NMR (400 MHz, DMSO-d$_6$) δ ppm 13.18 (br. s., 1H), 8.28 (br. s., 1H), 7.99 (s, 1H), 7.95 (s, 1H), 7.78 (s, 1H), 7.49 (d, J=8.38 Hz, 1H), 7.30-7.41 (m, 1H), 4.46-4.61 (m, 2H). LC-MS (ES$^-$) m/z 438.02, 440.05, 442.05 [M–1]. LC-MS (ES$^+$) m/z 439.93, 441.90, 443.94 [M+H]

Example 156

4-chloro-N-[(4-chloro-3-{[3-cyano-5-(2-propen-1-yl)phenyl]oxy}-2-fluorophenyl)methyl]-1'-1H-imidazole-5-carboxamide

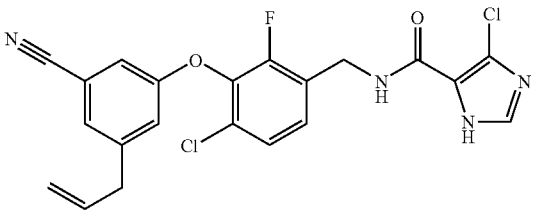

Step A: 3-{[3-(aminomethyl)-6-chloro-2-fluorophenyl]oxy}-5-(2-propen-1-yl)benzonitrile 3-{[3-(aminomethyl)-6-chloro-2-fluorophenyl]oxy}-5-bromobenzonitrile (0.300 g, 0.844 mmol), allyltributyl tin (0.414 mL, 1.350 mmol) and tetrakis(triphenylphosphine)palladium(0) (0.097 g, 0.084 mmol) were combined in DMF (7 mL), purged with nitrogen, and heated at 160° C. in a microwave reactor for 30 min. The reaction mixture was filtered through Celite, diluted with EtOAc, and washed four times with dilute aqueous NaHCO$_3$. The organic phase was isolated, dried over MgSO$_4$, filtered and concentrated to dryness. The residue was purified on 40 g silica gel eluted successively with EtOAc followed by 0 to 10% CH$_3$OH/DCM to give 3-{[3-(aminomethyl)-6-chloro-2-fluorophenyl]oxy}-5-(2-propen-1-yl)benzonitrile (0.145 g, 0.458 mmol, 54.3% yield) as a clear oil. 1H NMR (400 MHz, DMSO-d$_6$) δ ppm 7.45-7.53 (m, 2H), 7.42 (s, 1H), 7.22 (s, 1H), 7.13 (s, 1H), 5.87-6.00 (m, 1H), 5.04-5.14 (m, 2H), 3.76 (s, 2H), 3.41 (d, J=6.59 Hz, 2H), 2.18-2.46 (br. s., 2H). LC-MS (ES$^-$) m/z 315.20, 317.08 [M–1]. LC-MS (ES$^+$) m/z 317.31, 319.31 [M+H].

Step B: 4-chloro-N-[(4-chloro-3-{[3-cyano-5-(2-propen-1-yl)phenyl]oxy}-2-fluorophenyl)methyl]-1-({[2-(trimethylsilyl)ethyl]oxy}methyl)-1H-imidazole-5-carboxamide 3-{[3-(aminomethyl)-6-chloro-2-fluorophenyl]oxy}-5-(2-propen-1-yl)benzonitrile (0.113 g, 0.358 mmol), 4-chloro-1-({[2-(trimethylsilyl)ethyl]oxy}methyl)-1H-imidazole-5-carboxylic acid (0.099 g, 0.358 mmol), and DIEA (0.125 mL, 0.715 mmol) were combined in THF (4 mL) and stirred at 25° C. overnight. Additional 4-chloro-1-({[2-(trimethylsilyl)ethyl]oxy}methyl)-1H-imidazole-5-carboxylic acid (0.049 g, 0.179 mmol), EDC (0.069 g, 0.358 mmol) and THF (4.00 mL) were added to the reaction mixture and stirred at 50° C. overnight. The reaction mixture was concentrated to dryness and partitioned between DCM and saturated aqueous NaHCO$_3$. The organic phase was isolated, dried over MgSO$_4$, filtered and concentrated to dryness. The residue was purified on 40 g silica gel eluted with 20 to 70% EtOAc/hexanes to give 4-chloro-N-[(4-chloro-3-{[3-cyano-5-(2-propen-1-yl)phenyl]oxy}-2-fluorophenyl)methyl]-1-({[2-(trimethylsilyl)ethyl]oxy}methyl)-1H-imidazole-5-carboxamide (0.088 g, 0.153 mmol, 42.7% yield) as a clear oil. 1H NMR (400 MHz, DMSO-d$_6$) δ ppm 8.78 (t, J=5.81 Hz, 1H), 8.00 (s, 1H), 7.36-7.52 (m, 3H), 7.20 (s, 1H), 7.17 (s, 1H), 5.86-6.01 (m, 1H), 5.51 (s, 2H), 5.10 (d, J=5.49 Hz, 1H), 5.07 (s, 1H), 4.50 (d, J=5.77 Hz, 2H), 3.40 (m, 4H), 0.77 (t, J=8.10 Hz, 2H), –0.07 (s, 9 H). LC-MS (ES$^-$) m/z 573.22, 575.17 [M–1]. LC-MS (ES$^+$) m/z 575.15, 577.16 [M+H].

Step C: 4-chloro-N-[(4-chloro-3-{[3-cyano-5-(2-propen-1-yl)phenyl]oxy}-2-fluorophenyl)methyl]-1H-imidazole-5-carboxamide 4-chloro-N-[(4-chloro-3-{[3-cyano-5-(2-propen-1-yl)phenyl]oxy}-2-fluorophenyl)methyl]-1-({[2-(trimethylsilyl)ethyl]oxy}methyl)-1H-imidazole-5-carboxamide (0.034 g, 0.059 mmol) dissolved in DCM (2.5 mL) was treated with TFA (2.5 mL) at 25° C. for 3 days with stirring. The reaction mixture was concentrated to dryness and the residue was purified by mass-directed HPLC on a SunFire prep C-18 column eluted with 30 to 85% $CH_3CN/H_2O$ (0.1% formic acid buffer). Appropriate fractions were combined, concentrated to dryness, chased twice with ethanol and twice with toluene to remove residual water to give 4-chloro-N-[(4-chloro-3-{[3-cyano-5-(2-propen-1-yl)phenyl]oxy}-2-fluorophenyl)methyl]-1H-imidazole-5-carboxamide (0.022 g, 0.049 mmol, 84% yield) as a white solid. 1H NMR (400 MHz, DMSO-$d_6$) δ ppm 13.19 (br. s., 1H), 8.28 (br. s., 1H), 7.78 (s, 1H), 7.50 (d, J=8.52 Hz, 1H), 7.44 (s, 1H), 7.35 (t, J=7.62 Hz, 1H), 7.25 (br. s., 1H), 7.15 (br. s., 1H), 5.85-6.03 (m, 1H), 5.09 (d, J=6.46 Hz, 1H), 5.06 (s, 1H), 4.53 (d, J=4.39 Hz, 2H), 3.41 (d, J=6.46 Hz, 2H). LC-MS (ES⁻) m/z 443.10, 445.17 [M−1]. LC-MS (ES⁺) m/z 445.05, 447.08 [M+H].

Example 157

4-chloro-N-[(4-chloro-3-{[3-cyano-5-(cyclopropylmethyl)phenyl]oxy}-2-fluorophenyl)methyl]-1H-imidazole-5-carboxamide

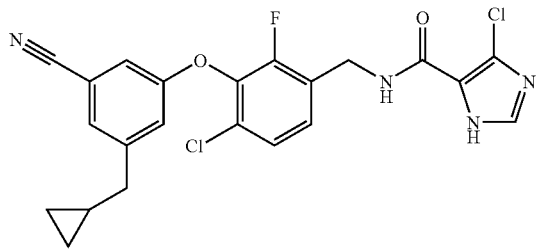

Step A: 4-chloro-N-[(4-chloro-3-{[3-cyano-5-(cyclopropylmethyl)phenyl]oxy}-2-fluorophenyl)methyl]-1-({[2-(trimethylsilyl)ethyl]oxy}methyl)-1H-imidazole-5-carboxamide To a mixture of 30% aqueous KOH (11 mL) and diethyl ether (11 mL) was added N-methyl-N-nitrosourea (0.097 g, 0.938 mmol) in one portion with stirring and cooling at 0° C. and the reaction mixture was maintained at this temperature for 20 min. The organic phase was isolated, dried over KOH pellets and added dropwise to a solution of 4-chloro-N-[(4-chloro-3-{[3-cyano-5-(2-propen-1-yl)phenyl]oxy}-2-fluorophenyl)methyl]-1-({[2-(trimethylsilyl)ethyl]oxy}methyl)-1H-imidazole-5-carboxamide (0.054 g, 0.094 mmol) and palladium(II) acetate (2.106 mg, 9.38 µmol) in diethyl ether (11.00 mL) with stirring and cooling at 0° C. The reaction mixture was stirred at 0° C. for 1 h and then allowed to warm to room temperature and stirred overnight at which time LC-MS indicated complete conversion to desired product.

Water and a small amount of acetic acid were added to the reaction mixture and stirred vigorously at room temperature for 1 h. The organic phase was isolated, washed with saturated aqueous $NaHCO_3$, dried over $MgSO_4$, filtered and concentrated to dryness. The residue was purified on 40 g silica gel eluted with 20 to 60% EtOAc/hexanes to give 4-chloro-N-[(4-chloro-3-{[3-cyano-5-(cyclopropylmethyl)phenyl]oxy}-2-fluorophenyl)methyl]-1-({[2-(trimethylsilyl)ethyl]oxy}methyl)-1H-imidazole-5-carboxamide (0.027 g, 0.046 mmol, 48.8% yield) as a clear oil. 1H NMR (400 MHz, DMSO-$d_6$) δ ppm 8.79 (t, J=5.49 Hz, 1H), 8.00 (s, 1H), 7.45-7.55 (m, 2H), 7.40 (t, J=7.87 Hz, 1H), 7.24 (s, 1H), 7.17 (s, 1H), 5.51 (s, 2H), 4.50 (d, J=5.49 Hz, 2H), 3.40 (t, J=8.06 Hz, 2H), 2.54 (d, 2H), 0.90-1.02 (m, 1H), 0.77 (t, J=8.01 Hz, 2H), 0.46 (d, J=7.14 Hz, 2H), 0.19 (d, J=4.40 Hz, 2H), −0.07 (s, 9H). LC-MS (ES⁻) m/z 587.16, 589.16 [M−1]. LC-MS (ES⁺) m/z 589.16, 591.16 [M+H].

Step B: 4-chloro-N-[(4-chloro-3-{[3-cyano-5-(cyclopropylmethyl)phenyl]oxy}-2-fluorophenyl)methyl]-1H-imidazole-5-carboxamide 4-chloro-N-[(4-chloro-3-{[3-cyano-5-(cyclopropylmethyl)phenyl]oxy}-2-fluorophenyl)methyl]-1-({[2-(trimethylsilyl)ethyl]oxy}methyl)-1H-imidazole-5-carboxamide (0.027 g, 0.046 mmol) dissolved in DCM (3 mL) was treated with TFA (3 mL) at 25° C. overnight with stirring. The reaction mixture was concentrated to dryness and the residue purified by mass-directed HPLC on a SunFire prep C-18 column eluted with 30 to 85% $CH_3CN/H_2O$ (0.1% formic acid buffer). Appropriate fractions were combined, concentrated to dryness, chased twice with ethanol and twice with toluene to remove residual water to give 4-chloro-N-[(4-chloro-3-{[3-cyano-5-(cyclopropylmethyl)phenyl]oxy}-2-fluorophenyl)methyl]-1H-imidazole-5-carboxamide (0.016 g, 0.035 mmol, 76% yield) as a white solid. 1H NMR (400 MHz, $CDCl_3$) δ ppm 11.31 (br. s., 1H), 7.61 (s, 1H), 7.20-7.36 (m, 4H), 7.14 (s, 1H), 6.87 (s, 1H), 4.72 (d, J=5.91 Hz, 2H), 2.56 (d, J=6.96 Hz, 2H), 0.84-1.03 (m, 1H), 0.53-0.63 (m, 2H), 0.14-0.27 (m, 2H). LC-MS (ES⁻) m/z 457.14, 459.12 [M−1]. LC-MS (ES⁺) m/z 459.09, 461.07 [M+H].

Example 158

4-chloro-N-[(4-chloro-3-{[3-cyano-5-(1-methylethenyl)phenyl]oxy}-2-fluorophenyl)methyl]-1H-imidazole-5-carboxamide

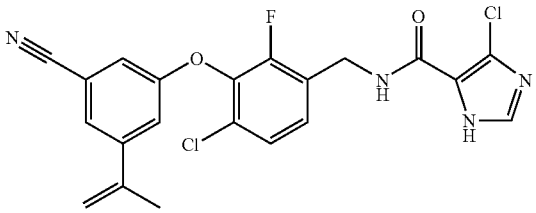

Step A: potassium isopropenyltrifluoroborate

To a solution of trimethylborate (16.72 mL, 150 mmol) in THF (62 mL) was added isopropylmagnesium bromide (0.5 M THF solution, 100 mL, 50.0 mmol) dropwise at 25° C. The reaction mixture was stirred for 3 h at 25° C., cooled in an ice bath, and treated with aqueous HCl (1 N, 125 mL, 125 mmol). the mixture was extracted with ether three times and the combined extracts were dried over $MgSO_4$, filtered and concentrated to a brown semi-solid. This material was triturated with ether and a white solid was filtered off and discarded. The filtrate was concentrated to dryness to give the crude boronic acid (3.9 g, 45 mmol) as a tan solid which rapidly darkened to brown. This material was dissolved in diethyl ether (62.0 mL) and treated with potassium hydrogen difluoride (13.67 g, 175 mmol) followed by slow, dropwise addition of water (5.40 mL, 300 mmol) over 1 h. the reaction mixture was concentrated to dryness and chased twice with toluene to remove residual water. The residue was triturated with acetone and the inorganics were filtered off. The filtrate was concentrated to ~50 mL and ether was added to precipitate the product. The precipitate was filtered off to give potassium isopropenyltrifluoroborate (3.88 g, 26.2 mmol, 52.4% yield) as a finely divided white solid. 1H NMR (400 MHz, DMSO-$d_6$) δ ppm 4.61-4.80 (m, 2H), 1.53 (s, 3H).

Step B: 3-{[3-(aminomethyl)-6-chloro-2-fluorophenyl]oxy}-5-(1-methylethenyl)benzonitrile 3-{[3-(aminomethyl)-6-chloro-2-fluorophenyl]oxy}-5-bromobenzonitrile (0.41 g, 1.153 mmol) was combined with potassium isopropenyltrifluoroborate (0.189 g, 1.268 mmol), 1,1'-bis(diphenylphosphino)ferrocenedichloropalladium(II) dichloromethane complex (0.034 g, 0.046 mmol) and TEA (0.241 mL, 1.730 mmol) in n-propanol (10 mL) and heated in a microwave reactor at 120° C. for 90 min. Additional potassium isopropenyltrifluoroborate (0.086 g, 0.577 mmol) was added to the reaction mixture which was heated in a microwave reactor at 120° C. for an additional 30 min. The reaction mixture was filtered through celite and concentrated to dryness. The residue was dissolved in DCM, washed with saturated aqueous $NaHCO_3$, dried over $MgSO_4$, filtered and concentrated to dryness. The crude material was purified on 40 g silica gel eluted with 0 to 10% $CH_3OH$/DCM to give 3-{[3-(aminomethyl)-6-chloro-2-fluorophenyl]oxy}-5-(1-methylethenyl)benzonitrile (0.140 g, 0.442 mmol, 38.3% yield) as a brown oil. 1H NMR (400 MHz, DMSO-$d_6$) δ ppm 7.74 (s, 1H), 7.46-7.54 (m, 2 H), 7.43 (s, 1H), 7.21 (s, 1H), 5.57 (s, 1H), 5.25 (s, 1H), 3.77 (s, 2H), 2.10 (s, 3H), 1.99 (br. s., 2H). LC-MS (ES$^+$) m/z 317.19, 319.17 [M+H].

Step C: 4-chloro-N-[(4-chloro-3-{[3-cyano-5-(1-methylethenyl)phenyl]oxy}-2-fluorophenyl)methyl]-1H-imidazole-5-carboxamide 3-{[3-(aminomethyl)-6-chloro-2-fluorophenyl]oxy}-5-(1-methylethenyl)benzonitrile (0.068 g, 0.215 mmol), 4-chloro-1H-imidazole-5-carboxylic acid (0.040 g, 0.273 mmol), and DIPEA (0.075 mL, 0.429 mmol) were combined in THF (6 mL) and treated with EDC (0.082 g, 0.429 mmol) at 50° C. for three days. The reaction mixture was concentrated to dryness and partitioned between EtOAc and brine. The organic phase was isolated, washed with saturated aqueous $NaHCO_3$, dried over $MgSO_4$, filtered and concentrated to dryness. The residue was purified on 40 g silica gel eluted with 40 to 100% EtOAc/hexanes to give impure product. This material was repurified by mass-directed HPLC on a SunFire prep C-18 column eluted with 30 to 85% $CH_3CN/H_2O$ (0.1% formic acid buffer). Appropriate fractions were combined, concentrated to dryness, chased twice with ethanol and twice with toluene to remove residual water to give 4-chloro-N-[(4-chloro-3-{[3-cyano-5-(1-methylethenyl)phenyl]oxy}-2-fluorophenyl)methyl]-1H-imidazole-5-carboxamide (0.013 g, 0.029 mmol, 13.60% yield) as a white solid. 1H NMR (400 MHz, DMSO-$d_6$) δ ppm 13.20 (br. s., 1H), 8.30 (br. s., 1H), 7.73-7.78 (m, 2H), 7.50 (d, J=8.52 Hz, 1H), 7.43 (s, 1H), 7.36 (t, J=7.76 Hz, 1H), 7.26 (s, 1H), 5.57 (s, 1H), 5.25 (s, 1H), 4.52 (d, J=5.36 Hz, 2H), 2.10 (s, 3H). LC-MS (ES$^-$) m/z 443.08, 445.16 [M−1]. LC-MS (ES$^+$) m/z 445.07, 447.07 [M+H].

Example 159

4-chloro-N-[(4-chloro-3-{[3-cyano-5-(1-methylethyl)phenyl]oxy}-2-fluorophenyl)methyl]-1H-imidazole-5-carboxamide

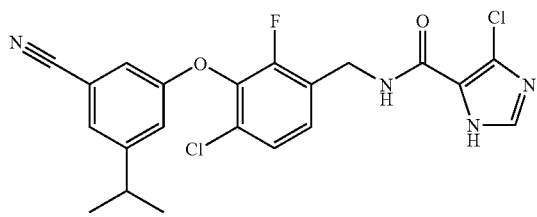

Step A: 3-{[3-(aminomethyl)-6-chloro-2-fluorophenyl]oxy}-5-(1-methylethyl)benzonitrile 3-{[3-(aminomethyl)-6-chloro-2-fluorophenyl]oxy}-5-(1-methylethenyl)benzonitrile (0.067 g, 0.212 mmol) dissolved in ethanol (10 mL) was treated with platinum(IV) oxide (0.050 g, 0.220 mmol) under hydrogen (1 atm) at 25° C. for 4 h. LC-MS indicates ~90% conversion but multiple impurities are present. The reaction mixture was filtered through Celite and concentrated to give crude 3-{[3-(aminomethyl)-6-chloro-2-fluorophenyl]oxy}-5-(1-methylethyl)benzonitrile as an amber oil which was used without further purification.

LC-MS (ES$^+$) m/z 319.24 [M+H]

Step B: 4-chloro-N-[(4-chloro-3-{[3-cyano-5-(1-methylethyl)phenyl]oxy}-2-fluorophenyl)methyl]-1H-imidazole-5-carboxamide 3-{[3-(aminomethyl)-6-chloro-2-fluorophenyl]oxy}-5-(1-methylethyl)benzonitrile (0.068 g, 0.213 mmol), 4-chloro-1H-imidazole-5-carboxylic acid (0.040 g, 0.273 mmol), and DIPEA (0.075 mL, 0.427 mmol) were combined in THF (6 mL) and treated with HATU (0.089 g, 0.235 mmol) at 25° C. overnight. The reaction mixture was concentrated to dryness and partitioned between DCM and water. The organic phase was isolated, dried over $MgSO_4$, filtered and concentrated to dryness. The residue was purified by mass-directed HPLC on a SunFire prep C-18 column eluted with 30 to 85% $CH_3CN/H_2O$ (0.1% formic acid buffer). Appropriate fractions were combined, concentrated to dryness, chased twice with ethanol and twice with toluene to remove residual water to give 4-chloro-N-[(4-chloro-3-{[3-cyano-5-(1-methylethyl)phenyl]oxy}-2-fluorophenyl)methyl]-1H-imidazole-5-carboxamide (0.0205 g, 0.046 mmol, 21.49% yield) as a clear oil. 1H NMR (400 MHz, DMSO-$d_6$) δ ppm 13.15 (br. s., 1H), 8.23 (br. s., 1H), 7.77 (s, 1H), 7.43-7.55 (m, 2H), 7.36 (t, J=7.71 Hz, 1H), 7.24 (br. s., 1H), 7.13 (br. s., 1H), 4.54 (d, J=4.99 Hz, 2H), 2.95 (spt, 1H), 1.18 (d, J=6.96 Hz, 6H). LC-MS (ES$^-$) m/z 445.09, 447.18 [M−1]. LC-MS (ES$^+$) m/z 447.08, 449.06 [M+H].

Example 160

N-({3-[(3-bromo-5-chlorophenyl)oxy]-4-chloro-2-fluorophenyl}methyl)-4-chloro-2-ethyl-1H-imidazole-5-carboxamide

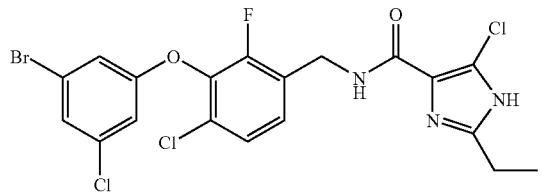

Step A: bis(1,1-dimethylethyl) {3-[(3-bromo-5-chlorophenyl)oxy]-2-fluoro-4-nitrophenyl}propanedioate Sodium hydride (60% dispersion in oil, 3.95 g, 98.6 mmol) was added to anhydrous THF (100 mL) and cooled to 0° C. under nitrogen. A solution of di-tert-butyl malonate (9.79 g, 45.3 mmol) in THF (20 mL) was added dropwise and the reaction mixture was stirred 30 min. A solution of 2-[(3-bromo-5-chlorophenyl)oxy]-3,4-difluoro-1-nitrobenzene (15.0 g, 41.1 mmol) was added dropwise in THF (50 mL) was added dropwise, the reaction was allowed to warm to RT and stirred for 90 min. The reaction was cooled to 0° C., a solution of saturated aqueous $NaHSO_4$ (200 mL) was added and the aqueous mixture was extracted with EtOAc (3×100 mL). The organic extracts were combined, dried over Na₂SO₄, filtered and evaporated to afford the title compound a brown solid. ¹H NMR (400 MHz, DMSO-d₆): δ ppm 8.05 (d, 1H), 7.58 (d, 1H), 7.48 (s, 1H), 7.20 (s, 1H), 7.12 (s, 1H), 3.82-3.80 (m, 1H), 1.35 (s, 18H).

Step B: {3-[(3-bromo-5-chlorophenyl)oxy]-2-fluoro-4-nitrophenyl}acetic acid

The crude bis(1,1-dimethylethyl) {3-[(3-bromo-5-chlorophenyl)oxy]-2-fluoro-4-nitrophenyl}propanedioate was dissolved in CH₂Cl₂ (100 mL) and TFA (50 mL) and heated to 40° C. for 3 h. The reaction mixture was cooled to RT and concentrated. Water (200 mL) and EtOAc (100 mL) were added, the layers were separated and the aqueous layer extracted with EtOAc (2×100 mL). The organic extracts were combined, dried over Na₂SO₄, filtered and evaporated to give the title compound as an oil. ¹H NMR (400 MHz, DMSO-d₆): δ ppm 12.17 (br s, 1H), 8.01 (dd, 1H), 7.58 (dd, 1H), 7.50 (s, 1H), 7.23 (s, 1H), 7.15 (s, 1H), 3.84 (s, 2H).

Step C: 2-[(3-bromo-5-chlorophenyl)oxy]-3-fluoro-4-methyl-1-nitrobenzene

The crude {3-[(3-bromo-5-chlorophenyl)oxy]-2-fluoro-4-nitrophenyl}acetic acid was dissolved in CH₃CN (150 mL) and Cu₂O (1.18 g, 8.22 mmol) was added. A condenser was attached and the heterogeneous mixture was heated to reflux for 3 h. The reaction mixture was cooled to RT, filtered through Celite and the solvent evaporated. The crude brown oil was purified by column chromatography (5% to 70% EtOAc/hexanes gradient) to afford the title compound (13.0 g, 88% over three steps) as a yellow oil. ¹H NMR (400 MHz, DMSO-d₆): δ ppm 7.94-7.91 (m, 1H), 7.49-7.45 (m, 2H), 7.22 (s, 1H), 7.14 (s, 1H), 2.34 (s, 3H).

Step D: {2-[(3-bromo-5-chlorophenyl)oxy]-3-fluoro-4-methylphenyl}amine

Sodium hydrosulfite (37.7 g, 216 mmol) dissolved in water (200 mL) was added dropwise to a vigorously stirred solution of 2-[(3-bromo-5-chlorophenyl)oxy]-3-fluoro-4-methyl-1-nitrobenzene (13.0 g, 36.1 mmol) dissolved in THF (100 mL). The reaction was stirred for 16 h at 40° C. The layers were separated and the aqueous phase was extracted with EtOAc (2×100 mL). The organic extracts were combined, dried over Na₂SO₄, filtered and concentrated. The crude oil was purified by column chromatography (5% to 100% EtOAc/hexanes gradient) to afford the title compound (5.0 g, 42%) as a light tan solid. ¹H NMR (400 MHz, DMSO-d₆): δ ppm 7.39-7.38 (m, 1H), 6.98-6.97 (m, 1H), 6.90-6.85 (m, 2H), 6.54-6.52 (m, 1H), 2.08 (s, 3H).

Step E: 2-[(3-bromo-5-chlorophenyl)oxy]-1-chloro-3-fluoro-4-methylbenzene

To an oven dried flask was added CuCl₂ (4.06 g, 30.2 mmol). The flask was placed under high vacuum, flushed with nitrogen and acetonitrile (30 mL) was added. t-Butyl nitrite (4.50 mL, 37.8 mmol) was added dropwise. The stirred solution was placed in an oil bath at 50° C. under gentle stream of nitrogen, heated for 5 min and a solution of {2-[(3-bromo-5-chlorophenyl)oxy]-3-fluoro-4-methylphenyl}amine in acetonitrile (40 mL) was added dropwise. The reaction was stirred for 0.5 h, cooled in an ice bath and poured into ice cold, aqueous HCl (1 N, 125 mL). EtOAc (100 mL) was added and the layers were separated. The aqueous layer was extracted with EtOAc (2×100 mL). The organic extracts were combined, dried over Na₂SO₄, filtered and evaporated. The crude material was purified by column chromatography (0% to 25% EtOAc/hexanes gradient) to afford the title compound (3.2 g, 60%) as a white solid. ¹H NMR (400 MHz, DMSO-d₆): δ ppm 7.48-7.47 m, 1H), 7.41-7.38 (m, 1H), 7.32-7.28 (m, 1H), 7.11-7.10 (m, 1H), 7.04-7.03 (m, 1H), 2.27 (s, 3H).

Step F: 2-[(3-bromo-5-chlorophenyl)oxy]-4-(bromomethyl)-1-chloro-3-fluorobenzene N-bromosuccinimide (1.95 g, 10.94 mmol) was added to a solution of 2-[(3-bromo-5-chlorophenyl)oxy]-1-chloro-3-fluoro-4-methylbenzene (3.20 g, 9.12 mmol) in CCl₄ (300 mL) at RT. The solution was heated to 90° C. for 5 min under N₂ and AIBN (0.070 g, 0.46 mmol) was added. After 4 h, more AIBN (0.070 g, 0.46 mmol) was added and the solution was heated at 90° C. for an additional 2 h. The reaction was cooled to 0° C., filtered through Celite and concentrated. The yellow oil was purified by column chromatography (0% to 30% EtOAc/hexanes gradient) to afford the title compound (3.2 g, 60%) as a clear oil ¹H NMR (400 MHz, DMSO-d₆): δ ppm 7.58-7.49 (m, 3H), 7.13-7.12 (m, 1H), 7.06-7.05 (m, 1H), 4.73 (s, 2H). In addition, 2.25 g (48%) of the di-brominated material, 12-[(3-bromo-5-chlorophenyl)oxy]-1-chloro-4-(dibromomethyl)-3-fluorobenzene was also obtained as a clear oil. ¹H NMR (400 MHz, DMSO-d₆): δ ppm 7.72-7.68 (m, 1H), 7.61 (dd, 1H), 7.51 (t, 1H), 7.47 (s, 1H), 7.19-7.18 (m, 1H), 7.11 (t, 1H).

Step G: ({3-[(3-bromo-5-chlorophenyl)oxy]-4-chloro-2-fluorophenyl}methyl)amine

To a solution of 2-[(3-bromo-5-chlorophenyl)oxy]-4-(bromomethyl)-1-chloro-3-fluorobenzene (2.0 g, 4.7 mmol) in CH₂Cl₂ (10 mL) was added ammonia in methanol (7N, 100 mL). The reaction mixture was stirred for 4 h and concentrated. The resulting crude material was triturated from water to afford the title compound (1.55 g, 92%) as a white solid. ¹H NMR (400 MHz, DMSO-d₅): δ ppm 7.57-7.49 (m, 3H), 7.12-7.11 (m, 1H), 7.05-7.04 (m, 1H), 5.99 (br s, 2H), 3.95 (s, 2H).

Step H: N-({3-[(3-bromo-5-chlorophenyl)oxy]-4-chloro-2-fluorophenyl}methyl)-4-chloro-2-ethyl-1H-imidazole-5-carboxamide ({3-[(3-bromo-5-chlorophenyl)oxy]-4-chloro-2-fluorophenyl}methyl)amine (296 mg, 0.81 mmol), HATU (418 mg, 1.10 mmol) and DIPEA (0.26 mL, 1.46 mmol) were dissolved in DMF (2 mL) and stirred overnight. The reaction was diluted with water (20 mL) and extracted with EtOAc (3×20 mL). The combined organic extracts were combined, dried over Na₂SO₄, filtered and concentrated. The crude material was purified by column chromatography (5% to 80% EtOAc/hexanes gradient) to afford the title compound (320 mg, 84%) as a white solid. ¹H NMR (400 MHz, CDCl₃): δ ppm 7.26-7.13 (m, 3H), 6.91 (s, 1H), 6.80 (s, 1H), 4.67-4.66 (m, 2H), 2.83-2.74 (m, 2H), 1.35-1.29 (m, 3H). MS: m/z 522.0 (M+1).

Example 161

4-chloro-N-[(4-chloro-3-{[3-chloro-5-(cyclopropylethynyl)phenyl]oxy}-2-fluorophenyl)methyl]-2-ethyl-1H-imidazole-5-carboxamide trifluoroacetate

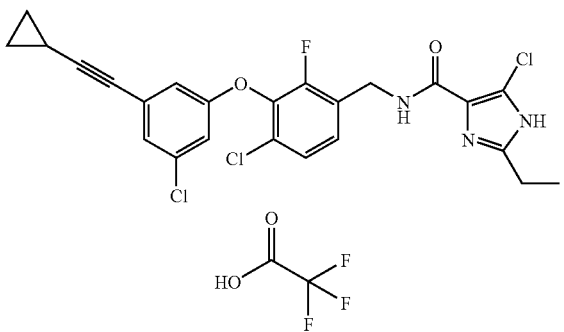

A solution of N-({3-[(3-bromo-5-chlorophenyl)oxy]-4-chloro-2-fluorophenyl}methyl)-4-chloro-2-ethyl-1H-imidazole-5-carboxamide (60 mg, 0.12 mmol), Pd(PPh₃)₂Cl₂ (4 mg, 0.006 mmol), CuI (1 mg, 0.0036 mmol) and cyclopropylacetylene (51 μL, 0.60 mmol) in triethylamine (1 mL) and DMF (0.5 mL) was heated at 90° C. in a sealed tube for 3 h. The reaction was cooled and the crude material purified by Reverse-Phase HPLC (water/acetonitrile with 0.1% TFA) to afford the title compound (45 mg, 61%) as a white solid. ¹H NMR (400 MHz, DMSO-d₆): δ ppm 8.13-8.08 (m, 1H), 7.45 (d, 1H), 7.29 (t, 1H), 7.15-7.14 (m, 1H), 7.00-6.99 (m, 1H), 6.72-6.71 (m, 1H), 4.48 (d, 1H), 2.55 (q, 2H), 1.52-1.44 (m, 1H), 1.13 (t, 3H), 0.86-0.81 (m, 2H), 0.71-0.67 (m, 2H). MS: m/z 506, 508 (M+1).

Example 162

4-chloro-N-({4-chloro-3-[(3-chloro-5-ethenylphenyl)oxy]-2-fluorophenyl}methyl)-2-ethyl-1H-imidazole-5-carboxamide

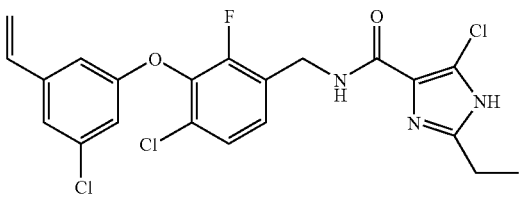

A solution of N-({3-[(3-bromo-5-chlorophenyl)oxy]-4-chloro-2-fluorophenyl}methyl)-4-chloro-2-ethyl-1H-imidazole-5-carboxamide (240 mg, 0.46 mmol), potassium vinyltrifluoroborate (122 mg, 0.92 mmol), PdCl₂(dppf)-DCM (15 mg, 0.0184 mmol) and triethylamine (0.13 mL, 0.92 mmol) in n-PrOH (5 mL). The reaction was heated at 100° C. for 6 h, cooled to rt and water was added (20 mL). The aqueous mixture was extracted with EtOAc (3×20 mL) and the organic extracts were combined, dried over Na₂SO₄, filtered and concentrated. The crude material was purified by column chromatography (5% to 100% EtOAc/hexanes gradient) to afford the title compound (177 mg, 82%) as a white solid. ¹H NMR (400 MHz, DMSO-d₆): δ ppm 8.14 (br s, 1H), 7.47 (d, 1H), 7.35-7.30 (m, 2H), 7.01 (s, 1H), 6.81 (d, 1H), 6.72-6.64 (m, 2H), 5.92 (d, 1H), 5.35 (d, 1H), 4.51 (d, 2H), 2.58 (q, 2H), 1.16 (t, 3H).

Example 163

4-chloro-N-{[4-chloro-3-({3-chloro-5-[(E)-2-cyanoethenyl]phenyl}oxy)-2-fluorophenyl]methyl}-2-ethyl-1H-imidazole-5-carboxamide

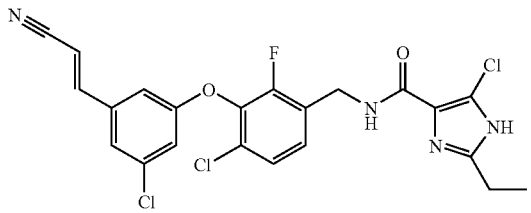

Step A: 4-chloro-N-({4-chloro-3-[(3-chloro-5-formylphenyl)oxy]-2-fluorophenyl}methyl)-2-ethyl-1H-imidazole-5-carboxamide A solution of 4-chloro-N-({4-chloro-3-[(3-chloro-5-ethenylphenyl)oxy]-2-fluorophenyl}methyl)-2-ethyl-1H-imidazole-5-carboxamide (80 mg, 0.17 mmol), osmium tetraoxide (2.5% in tBuOH, 35 μL, 0.003 mmol), sodium periodate (109 mg, 0.51 mmol) in THF (1 mL) and water (2 mL) was stirred at room temperature for 4 h. The reaction was concentrated to a green-black oil and purified by Reverse-Phase HPLC (water/acetonitrile with 0.1% TFA) to provide the product as the trifluoroacetate salt. The salt was dissolved in EtOAc (20 mL) and washed with saturated sodium bicarbonate (10 mL), dried over sodium sulfate, filtered and concentrated to afford the title compound (45 mg, 61%) as a clear oil. ¹H NMR (400 MHz, DMSO-d₆): δ ppm 9.90 (s, 1H), 8.11-8.08 (m, 1H), 7.72 (s, 1H), 7.51-7.46 (m, 2H), 7.36-7.31 (m, 1H), 7.24 (s, 1H), 4.52 (d, 2H), 2.57 (q, 2H), 1.14 (t, 3H).

Step B: 4-chloro-N-{[4-chloro-3-({3-chloro-5-[(E)-2-cyanoethenyl]phenyl}oxy)-2-fluorophenyl]methyl}-2-ethyl-1H-imidazole-5-carboxamide A solution of diethylphosphonoacetonitrile (15 μL, 0.094 mmol) in THF (1 mL) was cooled to 5° C. in an ice bath and potassium t-butoxide (1 M in THF, 94 μL, 0.094 mmol) was added dropwise. The reaction was stirred at 5° C. for 30 min and a solution of 4-chloro-N-({4-chloro-3-[(3-chloro-5-formylphenyl)oxy]-2-fluorophenyl}methyl)-2-ethyl-1H-imidazole-5-carboxamide (40 mg, 0.085 mmol) in THF (1 mL) was added dropwise. The reaction was stirred at 5° C. for 30 min, warmed to room temperature and stirred for an additional 60 min. The reaction was quenched with water (1 mL) and concentrated to a yellow oil. The crude material was purified by column chromatography (10% to 100% EtOAc/hexanes gradient) to afford the title compound (32 mg, 76%) as a white solid. ¹H NMR (400 MHz, DMSO-d₆): δ ppm 12.69 (s, 1H), 8.05 (t, 1H), 7.58 (d, 1H), 7.53 (s, 1H), 7.47-7.44 (m, 1H), 7.31 (t, 1H), 7.23 (s, 1H), 7.00 (s, 1H), 6.58 (d, 1H), 4.49 (d, 2H), 2.55 (q, 2H), 1.13 (t, 3H). MS: m/z 493, 495 (M+1).

Example 164

4-chloro-N-({4-chloro-3-[(3-chloro-5-cyclopropylphenyl)oxy]-2-fluorophenyl}methyl)-2-ethyl-1H-imidazole-5-carboxamide trifluoroacetate

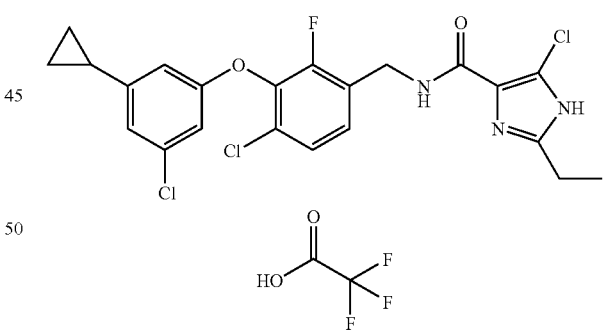

A 0.068 M solution of diazomethane in DCM (25 mL, 1.71 mmol) was added dropwise over 20 min to a solution of 4-chloro-N-({4-chloro-3-[(3-chloro-5-ethenylphenyl)oxy]-2-fluorophenyl}methyl)-2-ethyl-1H-imidazole-5-carboxamide (0.080 g, 0.17 mmol) and Pd(acac)₂ (0.005 g, 0.02 mmol) in Et₂O (15 mL) at RT under nitrogen. The reaction was stirred for 24 h under nitrogen. The mixture was filtered through Celite and concentrated. The crude product was purified by Reverse-Phase HPLC (water/acetonitrile with 0.1% TFA) three times to afford the title compound (17 mg, 21%) as a white powder. ¹H NMR (400 MHz, DMSO-d₆): δ ppm 12.72 (br s, 1H), 8.10 (t, 1H), 7.47 (d, 1H), 7.31 (t, 1H), 6.84

(s, 1H), 6.67 (s, 1H), 6.61 (s, 1H), 4.52 (d, 2H), 2.58 (t, 2H), 1.94-1.88 (m, 1H), 1.16 (t, 3H), 0.96-0.92 (m, 2H), 0.70-0.67 (m, 2H). MS: m/z 481.75, 483.75 (M+1).

Example 165

N-({4-Chloro-3-[(3-chloro-5-cyanophenyl)oxy]-2-fluorophenyl}methyl)-2-pyridinecarboxamide 1-oxide

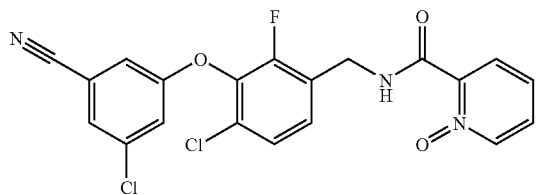

To a solution of N-[4-Chloro-3-(3-chloro-5-cyanophenoxy)-2-fluorobenzyl]pyridine-2-carboxamide (0.064 g, 0.154 mmol) in 4 mL of dichloromethane was added mCPBA (0.026 g, 0.154 mmol). The resulting mixture was stirred overnight at RT. The reaction mixture was washed with 15% Na₂CO₃ and the organic layer separated and evaporated. The solid was dissolved in DMF and diluted with MeOH to a volume of 2 mL. Purification was accomplished by reverse-phase HPLC (water/acetonitrile with 0.1% TFA) to afford the title compound (0.006 g, 9%) as a solid. ¹H NMR (400 MHz, CDCl₃) δ ppm 11.74-11.85 (m, 1H), 8.44 (dd, 1H), 8.26-8.30 (m, 1H), 7.46-7.52 (m, 1H), 7.40-7.45 (m, 1H), 7.32-7.38 (m, 2H), 7.24-7.29 (m, 1H), 7.16 (t, 1H), 7.01-7.04 (m, 1H), 4.74 (d, 2H). LCMS: m/z 431.9 (M+1).

Example 166

N-({4-chloro-3-[(3-chloro-5-cyanophenyl)oxy]-2-fluorophenyl}methyl)-5-{[2-(methylthio)ethyl]oxy}-1H-indole-2-carboxamide

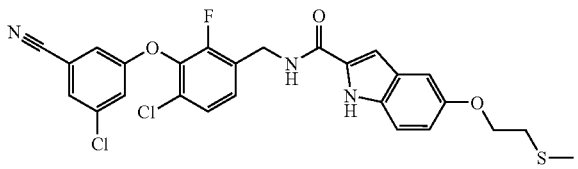

Step A: 1-(1,1-Dimethylethyl)2-ethyl 5-[(phenylmethyl)oxy]-1H-indole-1,2-dicarboxylate PS-DMAP (9.37 g, 16.8 mmol) was added to a THF solution of ethyl 5-[(phenylmethyl)oxy]-1H-indole-2-carboxylate (24.9 g, 84 mmol) followed by the addition of BOC₂O (23.5 mL, 101 mmol) and the reaction stirred at RT until no starting material remained as indicated by TLC. The resin was filtered off and the solvent evaporated to afford an oil. Purification was accomplished by silica gel column chromatography (0-20% EtOAc/hexanes) to afford the title compound (33.92 g, quant.) as a white solid. ¹H NMR (400 MHz, DMSO-d₆) δ ppm 7.86 (d, 1H), 7.42-7.48 (m, 2H), 7.38 (t, 2H), 7.28-7.34 (m, 2H), 7.16 (s, 1H), 5.12 (s, 2H), 4.29 (q, 2H), 1.54 (s, 9H), 1.29 (t, 3H). LCMS: m/z 294.6 (M-Boc).

Step B: 1-(1,1-Dimethylethyl)2-ethyl 5-hydroxy-1H-indole-1,2-dicarboxylate

Ammonium formate (54.1 g, 858 mmol) and 10% Pd/C (1.00 g, 0.470 mmol) were added to a solution of 1-(1,1-dimethylethyl)2-ethyl 5-[(phenylmethyl)oxy]-1H-indole-1,2-dicarboxylate (33.9 g, 86 mmol) in ethanol. The mixture was stirred at RT until TLC showed consumption of starting material. The mixture was filtered through celite and the ethanol evaporated to give an oil. The residue was partitioned between DCM and water. The organic layer was washed with sat. NaCl, dried over MgSO₄, filtered and evaporated onto silica. Purification was accomplished by silica gel column chromatography (0-40% EtOAc/hexanes) to afford the title compound (25.03 g, 96%) as a white solid. ¹H NMR (400 MHz, DMSO-d₆) δ ppm 9.36 (s, 1H), 7.75 (d, 1H), 7.08 (s, 1H), 6.96 (d, 1H), 6.91 (dd, 1H), 4.26 (q, 2H), 1.52 (s, 9H), 1.27 (t, 3H). LCMS: m/z 204.5 (M-Boc).

Step C: 1-(1,1-Dimethylethyl)2-ethyl 5-{[2-(methylthio)ethyl]oxy}-1H-indole-1,2-dicarboxylate 2-(Methylthio)ethanol (0.285 mL, 3.28 mmol) was added to a DCM solution of 1-(1,1-dimethylethyl)2-ethyl 5-hydroxy-1H-indole-1,2-dicarboxylate (0.500 g, 1.63 mmol), followed by the addition of triphenylphosphine (0.859 g, 3.28 mmol) and TBAD (0.754 g, 3.28 mmol). The resulting mixture was stirred for 1 hour at 45° C. The mixture was poured into water and EtOAc and the organic layer was separated. The organic layer was dried over MgSO₄, filtered and evaporated onto silica gel. Purification was accomplished by silica gel column chromatography (0-50% EtOAc/hexanes) to afford the title compound (0.512 g, 82%) ¹H NMR (400 MHz, CDCl₃) δ ppm 7.96 (d, 1H), 6.95-7.05 (m, 3H), 4.36 (q, 2H), 4.16 (t, 2H), 2.88 (t, 2H), 2.20 (s, 3H), 1.60 (s, 9 H), 1.37 (t, 3H).

Step D: Ethyl 5-{[2-(methylthio)ethyl]oxy}-1H-indole-2-carboxylate

A solution of 1-(1,1-dimethylethyl)2-ethyl 5-{[2-(methylthio)ethyl]oxy}-1H-indole-1,2-dicarboxylate (0.500 g, 1.31 mmol) in THF was treated with 4 M HCl in dioxane and stirred for 5 hours. The solvent was evaporated to an oil and the residue was dissolved in DCM and TFA was added and stirred until no starting material remained as evident by TLC. The mixture was evaporated to a solid and purification was accomplished by silica gel column chromatography (0-50% EtOAc/hexanes) to afford the title compound (0.228 g, 61%) as a white solid. ¹H NMR (400 MHz, CDCl₃) δ ppm 9.21-9.37 (m, 1H), 7.32 (d, 1H), 7.12-7.16 (m, 1H), 7.09 (d, 1H), 7.00 (dd, 1H), 4.42 (q, 2H), 4.19 (t, 2H), 2.91 (t, 2H), 2.22 (s, 3H), 1.42 (t, 3H). LCMS: m/z=279.9 (M+1).

Step E: 5-{[2-(Methylthio)ethyl]oxy}-1H-indole-2-carboxylic acid

A methanol solution of ethyl 5-{[2-(methylthio)ethyl]oxy}-1H-indole-2-carboxylate (0.099 g, 0.356 mmol) was treated with 1 N LiOH (4 mL). The reaction mixture turned cloudy and THF was added until the cloudiness disappeared. The reaction was heated to 70° C. until TLC showed consumption of the starting material. The reaction mixture was partitioned between EtOAc and water and the basic layer was separated. The basic layer was acidified with conc. HCl and extracted with EtOAc, the layers were separated and the EtOAc was evaporated to afford the title compound (0.037 g, 41%) as a white solid. ¹H NMR (400 MHz, Acetone-d₆) δ ppm 10.74 (br. s., 1H), 7.44 (d, 1H), 7.17 (d, 1H), 7.11 (s, 1H), 6.96 (dd, 1H), 4.19 (t, 2 H), 2.88 (t, 2H), 2.20 (s, 3H). LCMS: m/z=251.9 (M−1).

Step F: N-({4-chloro-3-[(3-chloro-5-cyanophenyl)oxy]-2-fluorophenyl}methyl)-5-{[2-(methylthio)ethyl]oxy}-1H-indole-2-carboxamide HATU (0.055 g, 0.145 mmol) was added as a solid to a solution of 3-{[3-(aminomethyl)-6-chloro-2-fluorophenyl]oxy}-5-chlorobenzonitrile (0.045 g, 0.145 mmol), 5-{[2-

(methylthio)ethyl]oxy}-1H-indole-2-carboxylic acid (0.036 g, 0.145 mmol) and DIPEA (0.025 mL, 0.145 mmol) in DMF (1 mL). After 2 hours the reaction mixture was poured into EtOAc and water and the layers were separated. The organic layer was dried over MgSO$_4$, filtered and the solvent evaporated. The residue was dissolved in MeOH and purification was accomplished by reverse-phase HPLC (water/acetonitrile with 0.1% TFA) to afford the title compound (0.041 g, 52%) as a white solid. $^1$H NMR (400 MHz, Acetone-d$_6$) δ ppm 10.64 (br. s., 1H), 8.28 (br. s., 1H), 7.61 (s, 1H), 7.33-7.51 (m, 5H), 7.00-7.13 (m, 2H), 6.89 (dd, 1H), 4.66 (d, 2 H), 4.15 (t, 2H), 2.85 (t, 2H), 2.17 (s, 3H). LC-MS (ES$^+$) m/z 544.4 [M+H].

Example 167

N-({4-chloro-3-[(3-chloro-5-cyanophenyl)oxy]-2-fluorophenyl}methyl)-2,3-dihydro-7H-[1,4]oxathiino[3,2-e]indole-8-carboxamide

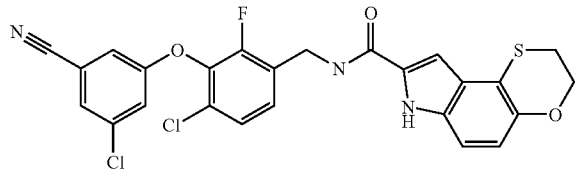

Step A: Ethyl 2,3-dihydro-7H-[1,4]oxathiino[3,2-e]indole-8-carboxylate

NCS (0.048 g, 0.358 mmol) was added to a DMF (2 mL) solution of ethyl 5-{[2-(methylthio)ethyl]oxy}-1H-indole-2-carboxylate (0.100 g, 0.358 mmol) and the reaction mixture stirred over the weekend at room temperature. The reaction mixture was partitioned between water and EtOAc and the organic layer was separated. The organic layer was dried over MgSO$_4$, filtered and evaporated onto silica. Purification was accomplished by silica gel column chromatography (0-50% EtOAc/hexanes) to afford the title compound (0.067 g, 71%) as a white solid. $^1$H NMR (400 MHz, CDCl$_3$) δ ppm 9.38 (br. s., 1H), 7.11 (s, 1H), 7.04 (d, 1H), 6.85 (d, 1H), 4.35-4.47 (m, 4 H), 3.16-3.24 (m, 2H), 1.41 (t, 3H). LCMS: m/z=264 (M+1).

Step B: 2,3-Dihydro-7H-[1,4]oxathiino[3,2-e]indole-8-carboxylic acid

A methanol solution of ethyl 2,3-dihydro-7H-[1,4]oxathiino[3,2-e]indole-8-carboxylate (0.067 g, 0.25 mmol) was treated with 1 N LiOH (4 mL). The reaction mixture turned cloudy and THF was added until the cloudiness disappeared. The reaction was heated to 70° C. until TLC showed consumption of the starting material. The reaction mixture was partitioned between EtOAc and water and the basic layer was separated. The basic layer was acidified with conc. HCl and extracted with EtOAc, the layers were separated and the EtOAc was evaporated to afford the title compound (0.047 g, 80%) as a white solid. $^1$H NMR (400 MHz, Acetone-d$_6$) δ ppm 10.85 (br. s., 1H), 7.19 (d, 1H), 7.01 (s, 1H), 6.82 (d, 1H), 4.37-4.46 (m, 2H), 3.20-3.30 (m, 2H). LCMS: m/z=235.9 (M+1).

Step C: N-({4-chloro-3-[(3-chloro-5-cyanophenyl)oxy]-2-fluorophenyl}methyl)-2,3-dihydro-7H-[1,4]oxathiino[3,2-e]indole-8-carboxamide HATU (0.061 g, 0.161 mmol) was added as a solid to a solution of 3-{[3-(aminomethyl)-6-chloro-2-fluorophenyl]oxy}-5-chlorobenzonitrile (0.050 g, 0.161 mmol), 2,3-dihydro-7H-[1,4]oxathiino[3,2-e]indole-8-carboxylic acid (0.038 g, 0.161 mmol) and DIPEA (0.028 mL, 0.161 mmol) in DMF (1 mL). After 2 hours the reaction mixture was poured into EtOAc and water and the organic layer separated. The organic layer was dried over MgSO$_4$, filtered and the solvent evaporated. The residue was dissolved in MeOH and purification was accomplished by reverse-phase HPLC (water/acetonitrile with 0.1% TFA) to afford the title compound (0.032 g, 38%) as a white solid. $^1$H NMR (400 MHz, Acetone-d$_6$) δ ppm 10.76 (br. s., 1H), 8.36 (t, 1H), 7.64 (t, 1H), 7.42-7.52 (m, 2H), 7.39-7.42 (m, 2H), 7.20 (dd, 1H), 7.00 (dd, 1H), 6.77 (d, 1H), 4.70 (d, 2H), 4.38-4.43 (m, 2H), 3.23-3.28 (m, 2H). LCMS: m/z=528.0 (M+1).

Example 168

N-({4-chloro-3-[(3-chloro-5-cyanophenyl)oxy]-2-fluorophenyl}methyl)-5-[(2-hydroxyethyl)oxy]-1H-indole-2-carboxamide

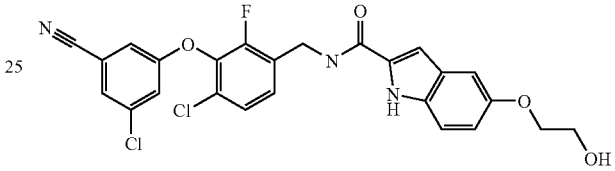

Step A: 1-(1,1-Dimethylethyl)2-ethyl 5-[(2-{[(1,1-dimethylethyl)(dimethyl)silyl]oxy}ethyl)oxy]-1H-indole-1,2-dicarboxylate Cesium carbonate (0.534 g, 1.63 mmol) and [(2-bromoethyl)oxy](1,1-dimethylethyl)dimethylsilane (0.351 mL, 1.63 mmol) were added to a solution of 1-(1,1-dimethylethyl)2-ethyl 5-hydroxy-1H-indole-1,2-dicarboxylate (0.500 g, 1.63 mmol) in DMF (10 mL). The reaction mixture was stirred at 45° C. for 6 hours and poured into EtOAc and water. The organic layer was washed with water, brine, dried over MgSO$_4$, filtered and the solvent evaporated. Purification was accomplished by silica gel column chromatography (0-50% EtOAc/hexanes) to afford the title compound (0.635 g, 84%) as an oil. $^1$H NMR (400 MHz, CDCl$_3$) δ ppm 7.95 (d, 1H), 6.94-7.07 (m, 3H), 4.33 (q, 2H), 4.02 (t, 2H), 3.94 (t, 2H), 1.58 (s, 9H), 1.35 (t, 3 H), 0.89 (s, 9H), 0.08 (s, 6H). LC-MS (ES$^+$) m/z 363.1 [M-Boc].

Step B: 5-[(2-Hydroxyethyl)oxy]-1H-indole-2-carboxylic acid

A methanol solution of 1-(1,1-dimethylethyl)2-ethyl 5-[(2-{[(1,1-dimethylethyl)(dimethyl)silyl]oxy}ethyl)oxy]-1H-indole-1,2-dicarboxylate (0.200 g, 0.431 mmol) was treated with 1 N LiOH (4 mL). A precipitate formed and THF was added to redissolve the material. The reaction was heated to 70° C. until the starting material was consumed, partitioned between EtOAc and water and the layers separated. The basic aqueous layer was acidified with conc. HCl and extracted with EtOAc. Purification was accomplished by silica gel column chromatography (0-100% EtOAc/hexanes, striped with MeOH) to afford the title compound (0.015 g, 16%) and 5-[(2-{[(1,1-dimethylethyl)(dimethyl)silyl]oxy}ethyl)oxy]-1H-indole-2-carboxylic acid (0.0114 g, 7%) $^1$H NMR (400 MHz, Acetone-d$_6$) δ ppm 10.73 (br. s., 1H), 7.43 (d, 1H), 7.15 (d, 1H), 7.10 (d, 1H), 6.96 (dd, 1H), 4.07 (t, 2H), 3.88 (t, 2H).

Step C: N-({4-chloro-3-[(3-chloro-5-cyanophenyl)oxy]-2-fluorophenyl}methyl)-5-[(2-hydroxyethyl)oxy]-1H-indole-2-carboxamide HATU (0.026 g, 0.069 mmol) was added to a DMF (1 mL) solution of 3-{[3-(aminomethyl)-6-chloro-2-fluorophenyl]

oxy}-5-chlorobenzonitrile (0.022 g, 0.069 mmol), 5-[(2-hydroxyethyl)oxy]-1H-indole-2-carboxylic acid (0.015 g, 0.069 mmol) and DIPEA (0.012 mL, 0.069 mmol). The reaction mixture was stirred for 2 h, poured into EtOAc and water and the layers separated. The organic layer was dried over MgSO₄, filtered and the solvent evaporated. The residue was dissolved in MeOH and purification was accomplished by reverse-phase HPLC (water/acetonitrile with 0.1% TFA) to afford the title compound (0.013 g, 37%) as a white solid ¹H NMR (400 MHz, DMSO-d₆) δ ppm 11.44 (s, 1H), 8.96 (t, 1H), 7.80 (s, 1H), 7.44-7.54 (m, 3H), 7.37 (t, 1H), 7.28 (d, 1H), 7.05 (s, 2H), 6.83 (dd, 1H), 4.80 (t, 1H), 4.54 (d, 2H), 3.94 (t, 2H), 3.70 (q, 2H).

Example 169

N-({4-Chloro-3-[(3-chloro-5-cyanophenyl)oxy]-2-fluorophenyl}methyl)-5-{[3-(methylthio)propyl]oxy}-1H-indole-2-carboxamide

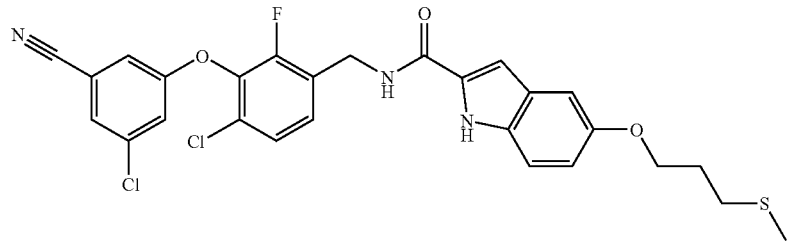

Step A: 1-(1,1-Dimethylethyl)2-ethyl 5-{[3-(methylthio)propyl]oxy}-1H-indole-1,2-dicarboxylate Triphenylphosphine (0.859 g, 3.28 mmol), and TBAD (0.754 g, 3.28 mmol) were added to a DCM solution of 1-(1,1-dimethylethyl)2-ethyl 5-hydroxy-1H-indole-1,2-dicarboxylate (0.50 g, 1.638 mmol) and 3-(methylthio)-1-propanol (0.348 g, 3.28 mmol). The resulting mixture was stirred at 45° C. for 1 hr. The mixture was poured into water and EtOAc and the layers were separated. The organic layer was dried over MgSO₄, filtered and evaporated onto silica gel. Purification was accomplished by silica gel column chromatography (0-50% EtOAc/hexanes) to afford the title compound (0.488 g, 76%). ¹H NMR (400 MHz, CDCl₃) δ ppm 7.90-7.99 (m, 1H), 6.95-7.04 (m, 3H), 4.35 (q, 2H), 4.07 (t, 2H), 2.69 (t, 2H), 2.10 (s, 3H), 2.05-2.10 (m, 2H), 1.60 (s, 9H), 1.37 (t, 3H). LCMS: m/z=392.0 (M−1).

Step B: 5-{[3-(Methylthio)propyl]oxy}-1H-indole-2-carboxylic acid

A methanol solution of 1-(1,1-dimethylethyl)2-ethyl 5-{[3-(methylthio)propyl]oxy}-1H-indole-1,2-dicarboxylate (0.488 g, 1.24 mmol) was treated with 1 N LiOH (4 mL). The reaction mixture turned cloudy, THF was added to redissolve the precipitate and the mixture was heated to 70° C. When no starting material remained as evident by TLC the reaction mixture was partitioned between EtOAc and water. The aqueous layer was separated and acidified with conc. HCl. The aqueous layer was extracted with EtOAc and the organic layer was evaporated to afford the title compound (0.263 g, 80%). ¹H NMR (400 MHz, Acetone-d₆) δ ppm 10.73 (br. s., 1H), 7.43 (d, 1H), 7.14 (d, 1H), 7.09-7.13 (m, 1H), 6.96 (dd, 1H), 4.09 (t, 2H), 2.68 (t, 2H), 2.08 (s, 3H), 2.04 (t, 2H). LCMS: m/z=264.1 (M−1).

Step C: N-({4-Chloro-3-[(3-chloro-5-cyanophenyl)oxy]-2-fluorophenyl}methyl)-5-{[3-(methylthio)propyl]oxy}-1H-indole-2-carboxamide HATU (0.061 g, 0.161 mmol) was added as a solid to a DMF (1 mL) solution of 3-{[3-(aminomethyl)-6-chloro-2-fluorophenyl]oxy}-5-chlorobenzonitrile (0.050 g, 0.161 mmol), 5-{[3-(methylthio)propyl]oxy}-1H-indole-2-carboxylic acid (0.043 g, 0.161 mmol) and DIPEA (0.028 mL, 0.161 mmol). After stirring for 2 hours the reaction mixture was poured into EtOAc and water and the layers separated. The organic layer was dried over MgSO₄, filtered and the solvent evaporated. The residue was dissolved in MeOH and purification was accomplished by reverse-phase HPLC (water/acetonitrile with 0.1% TFA) to afford the title compound (0.045 g, 50%) as a light yellow solid. ¹H NMR (400 MHz, DMSO-d₆) δ ppm 11.45 (s, 1H), 8.96 (t, 1H), 7.80 (s, 1H), 7.43-7.54 (m, 3H), 7.37 (t, 1H), 7.28 (d, 1H), 7.01-7.10 (m, 2H), 6.82 (dd, 1H), 4.54 (d, 2H), 4.00 (t, 2H), 2.61 (t, 2H), 2.04 (s, 3H), 1.89-2.01 (m, 2H). LCMS: m/z 558.1 (M+1).

Example 170

3-Bromo-N-({4-chloro-3-[(3-chloro-5-cyanophenyl)oxy]-2-fluorophenyl}methyl)-5-[(2-hydroxyethyl)oxy]-1H-indole-2-carboxamide

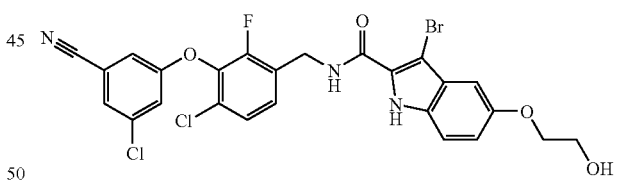

Step A: Ethyl 5-[(2-hydroxyethyl)oxy]-1H-indole-2-carboxylate

A solution of 1-(1,1-dimethylethyl)2-ethyl 5-[(2-{[(1,1-dimethylethyl)(dimethyl)silyl]oxy}ethyl)oxy]-1H-indole-1,2-dicarboxylate (0.389 g, 0.840 mmol) in THF (4 mL) was treated with 1N HCl (0.840 mL, 0.840 mmol) and the reaction mixture was stirred for several hours at room temp. TLC showed consumption of the starting material and 2 product spots. Solvents were evaporated and the residue dissolved in DCM (4 mL) and TFA (0.25 mL, 3.24 mmol) was added. TLC showed a single product spot. The solvents were evaporated to afford the title compound (0.224 g, 96%) as a grey solid. ¹H NMR (400 MHz, Acetone-d₆) δ ppm 10.74 (br. s., 1H), 7.41 (d, 1H), 7.32 (s, 1H), 7.12 (d, 1H), 7.06 (d, 1H), 6.94 (dd, 1H), 4.32 (q, 2H), 4.05 (t, 2H), 3.88 (t, 2H), 1.32 (t, 3H). LCMS: m/z 204.2 (M-45).

Step B: Ethyl 5-[(2-{[(1,1-dimethylethyl)(dimethyl)silyl]oxy}ethyl)oxy]-1H-indole-2-carboxylate DBU (0.203 mL, 1.34 mmol) was added to a solution of ethyl 5-[(2-hydroxyethyl)oxy]-1H-indole-2-carboxylate (0.224 g, 0.899 mmol) and TBDMS-Cl (0.203 g, 1.34 mmol) in THF (6 mL). The reaction was stirred at room temp until no starting material remained as evident by TLC. The THF was evaporated and the residue partitioned between DCM and water. The organic layer was separated, dried over MgSO₄, filtered and evaporated onto silica. Purification was accomplished by silica gel column chromatography (EtOAc/hexanes) to afford the title compound (0.255 g, 78%) as a white solid. $^1$H NMR (400 MHz, CDCl₃) δ ppm 8.82 (br. s., 1H), 7.29 (d, 1H), 7.12 (s, 1H), 7.08 (s, 1H), 6.96-7.04 (m, 1H), 4.39 (q, 2H), 4.06 (t, 2H), 3.95-4.02 (m, 2H), 1.40 (t, 3H), 0.91 (s, 9H), 0.10 (s, 6H).

Step C: Ethyl 3-bromo-5-[(2-{[(1,1-dimethylethyl)(dimethyl)silyl]oxy}ethyl)oxy]-1H-indole-2-carboxylate NBS (0.137 g, 0.771 mmol) was added to ethyl 5-[(2-{[(1,1-dimethylethyl)(dimethyl)silyl]oxy}ethyl)oxy]-1H-indole-2-carboxylate (0.255 g, 0.701 mmol) dissolved in DMF (2 mL) and the resulting mixture was stirred overnight at RT. The reaction mixture was partitioned between EtOAc and water. The organic layer was separated, dried over MgSO₄, filtered and the solvent evaporated. Purification was accomplished by silica gel column chromatography (0 to 50% EtOAc/hexanes) to afford the title compound (0.121 g, 39%) as an oily solid. $^1$H NMR (400 MHz, CDCl₃) δ ppm 8.90 (br. s., 1H), 7.27 (d, 1H), 7.02-7.07 (m, 1H), 7.01 (s, 1H), 4.43 (q, 2H), 4.11 (t, 2H), 4.00 (t, 2H), 1.43 (t, 3H), 0.91 (s, 9H), 0.11 (d, 6H). LC-MS (ES⁺) m/z 442.2 [M+H].

Step D: 3-Bromo-5-[(2-hydroxyethyl)oxy]-1H-indole-2-carboxylic acid

LiOH (1 N in water, 4 mL, 4 mmol) was added to a solution of ethyl 3-bromo-5-[(2-{[(1,1-dimethylethyl)(dimethyl)silyl]oxy}ethyl)oxy]-1H-indole-2-carboxylate (0.121 g, 0.275 mmol) in THF (4 mL) and methanol (4 mL). The solution was stirred at room temp overnight. The reaction mixture was evaporated to a residue and partitioned between EtOAc and 1 N HCl. The organic layer was separated, dried over MgSO₄, and evaporated to a crude solid to afford the title compound (0.081 g, 89%) as a white solid. $^1$H NMR (400 MHz, DMSO-d₆) δ ppm 13.14-13.33 (m, 1H), 11.97 (s, 1H), 7.34 (d, 1H), 6.97 (dd, 1H), 6.86 (s, 1H), 4.83 (t, 1H), 3.99 (t, 2H), 3.71 (q, 2H). LC-MS (ES⁺) m/z 301 [M+H].

Step E: 3-Bromo-N-({4-chloro-3-[(3-chloro-5-cyanophenyl)oxy]-2-fluorophenyl}methyl)-5-[(2-hydroxyethyl)oxy]-1H-indole-2-carboxamide HATU (0.061 g, 0.161 mmol) was added to a DMF (2 mL) solution of 3-bromo-5-[(2-hydroxyethyl)oxy]-1H-indole-2-carboxylic acid (0.048 g, 0.161 mmol), 3-{[3-(aminomethyl)-6-chloro-2-fluorophenyl]oxy}-5-chlorobenzonitrile (0.050 g, 0.161 mmol) and DIPEA (0.028 mL, 0.161 mmol). The solution was stirred overnight and partitioned between water and EtOAc. The organic was washed with a 15% aqueous solution of Na₂CO₃, dried over MgSO₄ and filtered. Evaporation of the EtOAc and trituration in acetone afforded the title compound (0.049 g, 47%) as a white solid. $^1$H NMR (400 MHz, DMSO-d₆) δ ppm 11.91 (s, 1H), 8.49 (t, 1H), 7.77-7.89 (m, 1H), 7.51-7.57 (m, 2H), 7.43-7.51 (m, 2H), 7.37 (d, 1H), 6.96 (ddd, 1H), 6.89 (s, 1H), 4.86 (t, 1H), 4.62 (d, 2H), 4.02 (t, 1H), 3.69-3.82 (m, 1H). LCMS: m/z=592.2 (M+1).

Example 171

3-Chloro-N-({4-chloro-3-[(3-chloro-5-cyanophenyl)oxy]-2-fluorophenyl}methyl)-4-formyl-1H-pyrrole-2-carboxamide

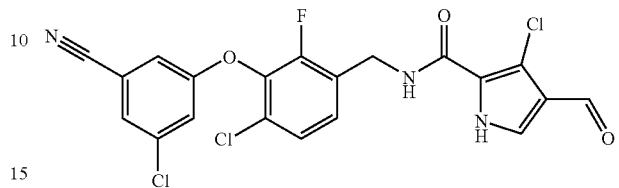

Step A: Methyl 3-chloro-4-formyl-1H-pyrrole-2-carboxylate

DMF (0.579 mL, 1.48 mmol) was cooled to 0° C. under nitrogen. POCl₃ (0.647 mL, 6.93 mmol) was added to the cold DMF and stirred at 0 oC, and a solid formed. Dichloroethane (2 mL) was added to the solid followed by the addition of methyl 3-chloro-1H-pyrrole-2-carboxylate (1.00 g, 6.26 mmol) in dichloroethane (2 mL). The reaction mixture was stirred for 10 minutes at 0° C. and heated to reflux until the starting material was no longer evident by TLC. The reaction mixture was cooled and partitioned between EtOAc and water. The organic layer was separated, washed with saturated NaHCO₃, dried over MgSO₄, filtered and the EtOAc evaporated. Purification was accomplished by silica gel column chromatography (0-30% EtOAc/hexanes) to afford the title compound (0.319 g, 27%), and methyl 3-chloro-5-formyl-1H-pyrrole-2-carboxylate (0.320 g, 27%). $^1$H NMR (400 MHz, Acetone-d₆) δ ppm 11.83 (br. s., 1H), 9.89 (s, 1H), 7.72 (s, 1H), 3.86 (s, 3H). LCMS: m/z=188.2 (M+1).

Step B: 3-Chloro-4-formyl-1H-pyrrole-2-carboxylic acid

LiOH (1 N in water, 2 mL, 2 mmol) was added to a solution of methyl 3-chloro-4-formyl-1H-pyrrole-2-carboxylate (0.050 g, 0.26 mmol) in THF (2 mL) and methanol (2 mL). The solution was stirred at RT overnight. The solvents were evaporated to afford a residue which was partitioned between EtOAc and 1 N HCl. The organic layer was separated, dried over MgSO₄, filtered and evaporated to a solid to afford the title compound (0.038 g, 83%) as a crude product which was used with no further purification. $^1$H NMR (400 MHz, Acetone-d₆) δ ppm 11.76 (br. s., 1H), 9.90 (s, 1H), 7.72 (d, 1H). LCMS: m/z=174.2 (M+1).

Step C: 3-Chloro-N-({4-chloro-3-[(3-chloro-5-cyanophenyl)oxy]-2-fluorophenyl}methyl)-4-formyl-1H-pyrrole-2-carboxamide HATU (0.061 g, 0.161 mmol) was added to a solution of 3-chloro-4-formyl-1H-pyrrole-2-carboxylic acid (0.028 g, 0.161 mmol), 3-{[3-(aminomethyl)-6-chloro-2-fluorophenyl]oxy}-5-chlorobenzonitrile (0.050 g, 0.161 mmol) and DIPEA (0.028 mL, 0.161 mmol) in DMF (2 mL). The solution was stirred overnight at RT. The reaction mixture was partitioned between water and EtOAc, followed by washing the organic layer with a 15% Na₂CO₃ solution and drying over MgSO₄. The solid was filtered off, and the solvent was evaporated. Purification was accomplished by silica gel column chromatography (EtOAc/hexanes) to give an orange film which was triturated in acetone to afford the title compound (0.014 g, 18%) as a white solid. $^1$H NMR (400 MHz, DMSO-d₆) δ ppm 12.66 (br. s., 1H), 9.75 (s, 1H), 8.27 (t, 1H), 7.77-7.82 (m, 1H), 7.73 (s, 1H), 7.46-7.51 (m, 2H), 7.44 (t, 1H), 7.36 (t, 1H), 4.54 (d, 2H). LCMS: m/z=464.3 (M−1).

Example 172

3-Chloro-N-({4-chloro-3-[(3-chloro-5-cyanophenyl)oxy]-2-fluorophenyl}methyl)-5-formyl-1H-pyrrole-2-carboxamide

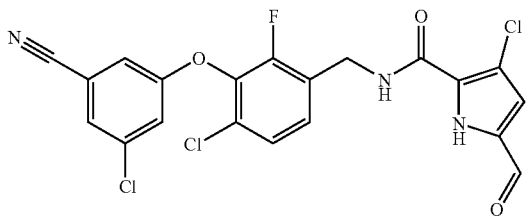

Step A: Methyl 3-chloro-5-formyl-1H-pyrrole-2-carboxylate

DMF (0.579 mL, 1.48 mmol) was cooled to 0° C. under nitrogen. POCl$_3$ (0.647 mL, 6.93 mmol) was added to the cold DMF and stirred at 0° C., and a solid formed. Dichloroethane (2 mL) was added to the solid followed by the addition of methyl 3-chloro-1H-pyrrole-2-carboxylate (1.00 g, 6.26 mmol) in dichloroethane (2 mL). The reaction mixture was stirred for 10 minutes at 0° C. and heated to reflux until the starting material was no longer evident by TLC. The reaction mixture was cooled and partitioned between EtOAc and water. The organic layer was separated, washed with saturated NaHCO$_3$, dried over MgSO$_4$, filtered and the EtOAc evaporated. Purification was accomplished by silica gel column chromatography (0-30% EtOAc/hexanes) to afford the title compound (0.320 g, 27%), and methyl 3-chloro-4-formyl-1H-pyrrole-2-carboxylate (0.319 g, 27%). $^1$H NMR (400 MHz, Acetone-d$_6$) δ ppm 11.95 (br. s., 1H), 9.72 (s, 1H), 7.02 (s, 1H), 3.87 (s, 3H). LCMS: m/z 188.1 (M+1).

Step B: 3-Chloro-5-formyl-1H-pyrrole-2-carboxylic acid

LiOH (2 mL, 2 mmol) was added to a solution of methyl 3-chloro-5-formyl-1H-pyrrole-2-carboxylate (0.050 g, 0.26 mmol) in THF (2 mL) and methanol (2 mL). The solution was stirred at room temperature overnight. The solvents were evaporated and the residue was partitioned between EtOAc and 1 N HCl. The organic layer was separated, dried over MgSO$_4$, filtered and evaporated to a solid to afford the title compound (0.0517 g) as a crude product which was used with no further purification. $^1$H NMR (400 MHz, Acetone-d$_6$) δ ppm 11.87 (br. s., 1H), 9.72 (s, 1H), 7.02 (s, 1H). LCMS: m/z 174.2 (M+1).

Step C: 3-Chloro-N-({4-chloro-3-[(3-chloro-5-cyanophenyl)oxy]-2-fluorophenyl}methyl)-5-formyl-1H-pyrrole-2-carboxamide HATU (0.061 g, 0.161 mmol) was added to a solution of 3-chloro-5-formyl-1H-pyrrole-2-carboxylic acid (0.028 g, 0.161 mmol), 3-{[3-(aminomethyl)-6-chloro-2-fluorophenyl]oxy}-5-chlorobenzonitrile (0.050 g, 0.161 mmol) and DIPEA (0.028 mL, 0.161 mmol) in DMF (2 mL). The solution was stirred overnight at RT. The reaction mixture was partitioned between water and EtOAc. The organic layer was washed with a 15% Na$_2$CO$_3$ solution and dried over MgSO$_4$. The solid was filtered off and the solvent was evaporated. Purification was accomplished by silica gel column chromatography (EtOAc/hexanes) to give an orange film which was triturated in acetone to afford the title compound (0.012 g, 15%) as a white solid. $^1$H NMR (400 MHz, DMSO-d6) δ ppm 12.88 (s, 1H), 9.57 (s, 1H), 8.53-8.71 (m, 1H), 7.74-7.86 (m, 1H), 7.47-7.52 (m, 2H), 7.38-7.46 (m, 2H), 7.04 (s, 1H), 4.52 (d, 1H). LCMS: m/z 466.2 (M+1).

Example 173

3-Chloro-N$^2$-({4-chloro-3-[(3-chloro-5-cyanophenyl)oxy]-2-fluorophenyl}methyl)-N$^5$-(2-hydroxyethyl)-1H-pyrrole-2,5-dicarboxamide0

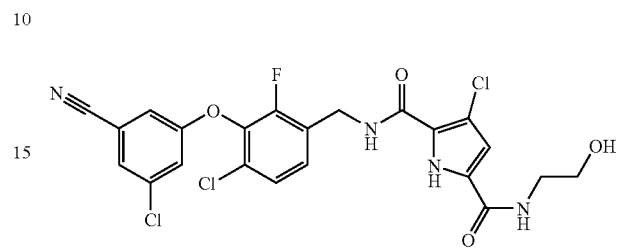

Step A: 4-Chloro-5-[(methyloxy)carbonyl]-1H-pyrrole-2-carboxylic acid

KMnO$_4$ (2.53 g, 16.0 mmol) was dissolved in acetone and water and added dropwise over a 2 hr period to a solution of methyl 3-chloro-5-formyl-1H-pyrrole-2-carboxylate (1.50 g, 8.00 mmol) in acetone (250 mL). After stirring for 4 hr the solution was poured into a solution of NaHSO$_3$ in 1N HCl. This was extracted with EtOAc and the organic layer was washed with water. The organic layer was dried over MgSO$_4$ and evaporated to afford the title compound (1.33 g, 82%) as a white solid. $^1$H NMR (400 MHz, DMSO-d$_6$) δ ppm 13.15 (br. s., 1H), 12.75 (br. s., 1H), 6.78 (d, 1H), 3.77 (s, 3 H). LCMS: m/z 203.9 (M+1).

Step B: Methyl 3-chloro-5-(chlorocarbonyl)-1H-pyrrole-2-carboxylate

Oxalyl chloride (0.430 mL, 4.91 mmol) was added to a solution of 4-chloro-5-[(methyloxy)carbonyl]-1H-pyrrole-2-carboxylic acid (0.500 g, 2.45 mmol) in DCM (50 mL). DMF (9.51 µl, 0.123 mmol) was added to the reaction mixture and the resulting suspension was stirred overnight. The solvent was evaporated to afford the title compound as a crude product (0.804 g) which was used with no further purification. $^1$H NMR (400 MHz, CDCl$_3$) δ ppm 11.02 (s, 1H), 7.11 (d, 1H), 3.97 (s, 3H).

Step C: Methyl 3-chloro-5-{[(2-hydroxyethyl)amino]carbonyl}-1H-pyrrole-2-carboxylate Ethanolamine (0.175 mL, 2.90 mmol) was added to a solution of methyl 3-chloro-5-(chlorocarbonyl)-1H-pyrrole-2-carboxylate (0.150 g, 0.580 mmol) in THF and the resulting solution stirred until no starting material was evident by TLC. Purification was accomplished by silica gel column chromatography (30-100% EtOAc/hexanes) to afford the title compound (0.082 g, 57%) as a white solid. $^1$H NMR (400 MHz, DMSO-d$_6$) δ ppm 12.37 (br. s., 1H), 8.42 (t, 1H), 6.80 (s, 1H), 4.75 (t, 1H), 3.78 (s, 3H), 3.46 (q, 2H), 3.27 (q, 2H). LCMS: m/z 245.4 (M−1).

Step D: 3-Chloro-5-{[(2-hydroxyethyl)amino]carbonyl}-1H-pyrrole-2-carboxylic acid LiOH (2 mL, 2 mmol) was added to a solution of methyl 3-chloro-5-{[(2-hydroxyethyl)amino]carbonyl}-1H-pyrrole-2-carboxylate (0.082 g, 0.33 mmol) in THF (2 mL) and methanol (2 mL). The solution was stirred at RT overnight. The solvent was evaporated and the residue partitioned between EtOAc and 1 N HCl. The organic layer was separated, dried over MgSO$_4$, filtered and evaporated to afford very little solid. The aqueous layer was evaporated to a residue and the salts extracted with methanol. The methanol was evaporated to afford the title compound (0.042 g, 54%). $^1$H NMR (400 MHz, DMSO-d$_6$) δ ppm 12.16 (br. s., 1H), 8.40 (t, 1H), 6.61-7.10 (m, 1H), 3.45 (t, 2H), 3.26 (q, 2H).

Step E: 3-Chloro-N$^2$-({4-chloro-3-[(3-chloro-5-cyanophenyl)oxy]-2-fluorophenyl}methyl)-N$^5$-(2-hydroxyethyl)-1H-pyrrole-2,5-dicarboxamide HATU (0.061 g, 0.161 mmol) was added to a DMF (2 mL) solution of 3-chloro-5-{[(2-hydroxyethyl)amino]carbonyl}-1H-pyrrole-2-carboxylic acid (0.037 g, 0.161 mmol), 3-{[3-(aminomethyl)-6-chloro-2-fluorophenyl]oxy}-5-chlorobenzonitrile (0.050 g, 0.161 mmol), and DIPEA (0.028 mL, 0.161 mmol). This solution was stirred overnight at RT. The reaction mixture was partitioned between water and EtOAc. The organic layer was washed with a 15% solution of Na$_2$CO$_3$, dried over MgSO$_4$, filtered and evaporated. The residue was subjected to silica gel column chromatography (EtOAc/hexanes) to afford an impure solid. A second purification was accomplished by reverse-phase HPLC (water/acetonitrile with 0.1% TFA) to afford the title compound (0.014 g, 15%) as a white solid. $^1$H NMR (400 MHz, Acetone-d$_6$) δ ppm 11.00 (br. s., 1H), 7.86 (d, 1H), 7.63 (s, 1H), 7.33-7.52 (m, 3H), 6.86 (d, 1H), 4.71 (d, 1H), 3.65 (t, 1H), 3.39-3.57 (m, 5H). LCMS: m/z 525.3 (M+1).

Example 174

3-Chloro-N$^2$-({4-chloro-3-[(3-chloro-5-cyanophenyl)oxy]-2-fluorophenyl}methyl)-1H-pyrrole-2,5-dicarboxamide

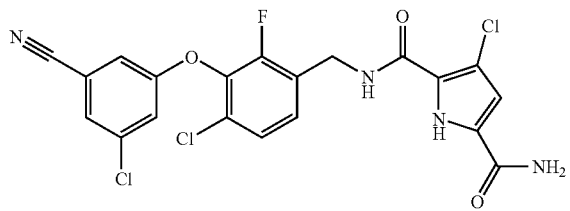

Step A: Methyl 5-(aminocarbonyl)-3-chloro-1H-pyrrole-2-carboxylate

Ammonia (5.8 mL, 2.9 mmol) was added to a solution of methyl 3-chloro-5-(chlorocarbonyl)-1H-pyrrole-2-carboxylate (0.15 g, 0.58 mmol) in THF and the resulting solution stirred until no starting material was evident by TLC. The solvent was evaporated and purification was accomplished by silica gel column chromatography (30 to 100% EtOAc/hexanes) to afford the title compound (0.060 g, 51%) as a white solid. $^1$H NMR (400 MHz, DMSO-d$_6$) δ ppm 12.29 (br. s., 1H), 7.82 (br. s., 1H), 7.47 (br. s., 1H), 6.80 (s, 1H), 3.77 (s, 3H). LCMS: m/z 201.4 (M−1).

Step B: 5-(Aminocarbonyl)-3-chloro-1H-pyrrole-2-carboxylic acid

LiOH (1 N in water, 2 mL, 2 mmol) was added to a solution of methyl 5-(aminocarbonyl)-3-chloro-1H-pyrrole-2-carboxylate (0.0602 g, 0.297 mmol) in THF (2 mL) and methanol (2 mL) and the solution was stirred at RT overnight. The reaction mixture was evaporated to a residue and partitioned with EtOAc and 1 N HCl. The organic layer was separated, dried over MgSO$_4$ and evaporated to a solid to afford the title compound (0.057 g, 77%) as a tan solid which was used with no further purification. $^1$H NMR (400 MHz, DMSO-d$_6$) δ ppm 12.07 (br. s., 1H), 7.80 (br. s., 1H), 7.43 (br. s., 1H), 6.57-6.89 (m, 1H).

Step C: 3-Chloro-N$^2$-({4-chloro-3-[(3-chloro-5-cyanophenyl)oxy]-2-fluorophenyl}methyl)-1H-pyrrole-2,5-dicarboxamide HATU (0.061 g, 0.161 mmol) was added to a solution of 5-(aminocarbonyl)-3-chloro-1H-pyrrole-2-carboxylic acid (0.030 g, 0.161 mmol), 3-{[3-(aminomethyl)-6-chloro-2-fluorophenyl]oxy}-5-chlorobenzonitrile (0.050 g, 0.161 mmol), and DIPEA (0.028 mL, 0.161 mmol) in DMF (2 mL). This solution was stirred overnight at RT. The reaction mixture was partitioned between water and EtOAc. The organic layer was washed with a 15% solution of Na$_2$CO$_3$, dried over MgSO$_4$, filtered and evaporated. Purification was accomplished by silica gel column chromatography (EtOAc/hexanes) to afford the title compound (0.023 g, 28%) as a white solid. $^1$H NMR (400 MHz, DMSO-d$_6$) δ ppm 12.08 (br. s., 1H), 8.48-8.74 (m, 1H), 7.72-7.98 (m, 2H), 7.27-7.62 (m, 5H), 6.83 (d, 1H), 4.48 (d, 2H). LCMS: m/z 481.0 (M+1).

Example 175

3-Chloro-N$^2$-({4-chloro-3-[(3-chloro-5-cyanophenyl)oxy]-2-fluorophenyl}methyl)-N$^5$-cyclopropyl-1H-pyrrole-2,5-dicarboxamide

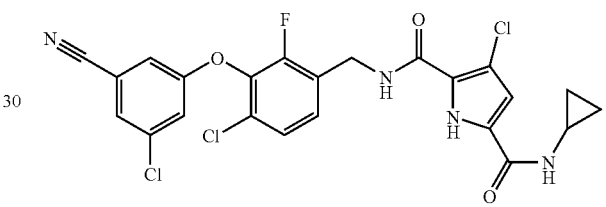

Step A: Methyl 3-chloro-5-[(cyclopropylamino)carbonyl]-1H-pyrrole-2-carboxylate

Cycloproplyamine (0.166 g, 2.90 mmol) was added to a solution of methyl 3-chloro-5-(chlorocarbonyl)-1H-pyrrole-2-carboxylate (0.150 g, 0.580 mmol) in THF and the resulting solution stirred until no starting material was evident by TLC. The solvent was evaporated and purification was accomplished by silica gel column chromatography (30-100% EtOAc/hexanes) to afford the title compound (0.099 g, 70%) as a white solid. $^1$H NMR (400 MHz, Acetone-d$_6$) δ ppm 10.81 (br. s., 1H), 7.71 (br. s., 1H), 6.78 (s, 1H), 3.84 (s, 3H), 2.79-2.92 (m, 1H), 0.73 (d, 2H), 0.57 (d, 2 H) LCMS: m/z 243.1 (M+1).

Step B: 3-Chloro-5-[(cyclopropylamino)carbonyl]-1H-pyrrole-2-carboxylic acid

LiOH (1 N in water, 2 mL, 2 mmol) was added to a solution of methyl 3-chloro-5-[(cyclopropylamino)carbonyl]-1H-pyrrole-2-carboxylate (0.0992 g, 0.409 mmol) in THF (2 mL) and methanol (2 mL) and the solution was stirred at RT overnight. The reaction mixture was evaporated to a residue and partitioned between EtOAc and 1 N HCl. The organic layer was separated, dried over MgSO$_4$ and evaporated to a solid to afford the title compound (0.072 g, 77%) as a white solid. $^1$H NMR (400 MHz, DMSO-d$_6$) δ ppm 13.08 (s, 1H), 12.05 (br. s., 1H), 8.32 (d, 1H), 6.73 (d, 1H), 2.71-2.81 (m, 1H), 0.62-0.72 (m, 2H), 0.42-0.53 (m, 2H). LCMS: m/z 229.2 (M+1).

Step C: 3-Chloro-N$^2$-({4-chloro-3-[(3-chloro-5-cyanophenyl)oxy]-2-fluorophenyl}methyl)-N$^5$-cyclopropyl-1H-pyrrole-2,5-dicarboxamide HATU (0.061 g, 0.161 mmol) was added to a solution of 3-chloro-5-[(cyclopropylamino)carbonyl]-1H-pyrrole-2- carboxylic acid (0.037 g, 0.161 mmol) and 3-{[3-(aminomethyl)-6-chloro-2-fluorophenyl]oxy}-5-chlorobenzonitrile (0.050 g, 0.161 mmol) and DIPEA (0.028 mL, 0.161 mmol) in DMF (2 mL). This solution was stirred overnight at RT. The reaction mixture was partitioned between water and EtOAc. The organic layer was washed with a 15% solution of $Na_2CO_3$, dried over $MgSO_4$, filtered and evaporated. The residue was subjected to silica gel column chromatography (EtOAc/hexanes) to afford an impure solid. A second purification by reverse-phase HPLC (water/acetonitrile with 0.1% TFA) afforded the title compound (0.0098 g, 11%) as a white solid. $^1$H NMR (400 MHz, DMSO-$d_6$) δ ppm 8.10-8.26 (m, 1H), 7.82 (br. s., 1H), 7.39-7.62 (m, 5H), 7.33 (d, 1H), 6.35 (br. s., 1H), 4.42 (br. s., 2H), 2.62-2.79 (m, 1H), 0.61 (d, 2H), 0.45 (br. s., 2H). LCMS: m/z 521.2 (M+1).

Example 176

3-Chloro-N-({4-chloro-3-[(3-chloro-5-cyanophenyl)oxy]-2-fluorophenyl}methyl)-5-(2-hydroxyethyl)-1H-pyrrole-2-carboxamide

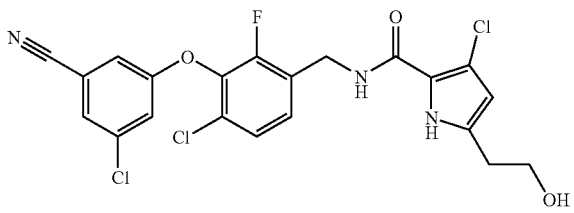

Step A: Methyl 3-chloro-5-ethenyl-1H-pyrrole-2-carboxylate

A suspension of methyl(triphenyl)phosphonium bromide (3.97 g, 11.1 mmol) in 20 mL of THF was cooled to −78° C. n-Butyllithium (1.6 M in Hexanes, 6.93 mL, 11.1 mmol) was added and the resulting yellow solution stirred for 20 minutes. A THF solution of methyl 3-chloro-5-formyl-1H-pyrrole-2-carboxylate (0.522 g, 2.78 mmol) was added and the reaction was warmed to RT. The reaction mixture was partitioned between EtOAc and water and the layers were separated. The organic layer was dried over $MgSO_4$, filtered and the solvent evaporated. Purification was accomplished by silica gel column chromatography (EtOAc/hexanes) to afford the title compound (0.210 g, 40%) as a white solid. $^1$H NMR (400 MHz, Acetone-$d_6$) δ ppm 11.05 (br. s., 1H), 6.62 (dd, 1H), 6.42 (d, 1H), 5.83 (d, 1H), 5.25 (d, 1H), 3.79 (s, 3H). LCMS: m/z=184.6 (M−1).

Step B: 3-Chloro-5-(2-hydroxyethyl)-1H-pyrrole-2-carboxylic acid

A stirred solution of methyl 3-chloro-5-ethenyl-1H-pyrrole-2-carboxylate (0.100 g, 0.539 mmol) in THF (5 mL) was treated with 9-BBN (5.39 mL, 2.15 mmol). The reaction was stirred at RT overnight. The reaction mixture was treated with 1 mL of 1N NaOH and 1 mL of 30% $H_2O_2$ and stirred. The reaction mixture was partitioned between EtOAc and a solution of sodium metabisulfite. The organic layer was separated, dried over $MgSO_4$ and evaporated to a residue. The residue was taken up in 1N LiOH (1 mL), MeOH (1 mL) and THF (1 mL) and heated until the acid was formed as seen on TLC. The reaction was evaporated, acidified and extracted with EtOAc. The organic layer was separated and dried over $MgSO_4$ to afford methyl 3-chloro-5-(2-hydroxyethyl)-1H-pyrrole-2-carboxylate (0.028 g, 27%) as a solid. LCMS: m/z=188.0 (M−1).

Step C: 3-Chloro-N-({4-chloro-3-[(3-chloro-5-cyanophenyl)oxy]-2-fluorophenyl}methyl)-5-(2-hydroxyethyl)-1H-pyrrole-2-carboxamide HATU (0.057 g, 0.15 mmol) was added to a solution of 3-{[3-(aminomethyl)-6-chloro-2-fluorophenyl]oxy}-5-chlorobenzonitrile (0.047 g, 0.15 mmol), 3-chloro-5-(2-hydroxyethyl)-1H-pyrrole-2-carboxylic acid (0.028 g, 0.15 mmol) and DIPEA (0.026 mL, 0.150 mmol) in DMF (2 mL). The resulting solution was stirred for 2 hours then partitioned between water and EtOAc. The organic layer was separated, dried over $MgSO_4$ and evaporated to a residue. The residue was purified by reverse-phase HPLC (water/acetonitrile with 0.1% TFA) to afford the title compound (0.0016 g, 2%) as a film. $^1$H NMR (400 MHz, Acetone-$d_6$) δ ppm 7.60-7.68 (m, 1H), 7.48-7.53 (m, 1H), 7.41-7.45 (m, 2H), 7.37-7.40 (m, 2H), 6.03 (d, 1H), 4.69 (d, 2H), 3.78 (t, 2 H), 2.82 (t, 2H). LCMS: m/z=479.9 (M−1).

Example 177

3-Chloro-$N^2$-({4-chloro-3-[(3-chloro-5-cyanophenyl)oxy]-2-fluorophenyl}methyl)-$N^5$-[2-(1-pyrrolidinyl)ethyl]-1H-pyrrole-2,5-dicarboxamide

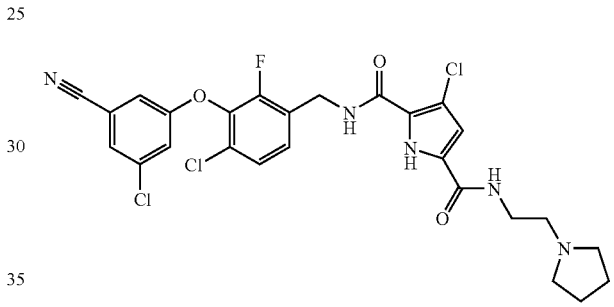

Step A: Methyl 3-chloro-5-({[2-(1-pyrrolidinyl)ethyl]amino}carbonyl)-1H-pyrrole-2-carboxylate A solution of methyl 3-chloro-5-(chlorocarbonyl)-1H-pyrrole-2-carboxylate (0.100 g, 0.387 mmol) in 4 mL of DCM was treated with [2-(1-pyrrolidinyl)ethyl]amine (0.110 g, 0.967 mmol). After 1 hour saturated $NaHCO_3$ was added and the mixture shaken. The DCM layer was separated, dried over $MgSO_4$ and evaporated onto silica gel. Purification was accomplished on silica with 0 to 10% MeOH in EtOAc to afford the title compound (0.080 g, 69%) as a white solid. $^1$H NMR (400 MHz, DMSO-$d_6$) δ ppm 8.38 (t, 1H), 6.80 (d, 1H), 3.78 (s, 3H), 3.32 (q, 2H), 2.52 (t, 2H), 2.45 (br. s., 4H), 1.65 (br. s., 4H). LCMS: m/z 298.2 (M−1).

Step B: 3-Chloro-$N^2$-({4-chloro-3-[(3-chloro-5-cyanophenyl)oxy]-2-fluorophenyl}methyl)-$N^5$-[2-(1-pyrrolidinyl)ethyl]-1H-pyrrole-2,5-dicarboxamide Methyl 3-chloro-5-({[2-(1-pyrrolidinyl)ethyl]amino}carbonyl)-1H-pyrrole-2-carboxylate (0.080 g, 0.268 mmol) was dissolved in THF and MeOH (2 mL of each). Potassium hydroxide (2 mL, 1 N) was added to the solution and heated to 60° C. After stirring overnight no reaction was observed. LiOH (2 mL, 1 N) was added and the reaction stirred at 60° C. overnight. The reaction mixture was evaporated to a solid and partitioned between EtOAc and 1 N HCl. The organic layer was separated, dried over $MgSO_4$, filtered and evaporated to a solid. The solid was added to a solution of 3-{[3-(aminomethyl)-6-chloro-2-fluorophenyl]oxy}-5-chlorobenzonitrile (0.050 g, 0.161 mmol) and DIPEA (0.031 mL, 0.241 mmol) in DMF (2 mL). HATU (0.092 g, 0.241 mmol) was added to the mixture and the reaction stirred for 2 hours.

The reaction mixture was partitioned between EtOAc and water and the layers separated. The organic layer was washed with 15% $Na_2CO_3$, dried over $MgSO_4$ and evaporated. Purification was accomplished by reverse-phase HPLC (water/acetonitrile with 0.1% TFA) to afford the title compound (0.008 g, 9%) as a solid. $^1$H NMR (400 MHz, Acetone-$d_6$) δ ppm 7.81-7.95 (m, 2H), 7.64 (t, 1H), 7.45-7.52 (m, 1H), 7.41-7.45 (m, 1H), 7.39 (d, 2H), 6.77 (s, 1H), 4.72 (d, 2H), 3.51 (q, 2H), 2.72-2.78 (m, 2H), 2.59-2.69 (m, 4H), 1.71-1.80 (m, 4H). LCMS: m/z 577.9 (M+1).

Example 178

N-({4-Chloro-3-[(3-chloro-5-cyanophenyl)oxy]-2-fluorophenyl}methyl)-5-methyl-2H-1,2,3-triazole-4-carboxamide

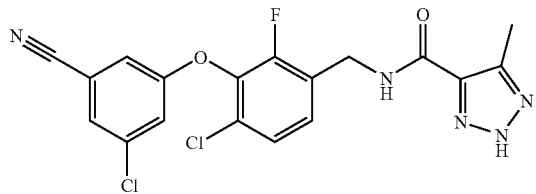

HATU (0.092 g, 0.241 mmol) was added to a solution of 3-{[3-(aminomethyl)-6-chloro-2-fluorophenyl]oxy}-5-chlorobenzonitrile (0.050 g, 0.161 mmol), 5-methyl-2H-1,2,3-triazole-4-carboxylic acid (0.022 g, 0.177 mmol) and DIPEA (0.042 mL, 0.241 mmol) in DMF (2 mL). The resulting solution was stirred overnight. The reaction mixture was partitioned between water and EtOAc. The organic layer was separated, dried over $MgSO_4$ and evaporated to a residue. Purification was accomplished by reverse-phase HPLC (water/acetonitrile with 0.1% TFA) to afford the title compound (0.0191 g, 28%) as a white solid. $^1$H NMR (400 MHz, DMSO-$d_6$) δ ppm 10.51 (s, 1H), 7.79 (d, 1H), 7.69 (t, 1H), 7.46-7.51 (m, 2H), 7.44 (d, 1H), 7.30 (t, 1H), 4.36 (d, 2H), 2.15 (s, 3H). LCMS: m/z 420.0 (M+1).

Example 179

5-Acetyl-3-chloro-N-({4-chloro-3-[(3-chloro-5-cyanophenyl)oxy]-2-fluorophenyl}methyl)-1H-pyrrole-2-carboxamide

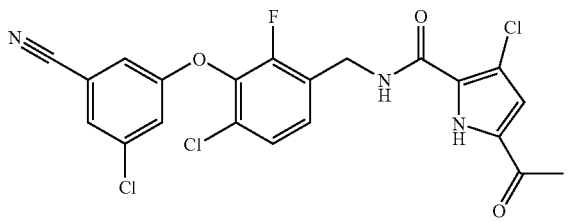

Step A: Methyl 5-acetyl-3-chloro-1H-pyrrole-2-carboxylate

A solution of methyl 3-chloro-1H-pyrrole-2-carboxylate (0.100 g, 0.627 mmol) in DCE (3 mL) was added to a suspension of $SnCl_2$ (0.238 g, 1.25 mmol) and methyl 3-chloro-1H-pyrrole-2-carboxylate (0.100 g, 0.627 mmol) in DCE (3 mL) at 0° C. The reaction was stirred for 10 min. at 0° C. then warmed to room temp over 2 hours. The reaction mixture was poured into water and EtOAc and the organic layer was separated, then washed with 1N sodium hydroxide, dried over $MgSO_4$, filtered and evaporated to a residue. Purification was accomplished on silica with EtOAc and hexanes to afford the title compound (0.034 g, 26%) as a solid, along with methyl 4-acetyl-3-chloro-1H-pyrrole-2-carboxylate (0.047 g, 37%) as a solid. $^1$H NMR (400 MHz, $CDCl_3$) δ ppm 9.90 (br. s., 1H), 6.79 (s, 1H), 3.89 (s, 3H), 2.43 (s, 3H). LCMS: m/z 200.0 (M−1).

Step B: 5-Acetyl-3-chloro-1H-pyrrole-2-carboxylic acid

Methyl 5-acetyl-3-chloro-1H-pyrrole-2-carboxylate (0.034 g, 0.169 mmol) was dissolved in THF (1 mL), methanol (1 mL) and 1N LiOH (1 mL). The reaction mixture was heated to 60° C. and stirred. The reaction mixture was evaporated and purification was accomplished by reverse-phase HPLC (water/acetonitrile with 0.1% TFA) to afford the title compound (0.030 g, 76%) as an impure product which was used with no further purification. LCMS: m/z 186.0 (M−1).

Step C: 5-Acetyl-3-chloro-N-({4-chloro-3-[(3-chloro-5-cyanophenyl)oxy]-2-fluorophenyl}methyl)-1H-pyrrole-2-carboxamide HATU (0.092 g, 0.241 mmol) was added to a solution of 3-{[3-(aminomethyl)-6-chloro-2-fluorophenyl]oxy}-5-chlorobenzonitrile (0.050 g, 0.161 mmol), 5-acetyl-3-chloro-1H-pyrrole-2-carboxylic acid (0.030 g, 0.161 mmol) and DIPEA (0.042 mL, 0.241 mmol) in DMF (2 mL). The resulting solution was stirred overnight. The reaction mixture was partitioned between water and EtOAc. The organic layer was separated, dried over $MgSO_4$ and evaporated to a residue. Purification was accomplished by reverse-phase HPLC (water/acetonitrile with 0.1% TFA) to afford the title compound (0.0127 g, 16%) as a white solid. $^1$H NMR (400 MHz, DMSO-$d_6$): δ ppm 3.29 (s, 3H) 4.48 (d, J=5.36 Hz, 2H) 7.10 (s, 1H) 7.36-7.56 (m, 4H) 7.80 (s, 1H) 8.71 (t, J=5.22 Hz, 1H) 12.31 (br. s., 1H). LCMS: m/z 477.9 (M−1).

Example 180

4-Acetyl-3-chloro-N-({4-chloro-3-[(3-chloro-5-cyanophenyl)oxy]-2-fluorophenyl}methyl)-1H-pyrrole-2-carboxamide

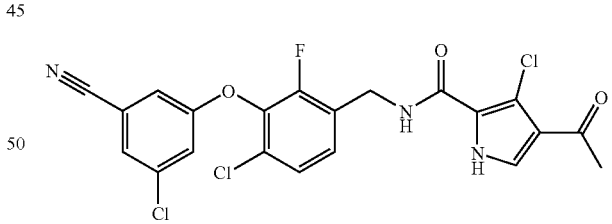

Step A: Methyl 4-acetyl-3-chloro-1H-pyrrole-2-carboxylate

A solution of methyl 3-chloro-1H-pyrrole-2-carboxylate (0.100 g, 0.627 mmol) in DCE (3 mL) was added to a suspension of $SnCl_2$ (0.238 g, 1.25 mmol) and methyl 3-chloro-1H-pyrrole-2-carboxylate (0.100 g, 0.627 mmol) in DCE (3 mL) at 0° C. The reaction was stirred for 10 min. at 0° C. then warmed to room temp over 2 hours. The reaction mixture was poured into water and EtOAc. The organic layer was separated, washed with 1N sodium hydroxide, dried over $MgSO_4$, filtered and evaporated to a residue. Purification was accomplished on silica with EtOAc and hexanes to afford the title compound (0.034 g, 26%) as a solid, along with methyl 4-acetyl-3-chloro-1H-pyrrole-2-carboxylate (0.047 g, 37%)

as a solid. $^1$H NMR (400 MHz, CDCl$_3$) δ ppm 10.19 (br. s., 1H), 7.34-7.84 (m, 1H), 3.90 (s, 3H), 2.52 (s, 3 H). LCMS: m/z 200.0 (M−1).

Step B: 4-Acetyl-3-chloro-1H-pyrrole-2-carboxylic acid

Methyl 5-acetyl-3-chloro-1H-pyrrole-2-carboxylate (0.034 g, 0.169 mmol) was dissolved in THF (1 mL), methanol (1 mL) and 1N LiOH (1 mL). The reaction mixture was heated to 60° C. and stirred. The reaction mixture was evaporated and purification was accomplished by reverse-phase HPLC (water/acetonitrile with 0.1% TFA) to afford the title compound (0.033 g, 67%) as an impure product which was used with no further purification. LCMS: m/z 187.9 (M+1).

Step C: 4-Acetyl-3-chloro-N-({4-chloro-3-[(3-chloro-5-cyanophenyl)oxy]-2-fluorophenyl}methyl)-1H-pyrrole-2-carboxamide HATU (0.092 g, 0.241 mmol) was added to a solution of 3-{[3-(aminomethyl)-6-chloro-2-fluorophenyl]oxy}-5-chlorobenzonitrile (0.050 g, 0.161 mmol), 4-acetyl-3-chloro-1H-pyrrole-2-carboxylic acid (0.030 g, 0.161 mmol) and DIPEA (0.042 mL, 0.241 mmol) in DMF (2 mL). The resulting solution was stirred overnight. The reaction mixture was partitioned between water and EtOAc. The organic layer was separated, dried over MgSO$_4$ and evaporated to a residue. Purification was accomplished by reverse-phase HPLC (water/acetonitrile with 0.1% TFA) to afford the title compound (0.0065 g, 7%) as a white solid. $^1$H NMR (400 MHz, Acetone-d$_6$) δ ppm ppm 11.46 (br. s., 1H), 7.88 (br. s., 1H), 7.79 (s, 1H), 7.63 (s, 1H), 7.36-7.50 (m, 4H), 4.73 (d, 2H), 2.41 (s, 3H). LCMS: m/z 480.0 (M+1).

Example 181

N-({4-Chloro-3-[(3-chloro-5-cyanophenyl)oxy]-2-fluorophenyl}methyl)-1,4-dihydropyrrolo[2,3-d]imidazole-5-carboxamide trifluoroacetate

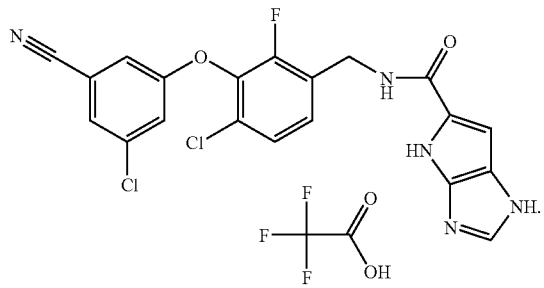

Step A: Ethyl 1-({[2-(trimethylsilyl)ethyl]oxy}methyl)-1,4-dihydropyrrolo[2,3-d]imidazole-5-carboxylate 1H-imidazole-4-carbaldehyde (1.05 g, 10.9 mmol) was added portion wise to a stirred suspension of NaH (0.437 g, 10.9 mmol) in 15 mL of DMF. After 1 hour a solution of SEM-Cl (1.93 mL, 10.9 mmol) in 3 mL of DMF was added dropwise over 10 minutes. The resulting solution was stirred for 3 hours at RT. The reaction mixture was partitioned between water and EtOAc. The organic layer was separated, dried over MgSO$_4$ and evaporated to yellow oil. Purification was accomplished by silica gel column chromatography (40-100% EtOAc/hexanes) to afford the SEM protected imidazole carbaldehyde (1.8 g, 7.9 mmol) as a mixture of regioisomers. The mixture was dissolved in 5 mL of ethanol and azidoacetate (7.8 g, 15.1 mmol) was added. This solution was added to a solution of sodium ethoxide (8.91 mL, 23.86 mmol) at −20° C. After the addition was complete, the solution was stirred at −10° C. for 3 hours. The reaction mixture was poured into a saturated solution of ammonium chloride and extracted with ether 2×100 mL. The extracts were combined, dried over MgSO$_4$, filtered and evaporated to an oil. Purification was accomplished by silica gel column chromatography (EtOAc/hexanes) to afford (1.111 g, 41% yield) of a yellow oil. The oil was dissolved in xylenes and heated to reflux for 3 hours. The solvent was evaporated under vacuum. Purification was accomplished by silica gel column chromatography (EtOAc/hexanes). The fractions collected contained multiple products and were combined. A second purification was accomplished by reverse-phase HPLC (water/acetonitrile with 0.1% TFA) to afford the title compound (0.088 g, 3%) as a solid. $^1$H NMR (400 MHz, CDCl$_3$) δ ppm 10.80 (d, 1H), 8.77 (s, 1H), 6.97 (s, 1H), 5.71 (s, 2H), 4.38 (q, 2H), 3.41-3.84 (m, 2H), 1.39 (t, 3H), 0.83-1.11 (m, 2H), −0.03 (s, 9H).

Step B: 1-({[2-(Trimethylsilyl)ethyl]oxy}methyl)-1,4-dihydropyrrolo[2,3-d]imidazole-5-carboxylic acid Ethyl 1-({[2-(trimethylsilyl)ethyl]oxy}methyl)-1,4-dihydropyrrolo[2,3-d]imidazole-5-carboxylate (0.088 g, 0.284 mmol) was dissolved in THF and MeOH. LiOH (1 mL, 1 mmol) was added to the solution and the reaction was heated to 60° C. When starting material was no longer evident by TLC the reaction was evaporated to afford the title compound (0.123 g, 77%) a white solid. This was used with no further purification. LCMS: m/z=280.0 (M−1).

Step B: N-({4-Chloro-3-[(3-chloro-5-cyanophenyl)oxy]-2-fluorophenyl}methyl)-1,4-dihydropyrrolo[2,3-d]imidazole-5-carboxamide trifluoroacetate HATU (0.092 g, 0.241 mmol) was added to a solution of DIPEA (0.042 ml, 0.241 mmol), 3-{[3-(aminomethyl)-6-chloro-2-fluorophenyl]oxy}-5-chlorobenzonitrile (0.050 g, 0.161 mmol) and 1-({[2-(trimethylsilyl)ethyl]oxy}methyl)-1,4-dihydropyrrolo[2,3-d]imidazole-5-carboxylic acid (0.045 g, 0.161 mmol) dissolved in DMF (2 ml). The resulting solution was stirred overnight. The reaction mixture was partitioned between water and EtOAc. The organic layer was separated, dried over MgSO$_4$ and evaporated to a residue. Purification was accomplished by reverse-phase HPLC (water/acetonitrile with 0.1% TFA) to afford a residue which was dissolved in DCM and TFA. This was stirred until LCMS showed complete removal of the SEM group. The solvent and acid were evaporated and the resulting solid washed with DCM and acetone to afford the title compound (0.0052 g, 6%) as a tan solid. $^1$H NMR (400 MHz, CD$_3$OD) δ ppm 8.65 (s, 1H), 7.55 (t, 1H), 7.36-7.43 (m, 2H), 7.27 (t, 1H), 7.20 (dd, 1H), 6.95 (s, 1H), 4.63 (s, 2H). $^{19}$F NMR (376 MHz, CD$_3$OD) δ ppm −77.52 (s, 3F), −133.01 (s, 1F). LCMS: m/z=442.0 (M−1).

Example 182

N-({4-chloro-3-[(3-chloro-5-cyanophenyl)oxy]phenyl}methyl)-4-(methyloxy)benzenesulfonamide

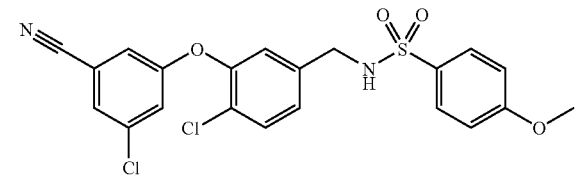

A solution of 3-{[5-(aminomethyl)-2-chlorophenyl]oxy}-5-chlorobenzonitrile (0.025 g, 0.085 mmol), 4-(methyloxy)benzenesulfonyl chloride, (0.025 g, 0.13 mmol) and DIPEA (0.05 mL, 0.25 mmol) in CH$_2$Cl$_2$ (2 mL) was stirred overnight. The solvent was concentrated and purification was accomplished by RP-HPLC (water/acetonitrile/0.1% TFA). The desired fractions were lyophilized and EtOAc (25 mL) and sat. NaHCO$_3$ (10 mL) were added. The layers were separated and the aqueous layer extracted with EtOAc (2×10 mL). The organic extracts were combined, dried over Na$_2$SO$_4$, filtered and concentrated to afford N-({4-chloro-3-[(3-chloro-5-cyanophenyl)oxy]phenyl}methyl)-4-(methyloxy) benzenesulfonamide (0.030 g, 75%) as a solid. $^1$H NMR (400 MHz, DMSO-d$_6$): δ ppm 8.03 (t, 1H), 7.80 (d, 1H), 7.66 (d, 2H), 7.51 (d, 1H), 7.38 (dd, 1H), 7.32 (t, 1H), 7.15 (dd, 1H), 6.99-7.10 (m, 3H), 3.96 (d, 2H), 3.78 (s, 3H). MS: m/z 485 (M+23).

Example 183

N-({1-chloro-3-[(3-chloro-5-cyanophenyl)oxy]-2-fluorophenyl}methyl)-4-(methyloxy)benzenesulfonamide

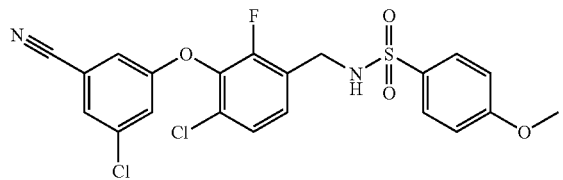

A solution of 3-{[3-aminomethyl)-6-chloro-2-fluorophenyl]oxy}-5-chlorobenzonitrile (0.030 g, 0.096 mmol), 4-(methyloxy)benzenesulfonyl chloride (0.034 g, 0.145 mmol) and DIPEA (0.025 mL, 0.145 mmol) in CH$_2$Cl$_2$ (2 mL) was stirred overnight. The solvent was concentrated and purification was accomplished by RP-HPLC (water/acetonitrile/0.1% TFA). The desired fractions were lyophilized and EtOAc (25 mL) and sat. NaHCO$_3$ (10 mL) were added. The layers were separated and the aqueous layer extracted with EtOAc (2×10 mL). The organic extracts were combined, dried over Na$_2$SO$_4$, filtered and concentrated to afford N-({4-chloro-3-[(3-chloro-5-cyanophenyl)oxy]-2-fluorophenyl}methyl)-4-(methyloxy)benzenesulfonamide (0.020 g, 43%) as a white solid. $^1$H NMR (400 MHz, DMSO-d$_6$): δ ppm 8.12 (s, 1H), 7.79 (s, 1H), 7.68 (m, 2H), 7.23-7.48 (m, 4H), 7.05 (m, 2H), 4.00 (d, 2H), 3.80 (s, 3H). MS: m/z 481.1 (M+1).

Example 184

N-({4-chloro-3-[(3-chloro-5-cyanophenyl)oxy]-2-fluorophenyl}methyl)-4-methyl-1H-pyrrole-2-carboxamide

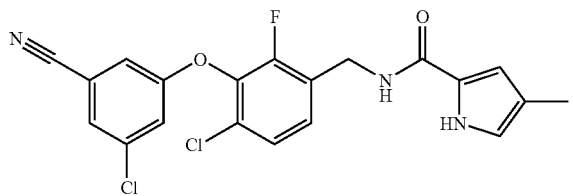

To a solution of ethyl 4-methyl-1H-pyrrole-2-carboxylate (0.022 g, 0.144 mmol) in THF/MeOH/H$_2$O (1:1:1, 1.5 mL) was added lithium hydroxide (0.034 g, 1.44 mmol) and the solution stirred at RT for 2 h. A 10% solution of citric acid (1 mL) and EtOAc (5 mL) were added. The aqueous layer was separated and extracted with EtOAc (2×5 mL). The organic layers were combined, dried over sodium sulfate, filtered, concentrated and placed under high vacuum to afford the crude carboxylic acid. To the crude intermediate was added HATU (0.034 g, 0.145 mmol), DIPEA (0.025 mL, 0.145 mmol), 3-{[3-aminomethyl)-6-chloro-2-fluorophenyl]oxy}-5-chlorobenzonitrile (0.030 g, 0.096 mmol), and DMF (1 mL). The reaction mixture was stirred overnight. Purification was accomplished by RPHPLC (water:acetonitrile with 0.1% TFA). The desired fractions were neutralized and extracted with EtOAC. The combined organics were dried over Na$_2$SO$_4$, filtered and concentrated to afford N-({4-chloro-3-[(3-chloro-5-cyanophenyl)oxy]-2-fluorophenyl}methyl)-4-methyl-1H-pyrrole-2-carboxamide (0.012 g, 20%) as a white solid. $^1$H NMR (400 MHz, DMSO-d$_6$): δ ppm 11.12 (br. s., 1H) 8.42 (t, J=5.40 Hz, 1H) 7.79 (d, 1H) 7.49 (d, 1H) 7.43-7.47 (m, 2H) 7.31 (t, 1H) 6.61 (d, 2H) 4.44 (d, 2H) 1.99 (s, 3H). MS: m/z 418.2 (M+1).

Example 185

N-({4-chloro-3-[(3-chloro-5-cyanophenyl)oxy]-2-fluorophenyl}methyl)-1H-pyrrolo[2,3-c]pyridine-2-carboxamide trifluoroacetate

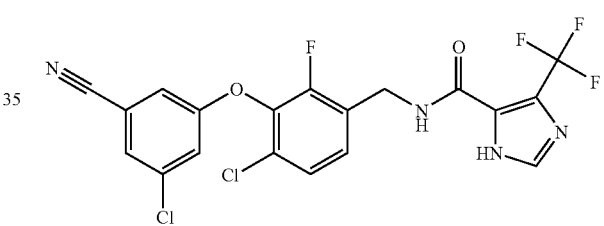

To a solution of ethyl 4-(trifluoromethyl)-1H-imidazole-5-carboxylate (0.030 g, 0.144 mmol) in THF/MeOH/H$_2$O (1:1:1, 1.5 mL) was added lithium hydroxide (0.034 g, 1.44 mmol) and the solution stirred at RT for 2 h. A 10% solution of citric acid (1 mL) and EtOAc (5 mL) were added. The aqueous layer was separated and extracted with EtOAc (2×5 mL). The organic layers were combined, dried over sodium sulfate, filtered, concentrated and placed under high vacuum to afford the crude carboxylic acid. To the crude intermediate was added HATU (0.050 g, 0.144 mmol), DIPEA (0.025 mL, 0.144 mmol), 3-{[3-aminomethyl)-6-chloro-2-fluorophenyl] oxy}-5-chlorobenzonitrile (0.030 g, 0.144 mmol), and DMF (1 mL). The reaction mixture was stirred overnight. Purification was accomplished by RPHPLC (water:acetonitrile with 0.1% TFA). The desired fractions were neutralized and extracted with EtOAC. The combined organics were dried over Na$_2$SO$_4$, filtered and concentrated to afford N-({4-chloro-3-[(3-chloro-5-cyanophenyl)oxy]-2-fluorophenyl}methyl)-4-(trifluoromethyl)-1H-imidazole-5-carboxamide (0.009 g, 13%) as a white solid. $^1$H NMR (400 MHz, DMSO-d$_6$): δ ppm 8.74-8.91 (m, 1H) 7.86-8.02 (m, 1H) 7.80 (d, 1H) 7.48 (s, 2H) 7.44 (s, 1H) 7.30-7.42 (m, 1H) 4.47 (d, 2H). MS: m/z 473.2 (M+1).

Example 186

N-({4-chloro-3-[(3-chloro-5-cyanophenyl)oxy]-2-fluorophenyl}methyl)-1H-pyrrolo[2,3-c]pyridine-2-carboxamide trifluoroacetate

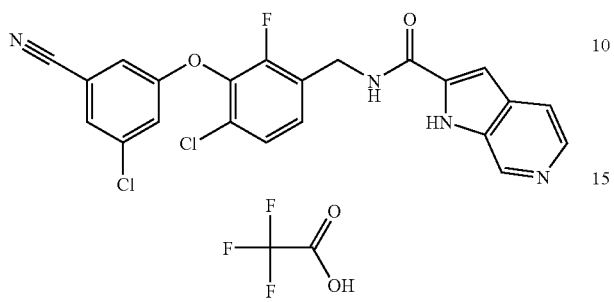

To a solution of ethyl 1H-pyrrolo[2,3-c]pyridine-2-carboxylate (0.025 g, 0.131 mmol) in THF/MeOH/H$_2$O (1:1:1, 1.5 mL) was added lithium hydroxide (0.031 g, 1.31 mmol) and the solution stirred at RT for 2 h. A 10% solution of citric acid (1 mL) and EtOAc (5 mL) were added. The aqueous layer was separated and extracted with EtOAc (2×5 mL). The organic layers were combined, dried over sodium sulfate, filtered, concentrated and placed under high vacuum to afford the crude carboxylic acid. To the crude intermediate was added HATU (0.050 g, 0.144 mmol), DIPEA (0.050 mL, 0.26 mmol), 3-{[3-aminomethyl)-6-chloro-2-fluorophenyl]oxy}-5-chlorobenzonitrile (0.040 g, 0.128 mmol), and DMF (1 mL). The reaction mixture was stirred overnight. Purification was accomplished by RPHPLC (water:acetonitrile with 0.1% TFA). The desired fractions were neutralized and extracted with EtOAC. The combined organics were dried over Na$_2$SO$_4$, filtered and concentrated to afford N-({4-chloro-3-[(3-chloro-5-cyanophenyl)oxy]-2-fluorophenyl}methyl)-1H-pyrrolo[2,3-c]pyridine-2-carboxamide trifluoroacetate (0.002 g, 2.6%) as a white solid. $^1$H NMR (400 MHz, DMSO-d$_6$): δ ppm 9.64 (s, 1H) 9.05 (s, 1H) 8.30 (d, 1H) 8.21 (d, 1H) 7.80 (s, 1H) 7.46-7.54 (m, 4H) 7.42 (t, 1H) 6.51 (br. s., 2H) 4.61 (br. s., 2H). MS: m/z 455.3 (M+1).

Example 187

3-bromo-N-({4-chloro-3-[(3-chloro-5-cyanophenyl)oxy]-2-fluorophenyl}methyl)-1H-pyrrolo[2,3-c]pyridine-2-carboxamide

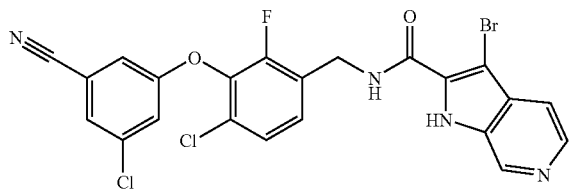

To a solution of 3-bromo-1H-pyrrolo[2,3-c]pyridine-2-carboxylic acid (0.019 g, 0.079 mmol) in DMF (1.0 mL) was added HATU (0.045 g, 0.011 mmol), DIPEA (0.021 mL, 0.011 mmol), 3-{[3-aminomethyl)-6-chloro-2-fluorophenyl]oxy}-5-chlorobenzonitrile (0.037 g, 0.011 mmol). The reaction mixture was stirred overnight. Purification was accomplished by RPHPLC (water:acetonitrile with 0.1% TFA). The desired fractions were neutralized and extracted with EtOAC. The combined organics were dried over Na$_2$SO$_4$, filtered and concentrated to afford 3-bromo-N-({4-chloro-3-[(3-chloro-5-cyanophenyl)oxy]-2-fluorophenyl}methyl)-1H-pyrrolo[2,3-c]pyridine-2-carboxamide (0.008 g, 19%) as a white solid. $^1$H NMR (400 MHz, DMSO-d$_6$): δ ppm 8.76-8.88 (m, 2H) 8.17-8.27 (m, 1H) 7.80 (s, 1H) 7.48 (d, 5H) 4.60 (d, 2H). MS: m/z 533.2 (M+1).

Example 188

N-({4-chloro-3-[(3-chloro-5-cyanophenyl)oxy]-2-fluorophenyl}methyl)-3-ethyl-1H-indole-2-carboxamide

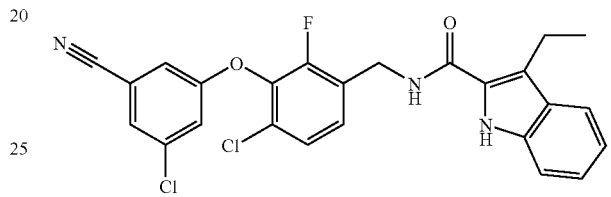

Step A: ethyl 3-ethyl-1H-indole-2-carboxylate

A solution of phenylhydrazine (1.0 g, 6.92 mmol) in absolute ethanol (50 mL) was placed in an oil bath at 60° C. and a reflux condenser attached. Ethyl 2-oxopentanoate (1.0 g, 6.94 mmol) (prepared according to Singh, J; Kissick, T. P.; Mueller, R. H. *Organic Preparations and Procedures International* (1989), 21(4), 501-4.) was added dropwise. The reaction mixture was heated to reflux and stirred overnight. The solution was cooled to RT and the solvent concentrated. Purification was accomplished by column chromatography (hexanes:EtOAc) to afford ethyl 3-ethyl-1H-indole-2-carboxylate (0.625 g, 41%) as a yellow solid. $^1$H NMR (400 MHz, DMSO-d$_6$): δ ppm 11.45 (s, 1H) 7.66 (d, 1H) 7.41 (d, 1H) 7.25 (t, 1H) 7.05 (t, 1H) 4.34 (q, 2H) 3.05 (q, 2H) 1.35 (t, 3H) 1.19 (t, 3H). MS: m/z 218.0 (M+1).

Step B: N-({4-chloro-3-[(3-chloro-5-cyanophenyl)oxy]-2-fluorophenyl}methyl)-3-ethyl-1H-indole-2-carboxamide To a solution of ethyl 3-ethyl-1H-indole-2-carboxylate (0.025 g, 0.108 mmol) in THF/MeOH/H$_2$O (1:1:1, 1.5 mL) was added lithium hydroxide (0.026 g, 1.08 mmol) and the solution stirred at RT for 3 h. A 10% solution of citric acid (1 mL) and EtOAc (5 mL) were added. The aqueous layer was separated and extracted with EtOAc (2×5 mL). The organic layers were combined, dried over sodium sulfate, filtered, concentrated and placed under high vacuum to afford the crude carboxylic acid. To the crude intermediate was added HATU (0.050 g, 0.131 mmol), DIPEA (0.025 mL, 0.131 mmol), 3-{[3-aminomethyl)-6-chloro-2-fluorophenyl]oxy}-5-chlorobenzonitrile (0.033 g, 0.131 mmol), and DMF (1 mL). The reaction mixture was stirred overnight. Purification was accomplished by RPHPLC (water:acetonitrile with 0.1% TFA). The desired fractions were neutralized and extracted with EtOAC. The combined organics were dried over Na$_2$SO$_4$, filtered and concentrated to afford N-({4-chloro-3-[(3-chloro-5-cyanophenyl)oxy]-2-fluorophenyl}methyl)-3-ethyl-1H-indole-2-carboxamide (0.021 g, 40%) as a white solid. $^1$H NMR (400 MHz, DMSO-d$_6$): δ ppm 11.14 (s, 1H) 8.46 (t, 1H) 7.83 (s, 1H) 7.63 (s, 1H) 7.53 (d, 2H) 7.44-7.50

(m, 2H) 7.38 (d, 1H) 7.20 (t, 1H) 7.05 (t, 1H) 4.57 (d, 2H) 3.02 (q, 2H) 1.15 (t, 3H). MS: m/z 482.3 (M+1).

Example 189

N-({4-chloro-3-[(3-chloro-5-cyanophenyl)oxy]-2-fluorophenyl}methyl)-3-propyl-1H-indole-2-carboxamide

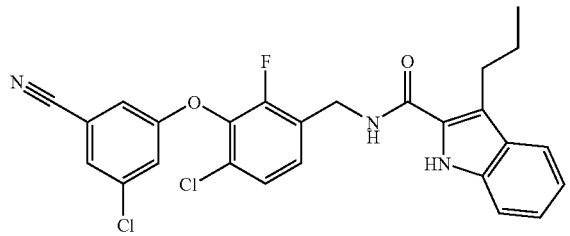

Step A: ethyl 3-propyl-1H-indole-2-carboxylate

A solution of phenylhydrazine (1.0 g, 6.92 mmol) in absolute ethanol (50 mL) was placed in an oil bath at 60° C. and a reflux condenser attached. Ethyl 2-oxohexanoate (1.0 g, 6.33 mmol) (prepared according to Singh, J; Kissick, T. P.; Mueller, R. H. *Organic Preparations and Procedures International* (1989), 21(4), 501-4.) was added dropwise. The reaction mixture was heated to reflux and stirred for 18 h. Water (25 mL) and EtOAc (25 mL) were added and the layers separated. The aqueous layer was extracted with EtOAc (2×25 mL), the organic layers combined, dried over sodium sulfate, filtered and concentrated. Trituration of the crude material (9:1 hexanes/EtOAc) afforded ethyl 3-propyl-1H-indole-2-carboxylate (0.850 g, 58%) as a yellow solid. $^1$H NMR (400 MHz, DMSO-d$_6$): δ ppm 11.46 (s, 1H) 7.65 (d, 1H) 7.40 (d, 1H) 7.25 (d, 1H) 7.04 (t, 1H) 4.33 (q, 2H) 3.02 (t, 2H) 1.56-1.67 (m, 2H) 1.35 (t, 3H) 0.91 (t, 3H). MS: m/z 232.0 (M+1).

Step B: N-({4-chloro-3-[(3-chloro-5-cyanophenyl)oxy]-2-fluorophenyl}methyl)-3-propyl-1H-indole-2-carboxamide To a solution of ethyl 3-propyl-1H-indole-2-carboxylate (0.025 g, 0.108 mmol) in THF/MeOH/H$_2$O (1:1:1, 1.5 mL) was added lithium hydroxide (0.026 g, 1.08 mmol) and the solution stirred at RT for 2 h. A 10% solution of citric acid (1 mL) and EtOAc (5 mL) were added. The aqueous layer was separated and extracted with EtOAc (2×5 mL). The organic layers were combined, dried over sodium sulfate, filtered, concentrated and placed under high vacuum to afford the crude carboxylic acid. To the crude intermediate was added HATU (0.050 g, 0.131 mmol), DIPEA (0.025 mL, 0.131 mmol), 3-{[3-aminomethyl)-6-chloro-2-fluorophenyl]oxy}-5-chlorobenzonitrile (0.033 g, 0.131 mmol), and DMF (1 mL). The reaction mixture was stirred overnight. Purification was accomplished by RPHPLC (water:acetonitrile with 0.1% TFA). The desired fractions were neutralized and extracted with EtOAC. The combined organics were dried over Na$_2$SO$_4$, filtered and concentrated to afford N-({4-chloro-3-[(3-chloro-5-cyanophenyl)oxy]-2-fluorophenyl}methyl)-3-propyl-1H-indole-2-carboxamide (0.021 g, 40%) as a white solid. $^1$H NMR (400 MHz, DMSO-d$_6$): δ ppm 11.18 (s, 1H) 8.49 (s, 1H) 7.86 (d, 1H) 7.63 (d, 1H) 7.55 (d, 2H) 7.46-7.52 (m, 2H) 7.41 (d, 1H) 7.22 (t, 1H) 7.06 (t, 1H) 4.60 (d, 2H) 3.02 (t, 2H) 1.56-1.63 (m, 2H) 0.87 (t, 3H). MS: m/z 496.3 (M+1).

Example 190

N-({4-chloro-3-[(3-chloro-5-cyanophenyl)oxy]-2-fluorophenyl}methyl)-3-(1-methylethyl)-1H-indole-2-carboxamide

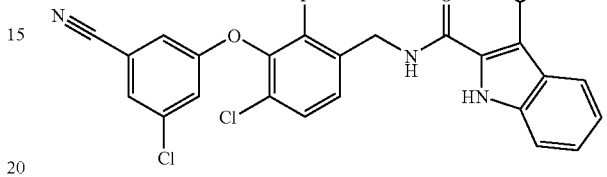

Step A: ethyl 3-(1-methylethyl)-1H-indole-2-carboxylate

A solution of phenylhydrazine (1.0 g, 6.92 mmol) in absolute ethanol (50 mL) was placed in an oil bath at 60° C. and a reflux condenser attached. Ethyl 4-methyl-2-oxopentanoate (1.0 g, 6.33 mmol) (prepared according to Singh, J; Kissick, T. P.; Mueller, R. H. *Organic Preparations and Procedures International* (1989), 21(4), 501-4.) was added dropwise. The reaction mixture was heated to reflux and stirred for 18 h. Water (25 mL) and EtOAc (25 mL) were added and the layers separated. The aqueous layer was extracted with EtOAc (2×25 mL), the organic layers combined, dried over sodium sulfate, filtered and concentrated. Purification was accomplished by column chromatography (hexanes/EtOAc) and RPHPLC. Neutralization and extraction of the desired fractions with EtOAc afforded ethyl 3-propyl-1H-indole-2-carboxylate (0.250 g) as a yellow solid. $^1$H NMR (400 MHz, DMSO-d$_6$): δ ppm 11.39 (s, 1H) 7.82 (d, 1H) 7.42 (d, 1H) 7.22 (t, 1H) 7.01 (t, 1H) 4.33 (q, 2H) 4.01-4.09 (m, 1H) 1.39 (d, 6H) 1.35 (t, 3H). MS: m/z 232.0 (M+1).

Step B: N-({4-chloro-3-[(3-chloro-5-cyanophenyl)oxy]-2-fluorophenyl}methyl)-3-(1-methylethyl)-1H-indole-2-carboxamide To a solution of ethyl 3-(1-methylethyl)-1H-indole-2-carboxylate (0.025 g, 0.108 mmol) in THF/MeOH/H$_2$O (1:1:1, 1.5 mL) was added lithium hydroxide (0.026 g, 1.08 mmol) and the solution stirred at RT for 3 h. A 10% solution of citric acid (1 mL) and EtOAc (5 mL) were added. The aqueous layer was separated and extracted with EtOAc (2×5 mL). The organic layers were combined, dried over sodium sulfate, filtered, concentrated and placed under high vacuum to afford the crude carboxylic acid. To the crude intermediate was added HATU (0.050 g, 0.131 mmol), DIPEA (0.025 mL, 0.131 mmol), 3-{[3-aminomethyl)-6-chloro-2-fluorophenyl]oxy}-5-chlorobenzonitrile (0.033 g, 0.131 mmol), and DMF (1 mL). The reaction mixture was stirred overnight. Purification was accomplished by RPHPLC (water:acetonitrile with 0.1% TFA). The desired fractions were neutralized and extracted with EtOAC. The combined organics were dried over Na$_2$SO$_4$, filtered and concentrated to afford N-({4-chloro-3-[(3-chloro-5-cyanophenyl)oxy]-2-fluorophenyl}methyl)-3-(1-methylethyl)-1H-indole-2-carboxamide (0.021 g, 40%) as a white solid. $^1$H NMR (400 MHz, DMSO-d$_6$): δ ppm 11.11 (s, 1H) 8.53 (br. s., 1H) 7.80 (d, 1H) 7.74 (d, 1H) 7.49-7.55 (m, 2H) 7.41-7.49 (m, 2H) 7.36

(d, 1H) 7.15 (t, 1H) 6.97 (t, 1H) 4.52 (d, 2H) 3.87-3.97 (m, 1H) 1.33 (d, 6H). MS: m/z 496.3 (M+1).

Example 191

N-({4-chloro-3-[(3-chloro-5-cyanophenyl)oxy]-2-fluorophenyl}methyl)-3-methyl-1H-pyrrole-2-carboxamide

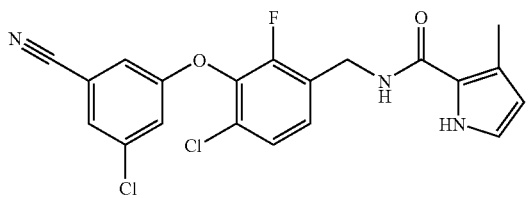

Step A: ethyl 3-hydroxy-3-methyl-1-[(4-methylphenyl)sulfonyl]prolinate

To a solution of 3-buten-2-one (4.75 mL, 58.3 mmol) in THF (100 mL) was added ethyl N-[(4-methylphenyl)sulfonyl]glycinate (15.0 g, 58.3 mmol) and DBU (19.0 mL, 128.3 mmol). The mixture was stirred overnight. Water (50 mL), diethyl ether (100 mL) and aqueous saturated sodium bicarbonate (50 ml) were added and stirred. The layers were separated and the aqueous layer extracted with diethyl ether (100 mL). The organic layers were combined, washed with aqueous 5% citric acid (50 mL), water (50 mL) and saturated NaCl, dried over magnesium sulfate, filtered and concentrated to afford a diastereomeric mixture of ethyl 3-hydroxy-3-methyl-1-[(4-methylphenyl)sulfonyl]prolinate (0.053 g, 60%) as an oil. $^1$H NMR (400 MHz, CDCl$_3$): δ ppm 7.63-7.77 (m, 2H) 7.28 (t, 2H) 4.09-4.24 (m, 1H) 3.97-4.03 (m, 1H) 3.68-3.75 (m, 1H) 3.50-3.64 (m, 1H) 3.31-3.43 (m, 1H) 2.35-2.43 (m, 3H) 2.02-2.14 (m, 1H) 1.82 (dt, 1H) 1.71 (dt, 1H) 1.20-1.29 (m, 5H). MS: m/z 326.0 (M−1).

Step B: ethyl 3-chloro-3-methyl-1-[(4-methylphenyl)sulfonyl]prolinate

Phosphorous oxychloride (11 mL, 118 mmol) was added dropwise to a solution of ethyl 3-hydroxy-3-methyl-1-[(4-methylphenyl)sulfonyl]prolinate (15.0 g, 45.8 mmol) in pyridine (100 mL). The reaction mixture was stirred for 36 h, poured onto ice (200 mL) and extracted with diethyl ether (2×100 mL). The organic layers were combined and washed with ice cold 5% HCl (100 mL), water (50 mL), saturated sodium bicarbonate (100 mL) and saturated NaCl (50 mL), dried over sodium sulfate filtered and concentrated to afford a diasteromeric mixture of ethyl 3-chloro-3-methyl-1-[(4-methylphenyl)sulfonyl]prolinate (15.0 g, 95%) as a white solid. $^1$H NMR (CHLOROFORM-d) δ ppm 7.69-7.83 (m, 2H) 7.31 (d, 2H) 5.38-5.53 (m, 1H) 4.96-5.26 (m, 1H) 4.51-4.92 (m, 1H) 4.11-4.31 (m, 4H) 4.02-4.12 (m, 1H) 3.60 (td, 1H) 3.34 (dt, 1H) 2.62-2.80 (m, 1H) 2.26-2.50 (m, 3H) 1.19-1.33 (m, 2H). MS: m/z 346.1 (M+1).

Step C: ethyl 3-methyl-1H-pyrrole-2-carboxylate

DBU (15.0 mL, 100 mmol) was added dropwise to a solution of ethyl 3-chloro-3-methyl-1-[(4-methylphenyl)sulfonyl]prolinate (15 g, 43 mmol) in THF (100 mL). The mixture was stirred overnight at RT. Diethyl ether (100 mL) and ice cold 5% HCl (100 mL) were added, the layers separated. The organic layer was washed again with washed with ice cold 5% HCl (100 mL) and water (50 mL) followed by saturated sodium bicarbonate (100 mL) and saturated NaCl (50 mL). The organic layer was dried over magnesium sulfate, filtered and concentrated to afford ethyl 3-methyl-1H-pyrrole-2-carboxylate (5.6 g, 84%) as a white solid. $^1$H NMR (400 MHz, DMSO-d$_6$) δ ppm 11.42 (br. s., 1H) 6.84 (t, 1H) 6.00 (t, 1H) 4.21 (q, 2H) 2.25 (s, 3H) 1.28 (t, 3 H). MS: m/z 153.9 (M+1).

Step D: N-({4-chloro-3-[(3-chloro-5-cyanophenyl)oxy]-2-fluorophenyl}methyl)-3-methyl-1H-pyrrole-2-carboxamide To a solution of ethyl 3-methyl-1H-pyrrole-2-carboxylate (0.025 g, 0.163 mmol) in THF/MeOH/H$_2$O (1:1:1, 1.5 mL) was added lithium hydroxide (0.040 g, 1.63 mmol) and the solution stirred at RT for 3 h. A 10% solution of citric acid (1 mL) and EtOAc (5 mL) were added. The aqueous layer was separated and extracted with EtOAc (3×15 mL). The organic layers were combined, dried over sodium sulfate, filtered, concentrated and placed under high vacuum to afford the crude carboxylic acid. To the crude intermediate was added HATU (0.075 g, 0.196 mmol), DIPEA (0.035 mL, 0.196 mmol), 3-{[3-aminomethyl)-6-chloro-2-fluorophenyl]oxy}-5-chlorobenzonitrile (0.050 g, 0.163 mmol), and DMF (1 mL). The reaction mixture was stirred overnight. Purification was accomplished by RPHPLC (water:acetonitrile with 0.1% TFA). The desired fractions were neutralized and extracted with EtOAC. The combined organics were dried over Na$_2$SO$_4$, filtered and concentrated to afford N-({4-chloro-3-[(3-chloro-5-cyanophenyl)oxy]-2-fluorophenyl}methyl)-3-methyl-1H-pyrrole-2-carboxamide (0.023 g, 34%) as a white solid. $^1$H NMR (400 MHz, DMSO-d$_6$): δ ppm 11.04 (br. s., 1H) 7.80 (d, 2H) 7.43-7.50 (m, 3H) 7.37 (d, 1H) 6.76 (br. s., 1H) 5.92 (s, 1H) 4.47 (d, 2H) 2.23 (s, 3H). MS: m/z 418.2 (M+1).

Example 192

4-chloro-N-({4-chloro-3-[(3-chloro-5-cyanophenyl)oxy]-2-fluorophenyl}methyl)-1H-pyrazole-5-carboxamide

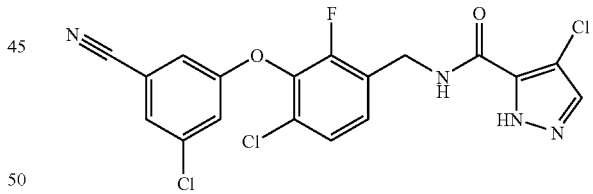

To a solution of 4-chloro-1H-pyrazole-5-carboxylic acid (0.025 g, 0.170 mmol) in DMF (1.0 mL) was added HATU (0.077 g, 0.205 mmol), DIPEA (0.035 mL, 0.205 mmol), 3-{[3-aminomethyl)-6-chloro-2-fluorophenyl]oxy}-5-chlorobenzonitrile (0.064 g, 0.205 mmol). The reaction mixture was stirred overnight. Purification was accomplished by RPHPLC (water:acetonitrile with 0.1% TFA). The desired fractions were neutralized and extracted with EtOAC. The combined organics were dried over Na$_2$SO$_4$, filtered and concentrated to afford 4-chloro-N-({4-chloro-3-[(3-chloro-5-cyanophenyl)oxy]-2-fluorophenyl}methyl)-1H-pyrazole-5-carboxamide (0.060 g, 80%) as a white solid. $^1$H NMR (400 MHz, DMSO-d$_6$): δ ppm 13.61 (br. s., 1H) 8.83 (t, 1H) 8.11 (s, 1H) 7.82 (s, 1H) 7.46-7.54 (m, 3H) 7.35 (t, 1H) 4.47 (d, 2H). MS: m/z 441.0 (M+1).

Example 193

N-({4-chloro-3-[(3-chloro-5-cyanophenyl)oxy]-2-fluorophenyl}methyl)-3,4,5-trimethyl-1H-pyrrole-2-carboxamide

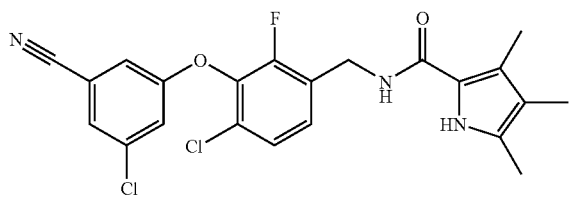

To a solution of ethyl 3,4,5-trimethyl-1H-pyrrole-2-carboxylate (0.020 g, 0.110 mmol) in THF/MeOH/H$_2$O (1:1:1, 1.5 mL) was added lithium hydroxide (0.025 g, 1.10 mmol) and the solution stirred overnight at RT. A 10% solution of citric acid (1 mL) and EtOAc (5 mL) were added. The aqueous layer was separated and extracted with EtOAc (3×10 mL). The organic layers were combined, dried over sodium sulfate, filtered, concentrated and placed under high vacuum to afford the crude carboxylic acid. To the crude intermediate was added HATU (0.050 g, 0.132 mmol), DIPEA (0.025 mL, 0.132 mmol), 3-{[3-aminomethyl)-6-chloro-2-fluorophenyl]oxy}-5-chlorobenzonitrile (0.040 g, 0.132 mmol), and DMF (1 mL). The reaction mixture was stirred overnight. Purification was accomplished by RPHPLC (water:acetonitrile with 0.1% TFA). The desired fractions were neutralized and extracted with EtOAc. The combined organics were dried over Na$_2$SO$_4$, filtered and concentrated to afford N-({4-chloro-3-[(3-chloro-5-cyanophenyl)oxy]-2-fluorophenyl}methyl)-3,4,5-trimethyl-1H-pyrrole-2-carboxamide (0.0035 g, 7%) as a white solid. $^1$H NMR (400 MHz, DMSO-d$_6$): δ ppm 10.63 (s, 1H) 7.82 (s, 1H) 7.71 (t, 1H) 7.43-7.53 (m, 3H) 7.37 (t, 1H) 4.47 (d, 2H) 2.15 (s, 3H) 2.09 (s, 3H) 1.82 (s, 3H). MS: m/z 446.1 (M+1).

Example 194

N-({4-chloro-3-[(3-chloro-5-cyanophenyl)oxy]-2-fluorophenyl}methyl)-3,4-diethyl-1H-pyrrole-2-carboxamide

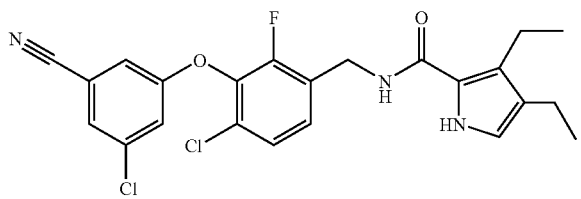

To a solution of ethyl 3,4-diethyl-1H-pyrrole-2-carboxylate (0.020 g, 0.102 mmol) in THF/MeOH/H$_2$O (1:1:1, 1.5 mL) was added lithium hydroxide (0.025 g, 1.10 mmol) and the solution stirred overnight at RT. A 10% solution of citric acid (1 mL) and EtOAc (5 mL) were added. The aqueous layer was separated and extracted with EtOAc (3×10 mL). The organic layers were combined, dried over sodium sulfate, filtered, concentrated and placed under high vacuum to afford the crude carboxylic acid. To the crude intermediate was added HATU (0.045 g, 0.123 mmol), DIPEA (0.020 mL, 0.123 mmol), 3-{[3-aminomethyl)-6-chloro-2-fluorophenyl]oxy}-5-chlorobenzonitrile (0.038 g, 0.123 mmol), and DMF (1 mL). The reaction mixture was stirred overnight. Purification was accomplished by RPHPLC (water:acetonitrile with 0.1% TFA). The desired fractions were neutralized and extracted with EtOAc. The combined organics were dried over Na$_2$SO$_4$, filtered and concentrated to afford N-({4-chloro-3-[(3-chloro-5-cyanophenyl)oxy]-2-fluorophenyl}methyl)-3,4-diethyl-1H-pyrrole-2-carboxamide (0.010 g, 21%) as a white solid. $^1$H NMR (400 MHz, DMSO-d$_6$): δ ppm 10.87 (br. s., 1H) 7.97 (t, 1H) 7.82 (s, 1H) 7.44-7.53 (m, 3H) 7.38 (t, 1H) 6.63 (s, 1H) 4.48 (d, 2H) 2.68 (q, 2H) 2.35 (q, 2H) 1.11 (t, 3H) 1.01 (t, 3H). MS: m/z 460.1 (M+1).

Example 195

N-({4-chloro-3-[(3-chloro-5-cyanophenyl)oxy]-2-fluorophenyl}methyl)-5-formyl-3-methyl-1H-pyrrole-2-carboxamide

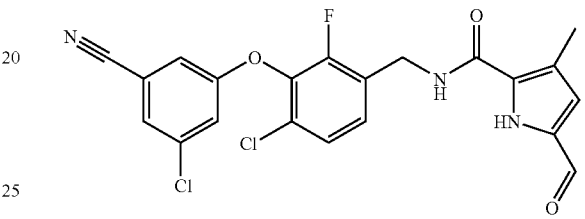

Step A: ethyl 5-formyl-3-methyl-1H-pyrrole-2-carboxylate

A flask with DMF (0.556 mL, 7.19 mmol) was cooled to 0° C. under nitrogen and phosphorous oxychloride (0.655 mL, 7.19 mmol) was added dropwise over 15 min. The solution was warmed to RT and diluted with dichloroethane (3 mL). The reaction mixture was cooled to 0° C. and ethyl 3-methyl-1H-pyrrole-2-carboxylate (1.0 g, 6.53 mmol) dissolved in dichloroethane (5 mL) was added dropwise over 1 h. The reaction mixture was warmed to RT over 15 min., placed in an oil bath @ 90° C. and heated for 15 min. The reaction mixture was cooled to RT, stirred additional 30 min., then cooled to 0° C. and an aqueous solution of sodium acetate (5 g in 6 mL) was added. Methylene chloride (20 mL) was added and the mixture vigorously stirred for 15 min. The organic layer was separated, washed with sat. sodium bicarbonate (2×10 mL), dried over sodium sulfate filtered and evaporated. Recrystallization from ethanol afforded (0.40 g) of a white solid. The filtrate was concentrated and purified by column chromatography (hexanes/EtOAc) to afford ethyl 5-formyl-3-methyl-1H-pyrrole-2-carboxylate (0.60 g total, 51%) and ethyl 4-formyl-3-methyl-1H-pyrrole-2-carboxylate (0.065 g, 5.5%) as white solids.

Ethyl 5-formyl-3-methyl-1H-pyrrole-2-carboxylate: $^1$H NMR (400 MHz, DMSO-d$_6$): δ ppm 12.64 (br. s., 1H) 9.66 (s, 1H) 6.80 (s, 1H) 4.29 (q, 2H) 2.28 (s, 3H) 1.32 (t, 3H). MS: m/z 182.3 (M+1).

Ethyl 4-formyl-3-methyl-1H-pyrrole-2-carboxylate: $^1$H NMR (400 MHz, DMSO-d$_6$): δ ppm 12.28 (br. s., 1H) 9.80 (s, 1H) 7.68 (d, 1H) 4.25 (q, 2H) 2.48 (s, 3H) 1.28 (t, 3 H). MS: m/z 182.3 (M+1).

Step B: N-({4-chloro-3-[(3-chloro-5-cyanophenyl)oxy]-2-fluorophenyl}methyl)-5-formyl-3-methyl-1H-pyrrole-2-carboxamide To a solution of ethyl 5-formyl-3-methyl-1H-pyrrole-2-carboxylate (0.02 g, 0.11 mmol) in THF/MeOH/H$_2$O (1:1:1, 1.5 mL) was added lithium hydroxide (0.025 g, 1.04 mmol) and the solution stirred at RT overnight. A 10% solution of citric acid (1 mL) and EtOAc (5 mL) were added. The aqueous layer was separated and extracted with EtOAc (3×10 mL). The organic layers were combined, dried over sodium sulfate, filtered, concentrated and placed under high vacuum to afford the crude carboxylic acid. To the crude intermediate was added HATU (0.050 g, 0.131 mmol), DIPEA (0.025 mL, 0.131 mmol), 3-{[3-aminomethyl)-6-chloro-2-fluorophenyl]oxy}-5-chlorobenzonitrile (0.040 g, 0.128 mmol), and DMF (1 mL). The reaction mixture was stirred overnight. Purification was accomplished by RPHPLC (water:acetonitrile with 0.1% TFA). The desired fractions were neutralized and extracted with EtOAc. The combined organics were dried over Na$_2$SO$_4$, filtered and concentrated to afford N-({4-chloro-3-[(3-chloro-5-cyanophenyl)oxy]-2-fluorophenyl}methyl)-5-formyl-3-methyl-1H-pyrrole-2-carboxamide (0.026 g, 34%) as a white solid, a portion of which was recrystallized from methanol. $^1$H NMR (400 MHz, DMSO-d$_6$): δ ppm 12.17 (br. s., 1H) 9.55 (s, 1H) 8.63 (t, 1H) 7.82 (s, 1H) 7.38-7.55 (m, 4H) 6.85 (s, 1H) 4.52 (d, 2H) 2.25-2.34 (m, 3H). MS: m/z 446.0 (M+1).

Example 196

N$^2$-({4-chloro-3-[(3-chloro-5-cyanophenyl)oxy]-2-fluorophenyl}methyl)-3-methyl-1H-pyrrole-2,5-dicarboxamide

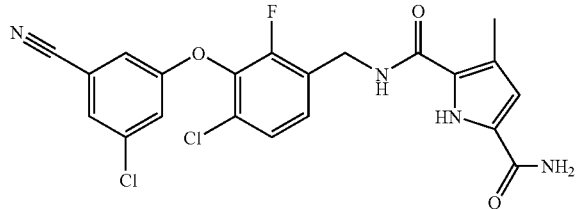

Step A: 5-[(ethyloxy)carbonyl]-4-methyl-1H-pyrrole-2-carboxylic acid

To a solution of ethyl 5-formyl-3-methyl-1H-pyrrole-2-carboxylate (0.25 g, 1.38 mmol) in t-BuOH (50 mL) was added 2-methylbutene as a 2M solution (24 mL, 48.3 mmol). In a separate flask sodium dihydrogen phosphate monohydrate (1.3 g, 9.42 mmol) and sodium chlorite (1.1 g, 12.2 mmol) were dissolved in water (30 mL). The aqueous solution was added to the alcoholic reaction mixture dropwise and stirred for 3 h. The solution was acidified with aqueous 1N HCl to a pH ~4 and EtOAc (100 mL) added. The layers were separated, the aqueous layer extracted with EtOAc (5×25 mL), the organic layers combined, dried over sodium sulfate, filtered and the volume reduced (~50 mL). Ethyl acetate (100 mL) was added and the solution extracted with sat. sodium bicarbonate (5×25 mL), the aqueous layers combined, acidified with 1N HCl to pH~4-5, saturated with NaCl and extracted with EtOAc (5×25 mL). The organic layers were combined, dried over sodium sulfate, filtered and evaporated to afford 5-[(ethyloxy)carbonyl]-4-methyl-1H-pyrrole-2-carboxylic acid (0.196 g, 72%) as a white solid along with 3-chloro-5-[(ethyloxy)carbonyl]-4-methyl-1H-pyrrole-2-carboxylic acid.

5-[(Ethyloxy)carbonyl]-4-methyl-1H-pyrrole-2-carboxylic acid: $^1$H NMR (400 MHz, DMSO-d$_6$): δ ppm 11.87 (br. s., 1H) 6.56 (s, 1H) 4.14-4.24 (m, 2H) 2.20 (s, 3H) 1.25 (t, 3H). MS: m/z 196.2 (M−1).

3-Chloro-5-[(ethyloxy)carbonyl]-4-methyl-1H-pyrrole-2-carboxylic acid: $^1$H NMR (400 MHz, DMSO-d$_6$): δ ppm 12.32 (br. s., 1H) 4.24 (q, 2H) 2.19 (s, 3H) 1.28 (t, 3H). MS: m/z 232.1 (M−1).

Step B: ethyl 5-(aminocarbonyl)-3-methyl-1H-pyrrole-2-carboxylate

To a solution of 5-[(ethyloxy)carbonyl]-4-methyl-1H-pyrrole-2-carboxylic acid (0.040 g, 0.203 mmol) in methylene chloride (1 ml) was added oxalyl chloride (0.020 mL, 0.223 mmol) and the reaction mixture was stirred for 15 min. The solvent was removed under reduced pressure, DMF (1 mL) and ammonia gas was bubbled through the solution for 5 min. The reaction was sealed with a rubber septum and stirred for 10 min. Purification was accomplished by RPHPLC (water:acetonitrile with 0.1% TFA). The desired fractions were collected and lypholized to afford ethyl 5-(aminocarbonyl)-3-methyl-1H-pyrrole-2-carboxylate (0.010 g, 25%) as a white solid. $^1$H NMR (400 MHz, CDCl$_3$): δ ppm 11.53 (br. s., 1H) 7.76 (br. s., 1H) 7.29 (br. s., 1H) 6.61 (s, 1H) 4.24 (d, 2H) 2.24 (s, 3H) 1.30 (t, 3H). MS: m/z 197.5 (M+1).

Step C: N$^2$-({4-chloro-3-[(3-chloro-5-cyanophenyl)oxy]-2-fluorophenyl}methyl)-3-methyl-1H-pyrrole-2,5-dicarboxamide To a solution of ethyl 5-(aminocarbonyl)-3-methyl-1H-pyrrole-2-carboxylate (0.010 g, 0.051 mmol) in THF/MeOH/H$_2$O (1:1:1, 1.5 mL) was added lithium hydroxide (0.012 g, 0.50 mmol) and the solution stirred overnight at RT. A 10% solution of citric acid (1 mL) and EtOAc (5 mL) were added. The aqueous layer was separated and extracted with EtOAc (3×15 mL). The organic layers were combined, dried over sodium sulfate, filtered, concentrated and placed under high vacuum to afford the crude carboxylic acid. To the crude intermediate was added HATU (0.024 g, 0.063 mmol), DIPEA (0.012 mL, 0.063 mmol), 3-{[3-aminomethyl)-6-chloro-2-fluorophenyl]oxy}-5-chlorobenzonitrile (0.019 g, 0.063 mmol), and DMF (1 mL). The reaction mixture was stirred overnight. Purification was accomplished by RPHPLC (water:acetonitrile with 0.1% TFA). The desired fractions were neutralized and extracted with EtOAc (3×10 mL). The combined organics were dried over Na$_2$SO$_4$, filtered and concentrated to afford N$^2$-({4-chloro-3-[(3-chloro-5-cyanophenyl)oxy]-2-fluorophenyl}methyl)-3-methyl-1H-pyrrole-2,5-dicarboxamide (0.005 g, 21%) as a white solid. $^1$H NMR (400 MHz, DMSO-d$_6$): δ ppm 11.54 (br. s., 1H) 8.61 (t, 1H) 7.82 (d, 1H) 7.71 (br. s., 1H) 7.44-7.56 (m, 3H) 7.41 (t, 1H) 7.21 (br. s., 1H) 6.63 (s, 1H) 4.48 (d, 2H) 2.26 (s, 3H). MS: m/z 461.0 (M+1).

Example 197

Ethyl 3-chloro-5-{[({4-chloro-3-[(3-chloro-5-cyanophenyl)oxy]-2-fluorophenyl}methyl)amino]carbonyl}-4-methyl-1H-pyrrole-2-carboxylate

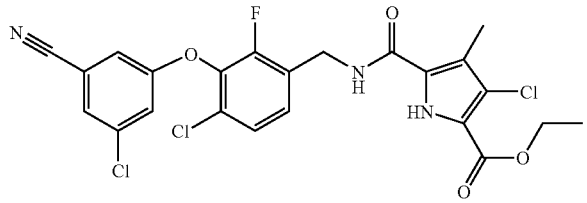

Step A: ethyl 5-formyl-4-methyl-1H-pyrrole-2-carboxylate

A flask with DMF (0.556 mL, 7.19 mmol) was cooled to 0° C. under nitrogen and phosphorous oxychloride (0.655 mL, 7.19 mmol) was added dropwise over 15 min. The solution was warmed to RT and dissolved in dichloroethane (3 mL). The reaction mixture was cooled to 0° C. and ethyl 4-methyl-1H-pyrrole-2-carboxylate (1.0 g, 6.53 mmol) dissolved in dichloroethane (5 mL) was added dropwise over 45 min. The reaction mixture was warmed to RT over 15 min., placed in an oil bath @ 90° C. and heated for 15 min. The reaction mixture was cooled to RT, stirred additional 30 min., then cooled to 0° C. and an aqueous solution of sodium acetate (1 g in 5 mL) was added. Methylene chloride (20 mL) was added and the mixture vigorously stirred for 15 min. The layers were separated, the aqueous layer extracted with methylene chloride (3×25 mL), the organic layers combined, washed with sat. sodium bicarbonate (3×25 mL), dried over sodium sulfate, filtered and evaporated. Recrystallization from ethyl acetate afforded (0.40 g) of a white solid. The filtrate was concentrated and purified by column chromatography (hexanes/EtOAc) to afford ethyl 5-formyl-4-methyl-1H-pyrrole-2-carboxylate (0.60 g total, 51%) as a white solid. $^1$H NMR (400 MHz, DMSO-$d_6$): δ ppm 12.6 (br. s., 1H). 9.79 (s, 1H) 6.70 (s, 1H) 4.28 (q, 2H) 2.29 (s, 3H) 1.29 (t, 3H) –2.31 (br. s., 1H). MS: m/z 180.5 (M−1).

Step B: 4-chloro-5-[(ethyloxy)carbonyl]-3-methyl-1H-pyrrole-2-carboxylic acid

To a solution of ethyl 5-formyl-4-methyl-1H-pyrrole-2-carboxylate (0.40 g, 2.21 mmol) in t-BuOH (25 mL) was added 2-methylbutene as a 2M solution (38 mL, 76.0 mmol). In a separate flask sodium dihydrogen phosphate monohydrate (2.1 g, 15.2 mmol) and sodium chlorite (1.8 g, 19.9 mmol) were dissolved in water (25 mL). The aqueous solution was added to the alcoholic reaction mixture dropwise and stirred for 3 h. Additional sodium dihydrogen phosphate monohydrate (1.05 g, 7.73 mmol) and sodium chlorite (0.9 g, 9.95 mmol) dissolved in water (10 mL) were added and the reaction mixture stirred an additional 2 h. The solution was acidified with aqueous 5% HCl to a pH ~4 and extracted with EtOAc (3×25 mL). The organic layers combined, dried over sodium sulfate, filtered and the solvent evaporated. Purification by column chromatography twice afforded 4-chloro-5-[(ethyloxy)carbonyl]-3-methyl-1H-pyrrole-2-carboxylic acid (0.10 g, 20%) as a white solid. $^1$H NMR (400 MHz, DMSO-$d_6$): δ ppm 12.32 (br. s., 1H) 4.24 (q, 2H) 2.19 (s, 3H) 1.28 (t, 3H). MS: m/z 232.1 (M+1).

Step C: ethyl 3-chloro-5-{[({4-chloro-3-[(3-chloro-5-cyanophenyl)oxy]-2-fluorophenyl}methyl)amino]carbonyl}-4-methyl-1H-pyrrole-2-carboxylate To a solution of 4-chloro-5-[(ethyloxy)carbonyl]-3-methyl-1H-pyrrole-2-carboxylic acid (0.10 g, 0.507 mmol) in DMF (1 mL) was added HATU (0.192 g, 0.507 mmol), DIPEA (0.090 mL, 0.507 mmol), 3-{[3-aminomethyl)-6-chloro-2-fluorophenyl]oxy}-5-chlorobenzonitrile (0.157 g, 0.507 mmol), and the reaction mixture was stirred overnight. Purification was accomplished by RPHPLC (water:acetonitrile with 0.1% TFA). The desired fractions were neutralized and extracted with EtOAc (3×15 mL). The combined organics were dried over $Na_2SO_4$, filtered and concentrated to afford ethyl 3-chloro-5-{[({4-chloro-3-[(3-chloro-5-cyanophenyl)oxy]-2-fluorophenyl}methyl)amino]carbonyl}-4-methyl-1H-pyrrole-2-carboxylate (0.075 g, 28%) as a white solid. $^1$H NMR (400 MHz, DMSO-$d_6$): δ ppm 12.18 (s, 1H) 8.79 (t, 1H) 7.83 (d, 1H) 7.50-7.56 (m, 2H) 7.48 (d, 1H) 7.43 (t, 1H) 4.51 (d, 2H) 4.31 (q, 2 H) 2.22 (s, 3H) 1.31 (t, 3H). MS: m/z 523.9 (M+1).

Example 198

$N^2$-({4-chloro-3-[(3-chloro-5-cyanophenyl)oxy]-2-fluorophenyl}methyl)-$N^5$,$N^5$,3-trimethyl-1H-pyrrole-2,5-dicarboxamide

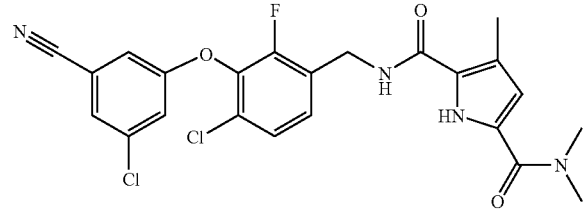

Step A: ethyl 5-[(dimethylamino)carbonyl]-3-methyl-1H-pyrrole-2-carboxylate

To a solution of 5-[(ethyloxy)carbonyl]-4-methyl-1H-pyrrole-2-carboxylic acid (0.160 g, 0.812 mmol) in DMF (4 ml) was added DIPEA (0.140 mL, 0.790 mmol). The reaction mixture was stirred and the solution was divided into four equal portions, one of which was added to a glass vial with a stir bar. To the vial was added a 2M solution of dimethylamine in THF (0.10 mL, 0.2 mmol) and HATU (0.075 g, 0.197 mmol) and the reaction mixture stirred overnight. Purification was accomplished by RPHPLC (water:acetonitrile with 0.1% TFA). The desired fractions were collected and lypholized to afford ethyl 5-[(dimethylamino)carbonyl]-3-methyl-1H-pyrrole-2-carboxylate (0.010 g, 22%) as a white solid. $^1$H NMR (400 MHz, DMSO-$d_6$): δ ppm 11.45 (br. s., 1H) 6.37 (d, 1H) 4.22 (q, 2H) 3.10 (br. s., 3H) 2.97 (br. s., 3H) 2.26 (s, 3H) 1.28 (t, 3H). MS: m/z 225.5 (M+1).

Step B: $N^2$-({4-chloro-3-[(3-chloro-5-cyanophenyl)oxy]-2-fluorophenyl}methyl)-$N^5$,$N^5$,3-trimethyl-1H-pyrrole-2,5-dicarboxamide To a solution of ethyl 5-[(dimethylamino)carbonyl]-3-methyl-1H-pyrrole-2-carboxylate (0.010 g, 0.045 mmol) in THF/MeOH/$H_2O$ (1:1:1, 1.5 mL) was added lithium hydroxide (0.012 g, 0.45 mmol) and the solution stirred overnight at RT. A 10% solution of citric acid (1 mL) and EtOAc (5 mL) were added. The aqueous layer was separated and extracted with EtOAc (3×10 mL). The organic layers were combined, dried over sodium sulfate, filtered, concentrated and placed under high vacuum to afford the crude carboxylic acid. To the crude intermediate was added HATU (0.020 g, 0.053 mmol), DIPEA (0.010 mL, 0.033 mmol), 3-{[3-aminomethyl)-6-chloro-2-fluorophenyl]oxy}-5-chlorobenzonitrile (0.017 g, 0.053 mmol), and DMF (1 mL). The reaction mixture was stirred overnight. Purification was accomplished by RPHPLC (water:acetonitrile with 0.1% TFA). The desired fractions were neutralized and extracted with EtOAc (3×10 mL). The combined organics were dried over $Na_2SO_4$, filtered and concentrated to afford $N^2$-({4-chloro-3-[(3-chloro-5-cyanophenyl)oxy]-2-fluorophenyl}methyl)-$N^5$,$N^5$,3-trimethyl-1H-pyrrole-2,5-dicarboxamide (0.010 g, 46%) as a white amorphous solid. $^1$H NMR (400 MHz, DMSO-$d_6$): δ ppm 11.48 (br. s., 1H) 8.60-8.76 (t, 1H) 7.79 (s, 1H) 7.48 (m, 3H) 7.39 (d, 1H) 6.43 (s, 1H) 4.45 (d, 2H) 3.14 (s, 3H) 3.13 (s, 3H) 2.25 (s, 3H). MS: m/z 489.0 (M+1).

Example 199

$N^2$-({4-chloro-3-[(3-chloro-5-cyanophenyl)oxy]-2-fluorophenyl}methyl)-$N^5$-(2-hydroxyethyl)-3-methyl-1H-pyrrole-2,5-dicarboxamide

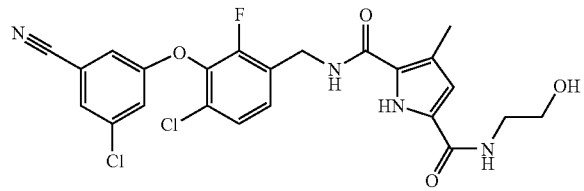

Step A: ethyl 5-{[(2-hydroxyethyl)amino]carbonyl}-3-methyl-1H-pyrrole-2-carboxylate To a solution of 5-[(ethyloxy)carbonyl]-4-methyl-1H-pyrrole-2-carboxylic acid (0.160 g, 0.812 mmol) in DMF (4 ml) was added DIPEA (0.140 mL, 0.790 mmol). The reaction mixture was stirred and the solution was divided into four equal portions, one of which was added to a glass vial with a stir bar. To the vial was added ethanolamine (0.012 mL, 0.2 mmol) and HATU (0.075 g, 0.197 mmol) and the reaction mixture stirred overnight. Purification was accomplished by RPHPLC (water:acetonitrile with 0.1% TFA). The desired fractions were collected and lypholized to afford ethyl 5-{[(2-hydroxyethyl)amino]carbonyl}-3-methyl-1H-pyrrole-2-carboxylate (0.010 g, 48%) as an oil. $^1$H NMR (400 MHz, DMSO-d$_6$): δ ppm 11.63 (br. s., 1H) 8.25-8.42 (m, 1H) 6.61 (s, 1H) 4.25 (q, 2H) 3.48 (t, 2H) 3.28 (q, 2H) 2.25 (s, 3H) 1.30 (t, 3H). MS: m/z 241.4 (M+1).

Step B: $N^2$-({4-chloro-3-[(3-chloro-5-cyanophenyl)oxy]-2-fluorophenyl}methyl)-$N^5$-(2-hydroxyethyl)-3-methyl-1H-pyrrole-2,5-dicarboxamide To a solution of ethyl 5-{[(2-hydroxyethyl)amino]carbonyl}-3-methyl-1H-pyrrole-2-carboxylate (0.010 g, 0.042 mmol) in THF/MeOH/H$_2$O (1:1:1, 1.5 mL) was added lithium hydroxide (0.012 g, 0.42 mmol) and the solution stirred overnight at RT. A 10% solution of citric acid (1 mL) and EtOAc (5 mL) were added. The aqueous layer was separated and extracted with EtOAc (3×10 mL). The organic layers were combined, dried over sodium sulfate, filtered, concentrated and placed under high vacuum to afford the crude carboxylic acid. To the crude intermediate was added HATU (0.019 g, 0.050 mmol), DIPEA (0.009 mL, 0.050 mmol), 3-{[3-aminomethyl)-6-chloro-2-fluorophenyl]oxy}-5-chlorobenzonitrile (0.015 g, 0.05 mmol), and DMF (1 mL). The reaction mixture was stirred overnight. Purification was accomplished by RPHPLC (water:acetonitrile with 0.1% TFA). The desired fractions were neutralized and extracted with EtOAc (3×10 mL). The combined organics were dried over Na$_2$SO$_4$, filtered and concentrated to afford $N^2$-({4-chloro-3-[(3-chloro-5-cyanophenyl)oxy]-2-fluorophenyl}methyl)-$N^5$-(2-hydroxyethyl)-3-methyl-1H-pyrrole-2,5-dicarboxamide (0.003 g, 14%) as an oil. $^1$H NMR (400 MHz, DMSO-d$_6$): δ ppm 11.57 (br. s., 1H) 8.61 (t, 1H) 8.23 (t, 1H) 7.82 (d, 1H) 7.45-7.55 (m, 3H) 7.40 (t, 1H) 6.64 (s, 1H) 4.73 (d, 1H) 4.48 (d, 2H) 3.47 (q, 2H) 3.23-3.31 (m, 2H) 2.26 (s, 3H). MS: m/z 505.0 (M+1).

Example 200

$N^2$-({4-chloro-3-[(3-chloro-5-cyanophenyl)oxy]-2-fluorophenyl}methyl)-3-methyl-$N^5$-(1-methylethyl)-1H-pyrrole-2,5-dicarboxamide

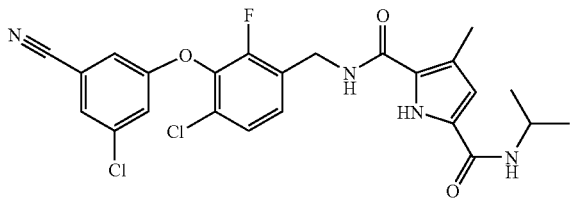

Step A: ethyl 3-methyl-5-{[(1-methylethyl)amino]carbonyl}-1H-pyrrole-2-carboxylate To a solution of 5-[(ethyloxy)carbonyl]-4-methyl-1H-pyrrole-2-carboxylic acid (0.160 g, 0.812 mmol) in DMF (4 ml) was added DIPEA (0.140 mL, 0.790 mmol). The reaction mixture was stirred and the solution was divided into four equal portions, one of which was added to a glass vial with a stir bar. To the vial was added isopropylamine (0.017 mL, 0.2 mmol) and HATU (0.075 g, 0.197 mmol) and the reaction mixture stirred overnight. Purification was accomplished by RPHPLC (water:acetonitrile with 0.1% TFA). The desired fractions were collected and lypholized to afford ethyl 3-methyl-5-{[(1-methylethyl)amino]carbonyl}-1H-pyrrole-2-carboxylate (0.010 g, 47%) as an oil. $^1$H NMR (400 MHz, DMSO-d$_6$): δ ppm 11.58 (br. s., 1H) 8.07 (s, 1H) 6.60 (s, 1H) 4.26 (q, 2H) 3.97-4.12 (m, 1H) 2.24 (s, 3H) 1.30 (t, 3H) 1.14 (d, 6H). MS: m/z 239.4 (M+1).

Step B: $N^2$-({4-chloro-3-[(3-chloro-5-cyanophenyl)oxy]-2-fluorophenyl}methyl)-3-methyl-$N^5$-(1-methylethyl)-1H-pyrrole-2,5-dicarboxamide To a solution of ethyl 3-methyl-5-{[(1-methylethyl)amino]carbonyl}-1H-pyrrole-2-carboxylate (0.010 g, 0.042 mmol) in THF/MeOH/H$_2$O (1:1:1, 1.5 mL) was added lithium hydroxide (0.012 g, 0.42 mmol) and the solution stirred overnight at RT. A 10% solution of citric acid (1 mL) and EtOAc (5 mL) were added. The aqueous layer was separated and extracted with EtOAc (3×10 mL). The organic layers were combined, dried over sodium sulfate, filtered, concentrated and placed under high vacuum to afford the crude carboxylic acid. To the crude intermediate was added HATU (0.019 g, 0.050 mmol), DIPEA (0.009 mL, 0.050 mmol), 3-{[3-aminomethyl)-6-chloro-2-fluorophenyl]oxy}-5-chlorobenzonitrile (0.015 g, 0.05 mmol), and DMF (1 mL). The reaction mixture was stirred overnight. Purification was accomplished by RPHPLC (water:acetonitrile with 0.1% TFA). The desired fractions were neutralized and extracted with EtOAc (3×10 mL). The combined organics were dried over Na$_2$SO$_4$, filtered and concentrated to afford $N^2$-({4-chloro-3-[(3-chloro-5-cyanophenyl)oxy]-2-fluorophenyl}methyl)-3-methyl-$N^5$-(1-methylethyl)-1H-pyrrole-2,5-dicarboxamide (0.0025 g, 12%) as an oil. $^1$H NMR (400 MHz, DMSO-d$_5$): δ ppm 11.50 (br. s., 1H) 8.56 (t, 1H) 7.96 (d, 1H) 7.79 (s, 1H) 7.29-7.54 (m, 4H) 6.64 (s, 1H) 4.45 (d, 2H) 3.96-4.05 (m, 1H) 2.23 (s, 3H) 1.10 (d, 6H). MS: m/z 503.1 (M+1).

Example 201

N-({4-chloro-3-[(3-chloro-5-cyanophenyl)oxy]-2-fluorophenyl}methyl)-3,5-dimethyl-4-nitro-1H-pyrrole-2-carboxamide

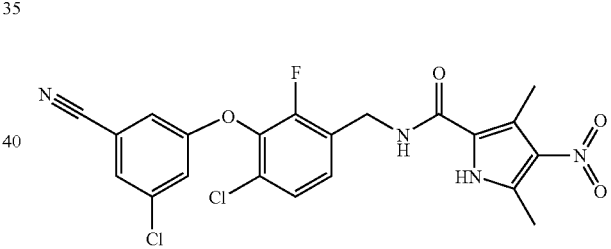

Step A: ethyl 3,5-dimethyl-4-nitro-1H-pyrrole-2-carboxylate

Nitric acid (70 w/w %, 5 mL) was added to ethyl 3,5-dimethyl-1H-pyrrole-2-carboxylate (1.0 g, 6.0 mmol) cooled to 0° C. The reaction mixture was stirred and allowed to warm to RT over 1 h. The reaction mixture was poured into an ice bath with sat. sodium bicarbonate (25 mL) and extracted with EtOAc (3×50 mL), the organic layers combined, dried over sodium sulfate, filtered and evaporated. Purification by column chromatography afforded ethyl 3,5-dimethyl-4-nitro-1H-pyrrole-2-carboxylate (0.185 g, 14%) as a white solid. $^1$H NMR (400 MHz, DMSO-d$_5$): δ ppm 12.49 (br. s., 1H) 4.26 (q, 2H) 2.51 (s, 3H) 2.50 (s, 3H) 1.28 (t, 3H). MS: m/z 213.3 (M+1).

Step B: N-({4-chloro-3-[(3-chloro-5-cyanophenyl)oxy]-2-fluorophenyl}methyl)-3,5-dimethyl-4-nitro-1H-pyrrole-2-carboxamide To a solution of ethyl 3,5-dimethyl-4-nitro-1H-pyrrole-2-carboxylate (0.025 g, 0.118 mmol) in THF/MeOH/H$_2$O (1:1:1, 1.5 mL) was added lithium hydroxide (0.028 g, 1.18 mmol) and the solution stirred overnight at RT. A 10% solution of citric acid (1 mL) and EtOAc (5 mL) were added. The aqueous layer was separated and extracted with EtOAc (3×10 mL). The organic layers were combined, dried over sodium sulfate, filtered, concentrated and placed under high vacuum to afford the crude carboxylic acid. To the crude intermediate was added HATU (0.053 g, 0.142 mmol), DIPEA (0.025 mL, 0.142 mmol), 3-{[3-aminomethyl)-6-chloro-2-fluorophenyl]oxy}-5-chlorobenzonitrile (0.044 g, 0.142 mmol), and DMF (1 mL). The reaction mixture was stirred overnight. Purification was accomplished by RPHPLC (water:acetonitrile with 0.1% TFA). The desired fractions were neutralized and extracted with EtOAc (3×10 mL). The combined organics were dried over $Na_2SO_4$, filtered and concentrated to afford N-({4-chloro-3-[(3-chloro-5-cyanophenyl)oxy]-2-fluorophenyl}methyl)-3,5-dimethyl-4-nitro-1H-pyrrole-2-carboxamide (0.002 g, 4%) as an oil. $^1$H NMR (400 MHz, DMSO-$d_6$): δ ppm 12.27 (br. s., 1H) 8.39 (t, 1H) 7.82 (s, 1H) 7.36-7.56 (m, 4 H) 4.51 (d, 2H) 2.47 (s, 6H). MS: m/z 475.2 (M−1).

Example 202

4-chloro-N-({4-chloro-3-[(3-chloro-5-cyanophenyl)oxy]-2-fluorophenyl}methyl)-3,5-dimethyl-1H-pyrrole-2-carboxamide

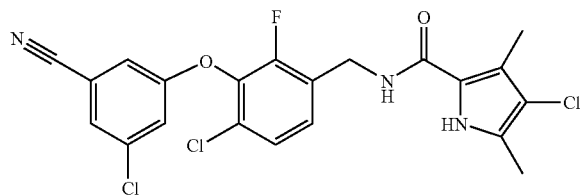

Step A: ethyl 4-chloro-3,5-dimethyl-1H-pyrrole-2-carboxylate

To a solution of ethyl 3,5-dimethyl-1H-pyrrole-2-carboxylate (0.100 g, 0.598 mmol) in DMF (2 ml) was added N-chlorosuccinimide (0.120 g, 0.897 mmol). The reaction mixture was stirred at RT for 4 h. The solvent was evaporated and purification by column chromatography (hexanes/EtOAc) afforded ethyl 4-chloro-3,5-dimethyl-1H-pyrrole-2-carboxylate (0.035 g, 29%) as a white solid. $^1$H NMR (400 MHz, DMSO-$d_6$): δ ppm 11.68 (br. s., 1H) 4.22 (q, 2H) 2.19 (s, 3H) 2.15 (s, 3H) 1.28 (t, 3H). MS: m/z 202.3 (M+1).

Step B: 4-chloro-N-({4-chloro-3-[(3-chloro-5-cyanophenyl)oxy]-2-fluorophenyl}methyl)-3,5-dimethyl-1H-pyrrole-2-carboxamide To a solution of ethyl 4-chloro-3,5-dimethyl-1H-pyrrole-2-carboxylate (0.030 g, 0.149 mmol) in THF/MeOH/$H_2O$ (1:1:1, 1.5 mL) was added lithium hydroxide (0.035 g, 1.50 mmol) and the solution stirred overnight at RT. A 10% solution of citric acid (1 mL) and EtOAc (5 mL) were added. The aqueous layer was separated and extracted with EtOAc (3×10 mL). The organic layers were combined, dried over sodium sulfate, filtered, concentrated and placed under high vacuum to afford the crude carboxylic acid. To the crude intermediate was added HATU (0.068 g, 0.224 mmol), DIPEA (0.031 mL, 0.224 mmol), 3-{[3-aminomethyl)-6-chloro-2-fluorophenyl]oxy}-5-chlorobenzonitrile (0.055 g, 0.224 mmol), and DMF (1 mL). The reaction mixture was stirred overnight. Purification was accomplished by RPHPLC (water:acetonitrile with 0.1% TFA). The desired fractions were neutralized and extracted with EtOAc (3×10 mL). The combined organics were dried over $Na_2SO_4$, filtered and concentrated. Further purification by column chromatography (hexanes/EtOAc) afforded 4-chloro-N-({4-chloro-3-[(3-chloro-5-cyanophenyl)oxy]-2-fluorophenyl}methyl)-3,5-dimethyl-1H-pyrrole-2-carboxamide (0.002 g, 3%) as a white solid. $^1$H NMR (400 MHz, DMSO-$d_6$): δ ppm 11.29 (br. s., 1H) 7.78-7.97 (m, 2H) 7.43-7.60 (m, 3H) 7.32-7.43 (m, 1H) 4.50 (d, 2H) 2.19 (s, 3H) 2.15 (s, 3H). MS: m/z 466.1 (M+1).

Example 203

N-({4-chloro-3-[(3-chloro-5-cyanophenyl)oxy]-2-fluorophenyl}methyl)-4-cyano-1H-imidazole-5-carboxamide

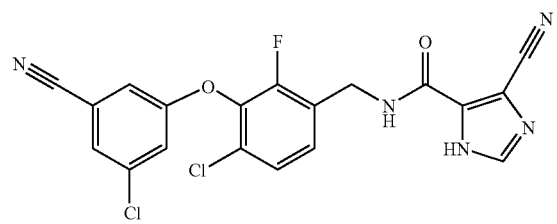

To a solution of ethyl 4-cyano-1H-imidazole-5-carboxylate (0.025 g, 0.152 mmol) in THF/MeOH/$H_2O$ (1:1:1, 1.5 mL) was added lithium hydroxide (0.036 g, 1.52 mmol) and the solution stirred overnight at RT. An aqueous solution of 2.5 N HCl (0.6 mL, 0.240 mmol) was added, the solvents evaporated, and the mixture was azeotroped with toluene (1 mL) and ether (2 mL) successively, and placed under high vacuum. To the crude intermediate dissolved in DMF (1 mL) was added HATU (0.063 g, 0.166 mmol), DIPEA (0.040 mL, 0.226 mmol), 3-{[3-aminomethyl)-6-chloro-2-fluorophenyl]oxy}-5-chlorobenzonitrile (0.052 g, 0.167 mmol). The reaction mixture was stirred 3 h. Purification was accomplished by RPHPLC (water:acetonitrile with 0.1% TFA). The desired fractions were lyophilized and triturated with ethyl acetate to afford N-({4-chloro-3-[(3-chloro-5-cyanophenyl)oxy]-2-fluorophenyl}methyl)-4-cyano-1H-imidazole-5-carboxamide (0.018 g, 28%) as a white solid. $^1$H NMR (400 MHz, DMSO-$d_6$): δ ppm 8.92-8.99 (m, 1H) 8.07 (s, 1H) 7.79 (s, 1H) 7.40-7.51 (m, 3H) 7.36 (t, 1H) 4.49 (d, 2H). MS: m/z 430.1 (M+1).

Example 204

3-bromo-N-({4-chloro-3-[(3-chloro-5-cyanophenyl)oxy]-2-fluorophenyl}methyl)-1H-pyrrole-2-carboxamide

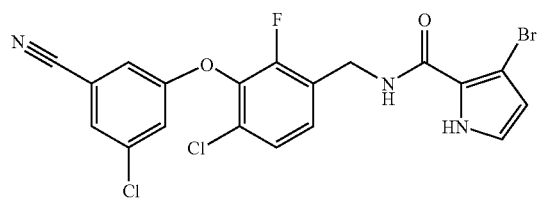

Step A: 3-bromo-1H-pyrrole-2-carboxylic acid

To a solution of 3-bromo-1H-pyrrole-2-carbaldehyde (0.44 g, 2.53 mmol) in tert-butanol (5.0 ml) was added 2-methyl-2-butene/2M in THF (5.09 ml, 48.0 mmol). To the reaction mixture was added sodium phosphate mono-$H_2O$ (2.461 g, 17.70 mmol) and sodium chlorite (2.058 g, 22.76 mmol) dissolved in water (5.00 ml) at RT over a period of 15 min. The solution was stirred overnight. The reaction mixture was acidified to pH~4 with 10% aqueous citric acid and extracted with EtOAc (5×30 mL). The organic layers were combined, dried over sodium sulfate filtered and evaporated. The crude material was triturated with minimal amount of EtOAc to afford 3-bromo-1H-pyrrole-2-carboxylic acid (0.35 g, 73% yield) as a tan solid. The filtrate solution was evaporated to afford an impure mixture of the product as an oil. $^1$H NMR (400 MHz, DMSO-d$_6$): δ ppm 12.55 (br. s., 1H) 12.00 (br. s., 1H) 6.96 (t, 1H) 6.26 (t, 1H). MS: m/z 188.0 (M−1).

Step B: 3-bromo-N-({4-chloro-3-[(3-chloro-5-cyanophenyl)oxy]-2-fluorophenyl}methyl)-1H-pyrrole-2-carboxamide To a solution of 3-bromo-1H-pyrrole-2-carboxylic acid (0.2 g, 0.684 mmol) in DMF (2 mL) was added HATU (0.48 g, 1.262 mmol), DIPEA (0.270 ml, 1.547 mmol) and 3-{[3-(aminomethyl)-6-chloro-2-fluorophenyl]oxy}-5-chlorobenzonitrile (0.39 g, 1.253 mmol). The reaction mixture was stirred at RT overnight. Water (5 ml) and EtOAc (10 mL) were added and the layers separated. The aqueous layer was extracted with EtOAc (3×10 mL), the organic layers combined, dried over sodium sulfate, filtered and evaporated. Purification was accomplished by RPHPLC. Further purification by RPHPLC was required. The desired fractions were collected, neutralized with sat. sodium bicarbonate and extracted with EtOAc (3×10 mL). The organic layers were combined, dried over sodium sulfate, filtered and evaporated to afford 3-bromo-N-({4-chloro-3-[(3-chloro-5-cyanophenyl)oxy]-2-fluorophenyl}methyl)-1H-pyrrole-2-carboxamide (0.029 g, 8.8% yield) as a white solid. $^1$H NMR (400 MHz, DMSO-d$_6$): δ ppm 11.87 (br. s., 1H) 7.96 (t, 1H) 7.83 (s, 1H) 7.46-7.54 (m, 3H) 7.40 (t, 1H) 6.96 (t, 1H) 6.25 (t, 1H) 4.56 (d, 2H). MS: m/z 479.9 (M−1).

Example 205

3-chloro-N$^2$-({4-chloro-3-[(3-chloro-5-cyanophenyl)oxy]-2-fluorophenyl}methyl)-1H-pyrrole-2,4-dicarboxamide

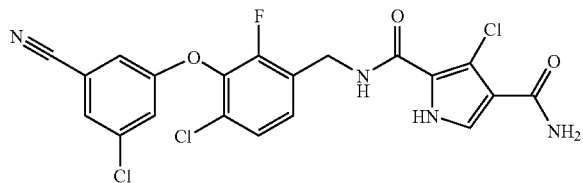

Step A: methyl 3-chloro-4-formyl-1H-pyrrole-2-carboxylate

A solution of phosphorous oxychloride (3.21 ml, 34.5 mmol) was added dropwise over a period of 15 min to a 0° C. solution of DMF (2.67 ml, 34.5 mmol) under nitrogen. The mixture was allowed to warm to RT and stirred for 30 min. Dichloroethane (20 mL) was added and the reaction mixture cooled to 0° C. A solution of methyl 3-chloro-1H-pyrrole-2-carboxylate (5 g, 31.3 mmol) in dichloroethane (20 mL) was added dropwise over 30 min. The reaction mixture was warmed to RT and allowed to stir for 1 h. The flask was placed in an oil bath at 90° C. and stirred for 30 min. The reaction mixture was cooled to RT, a solution of sodium acetate (25 g, 305 mmol) in water (25 mL) was added and stirred for 15 min. Methylene chloride (100 mL) was added and the layers separated. The aqueous layer was extracted with methylene chloride (2×25 mL), the organic layers were combined, dried over sodium sulfate, filtered and evaporated. The crude material was purified by column chromatography (hexanes: EtOAc; 10-100%) to afford three isolated materials. The first compound to elute was a mixture of starting materials and product. The second fraction to elute was evaporated and recrystallized from a minimal amount of EtOAc to afford methyl 3-chloro-5-formyl-1H-pyrrole-2-carboxylate (1.2 g, 6.40 mmol, 20% yield) as yellowish crystals. The third fraction to elute was evaporated and recrystallized from hexanes: EtOAc to afford methyl 3-chloro-4-formyl-1H-pyrrole-2-carboxylate (1.05 g, 18% yield) as a tan solid. Methyl 3-chloro-5-formyl-1H-pyrrole-2-carboxylate: $^1$H NMR (400 MHz, DMSO-d$_6$): 6 ppm 14.0 (br. s., 1H), 9.64 (d, 1H) 7.01 (s, 1H) 3.82 (s, 3H). MS: m/z 188.0 (M+1). Methyl 3-chloro-4-formyl-1H-pyrrole-2-carboxylate: $^1$H NMR (400 MHz, DMSO-d$_6$): 6 ppm 14.0 (br. s., 1H) 9.77 (s, 1H) 7.77 (s, 1H) 3.80 (s, 3H). MS: m/z 188.0 (M+1).

Step B: 4-chloro-5-[(methyloxy)carbonyl]-1H-pyrrole-3-carboxylic acid

To a solution of methyl 3-chloro-4-formyl-1H-pyrrole-2-carboxylate (0.5 g, 2.67 mmol) dissolved in tert-butanol (25 mL) was added 2-methyl-2-butene/2M in THF (20.26 mL, 40.5 mmol). A solution of sodium dihydrogen phosphate monoH2O (2.57 g, 18.66 mmol) and sodium chlorite (2.170 g, 23.99 mmol) in water (25.00 mL) was added dropwise over a period of 15 min. The solution was stirred at RT for 2.5 h. Aqueous citric acid (10 w/w %) was added until a pH of 4-5 was observed. EtOAc (50 mL) was added, the layers separated and the aqueous layer extracted with EtOAc (2×25 mL). The organic layers were combined, dried over sodium sulfate filtered and evaporated. The crude material was triturated with a minimal amount of EtOAc to afford 4-chloro-5-[(methyloxy)carbonyl]-1H-pyrrole-3-carboxylic acid (0.5 g, 92% yield) as a white solid. $^1$H NMR (400 MHz, DMSO-d$_6$): δ ppm 14.4 (br. s., 1H), 12.4 (br. s., 1H) 7.51 (d, 1H) 3.78 (s, 3H). MS: m/z 202.0 (M−1).

Step C: methyl 4-(aminocarbonyl)-3-chloro-1H-pyrrole-2-carboxylate

To a solution of 4-chloro-5-[(methyloxy)carbonyl]-1H-pyrrole-3-carboxylic acid (0.075 g, 0.368 mmol) in DMF (1 mL) was added DIPEA (0.097 mL, 0.553 mmol) and HATU (0.168 g, 0.442 mmol). Ammonia was bubbled through the reaction mixture for 5 min. and the reaction stirred at RT for 1 h. The crude material was purified by HPLC. The desired fractions were collected and lypholized to afford methyl 4-(aminocarbonyl)-3-chloro-1H-pyrrole-2-carboxylate (0.044 g, 59% yield) as a white solid. $^1$H NMR (400 MHz, DMSO-d$_6$): δ ppm 12.40-12.56 (m, 1H) 7.54 (d, 1H) 7.29 (br. s., 1H) 7.13 (br. s., 1H) 3.80 (s, 3H). MS: m/z 203.0 (M+1).

Step D: 3-chloro-N$^2$-({4-chloro-3-[(3-chloro-5-cyanophenyl)oxy]-2-fluorophenyl}methyl)-1H-pyrrole-2,4-dicarboxamide To a solution of methyl 4-(aminocarbonyl)-3-chloro-1H-pyrrole-2-carboxylate (0.04 g, 0.197 mmol) in THF (3 mL) and water (1 mL) was added lithium hydroxide (0.047 g, 1.974 mmol). The reaction mixture was stirred overnight at 35° C. The solvent was evaporated and the resulting solid placed under high vacuum. To the intermediate mixture was added DMF (1 mL), DIPEA (0.052 ml, 0.296 mmol), HATU (0.090 g, 0.237 mmol) and 3-{[3-(aminomethyl)-6-chloro-2-fluorophenyl]oxy}-5-chlorobenzonitrile (0.061 g, 0.197 mmol). The solution was stirred for 1 h at RT. Purification was accomplished by HPLC. The desired fractions were neutralized with saturated sodium bicarbonate, extracted with EtOAc (3×5 mL), the organic layers combined, dried over sodium sulfate, filtered and evaporated to afford 3-chloro-N$^2$-({4-chloro-3-[(3-chloro-5-cyanophenyl)oxy]-2-fluorophenyl}methyl)-1H-pyrrole-2,4-dicarboxamide (0.020 g, 21% yield) as a white solid. $^1$H NMR (400 MHz, DMSO-d$_6$): δ ppm 12.18 (br. s., 1H) 8.15 (t, 1H) 7.83 (d, 1H) 7.46-7.56 (m, 4H) 7.37 (t, 1H) 7.30 (br. s., 1H) 7.05 (br. s., 1H) 4.57 (d, 2H). MS: m/z 481.0 (M+1).

Example 206

3-chloro-N²-({4-chloro-3-[(3-chloro-5-cyanophenyl)oxy]-2-fluorophenyl}methyl)-N⁴-methyl-1H-pyrrole-2,4-dicarboxamide

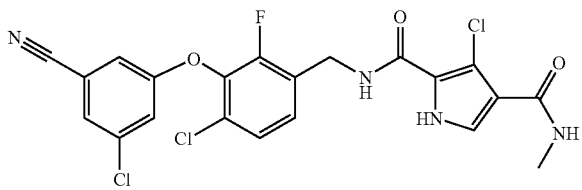

Step A: methyl 3-chloro-4-[(methylamino)carbonyl]-1H-pyrrole-2-carboxylate

To a solution of 4-chloro-5-[(methyloxy)carbonyl]-1H-pyrrole-3-carboxylic acid (0.075 g, 0.368 mmol) in DMF (1 ml) was added HATU (0.168 g, 0.442 mmol), DIPEA (0.097 ml, 0.553 mmol) and methyl amine (2M in THF) (0.276 ml, 0.553 mmol). The reaction mixture was stirred at RT overnight. Purification was accomplished by HPLC, the desired fractions collected and lypholized to afford methyl 3-chloro-4-[(methylamino)carbonyl]-1H-pyrrole-2-carboxylate (0.046 g, 57.6% yield) as a white solid. ¹H NMR (400 MHz, DMSO-d₆): δ ppm 12.39 (br. s., 1H) 7.73-7.83 (m, 1H) 7.46 (d, 1H) 3.80 (s, 3H) 2.70 (d, 3H). MS: m/z 217.0 (M+1).

Step B: 3-chloro-N²-({4-chloro-3-[(3-chloro-5-cyanophenyl)oxy]-2-fluorophenyl}methyl)-N⁴-methyl-1H-pyrrole-2,4-dicarboxamide To a solution of methyl 3-chloro-4-[(methylamino)carbonyl]-1H-pyrrole-2-carboxylate (0.04 g, 0.185 mmol) in THF (3 mL) and water (1 mL) was added lithium hydroxide (0.044 g, 1.847 mmol). The reaction mixture was stirred overnight at 35° C. The solvent was evaporated and the resulting solid placed under high vacuum. To the intermediate mixture was added DMF (1 mL), HATU (0.084 g, 0.222 mmol), DIPEA (0.048 ml, 0.277 mmol) and 3-{[3-(aminomethyl)-6-chloro-2-fluorophenyl]oxy}-5-chlorobenzonitrile (0.057 g, 0.185 mmol). The solution was stirred for 1.5 h at RT. Purification was accomplished by HPLC. The desired fractions were neutralized with saturated sodium bicarbonate, extracted with EtOAc (3×5 mL), the organic layers combined, dried over sodium sulfate, filtered and evaporated to afford 3-chloro-N²-({4-chloro-3-[(3-chloro-5-cyanophenyl)oxy]-2-fluorophenyl}methyl)-N⁴-methyl-1H-pyrrole-2,4-dicarboxamide (0.028 g, 31% yield) as a white solid. ¹H NMR (400 MHz, DMSO-d₆): δ ppm 12.14 (br. s., 1H) 8.13 (t, 1H) 7.81 (d, 1H) 7.74-7.79 (m, 1H) 7.44-7.53 (m, 3H) 7.35 (t, 1H) 7.40 (d, 1H) 4.54 (d, 2H) 2.68 (d, 3H). MS: m/z 495.1 (M+1).

Example 207

3-chloro-N²-({4-chloro-3-[(3-chloro-5-cyanophenyl)oxy]-2-fluorophenyl}methyl)-N⁴,N⁴-dimethyl-1H-pyrrole-2,4-dicarboxamide

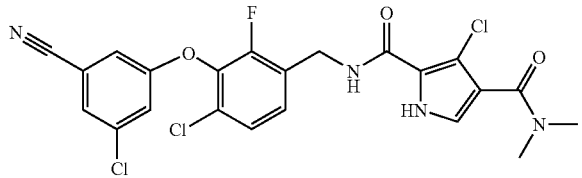

Step A: methyl 3-chloro-4-[(methylamino)carbonyl]-1H-pyrrole-2-carboxylate

To a solution of 4-chloro-5-[(methyloxy)carbonyl]-1H-pyrrole-3-carboxylic acid (0.075 g, 0.368 mmol) in DMF (1 ml) was added HATU (0.168 g, 0.442 mmol), DIPEA (0.097 ml, 0.553 mmol) and dimethyl amine (2M in THF) (0.276 ml, 0.553 mmol) and the reaction stirred at RT for 1 h. Purification was accomplished by HPLC to afford methyl 3-chloro-4-[(dimethylamino)carbonyl]-1H-pyrrole-2-carboxylate (0.042 g, 49% yield) as a white solid. ¹H NMR (400 MHz, DMSO-d₆) δ ppm 12.40 (br. s., 1H) 7.23 (d, 1H) 3.80 (s, 3H) 2.93 (s, 6H). MS: m/z 231.0 (M+1).

Step B: 3-chloro-N²-({4-chloro-3-[(3-chloro-5-cyanophenyl)oxy]-2-fluorophenyl}methyl)-N⁴,N⁴-dimethyl-1H-pyrrole-2,4-dicarboxamide To a solution of methyl 3-chloro-4-[(dimethylamino)carbonyl]-1H-pyrrole-2-carboxylate (0.038 g, 0.165 mmol) in THF (3 mL) and water (1 mL) was added lithium hydroxide (0.039 g, 1.648 mmol). The reaction mixture was stirred overnight at 35° C. The solvent was evaporated and the resulting solid placed under high vacuum. To the intermediate mixture was added DMF (1 mL), HATU (0.075 g, 0.198 mmol), DIPEA (0.043 ml, 0.247 mmol) and 3-{[3-(aminomethyl)-6-chloro-2-fluorophenyl]oxy}-5-chlorobenzonitrile (0.051 g, 0.165 mmol). The solution was stirred for 2 h at RT. Purication was accomplished by HPLC. The desired fractions were neutralized with saturated sodium bicarbonate, extracted with EtOAc (3×5 mL), the organic layers combined, dried over sodium sulfate, filtered and evaporated to afford 3-chloro-N²-({4-chloro-3-[(3-chloro-5-cyanophenyl)oxy]-2-fluorophenyl}methyl)-N⁴,N⁴-dimethyl-1H-pyrrole-2,4-dicarboxamide (0.0053 g, 6% yield) as a white solid. ¹H NMR (400 MHz, DMSO-d₆): δ ppm 12.16 (br. s., 1H) 8.13 (t, 1H) 7.83 (d, 1H) 7.46-7.54 (m, 3 H) 7.38 (t, 1H) 7.16 (d, 1H) 4.56 (d, 2H) 2.95 (s, 6H). MS: m/z 509.1 (M+1).

Example 208

3-chloro-N²-({4-chloro-3-[(3-chloro-5-cyanophenyl)oxy]-2-fluorophenyl}methyl)-N⁴-ethyl-1H-pyrrole-2,4-dicarboxamide

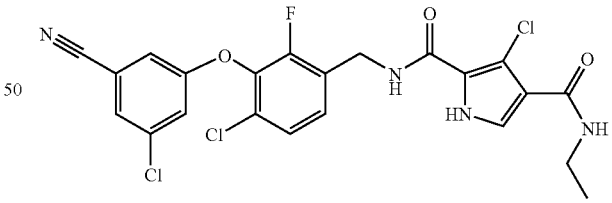

Step A: methyl 3-chloro-4-[(ethylamino)carbonyl]-1H-pyrrole-2-carboxylate

To a solution of 4-chloro-5-[(methyloxy)carbonyl]-1H-pyrrole-3-carboxylic acid (0.075 g, 0.368 mmol) in DMF (1 ml) was added DIPEA (0.193 ml, 1.105 mmol), HATU (0.168 g, 0.442 mmol), and ethyl amine (0.045 g, 0.553 mmol) and the reaction stirred at RT for 2 h. Purification was accomplished by HPLC to afford methyl 3-chloro-4-[(ethylamino)carbonyl]-1H-pyrrole-2-carboxylate (0.035 g, 41% yield) as a white solid. ¹H NMR (400 MHz, DMSO-d₆) δ ppm 12.45 (br. s., 1H) 7.81 (t, 1H) 7.48 (d, 1H) 3.80 (s, 3H) 3.20 (dd, 2H) 1.08 (t, 3H). MS: m/z 231.0 (M+1).

221

Step B: 3-chloro-N²-({4-chloro-3-[(3-chloro-5-cyanophenyl)oxy]-2-fluorophenyl}methyl)-N⁴-ethyl-1H-pyrrole-2,4-dicarboxamide To a solution of methyl 3-chloro-4-[(ethylamino)carbonyl]-1H-pyrrole-2-carboxylate (0.03 g, 0.130 mmol) in THF (3 mL) and water (1 mL) was added lithium hydroxide (0.031 g, 1.301 mmol). The reaction mixture was stirred overnight at 35° C. The solvent was evaporated and the resulting solid placed under high vacuum. To the intermediate mixture was added DMF (1 mL), HATU (0.059 g, 0.156 mmol), DIPEA (0.034 ml, 0.195 mmol) and 3-{[3-(aminomethyl)-6-chloro-2-fluorophenyl]oxy}-5-chlorobenzonitrile (0.040 g, 0.130 mmol). The solution was stirred for 2 h at RT. Purification was accomplished by HPLC. The desired fractions were neutralized with saturated sodium bicarbonate, extracted with EtOAc (3×5 mL), the organic layers combined, dried over sodium sulfate, filtered and evaporated to afford 3-chloro-N²-({4-chloro-3-[(3-chloro-5-cyanophenyl)oxy]-2-fluorophenyl}methyl)-N⁴-ethyl-1H-pyrrole-2,4-dicarboxamide (0.0033 g, 5% yield) as a white solid. ¹H NMR (400 MHz, DMSO-d₆): δ ppm 12.15 (br. s., 1H) 8.14 (s, 1H) 7.83 (d, 2H) 7.44-7.54 (m, 4H) 7.37 (s, 1H) 4.57 (d, 2H) 3.20 (dd, 2H) 1.08 (t, 3H). MS: m/z 509.2 (M+1).

Example 209

3-chloro-N²-({4-chloro-3-[(3-chloro-5-cyanophenyl)oxy]-2-fluorophenyl}methyl)-N⁴-(2-hydroxyethyl)-1H-pyrrole-2,4-dicarboxamide

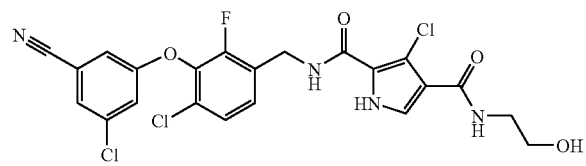

Step A: methyl 3-chloro-4-{[(2-hydroxyethyl)amino]carbonyl}-1H-pyrrole-2-carboxylate To a solution of 4-chloro-5-[(methyloxy)carbonyl]-1H-pyrrole-3-carboxylic acid (0.075 g, 0.368 mmol) in DMF (1 ml) was added DIPEA (0.097 ml, 0.553 mmol), HATU (0.168 g, 0.442 mmol) and ethanolamine (0.033 ml, 0.553 mmol) and the reaction stirred at RT for 3 h. Purification was accomplished by HPLC to afford methyl 3-chloro-4-{[(2-hydroxyethyl)amino]carbonyl}-1H-pyrrole-2-carboxylate (0.06 g, 53% yield) as a white solid. ¹H NMR (400 MHz, DMSO-d₆) δ ppm 12.45 (br. s., 1H) 7.78 (t, 1H) 7.52 (d, 1H) 4.28 (br. s., 1H) 3.80 (s, 3H) 3.56-3.68 (m, 1H) 3.46 (t, 1H) 3.25 (q, 1H) 3.07-3.21 (m, 1H). MS: m/z 247.0 (M+1).

Step B: 3-chloro-N²-({4-chloro-3-[(3-chloro-5-cyanophenyl)oxy]-2-fluorophenyl}methyl)-N⁴-(2-hydroxyethyl)-1H-pyrrole-2,4-dicarboxamide To a solution of methyl 3-chloro-4-{[(2-hydroxyethyl)amino]carbonyl}-1H-pyrrole-2-carboxylate (0.048 g, 0.195 mmol) in THF (3 mL) and water (1 mL) was added lithium hydroxide (0.047 g, 1.946 mmol). The reaction mixture was stirred overnight at 35° C. The solvent was evaporated and the resulting solid placed under high vacuum. To the intermediate mixture was added DMF (1 mL), HATU (0.089 g, 0.234 mmol), DIPEA (0.051 ml, 0.292 mmol) and 3-{[3-(aminomethyl)-6-chloro-2-fluorophenyl]oxy}-5-chlorobenzonitrile (0.061 g, 0.195 mmol). The solution was stirred for 4 h at RT. Purification was accomplished by HPLC. The desired fractions were neutralized with saturated sodium bicarbonate, extracted with EtOAc (3×5 mL), the organic layers combined, dried over sodium sulfate, filtered and evaporated to afford 3-chloro-N²-({4-chloro-3-[(3-chloro-5-cyanophenyl)oxy]-2-fluorophenyl}methyl)-N⁴-(2-hydroxyethyl)-1H-pyrrole-2,4-dicarboxamide (0.039 g, 38% yield) as a white solid. ¹H NMR (400 MHz, DMSO-d₆): δ ppm 12.25 (br. s., 1H) 8.15 (t, 1H) 7.83 (d, 1H) 7.78 (t, 1H) 7.51-7.56 (m, 2H) 7.48 (dt, 2H) 7.37 (t, 1H) 4.57 (d, 2H) 3.46 (t, 2H) 3.25 (q, 2H). MS: m/z 525.0 (M+1).

Example 210

4,6-dichloro-N-({4-chloro-3-[(3-chloro-5-cyanophenyl)oxy]-2-fluorophenyl}methyl)-1H-indole-2-carboxamide

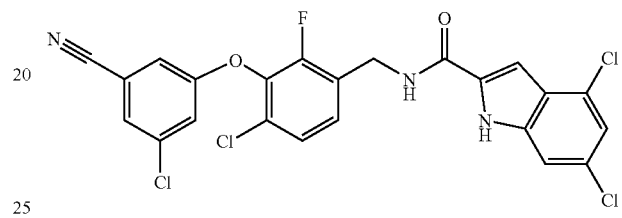

To a solution of 3-{[3-(aminomethyl)-6-chloro-2-fluorophenyl]oxy}-5-chlorobenzonitrile (0.050 g, 0.16 mmol) in dichloromethane (1.5 mL) was added 4,6-dichloro-1H-indole-2-carbonyl chloride (0.060 g, 0.24 mmol) and diisopropylethylamine (0.031 g, 0.24 mmol). The resulting suspension was stirred at RT for 45 min. The reaction mixture was diluted with dichloromethane and water. A solid precipitated which was filtered and dried under vacuum to give the title compound (0.069 g, 82%) as an off-white solid. ¹H NMR (400 MHz, DMSO-d₆) δ ppm 12.12 (br. s., 1H), 9.20 (br. s., 1H), 7.77-7.78 (m, 1H), 7.41-7.52 (m, 3H), 7.33-7.41 (m, 2H), 7.23-7.32 (m, 1H), 7.19-7.20 (m, 1H), 4.54 (s, 2H). ES-LCMS: m/z 522 (M−H).

Example 211

N-({4-chloro-3-[(3-chloro-5-cyanophenyl)oxy]-2-fluorophenyl}methyl)-5-[(N,N-dimethylglycyl)amino]-1H-indole-2-carboxamide

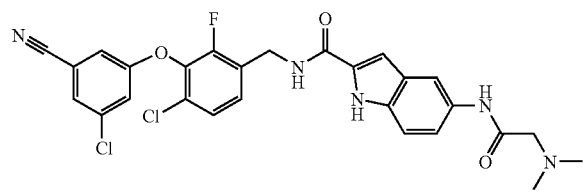

Step A: 1,1-dimethylethyl (2-{[({4-chloro-3-[(3-chloro-5-cyanophenyl)oxy]-2-fluorophenyl}methyl)amino]carbonyl}-1H-indol-5-yl)carbamate HATU (2.75 g, 7.23 mmol) was added to a solution of 3-{[3-(aminomethyl)-6-chloro-2-fluorophenyl]oxy}-5-chlorobenzonitrile (1.50 g, 4.82 mmol), 5-({[(1,1-dimethylethyl)oxy]carbonyl}amino)-1H-indole-2-carboxylic acid (1.33 g, 4.82 mmol) and diisopropylethylamine (1.26 mL, 7.23 mmol) in DMF (10 mL). The mixture was stirred at RT overnight. The reaction mixture was extracted with EtOAc and water and the organic layer was washed with water, dried over sodium sulfate and concentrated. The residue was purified by silica gel flash chromatography (5-50% EtOAc:hexane) to give an off-white solid which was triturated with EtOAc:hexane, filtered and dried to afford the title compound (1.36 g, 49%) as a white solid. ¹H NMR (400 MHz, DMSO-d₆) δ ppm 11.44 (s, 1H), 9.07 (br. s., 1H), 8.95 (t, 1H), 7.78 (s, 1H), 7.71 (br. s., 1H), 7.41-7.55 (m, 3H), 7.36 (t, 1H), 7.21-7.30 (m, 1H), 7.15 (d, 1H), 7.03 (s, 1H), 4.37-4.68 (m, 2H), 1.44 (s, 9H). ES-LCMS: m/z 569 (M+H).

Step B: 5-amino-N-({4-chloro-3-[(3-chloro-5-cyanophenyl)oxy]-2-fluorophenyl}methyl)-1H-indole-2-carboxamide trifluoroacetate Trifluoroacetic acid (5 mL, 64.9 mmol) was added to a solution of 1,1-dimethylethyl (2-{[({4-chloro-3-[(3-chloro-5-cyanophenyl)oxy]-2-fluorophenyl}methyl)amino]carbonyl}-1H-indol-5-yl)carbamate (1.36 g, 2.39 mmol) in dichloromethane (40 mL). The reaction mixture was stirred at RT overnight. The solvent was evaporated to give the title compound as a beige foam (1.35 g, 97%). ¹H NMR (400 MHz, DMSO-d₆) δ ppm 11.94 (s, 1H), 9.92 (br. s., 2H), 9.13 (t, 1H), 7.75-7.85 (m, 1H), 7.62 (d, 1H), 7.44-7.57 (m, 4H), 7.40 (t, 1H), 7.23 (d, 1H), 7.16 (dd, 1H), 4.57 (d, 2H). ES-LCMS: m/z 469 (M+H).

Step C: N-({4-chloro-3-[(3-chloro-5-cyanophenyl)oxy]-2-fluorophenyl}methyl)-5-[(N,N-dimethylglycyl)amino]-1H-indole-2-carboxamide BOP chloride (0.079 g, 0.309 mmol) was added to a solution of 5-amino-N-({4-chloro-3-[(3-chloro-5-cyanophenyl)oxy]-2-fluorophenyl}methyl)-1H-indole-2-carboxamide trifluoroacetate (0.060 g, 0.103 mmol), N,N-dimethylglycine (0.011 g, 0.103 mmol) and diisopropylethylamine (0.090 mL, 0.514 mmol) in DMF (1 mL). The mixture was stirred at RT for 1 hr. The reaction mixture was diluted with EtOAc and water. The organic layer was washed with water, dried over sodium sulfate, filtered and concentrated. The residue was triturated with methanol and dried under vacuum to give the title compound (0.016 g, 28%) as a white solid. ¹H NMR (400 MHz, DMSO-d₆) δ ppm 11.51 (br. s., 1H), 9.52 (br. s., 1H), 8.96 (t, 1H), 7.94 (s, 1H), 7.78 (s, 1H), 7.41-7.54 (m, 2H), 7.36 (t, 1H), 7.30 (s, 2H), 7.07 (s, 1H), 4.53 (d, 2H), 2.22 (s, 6H). ES MS: m/z 553 (M).

Example 212

N-({4-chloro-3-[(3-chloro-5-cyanophenyl)oxy]-2-fluorophenyl}methyl)-5-{[3-(1-piperidinyl)propanoyl]amino}-1H-indole-2-carboxamide trifluoroacetate BOP chloride (0.079 g, 0.309 mmol) was added to a solution of 5-amino-N-({4-chloro-3-[(3-chloro-5-cyanophenyl)oxy]-2-fluorophenyl}methyl)-1H-indole-2-carboxamide trifluoroacetate (0.060 g, 0.103 mmol), 3-(1-piperidinyl)propanoic acid (0.0162 g, 0.103 mmol) and diisopropylethylamine (0.090 mL, 0.514 mmol) in DMF (1 mL). The mixture was stirred at room temperature for 1 hr. The reaction mixture was extracted with ethyl acetate and water. The organic layer was washed with water, dried over sodium sulfate and concentrated. The residue was purified by reverse phase HPLC (acetonitrile:water with 0.% trifluoroacetic acid) to give 0.032 g (43%) of the title compound as a white solid. ¹H NMR (400 MHz, DMSO-d₆) δ ppm 11.56 (br. s., 1H), 10.01 (br. s., 1H), 9.01-9.18 (m, 1H), 8.97 (d, 1H), 7.92 (br. s., 1H), 7.68-7.84 (m, 1H), 7.40-7.56 (m, 2H), 7.27-7.41 (m, 2H), 7.15-7.28 (m, 1H), 7.08 (s, 1H), 4.36-4.68 (m, 2H), 3.22-3.48 (m, 4H), 2.67-2.98 (m, 4H), 1.72-1.87 (m, 2H), 1.48-1.71 (m, 3H), 1.20-1.43 (m, 1H). ES MS: m/z 608 (M+1).

Example 213

N-({4-chloro-3-[(3-chloro-5-cyanophenyl)oxy]-2-fluorophenyl}methyl)-5-({3-[(1,1-dimethylethyl)oxy]propanoyl}amino)-1H-indole-2-carboxamide

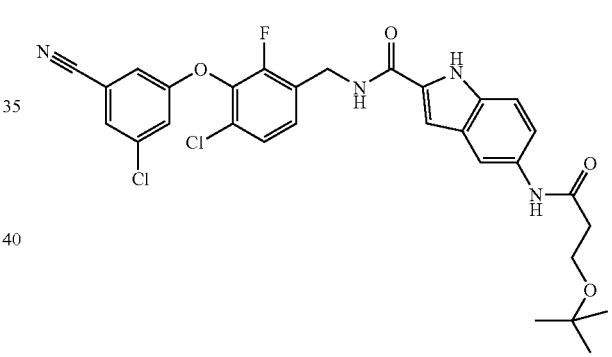

BOP chloride (0.079 g, 0.309 mmol) was added to a solution of 5-amino-N-({4-chloro-3-[(3-chloro-5-cyanophenyl)oxy]-2-fluorophenyl}methyl)-1H-indole-2-carboxamide trifluoroacetate (0.060 g, 0.103 mmol), 3-[(1,1-dimethylethyl)oxy]propanoic acid (0.015 mL, 0.103 mmol) and diisopropylethylamine (0.090 mL, 0.514 mmol) in DMF (1 mL). the mixture was stirred at room temperature for 1 hr. The reaction mixture was extracted with ethyl acetate and water.

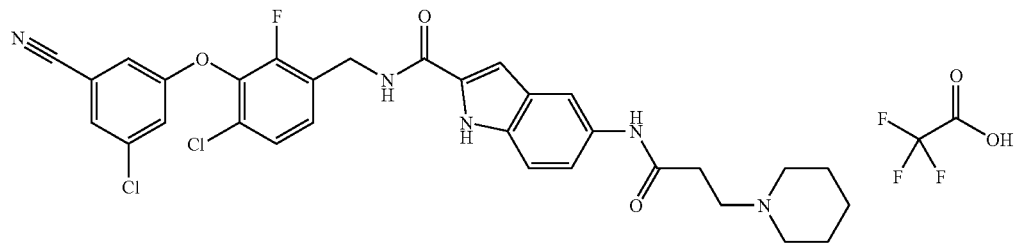

The organic layer was washed with water, dried over sodium sulfate and concentrated. The residue was purified by flash chromatography (hexane:ethyl acetate) to give the title compound (0.036 g, 58%) as a white solid. $^1$H NMR (400 MHz, DMSO-d$_6$) δ ppm 11.49 (s, 1H), 9.69 (s, 1H), 8.95 (t, 1H), 7.95 (s, 1H), 7.77 (d, 1H), 7.40-7.52 (m, 3H), 7.36 (t, 1H), 7.26-7.32 (m, 1H), 7.21 (d, 1H), 7.06 (s, 1H), 4.52 (d, 2H), 3.57 (t, 2H), 2.41 (t, 2H), 1.09 (s, 9H). ES MS: m/z 597 (M+1).

Example 214

N-({4-chloro-3-[(3-chloro-5-cyanophenyl)oxy]-2-fluorophenyl}methyl)-5-({[(2-{[2-(methyloxy)ethyl]oxy}ethyl)oxy]acetyl}amino)-1H-indole-2-carboxamide

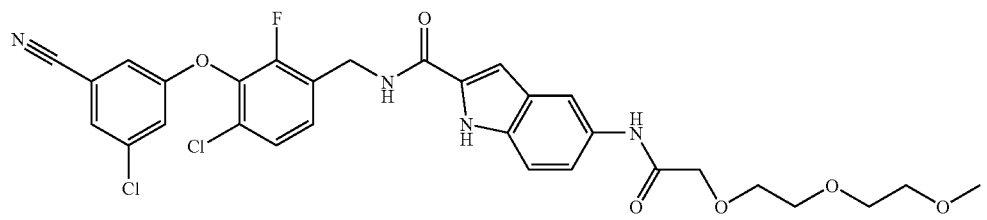

BOP chloride (0.079 g, 0.309 mmol) was added to a solution of 5-amino-N-({4-chloro-3-[(3-chloro-5-cyanophenyl)oxy]-2-fluorophenyl}methyl)-1H-indole-2-carboxamide trifluoroacetate (0.060 g, 0.103 mmol), [(2-{[2-(methyloxy)ethyl]oxy}ethyl)oxy]acetic acid (0.016 mL, 0.103 mmol) and diisopropylethylamine (0.090 mL, 0.514 mmol) in DMF (1 mL). The mixture was stirred at room temperature for 1 hr. The reaction mixture was diluted with ethyl acetate and water. The organic layer was washed with water, dried over sodium sulfate and concentrated. The residue was purified by reverse phase HPLC (acetonitrile:water with 0.1% trifluoroacetic acid) to give the title compound (0.027 g, 42%) as a white solid. $^1$H NMR (400 MHz, DMSO-d$_6$) δ ppm 11.54 (s, 1H), 9.39 (s, 1H), 8.97 (t, 1H), 7.92 (s, 1H), 7.78 (s, 1H), 7.49 (d, 1H), 7.46 (s, 1H), 7.42-7.45 (m, 1H), 7.33-7.40 (m, 1H), 7.31 (s, 2H), 7.09 (d, 1H), 4.53 (d, 2H), 4.02 (s, 2H), 3.61-3.66 (m, 2H), 3.56-3.60 (m, 2H), 3.53 (dd, 2H), 3.38-3.44 (m, 2H), 3.19 (s, 3H). ES MS: m/z 629 (M+1).

Example 215

N-({4-chloro-3-[(3-chloro-5-cyanophenyl)oxy]-2-fluorophenyl}methyl)-5-[(4-piperidinylcarbonyl)amino]-1H-indole-2-carboxamide trifluoroacetate Step A: 1,1-dimethylethyl 4-{[(2-{[({4-chloro-3-[(3-chloro-5-cyanophenyl)oxy]-2-fluorophenyl}methyl)amino]carbonyl}-1H-indol-5-yl)amino]carbonyl}-1-piperidinecarboxylate BOP chloride (0.079 g, 0.309 mmol) was added to a solution of 5-amino-N-({4-chloro-3-[(3-chloro-5-cyanophenyl)oxy]-2-fluorophenyl}methyl)-1H-indole-2-carboxamide trifluoroacetate (0.060 g, 0.103 mmol), 1-{[(1,1-dimethylethyl)oxy]carbonyl}-4-piperidinecarboxylic acid (0.0236 g, 0.103 mmol) and diisopropylethylamine (0.090 mL, 0.514 mmol) in DMF (1 mL). The mixture was stirred at room temperature for 1 hr. The reaction mixture was extracted with ethyl acetate and water. The organic layer was washed with water, dried over sodium sulfate and concentrated. The residue was purified by flash chromatography with hexane:ethyl acetate to give the title compound (0.029 g, 41%) as a white solid. $^1$H NMR (400 MHz, DMSO-d$_6$) δ ppm 11.50 (br. s., 1H), 9.72 (br. s., 1H), 8.95 (br. s., 1H), 7.95 (s, 1H), 7.78 (s, 1H), 7.41-7.52 (m, 2H), 7.36 (t, 1H), 7.25-7.32 (m, 1H), 7.21 (d, 1H), 7.06 (br. s., 1H), 4.52 (d, 2H), 3.85-4.17 (m, 2H), 2.58-2.94 (m, 2H), 1.63-1.85 (m, 2H), 1.41-1.53 (m, 2H), 1.36 (s, 9H). ES MS: m/z 680 (M+1).

Step B: N-({4-chloro-3-[(3-chloro-5-cyanophenyl)oxy]-2-fluorophenyl}methyl)-5-[(4-piperidinylcarbonyl)amino]-1H-indole-2-carboxamide trifluoroacetate Trifluoroacetic acid (0.5 mL, 6.49 mmol) was added to a suspension of 1,1-dimethylethyl-4-{[(2-{[({4-chloro-3-[(3-chloro-5cyanophenyl)oxy]-2-fluorophenyl}methyl)amno]carbonyl}-1H-indol-5-yl)amino]carbonyl}-1-piperidinecarboxylate (0.025 g, 0.037 mmol) in dichloromethane (1 mL). The resulting solution was stirred at room temperature for 1 hr. The solvent was evaporated to give the title compound (0.023 g, 90%) as a beige solid. $^1$H NMR (400 MHz, DMSO-d$_6$) δ ppm 11.53 (s, 1H), 9.84 (s, 1H), 8.97 (t, 1H), 8.42-8.61 (m, 1H), 8.20-8.37 (m, 1H), 7.93 (s, 1H), 7.78 (d, 1H), 7.40-7.53 (m, 2H), 7.36 (t, 1H), 7.26-7.33 (m, 1H), 7.17-7.25 (m, 1H), 7.07 (s, 1H), 4.52 (d, 2H), 3.24-3.42 (m, 2H), 2.75-3.05 (m, 2H), 2.51-2.67 (m, 1H), 1.85-2.04 (m, 2H), 1.61-1.85 (m, 2H). ES MS: m/z 580 (M+1).

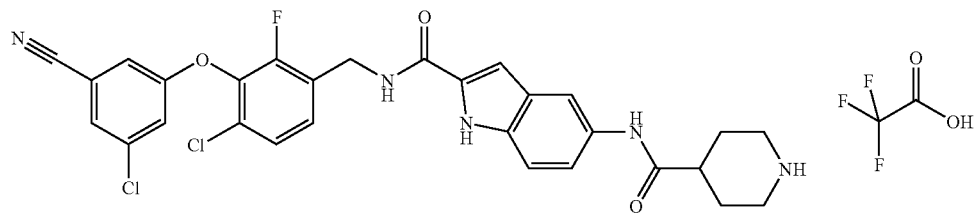

Example 216

N-({4-chloro-3-[(3-chloro-5-cyanophenyl)oxy]-2-fluorophenyl}methyl)-5-{[(2S)-2-piperidinylcarbonyl]amino}-1H-indole-2-carboxamide

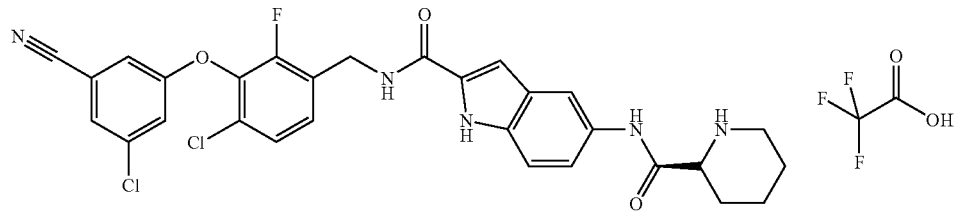

Step A: 1,1-dimethylethyl (2S)-2-{[(2-{[({4-chloro-3-[(3-chloro-5-cyanophenyl)oxy]-2-fluorophenyl}methyl)amino]carbonyl}-indol-5-yl)amino]carbonyl}-1-piperidinecarboxylate BOP chloride (0.079 g, 0.309 mmol) was added to a solution of 5-amino-N-({4-chloro-3-[(3-chloro-5-cyanophenyl)oxy]-2-fluorophenyl}methyl)-1H-indole-2-carboxamide trifluoroacetate (0.060 g, 0.103 mmol), (2S)-1-{[(1,1-dimethylethyl)oxy]carbonyl}-2-piperidinecarboxylic acid (0.0236 g, 0.103 mmol) and diisopropylethylamine (0.090 mL, 0.514 mmol) in DMF (1 mL). The mixture was stirred at room temperature for 1 hr. The reaction mixture was extracted with ethyl acetate and water. The organic layer was washed with water, dried over sodium sulfate and concentrated. The residue was purified by flash chromatography with hexane:ethyl acetate to give the partially pure (~85%) compound (0.028 g) as a clear resin.

Step B: N-({4-chloro-3-[(3-chloro-5-cyanophenyl)oxy]-2-fluorophenyl}methyl)-5-{[(2S)-2-piperidinylcarbonyl]amino}-1H-indole-2-carboxamide trifluoroacetate To a solution of 1,1-dimethylethyl (2S)-2-{[(2-{[({4-chloro-3-[(3-chloro-5-cyanophenyl)oxy]-2-fluorophenyl}methyl)amino]carbonyl}-1H-indol-5-yl)amino]carbonyl}-1-piperidinecarboxylate (0.025 g, 0.036 mmol) in dichloromethane (1 mL) was added trifluoroacetic acid (0.5 mL, 6.49 mmol). The mixture was stirred at room temperature for 1 hr. The solvent was evaporated and the residue was purified by reverse phase HPLC (acetonitrile:water with 0.1% TFA) to give the title compound (0.012 g, 47%) as a white solid. $^1$H NMR (400 MHz, DMSO-$d_6$) δ ppm 11.63 (br. s., 1H), 10.29 (s, 1H), 8.94-9.03 (m, 1H), 8.82-8.94 (m, 1H), 8.62-8.79 (m, 1H), 7.90 (s, 1H), 7.78 (s, 1H), 7.41-7.52 (m, 2H), 7.30-7.41 (m, 1H), 7.24 (d, 1H), 7.11 (s, 1H), 4.53 (d, 2H), 3.74-3.88 (m, 1H), 3.16-3.31 (m, 1H), 2.85-3.02 (m, 1H), 2.10-2.24 (m, 1H), 1.74-1.88 (m, 1H), 1.41-1.75 (m, 4H). ES MS: m/z 580 (M+1).

Example 217

N-({4-chloro-3-[(3-chloro-5-cyanophenyl)oxy]-2-fluorophenyl}methyl)-5-[(N,N-dimethyl-b-alanyl)amino]-1H-indole-2-carboxamide trifluoroacetate

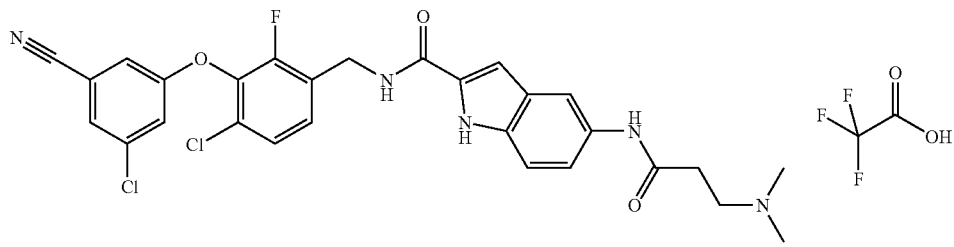

BOP chloride (0.079 g, 0.309 mmol) was added to a solution of 5-amino-N-({4-chloro-3-[(3-chloro-5-cyanophenyl)oxy]-2-fluorophenyl}methyl)-1H-indole-2-carboxamide trifluoroacetate (0.060 g, 0.103 mmol), N,N-dimethyl-beta-alanine (0.016 g, 0.103 mmol) and diisopropylethylamine (0.11 mL, 0.617 mmol) in DMF (1 mL). the mixture was stirred at room temperature for 1 hr. The reaction mixture was diluted with ethyl acetate and water. The organic layer was washed with water, dried over sodium sulfate and concentrated. The residue was triturated with methanol to give a white solid. Purification by reverse phase HPLC (acetonitrile:water with 0.1% TFA) gave the title compound (0.024 g, 34%) as a white solid. $^1$H NMR (400 MHz, DMSO-$d_6$) δ ppm 11.56 (s, 1H), 10.04 (s, 1H), 9.17-9.45 (m, 1H), 8.96 (t, 1H), 7.92 (s, 1H), 7.78 (s, 1H), 7.42-7.50 (m, 2H), 7.29-7.40 (m, 2H), 7.23 (d, 1H), 7.08 (s, 1H), 4.53 (d, 2H), 3.31-3.39 (m, 2H), 2.71-2.82 (m, 8H). ES MS: m/z 568 (M+1).

Example 218

N-({4-chloro-3-[(3-chloro-5-cyanophenyl)oxy]-2-fluorophenyl}methyl)-5-[(3-hydroxypropanoyl)amino]-1H-indole-2-carboxamide

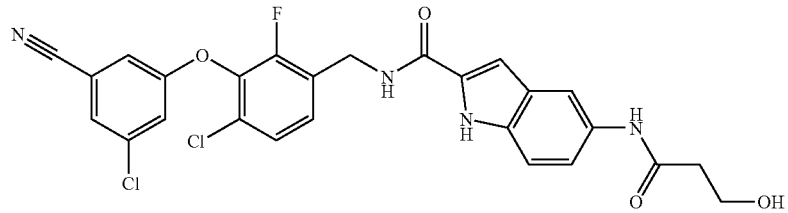

Step A: N-({4-chloro-3-[(3-chloro-5-cyanophenyl)oxy]-2-fluorophenyl}methyl)-5-({3-[(1,1-dimethylethyl)oxy]propanoyl}amino)-1H-indole-2-carboxamide.

BOP chloride (0.079 g, 0.309 mmol) was added to a solution of 5-amino-N-({4-chloro-3-[(3-chloro-5-cyanophenyl)oxy]-2-fluorophenyl}methyl)-1H-indole-2-carboxamide trifluoroacetate (0.060 g, 0.103 mmol), 3-[(1,1-dimethylethyl)oxy]propanoic acid (0.015 mL, 0.103 mmol) and diisopropylethylamine (0.090 mL, 0.514 mmol) in DMF (1 mL). The mixture was stirred at room temperature for 2 hr. The reaction mixture was extracted with ethyl acetate and water. The organic layer was washed with water, dried over sodium sulfate and concentrated. The residue was purified by flash chromatography (hexane:ethyl acetate) to give the title compound (0.041 g, 67%) as a white solid. ES MS: m/z 597 (M+1).

Step B: N-({4-chloro-3-[(3-chloro-5-cyanophenyl)oxy]-2-fluorophenyl}methyl)-5-[(3-hydroxypropanoyl)amino]-1H-indole-2-carboxamide N-({4-chloro-3-[(3-chloro-5-cyanophenyl)oxy]-2-fluorophenyl}methyl)-5-({3-[(1,1-dimethylethyl)oxy]propanoyl}amino)-1H-indole-2-carboxamide (0.040 g, 0.067 mmol) was dissolved in 4N HCl in dioxane (3 mL). The solution was heated at 100° C. overnight. The reaction mixture was cooled to room temperature and the solvent was evaporated. The residue was purified by reverse phase HPLC (acetonitrile:water with 0.1% TFA) to give the title compound (0.007 g, 19%) as a white powder. $^1$H NMR (400 MHz, DMSO-$d_6$) δ ppm 11.49 (br. s., 1H), 9.70 (s, 1H), 8.67-9.07 (m, 1H), 7.95 (s, 1H), 7.77 (s, 1H), 7.42-7.53 (m, 2H), 7.37 (d, 1H), 7.25-7.32 (m, 1H), 7.19-7.25 (m, 1H), 7.06 (s, 1H), 4.52 (d, 2H), 3.62-3.73 (m, 2H), 3.51-3.60 (m, 1H), 2.40 (t, 2H). ES MS: m/z 541 (M+1).

Example 219

N-({4-chloro-3-[(3-chloro-5-cyanophenyl)oxy]-2-fluorophenyl}methyl)-5-(glycylamino)-1H-indole-2-carboxamide trifluoroacetate

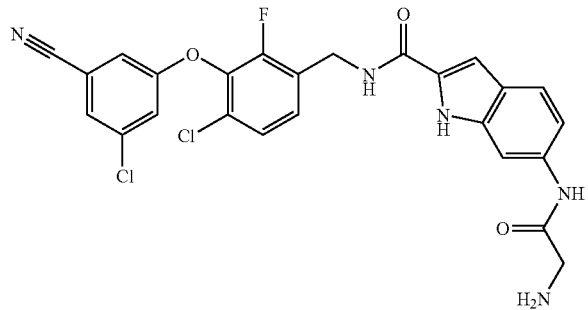

-continued

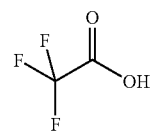

Step A: 1,1-dimethylethyl {2-[(2-{[({4-chloro-3-[(3-chloro-5-cyanophenyl)oxy]-2-fluorophenyl}methyl)amino]carbonyl}-1H-indol-5-yl)amino]-2-oxoethyl}carbamate BOP chloride (0.085 g, 0.334 mmol) was added to a solution of 6-amino-N-({4-chloro-3-[(3-chloro-5-cyanophenyl)oxy]-2-fluorophenyl}methyl)-1H-indole-2-carboxamide (0.065 g, 0.111 mmol), N-{[(1,1-dimethylethyl)oxy]carbonyl}glycine (0.0195 g, 0.111 mmol) and diisopropylethylamine (0.097 mL, 0.557 mmol) in DMF (1 mL). The mixture was stirred at room temperature for 1 hr, then extracted with ethyl acetate and water. The organic layer was washed with water, dried over sodium sulfate and concentrated. The residue was purified by flash chromatography (hexane:ethyl acetate) to give the title compound (0.031 g, 80% pure). ES MS: m/z 624 (M−1).

Step B: N-({4-chloro-3-[(3-chloro-5-cyanophenyl)oxy]-2-fluorophenyl}methyl)-6-(glycylamino)-1H-indole-2-carboxamide trifluoroacetate Trifluoroacetic acid (0.5 mL, 6.49 mmol) was added to a suspension of 1,1-dimethylethyl {2-[(2-{[({4-chloro-3-[(3-chloro-5-cyanophenyl)oxy]-2-fluorophenyl}methyl)amino]carbonyl}-1H-indol-5-yl)amino]-2-oxoethyl}carbamate (0.039 g, 0.062 mmol) in dichloromethane (1 mL). The resulting solution was stirred at room temperature overnight. The solvent was evaporated and the residue was purified by reverse phase HPLC (acetonitrile:water with 0.1% TFA) to give the title compound (0.020 g, 50%) as a white solid. $^1$H NMR (400 MHz, DMSO-$d_6$) δ ppm 11.60 (d, 1H), 10.37 (br. s., 1H), 8.75-9.21 (m, 1H), 8.01-8.18 (m, 3H), 7.92 (br. s., 1H), 7.81 (br. s., 1H), 7.53-7.61 (m, 1H), 7.43-7.54 (m, 2H), 7.33-7.43 (m, 1H), 7.13 (br. s., 1H), 5.74 (br. s., 1H), 4.31-4.69 (m, 2H), 3.61-3.94 (m, 2H). ES MS: m/z 526 (M+1).

Example 220

N-({4-chloro-3-[(3-chloro-5-cyanophenyl)oxy]-2-fluorophenyl}methyl)-6-({3-[(1,1-dimethylethyl)oxy]propanoyl}amino)-1H-indole-2-carboxamide

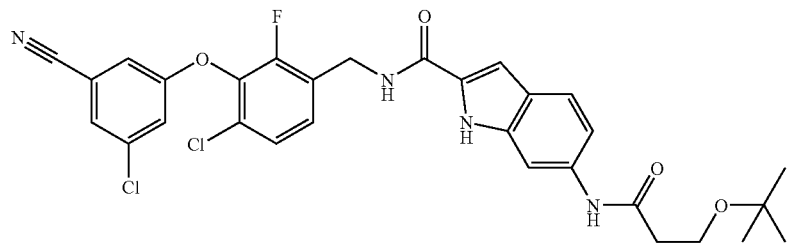

Step A: 1-(1,1-dimethylethyl)2-ethyl 6-nitro-1H-indole-1,2-dicarboxylate

Di-tert-butyl dicarbonate (2.139 g, 9.80 mmol) and N,N-dimethylaminopyridine (0.798 g, 6.53 mmol) were added to a solution of ethyl 6-nitro-1H-indole-2-carboxylate (1.53 g, 6.53 mmol) in dichloromethane (25 mL). The mixture was stirred at room temperature for 2 hrs. The solvent was evaporated to give the title compound as a tan solid (1.19 g, 54%). $^1$H NMR (400 MHz, CHLOROFORM-d) δ ppm 9.03 (d, 1H), 8.16 (dd, 1H), 7.70 (d, 1H), 7.10 (s, 1H), 4.42 (q, 2H), 1.67 (s, 9H), 1.37-1.45 (m, 3H).

Step B: 1-(1,1-dimethylethyl)2-ethyl 6-amino-1H-indole-1,2-dicarboxylate

Platinum (IV) oxide (0.039 g, 0.173 mmol) was added to a suspension of 1-(1,1-dimethylethyl)2-ethyl 6-nitro-1H-indole-1,2-dicarboxylate (1.16 g, 3.47 mmol) in ethanol (40 mL) in a pressure vessel. The mixture was evacuated and flushed with nitrogen, then with hydrogen (50 psi) and stirred for 1 hr. The reaction mixture was filtered through Celite and the solvent was evaporated. The residue was purified by flash chromatography (hexane:ethyl acetate) to give the title compound (0.796 g, 75%) as a yellow solid. $^1$H NMR (400 MHz, chloroform-d) δ ppm 7.37 (d, 1H), 7.32 (d, 1H), 7.01 (s, 1H), 6.61 (dd, 1H), 4.31 (q, 2H), 1.60 (s, 9H), 1.35 (t, 3H).

Step C: 1-(1,1-dimethylethyl)2-ethyl 6-({3-[(1,1-dimethylethyl)oxy]propanoyl}amino)-1H-indole-1,2-dicarboxylate BOP chloride (0.251 g, 0.986 mmol) was added to a solution of -(1,1-dimethylethyl) 2-ethyl 6-amino-1H-indole-1,2-dicarboxylate (0.100 g, 0.329 mmol), 3-[(1,1-dimethylethyl)oxy]propanoic acid (0.048 g, 0.329 mmol) and diisopropylethylamine (0.29 mL, 1.643 mmol) in DMF (2 mL). After 1 hr, the reaction mixture was extracted with ethyl acetate and water. The organic layer was washed with water, dried over sodium sulfate and concentrated. The residue was purified by flash chromatography (hexane:ethyl acetate) to give the title compound (0.070 g, 49%) as an off-white solid. $^1$H NMR (400 MHz, chloroform-d) δ ppm 8.96 (s, 1H), 8.49 (s, 1H), 7.49 (d, 1H), 7.18-7.30 (m, 1H), 4.36 (q, 2H), 3.72 (t, 2H), 2.63 (t, 2H), 1.65 (s, 9H), 1.37 (t, 3H), 1.29 (s, 9H). ES MS: m/z 433 (M+1).

Step D: 1-{[(1,1-dimethylethyl)oxy]carbonyl}-6-({3-[(1,1-dimethylethyl)oxy]propanoyl}amino)-1H-indole-2-carboxylic acid Lithium hydroxide (0.037 g, 1.55 mmol) was added to a solution of 1-(1,1-dimethylethyl)2-ethyl 6-({3-[(1,1-dimethylethyl)oxy]propanoyl}amino)-1H-indole-1,2-dicarboxylate (0.067 g, 0.155 mmol) in THF:methanol:water/3:1:1 (3 mL). The mixture was heated at 50° C. for 1 hr. The solvent was evaporated and the residue was dissolved in water, acidified with 1N aqueous HCl and extracted with ethyl acetate. The organic layer was dried over sodium sulfate and concentrated to give the title compound (0.051 g, 108%) as a white solid. $^1$H NMR (400 MHz, DMSO-d$_6$) δ ppm 11.40 (br. s., 1H), 9.82 (s, 1H), 7.94 (s, 1H), 7.44 (d, 1H), 7.04 (d, 1H), 6.85 (s, 1H), 3.57 (t, 2H), 2.33-2.48 (m, 2H), 1.09 (s, 9H). ES MS: m/z 305 (M+1).

Step E: N-({4-chloro-3-[(3-chloro-5-cyanophenyl)oxy]-2-fluorophenyl}methyl)-6-({3-[(1,1-dimethylethyl)oxy]propanoyl}amino)-1H-indole-2-carboxamide HATU (0.090 g, 0.237 mmol) was added to a solution of 3-{[3-(aminomethyl)-6-chloro-2-fluorophenyl]oxy}-5-chlorobenzonitrile (0.0491 g, 0.158 mmol), 1-{[(1,1-dimethylethyl)oxy]carbonyl}-6-({3-[(1,1-dimethylethyl)oxy]propanoyl}amino)-1H-indole-2-carboxylic acid (0.048 g, 0.158 mmol) and diisopropylethylamine (0.041 mL, 0.237 mmol) in DMF (1 mL). The mixture was stirred at room temperature overnight. The reaction mixture was extracted with ethyl acetate and water. The organic layer was washed with water, dried over sodium sulfate and concentrated. The residue was purified by flash chromatography (hexane:ethyl acetate) to give the title compound (0.055 g, 58%) as an off-white solid. $^1$H NMR (400 MHz, DMSO-d$_6$) δ ppm 11.47 (s, 1H), 9.81 (s, 1H), 8.89 (t, 1H), 7.94 (s, 1H), 7.78 (s, 1H), 7.39-7.53 (m, 4H), 7.36 (t, 1H), 7.03-7.12 (m, 2H), 4.52 (d, 2H), 3.57 (t, 2H), 2.36-2.49 (m, 2H), 1.10 (s, 9H). ES MS: m/z 597 (M+1).

Example 221

N-({4-chloro-3-[(3-chloro-5-cyanophenyl)oxy]-2-fluorophenyl}methyl)-6-[(3-hydroxypropanoyl)amino]-1H-indole-2-carboxamide

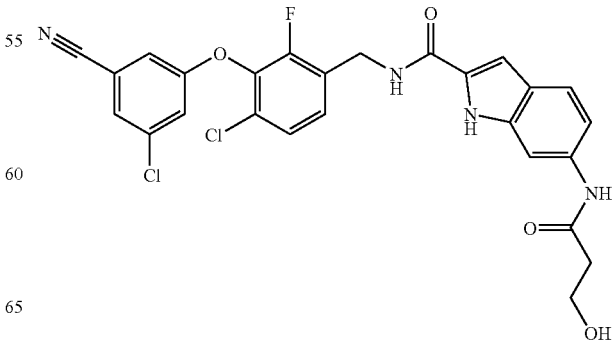

N-({4-chloro-3-[(3-chloro-5-cyanophenyl)oxy]-2-fluorophenyl}methyl)-6-({3-[(1,1-dimethylethyl)oxy]propanoyl}amino)-1H-indole-2-carboxamide (0.049 g, 0.082 mmol) was dissolved in 4N HCl in dioxane (3 mL). The mixture was heated in a 105° C. oil bath under a reflux condenser for 3 days. The solvent was evaporated and the residue was purified by reverse phase HPLC (acetonitrile:water with 0.1% TFA) to give the title compound (0.009 g, 20%) as a white solid. $^1$H NMR (400 MHz, DMSO-$d_6$) δ ppm 11.48 (br. s., 1H), 9.82 (s, 1H), 8.69-9.06 (m, 1H), 7.91-7.99 (m, 1H), 7.78 (s, 1H), 7.42-7.56 (m, 4H), 7.35 (t, 1H), 7.08 (d, 2H), 4.30-4.70 (m, 2H), 3.54-3.82 (m, 2H), 2.39-2.46 (m, 2H). ES MS: m/z 541 (M+1).

Example 222

N-({4-chloro-3-[(3-chloro-5-cyanophenyl)oxy]-2-fluorophenyl}methyl)-6-[(methylsulfonyl)amino]-1H-indole-2-carboxamide

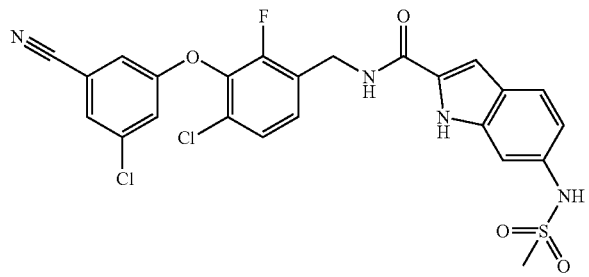

Step A: 1-(1,1-dimethylethyl)2-ethyl 6-[(methylsulfonyl)amino]-1H-indole-1,2-dicarboxylate Methanesulfonic anhydride (0.057 g, 0.329 mmol) was added to a solution of 1-(1,1-dimethylethyl)2-ethyl 6-amino-1H-indole-1,2-dicarboxylate (0.100 g, 0.329 mmol) and pyridine (0.027 mL, 0.334 mmol) in dichloromethane (5 mL), while stirring and cooling in an ice bath. The cooling bath was removed and stirring was continued at room temperature for 1 hr. The reaction mixture was diluted with dichloromethane and washed with 1N aqueous HCl. The organic layer was dried over sodium sulfate and concentrated. The residue was purified by flash chromatography (hexane:ethyl acetate) to give the title compound (0.118 g, 94%). $^1$H NMR (400 MHz, chloroform-d) δ ppm 8.02 (s, 1H), 7.54 (d, 1H), 7.14-7.21 (m, 1H), 7.13 (s, 1H), 7.07 (s, 1H), 4.37 (q, 2H), 3.03 (s, 3H), 1.63 (s, 9H), 1.38 (t, 3H). ES MS: m/z 381 (M−1).

Step B: 1-{[(1,1-dimethylethyl)oxy]carbonyl}-6-[(methylsulfonyl)amino]-1H-indole-2-carboxylic acid Lithium hydroxide (0.068 g, 2.85 mmol) was added to a solution of 1-(1,1-dimethylethyl)2-ethyl 6-[(methylsulfonyl)amino]-1H-indole-1,2-dicarboxylate (0.109 g, 0.285 mmol) in THF:methanol:water/3:1:1 (3 mL). The mixture was heated at 50° C. for 2 hrs. The solvent was evaporated and the residue was dissolved in water, acidified with 1N aqueous HCl and extracted with ethyl acetate. The organic layer was washed with water, dried over sodium sulfate and concentrated to give the title compound (0.040 g, 55%) as a white solid. $^1$H NMR (400 MHz, DMSO-$d_6$) δ ppm 12.92 (br. s., 1H), 11.41-11.79 (m, 1H), 9.32-9.73 (m, 1H), 7.48-7.57 (m, 1H), 7.31 (s, 1H), 6.94-7.00 (m, 1H), 6.88-6.94 (m, 1H), 2.88 (s, 3H). ES MS: m/z 253 (M−1).

Step C: N-({4-chloro-3-[(3-chloro-5-cyanophenyl)oxy]-2-fluorophenyl}methyl)-6-[(methylsulfonyl)amino]-1H-indole-2-carboxamide HATU (0.083 g, 0.218 mmol) was added to a solution of 3-{[3-(aminomethyl)-6-chloro-2-fluorophenyl]oxy}-5-chlorobenzonitrile (0.045 g, 0.146 mmol), 1-{[(1,1-dimethylethyl)oxy]carbonyl}-6-[(methylsulfonyl)amino]-1H-indole-2-carboxylic acid (0.037 g, 0.146 mmol) and diisopropylethylamine (0.038 mL, 0.218 mmol) in DMF (1 mL). The mixture was stirred at room temperature overnight. The reaction mixture was extracted with ethyl acetate and water. The organic layer wa sdired over sodium sulfate and concentrated. The residue was triturated with methanol to give the title compound (0.036 g, 45%) as a beige solid. $^1$H NMR (400 MHz, DMSO-$d_6$) δ ppm 11.56 (s, 1H), 9.53 (br. s., 1H), 8.94 (t, 1H), 7.78 (s, 1H), 7.52 (d, 1H), 7.48 (br. s., 1H), 7.45 (d, 1H), 7.35 (t, 1H), 7.31 (s, 1H), 7.10 (s, 1H), 6.91 (dd, 1H), 4.52 (d, 2 H), 2.87 (s, 3H). ES MS: m/z 547 (M+1).

Example 223

5-amino-3-chloro-N-({4-chloro-3-[(3-chloro-5-cyanophenyl)oxy]-2-fluorophenyl}methyl)-1H-indole-2-carboxamide trifluoroacetate

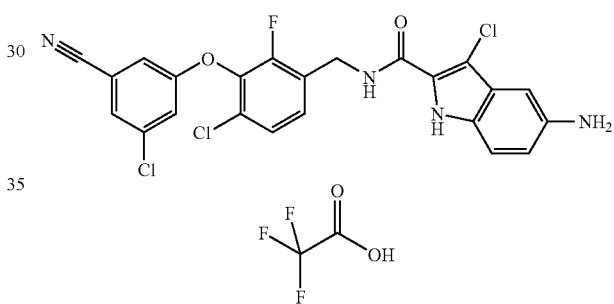

Step A: Ethyl 3-chloro-5-({[(1,1-dimethylethyl)oxy]carbonyl}amino)-1H-indole-2-carboxylate N-Chlorosuccinimide (0.044 g, 0.329 mmol) to a suspension of ethyl 5-({[(1,1-dimethylethyl)oxy]carbonyl}amino)-1H-indole-2-carboxylate (0.100 g, 0.329 mmol) in dichloromethane (5 mL). Methanol (2 mL) was added to complete solution. The mixture was stirred at room temperature overnight. The solvent was evaporated, the residue was dissolved in ethyl acetate and washed with water. The organic layer was dried over sodium sulfate and concentrated. The residue was purified by flash chromatography (hexane:ethyl acetate) to give the title compound (0.082 g, 74%). $^1$H NMR (400 MHz, DMSO-$d_6$) δ ppm 11.93 (s, 1H), 9.31 (br. s., 1H), 7.80 (br. s., 1H), 7.28-7.32 (m, 2H), 4.31 (q, 2H), 1.44 (s, 9H), 1.25-1.35 (m, 3H).

Step B: 3-chloro-5-({[(1,1-dimethylethyl)oxy]carbonyl}amino)-1H-indole-2-carboxylic acid Lithium hydroxide (0.032 g, 1.344 mmol) was added to a solution of ethyl 3-chloro-5-({[(1,1-dimethylethyl)oxy]carbonyl}amino)-1H-indole-2-carboxylate (0.059, 0.17 mmol) in THF:methanol:water/3:1:1 (3 mL). The mixture was stirred at room temperature overnight. The solvent was evaporated and the residue was dissolved in water, acidified with 1N aqueous HCl and extracted with ethyl acetate. The organic layer was dried over sodium sulfate and concentrated to give the title compound (0.054 g, ~75% pure).

Step C: 1,1-dimethylethyl (3-chloro-2-{[({4-chloro-3-[(3-chloro-5-cyanophenyl)oxy]-2-fluorophenyl}methyl)amino]carbonyl}-1H-indol-5-yl)carbamate HATU (0.119 g, 0.314 mmol) was added to a solution of 3-{[3-(aminomethyl)-6-chloro-2-fluorophenyl]oxy}-5-chlorobenzonitrile (0.055 g, 0.209 mmol), 3-chloro-5-({[(1,1-dimethylethyl)oxy]carbonyl}amino)-1H-indole-2-carboxylic acid (0.065 g, 0.209 mmol) and diisopropylethylamine (0.055 mL, 0.314 mmol) in DMF (1 mL). The mixture was stirred at room temperature overnight. The reaction mixture was extracted with ethyl acetate and water. The organic layer was washed with water, dried over sodium sulfate and concentrated. The residue was triturated with methanol to give the title compound (0.033 g, 26%). $^1$H NMR (400 MHz, DMSO-$d_6$) δ ppm 11.75 (s, 1H), 9.28 (br. s., 1H), 8.44 (t, 1H), 7.78 (br. s., 2H), 7.48 (d, 2H), 7.35-7.45 (m, 2H), 7.26-7.32 (m, 1H), 7.19-7.26 (m, 1H), 4.58 (d, 2H), 1.42 (s, 9H). ES MS: m/z 601 (M−1).

Step D: 5-amino-3-chloro-N-({4-chloro-3-[(3-chloro-5-cyanophenyl)oxy]-2-fluorophenyl}methyl)-1H-indole-2-carboxamide trifluoroacetate Trifluoroacetic acid (0.5 mL, 6.49 mmol) was added to a suspension of 1,1-dimethylethyl (3-chloro-2-{[({4-chloro-3-[(3-chloro-5-cyanophenyl)oxy]-2-fluorophenyl}methyl)amino]carbonyl}-1H-indol-5-yl)carbamate (0.030 g, 0.050 mmol) in dichloromethane (3 mL). The resulting solution was stirred at room temperature overnight. The solvent was evaporated and the residue was purified by reverse phase HPLC (acetonitrile:water with 0.1% TFA) to give the title compound (0.021 g, 59%). $^1$H NMR (400 MHz, DMSO-$d_6$) δ ppm 11.98-12.29 (m, 1H), 8.80-9.68 (m, 2H), 8.53-8.63 (m, 1H), 7.78-7.85 (m, 1H), 7.39-7.57 (m, 5H), 7.31-7.39 (m, 1H), 7.09-7.20 (m, 1H), 4.41-4.89 (m, 2H). ES MS: m/z 503 (M+1).

Example 224

5-amino-3-bromo-N-({4-chloro-3-[(3-chloro-5-cyanophenyl)oxy]-2-fluorophenyl}methyl)-1H-indole-2-carboxamide trifluoroacetate

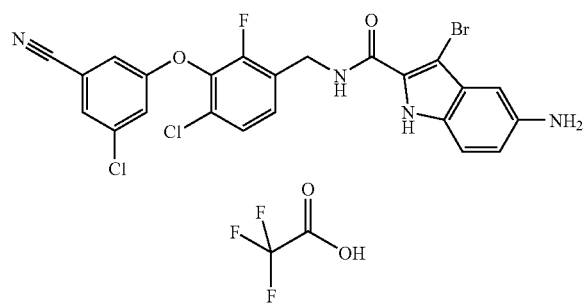

Step A: Ethyl 3-bromo-5-({[(1,1-dimethylethyl)oxy]carbonyl}amino)-1H-indole-2-carboxylate N-Bromosuccinimide (0.095 g, 0.536 mmol) was added to a solution of ethyl 5-({[(1,1-dimethylethyl)oxy]carbonyl}amino)-1H-indole-2-carboxylate (0.163 g, 0.536 mmol) in dichloromethane (5 mL). The mixture was stirred at room temperature overnight. The solvent was evaporated. The residue was taken up in ethyl acetate and washed with water. The organic layer was dried over sodium sulfate and concentrated to give the title compound (0.186 g, 48%) as an off-white solid. $^1$H NMR (400 MHz, chloroform-d) δ ppm 8.97 (br. s., 1H), 7.70 (s, 1H), 7.28-7.39 (m, 2H), 6.54 (br. s., 1H), 4.33-4.54 (m, 2H), 1.54 (s, 9H), 1.39-1.48 (m, 3H). ES MS: m/z 381, 383.

Step B: 3-bromo-5-({[(1,1-dimethylethyl)oxy]carbonyl}amino)-1H-indole-2-carboxylic acid Lithium hydroxide (0.113 g, 4.72 mmol) was added to a solution of ethyl 3-bromo-5-({[(1,1-dimethylethyl)oxy]carbonyl}amino)-1H-indole-2-carboxylate (0.181 g, 0.472 mmol) in THF:methanol:water/3:1:1 (5 mL). The mixture was stirred at room temperature overnight. The solvent was evaporated and the residue was taken up in water, acidified with 1 N aqueous HCl and extracted with ethyl acetate. The organic layer was dried over sodium sulfate and concentrated to give the title compound (0.151 g, 77%) as a beige solid. $^1$H NMR (400 MHz, DMSO-$d_6$) δ ppm 11.81 (br. s., 1H), 9.27 (br. s., 1H), 7.73 (br. s., 1H), 7.22-7.33 (m, 2H), 1.44-1.54 (m, 9H).

ES MS: m/z 352, 355.

Step C: 1,1-dimethylethyl (3-bromo-2-{[({4-chloro-3-[(3-chloro-5-cyanophenyl)oxy]-2-fluorophenyl}methyl)amino]carbonyl}-1H-indol-5-yl)carbamate HATU (0.231 g, 0.608 mmol) was added to a solution of 3-{[3-(aminomethyl)-6-chloro-2-fluorophenyl]oxy}-5-chlorobenzonitrile (0.126 g, 0.405 mmol), 3-bromo-5-({[(1,1-dimethylethyl)oxy]carbonyl}amino)-1H-indole-2-carboxylic acid (0.144 g, 0.405 mmol) and diisopropylethylamine (0.106 mL, 0.608 mmol) in DMF (3 mL). The mixture was stirred at room temperature for 1 hr. The reaction mixture was extracted with ethyl acetate and water. The organic layer was washed with water, dried over sodium sulfate and concentrated. The residue was triturated with methanol to give the title compound (0.086 g, 31%). $^1$H NMR (400 MHz, DMSO-$d_6$) δ ppm 11.84 (br. s., 1H), 9.27 (br. s., 1H), 8.45 (br. s., 1H), 7.66-7.84 (m, 2H), 7.38-7.56 (m, 4H), 7.17-7.34 (m, 2H), 4.57 (d, 2H), 1.14-1.62 (m, 9H).

Step D: 5-amino-3-bromo-N-({4-chloro-3-[(3-chloro-5-cyanophenyl)oxy]-2-fluorophenyl}methyl)-1H-indole-2-carboxamide trifluoroacetate Trifluoroacetic acid (0.5 mL, 6.49 mmol) was added to a suspension of 1,1-dimethylethyl (3-bromo-2-{[({4-chloro-3-[(3-chloro-5-cyanophenyl)oxy]-2-fluorophenyl}methyl)amino]carbonyl}-1H-indol-5-yl)carbamate (0.082 g, 0.126 mmol) in chloroform (2 mL). The resulting solution was stirred at room temperature overnight. The solvent was evaporated to give the title compound (0.100 g, 107%). $^1$H NMR (400 MHz, DMSO-$d_6$) δ ppm 12.34 (s, 1H), 9.86 (br. s., 2H), 8.66 (t, 1H), 7.78-7.84 (m, 1H), 7.56 (t, 1H), 7.41-7.52 (m, 5H), 7.25 (dd, 1H), 4.49-4.72 (m, 2H).

Example 225

3-chloro-N-{[4-chloro-2-fluoro-3-(1-naphthalenyloxy)phenyl]methyl}-1H-pyrrole-2-carboxamide

Step A: 1-[(2,3-difluoro-6-nitrophenyl)oxy]naphthalene

Sodium hydride (60% oil dispersion) (2.77 g, 69.4 mmol) was added to a solution of 1-naphthol (10.00 g, 69.4 mmol) in THF (200 mL) while cooling in an ice bath. The mixture was stirred at 0° C. for 30 min and 1,2,3-trifluoro-4-nitrobenzene (12.28 g, 69.4 mmol) was added and the mixture was allowed to warm to room temperature. After 2 hrs, the reaction mixture was poured into a mixture of ice and 10% aqueous HCl and was extracted with ethyl acetate. The organic layer was dried over sodium sulfate and the solvent was evaporated. The residue was purified by flash chromatography (hexane:ethyl acetate) to give the title compound (14.5 g, 69.4%). $^1$H NMR (400 MHz, chloroform-d) 6d ppm 8.31-8.45 (m, 1H), 7.82-7.99 (m, 2H), 7.54-7.66 (m, 3H), 7.30 (t, 1H), 7.17-7.26 (m, 1H), 6.61 (d, 1H).

Step B: bis(1,1-dimethylethyl) [2-fluoro-3-(1-naphthalenyloxy)-4-nitrophenyl]propanedioate Sodium hydride (60% oil dispersion) (4.07 g, 102 mmol) was added in portions to a solution of di-t-butyl malonate (11.01 g, 50.9 mmol) in THF (200 mL) at room temperature. After gas evolution ceased, 1-[(2,3-difluoro-6-nitrophenyl)oxy]naphthalene (13.94 g, 46.3 mmol), dissolved in THF (100 mL), was added. The reaction mixture was stirred at room temperature for 2 hrs and then poured on to ice and extracted with ethyl acetate. The organic layer was dried over sodium sulfate. The solvent was evaporated to give the title compound (26.59 g, 102%) as a yellow oil. $^1$H NMR (400 MHz, chloroform-d) δ ppm 8.33-8.44 (m, 1H), 7.83-7.95 (m, 2H), 7.51-7.65 (m, 4H), 7.23-7.34 (m, 1H), 6.60 (d, 1H), 4.82 (s, 1H), 1.49 (s, 18H). ESMS: m/z 497.

Step C: [2-fluoro-3-(1-naphthalenyloxy)-4-nitrophenyl]acetic acid

Trifluoroacetic acid (30 mL, 389 mmol) was added to a solution of bis(1,1-dimethylethyl) [2-fluoro-3-(1-naphthalenyloxy)-4-nitrophenyl]propanedioate (22.89, g, 46 mmol) in dichloromethane (250 mL). the mixture was heated under a reflux condenser at 45° C. for 4 hrs. The reaction mixture was cooled to room temperature and diluted with ethyl acetate and water. The organic layer was dried over sodium sulfate and concentrated to give the title compound (15.70 g, 100%). $^1$H NMR (400 MHz, chloroform-d) δ ppm 8.91 (br. s., 1H), 8.30-8.44 (m, 1H), 7.82-7.91 (m, 2 H), 7.51-7.62 (m, 3H), 7.21-7.35 (m, 2H), 6.58 (d, 1H), 3.82 (d, 2H). ES MS: m/z 340 (M−1).

Step D: 1-[(2-fluoro-3-methyl-6-nitrophenyl)oxy]naphthalene

Copper(I) oxide (1.258 g, 8.79 mmol) was added to a solution of [2-fluoro-3-(1-naphthalenyloxy)-4-nitrophenyl]acetic acid (15.70 g, 46 mmol) in acetonitrile (200 mL). The mixture was heated at 90° C. for 4 hrs. The reaction mixture was concentrated and the residue was purified by flash chromatography (hexane:ethyl acetate) to give the title compound (6.30 g, 36%). ES MS: m/z 298 (M+1), ~80% pure.

Step E: [3-fluoro-4-methyl-2-(1-naphthalenyloxy)phenyl]amine

A solution of sodium hydrosulfite (25.8 g, 125 mmol) in water (120 mL) was added dropwise to a solution of 1-[(2-fluoro-3-methyl-6-nitrophenyl)oxy]naphthalene (6.2 g, 20.86 mmol) in THF (60 mL) at room temperature. The mixture was stirred at room temperature for 2 hrs. The reaction mixture was extracted with ethyl acetate (3×50 mL) and the combined organic layers were washed with brine, dried over sodium sulfate and concentrated. The residue was purified by flash chromatography (hexane:ethyl acetate) to give the title compound (3.34 g, 60%) as a light tan oil. $^1$H NMR (400 MHz, chloroform-d) δ ppm 8.44-8.52 (m, 1H), 7.80-7.90 (m, 1H), 7.45-7.61 (m, 3H), 7.19-7.32 (m, 1H), 6.86 (t, 1H), 6.64 (d, 1H), 6.53 (dd, 1H), 3.59 (br. s., 2H), 2.19 (s, 3H). ES MS m/z 268 (M+1).

Step F: 1-[(6-chloro-2-fluoro-3-methylphenyl)oxy]naphthalene

To a suspension of copper(II) chloride (3.32 g, 24.69 mmol) in acetonitrile (15 mL) was added tert-butyl nitrite (3.67 mL, 30.9 mmol) dropwise at room temperature under nitrogen. After stirring for 5 min at room temperature, the mixture was heated in a 55° C. oil bath and [3-fluoro-4-methyl-2-(1-naphthalenyloxy)phenyl]amine (3.30 g, 12.35 mmol) was added dropwise. After complete addition, the reaction mixture was stirred at 55° C. for 5 min, then cooled to room temperature and extracted between cold 0.1 N HCl (100 mL) and ethyl acetate (100 mL). The aqueous layer was back extracted with ethyl acetate (2×25 mL). The combined organic layers were dried over sodium sulfate and concentrated. The residue was purified by flash chromatography (hexane:ethyl acetate) to give the desired product (1.70 g, 38%) as a yellow oil. $^1$H NMR (400 MHz, chlroform-d) δ ppm 8.44-8.55 (m, 1H), 7.87 (dd, 1H), 7.47-7.62 (m, 3H), 7.23-7.32 (m, 1H), 7.20 (dd, 1H), 7.05 (t, 1H), 6.51 (d, 1H), 2.31 (d, 3 H). ES MS: m/z 287 (M+1).

Step G: 1-{[3-(bromomethyl)-6-chloro-2-fluorophenyl]oxy}naphthalene

To a solution of 1-[(6-chloro-2-fluoro-3-methylphenyl)oxy]naphthalene (1.69 g, 5.89 mmol) in carbon tetrachloride (20 mL) was added N-bromosuccinimide (1.154 g, 6.48 mmol) and AIBN (0.048 g, 0.295 mmol). The mixture was heated at reflux overnight. The reaction mixture was filtered through Celite and the solvent was evaporated. The residue was purified by flash chromatography (hexane:ethyl acetate) to give the desired product (0.98 g, 45.5%) as a light yellow oil. $^1$H NMR (400 MHz, chloroform-d) δ ppm 8.43-8.51 (m, 1H), 7.84-7.92 (m, 1H), 7.53-7.64 (m, 3H), 7.23-7.34 (m, 3H), 6.50 (d, 1H), 4.50 (d, 2H).

Step H: {[4-chloro-2-fluoro-3-(1-naphthalenyloxy)phenyl]methyl}amine

To a solution of 1-{[3-(bromomethyl)-6-chloro-2-fluorophenyl]oxy}naphthalene (0.96 g, 2.63 mmol) in dichloromethane (10 mL) was added 7N ammonia in methanol (20 mL, 140 mmol). The mixture was stirred at room temperature overnight. The solvent was evaporated and the residue was triturated with dichloromethane to give the desired product (0.769 g, 87%) as an off-white solid. $^1$H NMR (400 MHz, DMSO-$d_6$) δ ppm 8.29-8.37 (m, 1H), 7.94-8.03 (m, 1H), 7.60-7.71 (m, 4H), 7.56 (t, 1H), 7.36 (t, 1H), 6.56 (d, 1H), 4.13 (s, 2H). ES MS: m/z 302 (M+1).

Step I: 3-chloro-N-{[4-chloro-2-fluoro-3-(1-naphthalenyloxy)phenyl]methyl}-1H-pyrrole-2-carboxamide HATU (0.113 g, 0.298 mmol) was added to a solution of {[4-chloro-2-fluoro-3-(1-naphthalenyloxy)phenyl]methyl}amine (0.060 g, 0.199 mmol) and 3-chloro-1H-pyrrole-2-carboxylic acid (0.0289 g, 0.199 mmol) nd diisopropylethylamine (0.052 mL, 0.298 mmol) and diisopropylethylamine (0.052 mL, 0.298 mmol) in DMF (1 mL). The mixture was stirred at room temperature for 1 hr. The reaction mixture was extracted with ethyl acetate and water. The organic layer was washed with water and brine, dried over sodium sulfate and concentrated. The residue was purified by reverse phase HPLC (acetonitrile:water with 0.1% TFA) to give the title compound (0.018 g, 21%) as a white solid. $^1$H NMR (400 MHz, DMSO-$d_6$) δ ppm 11.80 (br. s., 1H), 8.29-8.40 (m, 1H), 7.91-8.04 (m, 2H), 7.57-7.69 (m, 3H), 7.51 (dd, 1H), 7.35 (t, 2H), 6.93 (t, 1H), 6.52 (d, 1H), 6.19 (t, 1H), 4.54 (d, 2H). ES MS: m/z 429 (M+1).

Example 226

4-chloro-N-{[4-chloro-2-fluoro-3-(1-naphthalenyloxy)phenyl]methyl}-2-methyl-1H-imidazole-5-carboxamide trifluoroacetate

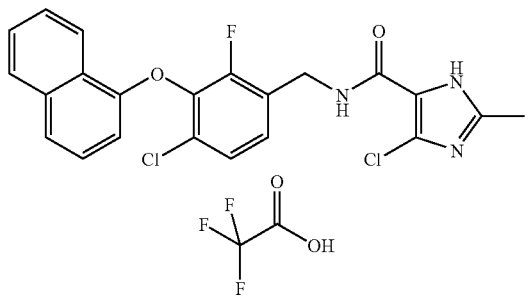

HATU (0.113 g, 0.298 mmol) was added to a solution of {[4-chloro-2-fluoro-3-(1-naphthalenyloxy)phenyl]methyl}amine (0.060 g, 0.199 mmol) and 4-chloro-2-methyl-1H-imidazole-5-carboxylic acid (0.031 g, 0.199 mmol) and diisopropylethylamine (0.052 mL, 0.298 mmol) in DMF (1 mL). The mixture was stirred at room temperature for 1 hr. The reaction mixture was extracted with ethyl acetate and water. The organic layer was washed with water and brine, dried over sodium sulfate and concentrated. The residue was purified by reverse phase HPLC (acetonitrile:water with 0.1% TFA) to give the title compound (0.026 g, 29%) as a white solid. $^1$H NMR (400 MHz, DMSO-$d_6$) δ ppm 8.30-8.40 (m, 1H), 8.12-8.21 (m, 1H), 7.98 (dd, 1H), 7.57-7.68 (m, 3H), 7.51 (dd, 1H), 7.34 (td, 2H), 6.52 (d, 1H), 4.52 (d, 2H), 2.41-2.56 (m, 3H). ES MS: m/z 444 (M+1).

Example 227

4-chloro-N-{[4-chloro-2-fluoro-3-(1-naphthalenyloxy)phenyl]methyl}-2-ethyl-1H-imidazole-5-carboxamide

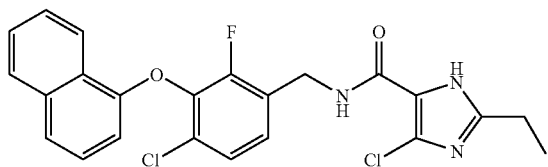

HATU (0.113 g, 0.298 mmol) was added to a solution of {[4-chloro-2-fluoro-3-(1-naphthalenyloxy)phenyl]methyl}amine (0.060 g, 0.199 mmol) and 4-chloro-2-ethyl-1H-imidazole-5-carboxylic acid (0.035 g, 0.199 mmol) and diisopropylethylamine (0.052 mL, 0.298 mmol) in DMF (1 mL). The mixture was stirred at room temperature for 1 hr. The reaction mixture was extracted with ethyl acetate and water. The organic layer was washed with water and brine, dried over sodium sulfate and concentrated. The residue was purified by reverse phase HPLC (acetonitrile:water with 0.1% TFA) to give the title compound (0.026 g, 26%) as a white solid. $^1$H NMR (400 MHz, DMSO-$d_6$) δ ppm 8.28-8.39 (m, 1H), 8.09-8.22 (m, 1H), 7.98 (dd, 1H), 7.57-7.69 (m, 3H), 7.51 (dd, 1H), 7.27-7.40 (m, 2H), 6.52 (d, 1H), 4.52 (d, 2H), 2.59 (q, 2H), 1.16 (t, 3H). ES MS: m/z 458 (M+1).

Example 228

4-chloro-N-{[4-chloro-2-fluoro-3-(1-naphthalenyloxy)phenyl]methyl}-2-cyclopropyl-1H-imidazole-5-carboxamide

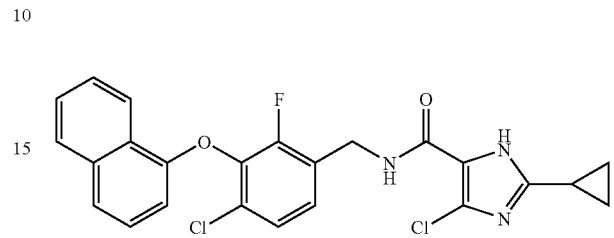

HATU (0.113 g, 0.298 mmol) was added to a solution of {[4-chloro-2-fluoro-3-(1-naphthalenyloxy)phenyl]methyl}amine (0.060 g, 0.199 mmol) and 4-chloro-2-cyclopropyl-1H-imidazole-5-carboxylic acid (0.037 g, 0.199 mmol) and diisopropylethylamine (0.052 mL, 0.298 mmol) in DMF (1 mL). The mixture was stirred at room temperature for 1 hr. The reaction mixture was extracted with ethyl acetate and water. The organic layer was washed with water and brine, dried over sodium sulfate and concentrated. The residue was purified by reverse phase HPLC (acetonitrile:water with 0.1% TFA) to give the title compound (0.016 g, 14%) as a white solid. $^1$H NMR (400 MHz, DMSO-$d_6$) δ ppm 8.284-8.37 (m, 1H), 8.00-8.13 (m, 1H), 7.95 (dd, 1H), 7.54-7.66 (m, 3H), 7.48 (dd, 1H), 7.25-7.37 (m, 2H), 6.49 (d, 1H), 4.33-4.62 (d, 2H), 1.75-2.03 (m, 1H), 0.85-0.93 (m, 2H), 0.77-0.84 (m, 2H). ES MS: m/z 470 (M+1).

Example 229

4-chloro-N-{[4-chloro-2-fluoro-3-(phenyloxy)phenyl]methyl}-2-methyl-1H-imidazole-5-carboxamide trifluoroacetate

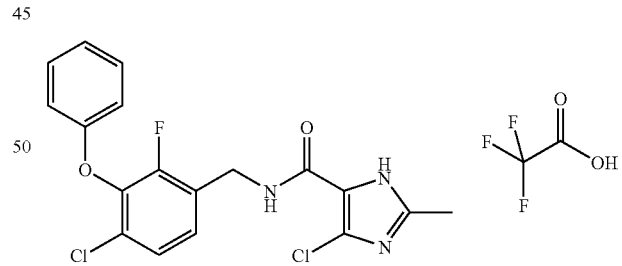

Step A: 1,2-difluoro-4-nitro-3-(phenyloxy)benzene

Sodium hydride (60% oil dispersion) (2.125 g, 53.1 mmol) was added in portions to a solution of phenol (5.00 g, 53.1 mmol) in THF (100 mL) while cooling in an ice bath. After 30 min, 1,2,3-trifluoro-4-nitrobenzene (6.11 mL, 53.1 mmol) was added. The mixture was stirred at RT overnight. The reaction mixture was poured on to ice/10% aqueous HCl and extracted with ethyl acetate. The organic layer was dried over sodium sulfate and the solvent was evaporated. Chromatography of the residue (ethyl acetate:hexane) gave the crude product (10.78 g, 43%) as a yellow oil.

Step B: bis(1,1-dimethylethyl) [2-fluoro-4-nitro-3-(phenyloxy)phenyl]propanedioate Sodium hydride (60% oil dispersion) (3.75 g, 94 mmol) was added in portions to a solution of di-t-butyl malonate (10.49 ml, 46.9 mmol) in THF (200 mL). After gas evolution subsided, a solution of 1,2-difluoro-4-nitro-3-(phenyloxy) benzene (10.70 g, 42.6 mmol) in THF (100 mL) was added. The mixture was stirred at room temperature for 2 hrs. The reaction mixture was poured into ice and extracted with ethyl acetate. The organic layer was dried over sodium sulfate and the solvent was evaporated. Chromatography of the residue (ethyl acetate:hexanes) gave the desires product (2.38 g, 12.5%) as a yellow oil. $^1$H NMR (400 MHz, chloroform-d) δ ppm 7.81 (dd, 1H), 7.53 (dd, 1H), 7.27-7.35 (m, 2H), 7.09 (t, 1H), 6.93 (d, 2H), 4.80 (s, 1H), 1.48 (s, 18H). ES MS: m/z 470 (M+23).

Step C: [2-fluoro-4-nitro-3-(phenyloxy)phenyl]acetic acid

Trifluoroacetic acid (3 mL, 38.9 mmol) was added to a solution of bis(1,1-dimethylethyl) [2-fluoro-4-nitro-3-(phenyloxy)phenyl]propanedioate (2.210 g, 4.94 mmol) in dichloromethane (20 mL). The mixture was heated at 45° C. overnight. The reaction mixture was diluted with ethyl acetate and water. The organic layer was dried over sodium sulfate and the solvent was evaporated to give the crude product (1.59 g, 89% yield) as a gummy solid. $^1$H NMR (400 MHz, chloroform-d) δ ppm 7.70-7.80 (m, 1H), 7.20-7.33 (m, 3H), 7.07 (t, 1H), 6.89 (d, 2H), 3.78 (s, 2H).

Step D: 2-fluoro-1-methyl-4-nitro-3-(phenyloxy)benzene

Copper(I) oxide (0.077 g, 0.536 mmol) was added to a solution of [2-fluoro-4-nitro-3-(phenyloxy)phenyl]acetic acid (1.560 g, 5.36 mmol) in acetonitrile (20 mL). The mixture was heated in a 90° C. oil bath for 1 h. The reaction mixture was cooled to RT and the solvent was evaporated. The residue was taken up in dichloromethane and filtered through Celite. Flash chromatography (ethyl acetate:hexanes) gave 2-fluoro-3-methyl-6-nitrophenyl phenyl ether (0.888 g, 63.7% yield) as a yellow oil. $^1$H NMR (400 MHz, CHLOROFORM-d) δ ppm 7.74 (dd, 1H), 7.27-7.36 (m, 2H), 7.18 (t, 1H), 7.09 (t, 1H), 6.92 (d, 2H), 2.38 (s, 3H). ES MS: m/z 246 (M−1).

Step E: [3-fluoro-4-methyl-2-(phenyloxy)phenyl]amine

A solution of sodium hydrosulfite (4.42 g, 21.45 mmol) in water (25 mL) was added dropwise to a solution of 2-fluoro-1-methyl-4-nitro-3-(phenyloxy)benzene (0.884 g, 3.58 mmol) in THF (10 mL). The mixture was stirred at room temperature overnight. The reaction mixture was extracted with ethyl acetate (3×25 mL). The combined organic layers were washed with brine and dried over sodium sulfate. The solvent was evaporated and the residue was purified by chromatography (ethyl acetate:hexane) to give [3-fluoro-4-methyl-2-(phenyloxy)phenyl]amine (0.444 g, 51.4%) as a colorless oil, which crystallized after standing overnight. $^1$H NMR (400 MHz, chloroform-d) δ ppm 7.23-7.33 (m, 2H), 7.03 (t, 1H), 6.94 (d, 2H), 6.83 (t, 1H), 6.51 (dd, 1H), 3.40 (br. s., 2H), 2.18 (d, 3H). ES MS: m/z 217.

Step F: 1-chloro-3-fluoro-4-methyl-2-(phenyloxy)benzene

To a suspension of copper(II) chloride (0.532 g, 3.96 mmol) in acetonitrile (4 mL) was added tert-butyl nitrite (0.588 ml, 4.95 mmol) dropwise at room temperature under nitrogen. After stirring at room temperature for 5 min, the mixture was heated in a 55° C. oil bath. A solution of [3-fluoro-4-methyl-2-(phenyloxy)phenyl]amine (0.430 g, 1.979 mmol) in acetonitrile (3 mL) was added dropwise. After complete addition, the reaction mixture was stirred at 55° C. for 5 min, then cooled to room temperature. The reaction mixture was extracted between ethyl acetate and cold 0.1M aqueous HCl. The aqueous layer was back-extracted once with ethyl acetate and the combined organic layers were dried over sodium sulfate. The solvent was evaporated. Chromatography of the residue (ethyl acetate:hexane) gave 0.294 g of partially purified desired product as a yellow oil $^1$H NMR (400 MHz, chloroform-d) δ ppm 7.28 (t, 2H), 7.09-7.16 (m, 1H), 7.04 (t, 1H), 6.98 (t, 1H), 6.88 (d, 2H), 2.26 (d, 3H).

Step G: 1-(bromomethyl)-4-chloro-2-fluoro-3-(phenyloxy)benzene

A mixture of 1-chloro-3-fluoro-4-methyl-2-(phenyloxy) benzene (0.500 g, 2.113 mmol), NBS (0.414 g, 2.324 mmol) and AIBN (0.017 g, 0.106 mmol) in carbon tetrachloride (8 mL) was heated at reflux overnight. The reaction mixture was cooled to RT and filtered through Celite. The solvent was evaporated. Chromatography of the residue gave the desired product (0.058 g, 9%) as a white solid. $^1$H NMR (400 MHz, chloroform-d) δ ppm 7.27-7.35 (m, 3H), 7.18-7.27 (m, 2H), 7.05-7.11 (m, 1H), 6.89 (d, 2H), 4.30-4.59 (m, 2H).

Step H: {[4-chloro-2-fluoro-3-(phenyloxy)phenyl] methyl}amine

A mixture of 1-(bromomethyl)-4-chloro-2-fluoro-3-(phenyloxy)benzene (0.058 g, 0.184 mmol) and 7M ammonia in methanol (3 mL, 21.00 mmol) in dichloromethane (1 mL) was stirred at room temperature overnight. The solvent was evaporated and the residue was triturated with dichloromethane to give the desired product (0.023 g, 47% yield). $^1$H NMR (400 MHz, DMSO-$d_5$) δ ppm 7.93 (br. s., 2H), 7.52-7.60 (m, 1H), 7.46 (t, 1H), 7.26-7.38 (m, 2H), 7.01-7.12 (m, 1H), 6.86 (d, 2H), 4.07 (s, 2 H). ES MS: m/z 252 (M+1).

Step I: 4-chloro-N-{[4-chloro-2-fluoro-3-(phenyloxy)phenyl]methyl}-2-methyl-1H-imidazole-5-carboxamide trifluoroacetate A mixture of {[4-chloro-2-fluoro-3-(phenyloxy)phenyl] methyl}amine (0.021 g, 0.083 mmol), 4-chloro-2-methyl-1H-imidazole-5-carboxylic acid (0.013 g, 0.083 mmol), HATU (0.038 g, 0.100 mmol) and DIPEA (0.017 mL, 0.100 mmol) in DMF (1 mL) was stirred at room temperature overnight. The crude reaction mixture was purified by reverse phase HPLC (acetonitrile:water with 0.1% TFA). The fractions containing product were lyophilized to give 4-chloro-N-{[4-chloro-2-fluoro-3-(phenyloxy)phenyl]methyl}-2-methyl-1H-imidazole-5-carboxamide (0.0077 g, 18%) (trifluoroacetate salt) as a white solid. $^1$H NMR (400 MHz, DMSO-$d_6$) d ppm 8.05-8.18 (m, 1H), 7.41-7.48 (m, 1H), 7.34 (t, 2H), 7.27 (t, 1H), 7.08 (t, 1H), 6.87 (d, 2 H), 4.49 (d, 2H), 2.24 (s, 3H). ES MS: m/z 394 (M+1).

Example 230

2-amino-4-chloro-N-({4-chloro-3-[(3-chloro-5-cyanophenyl)oxy]-2-fluorophenyl}methyl)-1H-imidazole-5-carboxamide trifluoroacetate

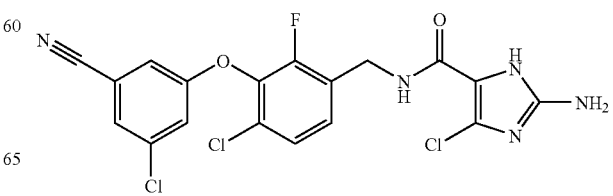

-continued

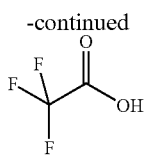

Step A: 3-bromo-1,1-bis(methyloxy)-2-propanone

A solution of 1,1-bis(methyloxy)-2-propanone (40.1 mL, 339 mmol) in 5% (v/v) methanol/acetonitrile (200 mL) was cooled to <5° C. while stirring. A 1 mL portion of a solution of bromine (17.44 mL, 339 mmol) in acetonitrile (30 mL) was added and the mixture was stirred until the solution was decolorized. The remainder of the bromine solution was added to the reaction mixture over 6-8 hrs while maintaining an internal temperature of <10° C. The mixture was stirred at RT overnight. Sodium bicarbonate (30.2 g, 360 mmol) was added and the mixture was stirred for 1 hr, then filtered. The filtrate was concentrated and t-butyl methyl ether (30 mL) and heptane (15 mL) were added. The mixture was washed with aqueous sodium bicarbonate (6.0 g in 60 mL water) and the organic layer was dried over sodium sulfate. The solvent was evaporated to give the title compound (47.03 g, 70%) as a yellow oil. $^1$H NMR (400 MHz, chloroform-d) δ ppm 4.64 (s, 1H), 4.13 (s, 2H), 3.35 (s, 6H).

Step B: 1,1-dimethylethyl[amino(imino)methyl]carbamate

A solution of tert-butyl dicarbonate (57.3 g, 263 mmol) in acetone (500 mL) was added to a solution of guanidine hydrochloride (100 g, 1050 mmol) and sodium hydroxide (84 g, 2100 mmol) in water (400 mL) at 0° C. The mixture was stirred at RT for 2 hrs. The acetone was removed by rotary evaporation and the remaining suspension was extracted with EtOAc (3×). The combined organic layers were dried over sodium sulfate and the solvent was evaporated to give 1,1-dimethylethyl [amino(imino)methyl]carbamate (42 g, 100%). $^1$H NMR (400 MHz, chloroform-d) δ ppm 6.08 (br. s., 4H), 1.44 (s, 9H).

Step C: 1,1-dimethylethyl 2-amino-4-[bis(methyloxy)methyl]-1H-imidazole-1-carboxylate To a solution of 1,1-dimethylethyl[amino(imino)methyl] carbamate (42.0 g, 264 mmol) in anhydrous THF (200 mL) was added a solution of 3-bromo-1,1-bis(methyloxy)-2-propanone (17.31 g, 88 mmol) in anhydrous THF (100 mL), under nitrogen. The mixture was heated at 50° C. for 2.5 hrs. The solvent was evaporated and the residue was purified by chromatography (EtOAc:hexanes) to give the title compound (9.81 g, 43%) as a tan solid. $^1$H NMR (400 MHz, chloroform-d) δ ppm 6.85 (s, 1H), 5.66 (br. s., 2H), 5.27 (s, 1H), 3.22-3.46 (m, 6H), 1.58 (s, 9H). ES MS: m/z 258 (M+1).

Step D: 1,1-dimethylethyl 2-(bis{[(1,1-dimethylethyl)oxy] carbonyl}amino)-4-[bis(methyloxy)methyl]-1H-imidazole-1-carboxylate Di-t-butyl dicarbonate (1.70 g, 7.77 mmol) was added to a solution of 1,1-dimethylethyl 2-amino-4-[bis(methyloxy) methyl]-1H-imidazole-1-carboxylate (1.00 g, 3.89 mmol) in dichloromethane (15 mL). A catalytic amount (a few mg) of DMAP was added. The mixture was stirred at RT for 1 hr. The reaction mixture was diluted with dichloromethane and washed with 1N aqueous HCl. The organic layer was dried over sodium sulfate and the solvent was evaporated to give the title compound (1.55 g, 87%) as a beige solid. $^1$H NMR (400 MHz, chloroform-d) δ pm 7.39 (s, 3H), 5.43 (s, 1H), 3.30 (s, 6H), 1.55 (s, 9H), 1.37 (s, 18H).

Step E: bis(1,1-dimethylethyl)(4-formyl-1H-imidazol-2-yl) imidodicarbonate

A catalytic amount of pyridinium p-toluenesulfonate was added to a solution of 1,1-dimethylethyl 2-(bis{[(1,1-dimethylethyl)oxy]carbonyl}amino)-4-[bis(methyloxy)methyl]-1H-imidazole-1-carboxylate (1.520 g, 3.32 mmol) in acetone:water/3:2 (25 mL). The mixture was stirred at RT for 3 days. The solvent was evaporated and the residue was purified by chromatography (EtOAc:hexanes) to give 0.680 g of the title compound (0.680 g, 66%). $^1$H NMR (400 MHz, chloroform-d) δ ppm 10.57 (br. s., 1H), 9.57 (s, 1H), 7.61 (s, 1H), 1.51 (s, 18H). ES MS: m/z 310 (M–H), 334 (M+Na).

Step F: bis(1,1-dimethylethyl)(4-chloro-5-formyl-1H-imidazol-2-yl)imidodicarbonate N-Chlorosuccinimide (0.346 g, 2.59 mmol) was added to a suspension of bis(1,1-dimethylethyl)(4-formyl-1H-imidazol-2-yl)imidodicarbonate (0.672 g, 2.158 mmol) in acetonitrile (10 mL). The mixture was heated at 60° C. for 2 hrs. The solvent was evaporated. Chromatography of the residue with ethyl acetate:hexane gave the title compound (0.086 g, 11%) as a white solid. $^1$H NMR (400 MHz, chloroform-d) δ ppm 10.38-10.79 (m, 1H), 9.6 (s, 1H), 1.52 (s, 18H). ES MS: m/z 345

Step G: 2-(bis{[(1,1-dimethylethyl)oxy]carbonyl}amino)-4-chloro-1H-imidazole-5-carboxylic acid A solution of sodium chlorite (0.217 g, 2.400 mmol) and sodium phosphate dibasic monohydrate (0.199 g, 1.440 mmol) in water (2 mL) was added to a solution of bis(1,1-dimethylethyl)(4-chloro-5-formyl-1H-imidazol-2-yl)imidodicarbonate (0.083 g, 0.240 mmol), 2-methyl-2-butene (2M in THF) (1.5 mL, 3.00 mmol), tert-butanol (1 mL) and THF (3 mL). The reaction mixture was extracted with EtOAc. The organic layer was dried over sodium sulfate and concentrated. The residue was triturated with ether to give a white solid which was dried under vacuum for 1 hr to give 0.043 g of a 50:50 mixture of 2-(bis{[(1,1-dimethylethyl)oxy] carbonyl}amino)-4-chloro-1H-imidazole-5-carboxylic acid and 4-chloro-2-({[(1,1-dimethylethyl)oxy]carbonyl} amino)-1H-imidazole-5-carboxylic acid. LCMS: m/z 362 and 262.

Step H: 2-amino-4-chloro-N-({4-chloro-3-[(3-chloro-5-cyanophenyl)oxy]-2-fluorophenyl}methyl)-1H-imidazole-5-carboxamide trifluoroacetate A mixture of 3-{[3-(aminomethyl)-6-chloro-2-fluorophenyl]oxy}-5-chlorobenzonitrile (0.041 g, 0.131 mmol), a 50:50 mixture of 2-(bis{[(1,1-dimethylethyl)oxy] carbonyl}amino)-4-chloro-1H-imidazole-5-carboxylic acid and 4-chloro-2-({[(1,1-dimethylethyl)oxy]carbonyl} amino)-1H-imidazole-5-carboxylic acid (0.047 g, 0.131 mmol), HATU (0.060 g, 0.157 mmol) and DIPEA (0.027 ml, 0.157 mmol) in DMF (1.5 mL) was stirred at RT overnight. The reaction mixture was extracted between EtOAc and water. The organic layer was washed with water and dried over sodium sulfate. The solvent was evaporated and the crude product was dissolved in dichloromethane (2 mL) and TFA (0.5 ml, 6.49 mmol) was added. The mixture was stirred at RT overnight. The solvent was evaporated and the residue was purified by reverse phase HPLC (acetonitrile:water with 0.1% TFA) to give the title compound (0.007 g, 6.2%) as a white solid. 1H NMR (400 MHz, DMSO-d$_6$) δ ppm 7.56 (dd, 1H), 7.41-7.52 (m, 3H), 6.66 (s, 1H), 3.73 (s, 2H), 1.88 (br. s., 2H). ES MS: m/z 454 (M+1)

Example 230B (Freebase): 2-amino-4-chloro-N-({4-chloro-3-[(3-chloro-5-cyanophenyl)oxy]-2-fluorophenyl}methyl)-1H-imidazole-5-carboxamide

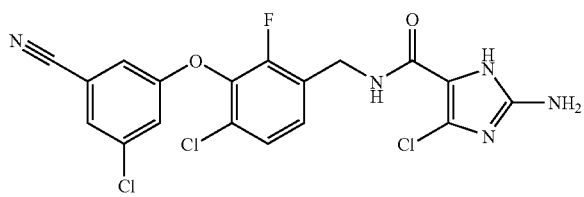

Route B:
Step A: 4-chloro-2-(methylthio)-1-({[2-(trimethylsilyl)ethyl]oxy}methyl)-1H-imidazole-5-carbaldehyde nBuLi (22.61 ml, 54.3 mmol) was added dropwise to a solution of 2-bromo-4,5-dichloro-1-({[2-(trimethylsilyl)ethyl]oxy}methyl)-1H-imidazole (18.78 g, 54.3 mmol) in tetrahydrofuran (THF) (200 ml) at −78° C. and the reaction mixture was stirred for 20 min. Dimethyl disulfide (4.82 ml, 54.3 mmol) was added dropwise slowly and stirring was continued for another 30 min. Additional nBuLi (22.61 ml, 54.3 mmol) was added to the solution and after another 20 min, DMF (8.40 ml, 109 mmol) was added slowly. The reaction mixture was stirred for 30 min, allowed to warm to RT, stirred overnight, and evaporated to half the volume. Sat'd NaHCO$_3$ (50 mL) and EtOAc (50 mL) were added and the aqueous layer was extracted with EtOAc. The organic phase was dried (Na$_2$SO$_4$), filtered, and purified by silica gel chromatography (0-30% EtOAc/hex) to afford the title compound (12.59 g, 76%) as a clear oil. 1H NMR (400 MHz, CHLOROFORM-d) δ ppm 9.69 (s, 1H), 5.66 (s, 2H), 3.52-3.65 (m, 2H), 2.71 (s, 3H), 0.88-1.01 (m, 2H), −0.01 (s, 9H).

Step B: 2-azido-4-chloro-1-({[2-(trimethylsilyl)ethyl]oxy}methyl)-1H-imidazole-5-carbaldehyde
mCPBA (23.26 g, 94 mmol) was added to a solution of 4-chloro-2-(methylthio)-1-({[2-(trimethylsilyl)ethyl]oxy}methyl)-1H-imidazole-5-carbaldehyde (12.59 g, 41.0 mmol) in dichloromethane (350 ml) at 0° C. After 1 h, the solution was removed from the ice bath and stirred at RT for 4 h. The solid was removed by filtration and sat'd NaHCO$_3$ was added to the filtrate and it was extracted with additional dichloromethane. The organic phase was dried (Na$_2$SO$_4$), filtered and concentrated to afford the sulfone as an off-white solid which was used without further purification. A solution of the sulfone and sodium azide (4.00 g, 61.5 mmol) in DMF (200 mL) was stirred for 1 h. Sat'd NaHCO$_3$ was added while cooling in an ice bath and the reaction mixture was extracted with CH$_2$Cl$_2$ (3×100 mL). The organic layer was dried (Na$_2$SO$_4$), filtered, concentrated, and purified by silica gel chromatography (0-30% EtOAc/hexanes) to provide the title compound as a yellow oil (8.53 g, 69%). 1H NMR (400 MHz, CHLOROFORM-d) δ ppm 9.73 (s, 1H), 5.52 (s, 2H), 3.55-3.67 (m, 2H), 0.87-0.98 (m, 2H), 0.00 (s, 9H).

Step C: 2-azido-4-chloro-1H-imidazole-5-carboxylic acid
A solution of NaClO$_2$ (21.7 g, 240 mmol) and NaH$_2$PO$_4$.2H$_2$O (19.9 g, 144 mmol) in H$_2$O (51 mL) was added to a stirred solution of 2-azido-4-chloro-1-({[2-(trimethylsilyl)ethyl]oxy}methyl)-1H-imidazole-5-carbaldehyde (7.2 g, 24.0 mmol) and 2-methyl-2-butene (144 mL of a 2M solution in THF, 2887 mmol) in THF (72 mL) and t-BuOH (17 mL). The reaction mixture was stirred at RT for 1 h and extracted with EtOAc. The organic layer was dried (Na$_2$SO$_4$), filtered and dried to provide 2-azido-4-chloro-1-({[2-(trimethylsilyl)ethyl]oxy}methyl)-1H-imidazole-5-carboxylic acid as a clear oil that was assumed to be quantitative and used without further purification. The above acid (1.40 mmol) was stirred in a solution of TFA (2.15 mL, 27.9 mmol) in CH$_2$Cl$_2$ (2 mL) for 1 h at RT. Sat'd NaHCO$_3$ was added and the mixture was washed with EtOAc. The aqueous layer was isolated, acidified with 1N HCl and extracted thoroughly with EtOAc. The organic layer was dried (Na$_2$SO$_4$), filtered, concentrated, and triturated with hexanes and again with diethyl ether to provide the title compound as a yellow solid. 1H NMR (400 MHz, DMSO-d$_6$) δ ppm 13.33 (br. s., 1H), 12.77 (br. s., 1H).

Step D: 2-amino-4-chloro-N-({4-chloro-3-[(3-chloro-5-cyanophenyl)oxy]-2-fluorophenyl}methyl)-1H-imidazole-5-carboxamide
A solution of 2-azido-4-chloro-1H-imidazole-5-carboxylic acid (0.26 g, 1.4 mmol), 3-{[3-(aminomethyl)-6-chloro-2-fluorophenyl]oxy}-5-chlorobenzonitrile (0.44 g, 1.40 mmol), 1-Ethyl-3-(3-dimethyllaminopropyl)carbodiimide hydrochloride (0.32 g, 1.68 mmol) and N-hydroxybenzotriazole (0.28 g, 1.82 mmol) was stirred at RT overnight. NaHCO$_3$ was added and the solution was extracted with 9:1 CH$_2$Cl$_2$:MeOH. The combined organic phase was dried (Na2SO4), filtered, and concentrated to give 2-azido-4-chloro-N-({4-chloro-3-[(3-chloro-5-cyanophenyl)oxy]-2-fluorophenyl}methyl)-1H-imidazole-5-carboxamide which was used without further purification after extraction. A solution of the above crude azide and catalytic Pd/CaCO$_3$ (poisoned with lead) in EtOAc (20 mL) was then stirred under 50 psi hydrogen gas for 2 h. The solution was filtered through celite, evaporated and purified by silica gel chromatography (0-10% MeOH/CH$_2$Cl$_2$) to afford the title compound as a white solid. 1H NMR (400 MHz, DMSO-d6) δ ppm 10.95 (s, 1H), 7.82 (s, 1H), 7.77 (t, J=5.86 Hz, 1H), 7.48-7.54 (m, 2H), 7.46 (t, J=2.01 Hz, 1H), 7.34 (t, J=7.97 Hz, 1H), 5.82 (s, 2H), 4.49 (d, J=5.77 Hz, 2H). ES-LCMS: m/z 454.0, 456.0, 458.0 (M+1).

Example 231

N-({4-bromo-3-[(3-chloro-5-cyanophenyl)oxy]-2-fluorophenyl}methyl)-4-chloro-2-methyl-1H-imidazole-5-carboxamide trifluoroacetate

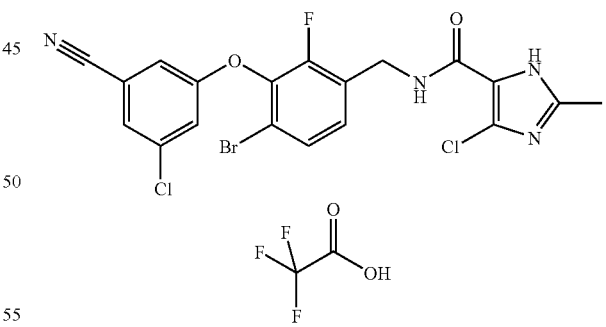

Step A: 3-[(6-bromo-2-fluoro-3-methylphenyl)oxy]-5-chlorobenzonitrile
t-Butyl nitrite (4.81 mL, 40.5 mmol) was added dropwise to a suspension of copper(II) bromide (7.23 g, 32.4 mmol) in acetonitrile (20 mL) at RT under nitrogen. The mixture was stirred for 5 min and then heated in a 55° C. oil bath. A solution of 3-[(6-amino-2-fluoro-3-methylphenyl)oxy]-5-chlorobenzonitrile (4.48 g, 16.19 mmol) in acetonitrile (25 mL) was added dropwise. After complete addition, the reaction mixture was stirred at 55° C. for 5 min and cooled to RT. Cold 0.5N HCl (150 mL) was added and the mixture was extracted with EtOAc. The combined organic layers were dried over sodium sulfate and the solvent was evaporated. Chromatography of the residue (EtOAc:hexane) gave 4.40 g of a mixture of desired product and dibrominated product as a white solid.

Step B: 3-{[6-bromo-3-(bromomethyl)-2-fluorophenyl]oxy}-5-chlorobenzonitrile

A mixture of 3-[(6-bromo-2-fluoro-3-methylphenyl)oxy]-5-chlorobenzonitrile (3.39 g, 9.95 mmol), NBS (1.949 g, 10.95 mmol) and AIBN (0.082 g, 0.498 mmol) in carbon tetrachloride (45 ml) was heated at reflux overnight. The reaction mixture was filtered through Celite and the filtrate was evaporated to dryness. Chromatography of the residue (EtOAc:hexane) gave 3-{[6-bromo-3-(bromomethyl)-2-fluorophenyl]oxy}-5-chlorobenzonitrile (1.35 g, 32.3% yield) as a colorless oil which crystallized to a white solid. 1H NMR (400 MHz, chloroform-d) δ ppm 7.44 (dd, 1H), 7.34 (s, 1H), 7.19-7.27 (m, 1H), 7.10-7.15 (m, 1H), 6.97 (s, 1H), 4.45 (s, 2H).

Step C: 3-{[3-(aminomethyl)-6-bromo-2-fluorophenyl]oxy}-5-chlorobenzonitrile

A mixture of 3-{[6-bromo-3-(bromomethyl)-2-fluorophenyl]oxy}-5-chlorobenzonitrile (1.330 g, 3.17 mmol) and 7M ammonia in methanol (20 mL, 140 mmol) in dichloromethane (20 mL) was stirred at RT overnight. The solvent was evaporated and the residue was triturated with dichloromethane and dried under vacuum to give 1.15 g of a white solid. Chromatography (dichloromethane:methanol) gave the desired product (0.507 g, 45%) as a white solid. 1H NMR (400 MHz, DMSO-$d_6$) δ ppm 8.13 (br. s., 1H), 7.80 (s, 1H), 7.72 (d, 1H), 7.46 (t, 1H), 7.42 (s, 1H), 4.07 (s, 2H).

Step D: N-({4-bromo-3-[(3-chloro-5-cyanophenyl)oxy]-2-fluorophenyl}methyl)-4-chloro-2-methyl-1H-imidazole-5-carboxamide trifluoroacetate A mixture of 3-{[3-(aminomethyl)-6-bromo-2-fluorophenyl]oxy}-5-chlorobenzonitrile (0.050 g, 0.141 mmol), 4-chloro-2-methyl-1H-imidazole-5-carboxylic acid (0.023 g, 0.141 mmol), HATU (0.064 g, 0.169 mmol) and DIPEA (0.029 mL0.169 mmol) in DMF (1 mL) was stirred at RT overnight. The crude reaction mixture was purified by reverse phase HPLC (acetonitrile:water with 0.1% TFA) to give the title compound trifluoroacetate (0.015 g, 17.5%) as a white solid. 1H NMR (400 MHz, DMSO-$d_6$) δ ppm 8.09 (br. s., 1H), 7.78 (s, 1H), 7.58 (d, 1H), 7.45 (s, 1H), 7.40 (s, 1H), 7.25 (t, 1H), 4.46 (d, 2H), 2.21 (s, 3H). ES MS: m/z 496, 498 (M+2).

Example 232

N-({4-bromo-3-[(3-chloro-5-cyanophenyl)oxy]-2-fluorophenyl}methyl)-4-chloro-2-methyl-1H-imidazole-5-carboxamide

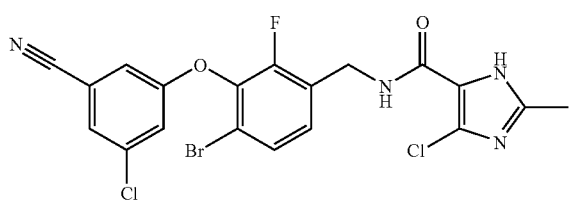

EDC (0.060 g, 0.311 mmol) and HOBT (0.042 g, 0.311 mmol) were added to a solution of 3-{[3-(aminomethyl)-6-bromo-2-fluorophenyl]oxy}-5-chlorobenzonitrile (0.111 g, 0.311 mmol) and 4-chloro-2-methyl-1H-imidazole-5-carboxylic acid (0.050 g, 0.311 mmol) in DMF (2 mL). The mixture was stirred at RT overnight. The reaction mixture was extracted with EtOAc and saturated sodium bicarbonate and the organic layer was dried over sodium sulfate and concentrated. Rerverse phase HPLC (acetonitrile:water with 0.1% formic acid) gave the title compound (0.019 g, 12%) as a white solid. $^1$H NMR (400 MHz, DMSO-$d_6$) δ ppm 12.86 (br. s., 1H), 8.17 (br. s., 1H), 7.77-7.88 (m, 1H), 7.57-7.66 (m, 1H), 7.46-7.55 (m, 1H), 7.44 (br. s., 1H), 7.22-7.35 (m, 1H), 4.37-4.70 (m, 2H), 2.28 (s, 3H). LCMS: m/z 497, 499.

Example 233

4-bromo-N-({4-bromo-3-[(3-chloro-5-cyanophenyl)oxy]-2-fluorophenyl}methyl)-2-methyl-1H-imidazole-5-carboxamide

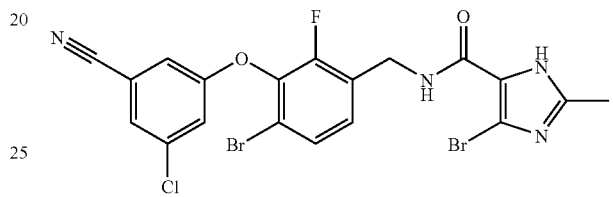

A mixture of 3-{[3-(aminomethyl)-6-bromo-2-fluorophenyl]oxy}-5-chlorobenzonitrile (0.050 g, 0.141 mmol), 4-bromo-2-methyl-1H-imidazole-5-carboxylic acid (0.029 g, 0.141 mmol), HATU (0.064 g, 0.169 mmol) and DIPEA (0.029 mL, 0.169 mmol) in DMF (1 mL) was stirred at RT overnight. The reaction mixture was extracted with EtOAc and water. The organic layer was dried over sodium sulfate and concentrated. The residue was purified by preparative LCMS (acetonitrile:water with 0.1% formic acid) to give the title compound (15 mg, 19.6%) as a white solid. 1H NMR (400 MHz, DMSO-$d_6$) δ ppm 8.17 (br. s., 1H), 7.77 (s, 1H), 7.57 (d, 1H), 7.45 (s, 1H), 7.40 (d, 1H), 7.25 (t, 1H), 4.18-4.59 (m, 2H), 2.21 (s, 3H). ES MS: m/z 541, 543.

Example 234

4-bromo-N-({4,5-dibromo-3-[(3-chloro-5-cyanophenyl)oxy]-2-fluorophenyl}methyl)-2-methyl-1H-imidazole-5-carboxamide trifluoroacetate

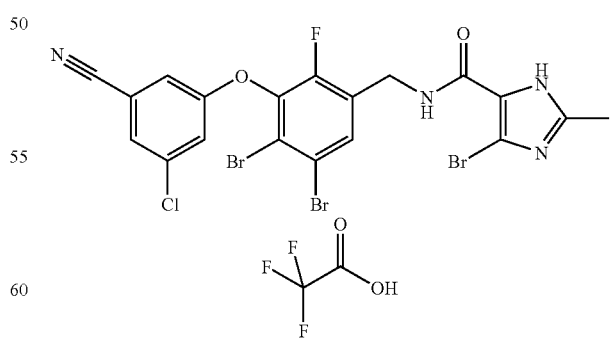

Step A: 3-chloro-5-{[2,3-dibromo-5-(bromomethyl)-6-fluorophenyl]oxy}benzonitrile To a mixture of 3-[(6-bromo-2-fluoro-3-methylphenyl)oxy]-5-chlorobenzonitrile and 3-[(5,6-bromo-2-fluoro-3- methylphenyl)oxy]-5-chlorobenzonitrile (1.000 g, approx 2.94 mmol) in carbon tetrachloride (15 mL) was added NBS (0.575 g, 3.23 mmol) and AIBN (0.024 g, 0.147 mmol). The mixture was heated at reflux overnight. The reaction mixture was filtered through Celite and the filtrate was evaporated to dryness. Chromatography of the residue (EtOAc:hexane) gave 0.345 g of the monobromo product (~90% mono, 10% dibromo) and 0.601 g of a mixture of dibromo product, SM and monobromo product. The latter material was combined with another batch containing a similar mixture. Chromatography (hexane:ethyl acetate) gave the title compound (0.195 g) as a white solid. $^1$H NMR (400 MHz, chloroform-d) δ ppm 7.67 (d, 1H), 7.33-7.39 (m, 1H), 7.12 (t, 1H), 6.97 (d, 1H), 4.40 (s, 2H).

Step B: 3-{[3-(aminomethyl)-5,6-dibromo-2-fluorophenyl]oxy}-5-chlorobenzonitrile A mixture of 3-chloro-5-{[2,3-dibromo-5-(bromomethyl)-6-fluorophenyl]oxy}benzonitrile (0.185 g, 0.371 mmol) and 7M ammonia in methanol (5 mL, 35.0 mmol) in dichloromethane (5 mL) was stirred at RT overnight. The solvent was evaporated and the residue was purified by chromatography (MeOH:dichloromethane) to give the desired product (37 mg, 19.5%) as a white solid. 1H NMR (400 MHz, methanol-$d_4$) δ ppm 7.80 (d, 1H), 7.52 (t, 1H), 7.25 (t, 1H), 7.20 (d, 1H), 3.82 (s, 2H).

Step C: 4-bromo-N-({4,5-dibromo-3-[(3-chloro-5-cyanophenyl)oxy]-2-fluorophenyl}methyl)-2-methyl-1H-imidazole-5-carboxamide trifluoroacetate EDC (0.017 g, 0.089 mmol) and HOBT (0.012 g, 0.089 mmol) were added to a solution of 3-{[3-(aminomethyl)-5,6-dibromo-2-fluorophenyl]oxy}-5-chlorobenzonitrile (0.035 g, 0.081 mmol) and 4-bromo-2-methyl-1H-imidazole-5-carboxylic acid (0.017 g, 0.081 mmol) in DMF. The reaction mixture was stirred overnight and purified by reverse phase HPLC (acetonitrile:water with 0. % TFA) to give the title compound (0.028 g, 47%) as a white powder. 1H NMR (400 MHz, DMSO-$d_6$) δ ppm 8.29 (br. s., 1H), 7.82 (s, 1H), 7.74 (d, 1H), 7.52-7.60 (m, 2H), 4.47 (d, 2H), 2.28 (s, 3H). ES MS m/z 622.

Example 235

2-amino-4-bromo-N-({4-chloro-3-[(3-chloro-5-cyanophenyl)oxy]-2-fluorophenyl}methyl)-1H-imidazole-5-carboxamide trifluoroacetate

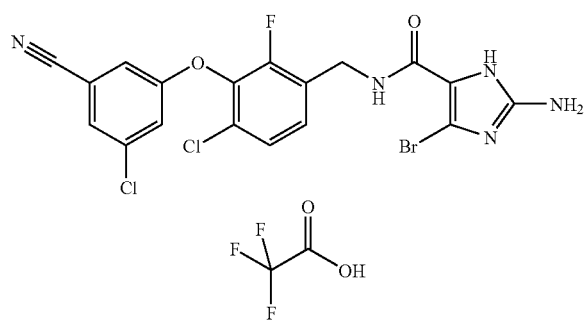

Step A: bis(1,1-dimethylethyl)(4-bromo-5-formyl-1H-imidazol-2-yl)imidodicarbonate NBS (0.206 g, 1.156 mmol) was added to a solution of bis(1,1-dimethylethyl)(4-formyl-1H-imidazol-2-yl)imidodicarbonate (0.300 g, 0.964 mmol) in DMF (3 mL). The mixture was heated at 50° C. for 3 hrs. The reaction mixture was diluted with EtOAc and washed 2x with water. The organic layer was dried over sodium sulfate and concentrated. Chromatography (EtOAc:hexane) gave the desired product (0.154 g, 41%) as a white solid. 1H NMR (400 MHz, chloroform-d) δ ppm 10.54 (br. s., 1H), 9.54 (s, 1H), 1.50 (s, 18H). ES MS: m/z 390.

Step B: 2-(bis{[(1,1-dimethylethyl)oxy]carbonyl}amino)-4-bromo-1H-imidazole-5-carboxylic acid A solution of sodium chlorite (0.348 g, 3.84 mmol) and sodium dihydrogenphosphate monohydrate (0.318 g, 2.306 mmol) in water (4 mL) was added to a solution of bis(1,1-dimethylethyl)(4-bromo-5-formyl-1H-imidazol-2-yl)imidodicarbonate (0.150 g, 0.384 mmol), 2-methyl-2-butene (2M in THF) (2.402 mL, 4.80 mmol), t-BuOH (2 mL) and THF (6 mL). The mixture was stirred at RT overnight and extracted with EtOAc. The organic layer was dried over sodium sulfate and concentrated. The residue was triturated with ether to give the desired product (0.047 g, 30%) as a white solid. ES MS: m/z 406 (M+1).

Step C: bis(1,1-dimethylethyl)(4-bromo-5-{[({4-chloro-3-[(3-chloro-5-cyanophenyl)oxy]-2-fluorophenyl}methyl)amino]carbonyl}-1H-imidazol-2-yl)imidodicarbonate EDC (0.022 g, 0.116 mmol) and HOBT (0.016 g, 0.116 mmol) were added to a solution of 3-{[3-(aminomethyl)-6-chloro-2-fluorophenyl]oxy}-5-chlorobenzonitrile (0.033 g, 0.106 mmol) and 2-(bis{[(1,1-dimethylethyl)oxy]carbonyl}amino)-4-bromo-1H-imidazole-5-carboxylic acid (0.043 g, 0.106 mmol) in DMF (2 mL). The mixture was stirred at RT overnight. Saturated sodium bicarbonate was added and the reaction mixture was extracted with EtOAc. The organic layer was dried over sodium sulfate and concentrated. Chromatography (MeOH:dichloromethane) gave the desired product (0.030 g, 34%) as a white solid.

Step D: 2-amino-4-bromo-N-({4-chloro-3-[(3-chloro-5-cyanophenyl)oxy]-2-fluorophenyl}methyl)-1H-imidazole-5-carboxamide trifluoroacetate TFA (3.30 μl, 0.043 mmol) was added to a solution of bis(1,1-dimethylethyl)(4-bromo-5-{[({4-chloro-3-[(3-chloro-5-cyanophenyl)oxy]-2-fluorophenyl}methyl)amino]carbonyl}-1H-imidazol-2-yl)imidodicarbonate (0.030 g, 0.043 mmol) in dichloromethane (2 mL). The mixture was stirred at RT overnight. The solvent was evaporated and the residue was purified by reverse phase HPLC (acetonitrile:water with 0. % TFA) to give the title compound (11 mg, 41%) as a white solid. 1H NMR (400 MHz, DMSO-$d_6$) δ ppm 8.02-8.12 (m, 1H), 7.80 (s, 1H), 7.46-7.53 (m, 2H), 7.44 (s, 1H), 7.35 (t, 1H), 6.61 (br. s., 2H), 4.47 (s, 2H). ES MS m/z 499.

Example 236

2-amino-4-bromo-N-({4-chloro-3-[(3-chloro-5-cyanophenyl)oxy]-2-fluorophenyl}methyl)-1H-imidazole-5-carboxamide

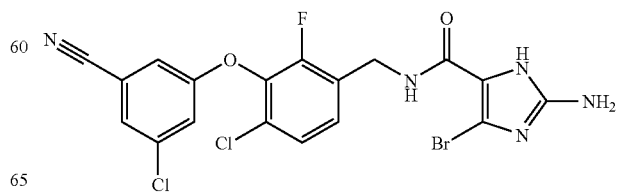

TFA (2 ml, 26.0 mmol) was added to a solution of bis(1,1-dimethylethyl)(4-bromo-5-{[({4-chloro-3-[(3-chloro-5-cyanophenyl)oxy]-2-fluorophenyl}methyl)amino]carbonyl}-1H-imidazol-2-yl)imidodicarbonate (1.130 g, 1.616 mmol) in dichloromethane (10 mL). The mixture was stirred at RT overnight. The reaction mixture was stirred with saturated aqueous sodium bicarbonate for 1 hr and the resulting solid was isolated by filtration. A portion (0.100 g) was recrystallized from ethanol to give the title compound (0.071 g, 9%). 1H NMR (400 MHz, DMSO-d$_6$) δ ppm 11.16 (br. s., 1H), 7.79-7.85 (m, 1H), 7.72-7.79 (m, 1H), 7.44-7.55 (m, 2H), 7.29-7.39 (m, 1H), 5.53 (br. s., 2H), 4.24-4.68 (m, 2H). ES MS: m/z 498, 500.

Example 237

2-amino-4-bromo-N-({4-bromo-3-[(3-chloro-5-cyanophenyl)oxy]-2-fluorophenyl}methyl)-1H-imidazole-5-carboxamide trifluoroacetate

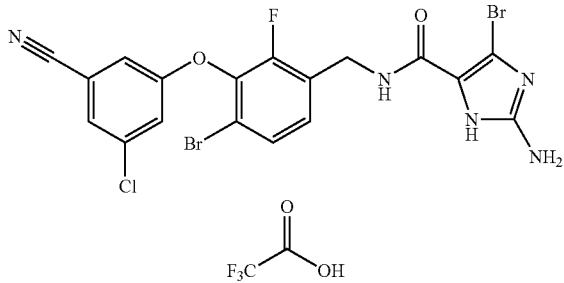

Step A: 4-bromo-2-(methylthio)-1-({[2-(trimethylsilyl)ethyl]oxy}methyl)-1H-imidazole-5-carbaldehyde The title compound (1.00 g, 73%) was obtained as a clear oil from 2,4,5-tribromo-1-({[2-(trimethylsilyl)ethyl]oxy}methyl)-1H-imidazole (1.70 g, 3.91 mmol) using a procedure and process similar to that described herein. 1H NMR (400 MHz, CHLOROFORM-d) δ ppm 9.63 (s, 1H) 5.67 (s, 2H) 3.56-3.64 (m, 2H) 2.72 (s, 3 H) 0.87-0.98 (m, 2H)-0.01 (s, 9H).

Step B: 4-bromo-2-(methylsulfonyl)-1-({[2-(trimethylsilyl)ethyl]oxy}methyl)-1H-imidazole-5-carbaldehyde mCPBA (0.40 g, 1.64 mmol) was added to a solution of 4-bromo-2-(methylthio)-1-({[2-(trimethylsilyl)ethyl]oxy}methyl)-1H-imidazole-5-carbaldehyde (0.23 g, 0.66 mmol) in CH$_2$Cl$_2$ (6.6 ml) at 0° C. After 2 h, the reaction mixture was stirred at RT for another 2 h. Sat'd NaHCO$_3$ was added and the solution was extracted with CH$_2$Cl$_2$ (3×10 mL). The organic layer was dried (Na$_2$SO$_4$), filtered, concentrated, and purified by silica gel chromatography (0-25% EtOAc/hexanes) to provide the title compound (0.21 g, 0.54 mmol) as a white solid. 1H NMR (400 MHz, CHLOROFORM-d) δ ppm 9.92 (s, 1H) 6.07 (s, 2H) 3.61-3.74 (m, 2H) 3.43 (s, 3H) 0.87-1.02 (m, 2H) 0.00 (s, 9H).

Step C: 2-azido-4-bromo-1-({[2-(trimethylsilyl)ethyl]oxy}methyl)-1H-imidazole-5-carbaldehyde The title compound (0.13 g, 71%) was obtained as a clear oil from 4-bromo-2-(methylsulfonyl)-1-({[2-(trimethylsilyl)ethyl]oxy}methyl)-1H-imidazole-5-carbaldehyde (0.21 g, 0.54 mmol) using a procedure and process similar to that described herein. 1H NMR (400 MHz, CHLOROFORM-d) δ ppm 9.64 (s, 1H) 5.50 (s, 2H) 3.58 (t, J=8.24 Hz, 2H) 0.91 (t, J=8.24 Hz, 2H) -0.02 (s, 9H).

Step D: 2-azido-4-bromo-N-({4-bromo-3-[(3-chloro-5-cyanophenyl)oxy]-2-fluorophenyl}methyl)-1-({[2-(trimethylsilyl)ethyl]oxy}methyl)-1H-imidazole-5-carboxamide The procedure and process are similar to that described herein except that 2-azido-4-bromo-1-({[2-(trimethylsilyl)ethyl]oxy}methyl)-1H-imidazole-5-carbaldehyde (0.13 g, 0.38 mmol) was employed to provide the acid as a clear oil which was used without further purification. The above acid and 3-{[3-(aminomethyl)-6-bromo-2-fluorophenyl]oxy}-5-chlorobenzonitrile (0.17 g, 0.38 mmol) were employed in a similar process described herein to prepare the title compound (0.15 g, 58%) as a clear oil. 1H NMR (400 MHz, CHLOROFORM-d) δ ppm 7.45 (dd, J=8.42, 1.28 Hz, 1H) 7.37 (s, 1H) 7.30 (d, J=7.32 Hz, 1H) 7.12-7.19 (m, 2H) 7.02 (s, 1H) 5.55 (s, 2H) 4.66 (d, J=5.86 Hz, 2H) 3.50-3.62 (m, 2H) 0.85-0.94 (m, 2H) -0.02 (s, 9H).

Step E: 2-amino-4-bromo-N-({4-bromo-3-[(3-chloro-5-cyanophenyl)oxy]-2-fluorophenyl}methyl)-1-({[2-(trimethylsilyl)ethyl]oxy}methyl)-1H-imidazole-5-carboxamide A solution of 2-azido-4-bromo-N-({4-bromo-3-[(3-chloro-5-cyanophenyl)oxy]-2-fluorophenyl}methyl)-1-({[2-(trimethylsilyl)ethyl]oxy}methyl)-1H-imidazole-5-carboxamide (0.030 g, 0.043 mmol) and catalytic palladium on Ca$_2$CO$_3$ (poisoned with lead) in THF (1 mL) was stirred under atmospheric hydrogen pressure overnight. The reaction mixture was filtered through celite and evaporated to give the title compound (0.029 mg, quant.) as a clear oil. 1H NMR (400 MHz, CHLOROFORM-d) δ ppm 7.43 (dd, J=8.47, 1.42 Hz, 1H) 7.31-7.37 (m, 1H) 7.21-7.26 (m, 1H) 7.11-7.17 (m, 1H) 7.06 (t, J=6.00 Hz, 1H) 7.01 (s, 1H) 5.69 (s, 2H) 4.85 (br. s., 2H) 4.63 (d, J=6.04 Hz, 2H) 3.59-3.68 (m, 2H) 0.86-0.94 (m, 2H) -0.03 (s, 9H).

Step F: 2-amino-4-bromo-N-({4-bromo-3-[(3-chloro-5-cyanophenyl)oxy]-2-fluorophenyl}methyl)-1H-imidazole-5-carboxamide trifluoroacetate The title compound (0.002 g, 7%) was obtained as a white solid from 2-amino-4-bromo-N-({4-bromo-3-[(3-chloro-5-cyanophenyl)oxy]-2-fluorophenyl}methyl)-1-({[2-(trimethylsilyl)ethyl]oxy}methyl)-1H-imidazole-5-carboxamide (0.029 g, 0.043 mmol) using a procedure and process similar to that described herein. Purification of the title compound was achieved by Reverse-Phase HPLC (water:acetonitrile with 0.1% TFA). 1H NMR (400 MHz, METHANOL-d4) δ ppm 7.51-7.61 (m, 2H) 7.34 (t, J=7.83 Hz, 1H) 7.24-7.29 (m, 1H) 7.19 (s, 1H) 4.62 (s, 2H). ES-LCMS: m/z 541.9, 543.8, 545.9 (M+1).

Example 238

2-amino-N-({4-chloro-3-[(3-chloro-5-cyanophenyl)oxy]-2-fluorophenyl}methyl)-1H-imidazole-4-carboxamide

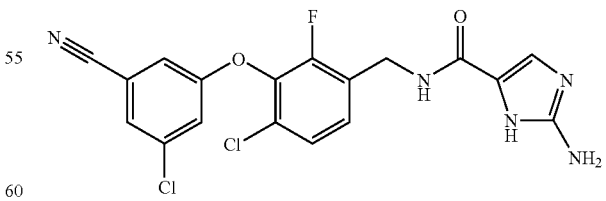

Step A: 2-(bis{[(1,1-dimethylethyl)oxy]carbonyl}amino)-1H-imidazole-4-carboxylic acid A solution of sodium chlorite (0.505 g, 5.59 mmol) and sodium dihydrogenphosphate monohydrate (0.463 g, 3.35 mmol) in water (4 mL) was added to a solution of bis(1,1-dimethylethyl)(4-formyl-1H-imidazol-2-yl)imidodicarbonate (0.174 g, 0.559 mmol), 2-methyl-2-butene (2M in THF) (3.49 mL, 6.99 mmol), t-BuOH (2 mL) and THF (6 mL). The mixture was stirred at RT overnight. The reaction mixture was extracted with ethyl acetate. The organic layer was dried over sodium sulfate and the solvent was evaporated. The residue was triturated with ether and the resulting white solid was dried under vacuum to give 0.098 g (53%) of the title compound. MS m/z 326 (M−1).

Step B: 2-amino-N-({4-chloro-3-[(3-chloro-5-cyanophenyl)oxy]-2-fluorophenyl}methyl)-1H-imidazole-4-carboxamide EDC (0.035 g, 0.183 mmol) and HOBT (0.025 g, 0.183 mmol) were added to a solution of 3-{[3-(aminomethyl)-6-chloro-2-fluorophenyl]oxy}-5-chlorobenzonitrile (0.048 g, 0.153 mmol) and 2-(bis{[(1,1-dimethylethyl)oxy]carbonyl}amino)-1H-imidazole-4-carboxylic acid (0.050 g, 0.153 mmol) in DMF (2 mL). The mixture was stirred at RT overnight. Saturated aqueous sodium bicarbonate was added and the reaction mixture was extracted with ethyl acetate. The organic layer was dried over sodium sulfate and concentrated to give crude bis(1,1-dimethylethyl)(4-{[({4-chloro-3-[(3-chloro-5-cyanophenyl)oxy]-2-fluorophenyl}methyl)amino]carbonyl}-1H-imidazol-2-yl)imidodicarbonate as an oil. Trifluoroacetic acid (0.3 mL, 3.89 mmol) was added to a solution of bis(1,1-dimethylethyl)(4-{[({4-chloro-3-[(3-chloro-5-cyanophenyl)oxy]-2-fluorophenyl}methyl)amino]carbonyl}-1H-imidazol-2-yl)imidodicarbonate (0.066 g, 0.106 mmol) in dichloromethane (2 mL). The mixture was stirred at RT overnight, concentrated and purified by reverse phase HPLC (acetonitrile:water with 0.1% formic acid) to give the title compound (0.017 g, 27%). $^1$H NMR (400 MHz, DMSO-$d_6$) δ ppm 8.09-8.18 (m, 2H), 7.81 (s, 1H), 7.51 (s, 1H), 7.44-7.50 (m, 2H), 7.30 (t, 1H), 7.10 (s, 1H), 5.45 (br. s., 2H), 4.44 (d, 2H). MS m/z 420 (M+1).

Example 239

2-amino-N-({4-bromo-3-[(3-chloro-5-cyanophenyl)oxy]-2-fluorophenyl}methyl)-4-chloro-1H-imidazole-5-carboxamide

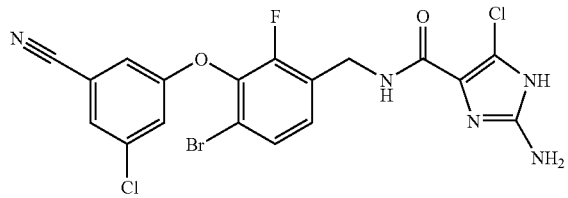

Route A:
Step A. 3-[(6-bromo-2-fluoro-3-methylphenyl)oxy]-5-chlorobenzonitrile t-Butyl nitrite (4.37 ml, 36.7 mmol) was added dropwise to a suspension of copper(II) bromide (6.83 g, 30.6 mmol) in MeCN (30 mL) at RT under an atmosphere of nitrogen. The mixture was stirred for 5 min then heated to 55° C. after which a solution of 3-[(6-amino-2-fluoro-3-methylphenyl)oxy]-5-chlorobenzonitrile (6.77 g, 24.47 mmol) in MeCN (30 mL) was added dropwise. The brown solution was stirred at 55° C. for 30 min then cooled to RT. Cold 0.5N HCl (150 mL) was added followed by ethyl acetate (400 mL). The organic layer was washed with brine (400 mL), dried over MgSO$_4$, filtered and concentrated to give 8.1 g (78%) of 3-[(6-bromo-2-fluoro-3-methylphenyl)oxy]-5-chlorobenzonitrile in ca. 80% purity. 1H NMR shows the desired product plus ~20% of a side product. Used as is in next experiment. 1H NMR (400 MHz, chloroform-d) δ ppm 7.31-7.41 (m, 2H), 7.11-7.20 (m, 1H), 7.02-7.11 (m, 1H), 7.00 (d, 1H), 2.31 (s, 3H).

Step B. 3-{[6-bromo-3-(bromomethyl)-2-fluorophenyl]oxy}-5-chlorobenzonitrile

A mixture of 3-[(6-bromo-2-fluoro-3-methylphenyl)oxy]-5-chlorobenzonitrile (8.1 g, 23.78 mmol), NBS (5.08 g, 28.5 mmol) and AIBN (0.195 g, 1.189 mmol) in CCl$_4$ (240 ml) was heated at 90° C. for 16 h under an atmosphere of nitrogen. The mixture was cooled to 0° C., filtered thru Celite and concentrated. The crude yellow oil was purified on silica gel (hexanes/ethyl acetate) to give 2.75 g (26%) of 3-{[6-bromo-3-(bromomethyl)-2-fluorophenyl]oxy}-5-chlorobenzonitrile as a clear oil. 1H NMR (400 MHz, chloroform-d) δ ppm 7.44 (dd, 1H), 7.34 (t, 1H), 7.18-7.32 (m, 1H), 7.13 (t, 1H), 6.89-7.05 (m, 1H), 4.45 (d, 2H).

Step C: 3-{[3-(aminomethyl)-6-bromo-2-fluorophenyl]oxy}-5-chlorobenzonitrile

A solution of 3-{[6-bromo-3-(bromomethyl)-2-fluorophenyl]oxy}-5-chlorobenzonitrile (2.5 g, 5.96 mmol) in tetrahydrofuran (THF) (50 mL) was added dropwise to a 7M solution of ammonia in MeOH (42.6 mL, 298 mmol) at RT under nitrogen. The reaction was stirred for 16 h then the reaction mixture was evaporated to dryness. Ethyl acetate and saturated aqueous sodium bicarbonate were added to the residue and the mixture was shaken in a separatory funnel. The organic layer was dried over sodium sulfate and the solvent was evaporated. The residue was purified by chromatography with hexane:ethyl acetate to give the title compound (0.453 g, 21%) as a white solid. 1H NMR (400 MHz, DMSO-$d_6$) δ ppm 7.76 (s, 1H), 7.56 (d, 1H), 7.39-7.46 (m, 2H), 7.37 (m, 1H), 3.70 (s, 2H), 1.85 (br. s., 2H).

Step D: 2-amino-N-({4-bromo-3-[(3-chloro-5-cyanophenyl)oxy]-2-fluorophenyl}methyl)-4-chloro-1H-imidazole-5-carboxamide trifluoroacetate EDC (0.029 g, 0.152 mmol) and HOBT (0.021 g, 0.152 mmol) were added to a solution of 3-{[3-(aminomethyl)-6-bromo-2-fluorophenyl]oxy}-5-chlorobenzonitrile (0.049 g, 0.138 mmol) and 2-(bis{[(1,1-dimethylethyl)oxy]carbonyl}amino)-4-chloro-1H-imidazole-5-carboxylic acid (0.050 g, 0.138 mmol) in DMF (2 mL). The mixture was stirred at RT for 1 hr. The reaction mixture was extracted with EtOAc and saturated sodium bicarbonate. The organic layer was dried over sodium sulfate and concentrated to an oil. Dichloromethane (2 mL) and trifluoroacetic acid (0.5 mL, 6.49 mmol) were added and the mixture was stirred at RT overnight. The solvent was evaporated and the residue was purified by reverse phase HPLC (acetonitrile:water with 0.1% formic acid) to give the title compound (0.0103 g, 18%). $^1$H NMR (400 MHz, DMSO-d6) δ ppm 11.05 (br. s., 1H), 7.75-7.85 (m, 2H), 7.61 (d, 1H), 7.49 (s, 1H), 7.43 (m, 1H), 7.21-7.32 (m, 1H), 5.82 (br. s., 2H), 4.47 (d, 2H). LCMS: m/z 499 (M+1).

Example 239

2-amino-N-({4-bromo-3-[(3-chloro-5-cyanophenyl)oxy]-2-fluorophenyl}methyl)-4-chloro-1H-imidazole-5-carboxamide

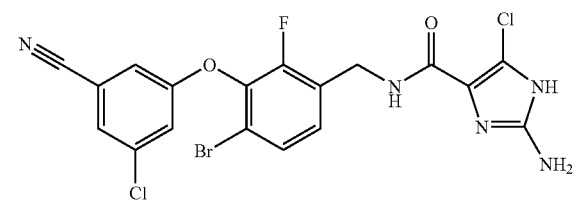

Route B:

Step A: 3-{[3-(azidomethyl)-6-bromo-2-fluorophenyl]oxy}-5-chlorobenzonitrile

Sodium azide (0.465 g, 7.16 mmol) was added to a solution of 3-{[6-bromo-3-(bromomethyl)-2-fluorophenyl]oxy}-5-chlorobenzonitrile (2.73 g, 6.51 mmol) in DMSO (20 mL). The mixture was stirred at RT overnight. The reaction mixture was diluted with EtOAc and washed with water (3×). The organic layer was dried over sodium sulfate and concentrated. The residue was purified by chromatography with hexane:ethyl acetate to give the title compound (2.05 g, 83%) as an oil. $^1$H NMR (400 MHz, chloroform-d) δ ppm 7.50 (dd, 1H), 7.35 (s, 1H), 7.18-7.26 (m, 1H), 7.14 (s, 1H), 6.99 (s, 1H), 4.41 (s, 2H).

Step B: 3-{[3-(aminomethyl)-6-bromo-2-fluorophenyl]oxy}-5-chlorobenzonitrile

Trimethylphosphine (1M in THF) (6.41 mL, 6.41 mmol) and water (0.384 mL, 21.36 mmol) were added to a solution of 3-{[3-(azidomethyl)-6-bromo-2-fluorophenyl]oxy}-5-chlorobenzonitrile (1.630 g, 4.27 mmol) in THF (30 mL) at RT. The mixture was stirred at RT overnight. The solvent was evaporated. The residue was purified by chromatography with dichloromethane:methanol to give the title compound (1.21 g, 79%) as a white solid. $^1$H NMR (400 MHz, DMSO-d$_6$) δ ppm 7.80 (s, 1H), 7.60 (dd, 1H), 7.43-7.51 (m, 2H), 7.41 (t, 1H), 3.75 (s, 2H), 1.92 (br. s., 2H).

Step C: 2-azido-N-({4-bromo-3-[(3-chloro-5-cyanophenyl)oxy]-2-fluorophenyl}methyl)-4-chloro-1H-imidazole-5-carboxamide EDC (0.331 g, 1.726 mmol) and HOBT (0.233 g, 1.726 mmol) were added to a solution of 3-{[3-(aminomethyl)-6-bromo-2-fluorophenyl]oxy}-5-chlorobenzonitrile (0.558 g, 1.569 mmol) and 2-azido-4-chloro-1H-imidazole-5-carboxylic acid (0.294 g, 1.569 mmol) in DMF (7 mL). The mixture was stirred at RT overnight. The reaction mixture was diluted with EtOAc and washed with water and brine and the organic layer was dried over sodium sulfate and concentrated to give the crude title compound (0.850 g) as a light yellow solid. This crude product was taken on to the next step without further purification.

Step D: 2-amino-N-({4-bromo-3-[(3-chloro-5-cyanophenyl)oxy]-2-fluorophenyl}methyl)-4-chloro-1H-imidazole-5-carboxamide Lindlar Catalyst (0.167 g, 0.078 mmol) was added to a suspension of 2-azido-N-({4-bromo-3-[(3-chloro-5-cyanophenyl)oxy]-2-fluorophenyl}methyl)-4-chloro-1H-imidazole-5-carboxamide (0.824 g, 1.569 mmol) in ethyl acetate (30 mL) in a pressure vessel. The vessel was evacuated and flushed with nitrogen, then evacuated and filled with hydrogen (50 psi). The reaction mixture was stirred for 7 h, then filtered through celite. The filtrate was evaporated to dryness and the residue was triturated with ethanol and dried under vacuum to give the title compound (0.350 g, 44%) as a white solid. $^1$H NMR (400 MHz, DMSO-d$_6$) δ ppm 10.95 (br. s., 1H), 7.80 (s, 1H), 7.76 (t, 1H), 7.60 (d, 1H), 7.48 (s, 1H), 7.42 (m, 1H), 7.26 (t, 1H), 5.79 (br. s., 2H), 4.45 (d, 2H). ES MS m/z 498 (M–H).

Example 240

2-amino-N-({4-bromo-3-[(3-cyano-5-methylphenyl)oxy]-2-fluorophenyl}methyl)-4-chloro-1H-imidazole-5-carboxamide trifluoroacetate

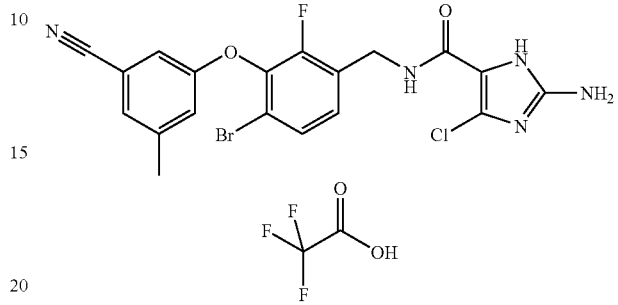

EDC (0.043 g, 0.225 mmol) and HOBT (0.030 g, 0.225 mmol) were added to a solution of 3-{[3-(aminomethyl)-6-chloro-2-fluorophenyl]oxy}-5-methylbenzonitrile (0.059 g, 0.205 mmol) and 2-(bis{[(1,1-dimethylethyl)oxy]carbonyl}amino)-4-chloro-1H-imidazole-5-carboxylic acid (0.074 g, 0.205 mmol) in DMF (2 mL). The mixture was stirred at RT overnight. Saturated sodium bicarbonate was added and the solution was extracted with EtOAc. The organic layer was dried over sodium sulfate and concentrated. The crude product was dissolved in dichloromethane (2 mL) and trifluoroacetic (0.3 mL, 3.89 mmol) was added. The mixture was stirred at RT overnight. The solvent was evaporated and the residue was purified by reverse phase HPLC to give the title compound (0.034 g, 44%) as a white solid. $^1$H NMR (400 MHz, DMSO-d$_6$) δ ppm 7.94-8.04 (m, 1H), 7.48 (d, 1H), 7.43 (s, 1H), 7.33 (t, 1H), 7.21 (br. s., 1H), 7.12 (s, 1H), 4.49 (d, 2H), 2.33 (s, 3H). ES MS m/z 434 (M+1).

Example 241

N-({4-bromo-3-[(3-chloro-5-cyanophenyl)oxy]-2-fluorophenyl}methyl)-4-chloro-2-(hydroxymethyl)-1H-imidazole-5-carboxamide

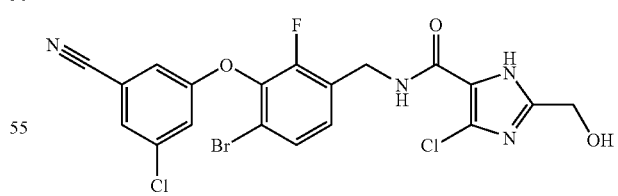

EDC (0.025 g, 0.131 mmol) and HOBT (0.018 g, 0.131 mmol) were added to a solution of 3-{[3-(aminomethyl)-6-bromo-2-fluorophenyl]oxy}-5-chlorobenzonitrile (0.042 g, 0.119 mmol) and 4-chloro-2-({[(1,1-dimethylethyl)(dimethyl)silyl]oxy}methyl)-1-({[2-(trimethylsilyl)ethyl]oxy}methyl)-1H-imidazole-5-carboxylic acid (0.050 g, 0.119 mmol) in DMF (2 mL). The mixture was stirred at RT for 4 hrs, saturated sodium bicarbonate was added and the solution was extracted with EtOAc. The organic layer was dried over sodium sulfate and concentrated. The crude product was dissolved in dichloromethane (2 mL) and trifluoroacetic acid (0.3 mL, 3.89 mmol) was added. The mixture was stirred at RT overnight. The solvent was evaporated and the residue was purified by reverse phase HPLC (acetonitrile: water with 0.1% formic acid) to give the title compound (0.030 g, 47%) as a white powder. $^1$H NMR (400 MHz, DMSO-$d_6$) δ ppm 12.99 (br. s., 1H), 8.32-8.41 (m, 1H), 7.79-7.84 (m, 1H), 7.57-7.65 (m, 1H), 7.47-7.52 (m, 1H), 7.44 (t, 1H), 7.31 (t, 1H), 5.54 (br. s., 1H), 4.45-4.53 (m, 2H), 4.37-4.44 (m, 2H). ES MS: m/z 512, 514.

Example 242

N-({4-chloro-3-[(3-chloro-5-cyanophenyl)oxy]-2-fluorophenyl}methyl)-5-methyl-2-oxo-2,3-dihydro-1H-imidazole-4-carboxamide

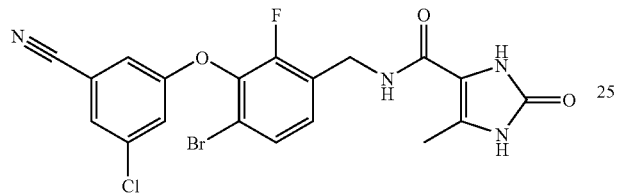

Step A: ethyl 5-methyl-2-oxo-2,3-dihydro-1H-imidazole-4-carboxylate

A mixture of ethyl (2E)-2-(hydroxyimino)-3-oxobutanoate (8.50 g, 53.41 mmol) and 10% Pd/C (0.42 g) in EtOH (25 mL) and a 1.5 M solution of HCl (40 mL) were stirred under hydrogen (50 psig) for 4 h. The vessel was carefully vented then the mixture was filtered through Celite which was subsequently washed with EtOH. The filtrate was concentrated slightly to remove some of the EtOH but the water bath was kept below 40° C. A 5M solution of aqueous HCl (5 mL) was added to the yellow solution and this was added dropwise to a solution of KOCN (6.50 g, 80.12 mmol) in water (25 mL) at RT. The reaction mixture was stirred at RT for 3 days then cooled to 0° C. After 2 h, the precipitate was filtered and washed with a cold 1:1 mixture of MeOH/water (20 mL) and dried under vacuum to afford 1.70 g (19%) of the title compound as a grey powder. 1H NMR (400 MHz, DMSO-$d_6$) δ ppm 10.61 (br. s., 1H), 10.14 (br. s., 1H), 4.16 (d, 2H), 2.20 (br. s., 3H), 1.23 (t, 3H). LCMS m/z 171.3 (M+H).

Step B. 5-methyl-2-oxo-2,3-dihydro-1H-imidazole-4-carboxylic acid

A solution of ethyl 5-methyl-2-oxo-2,3-dihydro-1H-imidazole-4-carboxylate (1.00 g, 5.88 mmol) in 3N NaOH (5.88 mL) was heated to 65° C. for 2 h then cooled to RT. The mixture was filtered then added dropwise to a stirred solution of concentrated $H_2SO_4$ (1.10 mL) in water (7.35 mL). The mixture was stirred for 2 h then filtered. The solid was washed with water (2×10 mL) then dried under vacuum to give 0.65 g (78%) of the title compound as a white solid. 1H NMR (400 MHz, DMSO-$d_6$) δ ppm 12.21 (d, 1H), 10.52 (br. s., 1H), 9.77-10.21 (m, 1H), 1.95-2.35 (m, 3H).

Step C. N-({4-chloro-3-[(3-chloro-5-cyanophenyl)oxy]-2-fluorophenyl}methyl)-5-methyl-2-oxo-2,3-dihydro-1H-imidazole-4-carboxamide DIPEA (0.20 mL, 1.16 mmol) was added to a mixture of 3-{[3-(aminomethyl)-6-chloro-2-fluorophenyl]oxy}-5-chlorobenzonitrile (0.15 g, 0.48 mmol), 5-methyl-2-oxo-2,3-dihydro-1H-imidazole-4-carboxylic acid (0.080 g, 0.58 mmol) and HATU (0.24 g, 0.63 mmol) in DMF (3 mL). The yellow solution was stirred at RT under nitrogen for 24 h then ethyl acetate (50 mL) and saturated sodium bicarbonate solution (100 mL) was added. The organic layer was separated, washed with saturated sodium bicarbonate solution (50 mL), water (50 mL), brine (50 mL) and dried over $MgSO_4$. The mixture was filtered and the solvent was removed under vacuum. The crude material was purified by Reverse Phase HPLC (MeCN/water+0.1% TFA) to give the title compound (0.20 g, 10%) as a white solid. 1H NMR (400 MHz, DMSO-$d_6$) δ ppm 10.42 (br. s., 1H), 9.75 (br. s., 1H), 7.74-7.95 (m, 2H), 7.42-7.57 (m, 3H), 7.37 (t, 1H), 4.44 (d, 2H), 2.20 (s, 3H). LCMS m/z 437.0 (M+H).

Example 243

N-({4-chloro-3-[(3-chloro-5-cyanophenyl)oxy]-2-fluorophenyl}methyl)-N-ethyl-1H-pyrrole-2-carboxamide

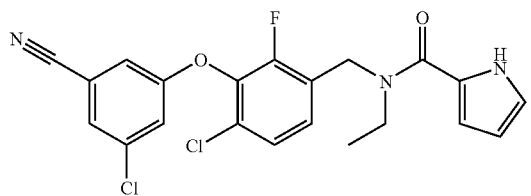

Step A: 3-chloro-5-({6-chloro-3-[(ethylamino)methyl]-2-fluorophenyl}oxy)benzonitrile A solution of 3-{[3-(bromomethyl)-6-chloro-2-fluorophenyl]oxy}-5-chlorobenzonitrile (0.50 g, 1.33 mmol) in THF (10 mL) was added dropwise to a 2M solution of $EtNH_2$ (6.67 mL, 13.33 mmol) in THF. The flask was sealed and stirred at RT overnight. Ethyl acetate (100 ml) and saturated $NaHCO_3$ solution (100 ml) were added. The organic layer was washed with brine (150 mL), dried over $MgSO_4$, filtered and concentrated to give the title compound (0.48 g, quant.) as a tan solid. 1H NMR shows title compound plus a little residual $EtNH_2$. 1H NMR (400 MHz, DMSO-$d_6$) δ ppm 8.04 (br. s., 1H), 7.83 (s, 1H), 7.62 (s, 2H), 7.45-7.55 (m, 2H), 4.14 (s, 2H), 2.95 (q, 2H), 1.18 (t, 3H). LCMS m/z 340.0 (M+H).

Step B. N-({4-chloro-3-[(3-chloro-5-cyanophenyl)oxy]-2-fluorophenyl}methyl)-N-ethyl-1H-pyrrole-2-carboxamide DMF (3 mL) and DIPEA (0.1 mL, 0.59 mmol) were added to a mixture of HATU (0.12 g, 0.32 mmol), 3-chloro-5-({6-chloro-3-[(ethylamino)methyl]-2-fluorophenyl}oxy)benzonitrile (0.10 g, 0.29 mmol) and 1H-pyrrole-2-carboxylic acid (0.05 g, 0.41 mmol). The yellow solution was stirred at RT under a nitrogen atmosphere for 48 h then ethyl acetate (100 ml) and saturated $NaHCO_3$ solution (100 ml) were added. The organic layer was washed with saturated $NaHCO_3$ solution (2×100 ml), brine (150 mL), dried over $MgSO_4$, filtered and concentrated. The crude material was purified by Reverse Phase HPLC (MeCN/water+0.1% TFA) to give the title compound (0.039 g, 31%) as a white solid. 1H NMR (400 MHz, DMSO-$d_6$) δ ppm 11.51 (s, 1H), 7.82 (br. s., 1H), 7.08-7.68 (m, 3H), 6.74-7.04 (m, 1H), 6.24-6.62 (m, 1H), 6.12 (d, 1H), 4.56-5.10 (m, 2H), 3.54-3.88 (m, 2H), 0.96-1.45 (m, 3H). LCMS m/z 433.9 (M+H).

Example 244

N-({4-chloro-3-[(3-chloro-5-cyanophenyl)oxy]-2-fluorophenyl}methyl)-N-ethyl-1H-imidazole-4-carboxamide

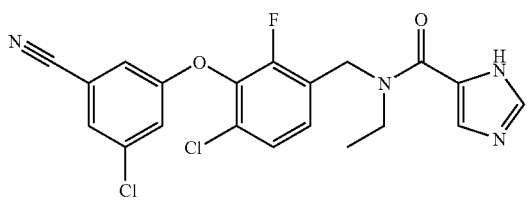

DMF (3 mL) and DIPEA (0.1 mL, 0.59 mmol) were added to a mixture of HATU (0.12 g, 0.32 mmol), 3-chloro-5-({6-chloro-3-[(ethylamino)methyl]-2-fluorophenyl}oxy)benzonitrile (0.10 g, 0.29 mmol) and 1H-imidazole-4-carboxylic acid (0.05 g, 0.41 mmol). The yellow solution was stirred at RT under a nitrogen atmosphere for 48 h then ethyl acetate (100 ml) and saturated NaHCO$_3$ solution (100 ml) were added. The organic layer was washed with saturated NaHCO$_3$ solution (2×100 ml), brine (150 mL), dried over MgSO$_4$, filtered and concentrated. The crude material was purified by Reverse Phase HPLC (MeCN/water+0.1% TFA) to give the title compound (0.046 g, 36%) as a white solid. 1H NMR (400 MHz, DMSO-d$_6$) δ ppm 8.47-8.80 (m, 1H), 7.89-8.03 (m, 1H), 7.82 (s, 1H), 7.44-7.56 (m, 3H), 7.33 (t, 1H), 4.69-5.18 (m, 2H), 3.33-3.79 (m, 2H), 1.01-1.27 (m, 3H). LCMS m/z 431.2 (M−H).

Example 245

4-bromo-N-({4-chloro-3-[(3-chloro-5-cyanophenyl)oxy]phenyl}methyl)-2-methyl-1H-imidazole-5-carboxamide

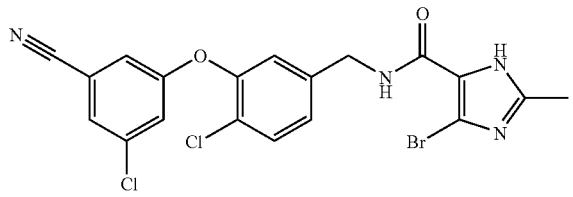

DMF (5 mL) was added to a mixture of 3-{[5-(aminomethyl)-2-chlorophenyl]oxy}-5-chlorobenzonitrile hydrochloride (0.125 g, 0.379 mmol), 4-bromo-2-methyl-1H-imidazole-5-carboxylic acid (0.093 g, 0.455 mmol) and HATU (0.173 g, 0.455 mmol). The mixture was stirred for 5 min then DIPEA (0.132 ml, 0.758 mmol) was added and the yellow solution was stirred at RT under an atmosphere of nitrogen for 2 h. Saturated aqueous NaHCO$_3$ solution (30 mL) and Et$_2$O (10 mL) was added and the suspension was filtered to give 0.50 g of an insoluble white solid. The filtrate was extracted with ethyl acetate (75 mL) and washed with saturated aqueous Na HCO$_3$ solution (2×50 mL), water (50 mL), brine (50 mL), dried over MgSO$_4$, filtered and concentrated. The crude material was purified on silica gel (hexanes/ethyl acetate) to give the title compound (0.075 g, 41%) in ca. 70% purity. The material was purified further by Reverse Phase HPLC (MeCN/H$_2$O+0.1% TFA) to give the title compound (0.043 g, 24%) as a white powder. 1H NMR (400 MHz, DMSO-d$_6$+ CD$_3$OD) δ ppm 7.66 (br. s., 1H), 7.54 (d, 1H), 7.16-7.35 (m, 4H), 4.44 (br. s., 2H), 2.25 (s, 3H). LCMS m/z 481.0 (M+H).

Example 246

4-bromo-N-({4-chloro-3-[(3-chloro-5-cyanophenyl)oxy]phenyl}methyl)-1H-imidazole-5-carboxamide

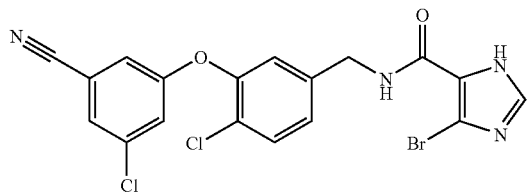

DMF (5 mL) was added to a mixture of 3-{[5-(aminomethyl)-2-chlorophenyl]oxy}-5-chlorobenzonitrile hydrochloride (0.115 g, 0.349 mmol), 4-bromo-1H-imidazole-5-carboxylic acid (0.070 g, 0.366 mmol) and HATU (0.159 g, 0.419 mmol). The mixture was stirred for 5 min then DIPEA (0.122 ml, 0.698 mmol) was added and the yellow solution was stirred at RT under an atmosphere of nitrogen for 2 h. Saturated aqueous NaHCO$_3$ solution (30 mL) and ethyl acetate (75 mL) were added. The organic layer was separated, washed with saturated aqueous NaHCO$_3$ solution (2×50 mL), water (50 mL), brine (50 mL), dried over MgSO$_4$, filtered and concentrated. The crude material was purified by Reverse Phase HPLC (MeCN/water+0.1% TFA) to give the title compound (0.026 g, 16%) as a white solid. 1H NMR (400 MHz, METHANOL-d$_4$) δ ppm 7.74 (br. s., 1H), 7.49-7.56 (m, 2H), 7.30 (d, 1H), 7.16-7.24 (m, 3H), 4.57 (br. s., 2H). LCMS m/z 467.1 (M+H).

Example 247

4-bromo-N-({3-[(3-chloro-5-cyanophenyl)oxy]-2,4-difluorophenyl}methyl)-1H-imidazole-5-carboxamide

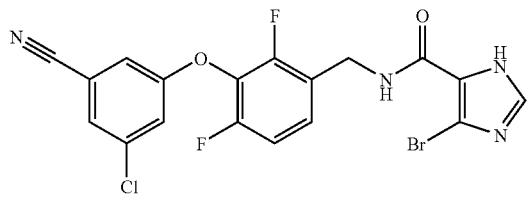

Step A: 3-chloro-5-[(2,6-difluoro-3-methylphenyl)oxy]benzonitrile

A 1M solution KOtBu in THF (4.41 mL, 4.41 mmol) was added to a solution of 2,6-difluoro-3-methylphenol (3 g, 20.82 mmol) in DMSO (10 mL) at 0° C. under an atmosphere of nitrogen. After 10 min, 3-chloro-5-fluorobenzonitrile (3.24 g, 20.82 mmol) and 18-CROWN-6 (0.550 g, 2.082 mmol) were added and the solution was heated to 135° C. After 6 h, the brown solution was cooled to RT and water (100 mL) and ethyl acetate (150 mL) were added. The organic layer was separated, washed with water (2×150 mL), brine (150 mL), dried over MgSO$_4$, filtered and concentrated. The residue was purfied on silica gel (hexanes/ethyl acetate) to give the title compound (4.05 g, 70%) as a white solid (N4011-11-100). 1H NMR (400 MHz, CHLOROFORM-d) δ ppm 7.36 (t, 1H), 7.20 (t, 1H), 7.05-7.14 (m, 2H), 6.93-7.00 (m, 1H), 2.31 (s, 3H).

Step B: 3-{[3-(bromomethyl)-2,6-difluorophenyl]oxy}-5-chlorobenzonitrile

A solution of 3-chloro-5-[(2,6-difluoro-3-methylphenyl)oxy]benzonitrile (4.05 g, 14.48 mmol) and NBS (3.09 g, 17.38 mmol) in carbon tetrachloride (500 mL) was degassed and heated to 90° C. under a nitrogen atmosphere. After ca. 5 min, AIBN (0.119 g, 0.724 mmol) was added and the solution was heated for 6 h. The solution was cooled to 0° C. then filtered through Celite. The filtrate was concentrated and the crude material was purified on silica gel (hexanes/ethyl acetate) to give the title compound (2.9 g, 56%) as a white solid. 1H NMR (400 MHz, CHLOROFORM-d) δ ppm 7.31-7.40 (m, 2H), 7.21 (t, 1H), 7.04-7.11 (m, 2H), 4.51 (s, 2H).

Step C: 3-{[3-(aminomethyl)-2,6-difluorophenyl]oxy}-5-chlorobenzonitrile

A 7M solution of ammonia in MeOH (45.8 mL, 321 mmol) was added to a solution of 3-{[3-(bromomethyl)-2,6-difluorophenyl]oxy}-5-chlorobenzonitrile (2.3 g, 6.41 mmol) in THF (30 mL) at RT. The reaction was capped and stirred for 16 h at RT then concentrated to dryness under vacuum. Ethyl acetate (200 mL) and saturated aqueous NaHCO$_3$ solution (300 mL) were added. The organic layer was separated, washed with saturated aqueous NaHCO$_3$ solution (2×200 mL), water (200 mL), brine (200 mL), dried over Na$_2$SO$_4$, filtered and concentrated to give a white solid. The crude product was purified on silica gel (10% MeOH/DCM) to give the title compound (1.63 g, 86%) as a white solid (N4011-13-100). 1H NMR (400 MHz, DMSO-d$_5$) δ ppm 7.82 (s, 1H), 7.40-7.66 (m, 3H), 7.31 (t, 1H), 3.75 (s, 2H), 1.86 (br. s., 2H).

Step D: 4-bromo-N-({3-[(3-chloro-5-cyanophenyl)oxy]-2,4-difluorophenyl}methyl)-1H-imidazole-5-carboxamide DMF (5 mL) was added to a mixture of 3-{[3-(aminomethyl)-2,6-difluorophenyl]oxy}-5-chlorobenzonitrile (0.093 g, 0.316 mmol), 4-chloro-1-({[2-(trimethylsilyl)ethyl]oxy}methyl)-1H-imidazole-5-carboxylic acid (0.105 g, 0.379 mmol) and HATU (0.144 g, 0.379 mmol). The mixture was stirred for 5 min then DIPEA (0.110 ml, 0.631 mmol) was added and the yellow solution was stirred at RT under an atmosphere of nitrogen for 16 h. LCMS shows the desired product (m/z 553). The DMF was removed under vacuum and the residue was dissolved in DCM (2 mL). TFA (1 mL) was added and the solution was stirred overnight then concentrated to dryness. The crude material was purified by Reverse Phase HPLC and the desired fractions were combined in a separatory funnel, washed with saturated aqueous NaHCO$_3$ solution (100 mL) and extracted with ethyl acetate (75 mL). The organic layer was separated, washed with saturated aqueous NaHCO$_3$ solution (50 mL), water (50 mL), brine (50 mL), dried over MgSO$_4$, filtered and concentrated to give the title compound (0.080 g, 60%) as a white powder. 1H NMR (400 MHz, DMSO-d$_6$+D$_2$O) δ ppm 7.67-7.87 (m, 2H), 7.44-7.60 (m, 2H), 7.22-7.41 (m, 2H), 4.50 (s, 2 H). LCMS m/z 424.0 (M+H).

Example 248

4-chloro-N-[(4-chloro-3-{[3-cyano-5-(2-propen-1-yl)phenyl]oxy}-2-fluorophenyl)methyl]-2-methyl-1H-imidazole-5-carboxamide trifluoroacetate

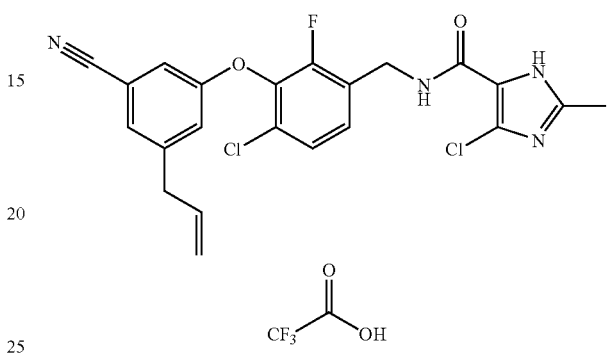

Step A: 3-{[3-(aminomethyl)-6-chloro-2-fluorophenyl]oxy}-5-(2-propen-1-yl)benzonitrile A mixture of 3-{[3-(aminomethyl)-6-chloro-2-fluorophenyl]oxy}-5-bromobenzonitrile (0.62 g, 1.744 mmol), tributyl(2-propen-1-yl)stannane (0.924 g, 2.79 mmol) and Pd(PPh$_3$)$_4$ (0.201 g, 0.174 mmol) in N,N-Dimethylformamide (DMF) (14 ml) was heated in a microwave reactor at 120° C. for 30 min. The vessel was cooled to RT and ethyl acetate (200 mL) and water (200 mL) were added. The organic layer was separated, washed with brine (200 mL), dried over MgSO$_4$, filtered and concentrated. The crude material was purified on silica gel (hexanes/ethyl acetate) to give 0.38 g of a mixture of 3-{[3-(aminomethyl)-6-chloro-2-fluorophenyl]oxy}-5-(2-propen-1-yl)benzonitrile and Bu$_3$SnBr. The material was used without further purification. N4011-30-100. 1H NMR (400 MHz, CHLOROFORM-d) δ ppm 7.20-7.29 (m, 2H), 7.17 (s, 1H), 7.02 (s, 1H), 6.84 (s, 1H), 5.78-5.96 (m, 1H), 5.01-5.18 (m, 2H), 3.91 (s, 2H), 3.37 (d, 2H).

Step B: 4-chloro-N-[(4-chloro-3-{[3-cyano-5-(2-propen-1-yl)phenyl]oxy}-2-fluorophenyl)methyl]-2-methyl-1H-imidazole-5-carboxamide trifluoroacetate A solution of 3-{[3-(aminomethyl)-6-chloro-2-fluorophenyl]oxy}-5-(2-propen-1-yl)benzonitrile (0.38 g, 1.200 mmol), 4-chloro-2-methyl-1H-imidazole-5-carboxylic acid (0.462 g, 1.440 mmol), EDC (0.276 g, 1.440 mmol) and HOBT (0.220 g, 1.440 mmol) in N,N-Dimethylformamide (DMF) (20 ml) were stirred at RT under an atmosphere of nitrogen for 16 h then ethyl acetate (100 mL) and saturated aqueous NaHCO$_3$ solution (100 mL) were added. The organic layer was separated, washed with saturated aqueous NaHCO$_3$ solution (100 mL), water (100 mL), dried over MgSO$_4$, filtered and concentrated. The crude material was purified on silica gel (hexanes/ethyl acetate) to give 0.40 g (73%) of the desired compound but in only ~70% purity. The material was further purified by Reverse Phase HPLC (MeCN/water+0.1% TFA) to give the title compound (0.14 g, 20%). 1H NMR (400 MHz, METHANOL-d$_4$) δ ppm 7.20-7.41 (m, 3H), 7.03 (s, 1H), 6.98 (s, 1H), 5.78-6.00 (m, 1H), 4.98-5.14 (m, 2H), 4.61 (s, 2H), 3.38 (d, 2H), 2.35 (s, 3H). LCMS m/z 457.1 (M−H).

Example 249

4-chloro-N-({3-[(3-chloro-5-cyanophenyl)oxy]-4-ethyl-2-fluorophenyl}methyl)-2-methyl-1H-imidazole-5-carboxamide

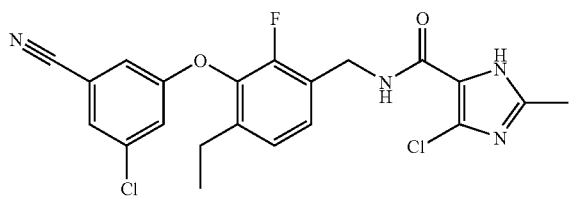

Step A: 1,1-dimethylethyl({4-bromo-3-[(3-chloro-5-cyanophenyl)oxy]-2-fluorophenyl}methyl)carbamate BOC₂O (2.183 ml, 9.40 mmol) was added to a solution of 3-{[3-(aminomethyl)-6-bromo-2-fluorophenyl]oxy}-5-chlorobenzonitrile (3.04 g, 8.55 mmol) in chloroform (75 ml) at 0° C. under nitrogen. The yellow solution was allowed to warm to RT and stirred for 24 h. Saturated NaHCO₃ solution (300 mL) and CH₂Cl₂ (200 mL) were added. The organic layer was separated, washed with brine solution (300 mL), dried over MgSO₄, filtered, concentrated and purified on silica gel (hexanes/ethyl acetate) to give the title compound (2.9 g, 71%) as a white solid. 1H NMR (400 MHz, CHLOROFORM-d) δ ppm 7.45 (dd, 1H), 7.36 (t, 1H), 7.24 (t, 1H), 7.15 (t, 1H), 6.99-7.02 (m, 1H), 4.97 (br. s., 1H), 4.37 (d, 2H), 1.46 (s, 9H).

Step B: 1,1-dimethylethyl({3-[(3-chloro-5-cyanophenyl)oxy]-4-ethenyl-2-fluorophenyl}methyl)carbamate A mixture of 1,1-dimethylethyl({4-bromo-3-[(3-chloro-5-cyanophenyl)oxy]-2-fluorophenyl}methyl)carbamate (0.64 g, 1.404 mmol), potassium vinyl trifluoroborate (0.282 g, 2.107 mmol), 1,1'-bis(diphenylphosphino)ferrocene-palladium(II)dichloride dichloromethane complex (0.046 g, 0.056 mmol) and triethylamine (0.294 ml, 2.107 mmol) in n-propanol (15 ml) were heated to 100° C. under an atmosphere of nitrogen for 4 h. The reaction cooled to RT and water (150 mL) and ethyl acetate (150 mL) were added. The organic layer was separated, washed with brine (150 mL), dried over MgSO₄, filtered through Celite and concentrated. The mixture was dissolved in n-propanol (15 ml) and potassium vinyl trifluoroborate (0.56 g, 4.22 mmol), 1,1'-bis(diphenylphosphino)ferrocene-palladium(II)dichloride dichloromethane complex (0.046 g, 0.056 mmol), and triethyl amine (0.63 g, 6.33 mmol) were added. The mixture was heated to 100° C. under an atmosphere of nitrogen for 8 h. The reaction was cooled to RT and water (150 mL) and ethyl acetate (150 mL) were added. The organic layer was separated, washed with brine (150 mL), dried over MgSO₄, filtered through Celite, concentrated and purified on silica gel (hexanes/ethyl acetate) to give the title compound (0.52 g, 83%) in ca. 90% purity. 1H NMR (400 MHz, CHLOROFORM-d) δ ppm 7.40 (d, 1H), 7.26-7.33 (m, 2H), 7.12 (t, 1H), 6.98 (d, 1H), 6.69 (dd, 1H), 5.82 (d, 1H), 5.36 (d, 1H), 4.97 (br. s., 1H), 4.38 (d, 2H), 1.46 (s, 9H).

Step C: 1,1-dimethylethyl({3-[(3-chloro-5-cyanophenyl)oxy]-4-ethyl-2-fluorophenyl}methyl)carbamate A mixture of 1,1-dimethylethyl({3-[(3-chloro-5-cyanophenyl)oxy]-4-ethenyl-2-fluorophenyl}methyl)carbamate (0.5 g, 1.241 mmol), diphenyl sulfide (0.021 ml, 0.124 mmol) and Pd/C (0.132 g, 0.124 mmol) in ethyl acetate (80 ml) and methanol (80 ml) was stirred at RT under an atmosphere of hydrogen gas (45 psi) for 3 h. The vessel was carefully vented and the mixture was filtered thru Celite and dried to give the title compound (0.5 g, 95%) as a white solid. 1H NMR (400 MHz, DMSO-d₆) δ ppm 7.76 (t, 1H), 7.29-7.43 (m, 3H), 7.18-7.23 (m, 2H), 4.16 (d, 2H), 2.45-2.53 (m, 2H), 1.38 (s, 9H), 1.08 (t, 3H). LCMS m/z 403.1 (M−H).

Step D: 3-{[3-(aminomethyl)-6-ethyl-2-fluorophenyl]oxy}-5-chlorobenzonitrile

TFA (1.903 ml, 24.70 mmol) was added to a solution of 1,1-dimethylethyl({3-[(3-chloro-5-cyanophenyl)oxy]-4-ethyl-2-fluorophenyl}methyl)carbamate (0.5 g, 1.235 mmol) in DCM (30 mL) at RT under an atmosphere of nitrogen. After 16 h, the solution was concentrated under vacuum. Saturated NaHCO₃ solution (100 mL) and ethyl acetate (100 mL) were added and the mixture was stirred for 1 h. The organic layer was separated, washed with water (100 mL), brine (100 mL), dried over Na₂SO₄, filtered and concentrated to give the title compound (0.38 g, >99%) as a brown oil. 1H NMR (400 MHz, CHLOROFORM-d) δ ppm 7.29-7.33 (m, 1H), 7.21-7.27 (m, 1H), 7.13 (t, 1H), 7.09 (d, 1H), 6.98 (s, 1H), 3.92 (s, 2H), 2.54 (d, 2H), 1.54 (d, 2H), 1.13-1.19 (m, 3H).

Step E: 4-chloro-N-({3-[(3-chloro-5-cyanophenyl)oxy]-4-ethyl-2-fluorophenyl}methyl)-2-methyl-1H-imidazole-5-carboxamide A solution of 3-{[3-(aminomethyl)-6-ethyl-2-fluorophenyl]oxy}-5-chlorobenzonitrile (0.075 g, 0.246 mmol), 4-chloro-2-methyl-1H-imidazole-5-carboxylic acid (0.040 g, 0.246 mmol), EDC (0.047 g, 0.246 mmol) and HOBT (0.038 g, 0.246 mmol) in DMF (4 ml) was stirred at RT under an atmosphere of nitrogen for 1 h then ethyl acetate (100 mL) and saturated aqueous NaHCO₃ solution (100 mL) were added. The organic layer was separated, washed with saturated aqueous NaHCO₃ solution (100 mL), water (100 mL), dried over MgSO₄, filtered and concentrated. The material was purified by Reverse Phase HPLC (MeCN/water+0.1% TFA). The desired product was washed with saturated NaHCO₃ solution and extraced with ethyl acetate. The organic layer was separated, washed with saturated aqueous NaHCO₃ solution (50 mL), water (50 mL), dried over MgSO₄, filtered and concentrated to give the title compound (0.052 g, 47%) as a white solid. 1H NMR (400 MHz, CHLOROFORM-d) δ ppm 11.06 (br. s., 1H), 7.29 (s, 1H), 7.20 (d, 1H), 7.03-7.12 (m, 3H), 6.97 (s, 1H), 4.67 (d, 2H), 2.53 (q, 2H), 2.37 (s, 3H), 1.13 (t, 3H). LCMS m/z 447.05 (M+H).

Example 250

4-chloro-N-({3-[(3-chloro-5-cyanophenyl)oxy]-4-ethyl-2-fluorophenyl}methyl)-1H-imidazole-5-carboxamide

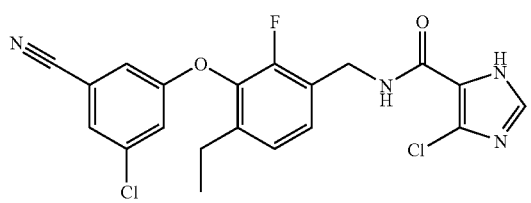

Step A: 4-chloro-N-({3-[(3-chloro-5-cyanophenyl)oxy]-4-ethyl-2-fluorophenyl}methyl)-1-({[2-(trimethylsilyl)ethyl]oxy}methyl)-1H-imidazole-5-carboxamide A solution of 3-{[3-(aminomethyl)-6-ethyl-2-fluorophenyl]oxy}-5-chlorobenzonitrile (0.075 g, 0.246 mmol), 4-chloro-1-({[2-(trimethylsilyl)ethyl]oxy}methyl)-1H-imidazole-5-carboxylic acid (0.075 g, 0.271 mmol), EDC (0.052 g, 0.271 mmol) and HOBT (0.041 g, 0.271 mmol) in DMF (4 ml) was stirred at RT under an atmosphere of nitrogen for 16 h then ethyl acetate (100 mL) and saturated aqueous NaHCO₃ solution (100 mL) were added. The organic layer was separated, washed with saturated aqueous NaHCO₃ solution (100 mL), water (100 mL), dried over MgSO₄, filtered and concentrated. The material was purified on silica gel (hexanes/ethyl acetate) to give the title compound (0.12 g, 74%) in ca. 85% purity. 1H NMR (400 MHz, CHLOROFORM-d) δ ppm 7.65 (s, 1H), 7.34 (t, 1H), 7.28-7.32 (m, 1H), 7.09-7.20 (m, 3H), 7.02 (d, 1H), 5.75 (s, 2H), 4.69 (d, 2H), 3.61 (t, 2H), 2.57 (q, 2H), 1.18 (t, 3H), 0.95 (t, 2H).

Step B: 4-chloro-N-({3-[(3-chloro-5-cyanophenyl)oxy]-4-ethyl-2-fluorophenyl}methyl)-1H-imidazole-5-carboxamide A solution of 5-chloro-N-({3-[(3-chloro-5-cyanophenyl)oxy]-4-ethyl-2-fluorophenyl}methyl)-1-({[2-(trimethylsilyl)ethyl]oxy}methyl)-1H-imidazole-4-carboxamide (0.12 g, 0.213 mmol) and TFA (1.641 ml, 21.29 mmol) were stirred at RT under an atmosphere of nitrogen for 16 h then the solution was concentrated under vacuum. The material was purified by Reverse Phase HPLC (MeCN/water+0.1% TFA). The desired product was washed with saturated NaHCO₃ solution and extracted with ethyl acetate. The organic layer was separated, washed with saturated aqueous NaHCO₃ solution (50 mL), water (50 mL), dried over MgSO₄, filtered and concentrated to give the title compound (0.059 g, 61%) as a white solid. 1H NMR (400 MHz, METHANOL-d₄) δ ppm 7.73 (s, 1H), 7.50 (s, 1H), 7.31 (t, 1H), 7.15-7.22 (m, 3H), 4.64 (s, 2H), 2.58 (q, 2H), 1.15 (t, 3H). LCMS m/z 434.1 (M+H).

Example 251

2-amino-4-chloro-N-({3-[(3-chloro-5-cyanophenyl)oxy]-4-ethyl-2-fluorophenyl}methyl)-1H-imidazole-5-carboxamide

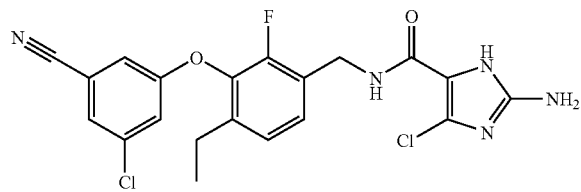

A solution of 3-{[3-(aminomethyl)-6-ethyl-2-fluorophenyl]oxy}-5-chlorobenzonitrile (0.075 g, 0.246 mmol), 2-azido-4-chloro-1H-imidazole-5-carboxylic acid (0.051 g, 0.271 mmol), EDC (0.052 g, 0.271 mmol) and HOBT (0.041 g, 0.271 mmol) in DMF (4 ml) was stirred at RT under an atmosphere of nitrogen for 16 h then ethyl acetate (100 mL) and saturated aqueous NaHCO₃ solution (100 mL) were added. The organic layer was separated, washed with saturated aqueous NaHCO₃ solution (100 mL), water (100 mL), dried over MgSO₄, filtered and concentrated. Ethyl acetate (20 mL) and Lindlar Catalyst (0.026 g, 0.247 mmol) were added and the mixture was stirred at RT under an atmosphere of hydrogen (55 psig) for 19 h. The vessel was carefully vented and the mixture was filtered thru Celite, concentrated purified by Reverse Phase HPLC (MeCN/water+0.1% TFA) to give the title compound (0.059 g, 51%) as a white solid. 1H NMR (400 MHz, DMSO-d₆) δ ppm 10.93 (s, 1H), 7.77 (t, 1H), 7.70 (t, 1H), 7.39 (s, 1H), 7.33 (t, 1H), 7.18-7.29 (m, 2H), 5.81 (s, 2H), 4.47 (d, 2H), 2.47-2.54 (m, 2H), 1.08 (t, 3H). LCMS m/z 450.1 (M+H).

Example 252

4-chloro-N-{[3-[(3-chloro-5-cyanophenyl)oxy]-4-(difluoromethyl)-2-fluorophenyl]methyl}-1H-imidazole-5-carboxamide

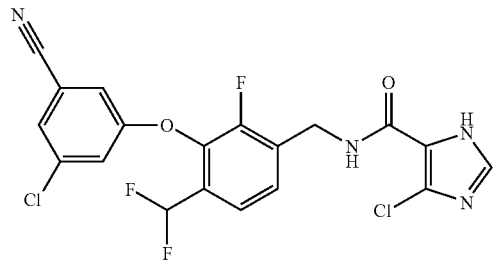

Step A: 1,1-dimethylethyl({3-[(3-chloro-5-cyanophenyl)oxy]-2-fluoro-4-formylphenyl}methyl)carbamate Osmium tetroxide (0.156 ml, 0.012 mmol) was added to a mixture of 1,1-dimethylethyl({3-[(3-chloro-5-cyanophenyl)oxy]-4-ethenyl-2-fluorophenyl}methyl)carbamate (0.25 g, 0.621 mmol) and sodium periodate (0.398 g, 1.862 mmol) in THF (4 ml) and water (2 ml). A white precipitate formed and the slurry was stirred at RT overnight. Water (75 mL) and ethyl acetate (75 mL) were added and the organic layer was separated, washed with water (75 mL), brine (75 mL), dried over MgSO₄, filtered and concentrated to give the title compound (0.153 g, 60%) as a white solid. 1H NMR (400 MHz, CHLOROFORM-d) δ ppm 10.16 (s, 1H), 7.77 (d, 1H), 7.46 (t, 1H), 7.39 (d, 1H), 7.19 (t, 1H), 7.07 (s, 1H), 5.05 (br. s., 1H), 4.46 (d, 2H), 1.46 (s, 9H).

Step B: 1,1-dimethylethyl {[3-[(3-chloro-5-cyanophenyl)oxy]-4-(difluoromethyl)-2-fluorophenyl]methyl}carbamate A solution of 1,1-dimethylethyl({3-[(3-chloro-5-cyanophenyl)oxy]-2-fluoro-4-formylphenyl}methyl)carbamate (0.15 g, 0.371 mmol) and DAST (0.098 ml, 0.741 mmol) in dichloromethane (6 ml) was stirred at RT for 16 h then water (15 mL) and ethyl acetate (25 mL) were added. The organic layer was washed with brine, dried over MgSO₄, filtered and concentrated to give the title compound (0.152 g, 94%) as a orange solid. 1H NMR (400 MHz, CHLOROFORM-d) δ ppm 7.39-7.52 (m, 2H), 7.37 (t, 1H), 7.15 (t, 1H), 7.03 (s, 1H), 6.76 (t, 1H), 4.98 (br. s., 1H), 4.42 (d, 2H), 1.46 (s, 9H).

Step C: 3-{[3-(aminomethyl)-6-(difluoromethyl)-2-fluorophenyl]oxy}-5-chlorobenzonitrile A solution of 1,1-dimethylethyl {[3-[(3-chloro-5-cyanophenyl)oxy]-4-(difluoromethyl)-2-fluorophenyl]methyl}carbamate (0.152 g, 0.356 mmol) and TFA (1.372 ml, 17.81 mmol) in dichloromethane (10 ml) was stirred for 16 h at RT under an atmosphere of nitrogen. The solution was concentrated under vacuum to give the title compound as an orange oil that was used without further purification. 1H NMR (400 MHz, CHLOROFORM-d) δ ppm 7.40-7.52 (m, 2H), 7.31 (s, 1H), 7.23-7.26 (m, 1H), 6.89 (s, 1H), 6.74 (t, 1H), 4.19 (br. s., 2H).

Step D: 4-chloro-N-{[3-[(3-chloro-5-cyanophenyl)oxy]-4-(difluoromethyl)-2-fluorophenyl]methyl}-imidazole-5-carboxamide A solution of 3-{[3-(aminomethyl)-6-(difluoromethyl)-2-fluorophenyl]oxy}-5-chlorobenzonitrile (0.08 g, 0.245 mmol), 4-chloro-1-({[2-(trimethylsilyl)ethyl]oxy}methyl)-1H-imidazole-5-carboxylic acid (0.068 g, 0.245 mmol), EDC (0.047 g, 0.245 mmol) and HOBT (0.037 g, 0.245 mmol) in DMF (4 ml) was stirred at RT under an atmosphere of nitrogen for 16 h then ethyl acetate (30 mL) and saturated aqueous NaHCO₃ solution (30 mL) were added. The organic layer was separated, washed with saturated aqueous NaHCO₃ solution (30 mL), water (30 mL), brine (30 mL), dried over MgSO₄, filtered and concentrated. A solution of this residue and TFA (0.019 ml, 0.246 mmol) in dichloromethane (10 ml) was stirred at RT under an atmosphere of nitrogen for 16 h. The solvent was removed under vacuum and the resulting oil was purified by Reverse Phase HPLC (MeCN/water+0.1% TFA). The desired compound was washed with saturated aqueous NaHCO₃ solution (25 mL) and extracted with ethyl acetate (25 mL). The organic layer was separated, washed with water (25 mL), brine (25 mL), dried over MgSO₄, filtered and concentrated to give the title compound (0.034 g, 30%) as a white powder. 1H NMR (400 MHz, METHANOL-d₄) δ ppm 7.73 (s, 1H), 7.44-7.63 (m, 3H), 7.27 (d, 2H), 6.92 (t, 1H), 4.70 (s, 2H). LC/MS m/z 453.2 (M−H).

Example 253

2-amino-4-chloro-N-{[3-[(3-chloro-5-cyanophenyl)oxy]-4-(difluoromethyl)-2-fluorophenyl]methyl}-1H-imidazole-5-carboxamide

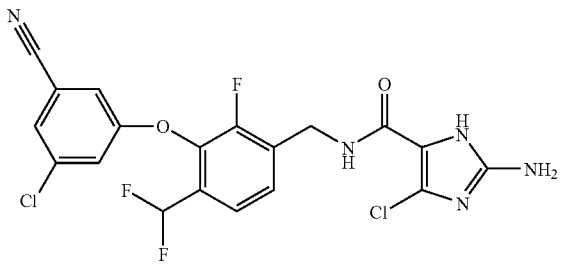

A solution of 3-{[3-(aminomethyl)-6-(difluoromethyl)-2-fluorophenyl]oxy}-5-chlorobenzonitrile (0.08 g, 0.245 mmol), 2-azido-4-chloro-1H-imidazole-5-carboxylic acid (0.046 g, 0.245 mmol), EDC (0.047 g, 0.245 mmol) and HOBT (0.037 g, 0.245 mmol) in N,N-Dimethylformamide (DMF) (4 ml) were stirred at RT under an atmosphere of nitrogen for 16 h then ethyl acetate (30 mL) and saturated aqueous NaHCO₃ solution (30 mL) were added. The organic layer was separated, washed with saturated aqueous NaHCO₃ solution (30 mL), water (30 mL), brine (30 mL), dried over MgSO₄, filtered and concentrated. A mixture of 2-azido-5-chloro-N-{[3-[(3-chloro-5-cyanophenyl)oxy]-4-(difluoromethyl)-2-fluorophenyl]methyl}-1H-imidazole-4-carboxamide (0.12 g, 0.242 mmol) and Lindlar Catalyst (5.15 mg, 0.048 mmol) in ethyl acetate (10 ml) was stirred at RT under hydrogen (55 psig) for 16 h. Next day TLC & LCMS show desired product and remaining starting material. More Lindlar Catalyst (5.15 mg, 0.048 mmol) was added and the mixture was stirred at RT under hydrogen (55 psig) for 6 h. The mixture was carefully vented, filtered thru Celite and concentrated under vacuum. The yellow solid was purified by Reverse Phase HPLC (MeCN/water+0.1 TFA) to give a white solid. The salt was stirred with ethyl acetate (15 mL) and saturated aqueous NaHCO₃ solution (15 mL) for 15 min. The organic layer was separated, washed with water (15 mL), brine (15 mL), dried over MgSO₄, filtered and concentrated to give 0.033 g (29%) of the title compound as a white powder. 1H NMR (400 MHz, METHANOL-d₄) δ ppm 7.39-7.62 (m, 3H), 7.27 (d, 2H), 6.92 (t, 1H), 4.66 (s, 2H). LCMS m/z 468.3 (M−H).

Example 254

4-chloro-N-{[3-[(3-chloro-5-cyanophenyl)oxy]-4-(difluoromethyl)-2-fluorophenyl]methyl}-2-methyl-1H-imidazole-5-carboxamide

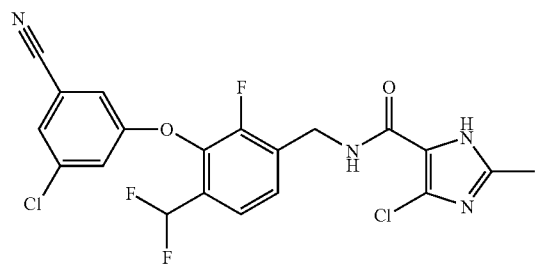

A solution of 3-{[3-(aminomethyl)-6-(difluoromethyl)-2-fluorophenyl]oxy}-5-chlorobenzonitrile (0.05 g, 0.153 mmol), 4-chloro-2-methyl-1H-imidazole-5-carboxylic acid (0.027 g, 0.168 mmol), EDC (0.032 g, 0.168 mmol) and HOBT (0.026 g, 0.168 mmol) in N,N-Dimethylformamide (DMF) (4 ml) were stirred at RT under an atmosphere of nitrogen for 16 h then ethyl acetate (30 mL) and saturated aqueous NaHCO₃ solution (30 mL) were added. The organic layer was separated, washed with saturated aqueous NaHCO₃ solution (30 mL), water (30 mL), brine (30 mL), dried over MgSO₄, filtered and concentrated. The crude material was purified by Reverse Phase HPLC (MeCN/water+0.1% TFA) to give the desired product as a TFA salt. The white solid was stirred with saturated aqueous NaHCO₃ solution (~10 mL) and ethyl acetate (30 mL) for 15 min then the organic layer was separated, washed with water (15 mL), brine (15 mL), dried over MgSO₄, filtered and concentrated to give 0.02 g (28%) of the title compound as a white solid. 1H NMR (400 MHz, METHANOL-d₄) δ ppm 7.43-7.62 (m, 3H), 7.21-7.35 (m, 2H), 6.75-7.10 (m, 1H), 4.69 (s, 2H), 2.36 (s, 3H). LCMS m/z 467.2 (M−H).

Example 255

N-({4-chloro-3-[(3-chloro-5-cyanophenyl)oxy]-2-fluorophenyl}methyl)-2,4-dimethyl-1H-imidazole-5-carboxamide

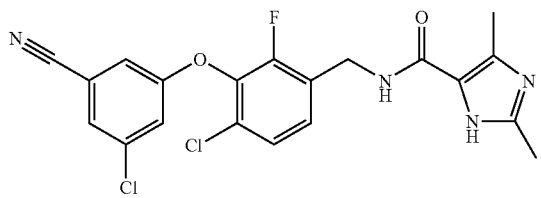

Step A: Ethyl 2-amino-3-oxobutanoate hydrochloride

Ethyl 2-amino-3-oxobutanoate hydrochloride was prepared as described in *J. Med. Chem.* 1996, 39, 957. LiHMDS (50 mL, 50 mmol, 1 M in THF) was slowly added to a solution of ethyl N-(diphenylmethylidene)glycinate in THF (62.5 mL)

at −78° C. under N₂. The yellow slurry was stirred for 45 min. and was then transferred via cannula to a solution of acetyl chloride (4.2 mL, 59 mmol) in THF (25 mL) at −78° C. Additional THF (125 mL) was added to the anion solution to facilitate transfer to the acetyl chloride solution. The reaction mixture was allowed to warm to RT and stirred for 4 h. The reaction was then quenched with 2 N HCl (57.5 mL). The THF was evaporated and the resultant aqueous solution was extracted with EtOAc (2×50 mL). The organic phases were discarded and the aqueous phase was concentrated in vacuo. The residue was treated with EtOH (75 mL) and filtered. The filtrate was concentrated in vacuo to give the title compound (9.6 g, >99%) as a light-yellow solid which was used in next step without purification.

Step B: Ethyl 2-(acetylamino)-3-oxobutanoate

4-Methylmorpholine (0.41 mL, 3.7 mmol) was added dropwise via a syringe pump to a mixture of ethyl 2-amino-3-oxobutanoate hydrochloride (565 mg, 3.12 mmol) and acetic anhydride (0.35 mL, 3.7 mmol) in DMF (2 mL) and THF (4 mL) at RT under N₂ over a period of 30 min. The reaction was stirred for 1 h and water was then added. It was extracted with EtOAc. The organic layer was washed with saturated sodium bicarbonate, HCl (1 N) and brine, dried over sodium sulfate and concentrated. The residue was purified by ISCO FC with 0-40% EtOAc in hexane to give the title compound (73 mg, 13%) as a light-yellow crystalline solid. $^1$H NMR (400 MHz, CDCl₃-d) δ ppm 6.60 (s, 1H) 5.22 (d, J=6.59 Hz, 1H) 4.25 (q, J=6.90 Hz, 2H) 2.36 (s, 3H) 2.04 (s, 3H) 1.28 (t, J=7.14 Hz, 2H).

Step C: Ethyl 2,4-dimethyl-1H-imidazole-5-carboxylate

Ammonium acetate (185 mg, 2.4 mmol) was added to a solution of ethyl 2-(acetylamino)-3-oxobutanoate (90 mg, 0.48 mmol) in acetic acid (1.0 mL). The mixture was heated to reflux overnight. After cooling, the solvent was evaporated under reduced pressure and the residue was taken up in saturated sodium bicarbonate and extracted with EtOAc. The organic layer was dried over sodium sulfate, and concentrated. The residue was purified by column chromatography (0-4% 2M NH3 solution of MeOH in DCM) to give the title compound (54 mg, 67%) as a white solid. $^1$H NMR (400 MHz, CDCl₃-d) δ ppm 4.30 (q, J=7.20 Hz, 2H) 2.44 (s, 3H) 2.38 (s, 3H) 1.34 (t, J=7.14 Hz, 3H). LCMS: m/z 169 (M+1).

Step D: 2,4-dimethyl-1H-imidazole-5-carboxylic acid

Lithium hydroxide (1.6 mL, 1.6 mmol, 1 M in H₂O) was added to a solution of ethyl 2,4-dimethyl-1H-imidazole-5-carboxylate (54 mg, 0.32 mmol) in THF:MeOH (4.8 mL/1.6 mL). The reaction mixture was heated at 70° C. for 4 h. The solvent was evaporated and dried in vacuo to give the title compound (mg, >99%) as a white solid which was directly used in the next step without purification.

Step E: N-({4-chloro-3-[(3-chloro-5-cyanophenyl)oxy]-2-fluorophenyl}methyl)-2,4-dimethyl-1H-imidazole-5-carboxamide HATU (365 mg, 0.96 mmol) was added to a solution of 3-{[3-(aminomethyl)-6-chloro-2-fluorophenyl]oxy}-5-chlorobenzonitrile (99 mg, 0.32 mmol), 5-(acetylamino)-1H-indole-2-carboxylic acid (45 mg, 0.32 mmol) and diisopropylethylamine (167 uL, 0.96 mmol) in DMF (2 mL). The reaction mixture was stirred at RT overnight and was extracted with ethyl acetate and water. The organic layer was washed with brine, dried over sodium sulfate and concentrated. The residue was purified by column chromatography (0-5% 2M NH3 solution of MeOH in DCM) and preparative TLC (5% 2M NH3 solution of MeOH in DCM) to afford the title compound (3.8 mg) as a white solid. $^1$H NMR (400 MHz, CDCl₃-d) δ ppm 8.82 (s, 1H) 7.53 (s, 1H) 7.30-7.38 (m, 2H) 7.21-7.26 (m, 1H) 7.13 (s, 1H) 7.01 (s, 1H) 4.61 (d, J=6.41 Hz, 2H) 2.54 (s, 3H) 2.35 (s, 3H). LCMS: m/z 433 (M+1).

Example 256

N-({4-chloro-3-[(3-chloro-5-cyanophenyl)oxy]-2-fluorophenyl}methyl)-2-ethyl-4-methyl-1H-imidazole-5-carboxamide

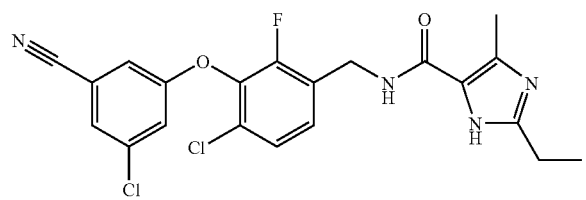

Step A: Ethyl 3-oxo-2-(propanoylamino)butanoate

HATU (1.41 g, 3.7 mmol) was added to a mixture of ethyl 2-amino-3-oxobutanoate hydrochloride (565 mg, 3.12 mmol) and propionic acid (280 uL, 3.7 mmol) in DMF (2 mL) and THF (4 mL) at RT under N₂. The reaction was stirred for 1 h and 4-methylmorpholine (0.41 mL, 3.7 mmol) was then added dropwise via a syringe pump to the above mixture. The reaction was stirred for 1 h and water was then added. It was extracted with EtOAc. The organic layer was washed with saturated sodium bicarbonate, HCl (1 N) and brine, dried over sodium sulfate and concentrated. The residue was purified by ISCO FC with 0-40% EtOAc in hexane to give the title compound (74 mg, 12%) as a light-yellow solid. $^1$H NMR (400 MHz, CDCl₃-d) δ ppm 6.61 (s, 1H) 5.20 (d, J=6.59 Hz, 1H) 4.22 (q, J=7.14 Hz, 2H) 2.34 (s, 3H) 2.26 (q, J=7.51 Hz, 2H) 1.25 (t, J=7.14 Hz, 3H) 1.11 (t, J=7.51 Hz, 3H).

Step B: Ethyl 2-ethyl-4-methyl-1H-imidazole-5-carboxylate

The reaction procedure and purification process are similar to that outlined herein except that ethyl 3-oxo-2-(propanoylamino)butanoate was used. The title compound (72 mg, 61%) as a light-yellow solid. $^1$H NMR (400 MHz, CDCl₃-d) δ ppm 4.30 (q, J=7.14 Hz, 2H) 2.72 (q, J=7.69 Hz, 2H) 2.45 (s, 3H) 1.33 (t, J=7.14 Hz, 3H) 1.29 (t, J=7.60 Hz, 3H). LCMS: m/z 183 (M+1).

Step C: 2-Ethyl-4-methyl-1H-imidazole-5-carboxylic acid

Lithium hydroxide (2 mL, 2 mmol, 1 M in H₂O) was added to a solution of ethyl 2-ethyl-4-methyl-1H-imidazole-5-carboxylate (72 mg, 0.39 mmol) in THF:MeOH (6 mL/2 mL). The reaction mixture was heated at 70° C. for 4 h. The solvent was evaporated and dried in vacuo to give the title compound (61.6 mg, >99%) as a white solid which was directly used in the next step without purification.

Step D: N-({4-chloro-3-[(3-chloro-5-cyanophenyl)oxy]-2-fluorophenyl}methyl)-2-ethyl-4-methyl-1H-imidazole-5-carboxamide HATU (114 mg, 0.3 mmol) was added to a solution of 3-{[3-(aminomethyl)-6-chloro-2-fluorophenyl]oxy}-5-chlorobenzonitrile (62 mg, 0.2 mmol), 5-(acetylamino)-1H-indole-2-carboxylic acid (31 mg, 0.2 mmol) and diisopropylethylamine (52 uL, 0.3 mmol) in DMF (1 mL). The reaction mixture was stirred at RT overnight and was extracted with ethyl acetate and water. The organic layer was washed with brine, dried over sodium sulfate and concentrated. The residue was purified by column chromatography (0-5% 2M NH3 solution of MeOH in DCM) and preparative TLC (5% 2M NH3 solution of MeOH in DCM) to afford the title compound (5.5 mg) as a white solid. $^1$H NMR (400 MHz, CDCl₃-d): δ ppm 8.85 (s, 1H) 7.54 (s, 1H) 7.31-7.38 (m, 2H) 7.20-7.27 (m, 1H) 7.14 (s, 1H) 7.01 (s, 1H) 4.62 (d, J=6.41 Hz, 2H) 2.67 (q, J=7.69 Hz, 2H) 2.55 (s, 3H) 1.29 (t, J=7.69 Hz, 3H). LCMS: m/z 447 (M+1).

Example 257

N-({4-chloro-3-[(3-chloro-5-cyanophenyl)oxy]-2-fluorophenyl}methyl)-4-methyl-2-(1-methylethyl)-1H-imidazole-5-carboxamide

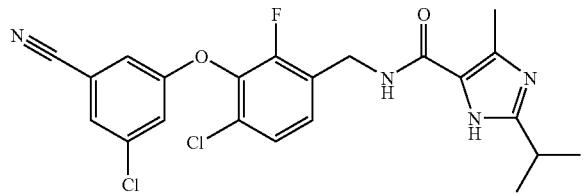

Step A: Ethyl 2-[(2-methylpropanoyl)amino]-3-oxobutanoate

The reaction procedure and purification process are similar to that outlined herein except that 2-methylpropanoic anhydride (0.6 mL, 3.6 mmol) was used to give 185 mg (29%) of the title compound as a light-yellow oil. 1H NMR (400 MHz, CHLOROFORM-d) δ ppm 6.58 (1H, br. s.) 5.20 (1H, d, J=6.4 Hz) 4.19-4.29 (2H, m) 2.46 (1H, dt, J=13.8, 6.9 Hz) 2.37 (3H, s) 1.28 (3H, t, J=7.1 Hz) 1.16 (3H, d, J=1.9 Hz) 1.14 (3H, d, J=1.8 Hz). LCMS: m/z 216 (M+1).

Step B: Ethyl 4-methyl-2-(1-methylethyl)-1H-imidazole-5-carboxylate

The reaction procedure and purification process are similar to that outlined herein except that ethyl 2-[(2-methylpropanoyl)amino]-3-oxobutanoate (185 mg, 0.86 mmol) was used to give (83 mg, 49%) of the title compound as a light-yellow solid. 1H NMR (400 MHz, CHLOROFORM-d) δ ppm 4.30 (2H, q, J=7.1 Hz) 3.04 (1H, dt, J=14.0, 7.0 Hz) 2.46 (3H, s) 1.28-1.36 (9H, m). LCMS: m/z 197 (M+1).

Step C: Ethyl 4-methyl-2-(1-methylethyl)-1-({[2-(trimethylsilyl)ethyl]oxy}methyl)-1H-imidazole-5-carboxylate A solution of 4-methyl-2-(1-methylethyl)-1H-imidazole-5-carboxylate (83 mg, 0.42 mmol) in THF (2.0 mL) was added dropwise to a suspension of NaH (60% in oil, 19.2 mg, 0.47 mmol) in THF (3.0 mL) at 0° C. under N₂. The mixture was allowed warm up to room temperature and stirred for 2 h, it was then cooled to 0° C. and {2-[(chloromethyl)oxy]ethyl}(trimethyl)silane (84 uL, 0.47 mmol) was added dropwise. The mixture was stirred overnight at room temperature and saturated sodium bicarbonate was added. DCM was added and the organic layer was dried over sodium sulfate and concentrated. The residue was purified by column chromatography (0-2% 2M NH3 solution of MeOH in DCM) to give the title compound (133 mg, 96%) as a yellow oil. 1H NMR (400 MHz, CHLOROFORM-d) δ ppm 5.16 (2H, s) 4.34 (2H, q, J=7.1 Hz) 3.44-3.51 (2H, m) 3.06 (1H, dt, J=13.8, 6.9 Hz) 2.54 (3H, s) 1.30-1.39 (9H, m) 0.84-0.92 (2H, m) −0.07--0.02 (9H, m). LCMS: m/z 327 (M+1).

Step D: 4-Methyl-2-(1-methylethyl)-1-({[2-(trimethylsilyl)ethyl]oxy}methyl)-1H-imidazole-5-carboxylic acid Lithium hydroxide (2 mL, 2 mmol, 1 M in H₂O) was added to a solution of ethyl 4-methyl-2-(1-methylethyl)-1-({[2-(trimethylsilyl)ethyl]oxy}methyl)-1H-imidazole-5-carboxylate (133 mg, 0.41 mmol) in THF:MeOH (6 mL/2 mL). The reaction mixture was heated at 40° C. and stirred overnight. The mixture was then acidified by H₃PO₄ (1N), extracted with 10% MeOH in CHCl₃ and the organic layer was dried over sodium sulfate. The solvent was evaporated and dried in vacuo to give the title compound (122 mg, >99%) as a yellow gel which was directly used in the next step without purification. LCMS: m/z 299 (M+1).

Step E: N-({4-chloro-3-[(3-chloro-5-cyanophenyl)oxy]-2-fluorophenyl}methyl)-4-methyl-2-(1-methylethyl)-1H-imidazole-5-carboxamide HATU (103 mg, 0.27 mmol) was added to a solution of 3-{[3-(aminomethyl)-6-chloro-2-fluorophenyl]oxy}-5-chlorobenzonitrile (56.2 mg, 0.18 mmol), 4-methyl-2-(1-methylethyl)-1-({[2-(trimethylsilyl)ethyl]oxy}methyl)-1H-imidazole-5-carboxylic acid (54 mg, 0.18 mmol) and diisopropylethylamine (47 uL, 0.27 mmol) in DMF (1 mL). The reaction mixture was stirred at RT overnight and the solvent was removed under vacuum. The residue was dried in vacuo and the residue was treated with TFA (0.5 mL) in DCM (1.0 mL) at RT and stirred overnight. Neutralized with saturated NaHCO₃ and extracted with 10% MeOH in DCM. The organic layer was dried over sodium sulfate and concentrated. The residue was purified by flash chromatography (0-5% 2M NH3 solution of MeOH in DCM) and HPLC to afford the title compound (50 mg, 60%) as a white solid. 1H NMR (400 MHz, CHLOROFORM-d) δ ppm 8.68 (1H, br. s.) 7.56 (1H, br. s.) 7.31-7.40 (2H, m) 7.23 (1H, s) 7.14 (1H, d, J=1.3 Hz) 7.02 (1H, s) 4.62 (2H, d, J=6.4 Hz) 2.96 (1H, dt, J=13.7, 6.8 Hz) 2.56 (3H, s) 1.30 (6H, d, J=7.0 Hz). LCMS: m/z 461 (M+1).

Example 258

N-({4-Chloro-3-[(3-chloro-5-cyanophenyl)oxy]-2-fluorophenyl}methyl)-2-cyclopropyl-4-methyl-1H-imidazole-5-carboxamide

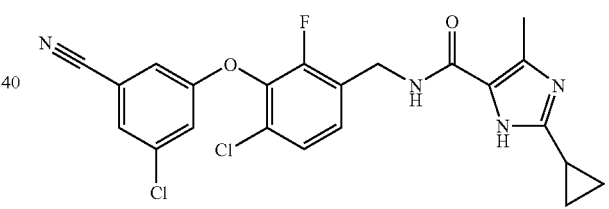

Step A: Cyclopropanecarboxylic anhydride

A solution of cyclopropanecarboxylic acid (5.0 g, 58 mmol) and DCC (6.13 g, 29 mmol) in DCM (60 mL) was stirred for 24 h at RT. The resulting white precipitate was filtered off through a pad of celite and the filtrate was evaporated under reduced pressure to yield the title compound as a white wax-like solid (4.38 g, 98%) which was directly used in the next step without purification.

Step B: Ethyl 2-[(cyclopropylcarbonyl)amino]-3-oxobutanoate

The reaction procedure and purification process are similar to that outlined herein except that cyclopropanecarboxylic anhydride (924 mg, 6.0 mmol) was used to give 326 mg (31%) of the title compound as a light-yellow solid. 1H NMR (400 MHz, CHLOROFORM-d) δ ppm 6.76 (1H, br.s.) 5.23 (1H, d, J=6.4 Hz) 4.25 (2H, qd, J=7.1, 2.7 Hz) 2.36 (3H, s) 1.49 (1H, td, J=8.2, 4.1 Hz) 1.28 (3H, t, J=7.1 Hz) 0.90-0.98 (2H, m) 0.77 (2H, m). LCMS: m/z 214 (M+1).

Step C: Ethyl 2-cyclopropyl-4-methyl-1H-imidazole-5-carboxylate

The reaction procedure and purification process are similar to that outlined herein except that ethyl 2-[(cyclopropylcarbonyl)amino]-3-oxobutanoate (326 mg, 1.53 mmol) was used give 124 mg (42%) of the title compound as a light-yellow solid. 1H NMR (400 MHz, CHLOROFORM-d) δ ppm 4.32 (2H, q, J=7.1 Hz) 2.46 (3H, s) 1.88-1.98 (1H, m) 1.35 (3H, t, J=7.1 Hz) 0.96-1.10 (4H, m). LCMS: m/z 195 (M+1).

Step D: Ethyl 2-cyclopropyl-4-methyl-1-({[2-(trimethylsilyl)ethyl]oxy}methyl)-1H-imidazole-5-carboxylate The reaction procedure and purification process are similar to that outlined herein except that ethyl 2-cyclopropyl-4-methyl-1H-imidazole-5-carboxylate (124 mg, 0.64 mmol) was used to give 186 mg (90%) of the title compound as a yellow oil. 1H NMR (400 MHz, CHLOROFORM-d) δ ppm 5.33 (2H, s) 4.35 (2H, q, J=7.1 Hz) 3.49-3.57 (2H, m) 2.57 (3H, s) 1.81-1.91 (1H, m) 1.38 (3H, t, J=7.1 Hz) 1.07-1.15 (2 H, m) 0.87-0.99 (4H, m) −0.01 (9H, s). LCMS: m/z 325 (M+1).

Step E: 2-Cyclopropyl-4-methyl-1-({[2-(trimethylsilyl)ethyl]oxy}methyl)-1H-imidazole-5-carboxylic acid The reaction procedure and purification process are similar to that outlined herein except that ethyl 2-cyclopropyl-4-methyl-1-({[2-(trimethylsilyl)ethyl]oxy}methyl)-1H-imidazole-5-carboxylate (186 mg, 0.57 mmol) was used to give 170 mg (>99%) of the title compound as a yellow gel which was directly used in the next step without purification. LCMS: m/z 297 (M+1).

Step F: N-({4-Chloro-3-[(3-chloro-5-cyanophenyl)oxy]-2-fluorophenyl}methyl)-2-cyclopropyl-4-methyl-1H-imidazole-5-carboxamide The reaction procedure and purification process are similar to that described herein except that 2-cyclopropyl-4-methyl-1-({[2-(trimethylsilyl)ethyl]oxy}methyl)-1H-imidazole-5-carboxylic acid (71.7 mg, 0.24 mmol) was used to give 80 mg (72%) of the title compound as a white solid. 1H NMR (400 MHz, CHLOROFORM-d) δ ppm 9.13 (1H, br. s.) 7.52 (1H, br. s.) 7.28-7.36 (2H, m) 7.19-7.24 (1H, m) 7.13 (1H, d, J=1.3 Hz) 7.01 (1H, s) 4.60 (2H, d, J=6.3 Hz) 2.50 (3H, s) 1.77-1.87 (1H, m) 0.86-0.96 (4H, m). LCMS: m/z 459 (M+1).

Example 259

N-({4-Chloro-3-[(3-chloro-5-cyanophenyl)oxy]-2-fluorophenyl}methyl)-4-ethyl-2-methyl-1H-imidazole-5-carboxamide

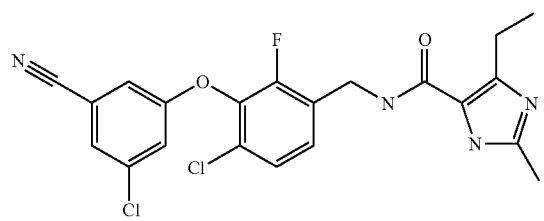

Step A: Ethyl 3-oxonorvalinate hydrochloride

The reaction procedure and purification process are similar to that outlined herein except that propanoyl chloride (3.44 mL, 39.5 mmol) was used to give 6.5 g (>99%) of the title compound as a light-yellow solid which was used in next step without purification.

Step B: Ethyl N-acetyl-3-oxonorvalinate

The reaction procedure and purification process are similar to that outlined herein except that ethyl 3-oxonorvalinate hydrochloride (970 mg, 5.0 mmol) was used. Water was added to the reaction mixture and it was then extracted with EtOAc. The organic layer was washed with saturated sodium bicarbonate, $H_3PO_4$ (1 N) and brine, dried over sodium sulfate and concentrated. The residue was purified on silica gel (0-40% EtOAc in hexane) to give the title compound (574 mg, 57%) as a white solid. 1H NMR (400 MHz, CHLOROFORM-d) δ ppm 6.59 (1H, br. s.) 5.22 (1H, d, J=6.6 Hz) 4.24 (2H, q, J=7.1 Hz) 2.60-2.84 (2H, m) 2.04 (3H, s) 1.28 (3H, t, J=7.1 Hz) 1.08 (3H, t). LCMS: m/z 202 (M+1).

Step C: Ethyl 4-ethyl-2-methyl-1H-imidazole-5-carboxylate

The reaction procedure and purification process are similar to that outlined herein except that ethyl N-acetyl-3-oxonorvalinate (574 mg, 2.73 mmol) was used. The title compound 286 mg (55%) was obtained as a white solid. 1H NMR (400 MHz, CHLOROFORM-d) δ ppm 4.30 (2H, q, J=7.1 Hz) 2.87 (2H, q, J=7.5 Hz) 2.39 (3H, s) 1.34 (3H, t, J=7.1 Hz) 1.22 (3H, t). LCMS: m/z 183 (M+1).

Step D: Ethyl 4-ethyl-2-methyl-1-({[2-(trimethylsilyl)ethyl]oxy}methyl)-1H-imidazole-5-carboxylate The reaction procedure and purification process are similar to that outlined herein except that ethyl 4-ethyl-2-methyl-1H-imidazole-5-carboxylate (282 mg, 1.55 mmol) was used to give 390 mg (81%) of the title compound as a yellow oil. 1H NMR (400 MHz, CHLOROFORM-d) δ ppm 5.17 (2H, s) 4.33-4.41 (2H, m) 3.45-3.53 (2H, m) 3.01 (2H, q, J=7.5 Hz) 2.46 (3H, s) 1.39 (3H, t, J=7.1 Hz) 1.20 (3H, t, J=7.5 Hz) 0.87-0.95 (2H, m) −0.01 (9H, s). LCMS: m/z 313 (M+1).

Step E: 4-Ethyl-2-methyl-1-({[2-(trimethylsilyl)ethyl]oxy}methyl)-1H-imid carboxylic acid The reaction procedure and purification process are similar to that outlined herein except that ethyl 4-ethyl-2-methyl-1-({[2-(trimethylsilyl)ethyl]oxy}methyl)-1H-imidazole-5-carboxylate (390 mg, 1.25 mmol) was used to give 353 mg (99%) of the title compound as an off-white gel which was directly used in the next step without purification.

Step F: N-({4-Chloro-3-[(3-chloro-5-cyanophenyl)oxy]-2-fluorophenyl}methyl)-4-ethyl-2-methyl-1H-imidazole-5-carboxamide The reaction procedure and purification process are similar to that outlined herein except that 4-ethyl-2-methyl-1-({[2-(trimethylsilyl)ethyl]oxy}methyl)-1H-imid carboxylic acid (71 mg, 0.25 mmol) was used to give 42.9 mg (38%) of the title compound as a white solid. 1H NMR (400 MHz, CHLOROFORM-d) δ ppm 8.74 (1H, br. s.) 7.60 (1H, br. s.) 7.31-7.38 (2H, m) 7.23 (1H, br. s.) 7.14 (1H, s) 7.01 (1H, s) 4.61 (2H, d, J=6.2 Hz) 3.05 (2H, q, J=7.5 Hz) 2.39 (3H, s) 1.24 (3H, t, J=7.6 Hz). LCMS: m/z 447 (M+1).

Example 260

N-({4-Chloro-3-[(3-chloro-5-cyanophenyl)oxy]-2-fluorophenyl}methyl)-4-ethyl-2-(1-methylethyl)-1H-imidazole-5-carboxamide

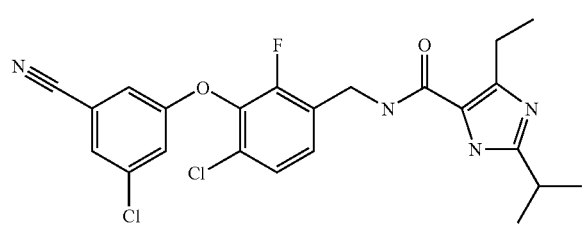

Step A: Ethyl N-(2-methylpropanoyl)-3-oxonorvalinate

The reaction procedure and purification process are similar to that outlined herein except that 2-methylpropanoic anhydride (1.0 mL, 6.0 mmol) was used to give 762 mg (66%) of the title compound as a white solid. 1H NMR (400 MHz, CHLOROFORM-d) δ ppm 6.59 (1H, br. s.) 5.20 (1H, d, J=6.5 Hz) 4.23 (2H, qd, J=7.1, 3.4 Hz) 2.61-2.84 (2H, m) 2.46 (1H, dt, J=13.8, 6.9 Hz) 1.27 (3H, t, J=7.1 Hz) 1.16 (3H, d, J=2.2 Hz) 1.14 (3H, d, J=2.2 Hz) 1.08 (3H, t, J=7.2 Hz). LCMS: m/z 230 (M+1).

Step B: Ethyl 4-ethyl-2-(1-methylethyl)-1H-imidazole-5-carboxylate

The reaction procedure and purification process are similar to that outlined herein except that ethyl N-(2-methylpropanoyl)-3-oxonorvalinate (762 mg, 3.32 mmol) was used to give 382 mg (55%) of the title compound as a white solid. 1H NMR (400 MHz, CHLOROFORM-d) δ ppm 9.16 (1H, br. s.) 4.31 (2H, q, J=7.1 Hz) 2.97-3.09 (1H, m) 2.80-2.92 (2H, m) 1.28-1.37 (9H, m) 1.21 (3H, t). LCMS: m/z 211 (M+1).

Step C: Ethyl 4-ethyl-2-(1-methylethyl)-1-({[2-(trimethylsilyl)ethyl]oxy}methyl)-1H-imidazole-5-carboxylate The reaction procedure and purification process are similar to that outlined herein except that ethyl 4-ethyl-2-(1-methylethyl)-1H-imidazole-5-carboxylate (380 mg, 1.81 mmol) was used to give 590 mg (96%) of the title compound as a yellow oil. 1H NMR (400 MHz, CHLOROFORM-d) δ ppm 5.15 (2H, s) 4.35 (2H, q, J=7.1 Hz) 3.45-3.52 (2H, m) 3.06 (1H, dt, J=13.8, 6.9 Hz) 2.96 (2H, q, J=7.4 Hz) 1.31-1.39 (9H, m) 1.17 (3H, t, J=7.5 Hz) 0.86-0.92 (2H, m) −0.03 (9H, s). LCMS: m/z 341 (M+1).

Step D: 4-Ethyl-2-(1-methylethyl)-1-({[2-(trimethylsilyl)ethyl]oxy}methyl)-1H-imidazole-5-carboxylic acid The reaction procedure and purification process are similar to that outlined herein except that ethyl 4-ethyl-2-(1-methylethyl)-1-({[2-(trimethylsilyl)ethyl]oxy}methyl)-1H-imidazole-5-carboxylate (590 mg, 1.73 mmol) was used to give 540 mg (>99%) of the title compound as a yellow gel which was directly used in the next step without purification.

Step E: N-({4-Chloro-3-[(3-chloro-5-cyanophenyl)oxy]-2-fluorophenyl}methyl)-4-ethyl-2-(1-methylethyl)-1H-imidazole-5-carboxamide The reaction procedure and purification process are similar to that outlined herein except that 4-ethyl-2-(1-methylethyl)-1-({[2-(trimethylsilyl)ethyl]oxy}methyl)-1H-imidazole-5-carboxylic acid (84 mg, 0.27 mmol) was used to give 77 mg (60%) of the title compound as a white solid. 1H NMR (400 MHz, CHLOROFORM-d) δ ppm 8.58 (1H, br. s.) 7.55 (1H, br. s.) 7.31-7.40 (2H, m) 7.23 (1H, br. s.) 7.14 (1H, d, J=1.5 Hz) 7.02 (1H, s) 4.62 (2H, d, J=6.3 Hz) 3.06 (2H, q, J=7.5 Hz) 2.91-3.01 (1H, m) 1.31 (6H, d, J=6.8 Hz) 1.25 (3H, t, J=7.5 Hz). LCMS: m/z 475 (M+1).

Example 261

N-({4-Chloro-3-[(3-chloro-5-cyanophenyl)oxy]-2-fluorophenyl}methyl)-2-cyclopropyl-4-ethyl-1H-imidazole-5-carboxamide

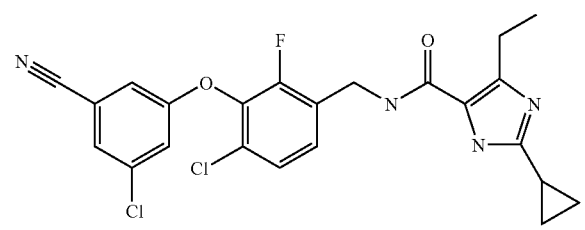

Step A: Ethyl N-(cyclopropylcarbonyl)-3-oxonorvalinate

The reaction procedure and purification process are similar to that outlined herein except that cyclopropanecarboxylic anhydride (920 mg, 6.0 mmol) was used to give 743 mg (65%) of the title compound as a white solid. 1H NMR (400 MHz, CHLOROFORM-d) δ ppm 6.76 (1H, br. s.) 5.23 (1H, d, J=6.6 Hz) 4.23 (2H, qd, J=7.1, 1.1 Hz) 2.59-2.84 (2H, m) 1.48 (1H, dq, J=8.3, 4.0 Hz) 1.27 (3H, t, J=7.1 Hz) 1.08 (3H, t, J=7.3 Hz) 0.91-0.97 (2H, m) 0.77 (2H, dd). LCMS: m/z 228 (M+1).

Step B: Ethyl 2-cyclopropyl-4-ethyl-1H-imidazole-5-carboxylate

The reaction procedure and purification process are similar to that outlined herein except that ethyl N-(cyclopropylcarbonyl)-3-oxonorvalinate (743 mg, 3.27 mmol) was used to give 254 mg (37%) of the title compound as a light-yellow solid. 1H NMR (400 MHz, CHLOROFORM-d) δ ppm 9.25 (1H, br. s.) 4.29 (2H, q, J=7.1 Hz) 2.82 (2 H, dd, J=1.7, 0.8 Hz) 1.82-1.93 (1H, m) 1.33 (3H, t, J=7.1 Hz) 1.19 (3H, t, J=7.6 Hz) 0.97 (4H, d). LCMS: m/z 433 (M+1). LCMS: m/z 209 (M+1).

Step C: Ethyl 2-cyclopropyl-4-ethyl-1-({[2-(trimethylsilyl)ethyl]oxy}methyl)-1H-imidazole-5-carboxy late The reaction procedure and purification process are similar to that outlined herein except that ethyl 2-cyclopropyl-4-ethyl-1H-imidazole-5-carboxylate (250 mg, 1.2 mmol) was used to give 371 mg (91%) of the title compound as a yellow oil. 1H NMR (400 MHz, CHLOROFORM-d) δ ppm 5.31 (2H, s) 4.32 (2H, q, J=7.1 Hz) 3.48-3.55 (2H, m) 2.97 (2H, q, J=7.4 Hz) 1.78-1.87 (1H, m) 1.35 (3H, t, J=7.1 Hz) 1.17 (3H, t, J=7.5 Hz) 1.08 (2H, dd, J=4.8, 2.1 Hz) 0.86-0.96 (4H, m) −0.03 (9H, s). LCMS: m/z 339 (M+1).

Step D: 2-Cyclopropyl-4-ethyl-1-({[2-(trimethylsilyl)ethyl]oxy}methyl)-1H-imidazole-5-carboxylic acid The reaction procedure and purification process are similar to that outlined herein except that ethyl 2-cyclopropyl-4-ethyl-1-({[2-(trimethylsilyl)ethyl]oxy}methyl)-1H-imidazole-5-carboxylate (370 mg, 1.09 mmol) was used to give 328 mg (97%) of the title compound as a yellow gel which was directly used in the next step without purification.

Step E: N-({4-Chloro-3-[(3-chloro-5-cyanophenyl)oxy]-2-fluorophenyl}methyl)-2-cyclopropyl-4-ethyl-1H-imidazole-5-carboxamide The reaction procedure and purification process are similar to that outlined herein except that 2-cyclopropyl-4-ethyl-1-({[2-(trimethylsilyl)ethyl]oxy}methyl)-1H-imidazole-5-carboxylic acid (71 mg, 0.23 mmol) was used to give 62 mg (57%) of the title compound as a white solid. 1H NMR (400 MHz, CHLOROFORM-d) δ ppm 8.67 (1H, br. s.) 7.50 (1H, br. s.) 7.30-7.37 (2H, m) 7.22 (1H, s) 7.13 (1H, d, J=1.0 Hz) 7.02 (1H, s) 4.61 (2H, d, J=6.3 Hz) 3.04 (2H, q, J=7.5 Hz) 1.78-1.88 (1H, m) 1.24 (3H, t, J=7.3 Hz) 0.95 (4H, m). LCMS: m/z 471 (M−1).

Example 262

4-Chloro-N-({4-chloro-3-[(3-chloro-5-cyanophenyl)oxy]-2-fluorophenyl}methyl)-2-(hydroxymethyl)-1H-imidazole-5-carboxamide

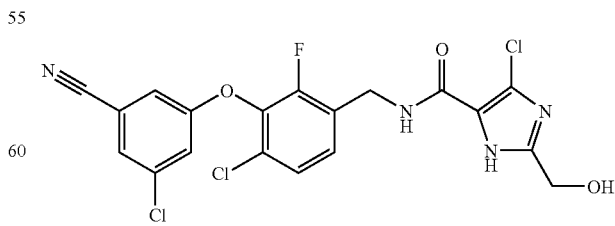

Step A: [4,5-Dichloro-1-({[2-(trimethylsilyl)ethyl]oxy}methyl)-1H-imidazol-2-yl]methanol nBuLi (2.0 mL, 3.2 mmol, 1.6 M in hexane) was added dropwise to a solution of 2-bromo-4,5-dichloro-1-({[2-(trimethylsilyl)ethyl]oxy}methyl)-1H-imidazole (1.1 g, 3.2 mmol) in THF (50 mL) at −78° C. under N₂. The mixture was stirred for 30 min and paraformaldehyde (960 mg, 32 mmol) was then added. The mixture was allowed warm up to room temperature and stirred for 6 h and then quenched by aqueous NH₄Cl. Extracted with EtOAc and the organic layer was dried over sodium sulfate and concentrated. The residue was purified by column chromatography (0-30% EtOAc in hexane) to give the title compound (614 mg, 65%) as a colorless oil. 1H NMR (400 MHz, CHLOROFORM-d) δ ppm 5.37 (2H, s) 4.70 (2H, d, J=1.2 Hz) 3.58 (2H, dd, J=8.9, 7.7 Hz) 0.89-0.96 (2H, m) 0.00 (9H, s). LCMS: m/z 297 (M+1).

Step B: 4,5-Dichloro-2-({[(1,1-dimethylethyl)(dimethyl)silyl]oxy}methyl)-1-({[2-(trimethylsilyl)ethyl]oxy}methyl)-1H-imidazole Imidazole (282 mg, 4.14 mmol) was added to a solution of [4,5-dichloro-1-({[2-(trimethylsilyl)ethyl]oxy}methyl)-1H-imidazol-2-yl]methanol (614 mg, 2.07 mmol) and chloro(1,1-dimethylethyl)dimethylsilane (345 mg, 2.28 mmol) in DCM (8 mL) at RT under N₂. The mixture was stirred overnight. Aqueous NH₄Cl was then added. Extracted with DMC and the extracts were dried over sodium sulfate and concentrated. The residue was purified by column chromatography (0-10% EtOAc in hexane) to give the title compound (845 mg, 99%) as a colorless oil. 1H NMR (400 MHz, CHLOROFORM-d) δ ppm 5.42 (2H, s) 4.74 (2H, s) 3.53-3.59 (2H, m) 0.87-0.95 (11H, m) 0.09 (6H, s) 0.00 (9H, s). LCMS: m/z 411 (M+1).

Step C: 4-Chloro-2-({[(1,1-dimethylethyl)(dimethyl)silyl]oxy}methyl)-1-({[2-(trimethylsilyl)ethyl]oxy}methyl)-1H-imidazole-5-carbaldehyde nBuLi (1.3 mL, 2.05 mmol, 1.57 M in hexane) was added dropwise to a solution of 4,5-dichloro-2-({[(1,1-dimethylethyl)(dimethyl)silyl]oxy}methyl)-1-({[2-(trimethylsilyl)ethyl]oxy}methyl)-1H-imidazole (842 mg, 2.05 mmol) in THF (30 mL) at −78° C. under N₂. The mixture was stirred for 30 min and DMF (1.0 mL) was then added dropwise. The mixture was stirred for 20 min and then allowed warm up to room temperature and stirred for 20 min. Quenched by aqueous NH₄Cl and extracted with EtOAc and the organic layer was dried over sodium sulfate and concentrated.

The residue was purified by column chromatography (0-10% EtOAc in hexane) to give the title compound (694 mg, 84%) as a colorless oil. 1H NMR (400 MHz, CHLOROFORM-d) δ ppm 9.80 (1H, s) 5.82 (2H, s) 4.79 (2H, s) 3.51-3.58 (2H, m) 0.82-0.90 (11H, m) 0.08 (6H, s) −0.05 (9H, s). LCMS: m/z 405 (M+1).

Step D: 4-Chloro-2-({[(1,1-dimethylethyl)(dimethyl)silyl]oxy}methyl)-1-({[2-(trimethylsilyl)ethyl]oxy}methyl)-1H-imidazole-5-carboxylic acid A solution of NaClO₂ (1.55 g, 17 mmol) and NaH₂PO₄·H₂O (1.42 g, 10.3 mmol) in H2O was added to a mixture of 4-chloro-2-({[(1,1-dimethylethyl)(dimethyl)silyl]oxy}methyl)-1-({[2-(trimethylsilyl)ethyl]oxy}methyl)-1H-imidazole-5-carbaldehyde (694 mg, 1.7 mmol), 2-methyl-2-butene (10.8 mL, 21.5 mmol, 2 M in THF), and tBuOH (1.33 mL) in THF (5.5 mL) at room temperature. The mixture was stirred overnight and separated and the aqueous layer was extracted with EtOAc. The combined extracts were dried over sodium sulfate and concentrated. The residue was purified by column chromatography (0-80% 0.1%) formic acid solution of EtOAc in DCM) to give the title compound (740 mg, >99%) as a white solid. 1H NMR (400 MHz, CHLOROFORM-d) δ ppm 5.83 (2H, s) 4.80 (2H, s) 3.56 (2H, t, J=8.1 Hz) 0.83-0.91 (11H, m) 0.08 (6H, s) −0.04 (9H, s). LCMS: m/z 421 (M+1).

Step E: 4-Chloro-N-({4-chloro-3-[(3-chloro-5-cyanophenyl)oxy]-2-fluorophenyl}methyl)-2-(hydroxymethyl)-1H-imidazole-5-carboxamide The reaction procedure and purification process are identical to that outlined herein except that 4-chloro-2-({[(1,1-dimethylethyl)(dimethyl)silyl]oxy}methyl)-1-({[2-(trimethylsilyl)ethyl]oxy}methyl)-1H-imidazole-5-carboxylic acid (373 mg, 1.75 mmol) was used. The title compound 458 mg (56%) was obtained as a white solid. 1H NMR (400 MHz, DMSO-d₆) δ ppm 8.29 (1H, br. s.) 7.80 (1H, s) 7.42-7.52 (3H, m) 7.36 (1H, br. s.) 5.51 (1H, t, J=5.6 Hz) 4.49 (2H, br. s.) 4.39 (2H, d, J=5.6 Hz). LCMS: m/z 469 (M+1).

Example 263

4-Chloro-N-({4-chloro-3-[(3-chloro-5-cyanophenyl)oxy]-2-fluorophenyl}methyl)-2-[(dimethylamino)methyl]-1H-imidazole-5-carboxamide trifluoroacetate

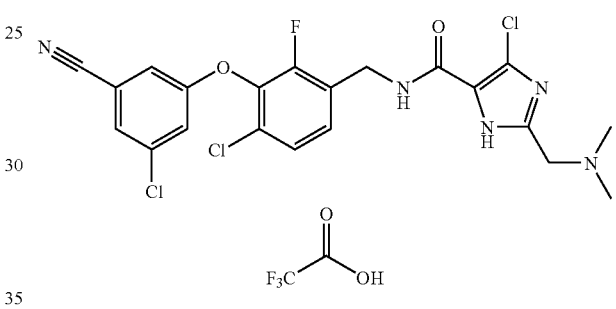

Step A: 4-Chloro-N-({4-chloro-3-[(3-chloro-5-cyanophenyl)oxy]-2-fluorophenyl}methyl)-2-formyl-1H-imidazole-5-carboxamide MnO₂ (2.5 g, 29 mmol) was added to a solution of 4-chloro-N-({4-chloro-3-[(3-chloro-5-cyanophenyl)oxy]-2-fluorophenyl}methyl)-2-(hydroxymethyl)-1H-imidazole-5-carboxamide (428 mg, 0.91 mmol) in DCM (30 mL) and 1,4-dioxane (5.0 mL). The mixture was stirred for 66 h and then the MnO₂ was filtered off by through a pad of celite. Resin with 10% MeCN in DCM and the filtrates were concentrated, dried in vacuo to give the crude product (128 m, 30%) which was used for the next step without purification.

Step B: 4-Chloro-N-({4-chloro-3-[(3-chloro-5-cyanophenyl)oxy]-2-fluorophenyl}methyl)-2-[(dimethylamino)methyl]-1H-imidazole-5-carboxamide General procedure for the reductive-amination reaction: the preparation of 4-chloro-N-({4-chloro-3-[(3-chloro-5-cyanophenyl)oxy]-2-fluorophenyl}methyl)-2-[(dimethylamino)methyl]-1H-imidazole-5-carboxamide is described as a example. NaBH(OAc)₃ was added to a solution of 4-chloro-N-({4-chloro-3-[(3-chloro-5-cyanophenyl)oxy]-2-fluorophenyl}methyl)-2-formyl-1H-imidazole-5-carboxamide (42 mg, 0.09 mmol) and dimethylamine (45 uL, 0.09 mmol, 2.0 M in THF) in DCE (5.0 mL) at room temperature under N₂. The reaction mixture was stirred overnight and then aqueous NaHCO3 was added. Extracted with 10% of MeOH in DCM and the combined extracts were over sodium sulfate and concentrated. The residue was purified by HPLC (Gilson) to give the title compound (19.8 mg, 37%) as a white solid as the TFA salt. 1H NMR (400 MHz, METHANOL-d₄) δ ppm 7.54 (1H, s) 7.32-7.42 (2H, m) 7.26 (1H, s) 7.18 (1H, s) 4.64 (2H, s) 4.36 (2H, s) 2.94 (6H, s). LCMS: m/z 496 (M+1).

Example 264

4-Chloro-N-({4-chloro-3-[(3-chloro-5-cyanophenyl)oxy]-2-fluorophenyl}methyl)-2-{[(2-hydroxyethyl)(methyl)amino]methyl}-1H-imidazole-5-carboxamide trifluoroacetate

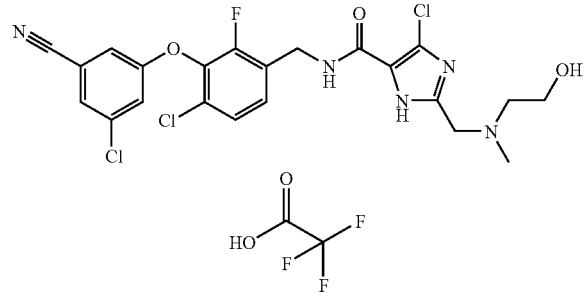

General procedure with the use of 4-chloro-N-({4-chloro-3-[(3-chloro-5-cyanophenyl)oxy]-2-fluorophenyl}methyl)-2-formyl-1H-imidazole-5-carboxamide (42 mg, 0.09 mmol) and 2-(methylamino)ethanol (7.2 uL, 0.09 mmol) to give the title compound (19 mg, 33%) as a white solid as the TFA salt. 1H NMR (400 MHz, METHANOL-d$_4$) δ ppm 7.54 (1H, s) 7.33-7.41 (2H, m) 7.26 (1H, s) 7.18 (1H, s) 4.64 (2H, s) 4.43 (2H, s) 3.89 (2H, t, J=4.6 Hz) 3.35 (2H, br. s.) 2.96 (3H, s). LCMS: m/z 526 (M+1).

Example 265

4-Chloro-N-({4-chloro-3-[(3-chloro-5-cyanophenyl)oxy]-2-fluorophenyl}methyl)-2-(1-piperidinylmethyl)-1H-imidazole-5-carboxamide

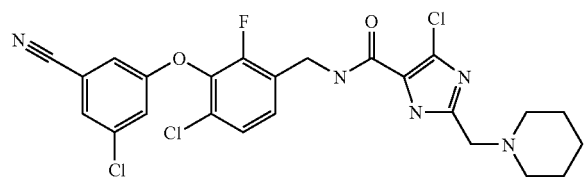

General procedure with the use of 4-chloro-N-({4-chloro-3-[(3-chloro-5-cyanophenyl)oxy]-2-fluorophenyl}methyl)-2-formyl-1H-imidazole-5-carboxamide (42 mg, 0.09 mmol) and piperidine (8.9 uL, 0.09 mmol) to give the title compound (21 mg, 36%) as a white solid as the TFA salt. 1H NMR (400 MHz, METHANOL-d$_4$) δ ppm 7.54 (1H, br. s.) 7.33-7.41 (2H, m) 7.26 (1H, br. s.) 7.18 (1H, s) 4.64 (2H, s) 4.31 (2H, s) 3.56 (2H, br. s.) 3.03 (2H, br. s.) 1.92 (2H, br. s.) 1.79 (3H, br. s.) 1.41-1.60 (1H, m). LCMS: m/z 536 (M+1).

Example 266

N-({4-chloro-3-[(3-chloro-5-cyanophenyl)oxy]-2-fluorophenyl}methyl)-4-fluoro-1H-imidazole-5-carboxamide

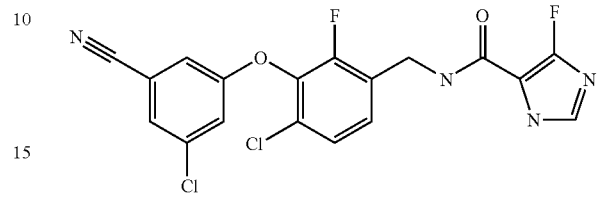

Step A: Ethyl 4-fluoro-1H-imidazole-5-carboxylate

Ethyl 4-fluoro-1H-imidazole-5-carboxylate was prepared as described in J. Org. Chem. 1984, 49, 1951. A solution of NaNO$_2$ (76 mg, 2.2 mmol) in minimum amount of H$_2$O was added to a solution of ethyl 4-amino-1H-imidazole-5-carboxylate (310 mg, 2.0 mmol) in 50% HBF$_4$ (7.0 mL) at −10° C. The reaction was stirred for 10 min and then irradiated with medium-pressure mercury vapor lamp (450 W) for 3 h at the same temperature. The mixture was neutralized with NaOH (5N) to Ph=5 while the temperature was maintained at −10° C. The resulting mixture was extracted with EtOAc and the extracts were over sodium sulfate and concentrated. The residue was purified by column chromatography (0-50% EtOAc in Hexane) to give the title compound (50 mg, 16%) as a white solid.

1H NMR (400 MHz, CHLOROFORM-d) δ ppm 10.02 (1H, br. s.) 7.37 (1H, s) 4.35 (2 H, q, J=7.1 Hz) 1.35 (3H, t). LCMS: m/z 159 (M+1).

Step B: Ethyl 4-fluoro-1-({[2-(trimethylsilyl)ethyl]oxy}methyl)-1H-imidazole-5-carboxylate The reaction procedure and purification process are similar to that outlined herein except that ethyl 4-fluoro-1H-imidazole-5-carboxylate (50 mg, 0.32 mmol) was used to give 30 mg (33%) of the title compound as a white solid. 1H NMR (400 MHz, CHLOROFORM-d) δ ppm 7.39 (1H, d, J=1.3 Hz) 5.59 (2H, s) 4.32 (2H, q, J=7.1 Hz) 3.52-3.59 (2H, m) 1.34 (3H, t, J=7.1 Hz) 0.86-0.94 (2H, m) −0.04 (9H, s).

Step C: 4-Fluoro-1-({[2-(trimethylsilyl)ethyl]oxy}methyl)-1H-imidazole-5-carboxylic acid The reaction procedure and purification process are similar to that outlined herein except that ethyl 4-fluoro-1-({[2-(trimethylsilyl)ethyl]oxy}methyl)-1H-imidazole-5-carboxylate (30 mg, 0.10 mmol) was used to give 27 mg (99%) of the title compound as a white solid which was directly used in the next step without purification. LCMS: m/z 259 (M−1).

Step D: N-({4-Chloro-3-[(3-chloro-5-cyanophenyl)oxy]-2-fluorophenyl}methyl)-4-fluoro-1H-imidazole-5-carboxamide The reaction procedure and purification process are similar to that outlined herein except that 4-fluoro-1-({[2-(trimethylsilyl)ethyl]oxy}methyl)-1H-imidazole-5-carboxylic acid (27 mg, 0.1 mmol) was used to give 52 mg (80%) of the title compound as a white solid. 1H NMR (400 MHz, METHANOL-d$_4$) δ ppm 7.53 (1H, s) 7.46 (1H, d, J=1.2 Hz) 7.30-7.40 (3H, m) 7.25 (1H, t, J=2.0 Hz) 7.21 (1H, s) 4.60 (2H, s). LCMS: m/z 423 (M+1).

Example 267

4-Chloro-N-({3-[(3-chloro-5-cyanophenyl)oxy]-2-fluoro-4-methylphenyl}methyl)-2-methyl-1H-imidazole-5-carboxamide

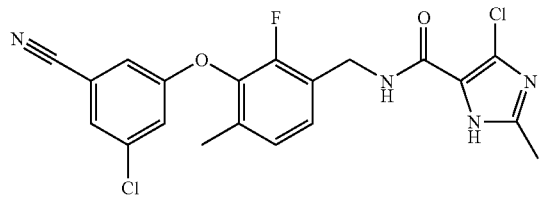

General Procedure for Negishi Cross-Coupling Reactions:

Me$_2$Zn (0.145 ml, 0.145 mmol, 1.0 M in) was added to a mixture of Pd(PPh$_3$)$_4$ (34.8 mg, 0.030 mmol) and N-({4-bromo-3-[(3-chloro-5-cyanophenyl)oxy]-2-fluorophenyl}methyl)-4-chloro-2-methyl-1H-imidazole-5-carboxamide (60 mg, 0.120 mmol) in THF (3.0 ml) in a seal tube at room temperature under N$_2$. The reaction mixture was heated to 80° C. and stirred overnight then cooled to RT and the solvent was removed under vacuum. The residue was dissolved in CH$_2$Cl$_2$ and aq.NaHCO$_3$ was added. The mixture was extracted with 10% MeOH in CH$_2$Cl$_2$. The organic layer was separated, dried over Na$_2$SO$_4$, filtered and concentrated to dryness. The crude product was purified by HPLC to give the title compound as a white solid (7 mg, 13%). 1H NMR (400 MHz, CHLOROFORM-d) δ ppm 11.34 (1H, br. s.) 7.31 (1H, s) 7.18 (1H, t, J=7.4 Hz) 7.03-7.13 (3H, m) 6.97 (1H, s) 4.68 (2H, d, J=5.9 Hz) 2.39 (3H, s) 2.18 (3H, s). LCMS: m/z 433 (M+1).

Example 268

4-Chloro-N-({3-[(3-chloro-5-cyanophenyl)oxy]-2-fluorophenyl}methyl)-2-methyl-1H-imidazole-5-carboxamide trifluoroacetate

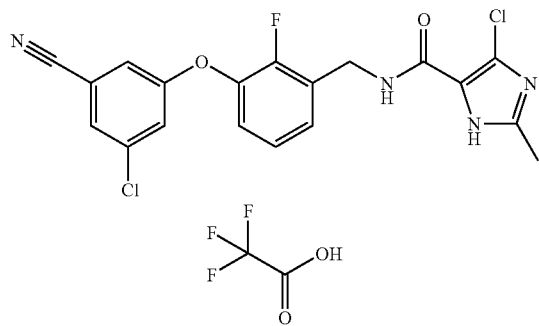

The reaction procedure was similar to that described in Example 267 except that Et$_2$Zn (0.13 mL, 0.15 mmol, 1.1 M in toluene) was used. The crude product was purified by HPLC to give the title compound as a white solid (2.7 mg, 4.2%, TFA salt). 1H NMR (400 MHz, METHANOL-d$_4$) δ ppm 7.59-7.67 (1H, m) 7.55 (1H, dd, J=7.3, 2.7 Hz) 7.51 (1H, s) 7.32 (1H, t, J=6.6 Hz) 7.20-7.29 (2 HT, m) 7.13-7.20 (1H, m) 4.66 (2H, s) 2.38 (3H, s). LCMS: m/z 419 (M+1).

Example 269

4-Chloro-N-({3-[(3-chloro-5-cyanophenyl)oxy]-4-ethenyl-2-fluorophenyl}methyl)-2-methyl-1H-imidazole-5-carboxamide

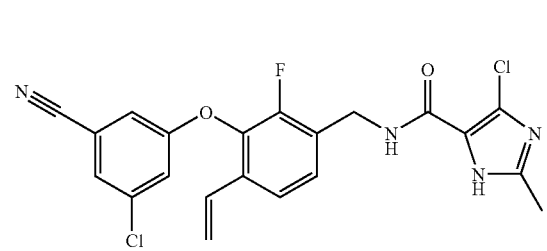

Et$_3$N (0.351 ml, 2.52 mmol) was added to a mixture of N-({4-bromo-3-[(3-chloro-5-cyanophenyl)oxy]-2-fluorophenyl}methyl)-4-chloro-2-methyl-1H-imidazole-5-carboxamide (251 mg, 0.504 mmol), potassium vinyltrifluoroborate (101 mg, 0.756 mmol) and 1,1'-bis(diphenylphosphino)ferrocene palladium (II) dichloride dichloromethane complex (41.1 mg, 0.050 mmol) in n-propanol (5 ml) under N$_2$. The mixture was heated to 100° C. and stirred for 4 h. Cooled down to RT and the reaction mixture was filtered through a pad of celite and concentrated to dryness. The residue was dissolved in EtOAC, washed with Sat. NaHCO$_3$, dried over Na$_2$SO$_4$. After filtration and concentration, the residue was purified by chromatography on silica gel eluted with 0-5% 2M NH$_3$ solution of MeOH in CH$_2$Cl$_2$ to give the title compound as a light-yellow solid (154 mg, 69%). 1H NMR (400 MHz, CHLOROFORM-d) δ ppm 11.33 (1H, br. s.) 7.40 (1H, d, J=8.2 Hz) 7.31 (1H, s) 7.26-7.29 (1H, m) 7.12 (2H, br. s.) 6.98 (1H, s) 6.69 (1H, dd, J=17.6, 11.2 Hz) 5.81 (1H, d, J=17.6 Hz) 5.37 (1H, d, J=11.1 Hz) 4.70 (2H, d, J=5.9 Hz) 2.39 (3H, s). LCMS: m/z 445 (M+1).

Example 270

4-Chloro-N-({3-[(3-chloro-5-cyanophenyl)oxy]-4-cyclopropyl-2-fluorophenyl}methyl)-2-methyl-1H-imidazole-5-carboxamide

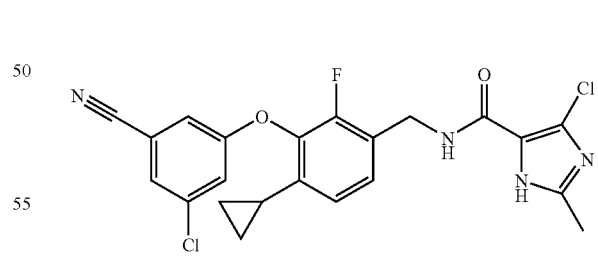

A ca. 0.07 M solution of CH$_2$N$_2$ (25.7 ml, 1.797 mmol) was added dropwise over ca. 20 min to a solution of 4-chloro-N-({3-[(3-chloro-5-cyanophenyl)oxy]-4-ethenyl-2-fluorophenyl}methyl)-2-methyl-1H-imidazole-5-carboxamide (80 mg, 0.180 mmol) and palladium (II) acetylacetonate (5.47 mg, 0.018 mmol) in diethyl ether (15 ml) at RT under N$_2$. The reaction mixture was stirred overnight. The reaction mixture was filtered through a pad of celite and concentrated to dryness. The crude residue was purified by HPLC (MeCN/ water+0.1% TFA) and subsequently converted to the freebase with aq.NaHCO₃ to give the title compound as a white solid (44 mg, 53%). 1H NMR (400 MHz, CHLOROFORM-d) δ ppm 10.88 (1H, br. s.) 7.31 (1H, s) 7.18 (1H, t, J=7.6 Hz) 7.15 (1H, t, J=1.9 Hz) 7.09 (1H, br. s.) 7.01 (1H, s) 6.70 (1H, d, J=8.2 Hz) 4.66 (2H, d, J=5.9 Hz) 2.40 (3H, s) 1.82-1.92 (1H, m) 0.87-0.95 (2H, m) 0.63-0.69 (2H, m). LCMS: m/z 459 (M+1).

Example 271

4-Chloro-N-({4-chloro-3-[(4-cyano-6-methyl-2-pyridinyl)oxy]-2-fluorophenyl}methyl)-2-methyl-1H-imidazole-5-carboxamide

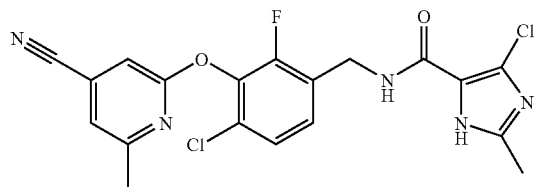

The reaction procedure and purification process were similar to that described in Example 267 except that 4-chloro-N-({4-chloro-3-[(6-chloro-4-cyano-2-pyridinyl)oxy]-2-fluorophenyl}methyl)-2-methyl-1H-imidazole-5-carboxamide (55 mg, 0.12 mmol) was used. The reaction was carried out at 60° C. for 2 h. The residue was purified by HPLC (MeCN/water+0.1% TFA) and subsequently converted to the freebase with aq.NaHCO₃ to give the title compound as a white solid (7.2 mg, 14%). 1H NMR (400 MHz, CHLOROFORM-d) δ ppm 11.26 (1H, br. s.) 7.17-7.24 (2H, m) 7.13 (1H, br. s.) 7.08 (2H, s) 4.69 (2H, d, J=5.9 Hz) 2.39 (3H, s) 2.35 (3H, s). LCMS: m/z 434 (M+1).

Example 272

4-Chloro-N-({4-chloro-3-[(4-cyano-6-ethenyl-2-pyridinyl)oxy]-2-fluorophenyl}methyl)-2-methyl-1H-imidazole-5-carboxamide

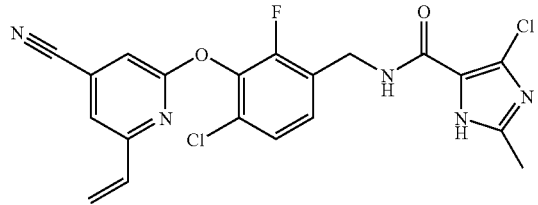

The reaction procedure and purification process were similar to that described in Example 269 except that 4-chloro-N-({4-chloro-3-[(6-chloro-4-cyano-2-pyridinyl)oxy]-2-fluorophenyl}methyl)-2-methyl-1H-imidazole-5-carboxamide (50 mg, 0.11 mmol) was used. The title compound was obtained as a light-yellow solid (34 mg, 69%). 1H NMR (400 MHz, CHLOROFORM-d) δ ppm 10.86 (1H, br. s.) 7.20-7.23 (1H, m) 7.17 (2H, d, J=1.9 Hz) 7.11 (1H, br. s.) 6.54 (1H, dd, J=17.2, 10.6 Hz) 5.93 (1H, d, J=17.0 Hz) 5.37 (1H, d, J=10.7 Hz) 4.69 (2H, d, J=5.8 Hz) 2.40 (3H, s). LCMS: m/z 446 (M+1).

Example 273

4-Chloro-N-({4-chloro-3-[(4-cyano-6-cyclopropyl-2-pyridinyl)oxy]-2-fluorophenyl}methyl)-2-methyl-1H-imidazole-5-carboxamide

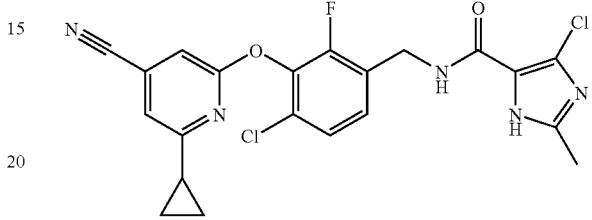

The reaction procedure was similar to that described in Example 270 except that 4-chloro-N-({4-chloro-3-[(4-cyano-6-ethenyl-2-pyridinyl)oxy]-2-fluorophenyl}methyl)-2-methyl-1H-imidazole-5-carboxamide (80 mg, 0.179 mmol) was used. The residue was purified by flash chromatography on silica gel eluted with 0-5% 2M NH₃ solution of MeOH in CH₂Cl₂ to give the title compound as a yellow solid (36 mg, 44%). 1H NMR (400 MHz, CHLOROFORM-d) δ ppm 11.22 (1H, br. s.) 7.16-7.24 (2H, m) 7.07-7.13 (2H, m) 7.02 (1H, s) 4.68 (2H, d, J=6.0 Hz) 2.39 (3H, s) 1.81-1.90 (1H, m) 0.77-0.84 (2H, m) 0.59-0.65 (2H, m). LCMS: m/z 460 (M+1).

Example 274

4-Chloro-N-({4-chloro-3-[(4-cyano-6-ethyl-2-pyridinyl)oxy]-2-fluorophenyl}methyl)-2-methyl-1H-imidazole-5-carboxamide

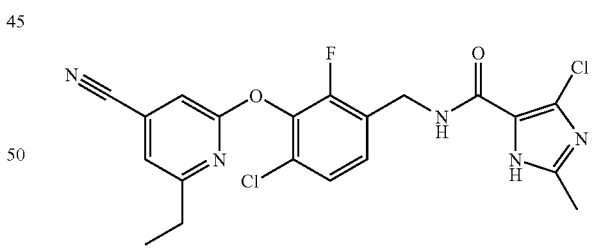

A solution of 4-chloro-N-({4-chloro-3-[(4-cyano-6-ethenyl-2-pyridinyl)oxy]-2-fluorophenyl}methyl)-2-methyl-1H-imidazole-5-carboxamide (53 mg, 0.119 mmol), diphenylsulfide (1.979 μl, 0.012 mmol) and palladium on carbon (12.64 mg, 0.012 mmol, 10%) in MeOH (8.0 ml) and ethyl acetate (8.00 ml) was reacted under H₂ (40 psi) overnight. The reaction mixture was filtered through a pad of celite and concentrated to dryness. The residue was purified by flash chromatography on silica gel eluted with 0-5% 2M NH₃ solution of MeOH in CH₂Cl₂ to give the title compound as a white solid (43 mg, 81%). 1H NMR (400 MHz, CHLOROFORM-d) δ ppm 10.82 (1H, br. s.) 7.17-7.24 (2H, m) 7.09

(2H, d, J=5.4 Hz) 4.68 (2H, d, J=6.0 Hz) 2.61 (2H, q, J=7.5 Hz) 2.39 (3H, s) 1.07 (3H, t). LCMS: m/z 448 (M+1).

Example 275

4-Chloro-N-({2-chloro-3-[(3-chloro-5-cyanophenyl)oxy]-4-fluorophenyl}methyl)-1H-imidazole-5-carboxamide

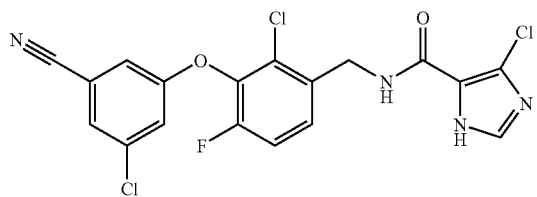

Step A: 3-Chloro-5-[(2-chloro-6-fluoro-3-methylphenyl)oxy]benzonitrile

The title compound was prepared as described herein using tBuOK (4.00 ml, 4.00 mmol), 2-chloro-6-fluoro-3-methylphenol (642 mg, 4.00 mmol), 3-chloro-5-fluorobenzonitrile (622 mg, 4.00 mmol) and 18-crown-6 (211 mg, 0.800 mmol) in dimethyl sulfoxide (16 ml) to give the title compound as a white solid (0.94 g, 79%). 1H NMR (400 MHz, CHLOROFORM-d) δ ppm 7.33 (1H, s) 7.12-7.19 (2H, m) 7.07 (1H, t, J=8.9 Hz) 6.98 (1H, s) 2.40 (3H, s). LCMS: m/z 294 (M−1).

Step B: 3-{[3-(Bromomethyl)-2-chloro-6-fluorophenyl]oxy}-5-chlorobenzonitrile

The title compound was prepared as described herein using 3-chloro-5-[(2-chloro-6-fluoro-3-methylphenyl)oxy]benzonitrile (940 mg, 3.17 mmol), NBS (593 mg, 3.33 mmol) and AIBN (26.1 mg, 0.159 mmol) in CCl₄ (30.0 ml) to give the title compound as a white solid (728 mg, 61%). 1H NMR (400 MHz, CHLOROFORM-d) δ ppm 7.41 (1H, dd, J=8.7, 5.3 Hz) 7.36 (1H, s) 7.18 (1H, s) 7.12-7.16 (1H, m) 6.99 (1H, s) 4.58 (2H, s). LCMS: m/z 375 (M+1).

Step C: 3-{[3-(Aminomethyl)-2-chloro-6-fluorophenyl]oxy}-5-chlorobenzonitrile

The title compound was prepared as described herein using 3-{[3-(bromomethyl)-2-chloro-6-fluorophenyl]oxy}-5-chlorobenzonitrile (728 mg, 1.941 mmol) and NH₃ in MeOH (27.7 ml, 194 mmol, 7.0 N) in CH₂Cl₂ (20 ml) to give the title compound as a white solid (602 mg, 100%) which was used for the next step without purification. 1H NMR (400 MHz, CHLOROFORM-d) δ ppm 7.37-7.43 (1H, m) 7.34 (1H, s) 7.12-7.21 (2H, m) 6.99 (1H, br. s.) 3.98 (2H, br. s.) 1.65-1.89 (2H, m). LCMS: m/z 311 (M+1).

Step D: 4-Chloro-N-({2-chloro-3-[(3-chloro-5-cyanophenyl)oxy]-4-fluorophenyl}methyl)-1H-imidazole-5-carboxamide The title compound was prepared as described herein using 3-{[3-(aminomethyl)-2-chloro-6-fluorophenyl]oxy}-5-chlorobenzonitrile (40 mg, 0.129 mmol), 4-chloro-1-({[2-(trimethylsilyl)ethyl]oxy}methyl)-1H-imidazole-5-carboxylic acid (35.6 mg, 0.129 mmol), EDC (29.6 mg, 0.154 mmol) and HOBT (29.5 mg, 0.193 mmol) in DMF (3.0 ml) to give the title compound as a white solid (43 mg, 76%). 1H NMR (400 MHz, CHLOROFORM-d) δ ppm 7.62 (1H, s) 7.40 (1H, dd, J=8.5, 5.4 Hz) 7.35 (2H, br. s.) 7.12-7.22 (2H, m) 7.00 (1H, s) 4.75 (2H, d). LCMS: m/z 439 (M+1).

Example 276

4-Chloro-N-({2-chloro-3-[(3-chloro-5-cyanophenyl)oxy]-4-fluorophenyl}methyl)-2-methyl-1H-imidazole-5-carboxamide

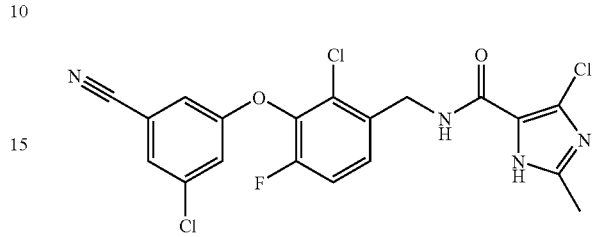

The title compound was prepared as described herein using 3-{[3-(aminomethyl)-2-chloro-6-fluorophenyl]oxy}-5-chlorobenzonitrile (40 mg, 0.129 mmol), 4-chloro-2-methyl-1H-imidazole-5-carboxylic acid (20.64 mg, 0.129 mmol), EDC (27.4 mg, 0.143 mmol) and HOBT (27.3 mg, 0.178 mmol) in DMF (3.0 ml) to give the title compound as a white solid (40 mg, 69%). 1H NMR (400 MHz, CHLOROFORM-d) δ ppm 10.42 (1H, br. s.) 7.46-7.54 (0H, m) 7.31-7.41 (2H, m) 7.16-7.23 (2H, m) 7.14 (1H, d, J=2.1 Hz) 7.00 (1H, s) 4.72 (2H, d, J=6.2 Hz) 2.41 (3H, s). LCMS: m/z 453 (M+1).

Example 277

4-Chloro-N-({2,4-dichloro-3-[(3-chloro-5-cyanophenyl)oxy]phenyl}methyl)-1H-imidazole-5-carboxamide

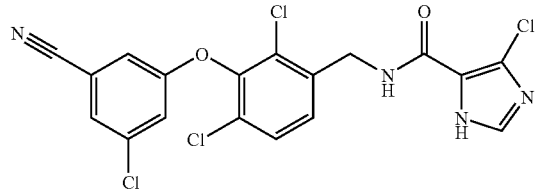

Step A: 4-Bromo-2,6-dichloro-3-methylphenol

Sulfuryl chloride (50.0 ml, 50.0 mmol, 1 M in CH₂Cl₂) was added to a solution of 4-bromo-3-methylphenol (3.74 g, 20 mmol) and di-iso-butylamine (0.349 ml, 2 mmol) in toluene (150 ml) at 70° C. The reaction mixture was stirred for 1 h and then cooled down to RT and concentrated under reduced pressure. The residue was dissolved in CH₂Cl₂, washed with HCl (1N) and then dried over Na₂SO₄. The residue was purified by chromatography on silica gel eluted with 0-5% EtOAc in hexane to give the title compound as a light-yellow solid (4.92 g, 96%). 1H NMR (400 MHz, CHLOROFORM-d) δ ppm 7.48 (1H, s) 5.83 (1H, s) 2.47 (3H, s). LCMS: m/z 254 (M−1).

Step B: 2,6-Dichloro-3-methylphenol

Zn powder (9.84 g, 150 mmol) was added to a solution of 4-bromo-2,6-dichloro-3-methylphenol (4.92 g, 19.22 mmol) in 10% NaOH (50 ml, 125 mmol). The reaction mixture was stirred for 1 h at 100° C. and then cooled down to RT. The Zn powder was filtered off and the filtrate was acidified with 10% HCl and extracted with CH₂Cl₂. The combined organic extracts were dried over Na$_2$SO$_4$, filtered and concentrated. The residue was purified by flash chromatography on silica gel eluted with 0-5% EtOAc in hexane to give the title compound as a colorless oil (2.98 g, 88%). 1H NMR (400 MHz, CHLOROFORM-d) δ ppm 7.14 (1H, d) 6.76 (1H, d) 5.83 (1H, s) 2.34 (3H, s). LCMS: m/z 175 (M−1).

Step C: 3-Chloro-5-[(2,6-dichloro-3-methylphenyl)oxy]benzonitrile

The title compound was prepared in a similar manner to that described herein using 2,6-dichloro-3-methylphenol (2.92 g, 16.49 mmol) to give the title compound as a white solid (1.57 g, 31%). 1H NMR (400 MHz, CHLOROFORM-d) δ ppm 7.29-7.34 (2H, m) 7.17 (1H, d) 7.10 (1H, t) 6.89-6.92 (1H, m) 2.42 (3H, s). LCMS: m/z 310 (M−1).

Step D: 3-{[3-(Bromomethyl)-2,6-dichlorophenyl]oxy}-5-chlorobenzonitrile

The title compound was prepared in a similar manner to that described herein using 3-chloro-5-[(2,6-dichloro-3-methylphenyl)oxy]benzonitrile (1.56 g, 4.99 mmol) to give the title compound as a white solid (1.24 g, 64%). 1H NMR (400 MHz, CHLOROFORM-d) δ ppm 7.41-7.46 (1H, m) 7.37-7.42 (1H, m) 7.35 (1H, s) 7.10 (1H, t) 6.92 (1H, s) 4.57 (2H, s). LCMS: m/z 391 (M+1).

Step E: 3-{[3-(Aminomethyl)-2,6-dichlorophenyl]oxy}-5-chlorobenzonitrile

The title compound was prepared in a similar manner to that described herein using 3-{[3-(bromomethyl)-2,6-dichlorophenyl]oxy}-5-chlorobenzonitrile (1.24 g, 3.17 mmol) to give the title compound as a white solid (1.04 g, 100%). 1H NMR (400 MHz, CHLOROFORM-d) δ ppm 7.37-7.46 (2H, m) 7.33 (1H, s) 7.10 (1H, s) 6.91 (1H, s) 3.98 (2H, s) 1.60 (2H, br. s.). LCMS: m/z 325 (M−1).

Step F: 4-Chloro-N-({2,4-dichloro-3-[(3-chloro-5-cyanophenyl)oxy]phenyl}methyl)-1H-imidazole-5-carboxamide The title compound was prepared in a similar manner to that described herein using 3-{[3-(aminomethyl)-2,6-dichlorophenyl]oxy}-5-chlorobenzonitrile (50 mg, 0.15 mmol) to give the title compound as a white solid (60 mg, 86%). 1H NMR (400 MHz, DMSO-d$_6$) δ ppm 13.09-13.31 (1H, m) 8.28 (1H, t) 7.79 (1H, s) 7.71 (1H, s) 7.65 (1H, d) 7.42 (1H, s) 7.36 (2H, dd) 4.53 (2H, d). LCMS: m/z 455 (M+1).

Example 278

4-Chloro-N-({2,4-dichloro-3-[(3-chloro-5-cyanophenyl)oxy]phenyl}methyl)-2-methyl-1H-imidazole-5-carboxamide

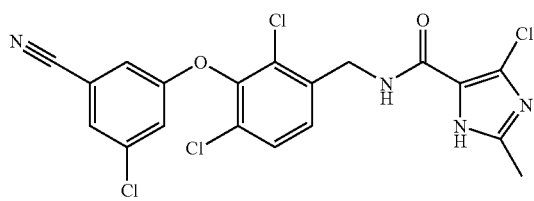

The title compound was prepared in a similar manner to that described herein using 3-{[3-(aminomethyl)-2,6-dichlorophenyl]oxy}-5-chlorobenzonitrile (50 mg, 0.15 mmol) to give the title compound as a white solid (60 mg, 84%). 1H NMR (400 MHz, CHLOROFORM-d) δ ppm 10.81 (1H, br. s.) 7.40-7.47 (1H, m) 7.31-7.37 (2H, m) 7.09 (1H, s) 6.93 (1H, s) 4.74 (2H, d, J=6.2 Hz) 2.41 (3H, s). LCMS: m/z 469 (M+1).

Example 279

4-Chloro-N-({4-chloro-3-[(2-chloro-6-cyano-4-pyridinyl)oxy]-2-fluorophenyl}methyl)-1H-imidazole-5-carboxamide

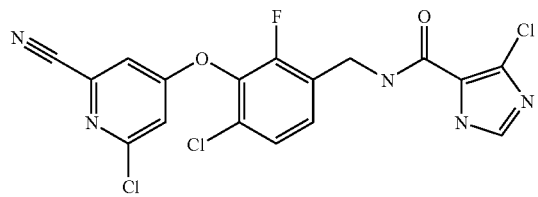

Step A: 2-Chloro-4-nitropyridine 1-oxide

TFAA (6.15 ml, 43.5 mmol) was slowly added to a solution of 2-chloro-4-nitropyridine (3.45 g, 21.76 mmol) and urea hydrogen peroxide (4.30 g, 45.7 mmol) in CH$_2$Cl$_2$ at 0° C. under N$_2$. The reaction was stirred for 30 min and then allowed to warm up to RT for 4 h. NH$_3$ gas was bubbled into the mixture for 5 min and then the organic layer was washed with sat. NaHCO$_3$, dried over Na$_2$SO$_4$, filtered and concentrated. The residue was purified by chromatography on silica gel eluted with 0-2% 2M NH$_3$ solution of MeOH in CH$_2$Cl$_2$ to give the product as a light-yellow solid (3.59 g, 95%). 1H NMR (400 MHz, CHLOROFORM-d) δ ppm 8.39 (1H, d) 8.36 (1H, d) 8.04 (1H, dd). LCMS: m/z 175 (M+1).

Step B: 6-Chloro-4-nitro-2-pyridinecarbonitrile 2-chloro-4-nitropyridine 1-oxide (1.8 g, 10.31 mmol) was slowly added to a solution of TMS-CN (4.98 ml, 37.1 mmol) in 1,2-dichloroethane (25 ml) at RT under N$_2$ and dimethylcarbamic chloride (3.41 ml, 37.1 mmol) was then slowly added. The mixture was stirred for at RT overnight then heated to 85° C. for 5 days. The reaction was cooled RT and sat. NaHCO$_3$ was added and then extracted with CH$_2$Cl$_2$. The organic was dried over Na$_2$SO$_4$, filtered and concentrated. The residue was purified by chromatography on silica gel eluted with 0-10% EtOAC in hexane to give the product as a white solid (0.79 g, 42%). 1H NMR (400 MHz, CHLOROFORM-d) δ ppm 7.63 (1H, d) 7.59 (1H, d).

Step C: 6-Chloro-4-[(6-chloro-2-fluoro-3-methylphenyl)oxy]-2-pyridinecarbonitrile The title compound was prepared in a similar manner to that described herein using 6-chloro-2-fluoro-3-methylphenol (0.60 g, 3.74 mmol) and 6-chloro-4-nitro-2-pyridinecarbonitrile (0.69 g, 3.74 mmol) to give the title compound as a white solid (0.98 g, 88%). 1H NMR (400 MHz, CHLOROFORM-d) δ ppm 7.20-7.24 (1H, m) 7.16 (1H, d) 7.14 (1H, d) 6.98 (1H, d) 2.33 (3H, d). LCMS: m/z 297 (M+1).

Step D: 4-{[3-(Bromomethyl)-6-chloro-2-fluorophenyl]oxy}-6-chloro-2-pyridinecarbonitrile The title compound was prepared in a similar manner to that described herein using 6-chloro-4-[(6-chloro-2-fluoro-3-methylphenyl)oxy]-2-pyridinecarbonitrile (500 mg, 1.68 mmol) to give the title compound as a colorless gel (359 mg, 57%). 1H NMR (400 MHz, CHLOROFORM-d) δ ppm 7.36-7.41 (1H, m) 7.32-7.35 (1H, m) 7.15 (1H, d) 6.99 (1H, d) 4.48 (2H, s). LCMS: m/z 376 (M+1).

Step E: 4-{[3-(aminomethyl)-6-chloro-2-fluorophenyl]oxy}-6-chloro-2-pyridinecarbonitrile The title compound was prepared in a similar manner to that described herein using 4-{[3-(bromomethyl)-6-chloro-2-fluorophenyl]oxy}-6-chloro-2-pyridinecarbonitrile (359 mg, 0.96 mmol) to give the title compound as a white solid (279 mg, 94%). 1H NMR (400 MHz, CHLOROFORM-d) δ ppm 7.39 (1H, t) 7.32 (1H, d) 7.15 (1H, d) 6.98 (1H, d) 3.96 (2H, s) 1.55-1.74 (2H, m). LCMS: m/z 312 (M+1).

Step F: 4-Chloro-N-({4-chloro-3-[(2-chloro-6-cyano-4-pyridinyl)oxy]-2-fluorophenyl}methyl)-1H-imidazole-5-carboxamide The title compound was prepared in a similar manner to that described herein using 4-{[3-(aminomethyl)-6-chloro-2-fluorophenyl]oxy}-6-chloro-2-pyridinecarbonitrile (50 mg, 0.16 mmol) to give the title compound as a white solid (34 mg, 48%). 1H NMR (400 MHz, DMSO-d$_6$) δ ppm 13.10 (1H, br. s.) 8.25 (1H, br. s.) 7.96 (1H, d) 7.76 (1H, s) 7.58 (1H, d) 7.52 (1H, d) 7.41 (1H, t) 4.52 (2H, br. s.). LCMS: m/z 440 (M+1).

Example 280

4-Chloro-N-({4-chloro-3-[(2-chloro-6-cyano-4-pyridinyl)oxy]-2-fluorophenyl}methyl)-2-methyl-1H-imidazole-5-carboxamide

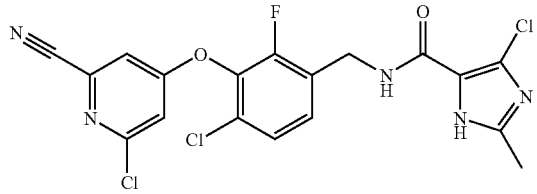

The title compound was prepared in a similar manner to that described herein using 4-{[3-(aminomethyl)-6-chloro-2-fluorophenyl]oxy}-6-chloro-2-pyridinecarbonitrile (50 mg, 0.16 mmol) to give the title compound as a white solid (30 mg, 42%). 1H NMR (400 MHz, DMSO-d$_6$) δ ppm 12.76 (1H, s) 8.06 (1H, t) 7.96 (1H, d) 7.58 (1H, d) 7.52 (1H, d) 7.39 (1H, t) 4.53 (2H, d) 2.24 (3H, s). LCMS: m/z 454 (M+1).

Example 281

2-Amino-4-chloro-N-({4-chloro-3-[(2-chloro-6-cyano-4-pyridinyl)oxy]-2-fluorophenyl}methyl)-1H-imidazole-5-carboxamide

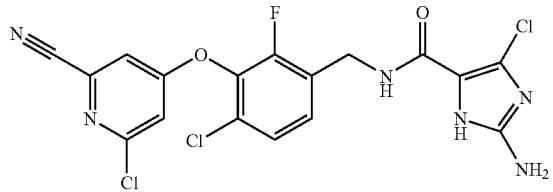

Step A: 2-Azido-4-chloro-N-({4-chloro-3-[(2-chloro-6-cyano-4-pyridinyl)oxy]-2-fluorophenyl}methyl)-1H-imidazole-5-carboxamide The title compound was prepared in a similar manner to that described herein using 2-azido-4-chloro-1H-imidazole-5-carboxylic acid (48 mg. 0.26 mmol) to give the title compound as a white solid (123 mg, >99%) which was used in the next step without purification. LCMS: m/z 481 (M+1).

Step B: 2-Amino-4-chloro-N-({4-chloro-3-[(2-chloro-6-cyano-4-pyridinyl)oxy]-2-fluorophenyl}methyl)-1H-imidazole-5-carboxamide The title compound was prepared in a similar manner to that described herein using 2-azido-4-chloro-N-({4-chloro-3-[(2-chloro-6-cyano-4-pyridinyl)oxy]-2-fluorophenyl}methyl)-1H-imidazole-5-carboxamide (123 mg, 0.255 mmol), a catalytic amount of Lindlar catalyst in EtOAc (15 ml) under H$_2$ (50 psi) to afford the title compound as a white powder (52 mg, 45%). 1H NMR (400 MHz, DMSO-d$_6$) δ ppm 10.96 (1H, s) 7.98 (1H, d) 7.78 (1H, t) 7.59 (1H, d) 7.53 (1H, d) 7.39 (1H, t) 5.83 (2H, s) 4.50 (2H, d). LCMS: m/z 455 (M+1).

Example 282

N-({4-chloro-3-[(3-chloro-5-cyanophenyl)oxy]-2-fluorophenyl}methyl)-1H-1,2,4-triazole-3-carboxamide

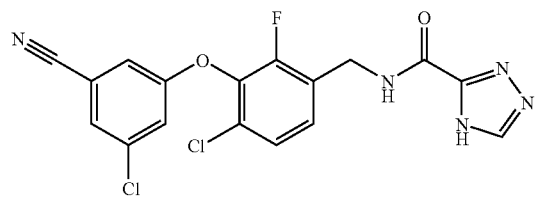

The title compound was prepared in a similar manner to that described herein using EDC (0.068 g, 0.354 mmol), HOBT (0.048 g, 0.354 mmol), 3-{[3-(aminomethyl)-6-chloro-2-fluorophenyl]oxy}-5-chlorobenzonitrile (0.100 g, 0.321 mmol) and 1H-1,2,4-triazole-3-carboxylic acid (0.036 g, 0.321 mmol) in DMF (2 mL) to give title compound (0.051 g, 39%) as a white solid. $^1$H NMR (400 MHz, DMSO-d$_6$) (95° C.) δ ppm 14.24 (br. s., 1H), 8.60 (br. s., 1H), 7.72 (s, 1H), 7.33-7.49 (m, 5H), 4.55 (d, 2H). ES MS: m/z 406 (M+1).

Example 283

4-chloro-N-[(4-chloro-3-{[3-cyano-5-(trifluoromethyl)phenyl]oxy}-2-fluorophenyl)methyl]-2-ethyl-1H-imidazole-5-carboxamide

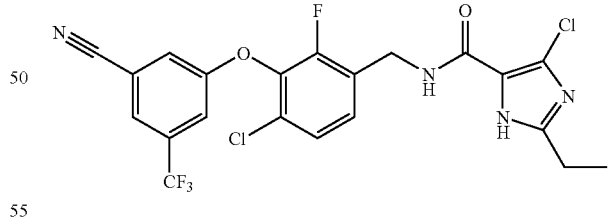

Step A: 3-[(6-chloro-2-fluoro-3-methylphenyl)oxy]-5-(trifluoromethyl)benzonitrile To a solution of 6-chloro-2-fluoro-3-methylphenol (8.49 g, 52.9 mmol) and 18-crown-6 (13.98 g, 52.9 mmol) in dimethyl sulfoxide (80 ml) was added potassium t-butoxide (20% wt solution in THF) (31.2 g, 55.5 mmol) (31.2 mL) and the mixture was stirred at rt for 30 minutes. Next, 3-fluoro-5-(trifluoromethyl)benzonitrile (10.00 g, 52.9 mmol) was added and the mixture was heated with stirring for 5 hours at 135° C. The reaction mixture was cooled to 0° C., poured into 700 mL water, and the precipitate was filtered off to give the title compound (12.6 g, 38.2 mmol, 72% yield) as a grey solid.

1H NMR (400 MHz, DMSO-$d_6$) δ ppm 8.10 (s, 1H), 7.80 (s, 1H), 7.74 (s, 1H), 7.39-7.49 (m, 1H), 7.34 (t, 1H), 2.28 (s, 3H).

Step B: 3-{[3-(bromomethyl)-6-chloro-2-fluorophenyl]oxy}-5-(trifluoromethyl)benzonitrile To a solution of 3-[(6-chloro-2-fluoro-3-methylphenyl)oxy]-5-(trifluoromethyl)benzonitrile (12.2 g, 37.0 mmol) and N-bromosuccinimide (6.59 g, 37.0 mmol) in carbon tetrachloride (300 mL) was added AIBN (0.304 g, 1.850 mmol) and the mixture was stirred at 75° C. for 4 hours. More AIBN (0.304 g, 1.850 mmol) was added and the reaction mixture was stirred overnight at 75° C. The mixture was filtered through a pad of Celite and the filtrate was concentrated. The crude oil was purified via silica gel chromatography to give 3-{[3-(bromomethyl)-6-chloro-2-fluorophenyl]oxy}-5-(trifluoromethyl)benzonitrile (7.33 g, 17.94 mmol, 49% yield). 1H NMR (400 MHz, CHLOROFORM-d) δ ppm 7.63 (s, 1H), 7.42 (s, 1H), 7.31-7.36 (m, 2H), 7.24 (d, 1H), 4.48 (s, 2H).

Step C: 3-{[3-(aminomethyl)-6-chloro-2-fluorophenyl]oxy}-5-(trifluoromethyl)benzonitrile A solution of 3-{[3-(bromomethyl)-6-chloro-2-fluorophenyl]oxy}-5-(trifluoromethyl)benzonitrile (5.00 g, 12.24 mmol) in DCM (15 ml) was added dropwise to ammonia (7.0 M solution in MeOH) (69.9 ml, 490 mmol) and the mixture was stirred overnight at rt. The solvent was removed and the crude material was neutralized to give 3-{[3-(aminomethyl)-6-chloro-2-fluorophenyl]oxy}-5-(trifluoromethyl)benzonitrile (4.22 g, 12.24 mmol, 100% yield) as a tan solid. 1H NMR (400 MHz, DMSO-$d_6$) δ ppm 8.24 (d, 2H), 8.15 (s, 1H), 7.76 (d, 2H), 7.62-7.69 (m, 1H), 7.54-7.61 (m, 1H), 4.12 (s, 2H).

Step D: 4-chloro-N-[(4-chloro-3-{[3-cyano-5-(trifluoromethyl)phenyl]oxy}-2-fluorophenyl)methyl]-2-ethyl-1H-imidazole-5-carboxamide To a mixture of 3-{[3-(aminomethyl)-6-chloro-2-fluorophenyl]oxy}-5-(trifluoromethyl)benzonitrile (197 mg, 0.573 mmol), 4-chloro-2-ethyl-1H-imidazole-5-carboxylic acid (100 mg, 0.573 mmol) and HATU (218 mg, 0.573 mmol) in DMF (4.0 ml) was added diisopropylethyl amine (0.200 ml, 1.146 mmol) and the mixture was stirred for 1 hr at rt. The reaction mixture was diluted with ethyl acetate and washed with water. The solvent was removed and the crude material was purified via silica gel chromatography to give 4-chloro-N-[(4-chloro-3-{[3-cyano-5-(trifluoromethyl)phenyl]oxy}-2-fluorophenyl)methyl]-2-ethyl-1H-imidazole-5-carboxamide (135 mg, 0.269 mmol, 47% yield). 1H NMR (400 MHz, DMSO-$d_6$) δ ppm 8.11 (s, 2H), 7.80 (s, 1H), 7.74 (s, 1H), 7.50 (dd, 1H), 7.36 (t, 1H), 4.52 (d, 2H), 2.58 (q, 2H), 1.16 (t, 3H). LC-MS (ES$^+$) m/z 501.10, [M+H].

Example 284

4-chloro-N-[(4-chloro-3-{[3-cyano-5-(trifluoromethyl)phenyl]oxy}-2-fluorophenyl)methyl]-2-methyl-1H-imidazole-5-carboxamide

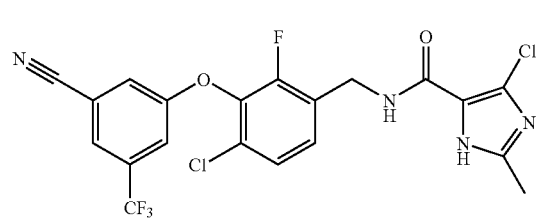

To a solution of 3-{[3-(aminomethyl)-6-chloro-2-fluorophenyl]oxy}-5-(trifluoromethyl)benzonitrile (27.9 mg, 0.081 mmol), 4-chloro-2-methyl-1H-imidazole-5-carboxylic acid (13.0 mg, 0.081 mmol) and HATU (30.8 mg, 0.081 mmol) in DMF (1.5 ml) was added diisopropylethyl amine (0.028 ml, 0.162 mmol) and the mixture was stirred for 1 hour at rt. The mixture was purified via reverse phase HPLC and neutralized to give 4-chloro-N-[(4-chloro-3-{[3-cyano-5-(trifluoromethyl)phenyl]oxy}-2-fluorophenyl)methyl]-2-methyl-1H-imidazole-5-carboxamide (25 mg, 0.051 mmol, 63% yield). 1H NMR (400 MHz, DMSO-$d_6$) δ ppm 8.05-8.14 (m, 2H), 7.77 (s, 1H), 7.71 (s, 1H), 7.47 (d, 1H), 7.33 (t, 1H), 4.49 (d, 2H), 2.21 (s, 3H). LC-MS (ES$^+$) m/z 486.94, [M+H].

Example 285

3-chloro-N-[(4-chloro-3-{[3-cyano-5-(trifluoromethyl)phenyl]oxy}-2-fluorophenyl)methyl]-1H-pyrrole-2-carboxamide

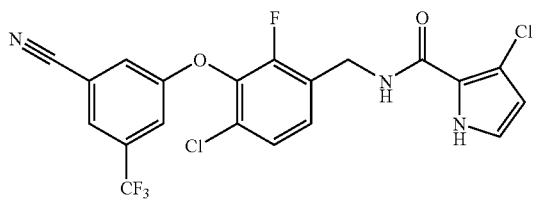

To a solution of 3-{[3-(aminomethyl)-6-chloro-2-fluorophenyl]oxy}-5-(trifluoromethyl)benzonitrile (71.0 mg, 0.206 mmol), 3-chloro-1H-pyrrole-2-carboxylic acid (30.0 mg, 0.206 mmol) and diisopropylethyl amine (0.036 ml, 0.206 mmol) in DMF (3.0 ml) was added HATU (78 mg, 0.206 mmol) and the reaction mixture was stirred at room temperature for 30 minutes. The mixture was diluted with EtOAc, washed with water and the solvent was removed. The crude material was purified via reverse phase HPLC to give 3-chloro-N-[(4-chloro-3-{[3-cyano-5-(trifluoromethyl)phenyl]oxy}-2-fluorophenyl)methyl]-1H-pyrrole-2-carboxamide (83 mg, 0.176 mmol, 85% yield). 1H NMR (400 MHz, DMSO-$d_6$) δ ppm 11.78 (t, 1H), 8.11 (s, 1H), 7.95 (t, 1H), 7.80 (s, 1H), 7.74 (s, 1H), 7.46-7.57 (m, 1H), 7.37 (t, 1H), 6.92 (t, 1H), 6.18 (t, 1H), 4.54 (d, 2H). LC-MS (ES$^+$) m/z 472.12, [M+H].

Example 286

4-bromo-N-[(4-chloro-3-{[3-cyano-5-(trifluoromethyl)phenyl]oxy}-2-fluorophenyl)methyl]-1H-imidazole-5-carboxamide

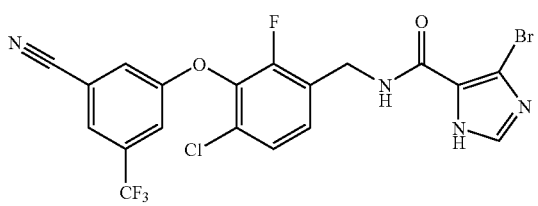

To a solution of 3-{[3-(aminomethyl)-6-chloro-2-fluorophenyl]oxy}-5-(trifluoromethyl)benzonitrile (36.1 mg, 0.105 mmol), 4-bromo-1H-imidazole-5-carboxylic acid (20.0 mg, 0.105 mmol) and diisopropylethyl amine (0.0366 mL, 0.210 mmol) in DMF (5 ml) was added HATU (39.8 mg, 0.105 mmol) and the mixture was stirred at rt for 30 minutes. The reaction mixture was diluted with EtOAc and washed with water. The solvent was removed and the crude material was purified via reverse phase HPLC to give 4-bromo-N-[(4-chloro-3-{[3-cyano-5-(trifluoromethyl)phenyl]oxy}-2-fluorophenyl)methyl]-1H-imidazole-5-carboxamide (11.0 mg, 0.021 mmol, 20% yield). 1H NMR (400 MHz, DMSO-$d_6$) δ ppm 8.27-8.50 (m, 1H), 8.11 (s, 1H), 7.76-7.89 (m, 2H), 7.74 (s, 1H), 7.50 (dd, 1H), 7.37 (t, 1H), 4.50 (d, 2H). LC-MS (ES$^+$) m/z 516.90, [M+H].

Example 287

4-bromo-N-[(4-chloro-3-{[3-cyano-5-(trifluoromethyl)phenyl]oxy}-2-fluorophenyl)methyl]-2-methyl-1H-imidazole-5-carboxamide trifluoroacetate

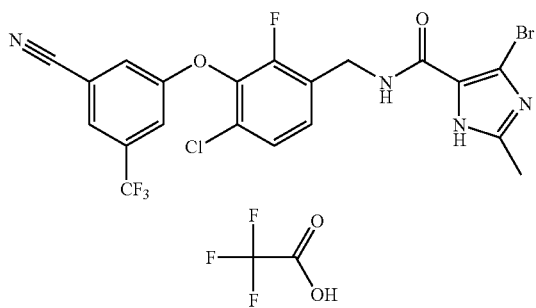

To a solution of 3-{[3-(aminomethyl)-6-chloro-2-fluorophenyl]oxy}-5-(trifluoromethyl)benzonitrile (33.6 mg, 0.098 mmol), 4-bromo-2-methyl-1H-imidazole-5-carboxylic acid (20 mg, 0.098 mmol) and HATU (37.1 mg, 0.098 mmol) in DMF (5 ml) was added diisopropylethyl amine (0.034 ml, 0.195 mmol) and the mixture was stirred for 20 minutes at rt. The mixture was diluted with EtOAc and washed with water. The solvent was removed and the crude material was purified via reverse phase HPLC to give 4-bromo-N-[(4-chloro-3-{[3-cyano-5-(trifluoromethyl)phenyl]oxy}-2-fluorophenyl)methyl]-2-methyl-1H-imidazole-5-carboxamide trifluoroacetate (15.0 mg, 0.023 mmol, 24% yield). 1H NMR (400 MHz, DMSO-$d_6$) δ ppm 8.23 (t, 1H), 8.11 (s, 1H), 7.79 (s, 1H), 7.74 (s, 1H), 7.50 (d, 1H), 7.36 (t, 1H), 4.49 (d, 2H), 2.26 (s, 3H). LC-MS (ES$^+$) m/z 531.10, [M+H].

Example 288

N-({3-[(3-bromo-5-chlorophenyl)oxy]-4-chloro-2-fluorophenyl}methyl)-4-chloro-1H-imidazole-5-carboxamide

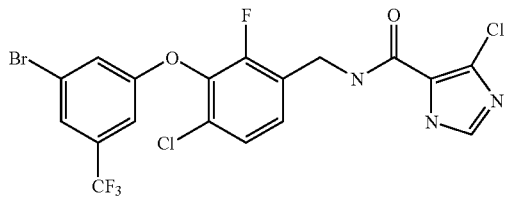

Step A: 2-[(3-bromo-5-chlorophenyl)oxy]-1-chloro-3-fluoro-4-methylbenzene

To a solution of 6-chloro-2-fluoro-3-methylphenol (7.67 g, 47.7 mmol) in DMSO (100 ml) was added potassium t-butoxide (1.0 M solution in THF) (50.1 ml, 50.1 mmol) and the mixture was stirred at room temperature for 30 minutes. Next, 1-bromo-3-chloro-5-fluorobenzene (10.0 g, 47.7 mmol) was added and the mixture was heated at 135° C. for 3 days. The reaction mixture was cooled to room temperature, diluted with EtOAc and washed with water. The solvent was removed to give 2-[(3-bromo-5-chlorophenyl)oxy]-1-chloro-3-fluoro-4-methylbenzene (9.54 g, 27.3 mmol, 57% yield) which was used in the next step without further purification. 1H NMR (400 MHz, DMSO-$d_6$) δ ppm 7.44 (s, 1H), 7.33-7.40 (m, 1H), 7.27 (t, 1H), 7.07 (s, 1H), 6.95-7.02 (m, 1H), 2.23 (d, 3H).

Step B: 2-[(3-bromo-5-chlorophenyl)oxy]-4-(bromomethyl)-1-chloro-3-fluorobenzene To a solution of 2-[(3-bromo-5-chlorophenyl)oxy]-1-chloro-3-fluoro-4-methylbenzene (9.69 g, 27.7 mmol) and NBS (4.93 g, 27.7 mmol) in carbon tetrachloride (250 ml) was added AIBN (0.227 g, 1.384 mmol) and the mixture was stirred at 80° C. overnight. An additional portion of AIBN (0.227 g, 1.384 mmol) was added and the mixture was stirred for another 4 hours. The mixture was cooled to rt, the solvent was removed and the crude material was purified via silica gel chromatography to give 2-[(3-bromo-5-chlorophenyl)oxy]-4-(bromomethyl)-1-chloro-3-fluorobenzene (5.78 g, 49% yield). 1H NMR (400 MHz, DMSO-$d_6$) δ ppm 7.38-7.67 (m, 3H), 7.10 (s, 1H), 6.98-7.07 (m, 1H), 4.70 (s, 2H)

Step C: ({3-[(3-bromo-5-chlorophenyl)oxy]-4-chloro-2-fluorophenyl}methyl)amine

To a flask containing ammonia (7.0 M solution in methanol) (132 ml, 927 mmol) was added a solution of 2-[(3-bromo-5-chlorophenyl)oxy]-4-(bromomethyl)-1-chloro-3-fluorobenzene (4.97 g, 11.59 mmol) in DCM (15 ml) dropwise and the mixture was stirred overnight at room temperature. The solvent was removed and the crude material was purified via silica gel chromatography to give ({3-[(3-bromo-5-chlorophenyl)oxy]-4-chloro-2-fluorophenyl}methyl)amine (3.70 g, 10.14 mmol, 87% yield). 1H NMR (400 MHz, DMSO-$d_6$) δ ppm 7.34-7.85 (m, 3H), 7.06 (s, 1H), 6.99 (t, 1H), 3.72 (s, 2H), 1.85 (s, 2H).

Step D: N-({3-[(3-bromo-5-chlorophenyl)oxy]-4-chloro-2-fluorophenyl}methyl)-4-chloro-1-({[2-(trimethylsilyl)ethyl]oxy}methyl)-1H-imidazole-5-carboxamide To a solution of ({3-[(3-bromo-5-chlorophenyl)oxy]-4-chloro-2-fluorophenyl}methyl)amine (667 mg, 1.828 mmol), 4-chloro-1-({[2-(trimethylsilyl)ethyl]oxy}methyl)-1H-imidazole-5-carboxylic acid (506 mg, 1.828 mmol) and diisopropylethyl amine (0.669 mL, 3.83 mmol) in DMF (20 ml) was added HATU (695 mg, 1.828 mmol) and the mixture was stirred for 30 minutes. The mixture was diluted with EtOAc and washed with water. The solvent was removed and the crude material was purified via silica gel chromatography to give N-({3-[(3-bromo-5-chlorophenyl)oxy]-4-chloro-2-fluorophenyl}methyl)-4-chloro-1-({[2-(trimethylsilyl)ethyl]oxy}methyl)-1H-imidazole-5-carboxamide (589 mg, 0.944 mmol, 52% yield). 1H NMR (400 MHz, DMSO-$d_6$) δ ppm 8.74 (t, 1H), 7.95 (s, 1H), 7.40-7.51 (m, 2H), 7.37 (t, 1H), 7.09 (t, 1H), 7.01 (t, 1H), 5.46 (s, 2H), 4.46 (d, 2H), 3.35 (t, 2H), 0.72 (t, 2H), −0.12 (s, 9H).

Step E: N-({3-[(3-bromo-5-chlorophenyl)oxy]-4-chloro-2-fluorophenyl}methyl)-4-chloro-1H-imidazole-5-carboxamide To a solution of N-({3-[(3-bromo-5-chlorophenyl)oxy]-4-chloro-2-fluorophenyl}methyl)-4-chloro-1-({[2-(trimethylsilyl)ethyl]oxy}methyl)-1H-imidazole-5-carboxamide (120 mg, 0.192 mmol) in DCM (5 ml) was added TFA (1.0 mL) and the mixture was stirred at room temperature for 3 hours. The solvent was removed and the crude material was purified via reverse phase HPLC to give N-({3-[(3-bromo-5-chlorophenyl)oxy]-4-chloro-2-fluorophenyl}methyl)-4-chloro-1H-imidazole-5-carboxamide (78 mg, 0.158 mmol, 82% yield). 1H NMR (400 MHz, DMSO-$d_6$) δ ppm 13.12 (d, 1H), 8.02-8.42 (m, 1H), 7.73 (s, 1H), 7.41-7.54 (m, 1H), 7.32 (t, 1H), 7.08-7.15 (m, 1H), 6.95-7.06 (m, 1H), 4.49 (d, 2H). LC-MS (ES$^+$) m/z 491.87, [M+H].

Example 289

4-chloro-N-({4-chloro-3-[(3-chloro-5-methylphenyl)oxy]-2-fluorophenyl}methyl)-1H-imidazole-5-carboxamide

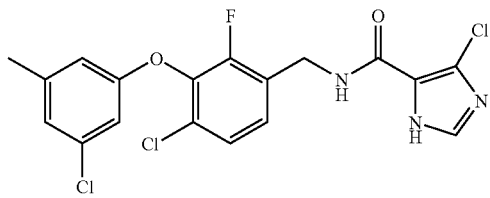

Step A: 4-chloro-N-({4-chloro-3-[(3-chloro-5-methylphenyl)oxy]-2-fluorophenyl}methyl)-1-({[2-(trimethylsilyl)ethyl]oxy}methyl)-1H-imidazole-5-carboxamide To a solution of N-({3-[(3-bromo-5-chlorophenyl)oxy]-4-chloro-2-fluorophenyl}methyl)-4-chloro-1-({[2-(trimethylsilyl)ethyl]oxy}methyl)-1H-imidazole-5-carboxamide (112 mg, 0.180 mmol) and 1,1′-bis(diphenylphosphino)ferrocene-dichloropalladium(II) dichloromethane complex (7.33 mg, 8.98 μmol) in THF (5 ml) at 0° C. was added DIBAL-H (1.0 M solution in dichloromethane) (0.018 ml, 0.018 mmol), followed by dimethylzinc (1.0 M solution in heptane) (0.197 ml, 0.197 mmol), and the reaction mixture was stirred with heating at 60° C. for one hour. The mixture was diluted with EtOAc and washed with water. The solvent was removed and the crude material was purified via silica gel chromatography to give 4-chloro-N-({4-chloro-3-[(3-chloro-5-methylphenyl)oxy]-2-fluorophenyl}methyl)-1-({[2-(trimethylsilyl)ethyl]oxy}methyl)-1H-imidazole-5-carboxamide (75 mg, 0.134 mmol, 75% yield). 1H NMR (400 MHz, DMSO-$d_5$) δ ppm 8.72-8.86 (m, 1H), 7.98 (s, 1H), 7.45 (dd, J=8.6, 1.4 Hz, 1H), 7.30-7.40 (m, 1H), 7.01 (s, 1H), 6.71 (d, 2H), 5.49 (s, 2H), 4.47 (d, 2H), 3.38 (t, 2 H), 2.25 (s, 3H), 0.75 (t, 2H), −0.09 (s, 9H Step B: 4-chloro-N-({4-chloro-3-[(3-chloro-5-methylphenyl)oxy]-2-fluorophenyl}methyl)-1H-imidazole-5-carboxamide To a solution of 4-chloro-N-({4-chloro-3-[(3-chloro-5-methylphenyl)oxy]-2-fluorophenyl}methyl)-1-({[2-(trimethylsilyl)ethyl]oxy}methyl)-1H-imidazole-5-carboxamide (73.0 mg, 0.131 mmol) in DCM (5 ml) was added TFA (1.5 mL) and the reaction mixture was stirred for 4 hours at room temperature. The reaction was quenched with saturated sodium bicarbonate and the organic layer was separated. The solvent was removed and the crude material was purified via silica gel chromatography to give 4-chloro-N-({4-chloro-3-[(3-chloro-5-methylphenyl)oxy]-2-fluorophenyl}methyl)-1H-imidazole-5-carboxamide (32 mg, 0.075 mmol, 57% yield). 1H NMR (400 MHz, DMSO-$d_5$) δ ppm 12.74-13.45 (m, 1H), 7.97-8.44 (m, 1H), 7.73 (s, 1H), 7.44 (d, 1H), 7.29 (t, 1H), 6.98 (s, 1H), 6.69 (d, 2H), 4.27-4.76 (m, 2 H), 2.23 (s, 3H). LC-MS (ES+) m/z 427.91, [M+H].

Example 290

4-chloro-N-({4-chloro-3-[(3-chloro-5-ethylphenyl)oxy]-2-fluorophenyl}methyl)-1H-imidazole-5-carboxamide

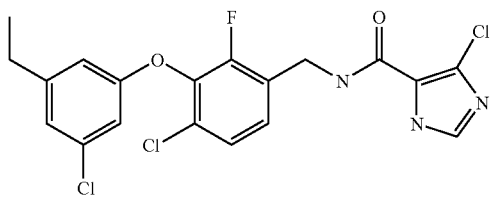

Step A: 4-chloro-N-({4-chloro-3-[(3-chloro-5-ethylphenyl)oxy]-2-fluorophenyl}methyl)-1-({[2-(trimethylsilyl)ethyl]oxy}methyl)-1H-imidazole-5-carboxamide To a solution of N-({3-[(3-bromo-5-chlorophenyl)oxy]-4-chloro-2-fluorophenyl}methyl)-4-chloro-1-({[2-(trimethylsilyl)ethyl]oxy}methyl)-1H-imidazole-5-carboxamide (112 mg, 0.180 mmol) and 1,1′-bis(diphenylphosphino)ferrocene-dichloropalladium(II) dichloromethane complex (7.33 mg, 8.98 μmol) in THF (10 ml) was added DIBAL-H (1.0 M solution in DCM) (2.55 mg, 0.018 mmol), followed by diethylzinc (1.0 M solution in heptane) (22.18 mg, 0.180 mmol). The reaction mixture was stirred for one hour at 60° C., cooled to room temperature, diluted with EtOAc and washed with water. The solvent was removed and the crude material (64 mg) was used directly in the next step without purification. LC-MS (ES+) m/z 572 [M+H].

Step B: 4-chloro-N-({4-chloro-3-[(3-chloro-5-ethylphenyl)oxy]-2-fluorophenyl}methyl)-1H-imidazole-5-carboxamide To a solution of 4-chloro-N-({4-chloro-3-[(3-chloro-5-ethylphenyl)oxy]-2-fluorophenyl}methyl)-1-({[2-(trimethylsilyl)ethyl]oxy}methyl)-1H-imidazole-5-carboxamide (64 mg, 0.112 mmol) in DCM (5 ml) was added TFA (2.0 ml) and the reaction mixture was stirred for 5 hours at room temperature. The reaction was quenched with saturated sodium bicarbonate and the organic layer was separated. The solvent was removed and the crude material was purified via silica gel chromatography to give 4-chloro-N-({4-chloro-3-[(3-chloro-5-ethylphenyl)oxy]-2-fluorophenyl}methyl)-1H-imidazole-5-carboxamide (28 mg, 0.063 mmol, 57% yield). 1H NMR (400 MHz, DMSO-$d_5$) δ ppm 12.83-13.43 (m, 1H), 8.20 (d, 1H), 7.73 (s, 1H), 7.44 (d, 1H), 7.29 (t, 1H), 7.01 (s, 1H), 6.73 (s, 1H), 6.66 (s, 1H), 4.48 (d, 2H), 2.53 (q, 2H), 1.08 (t, 3H). LC-MS (ES+) m/z 441.59, [M+H].

Example 291

4-chloro-N-{[4-chloro-3-({3-chloro-5-[(E)-2-cyanoethenyl]phenyl}oxy)-2-fluorophenyl]methyl}-1H-imidazole-5-carboxamide

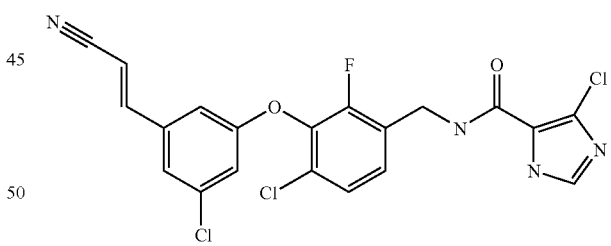

Step A: 4-chloro-N-({4-chloro-3-[(3-chloro-5-ethenylphenyl)oxy]-2-fluorophenyl}methyl)-1-({[2-(trimethylsilyl)ethyl]oxy}methyl)-1H-imidazole-5-carboxamide To a solution of N-({3-[(3-bromo-5-chlorophenyl)oxy]-4-chloro-2-fluorophenyl}methyl)-4-chloro-1-({[2-(trimethylsilyl)ethyl]oxy}methyl)-1H-imidazole-5-carboxamide (320 mg, 0.513 mmol), potassium vinyl trifluoroborate (69.2 mg, 0.513 mmol) and TEA (0.214 ml, 1.539 mmol) in n-propanol (3 ml) was added 1,1′-bis(diphenylphosphino)ferrocene-dichloropalladium(II) dichloromethane complex (84 mg, 0.103 mmol) and the reaction mixture was stirred at 100° C. for 4 hours. The mixture was adsorbed onto silica gel and the crude material was purified via silica gel chromatography to give 4-chloro-N-({4-chloro-3-[(3-chloro-5-ethenylphenyl)

oxy]-2-fluorophenyl}methyl)-1-({[2-(trimethylsilyl)ethyl] oxy}methyl)-1H-imidazole-5-carboxamide (246 mg, 0.431 mmol, 84% yield). 1H NMR (400 MHz, DMSO-d$_6$) δ ppm 8.74 (t, 1H), 7.95 (s, 1H), 7.40-7.55 (m, 1H), 7.22-7.39 (m, 2H), 6.99 (s, 1H), 6.72-6.81 (m, 1H), 6.64 (dd, 1H), 5.89 (d, 1H), 5.46 (s, 2H), 5.32 (d, 1H), 4.45 (d, 2H), 3.35 (t, 2H), 0.72 (t, 2H), −0.12 (s, 9H).

Step B: 4-chloro-N-({4-chloro-3-[(3-chloro-5-formylphenyl)oxy]-2-fluorophenyl}methyl)-1-({[2-(trimethylsilyl)ethyl]oxy}methyl)-1H-imidazole-5-carboxamide To a solution of 4-chloro-N-({4-chloro-3-[(3-chloro-5-ethenylphenyl)oxy]-2-fluorophenyl}methyl)-1-({[2-(trimethylsilyl)ethyl]oxy}methyl)-1H-imidazole-5-carboxamide (240 mg, 0.420 mmol) and sodium periodate (270 mg, 1.261 mmol) in dioxane (5 mL) and water (3 ml) was added osmium tetroxide (2.5% solution in t-butanol) (0.106 ml, 8.44 μmol) and the mixture was stirred at room temperature for 5 hours. The mixture was diluted with EtOAc, washed with water and the solvent was removed. The crude material was purified via silica gel chromatography to give 4-chloro-N-({4-chloro-3-[(3-chloro-5-formylphenyl)oxy]-2-fluorophenyl}methyl)-1-({[2-(trimethylsilyl)ethyl]oxy}methyl)-1H-imidazole-5-carboxamide (189 mg, 0.330 mmol, 78% yield). 1H NMR (400 MHz, DMSO-d$_6$) δ ppm 9.92 (s, 1H), 8.79 (t, 1H), 8.00 (s, 1H), 7.65-7.82 (m, 1H), 7.48-7.57 (m, 1H), 7.37-7.49 (m, 2H), 7.28 (d, 1H), 5.51 (s, 2H), 4.51 (d, 2H), 3.21-3.60 (m, 2H), 0.77 (t, 2H), −0.07 (s, 9H)

Step C: 4-chloro-N-{[4-chloro-3-({3-chloro-5-[(E)-2-cyanoethenyl]phenyl}oxy)-2-fluorophenyl]methyl}-1-({[2-(trimethylsilyl)ethyl]oxy}methyl)-1H-imidazole-5-carboxamide To a solution of diethyl cyanomethylphosphonate (56.1 mg, 0.317 mmol) in THF (5 mL) at 0° C. was added potassium t-butoxide (1.0 M solution in THF) (0.317 ml, 0.317 mmol) and the mixture was stirred at 0° C. for 30 minutes. Next, 4-chloro-N-({4-chloro-3-[(3-chloro-5-formylphenyl)oxy]-2-fluorophenyl}methyl)-1-({[2-(trimethylsilyl)ethyl] oxy}methyl)-1H-imidazole-5-carboxamide (165 mg, 0.288 mmol) was added and the reaction mixture was stirred at room temperature for 2 hours. The mixture was diluted with EtOAc and washed with water. The solvent was removed and the crude material was purified via silica gel chromatography to give 4-chloro-N-{[4-chloro-3-({3-chloro-5-[(E)-2-cyanoethenyl]phenyl}oxy)-2-fluorophenyl]methyl}-1-({[2-(trimethylsilyl)ethyl]oxy}methyl)-1H-imidazole-5-carboxamide (113 mg, 0.190 mmol, 66% yield). 1H NMR (400 MHz, DMSO-d$_6$) δ ppm 8.74 (t, 1H), 7.95 (s, 1H), 7.54 (d, 2H), 7.41-7.48 (m, 1H), 7.36 (t, 1H), 7.23 (s, 1H), 6.97 (s, 1H), 6.58 (d, 1H), 5.47 (s, 2H), 4.45 (d, 2H), 3.36 (t, 2H), 0.72 (t, 2H), −0.12 (s, 9H).

Step D: 4-chloro-N-{[4-chloro-3-({3-chloro-5-[(E)-2-cyanoethenyl]phenyl}oxy)-2-fluorophenyl]methyl}-1H-imidazole-5-carboxamide To a solution of 4-chloro-N-{[4-chloro-3-({3-chloro-5-[(E)-2-cyanoethenyl]phenyl}oxy)-2-fluorophenyl]methyl}-1-({[2-(trimethylsilyl)ethyl]oxy}methyl)-1H-imidazole-5-carboxamide (106 mg, 0.178 mmol) in DCM (5 ml) was added TFA (2.0 mL) and the reaction mixture was stirred at room temperature for 6 hours. The solvent was removed and the crude material was purified via reverse phase HPLC to give 4-chloro-N-{[4-chloro-3-({3-chloro-5-[(E)-2-cyanoethenyl]phenyl}oxy)-2-fluorophenyl]methyl}-1H-imidazole-5-carboxamide (72 mg, 0.155 mmol, 87% yield). 1H NMR (400 MHz, DMSO-d$_6$) δ ppm 12.81-13.40 (m, 1H), 8.08-8.51 (m, 1H), 7.72 (s, 1H), 7.51-7.62 (m, 2H), 7.45 (d, 1H), 7.31 (t, 1H), 7.23 (s, 1H), 7.00 (s, 1H), 6.58 (d, 1H), 4.48 (d, 2H). LC-MS (ES$^+$) m/z 464.94, [M+H].

Example 292

4-chloro-N-[(4-chloro-3-{[3-chloro-5-(2-cyanoethyl) phenyl]oxy}-2-fluorophenyl)methyl]-1H-imidazole-5-carboxamide

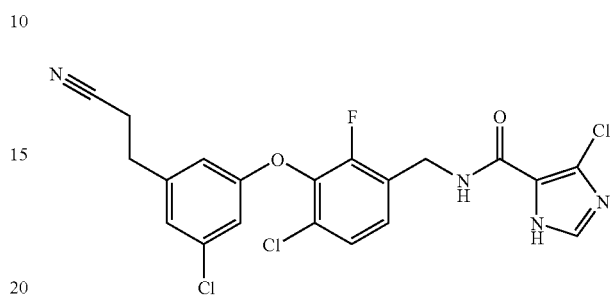

A solution of 4-chloro-N-{[4-chloro-3-({3-chloro-5-[(E)-2-cyanoethenyl]phenyl}oxy)-2-fluorophenyl]methyl}-1H-imidazole-5-carboxamide (32 mg, 0.069 mmol), diphenylsulfide (1.145 μl, 6.87 μmol) and Pd/C (7.31 mg, 6.87 μmol) in methanol (5 ml) and ethyl acetate (5 ml) was stirred under hydrogen gas (45 psi pressure) overnight. The palladium was filtered off, the solvent was removed and the crude material was purified via silica gel chromatography to give 4-chloro-N-[(4-chloro-3-{[3-chloro-5-(2-cyanoethyl)phenyl]oxy}-2-fluorophenyl)methyl]-1H-imidazole-5-carboxamide (22 mg, 0.047 mmol, 69% yield). 1H NMR (400 MHz, METHANOL-d$_4$) δ ppm 7.69 (s, 1H), 7.15-7.40 (m, 2H), 7.04 (s, 1H), 6.77 (s, 1H), 6.73 (s, 1H), 4.61 (s, 2H), 2.87 (t, 2H), 2.69 (t, 2H). LC-MS (ES$^+$) m/z 467.02, [M+H].

Example 293

4-chloro-N-({4-chloro-3-[(3-chloro-5-ethynylphenyl)oxy]-2-fluorophenyl}methyl)-1H-imidazole-5-carboxamide

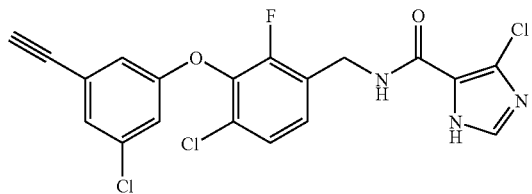

Step A: 4-chloro-N-{[4-chloro-3-({3-chloro-5-[(trimethylsilyl)ethynyl]phenyl}oxy)-2-fluorophenyl]methyl}-1-({[2-(trimethylsilyl)ethyl]oxy}methyl)-1H-imidazole-5-carboxamide To a solution of N-({3-[(3-bromo-5-chlorophenyl)oxy]-4-chloro-2-fluorophenyl}methyl)-4-chloro-1-({[2-(trimethylsilyl)ethyl]oxy}methyl)-1H-imidazole-5-carboxamide (145 mg, 0.232 mmol), copper iodide (2.213 mg, 0.012 mmol) and TEA (162 μL, 1.162 mmol) in THF (8 ml) was added trimethylsilylacetylene (43 μL, 0.302 mmol) and the reaction mixture was degassed for 5 minutes with nitrogen. The resulting mixture was heated with stirring at 60° C. for 4 hours under nitrogen. The solvent was removed and the crude material was purified via silica gel chromatography to give 4-chloro-N-{[4-chloro-3-({3-chloro-5-[(trimethylsilyl)ethynyl]phenyl}oxy)-2-fluorophenyl]methyl}-1-({[2-(trimethylsilyl)ethyl]oxy}methyl)-1H-imidazole-5-carboxamide (121 mg, 0.189 mmol, 81% yield). 1H NMR (400 MHz, DMSO-d$_6$) δ ppm 8.74 (t, 1H), 7.95 (s, 1H), 7.41-7.48 (m, 1H), 7.36 (t, 1H), 7.25 (s, 1H), 7.09 (t, 1H), 6.79 (s, 1H), 5.46 (s, 2H), 4.46 (d, 2H), 3.35 (t, 2H), 0.72 (t, 2H), 0.08-0.31 (m, 9H), −0.12 (s, 9H).

Step B: 4-chloro-N-({4-chloro-3-[(3-chloro-5-ethynylphenyl)oxy]-2-fluorophenyl}methyl)-1-({[2-(trimethylsilyl)ethyl]oxy}methyl)-1H-imidazole-5-carboxamide To a solution of 4-chloro-N-{[4-chloro-3-({3-chloro-5-[(trimethylsilyl)ethynyl]phenyl}oxy)-2-fluorophenyl]methyl}-1-({[2-(trimethylsilyl)ethyl]oxy}methyl)-1H-imidazole-5-carboxamide (120 mg, 0.187 mmol) in THF (5 ml) was added TBAF (1.0 M solution in THF) (0.281 ml, 0.281 mmol) and the reaction mixture was stirred for 2 hours. The reaction mixture was diluted with EtOAc and washed with water. The solvent was removed and the crude material was purified via silica gel chromatography to give 4-chloro-N-({4-chloro-3-[(3-chloro-5-ethynylphenyl)oxy]-2-fluorophenyl}methyl)-1-({[2-(trimethylsilyl)ethyl]oxy}methyl)-1H-imidazole-5-carboxamide (103 mg, 0.181 mmol, 97% yield). LC-MS (ES$^-$) m/z 566 [M−H].

Step C: 4-chloro-N-({4-chloro-3-[(3-chloro-5-ethynylphenyl)oxy]-2-fluorophenyl}methyl)-1H-imidazole-5-carboxamide To a solution of 4-chloro-N-({4-chloro-3-[(3-chloro-5-ethynylphenyl)oxy]-2-fluorophenyl}methyl)-1-({[2-(trimethylsilyl)ethyl]oxy}methyl)-1H-imidazole-5-carboxamide (98.0 mg, 0.172 mmol) in DCM (5 ml) was added TFA (2.0 ml) and the reaction mixture was stirred at rt for 3 hours. The reaction was quenched with saturated sodium bicarbonate, diluted with EtOAc, and the organic layer was separated. The solvent was removed and the crude material was purified via silica gel chromatography to give 4-chloro-N-({4-chloro-3-[(3-chloro-5-ethynylphenyl)oxy]-2-fluorophenyl}methyl)-1H-imidazole-5-carboxamide (50.0 mg, 0.114 mmol, 66% yield) 1H NMR (400 MHz, DMSO-d$_6$) δ ppm 8.09-8.30 (m, 1H), 7.73 (s, 1H), 7.45 (d, 1H), 7.22-7.36 (m, 2H), 7.08 (s, 1H), 6.88 (s, 1H), 4.49 (d, 2H), 4.37 (s, 1H). LC-MS (ES$^+$) m/z 438.01, [M+H].

Example 294

4-chloro-N-[(4-chloro-3-{[3-cyano-5-(trifluoromethyl)phenyl]oxy}-2-fluorophenyl)methyl]-1H-imidazole-5-carboxamide

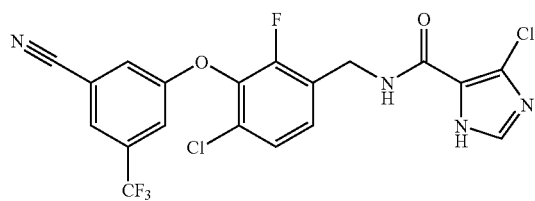

Step A: 4-chloro-N-[(4-chloro-3-{[3-cyano-5-(trifluoromethyl)phenyl]oxy}-2-fluorophenyl)methyl]-1-({[2-(trimethylsilyl)ethyl]oxy}methyl)-1H-imidazole-5-carboxamide To a solution of 3-{[3-(aminomethyl)-6-chloro-2-fluorophenyl]oxy}-5-(trifluoromethyl)benzonitrile (85.0 mg, 0.247 mmol), 4-chloro-1-({[2-(trimethylsilyl)ethyl]oxy}methyl)-1H-imidazole-5-carboxylic acid (68.3 mg, 0.247 mmol) and HATU (94 mg, 0.247 mmol) in DMF (5 ml) was added diisopropylethyl amine (0.086 ml, 0.493 mmol) and the reaction mixture was stirred for 30 minutes at rt. The reaction mixture was diluted with EtOAc and washed with water. The solvent was removed and the crude material was purified via silica gel chromatography to give 4-chloro-N-[(4-chloro-3-{[3-cyano-5-(trifluoromethyl)phenyl]oxy}-2-fluorophenyl)methyl]-1-({[2-(trimethylsilyl)ethyl]oxy}methyl)-1H-imidazole-5-carboxamide (97 mg, 0.161 mmol, 65% yield). 1H NMR (400 MHz, DMSO-d$_6$) δ ppm 8.74 (t, 1H), 8.09 (s, 1H), 7.95 (s, 1H), 7.74 (s, 1H), 7.70 (s, 1H), 7.43-7.53 (m, 1H), 7.39 (t, 1H), 5.47 (s, 2H), 4.46 (d, 2H), 3.35 (t, 2H), 0.59-0.81 (m, 2H), −0.12 (s, 9H).

Step B: 4-chloro-N-[(4-chloro-3-{[3-cyano-5-(trifluoromethyl)phenyl]oxy}-2-fluorophenyl)methyl]-1H-imidazole-5-carboxamide To a solution of 4-chloro-N-[(4-chloro-3-{[3-cyano-5-(trifluoromethyl)phenyl]oxy}-2-fluorophenyl)methyl]-1-({[2-(trimethylsilyl)ethyl]oxy}methyl)-1H-imidazole-5-carboxamide (97 mg, 0.161 mmol) in DCM (7 ml) was added TFA (3 ml) and the reaction mixture was stirred at rt for 2 hours. The reaction mixture was quenched with saturated sodium bicarbonate and the organic layer was separated. The solvent was removed and the crude material was purified via silica gel chromatography to give 4-chloro-N-[(4-chloro-3-{[3-cyano-5-(trifluoromethyl)phenyl]oxy}-2-fluorophenyl)methyl]-1H-imidazole-5-carboxamide (45 mg, 0.095 mmol, 59% yield). 1H NMR (400 MHz, METHANOL-d$_4$) δ ppm 7.82 (s, 1H), 7.69 (s, 1H), 7.47-7.53 (m, 2H), 7.35-7.42 (m, 2H), 4.63 (s, 2H). LC-MS (ES$^+$) m/z 473.07, [M+H].

Example 295

N-({3-[(3-butyl-5-chlorophenyl)oxy]-4-chloro-2-fluorophenyl}methyl)-4-chloro-1H-imidazole-5-carboxamide

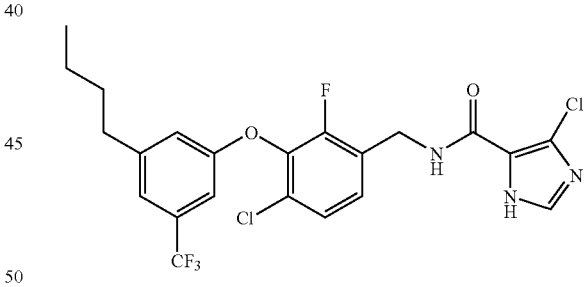

Step A: ({3-[(3-butyl-5-chlorophenyl)oxy]-4-chloro-2-fluorophenyl}methyl)amine

To a solution of ({3-[(3-bromo-5-chlorophenyl)oxy]-4-chloro-2-fluorophenyl}methyl)amine (300 mg, 0.822 mmol) and tetrakis(triphenylphosphine)palladium(0) (950 mg, 0.822 mmol) in THF (4 ml) was added n-butyl zinc bromide (0.5 M solution in THF) (1.644 ml, 0.822 mmol) and the reaction mixture was heated at 60° C. for one hour. The reaction mixture was diluted with EtOAc and washed with water. The solvent was removed and the crude material was purified via silica gel chromatography to give ({3-[(3-butyl-5-chlorophenyl)oxy]-4-chloro-2-fluorophenyl}methyl)amine (210 mg, 0.614 mmol, 75% yield). 1H NMR (400 MHz, DMSO-d$_6$) δ ppm 7.43 (s, 2H), 6.97 (s, 1H), 6.68 (s, 1H), 6.64 (s, 1H), 3.71 (s, 2H), 2.50 (t, 2H), 1.88 (br. s., 2H), 1.45 (quin, 2H), 1.14-1.29 (m, 2H), 0.82 (t, 3H).

Step B: N-({3-[(3-butyl-5-chlorophenyl)oxy]-4-chloro-2-fluorophenyl}methyl)-4-chloro-1-({[2-(trimethylsilyl)ethyl]oxy}methyl)-1H-imidazole-5-carboxamide To a solution of ({3-[(3-butyl-5-chlorophenyl)oxy]-4-chloro-2-fluorophenyl}methyl)amine (105 mg, 0.307 mmol), 4-chloro-1-({[2-(trimethylsilyl)ethyl]oxy}methyl)-1H-imidazole-5-carboxylic acid (85 mg, 0.307 mmol) and HATU (117 mg, 0.307 mmol) in DMF (3 ml) was added diisopropylethyl amine (0.107 ml, 0.614 mmol) and the reaction mixture was stirred at rt for 45 minutes. The reaction mixture was diluted with EtOAc and washed with water. The solvent was removed and the crude material was purified via silica gel chromatography to give N-({3-[(3-butyl-5-chlorophenyl)oxy]-4-chloro-2-fluorophenyl}methyl)-4-chloro-1-({[2-(trimethylsilyl)ethyl]oxy}methyl)-1H-imidazole-5-carboxamide (151 mg, 0.251 mmol, 82% yield). 1H NMR (400 MHz, DMSO-$d_6$) δ ppm 8.73 (t, 1H), 7.95 (s, 1H), 7.39-7.46 (m, 1H), 7.34 (t, 1H), 6.99 (s, 1H), 6.70 (s, 1H), 6.66 (s, 1H), 5.47 (s, 2H), 4.45 (d, 2H), 3.36 (t, 2H), 2.50 (t, 2H), 1.46 (t, 2H), 1.16-1.28 (m, 2H), 0.82 (t, 3 H), 0.73 (t, 2H), −0.12 (s, 9H).

Step C: N-({3-[(3-butyl-5-chlorophenyl)oxy]-4-chloro-2-fluorophenyl}methyl)-4-chloro-1H-imidazole-5-carboxamide To a solution of N-({3-[(3-butyl-5-chlorophenyl)oxy]-4-chloro-2-fluorophenyl}methyl)-4-chloro-1-({[2-(trimethylsilyl)ethyl]oxy}methyl)-1H-imidazole-5-carboxamide (148 mg, 0.246 mmol) in DCM (5 ml) was added TFA (3.0 ml) and the reaction mixture was stirred at rt for 2 hours. The reaction mixture was neutralized with saturated sodium bicarbonate, diluted with EtOAc, and the organic layer was separated. The solvent was evaporated and the crude material was purified via silica gel chromatography to give N-({3-[(3-butyl-5-chlorophenyl)oxy]-4-chloro-2-fluorophenyl}methyl)-4-chloro-1H-imidazole-5-carboxamide (94 mg, 0.200 mmol, 81% yield). 1H NMR (400 MHz, METHANOL-$d_4$) δ ppm 7.69 (s, 1H), 7.24-7.37 (m, 2H), 6.90 (s, 1H), 6.56-6.66 (m, 2H), 4.62 (s, 2H), 2.53 (t, 2H), 1.51 (qd, 2H), 1.20-1.35 (m, 2H), 0.88 (t, 3H). LC-MS (ES$^+$) m/z 469.93, [M+H].

Example 296

4-chloro-N-[(4-chloro-3-{[3-chloro-5-(cyclopropylethynyl)phenyl]oxy}-2-fluorophenyl)methyl]-1H-imidazole-5-carboxamide

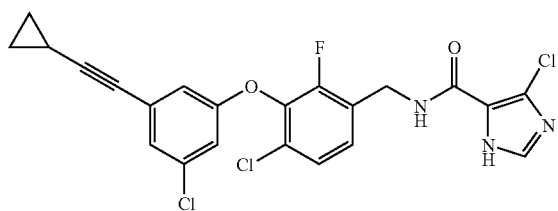

To a solution of N-({3-[(3-bromo-5-chlorophenyl)oxy]-4-chloro-2-fluorophenyl}methyl)-4-chloro-1H-imidazole-5-carboxamide (125 mg, 0.253 mmol), tetrakistriphenylphosphine palladium(0) (35.6 mg, 0.051 mmol), copper(I) iodide (4.82 mg, 0.025 mmol) and TEA (0.177 ml, 1.266 mmol) in THF (5 ml) was added cyclopropylacetylene (0.043 ml, 0.507 mmol) and the reaction mixture was stirred for 5 hours at 60° C. The reaction mixture was adsorbed onto silica gel and the crude material was purified via silica gel chromatography to give 4-chloro-N-[(4-chloro-3-{[3-chloro-5-(cyclopropylethynyl)phenyl]oxy}-2-fluorophenyl)methyl]-1H-imidazole-5-carboxamide (95 mg, 0.198 mmol, 78% yield). 1H NMR (400 MHz, METHANOL-$d_4$) δ ppm 7.70 (s, 1H), 7.21-7.39 (m, 2H), 7.02 (s, 1H), 6.81 (s, 1H), 6.64 (s, 1H), 4.62 (br. s., 2H), 1.35-1.50 (m, 1H), 0.78-0.90 (m, 2H), 0.57-0.77 (m, 2H). LC-MS (ES$^+$) m/z 477.87, [M+H].

Example 297

4-chloro-N-({4-chloro-3-[(3-chloro-5-cyclopropylphenyl)oxy]-2-fluorophenyl}methyl)-1H-imidazole-5-carboxamide

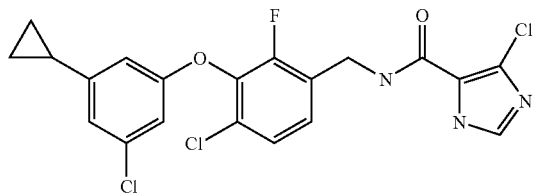

Step A: ({4-chloro-3-[(3-chloro-5-cyclopropylphenyl)oxy]-2-fluorophenyl}methyl)amine To a solution of ({3-[(3-bromo-5-chlorophenyl)oxy]-4-chloro-2-fluorophenyl}methyl)amine (0.460 g, 1.260 mmol) and tetrakis(triphenylphosphine)palladium(0) (0.029 g, 0.025 mmol) in THF (10 ml) was added cyclopropylzinc bromide (0.5 M solution in THF) (6.30 ml, 3.15 mmol) and the reaction mixture was stirred at 60° C. for 1 hour. The reaction mixture was diluted with EtOAc and washed with water. The solvent was removed and the crude material was purified via silica gel chromatography to give ({4-chloro-3-[(3-chloro-5-cyclopropylphenyl)oxy]-2-fluorophenyl}methyl)amine (0.281 g, 0.861 mmol, 68% yield). 1H NMR (400 MHz, METHANOL-$d_4$) d ppm 7.20-7.44 (m, 3H), 6.76 (s, 1H), 6.54 (s, 1H), 3.86 (s, 2H), 1.74-2.05 (m, 1H), 0.83-1.08 (m, 2H), 0.40-0.76 (m, 2H).

Step B: 4-chloro-N-({4-chloro-3-[(3-chloro-5-cyclopropylphenyl)oxy]-2-fluorophenyl}methyl)-1-({[2-(trimethylsilyl)ethyl]oxy}methyl)-1H-imidazole-5-carboxamide To a solution of ({4-chloro-3-[(3-chloro-5-cyclopropylphenyl)oxy]-2-fluorophenyl}methyl)amine (86 mg, 0.264 mmol), 4-chloro-1-({[2(trimethylsilyl)ethyl]oxy}methyl)-1H-imidazole-5-carboxylic acid (73.0 mg, 0.264 mmol) and HATU (100 mg, 0.264 mmol) in DMF (5 ml) was added diisopropylethyl amine (0.092 ml, 0.527 mmol) and the reaction mixture was stirred at rt for 45 minutes. The reaction mixture was diluted with EtOAc and washed with water. The solvent was removed and the crude material was purified via silica gel chromatography to give the desired compound which was only ~85% pure. This was purified via reverse phase HPLC to give 4-chloro-N-({4-chloro-3-[(3-chloro-5-cyclopropylphenyl)oxy]-2-fluorophenyl}methyl)-1-({[2-(trimethylsilyl)ethyl]oxy}methyl)-1H-imidazole-5-carboxamide (98 mg, 0.168 mmol, 64% yield).

Step C: 4-chloro-N-({4-chloro-3-[(3-chloro-5-cyclopropylphenyl)oxy]-2-fluorophenyl}methyl)-1H-imidazole-5-carboxamide To a solution of 4-chloro-N-({4-chloro-3-[(3-chloro-5-cyclopropylphenyl)oxy]-2-fluorophenyl}methyl)-1-({[2-(trimethylsilyl)ethyl]oxy}methyl)-1H-imidazole-5-carboxamide (94 mg, 0.161 mmol) in DCM (6 ml) was added TFA (3.0 ml) and the reaction mixture was stirred at rt for 1 hour. The solvent was removed and the crude material was purified via reverse phase HPLC to give 4-chloro-N-({4-chloro-3-[(3- chloro-5-cyclopropylphenyl)oxy]-2-fluorophenyl}methyl)-1H-imidazole-5-carboxamide (45 mg, 0.099 mmol, 62% yield). 1H NMR (400 MHz, METHANOL-d₄) δ ppm 7.70 (s, 1H), 7.25-7.39 (m, 2H), 6.76 (s, 1H), 6.56 (s, 1H), 6.53 (s, 1H), 4.63 (s, 2H), 1.67-2.00 (m, 1H), 0.96 (dd, 2H), 0.63 (dd, 2H). LC-MS (ES⁺) m/z 454.02, [M+H].

Example 298

4-chloro-N-[(4-chloro-3-{[3-chloro-5-(3-hydroxy-1-propyn-1-yl)phenyl]oxy}-2-fluorophenyl)methyl]-1H-imidazole-5-carboxamide

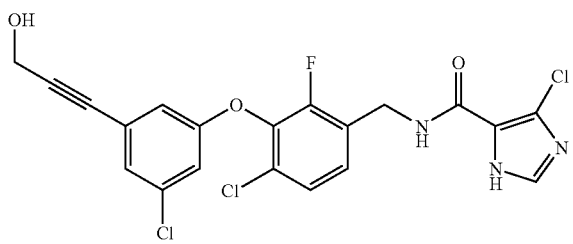

To a solution of N-({3-[(3-bromo-5-chlorophenyl)oxy]-4-chloro-2-fluorophenyl}methyl)-4-chloro-1H-imidazole-5-carboxamide (100 mg, 0.203 mmol), dichlorobisthiphenylphosphinepalladium(II) (14.22 mg, 0.020 mmol), copper (I) iodide (1.929 mg, 10.13 μmol) and TEA (0.141 ml, 1.013 mmol) in THF (5 ml) was added propargyl alcohol (22.72 mg, 0.405 mmol) and the reaction mixture was stirred at 60° C. overnight. The reaction mixture was diluted with EtOAc and washed with water. The solvent was removed and the crude material was purified via silica gel chromatography to give 4-chloro-N-[(4-chloro-3-{[3-chloro-5-(3-hydroxy-1-propyn-1-yl)phenyl]oxy}-2-fluorophenyl)methyl]-1H-imidazole-5-carboxamide (18 mg, 0.038 mmol, 19% yield).

1H NMR (400 MHz, DMSO-d₆) δ ppm 8.14-8.35 (m, 1H), 7.75 (s, 1H), 7.48 (d, 1H), 7.33 (t, 1H), 7.23 (s, 1H), 7.12 (s, 1H), 6.77 (s, 1H), 5.34 (t, 1H), 4.36-4.59 (m, 2H), 4.24 (d, 2H). LC-MS (ES⁺) m/z 467.98, [M+H].

Example 299

N-({3-[(3-bromo-5-cyanophenyl)oxy]-4-chloro-2-fluorophenyl}methyl)-4-chloro-2-methyl-1H-imidazole-5-carboxamide

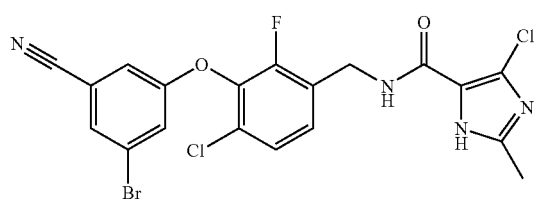

To a solution of 3-{[3-(aminomethyl)-6-chloro-2-fluorophenyl]oxy}-5-bromobenzonitrile (900 mg, 2.53 mmol) and 4-chloro-2-methyl-1H-imidazole-5-carboxylic acid (813 mg, 2.53 mmol) in DMF (10 ml) was added HOBT (388 mg, 2.53 mmol) and EDC (485 mg, 2.53 mmol) and the reaction mixture was stirred for 6 hours at rt. The reaction mixture was diluted with EtOAc and washed with water. The solvent was removed and the crude material was purified via silica gel chromatography to give N-({3-[(3-bromo-5-cyanophenyl) oxy]-4-chloro-2-fluorophenyl}methyl)-4-chloro-2-methyl-1H-imidazole-5-carboxamide (0.560 g, 1.124 mmol, 44% yield). 1H NMR (400 MHz, METHANOL-d₄) δ ppm 7.68 (s, 1H), 7.29-7.45 (m, 3H), 7.25 (s, 1H), 4.63 (s, 2H), 2.34 (s, 3H). LC-MS (ES⁺) m/z 496.87, [M+H].

Example 300

4-chloro-N-[(4-chloro-3-{[3-cyano-5-(difluoromethyl)phenyl]oxy}-2-fluorophenyl)methyl]-2-methyl-1H-imidazole-5-carboxamide trifluoroacetate

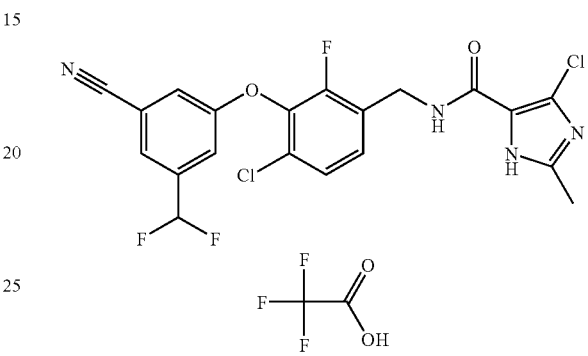

Step A: 4-chloro-N-({4-chloro-3-[(3-cyano-5-ethenylphenyl)oxy]-2-fluorophenyl}methyl)-2-methyl-1H-imidazole-5-carboxamide To a solution of N-({3-[(3-bromo-5-cyanophenyl)oxy]-4-chloro-2-fluorophenyl}methyl)-4-chloro-2-methyl-1H-imidazole-5-carboxamide (0.480 g, 0.964 mmol), potassium vinyltrifluoroborate (0.194 g, 1.445 mmol) and 1,1'-bis(diphenylphosphino)ferrocenedichloropalladium(II) dichloromethane complex (0.079 g, 0.096 mmol) in n-propanol (8 ml) was added TEA (0.672 ml, 4.82 mmol) and the reaction mixture was heated at 100° C. for 4 hours. The reaction mixture was diluted with EtOAc and washed with water. The solvent was removed and the crude material was purified via silica gel chromatography to give 4-chloro-N-({4-chloro-3-[(3-cyano-5-ethenylphenyl)oxy]-2-fluorophenyl}methyl)-2-methyl-1H-imidazol e-5-carboxamide (0.263 g, 0.591 mmol, 61% yield). 1H NMR (400 MHz, DMSO-d₆) δ ppm 8.05 (t, 1H), 7.77 (s, 1H), 7.47 (d, 1H), 7.40 (br. s., 1H), 7.32 (t, 1H), 7.26 (br. s., 1H), 6.72 (dd, 1H), 6.01 (d, 1H), 5.41 (d, 1H), 4.51 (d, 2H), 2.23 (s, 3H).

Step B: 4-chloro-N-({4-chloro-3-[(3-cyano-5-formylphenyl)oxy]-2-fluorophenyl}methyl)-2-methyl-1H-imidazole-5-carboxamide To a solution of 4-chloro-N-({4-chloro-3-[(3-cyano-5-ethenylphenyl)oxy]-2-fluorophenyl}methyl)-2-methyl-1H-imidazole-5-carboxamide (0.260 g, 0.584 mmol) and sodium periodate (0.375 g, 1.752 mmol) in THF (4 ml) and water (2 ml) was added osmium tetroxide (2.5 weight % in t-butanol) (0.147 ml, 0.012 mmol) and the reaction mixture was stirred at rt for 3 hours. The reaction mixture was diluted with EtOAc and washed with water. The solvent was removed and the crude material was purified via silica gel chromatography to give 4-chloro-N-({4-chloro-3-[(3-cyano-5-formylphenyl)oxy]-2-fluorophenyl}methyl)-2-methyl-1H-imidazole-5-carboxamide (0.245 g, 0.548 mmol, 94% yield). 1H NMR (400 MHz, DMSO-d₆) δ ppm 9.95 (s, 1H), 8.12 (s, 1H), 8.07 (s, 1H), 7.92 (s, 1H), 7.45-7.56 (m, 1H), 7.27-7.44 (m, 1H), 6.91 (d, 1H), 4.52 (d, 2H), 2.23 (s, 3H).

Step C: 4-chloro-N-[(4-chloro-3-{[3-cyano-5-(difluoromethyl)phenyl]oxy}-2-fluorophenyl)methyl]-2-methyl-1H-imidazole-5-carboxamide trifluoroacetate To a solution of 4-chloro-N-({4-chloro-3-[(3-cyano-5-formylphenyl)oxy]-2-fluorophenyl}methyl)-2-methyl-1H-imidazole-5-carboxamide (0.050 g, 0.112 mmol) in DCM (5 ml) was added diethyl ammonium sulfurtrifluoride (0.030 ml, 0.224 mmol) and the reaction mixture was stirred at rt for one hour. The reaction mixture was diluted with EtOAc and washed with water. The solvent was removed and the crude material was purified via reverse phase HPLC to give 4-chloro-N-[(4-chloro-3-{[3-cyano-5-(difluoromethyl)phenyl]oxy}-2-fluorophenyl)methyl]-2-methyl-1H-imidazole-5-carboxamide trifluoroacetate (0.016 g, 0.027 mmol, 25% yield) 1H NMR (400 MHz, METHANOL-$d_4$) δ ppm 7.65 (s, 1H), 7.27-7.46 (mh, 4H), 6.81 (t, 1H), 4.63 (s, 2 H), 2.34 (s, 3H). LC-MS (ES+) m/z 469.02, [M+H].

Example 301

4-chloro-N-[(4-chloro-3-{[3-cyano-5-(hydroxymethyl)phenyl]oxy}-2-fluorophenyl)methyl]-2-methyl-1H-imidazole-5-carboxamide

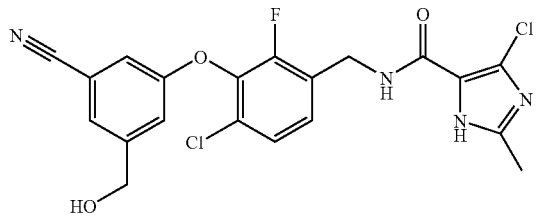

To a solution of 4-chloro-N-({4-chloro-3-[(3-cyano-5-formylphenyl)oxy]-2-fluorophenyl}methyl)-2-methyl-1H-imidazole-5-carboxamide (0.178 g, 0.398 mmol) in methanol (5 ml) at 0° C. was added sodium borohydride (0.015 g, 0.398 mmol) and the reaction mixture was allowed to warm to rt over 30 minutes. The reaction mixture was neutralized with saturated sodium bicarbonate, diluted with EtOAc, and the organic layer was separated. The solvent was evaporated and the crude material was purifed via silica gel chromatography to give 4-chloro-N-[(4-chloro-3-{[3-cyano-5-(hydroxymethyl)phenyl]oxy}-2-fluorophenyl)methyl]-2-methyl-1H-imidazole-5-carboxamide (0.135 g, 0.300 mmol, 76% yield). 1H NMR (400 MHz, METHANOL-$d_4$) δ ppm 7.39 (s, 1H), 7.27-7.38 (m, 2H), 7.18 (s, 1H), 7.08 (s, 1H), 4.60 (s, 2 H), 4.58 (s, 2H), 2.32 (s, 3H). LC-MS (ES+) m/z 448.94, [M+H].

Example 302

4-chloro-N-[(4-chloro-3-{[3-cyano-5-(fluoromethyl)phenyl]oxy}-2-fluorophenyl)methyl]-2-methyl-1H-imidazole-5-carboxamide trifluoroacetate

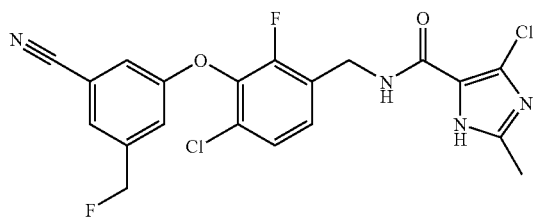

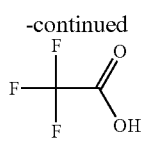

To a solution of 4-chloro-N-[(4-chloro-3-{[3-cyano-5-(hydroxymethyl)phenyl]oxy}-2-fluorophenyl)methyl]-2-methyl-1H-imidazole-5-carboxamide (0.050 g, 0.111 mmol) in DCM (5 ml) was added diethylammonium sulfurtrifluoride (0.029 ml, 0.223 mmol) and the reaction mixture was stirred at rt for 40 minutes. The reaction mixture was neutralized with saturated sodium bicarbonate, diluted with EtOAc, and the organics layer was separated. The solvent was evaporated and the crude material was purifed via reverse phase HPLC to give 4-chloro-N-[(4-chloro-3-{[3-cyano-5-(fluoromethyl)phenyl]oxy}-2-fluorophenyl)methyl]-2-methyl-1H-imidazole-5-carboxamide trifluoroacetate (0.013 g, 0.023 mmol, 21% yield). 1H NMR (400 MHz, METHANOL-$d_4$) δ ppm 7.47 (s, 1H), 7.28-7.42 (m, 2H), 7.11-7.26 (m, 2H), 5.45 (s, 1H), 5.33 (s, 1H), 4.62 (s, 2H), 2.34 (s, 3H). LC-MS (ES+) m/z 451.05, [M+H].

Example 303

N-({5-bromo-4-chloro-3-[(3-chloro-5-cyanophenyl)oxy]-2-fluorophenyl}methyl)-4-chloro-2-methyl-1H-imidazole-5-carboxamide trifluoroacetate

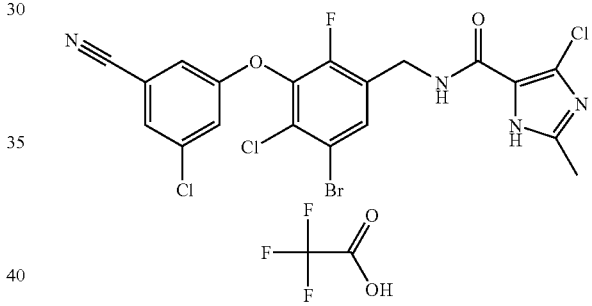

Step A: 3-[(2-amino-3-bromo-6-fluoro-5-methylphenyl)oxy]-5-chlorobenzonitrile

To a solution of 3-[(6-amino-2-fluoro-3-methylphenyl)oxy]-5-chlorobenzonitrile (7.422 g, 26.8 mmol) and ammonium acetate (0.207 g, 2.68 mmol) in acetonitrile (150 ml) was added NBS (5.01 g, 28.2 mmol) and the reaction mixture was stirred for two hours at rt. The solvent was removed and the crude material was purified via silica gel chromatography to give 3-[(2-amino-3-bromo-6-fluoro-5-methylphenyl)oxy]-5-chlorobenzonitrile (8.379 g, 23.56 mmol, 88% yield). 1H NMR (400 MHz, DMSO-$d_6$) δ ppm 7.71 (s, 1H), 7.33 (s, 1H), 7.23-7.30 (m, 2H), 5.31 (s, 2H), 2.08 (s, 3 H).

Step B: 3-[(3-bromo-2-chloro-6-fluoro-5-methylphenyl)oxy]-5-chlorobenzonitrile

To a solution of copper(II)chloride (3.02 g, 22.50 mmol) and tert-butyl nitrite (3.34 ml, 28.1 mmol) in 40 mL acetonitrile at 55° C. was added a solution of 3-[(2-amino-3-bromo-6-fluoro-5-methylphenyl)oxy]-5-chlorobenzonitrile (4.00 g, 11.25 mmol) in 60 mL acetonitrile and the reaction mixture was stirred at 55° C. for 30 minutes. The reaction was quenched with 5% HCl, diluted with EtOAc and the organics were separated. The solvent was removed and the crude material was purified via silica gel chromatography to give 3-[(3-bromo-2-chloro-6-fluoro-5-methylphenyl)oxy]-5-chlorobenzonitrile (2.75 g, 7.33 mmol, 65% yield). 1H NMR (400 MHz, DMSO-$d_6$) δ ppm 7.73-7.86 (m, 2H), 7.56 (s, 2H), 2.26 (s, 3H)

Step C: 3-{[3-bromo-5-(bromomethyl)-2-chloro-6-fluorophenyl]oxy}-5-chlorobenzonitrile To a solution of 3-[(3-bromo-2-chloro-6-fluoro-5-methylphenyl)oxy]-5-chlorobenzonitrile (2.74 g, 7.31 mmol) and NBS (1.300 g, 7.31 mmol) in carbon tertrachloride (200 ml) was added AIBN (0.060 g, 0.365 mmol) and the reaction mixture was stirred at 80° C. overnight. The solvent was removed and the crude material was purified via silica gel chromatography to give the title compound 3-{[3-bromo-5-(bromomethyl)-2-chloro-6-fluorophenyl]oxy}-5-chlorobenzonitrile (1.04 g, 1.604 mmol, 22% yield). 1H NMR (400 MHz, DMSO-$d_6$) δ ppm 8.01 (d, 1H), 7.79 (s, 1H), 7.58 (s, 2H), 4.68 (s, 2H)

Step D: 3-{[3-(aminomethyl)-5-bromo-6-chloro-2-fluorophenyl]oxy}-5-chlorobenzonitrile To an ammonia (7.0 M solution in MeOH) (60.0 ml, 2771 mmol) solution was added 3-{[3-bromo-5-(bromomethyl)-2-chloro-6-fluorophenyl]oxy}-5-chlorobenzonitrile in DCM (40 ml) dropwise at 0° C. and the reaction mixture was allowed to warm to rt overnight. The solvent was removed, the residue dissolved in EtOAc and the mixture was neutralized with saturated sodium bicarbonate. The solvent was removed and the crude material was purified via silica gel chromatography to give the title compound 3-{[3-(aminomethyl)-5-bromo-6-chloro-2-fluorophenyl]oxy}-5-chlorobenzonitrile (801 mg, 2.054 mmol, 95% yield). 1H NMR (400 MHz, DMSO-$d_6$) δ ppm 7.88 (d, 1H), 7.77 (s, 1H), 7.25-7.60 (m, 2H), 3.72 (s, 2H), 1.98 (br. s., 2H)

Step E: N-({5-bromo-4-chloro-3-[(3-chloro-5-cyanophenyl)oxy]-2-fluorophenyl}methyl)-4-chloro-2-methyl-1H-imidazole-5-carboxamide trifluoroacetate To a solution of 3-{[3-(aminomethyl)-5-bromo-6-chloro-2-fluorophenyl]oxy}-5-chlorobenzonitrile (400 mg, 1.026 mmol), 4-chloro-2-methyl-1H-imidazole-5-carboxylic acid (165 mg, 1.026 mmol), and HOBT (157 mg, 1.026 mmol) in DMF (3 ml) was added EDC (197 mg, 1.026 mmol) and the reaction mixture was stirred at rt for 3 hours. The solvent was removed and the crude material was purified via reverse phase HPLC to give N-({5-bromo-4-chloro-3-[(3-chloro-5-cyanophenyl)oxy]-2-fluorophenyl}methyl)-4-chloro-2-methyl-1H-imidazole-5-carboxamide trifluoroacetate (268 mg, 0.414 mmol, 40% yield). 1H NMR (400 MHz, METHANOL-$d_4$) δ ppm 7.67 (d, 1H), 7.54 (s, 1H), 7.28 (s, 1H), 7.24 (s, 1H), 4.60 (s, 2H), 2.34 (s, 3H). LC-MS (ES$^+$) m/z 530.92, [M+H].

Example 304

4-chloro-N-({4-chloro-3-[(3-chloro-5-cyanophenyl)oxy]-5-cyano-2-fluorophenyl}methyl)-2-methyl-1H-imidazole-5-carboxamide trifluoroacetate

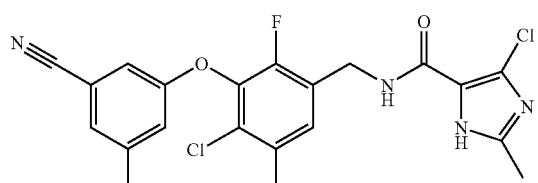

A solution of N-({5-bromo-4-chloro-3-[(3-chloro-5-cyanophenyl)oxy]-2-fluorophenyl}methyl)-4-chloro-2-methyl-1H-imidazole-5-carboxamide (70 mg, 0.131 mmol), zinc cyanide (7.72 mg, 0.066 mmol) and tetrakis(triphenylphosphine)palladium(0) (30.4 mg, 0.026 mmol) in DMF (1.5 ml) was irradiated for 35 minutes at 130° C. in a microwave reactor. The reaction mixture was purified via reverse phase HPLC to give 4-chloro-N-({4-chloro-3-[(3-chloro-5-cyanophenyl)oxy]-5-cyano-2-fluorophenyl}methyl)-2-methyl-1H-imidazole-5-carboxamide trifluoroacetate (5.8 mg, 9.79 μmol, 7% yield) as the TFA salt. 1H NMR (400 MHz, METHANOL-$d_4$) δ ppm 7.79 (d, 1H), 7.58 (s, 1H), 7.37 (s, 1H), 7.32 (s, 1H), 4.62 (s, 2H), 2.33 (s, 3H). LC-MS (ES$^+$) m/z 477.95, [M+H].

Example 305

4-chloro-N-({4-chloro-3-[(3-cyano-5-methylphenyl)oxy]-2-fluorophenyl}methyl)-2-methyl-1H-imidazole-5-carboxamide trifluoroacetate

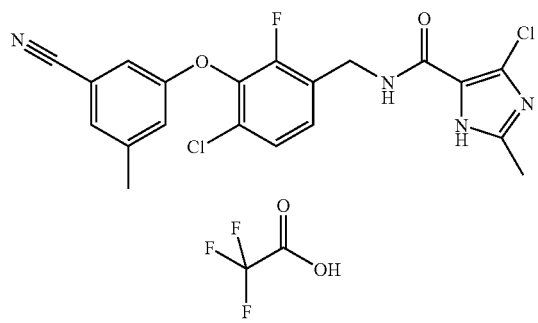

To a solution of N-({3-[(3-bromo-5-cyanophenyl)oxy]-4-chloro-2-fluorophenyl}methyl)-4-chloro-2-methyl-1H-imidazole-5-carboxamide (73.0 mg, 0.147 mmol) and tetrakis(triphenylphosphine)palladium(0) (169 mg, 0.147 mmol) in THF (10.0 ml) was added dimethyl zinc (1.0 M solution in toluene) (0.220 ml, 0.220 mmol) and the reaction mixture was stirred for one hour at 60° C. The mixture was filtered through a pad of celite, diluted with EtOAc and washed with water. The solvent was removed and the crude material was purified via reverse phase HPLC to give 4-chloro-N-({4-chloro-3-[(3-cyano-5-methylphenyl)oxy]-2-fluorophenyl}methyl)-2-methyl-1H-imidazole-5-carboxamide trifluoroacetate (11.5 mg, 0.021 mmol, 14% yield). 1H NMR (400 MHz, METHANOL-$d_4$) δ ppm 7.21-7.42 (m, 3H), 7.03 (s, 1H), 6.97 (s, 1H), 4.62 (s, 2H), 2.35 (s, 6H). LC-MS (ES$^+$) m/z 433.04, [M+H].

Example 306

4-chloro-N-({4-chloro-3-[(2,5-dichloro-3-cyanophenyl)oxy]-2-fluorophenyl}methyl)-2-methyl-1H-imidazole-5-carboxamide trifluoroacetate

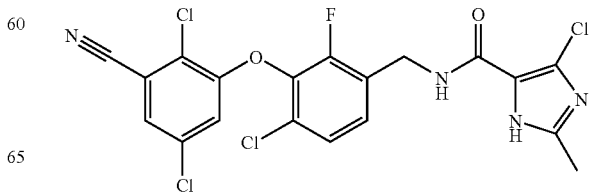

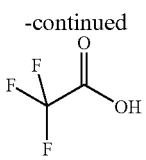

To a solution of 3-{[3-(aminomethyl)-6-chloro-2-fluorophenyl]oxy}-2,5-dichlorobenzonitrile (60 mg, 0.174 mmol), 4-chloro-2-methyl-1H-imidazole-5-carboxylic acid (27.9 mg, 0.174 mmol) and HOBT (26.6 mg, 0.174 mmol) was added EDC (33.3 mg, 0.174 mmol) and the reaction mixture was stirred at rt for 2 hours. The reaction mixture was diluted with EtOAc and washed with water. The solvent was removed and the crude material was purified via reverse phase HPLC to give 4-chloro-N-({4-chloro-3-[(2,5-dichloro-3-cyanophenyl)oxy]-2-fluorophenyl}methyl)-2-methyl-1H-imidazole-5-carboxamide (28 mg, 0.046 mmol, 27% yield) as the TFA salt. 1H NMR (400 MHz, METHANOL-d$_4$) δ ppm 7.66 (d, 1H), 7.29-7.49 (m, 2H), 6.97 (s, 1H), 4.64 (s, 2H), 2.34 (s, 3H). LC-MS (ES$^+$) m/z 486.93, [M+H].

Example 307

2-amino-4-chloro-N-({4-chloro-3-[(3-cyano-5-cyclopropylphenyl)oxy]-2-fluorophenyl}methyl)-1H-imidazole-5-carboxamide trifluoroacetate

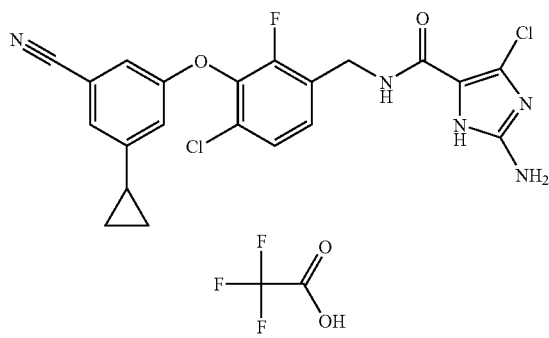

Step A: 1,1-dimethylethyl({3-[(3-bromo-5-cyanophenyl)oxy]-4-chloro-2-fluorophenyl}methyl)carbamate To a solution of 3-{[3-(aminomethyl)-6-chloro-2-fluorophenyl]oxy}-5-bromobenzonitrile (3.00 g, 8.44 mmol) in DCM (60 ml) at 0° C. was added BOC-Anhydride (1.959 ml, 8.44 mmol) and the reaction mixture was stirred overnight at rt. The solvent was removed to give 1,1-dimethylethyl({3-[(3-bromo-5-cyanophenyl)oxy]-4-chloro-2-fluorophenyl}methyl)carbamate (3.84 g, 8.43 mmol, 100% yield). 1H NMR (400 MHz, DMSO-d$_6$) δ ppm 7.88 (s, 1H), 7.35-7.59 (m, 4H), 7.26 (t, 1H), 4.14 (d, 2H), 1.34 (s, 9H).

Step B: 1,1-dimethylethyl({4-chloro-3-[(3-cyano-5-ethenylphenyl)oxy]-2-fluorophenyl}methyl)carbamate To a solution of 1,1-dimethylethyl({3-[(3-bromo-5-cyanophenyl)oxy]-4-chloro-2-fluorophenyl}methyl)carbamate (3.80 g, 8.34 mmol), potassium vinyltrifluoroborate (1.125 g, 8.34 mmol) and 1,1'-bis(diphenylphosphino)ferrocenedichloropalladium(II) dichloromethane complex (0.340 g, 0.417 mmol) in propanol (30 ml) was added TEA (5.81 ml, 41.7 mmol) and the reaction mixture was stirred at 100° C. for 7 hours. The reaction mixture was diluted with EtOAc and washed with water. The solvent was removed and the crude material was purified via silica gel chromatography to give 1,1-dimethylethyl({4-chloro-3-[(3-cyano-5-ethenylphenyl)oxy]-2-fluorophenyl}methyl)carbamate (1.78 g, 4.42 mmol, 53% yield). 1H NMR (400 MHz, DMSO-d$_6$) δ ppm 7.74 (s, 1H), 7.34-7.55 (m, 3H), 7.18-7.35 (m, 2H), 6.70 (dd, 1H), 5.99 (d, 1H), 5.39 (d, 1H), 4.14 (d, 2H), 1.28-1.45 (m, 9H).

Step C: 1,1-dimethylethyl({4-chloro-3-[(3-cyano-5-cyclopropylphenyl)oxy]-2-fluorophenyl}methyl)carbamate N-methyl-N-nitrosourea (4.56 g, 44.2 mmol) was added slowly as a solid to a mixture of DCM (650 ml) and potassium hydroxide (in 450 mL water) (136 g, 2430 mmol) 0° C. The mixture was stirred for 30 minutes at 0° C., then poured into a separatory funnel containing ice. The organic layer was separated and dried over KOH pellets to give a 0.068 M solution of diazomethane. This solution was added dropwise to a solution of 1,1-dimethylethyl({4-chloro-3-[(3-cyano-5-ethenylphenyl)oxy]-2-fluorophenyl}methyl)carbamate (1.78 g, 4.42 mmol) and palladium(II)acetylacetonate (0.134 g, 0.442 mmol) in DCM (30 mL) and the reaction mixture was stirred at 0° C. for one 3 hours. The reaction was quenched with 4 mL acetic acid and the organics were separated. The solvent was removed and the crude material was purified via silica gel chromatography to give 1,1-dimethylethyl({4-chloro-3-[(3-cyano-5-cyclopropylphenyl)oxy]-2-fluorophenyl}methyl)carbamate (886 mg, 2.125 mmol, 48% yield). 1H NMR (400 MHz, DMSO-d$_6$) δ ppm 7.36-7.51 (m, 2H), 7.14-7.31 (m, 2 H), 7.03 (d, 2H), 4.14 (d, 2H), 1.34 (s, 9H), 1.24 (s, 1H), 0.85-1.04 (m, 2H), Step D: 3-{[3-(aminomethyl)-6-chloro-2-fluorophenyl]oxy}-5-cyclopropylbenzonitrile To a solution of 1,1-dimethylethyl({4-chloro-3-[(3-cyano-5-cyclopropylphenyl)oxy]-2-fluorophenyl}methyl)carbamate (880 mg, 2.111 mmol) dissolved in DCM (15 ml) was added TFA (5.0 ml) and the reaction mixture was stirred for 30 minutes at RT. The reaction mixture was neutralized with saturated sodium bicarbonate, diluted with EtOAc, and the organics layer was separated. The solvent was evaporated and the crude material was purifed via silica gel chromatography to give 3-{[3-(aminomethyl)-6-chloro-2-fluorophenyl]oxy}-5-cyclopropylbenzonitrile (594 mg, 1.875 mmol, 89% yield). 1H NMR (400 MHz, DMSO-d$_6$) δ ppm 7.38-7.52 (m, 2H), 7.22 (s, 1H), 7.04 (d, 2H), 3.73 (s, 2H), 1.91-2.01 (m, 1H), 1.89 (br. s., 2H), 0.89-1.04 (m, 2H), 0.64-0.81 (m, 2H).

Step E: bis(1,1-dimethylethyl)(4-chloro-5-{[({4-chloro-3-[(3-cyano-5-cyclopropylphenyl)oxy]-2-fluorophenyl}methyl)amino]carbonyl}-1H-imidazol-2-yl)imidodicarbonate To a solution of 3-{[3-(aminomethyl)-6-chloro-2-fluorophenyl]oxy}-5-cyclopropylbenzonitrile (95 mg, 0.299 mmol), 2-(bis{[(1,1-dimethylethyl)oxy]carbonyl}amino)-4-chloro-1H-imidazole-5-carboxylic acid (120 mg, 0.299 mmol) and HOBT (45.7 mg, 0.299 mmol) in DMF (3 ml) was added EDC (57.2 mg, 0.299 mmol) and the reaction mixture was stirred at RT for 45 minutes. The reaction mixture was diluted with EtOAc and washed with water. The solvent was removed and the crude material bis(1,1-dimethylethyl)(4-chloro-5-{[({4-chloro-3-[(3-cyano-5-cyclopropylphenyl)oxy]-2-fluorophenyl}methyl)amino]carbonyl}-1H-imidazol-2-yl)imidodicarbonate (165 mg, 0.250 mmol, 84% yield) was used directly in the next step. LC-MS (ES$^+$) m/z 660 [M+H].

Step F: 2-amino-4-chloro-N-({4-chloro-3-[(3-cyano-5-cyclopropylphenyl)oxy]-2-fluorophenyl}methyl)-1H-imidazole-5-carboxamide trifluoroacetate To a solution of bis(1,1-dimethylethyl)(4-chloro-5-{[({4-chloro-3-[(3-cyano-5-cyclopropylphenyl)oxy]-2-fluorophenyl}methyl)amino]carbonyl}-1H-imidazol-2-yl)imidodicarbonate (161 mg, 0.244 mmol) in DCM (5 ml) was added TFA (2.5 ml) and the reaction mixture was stirred at RT for 3 hours. The solvent was removed and the crude material was purified via reverse phase HPLC to give 2-amino-4-chloro-N-({4-chloro-3-[(3-cyano-5-cyclopropylphenyl)oxy]-2-fluorophenyl}methyl)-1H-imidazole-5-carboxamide trifluoroacetate (59 mg, 0.103 mmol, 42% yield).

1H NMR (400 MHz, METHANOL-$d_4$) δ ppm 7.25-7.39 (m, 2H), 7.12 (s, 1H), 6.93 (s, 1H), 6.85 (s, 1H), 4.58 (s, 2H), 1.77-1.97 (m, 1H), 0.91-1.14 (m, 2H), 0.55-0.84 (m, 2H). LC-MS (ES$^+$) m/z 460.04, [M+H].

Example 308

4-chloro-N-({4-chloro-3-[(3-cyano-5-cyclopropylphenyl)oxy]-2-fluorophenyl}methyl)-2-methyl-1H-imidazole-5-carboxamide trifluoroacetate

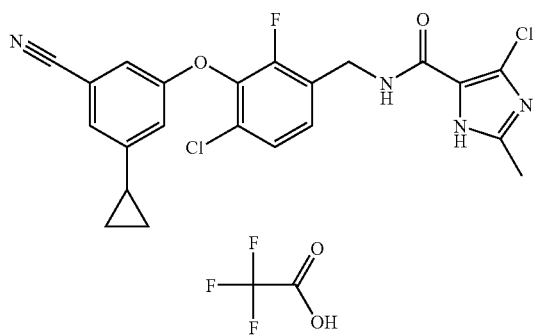

To a solution of 3-{[3-(aminomethyl)-6-chloro-2-fluorophenyl]oxy}-5-cyclopropylbenzonitrile (80 mg, 0.253 mmol), 4-chloro-2-methyl-1H-imidazole-5-carboxylic acid (40.6 mg, 0.253 mmol) and HOBT (38.7 mg, 0.253 mmol) in DMF (4.5 ml) was added EDC (48.4 mg, 0.253 mmol) and the reaction mixture was stirred at RT for 2 hours. The reaction mixture was purified via reverse phase HPLC to give 4-chloro-N-({4-chloro-3-[(3-cyano-5-cyclopropylphenyl)oxy]-2-fluorophenyl}methyl)-2-methyl-1H-imidazole-5-carboxamide trifluoroacetate (49 mg, 0.085 mmol, 34% yield). 1H NMR (400 MHz, METHANOL-$d_4$) δ ppm 7.24-7.46 (m, 2H), 7.13 (s, 1H), 6.94 (s, 1H), 6.88 (s, 1H), 4.62 (s, 2H), 2.37 (s, 3H), 1.81-2.00 (m, 1H), 0.93-1.15 (m, 2H), 0.47-0.82 (m, 2H). LC-MS (ES$^+$) m/z 459.04, [M+H].

Example 309

4-chloro-N-[(4-chloro-3-{[3-cyano-5-(difluoromethyl)phenyl]oxy}-2-fluorophenyl)methyl]-1H-imidazole-5-carboxamide

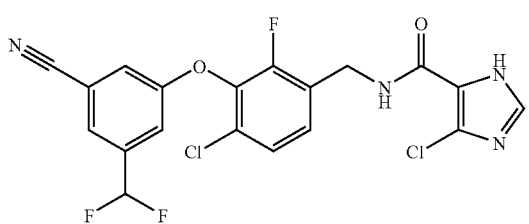

Step A: 4-chloro-N-({4-chloro-3-[(3-cyano-5-ethenylphenyl)oxy]-2-fluorophenyl}methyl)-1-({[2-(trimethyl silyl)ethyl]oxy}methyl)-1H-imidazole-5-carboxamide To a solution of 3-{[3-(aminomethyl)-6-chloro-2-fluorophenyl]oxy}-5-ethenylbenzonitrile (630 mg, 2.081 mmol), 4-chloro-1-({[2-(trimethylsilyl)ethyl]oxy}methyl)-1H-imidazole-5-carboxylic acid (576 mg, 2.081 mmol) and HOBT (414 mg, 2.71 mmol) in DMF (10.0 ml) was added EDC (479 mg, 2.497 mmol) and the reaction mixture was stirred at rt for 30 minutes. The reaction mixture was diluted with EtOAc and washed with water. The solvent was removed and the crude material was purified via silica gel chromatography to give 4-chloro-N-({4-chloro-3-[(3-cyano-5-ethenylphenyl)oxy]-2-fluorophenyl}methyl)-1-({[2-(trimethylsilyl)ethyl] oxy}methyl)-1H-imidazole-5-carboxamide (1125 mg, 2.004 mmol, 96% yield), 1H NMR (400 MHz, DMSO-$d_6$) δ ppm 8.76 (t, 1H), 7.92 (s, 1H), 7.77 (s, 1H), 7.43-7.49 (m, 1H), 7.32-7.42 (m, 2H), 7.22 (s, 1H), 6.72 (dd, 1H), 6.02 (d, 1H), 5.48 (s, 2H), 5.41 (d, 1H), 4.47 (d, 2H), 3.37 (t, 2H), 0.74 (t, 2H), −0.10 (s, 9H)

Step B: 4-chloro-N-({4-chloro-3-[(3-cyano-5-formylphenyl)oxy]-2-fluorophenyl}methyl)-1-({[2-(trimethylsilyl)ethyl] oxy}methyl)-1H-imidazole-5-carboxamide To a solution of 4-chloro-N-({4-chloro-3-[(3-cyano-5-ethenylphenyl)oxy]-2-fluorophenyl}methyl)-1-({[2-(trimethylsilyl)ethyl]oxy}methyl)-1H-imidazole-5-carboxamide (1.12 g, 1.995 mmol) and sodium periodate (1.280 g, 5.98 mmol) in THF (20 ml) and Water (10 ml) was added osmium tetroxide (2.5 wt % 2-butanol) (0.501 ml, 0.040 mmol) and the reaction mixture was stirred at rt for 5 hours. The reaction mixture was diluted with EtOAc and washed with water. The solvent was removed and the crude material was purified via silica gel chromatography to give 4-chloro-N-({4-chloro-3-[(3-cyano-5-formylphenyl)oxy]-2-fluorophenyl}methyl)-1-({[2-(trimethylsilyl)ethyl]oxy}methyl)-1H-imidazole-5-carboxamide (930 mg, 1.650 mmol, 83% yield). 1H NMR (400 MHz, METHANOL-$d_4$) δ ppm 9.94 (s, 1H), 8.71 (d, 1H), 8.00 (s, 1H), 7.90 (s, 1H), 7.61 (d, 1H), 7.34-7.47 (m, 2H), 5.59 (s, 2H), 4.47-4.70 (m, 2H), 3.50 (t, 2H), 0.83 (t, 2H), −0.05 (s, 9H).

Step C: 4-chloro-N-[(4-chloro-3-{[3-cyano-5-(difluoromethyl)phenyl]oxy}-2-fluorophenyl)methyl]-1-({[2-(trimethylsilyl)ethyl]oxy}methyl)-1H-imidazole-5-carboxamide to a solution of 4-chloro-N-({4-chloro-3-[(3-cyano-5-formylphenyl)oxy]-2-fluorophenyl}methyl)-1-({[2-(trimethylsilyl)ethyl]oxy}methyl)-1H-imidazole-5-carboxamide (100 mg, 0.177 mmol) in DCM (6 ml) was added DAST (0.047 ml, 0.355 mmol) and the reaction mixture was stirred at RT for two days. The reaction mixture was diluted with EtOAc and washed with water. The solvent was removed and the crude material 4-chloro-N-[(4-chloro-3-{[3-cyano-5-(difluoromethyl)phenyl]oxy}-2-fluorophenyl)methyl]-1-({[2-(trimethylsilyl)ethyl]oxy}methyl)-1H-imidazole-5-carboxamide (83 mg, 0.142 mmol, 80% yield) was used directly in the next step. 1H NMR (400 MHz, DMSO-$d_6$) δ ppm 8.58-8.94 (m, 1H), 7.98 (s, 1H), 7.84 (s, 1H), 7.66 (s, 1H), 7.33-7.57 (m, 3H), 6.81-7.25 (m, 1H), 5.49 (s, 2H), 4.49 (d, 2H), 3.38 (t, 2H), 0.75 (t, 2H), −0.09 (s, 9 H).

Step D: 4-chloro-N-[(4-chloro-3-{[3-cyano-5-(difluoromethyl)phenyl]oxy}-2-fluorophenyl)methyl]-1H-imidazole-5-carboxamide To a solution of 4-chloro-N-[(4-chloro-3-{[3-cyano-5-(difluoromethyl)phenyl]oxy}-2-fluorophenyl)methyl]-1-({[2-(trimethylsilyl)ethyl]oxy}methyl)-1H-imidazole-5-carboxamide (81 mg, 0.138 mmol) dissolved in DCM (5 ml) was added TFA (2.00 ml) and the reaction mixture was stirred at RT for 2 hours. The solvent was removed and the crude material was purified via reverse phase HPLC to give 4-chloro-N-[(4-chloro-3-{[3-cyano-5-(difluoromethyl)phenyl]oxy}-2-fluorophenyl)methyl]-1H-imidazole-5-carboxamide (56 mg, 0.123 mmol, 89% yield). 1H NMR (400 MHz, METHANOL-d₄) δ ppm 7.77 (s, 1H), 7.65 (s, 1H), 7.23-7.50 (m, 4H), 6.81 (t, 1H), 4.64 (s, 2H). LC-MS (ES⁺) m/z 454.97, [M+H].

Example 310

4-chloro-N-({4-chloro-3-[(3-cyano-5-ethynylphenyl)oxy]-2-fluorophenyl}methyl)-1H-imidazole-5-carboxamide

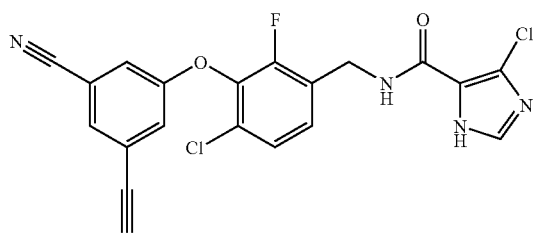

Step A: 4-chloro-N-({4-chloro-3-[(3-cyano-5-ethynyl phenyl)oxy]-2-fluorophenyl}methyl)-1-({[2-(trimethylsilyl)ethyl]oxy}methyl)-1H-imidazole-5-carboxamide To a solution of 4-chloro-N-({4-chloro-3-[(3-cyano-5-formylphenyl)oxy]-2-fluorophenyl}methyl)-1-({[2-(trimethylsilyl)ethyl]oxy}methyl)-1H-imidazole-5-carboxamide (90 mg, 0.160 mmol) and potassium carbonate (66.2 mg, 0.479 mmol) in Methanol (5 ml) was added dimethyl-1-diazo-2-oxopropylphosphonate (46.0 mg, 0.240 mmol) and the reaction mixture was stirred at RT overnight. The reaction mixture was diluted with EtOAc and washed with water. The solvent was removed and the crude material was purified via silica gel chromatography to give 4-chloro-N-({4-chloro-3-[(3-cyano-5-ethynylphenyl)oxy]-2-fluorophenyl}methyl)-1-({[2-(trimethylsilyl)ethyl]oxy}methyl)-1H-imidazole-5-carboxamide (48 mg, 0.086 mmol, 54% yield). 1H NMR (400 MHz, METHANOL-d₄) δ ppm 7.87 (s, 1H), 7.54 (s, 1H), 7.31-7.45 (m, 2H), 7.25 (s, 1H), 7.20 (s, 1H), 5.57 (s, 3H), 4.59 (s, 2H), 3.75 (s, 1H), 3.47 (t, 2H), 0.80 (t, 2H), −0.07 (s, 9H).

Step B: 4-chloro-N-({4-chloro-3-[(3-cyano-5-ethynylphenyl)oxy]-2-fluorophenyl}methyl)-1H-imidazole-5-carboxamide To a solution of 4-chloro-N-({4-chloro-3-[(3-cyano-5-ethynylphenyl)oxy]-2-fluorophenyl}methyl)-1-({[2-(trimethylsilyl)ethyl]oxy}methyl)-1H-imidazole-5-carboxamide (44.0 mg, 0.079 mmol) in DCM (6 ml) was added TFA (2.0 mL) and the reaction mixture was stirred at rt for one hour. The solvent was removed and the crude material was purified via reverse phase HPLC to give 4-chloro-N-({4-chloro-3-[(3-cyano-5-ethynylphenyl)oxy]-2-fluorophenyl}methyl)-1H-imidazole-5-carboxamide (23 mg, 0.042 mmol, 54% yield). 1H NMR (400 MHz, METHANOL-d₄) δ ppm 7.72 (s, 1H), 7.53 (s, 1H), 7.29-7.40 (m, 2H), 7.25 (s, 1H), 7.20 (s, 1H), 4.63 (s, 2H), 3.74 (s, 1H). LC-MS (ES⁺) m/z 429.00, [M+H].

Example 311

4-chloro-N-{[4-chloro-3-({3-cyano-5-[(dimethylamino)methyl]phenyl}oxy)-2-fluorophenyl]methyl}-1H-imidazole-5-carboxamide trifluoroacetate

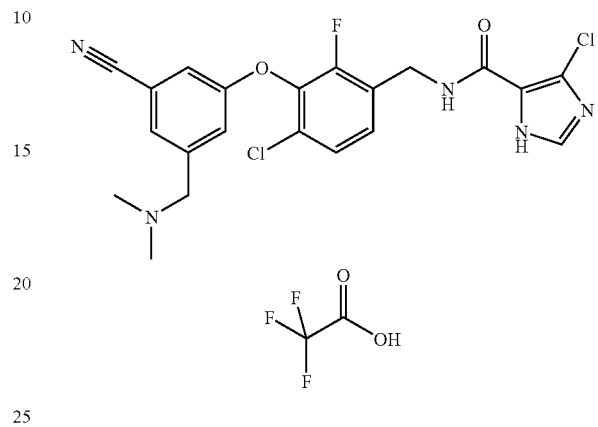

Step A: 4-chloro-N-{[4-chloro-3-({3-cyano-5-[(dimethylamino)methyl]phenyl}oxy)-2-fluorophenyl]methyl}-1-({[2-(trimethylsilyl)ethyl]oxy}methyl)-1H-imidazole-5-carboxamide to a solution of 4-chloro-N-({4-chloro-3-[(3-cyano-5-formylphenyl)oxy]-2-fluorophenyl}methyl)-1-({[2-(trimethylsilyl)ethyl]oxy}methyl)-1H-imidazole-5-carboxamide (90 mg, 0.160 mmol) and dimethyl amine (2.0 M solution in THF) (0.160 ml, 0.319 mmol) in 1,2-Dichloroethane (DCE) (5 ml) was added sodium triacetoxyborohydride (47.4 mg, 0.224 mmol) and the reaction mixture was stirred at RT for 4 hours. The reaction mixture was diluted with EtOAc and washed with water. The solvent was removed and the crude material was purified via silica gel chromatography to give 4-chloro-N-{[4-chloro-3-({3-cyano-5-[(dimethylamino)methyl]phenyl}oxy)-2-fluorophenyl]methyl}-1-({[2-(trimethylsilyl)ethyl]oxy}methyl)-1H-imidazole-5-carboxamide (85 mg, 0.143 mmol, 90% yield). 1H NMR (400 MHz, METHANOL-d₄) δ ppm 7.88 (s, 1H), 7.31-7.43 (m, 3H), 7.19 (s, 1H), 7.12 (s, 1H), 5.58 (s, 2H), 4.59 (s, 2H), 3.38-3.60 (m, 4H), 2.19 (s, 6H), 0.81 (t, 2H), −0.07 (s, 9H)

Step B: 4-chloro-N-{[4-chloro-3-({3-cyano-5-[(dimethylamino)methyl]phenyl}oxy)-2-fluorophenyl]methyl}-1H-imidazole-5-carboxamide trifluoroacetate To a solution of 4-chloro-N-{[4-chloro-3-({3-cyano-5-[(dimethylamino)methyl]phenyl}oxy)-2-fluorophenyl]methyl}-1-({[2-(trimethylsilyl)ethyl]oxy}methyl)-1H-imidazole-5-carboxamide (82 mg, 0.138 mmol) in DCM (6.0 ml) was added TFA (2.00 mL) and the reaction mixture was stirred ar RT for one hour. The solvent was removed and the crude material was purified via reverse phase HPLC to give 4-chloro-N-{[4-chloro-3-({3-cyano-5-[(dimethylamino)methyl]phenyl}oxy)-2-fluorophenyl]methyl}-1H-imidazole-5-carboxamide trifluoroacetate (29 mg, 0.050 mmol, 36% yield). 1H NMR (400 MHz, METHANOL-d₄) δ ppm 7.72 (s, 1H), 7.62 (s, 1H), 7.27-7.49 (m, 4H), 4.63 (s, 2H), 4.35 (s, 2H), 2.85 (s, 6H). LC-MS (ES⁺) m/z 462.08, [M+H].

Example 312

N-({3-[(3-acetyl-5-cyanophenyl)oxy]-4-chloro-2-fluorophenyl}methyl)-2-amino-4-chloro-1H-imidazole-5-carboxamide

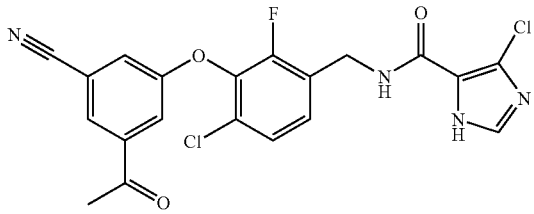

Step A: N-({3-[(3-acetyl-5-cyanophenyl)oxy]-4-chloro-2-fluorophenyl}methyl)-4-chloro-1-({[2-(trimethylsilyl)ethyl]oxy}methyl)-1H-imidazole-5-carboxamide To a solution of N-({3-[(3-bromo-5-cyanophenyl)oxy]-4-chloro-2-fluorophenyl}methyl)-4-chloro-1-({[2-(trimethylsilyl)ethyl]oxy}methyl)-1H-imidazole-5-carboxamide (500 mg, 0.814 mmol), tetraethylammoniumchloride (409 mg, 2.442 mmol) and dichlorobistriphenyl phosphinepalladium (II) (57.1 mg, 0.081 mmol) was added tributyl[1-(ethyloxy)ethenyl]stannane (0.302 mL, 0.894 mmol) and the reaction mixture was stirred at 80° C. overnight. The reaction mixture was cooled to RT, diluted with EtOAc and washed with water. The solvent was evaporated and the residue was dissolved in THF (7.00 mL) and HCl (1.0 M solution) (4 mL, 4.00 mmol) was added. The resulting mixture was stirred for 4 hours at RT. EtOAc was added and the organics were separated. The solvent was removed and the crude material was purifed via silica gel chromatography to give N-({3-[(3-acetyl-5-cyanophenyl)oxy]-4-chloro-2-fluorophenyl}methyl)-4-chloro-1-({[2-(trimethylsilyl)ethyl]oxy}methyl)-1H-imidazole-5-carboxamide (384 mg, 0.665 mmol, 82% yield). 1H NMR (400 MHz, METHANOL-$d_4$) δ ppm 8.08 (s, 1H), 7.90 (s, 1H), 7.70 (s, 1H), 7.33-7.49 (m, 3H), 5.59 (s, 2H), 4.61 (s, 2H), 3.49 (t, 2H), 2.60 (s, 3 H), 0.83 (t, 2H), −0.12-0.01 (m, 9H).

Step B: N-({3-[(3-acetyl-5-cyanophenyl)oxy]-4-chloro-2-fluorophenyl}methyl)-2-amino-4-chloro-1H-imidazole-5-carboxamide To a solution of N-({3-[(3-acetyl-5-cyanophenyl)oxy]-4-chloro-2-fluorophenyl}methyl)-4-chloro-1-({[2-(trimethylsilyl)ethyl]oxy}methyl)-1H-imidazole-5-carboxamide (209 mg, 0.362 mmol) dissolved in DCM (6 ml) was added TFA (3 mL) and the reaction mixture was stirred at RT for 3 hours. The solvent was removed and the crude material was purified via reverse phase HPLC to give N-({3-[(3-acetyl-5-cyanophenyl)oxy]-4-chloro-2-fluorophenyl}methyl)-2-amino-4-chloro-1H-imidazole-5-carboxamide trifluoroacetate (153 mg, 0.342 mmol, 95% yield). 1H NMR (400 MHz, METHANOL-$d_4$) δ ppm 8.07 (s, 1H), 7.77 (s, 1H), 7.69 (s, 1H), 7.49 (s, 1H), 7.30-7.44 (m, 2H), 4.64 (s, 2H), 2.59 (s, 3H). LC-MS (ES$^-$) m/z 445.09, [M−H].

Example 313

4-chloro-N-[(4-chloro-3-{[3-cyano-5-(1,1-difluoroethyl)phenyl]oxy}-2-fluorophenyl)methyl]-1H-imidazole-5-carboxamide

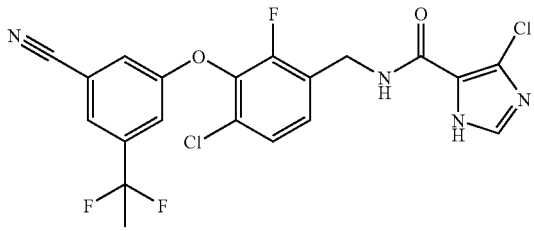

Step A: 4-chloro-N-[(4-chloro-3-{[3-cyano-5-(1,1-difluoroethyl)phenyl]oxy}-2-fluorophenyl)methyl]-1-({[2-(trimethylsilyl)ethyl]oxy}methyl)-1H-imidazole-5-carboxamide To a solution of N-({3-[(3-acetyl-5-cyanophenyl)oxy]-4-chloro-2-fluorophenyl}methyl)-4-chloro-1-({[2-(trimethylsilyl)ethyl]oxy}methyl)-1H-imidazole-5-carboxamide (175 mg, 0.303 mmol) in DCM (3 ml) was added DAST (0.080 ml, 0.606 mmol) and the reaction mixture was stirred at RT for 5 days. The reaction mixture was diluted with EtOAc and washed with water. The solvent was removed and the crude material was purified via silica gel chromatography to give 4-chloro-N-[(4-chloro-3-{[3-cyano-5-(1,1-difluoroethyl)phenyl]oxy}-2-fluorophenyl)methyl]-1-({[2-(trimethylsilyl)ethyl]oxy}methyl)-1H-imidazole-5-carboxamide (61 mg, 0.102 mmol, 34% yield). 1H NMR (400 MHz, METHANOL-$d_4$) δ ppm 8.70 (t, 1H), 7.89 (s, 1H), 7.63 (s, 1H), 7.33-7.44 (m, 3H), 7.26 (s, 1H), 5.58 (s, 2H), 4.60 (d, 2H), 3.48 (t, 2 H), 1.91 (t, 3H), 0.81 (t, 2H), −0.19-0.00 (m, 9H).

Step B: 4-chloro-N-[(4-chloro-3-{[3-cyano-5-(1,1-difluoroethyl)phenyl]oxy}-2-fluorophenyl)methyl]-1H-imidazole-5-carboxamide To a solution of 4-chloro-N-[(4-chloro-3-{[3-cyano-5-(1,1-difluoroethyl)phenyl]oxy}-2-fluorophenyl)methyl]-1-({[2-(trimethylsilyl)ethyl]oxy}methyl)-1H-imidazole-5-carboxamide (59 mg, 0.098 mmol) in DCM (6 ml) was added TFA (2.0 mL) and the reaction mixture was stirred at RT for 3 hours. The reaction mixture was purified via reverse phase HPLC to give 4-chloro-N-[(4-chloro-3-{[3-cyano-5-(1,1-difluoroethyl)phenyl]oxy}-2-fluorophenyl)methyl]-1H-imidazole-5-carboxamide (28 mg, 0.060 mmol, 61% yield). 1H NMR (400 MHz, METHANOL-$d_4$) δ ppm 7.72 (s, 1H), 7.63 (s, 1H), 7.30-7.42 (m, 3H), 7.28 (s, 1H), 4.63 (s, 2H), 1.90 (t, 3H). LC-MS (ES$^+$) m/z 469.08, [M+H].

Example 314

4-chloro-N-[(4-chloro-3-{[3-cyano-5-(hydroxymethyl)phenyl]oxy}-2-fluorophenyl)methyl]-1H-imidazole-5-carboxamide

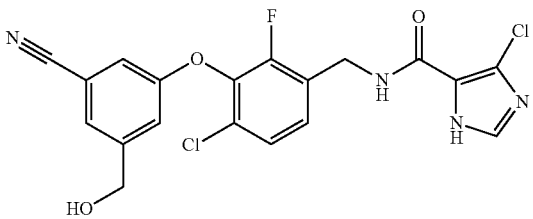

To a solution of 4-chloro-N-[(4-chloro-3-{[3-cyano-5-(hydroxymethyl)phenyl]oxy}-2-fluorophenyl)methyl]-1H-imidazole-5-carboxamide (53.0 mg, 0.094 mmol) in DCM (5 ml) was added TFA (2.0 mL) and the reaction mixture was stirred at RT for 4 hours. The solvent was removed and the crude material was purified via reverse phase HPLC to give 4-chloro-N-[(4-chloro-3-{[3-cyano-5-(hydroxymethyl)phenyl]oxy}-2-fluorophenyl)methyl]-1H-imidazole-5-carboxamide (37 mg, 0.085 mmol, 91% yield). 1H NMR (400 MHz, METHANOL-$d_4$) δ ppm 7.73 (s, 1H), 7.41 (s, 1H), 7.29-7.39 (m, 2H), 7.19 (s, 1H), 7.10 (s, 1H), 4.63 (s, 2H), 4.60 (s, 2H). LC-MS (ES$^+$) m/z 435.01, [M+H].

Example 315

4-chloro-N-[(4-chloro-3-{[3-cyano-5-(cyclopropylethynyl)phenyl]oxy}-2-fluorophenyl)methyl]-1H-imidazole-5-carboxamide

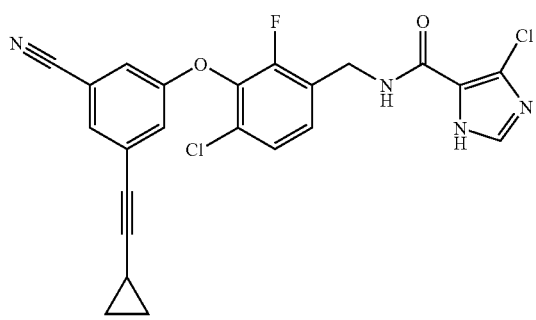

To a solution of N-({3-[(3-bromo-5-cyanophenyl)oxy]-4-chloro-2-fluorophenyl}methyl)-4-chloro-1H-imidazole-5-carboxamide (95.0 mg, 0.196 mmol), cyclopropylacetylene (25.9 mg, 0.392 mmol), copper(I) iodide (1.869 mg, 9.81 µmol) and Palladiumbischlorobistriphenylphosphine(II) (10.25 mg, 0.020 mmol) in THF (6 ml) was added TEA (0.137 ml, 0.981 mmol) and the reaction mixture was irradiated in a personal microwave reactor for 10 minutes at 120° C. The solvent was removed and the crude material was purified via reverse phase HPLC to give 4-chloro-N-[(4-chloro-3-{[3-cyano-5-(cyclopropylethynyl)phenyl]oxy}-2-fluorophenyl)methyl]-1H-imidazole-5-carboxamide (48 mg, 0.102 mmol, 52% yield). 1H NMR (400 MHz, DMSO-$d_6$) δ ppm 8.28 (br. s., 1H), 7.76 (s, 1H), 7.59 (s, 1H), 7.39-7.53 (m, 2H), 7.34 (t, 1H), 7.14 (s, 1H), 4.51 (d, 2H), 1.47-1.64 (m, 1H), 0.83-1.01 (m, 2H), 0.71-0.81 (m, 2H). LC-MS (ES$^+$) m/z 469.09, [M+H].

Example 316

4-chloro-N-[(4-chloro-3-{[3-cyano-5-(3-methyl-1-butyn-1-yl)phenyl]oxy}-2-fluorophenyl)methyl]-1H-imidazole-5-carboxamide

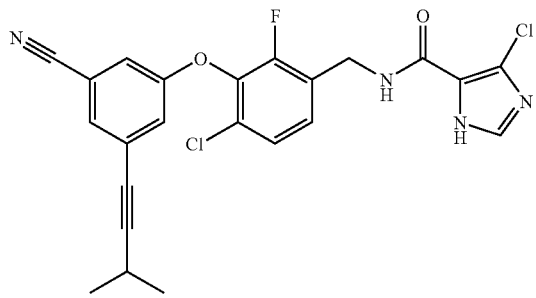

To a solution of N-({3-[(3-bromo-5-cyanophenyl)oxy]-4-chloro-2-fluorophenyl}methyl)-4-chloro-1H-imidazole-5-carboxamide (95 mg, 0.196 mmol), Palladium dichloropisttriphenylphosphine (103 mg, 0.196 mmol), 3-methyl-1-butyne (26.7 mg, 0.392 mmol) and copper(I) iodide (1.869 mg, 9.81 µmol) in THF (4 ml) was added TEA (0.141 ml, 1.012 mmol) and the reaction mixture was irradiated in a personal microwave reactor for 10 minutes at 120° C. The solvent was removed and the crude material was purified via reverse phase HPLC to give 4-chloro-N-[(4-chloro-3-{[3-cyano-5-(3-methyl-1-butyn-1-yl)phenyl]oxy}-2-fluorophenyl)methyl]-1H-imidazole-5-carboxamide (49 mg, 0.104 mmol, 53% yield). 1H NMR (400 MHz, DMSO-$d_6$) δ ppm 8.25 (d, 1H), 7.73 (s, 1H), 7.57 (s, 1H), 7.41-7.50 (m, 2H), 7.32 (t, 1H), 7.11 (s, 1H), 4.49 (d, 2H), 2.76 (dt, 1H), 1.15 (d, 6H). LC-MS (ES$^+$) m/z 471.13, [M+H].

Example 317

4-chloro-N-[(4-chloro-3-{[3-cyano-5-(1-propyn-1-yl)phenyl]oxy}-2-fluorophenyl)methyl]-1H-imidazole-5-carboxamide

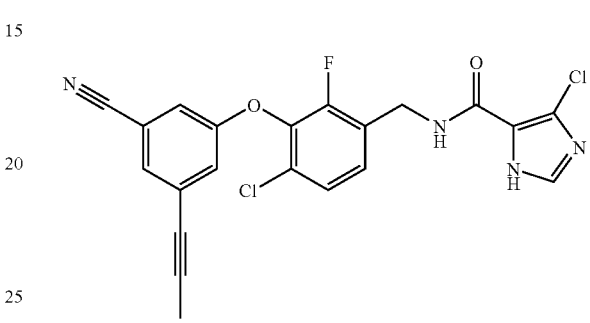

To a solution of N-({3-[(3-bromo-5-cyanophenyl)oxy]-4-chloro-2-fluorophenyl}methyl)-4-chloro-1H-imidazole-5-carboxamide (70.0 mg, 0.145 mmol), Palladium dichlorobistriphenylphosphine(II) (7.55 mg, 0.014 mmol), copper(I) iodide (1.377 mg, 7.23 µmol) and TEA (0.101 ml, 0.723 mmol) in THF (4 ml) was bubbled 1-propyne (11.59 mg, 0.289 mmol) for 5 minutes and the reaction mixture was irradiated in a personal microwave reactor for 10 minutes at 120° C. The solvent was removed and the crude material was purified via reverse phase HPLC to give 4-chloro-N-[(4-chloro-3-{[3-cyano-5-(1-propyn-1-yl)phenyl]oxy}-2-fluorophenyl)methyl]-1H-imidazole-5-carboxamide (29 mg, 0.065 mmol, 45% yield). 1H NMR (400 MHz, METHANOL-$d_4$) δ ppm 7.60-7.81 (m, 1H), 7.40 (s, 1H), 7.28-7.38 (m, 3H), 7.16 (s, 1H), 7.05 (s, 1H), 4.62 (s, 2H), 1.99 (s, 3H). LC-MS (ES$^+$) m/z 443.13, [M+H].

Example 318

N-[(3-{[3-(1-butyn-1-yl)-5-cyanophenyl]oxy}-4-chloro-2-fluorophenyl)methyl]-4-chloro-1H-imidazole-5-carboxamide

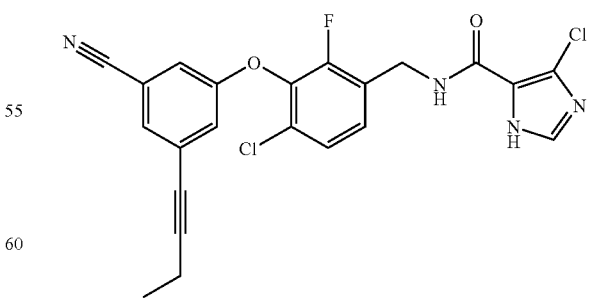

To a solution of N-({3-[(3-bromo-5-cyanophenyl)oxy]-4-chloro-2-fluorophenyl}methyl)-4-chloro-1H-imidazole-5-carboxamide (65 mg, 0.134 mmol), Palladium dichlorobistriphenylphosphine(II) (7.01 mg, 0.013 mmol), copper(I)

iodide (25.6 mg, 0.134 mmol) and TEA (0.019 ml, 0.134 mmol) in THF (5 ml) was bubbled 1-butyne (7.26 mg, 0.134 mmol) for 5 minutes and the reaction mixture was irradiated in a personal microwave reactor for 10 minutes at 120° C. The solvent was removed and the crude material was purified via reverse phase HPLC to give N-[(3-{[3-(1-butyn-1-yl)-5-cyanophenyl]oxy}-4-chloro-2-fluorophenyl)methyl]-4-chloro-1H-imidazole-5-carboxamide (17 mg, 0.037 mmol, 28% yield). 1H NMR (400 MHz, METHANOL-d4) δ ppm 7.71 (br. s., 1H), 7.40 (s, 1H), 7.28-7.39 (m, 3H), 7.17 (s, 1H), 7.05 (s, 1H), 4.62 (s, 2H), 2.38 (q, 2H), 1.17 (t, 3H). LC-MS (ES$^+$) m/z 457.14, [M+H].

Example 319

4-chloro-N-{[4-chloro-3-({3-chloro-5-[(3R)-3-hydroxy-1-butyn-1-yl]phenyl}oxy)-2-fluorophenyl]methyl}-1H-imidazole-5-carboxamide

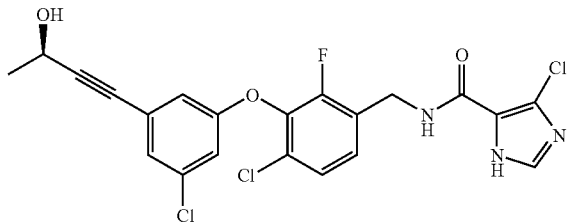

To a solution of N-({3-[(3-bromo-5-chlorophenyl)oxy]-4-chloro-2-fluorophenyl}methyl)-4-chloro-1H-imidazole-5-carboxamide (70 mg, 0.142 mmol), palladiumbisdichlorobistriphenylphosphine (9.96 mg, 0.014 mmol), copper(I) iodide (1.351 mg, 7.09 μmol) and TEA (0.099 ml, 0.710 mmol) in THF (6 ml) was added (2R)-3-butyn-2-ol (24.85 mg, 0.355 mmol) and the reaction mixture was irradiated in a personal microwave reaction for 10 minutes at 120° C. The reaction mixture was diluted with EtOAc and washed with water. The solvent was removed and the crude material was purified via reverse phase HPLC to give 4-chloro-N-{[4-chloro-3-({3-chloro-5-[(3R)-3-hydroxy-1-butyn-1-yl]phenyl}oxy)-2-fluorophenyl]methyl}-1H-imidazole-5-carboxamide (16 mg, 0.033 mmol, 23% yield). 1H NMR (400 MHz, METHANOL-d$_4$) δ ppm 7.24-7.45 (m, 3H), 7.11 (s, 1H), 6.89 (s, 1H), 6.74 (s, 1H), 4.47-4.70 (m, 3H), 1.41 (d, 3H). LC-MS (ES$^+$) m/z 482.03, [M+H].

Example 320

4-chloro-N-{[4-chloro-3-({3-chloro-5-[(3S)-3-hydroxy-1-butyn-1-yl]phenyl}oxy)-2-fluorophenyl]methyl}-1H-imidazole-5-carboxamide

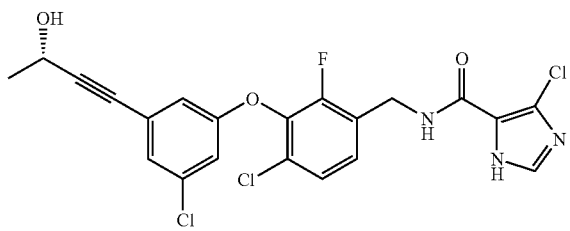

A solution of N-({3-[(3-bromo-5-chlorophenyl)oxy]-4-chloro-2-fluorophenyl}methyl)-4-chloro-1H-imidazole-5-carboxamide (86 mg, 0.174 mmol), (2S)-3-butyn-2-ol (30.5 mg, 0.436 mmol), palladiumbisdichlorobistriphenylphosphine (12.23 mg, 0.017 mmol), copper(I) iodide (1.659 mg, 8.71 μmol) and TEA (0.121 ml, 0.871 mmol) in THF (3 ml) was irradiated in the microwave for 10 minutes at 120° C. The reaction mixture was diluted with EtOAc and washed with water. The solvent was removed and the crude material was purified via reverse phase HPLC to give 4-chloro-N-{[4-chloro-3-({3-chloro-5-[(3S)-3-hydroxy-1-butyn-1-yl]phenyl}oxy)-2-fluorophenyl]methyl}-1H-imidazole-5-carboxamide (37 mg, 0.077 mmol, 44% yield). 1H NMR (400 MHz, METHANOL-d$_4$) δ ppm 7.54-7.94 (m, 1H), 7.26-7.47 (m, 2 H), 7.11 (s, 1H), 6.89 (s, 1H), 6.74 (s, 1H), 4.24-4.71 (m, 3H), 1.41 (d, 3H). LC-MS (ES$^+$) m/z 481.95, [M+H].

Example 321

N-({3-[(5-bromo-4-fluoro-2-nitrophenyl)oxy]-4-chloro-2-fluorophenyl}methyl)-4-chloro-1H-imidazole-5-carboxamide

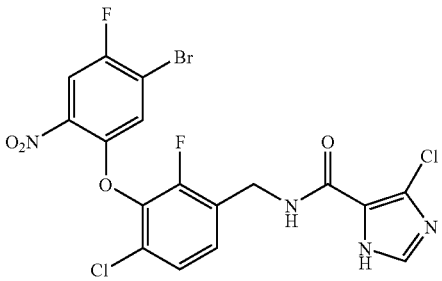

Step A: 2-[(5-bromo-4-fluoro-2-nitrophenyl)oxy]-1-chloro-3-fluoro-4-methylbenzene To a solution of 6-chloro-2-fluoro-3-methylphenol (12.8 g, 80 mmol) and 18-crown-6 (4.21 g, 15.94 mmol) in DMSO (100 ml) at 0° C. was added potassium tert-butoxide (1.0 M solution in THF) (80 ml, 80 mmol) and the reaction mixture was stirred at RT for 30 minutes. Next, 1-bromo-2,5-difluoro-4-nitrobenzene (19.4 g, 80 mmol) was added dropwise (in solution of 60 mL DMSO) and the reaction mixture was stirred overnight at RT. The reaction mixture was diluted with EtOAc and washed with water. The solvent was removed and the crude material was triturated with methanol to give 2-[(5-bromo-4-fluoro-2-nitrophenyl)oxy]-1-chloro-3-fluoro-4-methylbenzene (21.3 g, 56.3 mmol, 71% yield). 1H NMR (400 MHz, DMSO-d$_6$) δ ppm 8.26 (d, 1H), 7.34-7.40 (m, 1H), 7.21-7.34 (m, 2H), 2.23 (d, 3H).

Step B: 2-[(5-bromo-4-fluoro-2-nitrophenyl)oxy]-4-(bromomethyl)-1-chloro-3-fluorobenzene A solution of 2-[(5-bromo-4-fluoro-2-nitrophenyl)oxy]-1-chloro-3-fluoro-4-methylbenzene (1.00 g, 2.64 mmol), NBS (0.517 g, 2.91 mmol) and benzoyl peroxide (0.032 g, 0.132 mmol) in carbon tetrachloride (30 ml) was heated overnight at 85° C. The solvent was removed and the crude material was purified via silica gel chromatography to give 2-[(5-bromo-4-fluoro-2-nitrophenyl)oxy]-4-(bromomethyl)-1-chloro-3-fluorobenzene (695 mg, 1.519 mmol, 58% yield). 1H NMR (400 MHz, DMSO-d$_6$) δ ppm 8.32 (d, 1H), 7.50-7.60 (m, 2H), 7.40 (d, 1H), 4.73 (s, 2H).

Step C: ({3-[(5-bromo-4-fluoro-2-nitrophenyl)oxy]-4-chloro-2-fluorophenyl}methyl)amine To an ammonia (7.0 N solution in methanol) (50 ml, 350 mmol) solution at 0° C. was added 2-[(5-bromo-4-fluoro-2-nitrophenyl)oxy]-4-(bromomethyl)-1-chloro-3-fluorobenzene (695 mg, 1.519 mmol) dropwise in solution of DCM (10 ml) and the reaction was allowed to stir at RT overnight. The solvent was removed and the crude material was used directly in the next step without further purification. 1H NMR (400 MHz, DMSO-$d_6$) δ ppm 8.30 (d, 1H), 7.40-7.60 (m, 2H), 7.28 (d, 1H), 6.53 (br. s., 2H), 3.93 (s, 2H).

Step D: N-({3-[(5-bromo-4-fluoro-2-nitrophenyl)oxy]-4-chloro-2-fluorophenyl}methyl)-4-chloro-1-({[2-(trimethylsilyl)ethyl]oxy}methyl)-1H-imidazole-5-carboxamide To a solution of ({3-[(5-bromo-4-fluoro-2-nitrophenyl)oxy]-4-chloro-2-fluorophenyl}methyl)amine (690 mg, 1.454 mmol), 4-chloro-1-({[2-(trimethylsilyl)ethyl]oxy}methyl)-1H-imidazole-5-carboxylic acid (403 mg, 1.454 mmol) and HOBT (267 mg, 1.745 mmol) in DMF (4 ml) was added EDC (335 mg, 1.745 mmol) and the reaction mixture was stirred at RT for 45 minutes. The reaction mixture was diluted with EtOAc and washed with water. The solvent was removed and the crude material (942 mg) was used directly in the next step. 1H NMR (400 MHz, DMSO-$d_6$) δ ppm 8.77 (t, 1H), 8.32 (d, 1H), 7.98 (s, 1H), 7.45-7.56 (m, 1H), 7.41 (t, 1H), 7.31 (d, 1H), 5.49 (s, 2H), 4.48 (d, 2H), 3.38 (t, 2H), 0.74 (t, 2H), −0.09 (s, 9H).

Step E: N-({3-[(5-bromo-4-fluoro-2-nitrophenyl)oxy]-4-chloro-2-fluorophenyl}methyl)-4-chloro-1H-imidazole-5-carboxamide To a solution of N-({3-[(5-bromo-4-fluoro-2-nitrophenyl)oxy]-4-chloro-2-fluorophenyl}methyl)-4-chloro-1-({[2-(trimethylsilyl)ethyl]oxy}methyl)-1H-imidazole-5carboxamide (55.0 mg, 0.084 mmol) in DCM (6 ml) was added TFA (3.00 ml) and the reaction mixture was stirred at RT for 2 hours. The solvent was removed and the crude material was purified via reverse phase HPLC to give N-({3-[(5-bromo-4-fluoro-2-nitrophenyl)oxy]-4-chloro-2-fluorophenyl}methyl)-4-chloro-1H-imidazole-5-carboxamide (33 mg, 0.063 mmol, 75% yield). 1H NMR (400 MHz, METHANOL-$d_4$) δ ppm 8.03 (d, 1H), 7.74 (s, 1H), 7.32-7.45 (m, 2H), 7.10 (d, 1H), 4.65 (s, 2 H). LC-MS (ES$^+$) m/z 520.92, [M+H].

Example 322

4-chloro-N-({4-chloro-3-[(5-cyano-4-fluoro-2-nitrophenyl)oxy]-2-fluorophenyl}methyl)-1H-imidazole-5-carboxamide

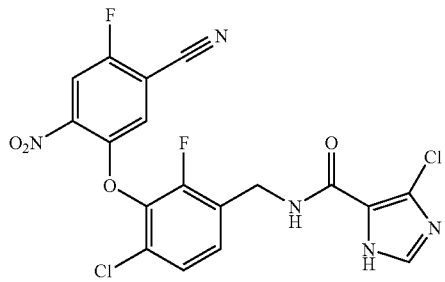

Step A: (4-chloro-N-({4-chloro-3-[(5-cyano-4-fluoro-2-nitrophenyl)oxy]-2-fluorophenyl}methyl)-1-({[2-(trimethylsilyl)ethyl]oxy}methyl)-1H-imidazole-5-carboxamide To a solution of N-({3-[(5-bromo-4-fluoro-2-nitrophenyl)oxy]-4-chloro-2-fluorophenyl}methyl)-4-chloro-1-({[2-(trimethylsilyl)ethyl]oxy}methyl)-1H-imidazole-5-carboxamide (83.0 mg, 0.127 mmol) and zinc cyanide (19.42 mg, 0.165 mmol) in DMF (3 ml) was added tetrakis(triphenylphosphine)palladium(0) (14.70 mg, 0.013 mmol) and the reaction mixture was irradiated in a personal microwave reactor for 15 minutes at 130° C. The reaction mixture was diluted with EtOAc and washed with water. The solvent was removed and the crude material (4-chloro-N-({4-chloro-3-[(5-cyano-4-fluoro-2-nitrophenyl)oxy]-2-fluorophenyl}methyl)-1-({[2-(trimethylsilyl)ethyl]oxy}methyl)-1H-imidazole-5-carboxamide (81 mg) was used directly in the next step without purification. LC-MS (ES$^+$) m/z 598 [M+H].

Step B: 4-chloro-N-({4-chloro-3-[(5-cyano-4-fluoro-2-nitrophenyl)oxy]-2-fluorophenyl}methyl)-1H-imidazole-5-carboxamide To a solution of 4-chloro-N-({4-chloro-3-[(5-cyano-4-fluoro-2-nitrophenyl)oxy]-2-fluorophenyl}methyl)-1-({[2-(trimethylsilyl)ethyl]oxy}methyl)-1H-imidazole-5-carboxamide (78.0 mg, 0.085 mmol) in DCM (7 ml) was added TFA (3.0 mL) and the reaction mixture was stirred at RT for 2 hours. The solvent was removed and the crude material was purified via reverse phase HPLC to give 4-chloro-N-({4-chloro-3-[(5-cyano-4-fluoro-2-nitrophenyl)oxy]-2-fluorophenyl}methyl)-1H-imidazole-5-carboxamide (39 mg, 0.083 mmol, 98% yield). 1H NMR (400 MHz, METHANOL-$d_4$) δ ppm 8.14 (d, 1H), 7.75 (s, 1H), 7.27-7.50 (m, 3H), 4.64 (s, 2H). LC-MS (ES$^+$) m/z 468.07, [M+H].

Example 323

N-({3-[(2-amino-5-cyano-4-fluorophenyl)oxy]-4-chloro-2-fluorophenyl}methyl)-4-chloro-1H-imidazole-5-carboxamide

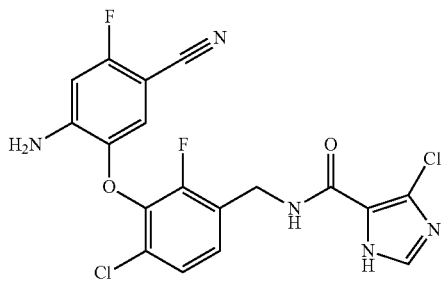

Step A: N-({3-[(2-amino-5-cyano-4-fluorophenyl)oxy]-4-chloro-2-fluorophenyl}methyl)-4-chloro-1-({[2-(trimethylsilyl)ethyl]oxy}methyl)-1H-imidazole-5-carboxamide To a solution of 4-chloro-N-({4-chloro-3-[(5-cyano-4-fluoro-2-nitrophenyl)oxy]-2-fluorophenyl}methyl)-1-({[2-(trimethylsilyl)ethyl]oxy}methyl)-1H-imidazole-5-carboxamide (450 mg, 0.752 mmol) in THF (3 ml) was added sodium hydrosulfite (85% tech.) (924 mg, 4.51 mmol) in solution of Water (6.00 ml) and the reaction mixture was stirred at 60° C. for one hour. The reaction mixture was diluted with EtOAc and washed with water. The solvent was removed and the crude material was purified via silica gel chromatography to give N-({3-[(2-amino-5-cyano-4-fluorophenyl)oxy]-4-chloro-2-fluorophenyl}methyl)-4-chloro-1-({[2-(trimethylsilyl)ethyl]oxy}methyl)-1H-imidazole-5-carboxamide (386 mg, 0.679 mmol, 90% yield). 1H NMR (400 MHz, DMSO-$d_6$) δ ppm 8.76 (t, 1H), 7.98 (s, 1H), 7.39-7.49 (m, 1H), 7.34 (t, 1H), 6.70 (s, 2H), 6.56-6.68 (m, 2H), 5.49 (s, 2H), 4.47 (d, 2H), 3.39 (t, 2H), 0.75 (t, 2H), −0.08 (s, 9H).

Step B: N-({3-[(2-amino-5-cyano-4-fluorophenyl)oxy]-4-chloro-2-fluorophenyl}methyl)-4-chloro-1H-imidazole-5-carboxamide To a solution of N-({3-[(2-amino-5-cyano-4-fluorophenyl)oxy]-4-chloro-2-fluorophenyl}methyl)-4-chloro-1-({[2-(trimethylsilyl)ethyl]oxy}methyl)-1H-imidazole-5-carboxamide (35 mg, 0.062 mmol) in DCM (6 ml) was added TFA (3.0 mL) and the reaction mixture was stirred for 3 hours at RT. The solvent was removed and the crude material was purified via reverse phase HPLC and neutralized to give N-({3-[(2-amino-5-cyano-4-fluorophenyl)oxy]-4-chloro-2-fluorophenyl}methyl)-4-chloro-1H-imidazole-5-carboxamide (9.0 mg, 0.021 mmol, 33% yield). 1H NMR (400 MHz, METHANOL-$d_4$) δ ppm 7.70 (s, 1H), 7.20-7.42 (m, 2H), 6.58 (d, 1H), 6.49 (d, 1H), 4.62 (s, 2H). LC-MS (ES$^+$) m/z 438.13, [M+H].

Example 324

4-chloro-N-({4-chloro-3-[(3-cyano-4-fluorophenyl)oxy]-2-fluorophenyl}methyl)-1H-imidazole-5-carboxamide

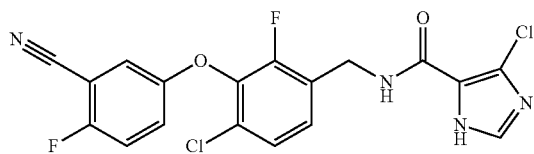

Step A: 4-chloro-N-({4-chloro-3-[(3-cyano-4-fluorophenyl)oxy]-2-fluorophenyl}methyl)-1-({[2-(trimethylsilyl)ethyl]oxy}methyl)-1H-imidazole-5-carboxamide To a solution of N-({3-[(2-amino-5-cyano-4-fluorophenyl)oxy]-4-chloro-2-fluorophenyl}methyl)-4-chloro-1-({[2-(trimethylsilyl)ethyl]oxy}methyl)-1H-imidazole-5-carboxamide (110 mg, 0.194 mmol) in Acetonitrile (8 ml) was added tert butyl nitrite (0.046 ml, 0.387 mmol) and the reaction mixture was stirred at RT for 1 hour. The reaction mixture was diluted with EtOAc and washed with water. The solvent was removed and the crude material was purified via silica gel chromatography to give 4-chloro-N-({4-chloro-3-[(3-cyano-4-fluorophenyl)oxy]-2-fluorophenyl}methyl)-1-({[2-(trimethylsilyl)ethyl]oxy}methyl)-1H-imidazole-5-carboxamide (49 mg, 0.089 mmol, 46% yield). 1H NMR (400 MHz, DMSO-$d_6$) δ ppm 8.76 (t, 1H), 7.98 (s, 1H), 7.42-7.59 (m, 3H), 7.29-7.42 (m, 2H), 5.49 (s, 2H), 4.48 (d, 2H), 3.38 (t, 2H), 0.75 (t, 2 H), −0.09 (s, 9H).

Step B: 4-chloro-N-({4-chloro-3-[(3-cyano-4-fluorophenyl)oxy]-2-fluorophenyl}methyl)-1H-imidazole-5-carboxamide To a solution of 4-chloro-N-({4-chloro-3-[(3-cyano-4-fluorophenyl)oxy]-2-fluorophenyl}methyl)-1-({[2-(trimethylsilyl)ethyl]oxy}methyl)-1H-imidazole-5-carboxamide (45 mg, 0.081 mmol) in DCM (4 ml) was added TFA (2.0 mL) and the reaction mixture was stirred at RT for 2 hours. The solvent was removed and the crude material was purified via reverse phase HPLC to give 4-chloro-N-({4-chloro-3-[(3-cyano-4-fluorophenyl)oxy]-2-fluorophenyl}methyl)-1H-imidazole-5-carboxamide (19 mg, 0.045 mmol, 55% yield). 1H NMR (400 MHz, METHANOL-$d_4$) δ ppm 7.74 (s, 1H) 7.29-7.40 (m, 3H) 7.13-7.29 (m, 2H) 4.61 (s, 2H). LC-MS (ES$^+$) m/z 423.12, [M+H].

Example 325

N-({3-[(2-amino-3-chloro-5-cyano-4-fluorophenyl)oxy]-4-chloro-2-fluorophenyl}methyl)-4-chloro-1H-imidazole-5-carboxamide

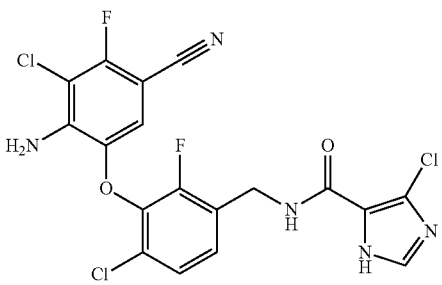

To a solution of N-({3-[(2-amino-5-cyano-4-fluorophenyl)oxy]-4-chloro-2-fluorophenyl}methyl)-4-chloro-1-({[2-(trimethylsilyl)ethyl]oxy}methyl)-1H-imidazole-5-carboxamide (188 mg, 0.331 mmol) and ammonium acetate (2.55 mg, 0.033 mmol) in Acetonitrile (4 ml) was added NCS (46.4 mg, 0.347 mmol) and the reaction mixture was stirred at 70° C. for 5 hours. The solvent was removed and the crude material was eluted through a plug of silica gel to give 125 mg of an inseparable mixture of product/starting material (approximately 7/1 by LCMS). This mixture was dissolved in DCM (4.00 ml) and treated with TFA (2.0 ml) for 2 hours at RT. The solvent was removed and the crude material was purified via reverse phase HPLC and neutralized to give N-({3-[(2-amino-3-chloro-5-cyano-4-fluorophenyl)oxy]-4-chloro-2-fluorophenyl}methyl)-4-chloro-1H-imidazole-5-carboxamide (74 mg, 0.157 mmol, 47% yield). 1H NMR (400 MHz, DMSO-$d_6$) δ ppm 8.19 (br. s., 1H), 7.73 (s, 1H), 7.43 (d, 1H), 7.29 (t, 1H), 6.98 (s, 2H), 6.81 (d, 1H), 4.48 (d, 2H). LC-MS (ES$^+$) m/z 472.01, [M+H].

Example 326

4-chloro-N-({4-chloro-3-[(3-chloro-5-cyano-4-fluorophenyl)oxy]-2-fluorophenyl}methyl)-1H-imidazole-5-carboxamide

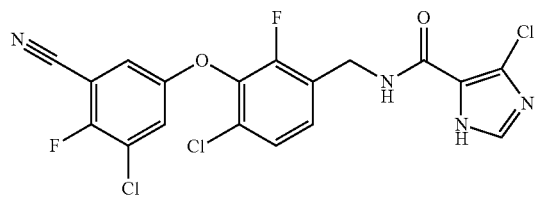

To a solution of N-({3-[(2-amino-3-chloro-5-cyano-4-fluorophenyl)oxy]-4-chloro-2-fluorophenyl}methyl)-4-chloro-1H-imidazole-5-carboxamide (38 mg, 0.080 mmol) in Acetonitrile (10 ml) was added tert-butyl nitrite (0.021 ml, 0.161 mmol) and the reaction mixture was stirred at RT for 2 hours. The reaction was quenched with methanol, the solvent was removed and the crude material was purified via reverse phase HPLC to give 4-chloro-N-({4-chloro-3-[(3-chloro-5-cyano-4-fluorophenyl)oxy]-2-fluorophenyl}methyl)-1H-imidazole-5-carboxamide (17 mg, 0.037 mmol, 46% yield). 1H NMR (DMSO-$d_6$) δ ppm 8.25 (br. s., 1H) 7.74 (s, 1H) 7.69 (dd, 1H) 7.60 (t, 1H) 7.45 (d, 1H) 7.32 (t, 1H) 4.48 (d, 2H). LC-MS (ES$^+$) m/z 457.05, [M+H].

Example 327

2-amino-4-chloro-N-[(4-chloro-3-{[3-cyano-5-(difluoromethyl)phenyl]oxy}-2-fluorophenyl)methyl]-1H-imidazole-5-carboxamide trifluoroacetate

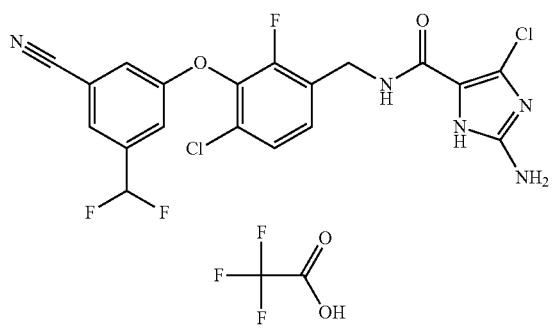

Step A: 1,1-dimethylethyl({4-chloro-3-[(3-cyano-5-formylphenyl)oxy]-2-fluorophenyl}methyl)carbamate To a solution of 1,1-dimethylethyl({4-chloro-3-[(3-cyano-5-ethenylphenyl)oxy]-2-fluorophenyl}methyl)carbamate (600 mg, 1.489 mmol) in THF (8 ml) and Water (4.00 ml) was added sodium periodate (956 mg, 4.47 mmol) and osmium tetroxide (2.5 wt % in 2-butanol) (0.374 ml, 0.030 mmol) and the reaction mixture was stirred at rt for 3 hours. The reaction mixture was diluted with EtOAc and washed with water. The solvent was removed and the crude material was purified via silica gel chromatography to give 1,1-dimethylethyl({4-chloro-3-[(3-cyano-5-formylphenyl)oxy]-2-fluorophenyl}methyl)carbamate (595 mg, 1.470 mmol, 99% yield). 1H NMR (400 MHz, DMSO-$d_6$) δ ppm 9.95 (s, 1H), 8.12 (s, 1H), 7.90 (s, 1H), 7.58-7.67 (m, 1H), 7.41-7.55 (m, 2H), 7.31 (t, 1H), 4.18 (d, 2H), 1.35 (s, 9H).

Step B: 1,1-dimethylethyl[(4-chloro-3-{[3-cyano-5-(difluoromethyl)phenyl]oxy}-2-fluorophenyl)methyl]carbamate To a solution of 1,1-dimethylethyl({4-chloro-3-[(3-cyano-5-formylphenyl)oxy]-2-fluorophenyl}methyl)carbamate (595 mg, 1.470 mmol) in DCM (15 ml) was added DAST (0.291 ml, 2.205 mmol) and the reaction mixture was stirred at RT for 5 hours. The reaction mixture was diluted with EtOAc and washed with water. The solvent was removed and the crude material was purified via silica gel chromatography to give 1,1-dimethylethyl[(4-chloro-3-{[3-cyano-5-(difluoromethyl)phenyl]oxy}-2-fluorophenyl)methyl]carbamate (215 mg, 0.504 mmol, 34% yield). 1H NMR (DMSO-$d_6$) δ ppm 7.83 (s, 1H) 7.68 (br. s., 1H) 7.41-7.55 (m, 3H) 7.29 (t, 1H) 6.88-7.22 (m, 1H) 4.18 (d, 2H) 1.37 (s, 9H).

Step C: 3-{[3-(aminomethyl)-6-chloro-2-fluorophenyl]oxy}-5-(difluoromethyl)benzonitrile trifluoroacetate To a solution of 1,1-dimethylethyl[(4-chloro-3-{[3-cyano-5-(difluoromethyl)phenyl]oxy}-2-fluorophenyl)methyl]carbamate (210 mg, 0.492 mmol) in DCM (10 ml) was added TFA (3.0 mL, 38.9 mmol) and the reaction mixture was stirred at RT for 30 minutes. The solvent was removed and the crude material 3-{[3-(aminomethyl)-6-chloro-2-fluorophenyl]oxy}-5-(difluoromethyl)benzonitrile trifluoroacetate (183 mg, 0.415 mmol, 84% yield) was used directly in the next step without purification. 1H NMR (DMSO-$d_6$) d ppm 8.24 (br. s., 2H) 7.84 (s, 1H) 7.44-7.75 (m, 4H) 6.54-7.28 (m, 1H) 4.09 (d, 2H).

Step D: 2-azido-4-chloro-N-[(4-chloro-3-{[3-cyano-5-(difluoromethyl)phenyl]oxy}-2-fluorophenyl)methyl]-1H-imidazole-5-carboxamide trifluoroacetate To a solution of 3-{[3-(aminomethyl)-6-chloro-2-fluorophenyl]oxy}-5-(difluoromethyl)benzonitrile hydrochloride (58 mg, 0.132 mmol), 2-azido-4-chloro-1H-imidazole-5-carboxylic acid (24.68 mg, 0.132 mmol), Hunig'sBase (0.046 ml, 0.263 mmol) and HOBT (20.15 mg, 0.132 mmol) in DMF (6 ml) was added EDC (25.2 mg, 0.132 mmol) and the reaction mixture was stirred at RT for 3 hours. The solvent was removed and the crude material was purified via reverse phase HPLC to give 2-azido-4-chloro-N-[(4-chloro-3-{[3-cyano-5-(difluoromethyl)phenyl]oxy}-2-fluorophenyl)methyl]-1H-imidazole-5-carboxamide trifluoroacetate (58 mg, 0.095 mmol, 72.2% yield). 1H NMR (DMSO-$d_6$) d ppm 8.13 (br. s., 1H) 7.81 (s, 1H) 7.67 (s, 1H) 7.48 (d, 1H) 7.43 (s, 1H) 7.28-7.39 (m, 1H) 7.03 (t, 1H) 4.48 (d, 2H). LC-MS (ES$^+$) m/z 496.06, [M+H].

Step E: 2-amino-4-chloro-N-[(4-chloro-3-{[3-cyano-5-(difluoromethyl)phenyl]oxy}-2-fluorophenyl)methyl]-1H-imidazole-5-carboxamide trifluoroacetate To a solution of 2-azido-4-chloro-N-[(4-chloro-3-{[3-cyano-5-(difluoromethyl)phenyl]oxy}-2-fluorophenyl)methyl]-1H-imidazole-5-carboxamide trifluoroacetate (39.0 mg, 0.079 mmol) in THF (6 ml) was added water (2.83 µl, 0.157 mmol) followed by trimethyl phosphine (2.0 M solution in THF) (0.039 ml, 0.079 mmol) and the reaction mixture was stirred at RT for 15 minutes. The solvent was removed and the crude material was purified via reverse phase HPLC to give 2-amino-4-chloro-N-[(4-chloro-3-{[3-cyano-5-(difluoromethyl)phenyl]oxy}-2-fluorophenyl)methyl]-1H-imidazole-5-carboxamide trifluoroacetate (28 mg, 0.048 mmol, 61.0% yield). $^1$H NMR (DMSO-$d_6$) δ ppm 7.76-7.88 (m, 2H) 7.68 (s, 1H) 7.39-7.54 (m, 2H) 7.31 (t, 1H) 6.84-7.20 (m, 1H) 5.97 (br.s., 2H) 4.45 (d, 2H). LC-MS (ES$^+$) m/z 470.05 [M+H].

Example 328

4-chloro-N-({4-chloro-3-[(4-cyano-2-fluorophenyl)oxy]-2-fluorophenyl}methyl)-2-methyl-1H-imidazole-5-carboxamide

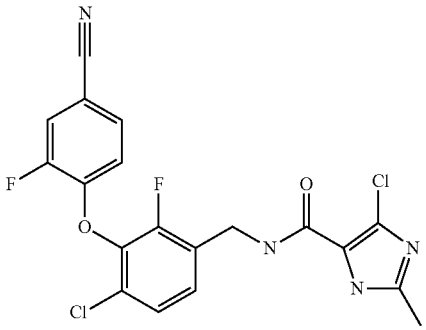

Step A: 4-[(6-chloro-2-fluoro-3-methylphenyl)oxy]-3-fluorobenzonitrile

To a solution of 6-chloro-2-fluoro-3-methylphenol (3.25 g, 20.24 mmol) and 18-crown-6 (0.535 g, 2.024 mmol) in DMSO (40 ml) was added potassium tert-butoxide (20 wt % in THF) (12.49 g, 22.26 mmol) and the reaction mixture was stirred at rt for 30 minutes. Next, 4-bromo-3-fluorobenzonitrile (4.05 g, 20.24 mmol) was added and the reaction mixture stirred at 135° C. for 3 days. The reaction mixture was diluted with EtOAc and washed with water. The solvent was removed and the crude material was purified via silica gel chromatography to give 4-[(6-chloro-2-fluoro-3-methylphenyl)oxy]-3-fluorobenzonitrile (4.56 g, 16.30 mmol, 81% yield). 1H NMR (400 MHz, DMSO-$d_6$) δ ppm 8.05 (dd, 1H), 7.59 (d, 1H), 7.35-7.43 (m, 1H), 7.30 (t, 1H), 6.89 (t, 1H), 2.24 (d, 3H).

Step B: 4-{[3-(bromomethyl)-6-chloro-2-fluorophenyl]oxy}-3-fluorobenzonitrile

To a solution of 4-[(6-chloro-2-fluoro-3-methylphenyl)oxy]-3-fluorobenzonitrile (2.41 g, 8.62 mmol) and NBS (1.534 g, 8.62 mmol) in carbon tetrachloride (150 ml) was added AIBN (1.415 g, 8.62 mmol) and the reaction mixture was stirred at 80° C. overnight. The solvent was removed and the crude material was purified via silica gel chromatography to give 4-{[3-(bromomethyl)-6-chloro-2-fluorophenyl]oxy}-3-fluorobenzonitrile (1.60 g, 4.46 mmol, 52% yield). 1H NMR (400 MHz, DMSO-$d_6$) δ ppm 8.08 (dd, 1H), 7.62 (d, 1H), 7.48-7.59 (m, 2H), 6.92 (t, 1H), 4.70 (s, 2H).

Step C: 4-{[3-(aminomethyl)-6-chloro-2-fluorophenyl]oxy}-3-fluorobenzonitrile

To a solution of ammonia (7.0 N solution in MeOH) (47.5 ml, 332 mmol) was added dropwise 4-{[3-(bromomethyl)-6-chloro-2-fluorophenyl]oxy}-3-fluorobenzonitrile (1.49 g, 4.16 mmol) in solution of 20 mL DCM. The mixture was stirred overnight and the solvent was removed to give 4-{[3-(aminomethyl)-6-chloro-2-fluorophenyl]oxy}-3-fluorobenzonitrile hydrobromide (1.26 g, 3.35 mmol, 81% yield). 1H NMR (400 MHz, DMSO-$d_6$) d ppm 8.10 (dd, 1H), 7.66 (d, 1H), 7.57-7.63 (m, 1H), 7.54 (t, 1H), 7.02 (br. s., 2H), 6.93 (t, 1H), 4.00 (s, 2H). 1H NMR (400 MHz, DMSO-$d_6$) δ ppm 8.10 (dd, 1H), 7.66 (d, 1H), 7.57-7.63 (m, 1H), 7.54 (t, 1H), 7.02 (br. s., 2H), 6.93 (t, 1H), 4.00 (s, 2H).

Step D: 4-chloro-N-({4-chloro-3-[(4-cyano-2-fluorophenyl)oxy]-2-fluorophenyl}methyl)-2-methyl-1H-imidazole-5-carboxamide To a solution of 4-{[3-(aminomethyl)-6-chloro-2-fluorophenyl]oxy}-3-fluorobenzonitrile (40.0 mg, 0.136 mmol), 4-chloro-2-methyl-1H-imidazole-5-carboxylic acid (21.79 mg, 0.136 mmol) and HATU (51.6 mg, 0.136 mmol) in DMF (3 ml) was added diisopropylethyl amine (0.047 ml, 0.271 mmol) and the reaction mixture was stirred at rt for 15 minutes. The reaction mixture was purified via reverse phase HPLC and neutralized to give 4-chloro-N-({4-chloro-3-[(4-cyano-2-fluorophenyl)oxy]-2-fluorophenyl}methyl)-2-methyl-1H-imidazole-5-carboxamide (13 mg, 0.030 mmol, 22% yield) 1H NMR (400 MHz, METHANOL-$d_4$) δ ppm 7.73 (d, 1H), 7.47 (d, 1H), 7.29-7.42 (m, 2H), 6.87 (t, 1H), 4.52-4.73 (m, 2H), 2.34 (s, 3H). LC-MS (ES$^+$) m/z 437.11, [M+H].

Example 329

4-bromo-N-({4-chloro-3-[(3-chloro-5-cyanophenyl)oxy]-2-fluorophenyl}methyl)-1H-imidazole-5-carboxamide

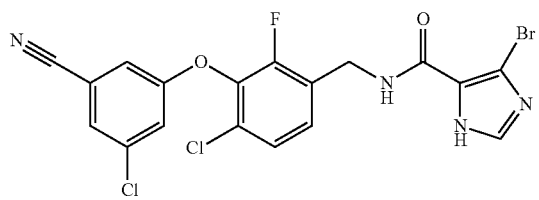

Step A: 2,4,5-tribromo-1-({[2-(trimethylsilyl)ethyl]oxy}methyl)-1H-imidazole

A solution of 2,4,5-tribromo-1H-imidazole (3.00 g, 9.84 mmol) in THF (25 mL) was added slowly to a 0° C. solution of NaH (0.41 g of a 60% suspension in mineral oil, 10.34 mmol) in THF (10 mL). The reaction mixture was stirred for 2 h at RT, cooled to 0° C., SEMCl (1.83 mL, 10.34 mmol) was added dropwise, and stirring was continued overnight. Sat'd NaHCO$_3$ was added and the solution was extracted with CH$_2$Cl$_2$. The organic layer was dried (Na$_2$SO$_4$), filtered and purified by silica gel chromatography (2-25% EtOAc/hexanes) to afford the title compound (4.21 g, 98%) as a white solid. 1H NMR (400 MHz, CHLOROFORM-d) δ ppm 5.34 (s, 2H), 3.62 (t, J=8.15 Hz, 2H), 0.95 (t, J=8.10 Hz, 2H), 0.02 (s, 9H).

Step B: 4-bromo-1-({[2-(trimethylsilyl)ethyl]oxy}methyl)-1H-imidazole-5-carbaldehyde nBuLi (4.9 mL of a 2.37 M solution in hexanes, 11.73 mmol) was added dropwise to a −78° C. solution of 2,4,5-tribromo-1-({[2-(trimethylsilyl)ethyl]oxy}methyl)-1H-imidazole (5.10 g, 11.73 mmol) in THF (120 mL). The reaction mixture was stirred for 20 min and TMSCl (1.49 mL, 11.73 mmol) was added dropwise. The cooling bath was removed and the reaction mixture was allowed to warm to RT over 2 h. After 4 h at RT, the solution was cooled to −78° C. and nBuLi (4.9 mL of a 2.37 M solution in hexanes, 11.73 mmol) was added dropwise. After 20 min, DMF (4.9 mL, 58.66 mmol) was added dropwise and the reaction was stirred at RT overnight, quenched by addition of sat'd NH$_4$Cl and extracted with EtOAc. The organic phase was dried (Na$_2$SO$_4$), filtered, and purified by silica gel chromatography (0-30% EtOAc/hexanes) to afford the title compound (1.93 g, 54%) as a yellow oil. 1H NMR (400 MHz, CHLOROFORM-d) δ ppm 9.80 (s, 1H), 7.78 (s, 1H), 5.68 (s, 2H), 3.62 (t, J=8.29 Hz, 2H), 0.95 (t, J=8.29 Hz, 2H), 0.00 (s, 9H).

Step C: 4-bromo-1-({[2-(trimethylsilyl)ethyl]oxy}methyl)-1H-imidazole-5-carboxylic acid A solution of NaClO$_2$ (5.73 g, 63.3 mmol) and NaH$_2$PO$_4$·H$_2$O (5.24 g, 38.0 mmol) in H$_2$O (13.6 mL) and t-BuOH (4.5 mL) was added to a solution of 4-bromo-1-({[2-(trimethylsilyl)ethyl]oxy}methyl)-1H-imidazole-5-carbaldehyde (1.93 g, 6.3 mmol) and 2-methyl-2-butene (38.0 mL of a 2M solution in THF, 76.0 mmol) in THF (19.0 mL). The reaction mixture was stirred at RT overnight and extracted with EtOAc. The organic layer was dried (Na$_2$SO$_4$), filtered and dried to provide the title compound as a white solid that was assumed to be quantitative and used without further purification. 1H NMR (400 MHz, METHANOL-$d_4$) δ ppm 7.98 (s, 1H), 5.70 (s, 2H), 3.58 (t, J=7.8 Hz, 2H), 0.89 (t, J=7.8 Hz, 2H), −0.03 (s, 9H).

Step D: 4-bromo-N-({4-chloro-3-[(3-chloro-5-cyanophenyl)oxy]-2-fluorophenyl}methyl)-1H-imidazole-5-carboxamide The title compound (0.18 g, 53%) was obtained as a white solid from 2,4,5-tribromo-1-({[2-(trimethylsilyl)ethyl]oxy}methyl)-1H-imidazole (0.32 g, 1.04 mmol) using a procedure and process similar to that described herein. The above acid and 3-{[3-(aminomethyl)-6-chloro-2-fluorophenyl]oxy}-5-chlorobenzonitrile (0.17 g, 0.55 mmol) were employed in a similar process described herein to prepare the title compound (0.19 g, 70%) as a white solid after deprotection and purification by silica gel chromatography (0-3% MeOH (2M NH$_3$)/CH$_2$Cl$_2$). 1H NMR (400 MHz, METHANOL-$d_4$) δ ppm 7.76 (s, 1H), 7.56 (s, 1H), 7.36-7.44 (m, 2H), 7.27 (s, 1H), 7.24 (s, 1H), 4.65 (s, 2H). ES-LCMS: m/z 483.0, 484.9, 486.9 (M+1).

Example 330

N-({4-chloro-3-[(3-chloro-5-cyanophenyl)oxy]-2-fluorophenyl}methyl)-4-(hydroxymethyl)-1H-imidazole-2-carboxamide

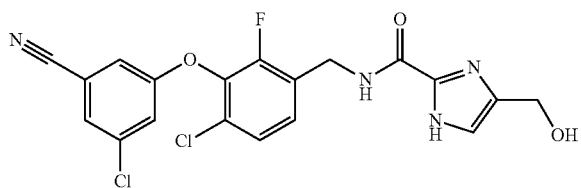

Step A: 4-({[(1,1-dimethylethyl)(dimethyl)silyl]oxy}methyl)-1H-imidazole

A solution of 1H-imidazol-4-ylmethanol (2 g, 20.4 mmol), TBSCl (3.7 g, 24.5 mmol), and imidazole (2.1 g, 30.6 mmol) in DMF (20 mL) was stirred at 50° C. for 20 h. Sat'd NaHCO$_3$ was added and the solution was extracted with CH$_2$Cl$_2$. The organic layer was dried (Na$_2$SO$_4$), filtered and purified by silica gel chromatography (0-10% MeOH (2M NH$_3$) in CH$_2$Cl$_2$) to afford the title compound (3.5 g, 82%) as a clear oil. $^1$H NMR (400 MHz, CHLOROFORM-d) δ ppm 7.64-7.73 (m, 1H), 6.97 (s, 1H), 4.76 (s, 2H), 0.92 (s, 9H), 0.10 (s, 6H).

Step B: 4-({[(1,1-dimethylethyl)(dimethyl)silyl]oxy}methyl)-1-({[2-(trimethylsilyl)ethyl]oxy}methyl)-1H-imidazole (+isomer)

60% NaH (0.4 g, 10 mmol) was added in two portions to a solution of 4-({[(1,1-dimethylethyl)(dimethyl)silyl]oxy}methyl)-1H-imidazole in DMF at 0° C. The reaction mixture was stirred at rt for 2 h and SEMCl (1.8 mL, 10 mmol) was added dropwise. After 20 h at RT, sat'd NaHCO$_3$ was added and the solution was extracted with CH$_2$Cl$_2$. The organic layer was dried (Na$_2$SO$_4$), filtered and purified by silica gel chromatography (0-60% EtOAc/hex) to afford the title compound (2.3 g, 70%) as a yellow oil and as a mixture of the expected two isomers. Major isomer: $^1$H NMR (400 MHz, CHLOROFORM-d) δ ppm 7.64-7.70 (m, 1H), 6.99 (s, 1H), 5.39 (s, 2H), 4.73 (s, 2H), 3.49 (m, 2H), 0.91-0.93 (m, 2H), 0.90 (s, 9H), 0.08 (s, 6H), −0.01 (s, 9H).

Step C: Ethyl 4-({[(1,1-dimethylethyl)(dimethyl)silyl]oxy}methyl)-1-({[2-(trimethylsilyl)ethyl]oxy}methyl)-1H-imidazole-2-carboxylate (+isomer)

nBuLi (2.2 mL of a 1.9M solution in hexanes, 4.2 mmol) was added dropwise to a −78° C. solution of 4-({[(1,1-dimethylethyl)(dimethyl)silyl]oxy}methyl)-1-({[2-(trimethylsilyl)ethyl]oxy}methyl)-1H-imidazole (1.20 g, 3.5 mmol) in THF (10 mL). The reaction mixture was stirred at −60° C. for 2 h, cooled to −78° C. and ethyl chloroformate (0.70 mL, 7.3 mmol) was added dropwise. The solution was allowed to warm to RT, quenched by addition of sat'd NaHCO$_3$ and extracted with CH$_2$Cl$_2$. The organic phase was dried (Na$_2$SO$_4$), filtered, and purified by silica gel chromatography (0-50% EtOAc/hex) to afford the title compound (1.21 g, 83%) as a light brown oil and as a mixture of the expected two isomers. Major isomer: $^1$H NMR (400 MHz, CHLOROFORM-d) δ ppm 7.05 (s, 1H), 5.90 (s, 2H), 4.75 (s, 2H), 4.34-4.43 (m, 2H) 3.48-3.58 (m, 2H) 1.40 (t, J=7.15 Hz, 3H), 0.91-0.89 (m, 2H), 0.87 (s, 9H), 0.06 (s, 6H), −0.06 (s, 9H).

Step D: N-({4-chloro-3-[(3-chloro-5-cyanophenyl)oxy]-2-fluorophenyl}methyl)-4-(hydroxymethyl)-1H-imidazole-2-carboxamide A solution of ethyl 4-({[(1,1-dimethylethyl)(dimethyl)silyl]oxy}methyl)-1-({[2-(trimethylsilyl)ethyl]oxy}methyl)-1H-imidazole-2-carboxylate (0.201 g, 0.49 mmol) in 6N KOH (0.10 mL, 0.6 mmol) and ethanol (1.5 mL) was stirred at RT for 30 mins and evaporated to dryness. The residue was stirred with 3-{[3-(aminomethyl)-6-chloro-2-fluorophenyl]oxy}-5-chlorobenzonitrile (0.10 g, 0.32 mmol), HATU (0.203 g, 0.53 mmol) and DIEA (0.085 mL, 0.49 mmol) in DMF (3 mL) at RT overnight. Sat'd NaHCO$_3$ was added and the aqueous layer was extracted with CH$_2$Cl$_2$. The organic phase was dried (Na$_2$SO$_4$), filtered, and purified by silica gel chromatography (0-50% EtOAc/hex) to afford N-({4-chloro-3-[(3-chloro-5-cyanophenyl)oxy]-2-fluorophenyl}methyl)-4-({[(1,1-dimethylethyl)(dimethyl)silyl]oxy}methyl)-1-({[2-(trimethylsilyl)ethyl]oxy}methyl)-1H-imidazole-2-carboxamide (0.13 mg, 58%) as a brown oil and as a mixture of the expected two isomers. This material was stirred in TBAF (2 mL of a 1N solution in THF, 0.2 mmol) for 1 h. Sat'd NaHCO$_3$ was added and the aqueous layer was extracted with CH$_2$Cl$_2$. The residue was stirred with TFA (0.4 mL) in EtOH (0.02 mL) and CH$_2$Cl$_2$ (0.8 mL) for 8 h and the solution was evaporated and purified by silica gel chromatography (0-100% EtOAc/hexs, then 0-5% MeOH (2M NH$_3$)/CH$_2$Cl$_2$) to provide the title compound (0.0163 g, 20%) as a white solid. 1H NMR (400 MHz, METHANOL-d$_4$) δ ppm 7.55 (t, J=1.51 Hz, 1H), 7.35-7.43 (m, 2 H), 7.28 (t, J=2.06 Hz, 1H), 7.22-7.26 (m, 1H), 7.15 (br. s., 1H), 4.64 (s, 2H), 4.57 (s, 2H). ES-LCMS: m/z 435.1, 437.0 (M+1).

Example 331

N-({4-chloro-3-[(3-chloro-5-cyanophenyl)oxy]-2-fluorophenyl}methyl)-4-(4-morpholinylmethyl)-1H-imidazole-2-carboxamide

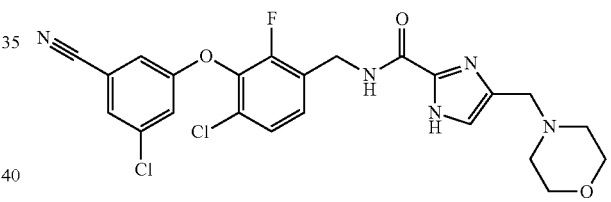

Step A: N-({4-chloro-3-[(3-chloro-5-cyanophenyl)oxy]-2-fluorophenyl}methyl)-4-formyl-1H-imidazole-2-carboxamide A solution of N-({4-chloro-3-[(3-chloro-5-cyanophenyl)oxy]-2-fluorophenyl}methyl)-4-(hydroxymethyl)-1H-imidazole-2-carboxamide (0.40 g, 0.92 mmol) and MnO$_2$ (0.80 g, 9.2 mmol) in CH$_2$Cl$_2$ (10 mL) was stirred at RT for 2 h. The solution was filtered through celite and evaporated to provide the crude title compound which was used without further purification.

Step B: N-({4-chloro-3-[(3-chloro-5-cyanophenyl)oxy]-2-fluorophenyl}methyl)-4-(4-morpholinylmethyl)-1H-imidazole-2-carboxamide A solution of N-({4-chloro-3-[(3-chloro-5-cyanophenyl)oxy]-2-fluorophenyl}methyl)-4-formyl-1H-imidazole-2-carboxamide (0.11 mmol), morpholine (0.020 mL, 0.22 mmol), NaBH(OAc)$_3$ (0.047 g, 0.22 mmol) in CH$_2$Cl$_2$ (1.5 mL) was stirred at RT overnight. Sat'd NaHCO$_3$ was added and the solution was extracted with CH$_2$Cl$_2$. The organic phase was dried (Na$_2$SO$_4$), filtered, and purified by Reverse-Phase HPLC (water:acetonitrile with 0.1% TFA) and silica gel chromatography to afford the title compound (0.006 g, 11%) as a white solid. $^1$H NMR (400 MHz, METHANOL-d$_4$) δ ppm 7.55 (t, J=1.47 Hz, 1H), 7.36-7.42 (m, 2H), 7.28 (t, J=2.06 Hz, 1H), 7.22-7.25 (m, 1H), 7.20 (br. s., 1H), 4.63 (s, 2H), 3.65-3.75 (m, 4H), 3.54 (br. s., 2H), 2.44-2.60 (m, 4H). ES-LCMS: m/z 504.1, 506.0 (M+1).

Example 332

N-({4-chloro-3-[(3-chloro-5-cyanophenyl)oxy]-2-fluorophenyl}methyl)-(4-2-hydroxyethyl)-1H-imidazole-2-carboxamide

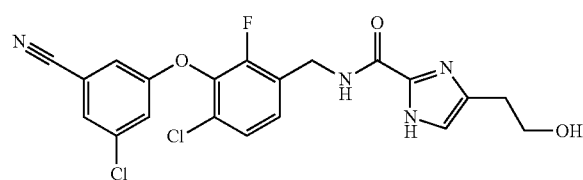

Step A: methyl 1H-imidazol-4-ylacetate

Thionyl chloride (3 mL, 41.1 mmol) was added slowly over the course of 30 mins to a 0° C. solution of imidazole acetic acid sodium salt (1.84 g, 10.0 mmol) in MeOH (40 mL) and the solution was stirred at RT overnight and evaporated. Aqueous NH$_4$OH was slowly added and the solution was extracted with 9:1 CH$_2$Cl$_2$:MeOH to provide the title compound (1.18 g, 84%) as a yellow oil. $^1$H NMR (400 MHz, CHLOROFORM-d) δ ppm 7.69 (d, J=5.22 Hz, 1H), 7.02 (br. s., 1H), 3.63-3.82 (m, 5H).

Step B: methyl[1-({[2-(trimethylsilyl)ethyl]oxy}methyl)-1H-imidazol-4-yl]acetate (+isomer)

60% dispersion of NaH in mineral oil (0.40 g, 10.0 mmol) was added slowly to a 0° C. solution of methyl 1H-imidazol-4-ylacetate (1.18 g, 8.4 mmol) in DMF (20 mL). The solution was stirred at RT for 2 h, cooled to 0° C., and SEMCl (1.5 mL, 8.5 mmol) was added dropwise. The reaction mixture was stirred for 3 days at RT. Sat'd NaHCO$_3$ was added and the solution was extracted with CH$_2$Cl$_2$. The organic phase was dried (Na$_2$SO$_4$), filtered, and purified by silica gel chromatography (0-100% EtOAc/hexanes) to provide the title compound (1.44 g, 5.3 mmol) as a brown oil as a mixture of expected isomers. Major isomer: $^1$H NMR (400 MHz, CHLOROFORM-d) δ ppm 7.54 (s, 1H), 7.01 (s, 1H), 5.23 (s, 2H), 3.72 (d, J=3.02 Hz, 5H), 3.44-3.54 (m, 2H), 0.83-0.95 (m, 2H), −0.01 (s, 9H).

Step C: 4-(2-{[(1,1-dimethylethyl)(diphenyl)silyl]oxy}ethyl)-1-({[2-(trimethylsilyl)ethyl]oxy}methyl)-1H-imidazole A solution of methyl[1-({[2-(trimethylsilyl)ethyl]oxy}methyl)-1H-imidazol-4-yl]acetate (1.44 g, 5.3 mmol) and LAH (10.6 mL of a 1M solution in THF, 10.6 mmol) in THF (30 mL) was heated under reflux for 7 h. 1M Na2CO3 was added dropwise until the residual LAH was quenched and the solution was stirred with CH$_2$Cl$_2$ overnight and filtered through celite. The filtrate was concentrated to give the alcohol as a light brown oil. A solution of this alcohol, imidazole (0.28 g, 4.0 mmol) and TBDPSCl (0.85 mL, 3.27 mmol) in DMF (3.5 mL) was stirred at RT for 6 h. The solvent was evaporated and the residue was purified by silica gel chromatography (10-100% EtOAc/hexanes) to provide the title compound (0.56 g, 22%) as a clear oil and as a mixture of expected isomers. Major isomer: $^1$H NMR (400 MHz, CHLOROFORM-d) δ ppm 7.61 (d, J=6.96 Hz, 4H), 7.48 (s, 1H), 7.34-7.44 (m, 6H), 6.87 (s, 1H), 5.16 (s, 2H), 3.86 (t, J=6.64 Hz, 2H), 3.39 (t, J=8.15 Hz, 2H), 2.91 (t, J=6.68 Hz, 2H), 1.04 (s, 9H), 0.84 (t, J=8.15 Hz, 2H), −0.02 (s, 9H)

Step D: ethyl 4-(2-{[(1,1-dimethylethyl)(diphenyl)silyl]oxy}ethyl)-1-({[2-(trimethylsilyl)ethyl]oxy}methyl)-1H-imidazole-2-carboxylate The procedure and process are similar to that described herein except that 4-(2-{[(1,1-dimethylethyl)(diphenyl)silyl]oxy}ethyl)-1-({[2-(trimethylsilyl)ethyl]oxy}methyl)-1H-imidazole (0.56 g, 1.15 mmol) was employed to provide the title compound (0.52 g, 81%) as a yellow oil and as a mixture of expected isomers. Major isomer: $^1$H NMR (400 MHz, CHLOROFORM-d) δ ppm 7.63 (d, J=6.78 Hz, 4H), 7.30-7.47 (m, 6H), 7.10 (s, 1H), 5.73 (s, 2H), 4.37-4.48 (m, 2H), 3.89-3.99 (m, 2H), 3.47-3.60 (m, 2H), 2.89-2.98 (m, 2H), 1.35-1.50 (m, 3H), 1.04 (s, 9H), −0.03 (s, 9H).

Step E: N-({4-chloro-3-[(3-chloro-5-cyanophenyl)oxy]-2-fluorophenyl}methyl)-4-(2-hydroxyethyl)-1H-imidazole-2-carboxamide The procedure and process are similar to that described herein except that ethyl 4-(2-{[(1,1-dimethylethyl)(diphenyl)silyl]oxy}ethyl)-1-({[2-(trimethylsilyl)ethyl]oxy}methyl)-1H-imidazole-2-carboxylate (0.52 g, 0.94 mmol) was employed to provide the title compound (0.086 g, 21% overall) as a white solid. $^1$H NMR (400 MHz, METHANOL-d$_4$) δ ppm 7.54 (s, 1H), 7.33-7.42 (m, 2H), 7.25-7.29 (m, 1H), 7.23 (s, 1H), 7.00 (br. s., 1H), 4.62 (s, 2H), 3.79 (t, J=6.68 Hz, 2H), 2.82 (t, 2H). ES-LCMS: m/z 449.0, 451.0 (M+1).

Example 333

N-({4-chloro-3-[(3-chloro-5-cyanophenyl)oxy]-2-fluorophenyl}methyl)-2-methyl-1H-imidazole-4-carboxamide trifluoroacetate

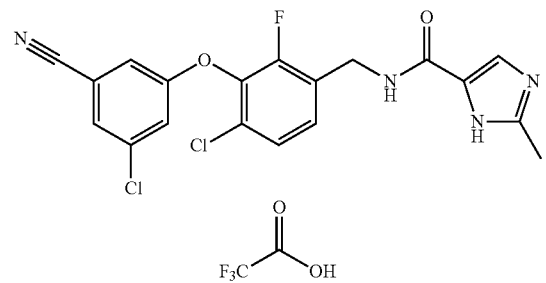

A solution of NaClO$_2$ (2.5 g, 27.5 mmol) and NaH$_2$PO4.H$_2$O (2.3 g, 16.3 mmol) in water (6.1 mL) was added to a solution of 4-formyl-2-methylimidazole (0.30 g, 2.72 mmol), 2-methyl-2-butene (17.0 mL of a 2M solution in THF, 34.0 mmol), tBuOH (2.0 mL), and THF (8.5 mL). The solution was stirred at RT for 3 h. EtOAc (10 mL) was added and the resulting solid was filtered and dried to provide 2-methyl-1H-imidazole-4-carboxylic acid (0.33 g, 97%) as a white solid which was used without further purification. A solution of the above acid (0.035 g, 0.28 mmol) in oxalyl chloride (0.15 mL, 1.67 mmol) was heated under reflux for 1 h and then evaporated to dryness. The residue was stirred with 3-{[3-(aminomethyl)-6-chloro-2-fluorophenyl]oxy}-5-chlorobenzonitrile (0.061 g, 0.28 mmol) in CH$_3$CN (3. mL), DMF (1 mL), and DIEA (0.4 mL, 2.3 mmol) at RT overnight. Aqueous Na2CO3 was added, and the solution was extracted with 9:1 CH$_2$Cl$_2$:MeOH. The organic phase was dried (Na$_2$SO$_4$), filtered, and purified by Reverse-Phase HPLC (water:acetonitrile with 0.1% TFA) to provide the title compound (0.010 g, 7%) as an off-white solid. $^1$H NMR (400 MHz, DMSO-d$_6$) δ ppm 9.15 (br. s., 1H), 7.93 (s, 1H), 7.83 (t, J=1.47 Hz, 1H), 7.49-7.55 (m, 2H), 7.48 (t, J=2.11 Hz, 1H), 7.39 (t, J=7.97 Hz, 1H), 4.55 (d, J=5.59 Hz, 2H), 2.54 (s, 3H). ES-LCMS: m/z 419.3, 421.3 (M+1).

Example 334

N-({4-chloro-3-[(3-chloro-5-cyanophenyl)oxy]-2-fluorophenyl}methyl)-4-methyl-1H-imidazole-5-carboxamide

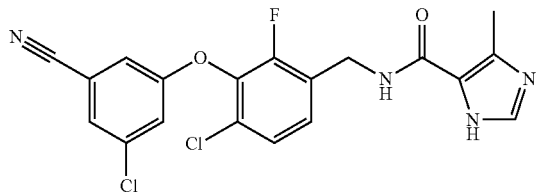

Step A: 5-methyl-1-({[2-(trimethylsilyl)ethyl]oxy}methyl)-1H-imidazole-4-carbaldehyde (+isomer)

A solution of 4-methyl-1H-imidazole-5-carbaldehyde (1.00 g, 9.1 mmol) in DMF (25 mL) was added dropwise to a 0° C. solution of NaH (0.36 g of a 60% dispersion in mineral oil, 9.1 mmol) in DMF (10 mL). The reaction mixture was stirred for 2 h at RT, cooled to 0° C. and treated with a solution of SEMCl (1.6 mL, 9.1 mmol) in THF (10 mL). After stirring overnight at RT, the solution was quenched by the addition of water and extracted with CH$_2$Cl$_2$. The organic phase was dried (Na$_2$SO$_4$), filtered, and purified by silica gel chromatography (10-70% EtOAc/hexanes) to provide the title compound (2.11 g, 97%) as a clear oil and as a mixture of expected isomers. Major isomer: 1H NMR (400 MHz, CHLOROFORM-d) δ ppm 9.89 (s, 1H), 7.84 (s, 1H), 5.67 (s, 2H), 3.57-3.65 (m, 2H), 2.57 (s, 3H), 0.87-0.99 (m, 2H), 0.00 (d, J=0.73 Hz, 9H).

Step B: 5-methyl-1-({[2-(trimethylsilyl)ethyl]oxy}methyl)-1H-imidazole-4-carboxylic acid The title compound was obtained from 5-methyl-1-({[2-(trimethylsilyl)ethyl]oxy}methyl)-1H-imidazole-4-carbaldehyde using a procedure and process similar to that described herein. The title compound, which was a single isomer, precipitated out of solution as a white solid (0.48 g, 45%) and was collected by filtration. 1H NMR (400 MHz, DMSO-d$_6$) δ ppm 7.77 (s, 1H), 5.33 (s, 2H), 3.46 (t, J=7.90 Hz, 2H), 2.46 (s, 3H), 0.84 (t, J=7.90 Hz, 2H), −0.05 (s, 9H).

Step C: N-({4-chloro-3-[(3-chloro-5-cyanophenyl)oxy]-2-fluorophenyl}methyl)-4-methyl-1H-imidazole-5-carboxamide The procedure and process are similar to that described herein except that 5-methyl-1-({[2-(trimethylsilyl)ethyl]oxy}methyl)-1H-imidazole-4-carboxylic acid (0.077 g, 0.30 mmol) and 3-{[3-(aminomethyl)-6-chloro-2-fluorophenyl]oxy}-5-chlorobenzonitrile (0.093 g, 0.30 mmol) were employed to provide the title compound (0.32 g, 25% overall) as a white solid after deprotection and purification by Reverse-Phase HPLC (water:acetonitrile with 0.1% NH$_4$OH. $^1$H NMR (400 MHz, DMSO-d$_6$) δ ppm 12.29 (br. s., 1H), 8.43 (t, J=5.84 Hz, 1H), 7.82 (s, 1H), 7.57 (s, 1H), 7.44-7.54 (m, 3H), 7.32 (t, J=7.83 Hz, 1H), 4.45 (d, J=6.04 Hz, 2H), 2.43 (s, 3H). ES-LCMS: m/z 419.0, 421.0 (M+1).

Example 335

4-bromo-N-({4-chloro-3-[(3-chloro-5-cyanophenyl)oxy]-2-fluorophenyl}methyl)-2-ethyl-1H-imidazole-5-carboxamide

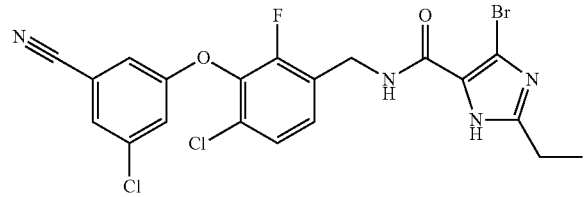

Step A: 4-bromo-2-ethyl-1-({[2-(trimethylsilyl)ethyl]oxy}methyl)-1H-imidazole-5-carbaldehyde n-BuLi (1.42 mL of a 1.6 M solution in hexanes, 2.24 mmol) was added dropwise to a −78° C. solution of 2,4,5-tribromo-1-({[2-(trimethylsilyl)ethyl]oxy}methyl)-1H-imidazole (0.98 g, 2.24 mmol) in THF (46 mL). The reaction mixture was stirred for 30 min and bromoethane (0.17 mL, 2.24 mmol) was added dropwise. The solution was stirred for 4 h at RT, cooled to −78° C., and n-BuLi (1.42 mL of a 1.6 M solution in hexanes, 2.24 mmol) was added dropwise. After 30 mins, DMF (2 mL, 23.9 mmol) was added. The reaction mixture was allowed to warm to RT, quenched by addition of sat'd NH$_4$Cl and extracted with CH$_2$Cl$_2$. The organic phase was dried (Na$_2$SO$_4$), filtered, and purified by silica gel chromatography (0-70% EtOAc/hex) to afford the title compound (0.16 g, 22%) as a clear oil. 1H NMR (400 MHz, CHLOROFORM-d) δ ppm 9.69 (s, 1H), 5.70 (s, 2H), 3.50-3.60 (m, 2H), 2.79 (q, J=7.51 Hz, 2H), 1.35 (t, J=7.56 Hz, 3H), 0.78-0.98 (m, 2H), −0.04 (s, 9H).

Step B: 4-bromo-N-({4-chloro-3-[(3-chloro-5-cyanophenyl)oxy]-2-fluorophenyl}methyl)-2-ethyl-1H-imidazole-5-carboxamide The procedure and process are similar to that described herein except that 4-bromo-2-ethyl-1-({[2-(trimethylsilyl)ethyl]oxy}methyl)-1H-imidazole-5-carbaldehyde (0.16 g, 0.49 mmol) was employed to provide the acid as a clear oil which was used without further purification. The above acid and 3-{[3-(aminomethyl)-6-chloro-2-fluorophenyl]oxy}-5-chlorobenzonitrile (0.15 g, 0.49 mmol) were employed in a similar process described herein to prepare the title compound (0.18 g, 47%) as a white solid after deprotection and purification by Reverse-Phase HPLC (water:acetonitrile with 0.1% TFA) followed by neutralization. $^1$H NMR (400 MHz, CHLOROFORM-d) δ ppm 11.21-11.75 (m, 1H), 7.34-7.41 (m, 2H), 7.24-7.33 (m, 2H), 7.15 (t, J=2.11 Hz, 1H), 7.02 (dd, J=2.29, 1.28 Hz, 1H), 4.72 (d, J=6.14 Hz, 2H), 2.72 (q, J=7.64 Hz, 2H), 1.28 (t, J=7.65 Hz, 3H). ES-LCMS: m/z 511.03, 513.0, 515.0 (M+1).

Example 336

4-bromo-N-({4-chloro-3-[(3-chloro-5-cyanophenyl)oxy]-2-fluorophenyl}methyl)-2-(hydroxymethyl)-1H-imidazole-5-carboxamide

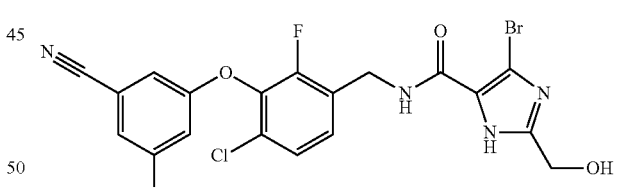

Step A: [4,5-dibromo-1-({[2-(trimethylsilyl)ethyl]oxy}methyl)-1H-imidazol-2-yl]methanol n-BuLi (3.16 mL of a 1.6 M solution in hexanes, 4.96 mmol) was added dropwise to a −78° C. solution of 2,4,5-tribromo-1-({[2-(trimethylsilyl)ethyl]oxy}methyl)-1H-imidazole (2.16 g, 4.96 mmol) in THF (50 mL). After 30 min, paraformaldehyde (0.74 g, 24.82 mmol) was added. The reaction mixture was warmed to RT, stirred overnight, quenched by addition of sat'd NH$_4$Cl and extracted with EtOAc. The organic phase was dried (Na$_2$SO$_4$), filtered, and purified by silica gel chromatography (5-60% EtOAc/hex) to afford the title compound (0.57 g, 302%) as a clear oil. 1H NMR (400 MHz, CHLOROFORM-d) δ ppm 5.44 (d, J=0.46 Hz, 2H), 4.74-4.88 (m, 2H), 3.49-3.69 (m, 2H), 0.88-1.02 (m, 2H), −0.13-0.22 (m, 9H).

Step B: 4,5-dibromo-2-({[(1,1-dimethylethyl)(dimethyl)silyl]oxy}methyl)-1-({[2-(trimethylsilyl)ethyl]oxy}methyl)-1H-imidazole The title compound (0.58 g, 79%) was obtained as a clear oil from [4,5-dibromo-1-({[2-(trimethylsilyl)ethyl]oxy}methyl)-1H-imidazol-2-yl]methanol (0.47 g, 1.47 mmol) using a procedure and process similar to that described herein. 1H NMR (400 MHz, CHLOROFORM-d) δ ppm 5.48 (s, 2H), 4.82 (br. s., 2H), 3.58 (t, J=8.03 Hz, 2H), 0.74-1.05 (m, 11H), 0.11 (s, 6H), 0.01 (s, 9H).

Step C: 4-bromo-2-({[(1,1-dimethylethyl)(dimethyl)silyl]oxy}methyl)-1-({[2-(trimethylsilyl)ethyl]oxy}methyl)-1H-imidazole-5-carbaldehyde The title compound (0.45 g, 88%) was obtained as a clear oil from 4,5-dibromo-2-({[(1,1-dimethylethyl)(dimethyl)silyl]oxy}methyl)-1-({[2-(trimethylsilyl)ethyl]oxy}methyl)-1H-imidazole (0.57 g, 1.14 mmol) using a procedure and process similar to that described herein. 1H NMR (400 MHz, CHLOROFORM-d) δ ppm 9.77 (s, 1H), 5.86 (s, 2H), 4.84 (s, 2H), 3.47-3.67 (m, 2H), 0.89 (s, 11H), 0.10 (s, 6H), −0.02 (s, 9H).

Step D: 4-bromo-N-({4-chloro-3-[(3-chloro-5-cyanophenyl)oxy]-2-fluorophenyl}methyl)-2-(hydroxymethyl)-1H-imidazole-5-carboxamide The procedure and process are similar to that described herein except that 4-bromo-2-({[(1,1-dimethylethyl)(dimethyl)silyl]oxy}methyl)-1-({[2-(trimethylsilyl)ethyl]oxy}methyl)-1H-imidazole-5-carbaldehyde (0.45 g, 1.00 mmol) was employed to provide the acid as a clear oil which was used without further purification. The above acid and 3-{[3-(aminomethyl)-6-chloro-2-fluorophenyl]oxy}-5-chlorobenzonitrile (0.31 g, 1.00 mmol) were employed in a similar process described herein to prepare the title compound (0.28 g, 44%) as a white solid after deprotection and purification by Reverse-Phase HPLC (water:acetonitrile with 0.1% TFA) followed by neutralization. 1H NMR (400 MHz, METHANOL-$d_4$) δ ppm 7.88 (s, 1H), 7.54 (s, 1H), 7.35-7.43 (m, 2H), 7.24-7.28 (m, 1H), 7.22 (s, 1H), 4.64 (s, 2H), 4.60 (s, 2 H). ES-LCMS: m/z 513.0, 515.0, 517.0 (M+1).

Example 337

4-bromo-5-{[({4-chloro-3-[(3-chloro-5-cyanophenyl)oxy]-2-fluorophenyl}methyl)amino]carbonyl}-1H-imidazole-2-carboxylic acid

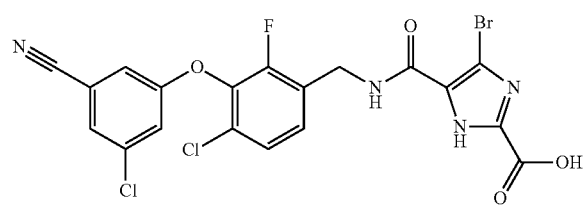

Step A: 4-bromo-N-({4-chloro-3-[(3-chloro-5-cyanophenyl)oxy]-2-fluorophenyl}methyl)-2-formyl-1H-imidazole-5-carboxamide The title compound (0.19 g, 83%) was obtained as a white solid from 4-bromo-N-({4-chloro-3-[(3-chloro-5-cyanophenyl)oxy]-2-fluorophenyl}methyl)-2-(hydroxymethyl)-1H-imidazole-5-carboxamide (0.23 g, 0.44 mmol) using a procedure and process similar to that described herein. 1H NMR (400 MHz, CHLOROFORM-d) δ ppm 11.43 (br. s., 1H), 9.74 (s, 1H), 7.29-7.47 (m, 3H), 7.17 (t, J=2.11 Hz, 1H), 7.03 (br. s., 1H), 4.75-4.85 (m, 2H).

Step B: 4-bromo-5-{[({4-chloro-3-[(3-chloro-5-cyanophenyl)oxy]-2-fluorophenyl}methyl)amino]carbonyl}-1H-imidazole-2-carboxylic acid The title compound (0.013 g, 35%) was obtained as a white solid from 4-bromo-N-({4-chloro-3-[(3-chloro-5-cyanophenyl)oxy]-2-fluorophenyl}methyl)-2-formyl-1H-imidazole-5-carboxamide (0.035 g, 0.07 mmol) using a procedure and process similar to that described herein. Purification was achieved using Reverse-Phase HPLC (water:acetonitrile with 0.1% TFA. 1H NMR (400 MHz, METHANOL-$d_4$) δ ppm 7.52-7.56 (m, 1H), 7.36-7.43 (m, 2H), 7.27 (t, J=2.06 Hz, 1H), 7.24 (dd, 1H), 4.63 (s, 2H). ES-LCMS: m/z 526.9, 529.1, 531.0 (M+1).

Example 338

4-bromo-N-({4-chloro-3-[(3-chloro-5-cyanophenyl)oxy]-2-fluorophenyl}methyl)-2-[(dimethylamino)methyl]-1H-imidazole-5-carboxamide bis(trifluoroacetate)

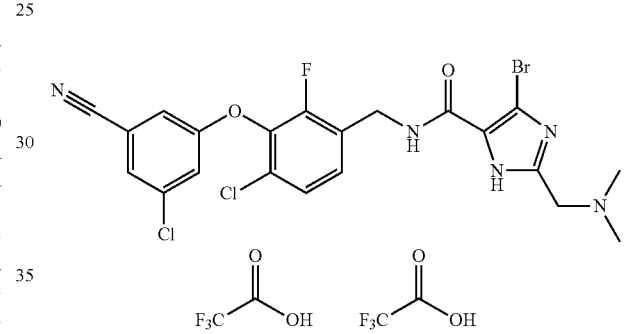

The title compound (0.021 g, 37%) was obtained as a white solid from 4-bromo-N-({4-chloro-3-[(3-chloro-5-cyanophenyl)oxy]-2-fluorophenyl}methyl)-2-formyl-1H-imidazole-5-carboxamide (0.038 g, 0.074 mmol) and dimethylamine (0.4 mL of a 2M solution in THF, 0.74 mmol) using a procedure and process similar to that described herein. Purification was achieved using Reverse-Phase HPLC (water:acetonitrile with 0.1% TFA). 1H NMR (400 MHz, METHANOL-$d_4$) δ ppm 7.53-7.58 (m, 1H), 7.35-7.43 (m, 2H), 7.28 (t, J=2.11 Hz, 1H), 7.20 (dd, J=2.15, 1.24 Hz, 1H), 4.65 (s, 2H), 4.39 (s, 2H), 2.97 (s, 6H). ES-LCMS: m/z 540.0, 542.1, 544.1 (M+1).

Example 339

4-bromo-N-({4-chloro-3-[(3-chloro-5-cyanophenyl)oxy]-2-fluorophenyl}methyl)-2-[(methyloxy)methyl]-1H-imidazole-5-carboxamide

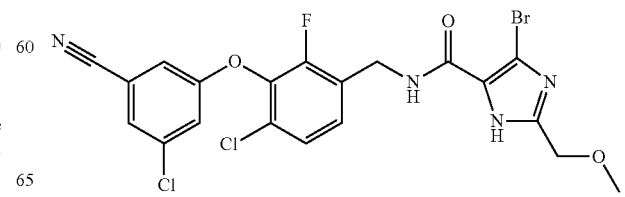

Step A: 4,5-dibromo-2-[(methyloxy)methyl]-1-({[2-(trimethylsilyl)ethyl]oxy}methyl)-1H-imidazole NaH (0.016 g of a 60% dispersion in mineral oil, 0.41 mmol) was added to a 0° C. solution of [4,5-dibromo-1-({[2-(trimethylsilyl)ethyl]oxy}methyl)-1H-imidazol-2-yl]ethanol (0.15 g, 0.39 mmol) in THF (2 mL). The solution was stirred at RT for 30 mins, recooled to 0° C. and iodomethane was added (0.052 mL, 0.78 mmol). After 2 h at RT, the reaction mixture was quenched by addition of sat'd NaHCO$_3$ and extracted with CH$_2$Cl$_2$. The organic phase was dried (Na$_2$SO$_4$), filtered, and purified by silica gel chromatography (0-30% EtOAc/hex) to afford the title compound (0.084 g, 54%) as clear oil. 1H NMR (400 MHz, CHLOROFORM-d) δ ppm 5.39 (s, 2H), 4.55 (s, 2H), 3.57 (t, J=8.19 Hz, 2H), 3.35 (s, 3H), 0.91 (t, J=8.15 Hz, 2H), −0.01 (s, 9H).

Step B: 4-bromo-2-[(methyloxy)methyl]-1-({[2-(trimethylsilyl)ethyl]oxy}methyl)-1H-imidazole-5-carbaldehyde The title compound (0.045 g, 61%) was obtained as a clear oil from 4,5-dibromo-2-[(methyloxy)methyl]-1-({[2-(trimethylsilyl)ethyl]oxy}methyl)-1H-imidazole (0.084 g, 0.24 mmol) using a procedure and process similar to that described herein. 1H NMR (400 MHz, CHLOROFORM-d) δ ppm 9.78 (s, 1H), 5.81 (s, 2H), 4.62 (s, 2H), 3.53-3.64 (m, 2H), 3.41 (s, 3H), 0.87-0.95 (m, 2H), −0.02 (s, 9H).

Step C: 4-bromo-N-({4-chloro-3-[(3-chloro-5-cyanophenyl)oxy]-2-fluorophenyl}methyl)-2-[(methyloxy)methyl]-1H-imidazole-5-carboxamide The procedure and process are similar to that described herein except that 4-bromo-2-[(methyloxy)methyl]-1-({[2-(trimethylsilyl)ethyl]oxy}methyl)-1H-imidazole-5-carbaldehyde (0.045 g, 0.11 mmol) was employed to provide the acid as a clear oil which was used without further purification. The above acid and 3-{[3-(aminomethyl)-6-chloro-2-fluorophenyl]oxy}-5-chlorobenzonitrile (0.035 g, 0.11 mmol) were employed in a similar process described herein to prepare the title compound (0.045 g, 76%) as a white solid after deprotection and purification by Reverse-Phase HPLC (water:acetonitrile with 0.1% TFA) followed by neutralization. 1H NMR (400 MHz, DMSO-d$_6$) δ ppm 12.98-13.57 (m, 1H), 8.31 (br. s., 1H), 7.82 (s, 1H), 7.43-7.59 (m, 3H), 7.38 (br. s., 1H), 4.50 (br. s., 2H), 4.37 (s, 2H), 3.28 (s, 3H). ES-LCMS: m/z 527.0, 529.0, 531.0 (M+1).

Example 340

4-bromo-N-({4-chloro-3-[(3-chloro-5-cyanophenyl)oxy]-2-fluorophenyl}methyl)-2-(1-hydroxyethyl)-1H-imidazole-5-carboxamide

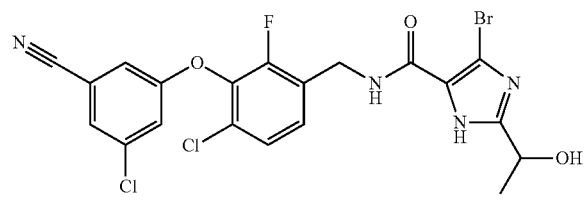

Step A: 1-[4,5-dibromo-1-({[2-(trimethylsilyl)ethyl]oxy}methyl)-1H-imidazol-2-yl]ethanol The title compound (1.28 g, 77%) was obtained as a clear oil from 2,4,5-tribromo-1-({[2-(trimethylsilyl)ethyl]oxy}methyl)-1H-imidazole (2.04 g, 4.68 mmol) and acetaldehyde (1.3 mL, 23.4 mmol) using a procedure and process similar to that described herein. 1H NMR (400 MHz, CHLOROFORM-d) δ ppm 5.34-5.51 (m, 2H), 4.94-5.05 (m, 1H), 3.61 (t, J=8.24 Hz, 2H), 1.65 (d, J=6.50 Hz, 3H), 0.93 (t, J=8.24 Hz, 2H), 0.01 (s, 9H).

Step B: 4,5-dibromo-2-(1-{[(1,1-dimethylethyl)(dimethyl)silyl]oxy}ethyl)-1-({[2-(trimethylsilyl)ethyl]oxy}methyl)-1H-imidazole The title compound (1.36 g, 82%) was obtained as a clear oil from 1-[4,5-dibromo-1-({[2-(trimethylsilyl)ethyl]oxy}methyl)-1H-imidazol-2-yl]ethanol (1.28 g, 3.21 mmol) using a procedure and process similar to that described herein. 1H NMR (400 MHz, CHLOROFORM-d) δ ppm 5.70 (d, J=10.44 Hz, 1H), 5.33 (d, J=10.44 Hz, 1H), 5.14 (q, J=6.47 Hz, 1H), 3.63 (t, J=8.24 Hz, 2H), 1.59 (d, J=6.59 Hz, 3H), 0.90-1.01 (m, 2H), 0.88 (s, 9H), 0.08 (s, 3H), 0.02 (s, 12H).

Step C: 4-bromo-2-(1-{[(1,1-dimethylethyl)(dimethyl)silyl]oxy}ethyl)-1-({[2-(trimethylsilyl)ethyl]oxy}methyl)-1H-imidazole-5-carbaldehyde The title compound (1.36 g, 82%) was obtained as a clear oil from 4,5-dibromo-2-(1-{[(1,1-dimethylethyl)(dimethyl)silyl]oxy}ethyl)-1-({[2-(trimethylsilyl)ethyl]oxy}methyl)-1H-imidazole (1.36 g, 2.64 mmol) using a procedure and process similar to that described herein. 1H NMR (400 MHz, CHLOROFORM-d) δ ppm 9.76 (s, 1H), 5.80-6.02 (m, 2H), 5.18 (q, J=6.41 Hz, 1H), 3.63 (t, J=8.29 Hz, 2H), 1.61 (d, J=6.50 Hz, 3H), 0.81-1.00 (m, 11H), 0.09 (s, 3H), 0.03 (s, 3H), 0.00 (s, 9H).

Step D: 4-bromo-N-({4-chloro-3-[(3-chloro-5-cyanophenyl)oxy]-2-fluorophenyl}methyl)-2-(1-hydroxyethyl)-1H-imidazole-5-carboxamide The procedure and process are similar to that described herein except that 4-bromo-2-(1-{[(1,1-dimethylethyl)(dimethyl)silyl]oxy}ethyl)-1-({[2-(trimethylsilyl)ethyl]oxy}methyl)-1H-imidazole-5-carbaldehyde (0.75 g, 1.63 mmol) was employed to provide the acid as a clear oil which was used without further purification. The above acid and 3-{[3-(aminomethyl)-6-chloro-2-fluorophenyl]oxy}-5-chlorobenzonitrile (0.51 g, 1.63 mmol) were employed in a similar process described herein to prepare the title compound (0.36 g, 42%) as a white solid after deprotection and purification by Reverse-Phase HPLC (water:acetonitrile with 0.1% TFA) followed by neutralization. 1H NMR (400 MHz, CHLOROFORM-d) δ ppm 7.46 (t, J=5.49 Hz, 1H), 7.28-7.40 (m, 3H), 7.19 (t, J=2.06 Hz, 1H), 7.02 (s, 1H), 4.99-5.10 (m, 1H), 4.71 (d, J=5.91 Hz, 2H), 1.61 (d, J=6.73 Hz, 3H). ES-LCMS: m/z 527.1, 529.1, 531.1 (M+1).

Example 341

2-acetyl-4-bromo-N-({4-chloro-3-[(3-chloro-5-cyanophenyl)oxy]-2-fluorophenyl}methyl)-1H-imidazole-5-carboxamide

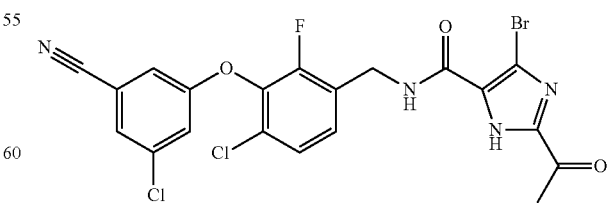

The title compound (0.055 g, 53%) was obtained as a white solid by MnO$_2$ oxidation of 4-bromo-N-({4-chloro-3-[(3-chloro-5-cyanophenyl)oxy]-2-fluorophenyl}methyl)-2-(1-hydroxyethyl)-1H-imidazole-5-carboxamide using a similar

339 process to that described herein. 1H NMR (400 MHz, DMSO-d$_6$) δ ppm 14.51 (br. s., 1H), 8.72-8.79 (m, 1H), 7.83 (s, 1H), 7.45-7.56 (m, 3H), 7.31-7.41 (m, 1H), 4.51 (br. s., 2H), 2.55 (s, 3 H). ES-LCMS: m/z 524.8, 526.8, 528.7 (M+1).

Example 342

4-bromo-N-({4-chloro-3-[(3-chloro-5-cyanophenyl) oxy]-2-fluorophenyl}methyl)-2-(2-hydroxyethyl)-1H-imidazole-5-carboxamide

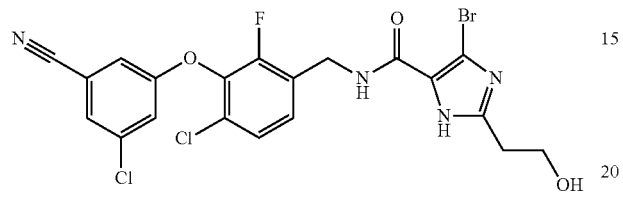

Step A: 2-[4,5-dibromo-1-({[2-(trimethylsilyl)ethyl] oxy}methyl)-1H-imidazol-2-yl]ethanol n-BuLi (4.30 mL of a 1.6 M solution in hexanes, 6.80 mmol) was added dropwise to a −78° C. solution of 2,4,5-tribromo-1-({[2-(trimethylsilyl)ethyl]oxy}methyl)-1H-imidazole (2.96 g, 6.80 mmol) in THF (55 mL). After 25 min, oxirane gas was bubbled through the solution for 25 mins. The reaction mixture was allowed to warm slowly to RT, stirred overnight, quenched by addition of sat'd NH$_4$Cl and extracted with CH$_2$Cl$_2$. The organic phase was dried (Na$_2$SO$_4$), filtered, and purified by silica gel chromatography (5-50% EtOAc/hex) to afford the title compound (0.83 g, 31%) as a yellow oil. 1H NMR (400 MHz, CHLOROFORM-d) δ ppm 5.36 (s, 2H), 3.82 (t, J=6.09 Hz, 2H), 3.55 (dd, J=8.94, 7.65 Hz, 2H), 3.10 (br. s., 1H), 2.90 (t, J=6.09 Hz, 2H), 0.85-0.98 (m, 2H), −0.02 (s, 9H).

Step B: 4,5-dibromo-2-(2-{[(1,1-dimethylethyl)(dimethyl) silyl]oxy}ethyl)-1-({[2-(trimethylsilyl)ethyl]oxy}methyl)-1H-imidazole The title compound (0.70 g, 66%) was obtained as a clear oil from 2-[4,5-dibromo-1-({[2-(trimethylsilyl)ethyl] oxy}methyl)-1H-imidazol-2-yl]ethanol (0.83 g, 2.09 mmol) using a procedure and process similar to that described herein. 1H NMR (400 MHz, CHLOROFORM-d) δ ppm 5.33 (s, 2H), 3.70-3.77 (m, 2H), 3.47-3.55 (m, 2H), 2.81-2.91 (m, 2H), 0.84-0.95 (m, 2H), 0.80 (s, 9H), −0.08--0.02 (m, 15H).

Step C: 4-bromo-2-(2-{[(1,1-dimethylethyl)(dimethyl)silyl] oxy}ethyl)-1-({[2-(trimethylsilyl)ethyl]oxy}methyl)-1H-imidazole-5-carbaldehyde The title compound (0.70 g, 66%) was obtained as a clear oil from 4,5-dibromo-2-(2-{[(1,1-dimethylethyl)(dimethyl) silyl]oxy}ethyl)-1-({[2-(trimethylsilyl)ethyl]oxy}methyl)-1H-imidazole (0.70 g, 1.37 mmol) using a procedure and process similar to that described herein. 1H NMR (400 MHz, CHLOROFORM-d) δ ppm 9.66 (s, 1H), 5.90 (s, 2H), 3.84 (t, J=6.19 Hz, 2H), 3.48-3.60 (m, 2H), 2.97 (t, J=6.19 Hz, 2H), 0.85-0.92 (m, 2H), 0.81 (s, 9H), −0.03 (s, 9H), −0.05 (s, 6H).

Step D: 4-bromo-N-({4-chloro-3-[(3-chloro-5-cyanophenyl) oxy]-2-fluorophenyl}methyl)-2-(2-hydroxyethyl)-1H-imidazole-5-carboxamide The procedure and process are similar to that described herein except that 4-bromo-2-(2-{[(1,1-dimethylethyl)(dimethyl)silyl]oxy}ethyl)-1-({[2-(trimethylsilyl)ethyl]oxy} methyl)-1H-imidazole-5-carbaldehyde (0.28 g, 0.60 mmol) was employed to provide the crude acid as a clear oil which was used without further purification. The above acid and 3-{[3-(aminomethyl)-6-chloro-2-fluorophenyl]oxy}-5-chlorobenzonitrile (0.19 g, 0.60 mmol) were employed in a similar process described herein to prepare the title compound (0.05 g, 2%) as a white solid after deprotection and multiple purifications by Reverse-Phase HPLC (water:acetonitrile with 0.1% TFA) and silica gel chromatography (0-5% MeOH/CH$_2$Cl$_2$). 1H NMR (400 MHz, CHLOROFORM-d) δ ppm 11.20 (br. s., 1H), 7.57-7.68 (m, 1H), 7.35 (t, J=1.51 Hz, 1H), 7.26-7.32 (m, 2H), 7.16 (t, J=2.11 Hz, 1H), 6.98-7.03 (m, 1H), 4.64 (d, J=6.23 Hz, 2H), 3.91 (t, J=5.64 Hz, 2H), 2.87 (t, J=5.64 Hz, 2H). ES-LCMS: m/z 527.2, 529.2, 531.3 (M+1).

Example 343

4-bromo-N-({4-chloro-3-[(3-chloro-5-cyanophenyl) oxy]-2-fluorophenyl}methyl)-2-{[(2-hydroxyethyl) oxy]methyl}-1H-imidazole-5-carboxamide

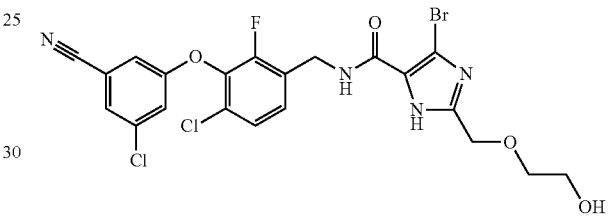

Step A: 4,5-dibromo-2-{[(2-{[(1,1-dimethylethyl)(dimethyl) silyl]oxy}ethyl)oxy]methyl}-1-({[2-(trimethylsilyl)ethyl] oxy}methyl)-1H-imidazole The title compound (0.12 g, 23%) was obtained as a clear oil from [4,5-dibromo-1-({[2-(trimethylsilyl)ethyl] oxy}methyl)-1H-imidazol-2-yl]methanol (0.37 g, 0.95 mmol), [(2-bromoethyl)oxy](1,1-dimethylethyl)dimethylsilane (1.0 g, 4.2 mmol), and NaH (0.042 g of a 60% dispersion in mineral oil, 1.10 mmol) using a procedure and process similar to that described herein with the modification that the reaction mixture was heated at 55° C. for 8 h. 1H NMR (400 MHz, CHLOROFORM-d) δ ppm 5.44 (s, 2H), 4.66 (s, 2H), 3.74 (t, J=4.90 Hz, 2H), 3.50-3.59 (m, 4H), 0.85-0.95 (m, 11H), 0.05 (s, 6H), 0.00 (s, 9H).

Step B: 4-bromo-2-{[(2-{[(1,1-dimethylethyl)(dimethyl)silyl]oxy}ethyl)oxy]methyl}-1-({[2-(trimethylsilyl)ethyl] oxy}methyl)-1H-imidazole-5-carbaldehyde 3N EtMgBr (0.086 mL of a 3N solution in diethyl ether, 0.26 mmol) was added to a solution of 4,5-dibromo-2-{[(2-{[(1,1-dimethylethyl)(dimethyl)silyl]oxy}ethyl)oxy]methyl}-1-({[2-(trimethylsilyl)ethyl]oxy}methyl)-1H-imidazole (0.12 g, 0.21 mmol) in THF (2 mL). The reaction mixture was stirred for 3 h, DMF was added (0.5 mL, 4.9 mmol), and stirring was continued overnight. The solution was quenched by addition of sat'd NH$_4$Cl and extracted with EtOAc and CH$_2$Cl$_2$. The organic phase was dried (Na$_2$SO$_4$), filtered, and purified by silica gel chromatography (0-30% EtOAc/hex) to afford the title compound (0.073 g, 69%) as a clear oil. 1H NMR (400 MHz, CHLOROFORM-d) δ ppm 9.77 (s, 1H), 5.84 (s, 2H), 5.27-5.47 (m, 1H), 4.60-4.77 (m, 1H), 3.74 (ddd, J=9.16, 4.85, 4.67 Hz, 2H), 3.47-3.62 (m, 4H), 0.83-0.95 (m, 11H), 0.04 (s, 6H), −0.06-0.01 (m, 9H).

Step C: 4-bromo-N-({4-chloro-3-[(3-chloro-5-cyanophenyl)oxy]-2-fluorophenyl}methyl)-2-{[(2-hydroxyethyl)oxy]methyl}-1H-imidazole-5-carboxamide The procedure and process are similar to that described herein except that 4-bromo-2-{[(2-{[(1,1-dimethylethyl)(dimethyl)silyl]oxy}ethyl)oxy]methyl}-1-({[2-(trimethylsilyl)ethyl]oxy}methyl)-1H-imidazole-5-carbaldehyde (0.073 g, 0.15 mmol) was employed to provide the acid as a clear oil which was used without further purification. The above acid and 3-{[3-(aminomethyl)-6-chloro-2-fluorophenyl]oxy}-5-chlorobenzonitrile (0.046 g, 0.15 mmol) were employed in a similar process described herein to prepare the title compound (0.016 g, 19%) as a white solid after deprotection and purification by Reverse-Phase HPLC (water:acetonitrile with 0.1% TFA) followed by neutralization. 1H NMR (400 MHz, METHANOL-$d_4$) δ ppm 7.56 (d, J=1.28 Hz, 1H), 7.35-7.44 (m, 2H), 7.26-7.29 (m, 1H), 7.24 (br. s., 1H), 4.65 (s, 2H), 4.57 (s, 2H), 3.69-3.74 (m, 2H), 3.59-3.63 (m, 2H). ES-LCMS: m/z 557.0, 559.0, 561.0 (M+1).

Example 344

4-bromo-N-({4-chloro-3-[(3-chloro-5-cyanophenyl)oxy]-2-fluorophenyl}methyl)-2-[3-(methyloxy)propyl]-1H-imidazole-5-carboxamide

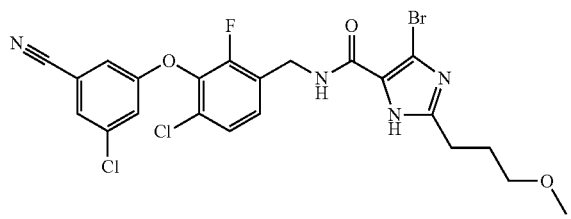

Step A: 4,5-dibromo-2-[3-(methyloxy)propyl]-1-({[2-(trimethylsilyl)ethyl]oxy}methyl)-1H-imidazole The title compound (0.17 g, 35%) was obtained as a yellow oil from 2,4,5-tribromo-1-({[2-(trimethylsilyl)ethyl]oxy}methyl)-1H-imidazole (0.48 g, 1.11 mmol) and 3-bromopropyl methyl ether (0.20 g, 1.31 mmol) using a procedure and process similar to that described herein. 1H NMR (400 MHz, CHLOROFORM-d) δ ppm 5.27 (s, 2H), 3.52-3.61 (m, 2H), 3.43 (t, J=5.95 Hz, 2H), 3.32 (s, 3H), 2.84 (t, J=7.55 Hz, 2H), 2.00-2.09 (m, 2H), 0.86-0.97 (m, 2H), 0.00 (s, 9H).

Step B: 4-bromo-2-[3-(methyloxy)propyl]-1-({[2-(trimethylsilyl)ethyl]oxy}methyl)-1H-imidazole-5-carbaldehyde The title compound (0.084 g, 58%) was obtained as a clear oil from 4,5-dibromo-2-[3-(methyloxy)propyl]-1-({[2-(trimethylsilyl)ethyl]oxy}methyl)-1H-imidazole (0.17 g, 0.38 mmol) using a procedure and process similar to that described herein. 1H NMR (400 MHz, CHLOROFORM-d) δ ppm 9.69 (s, 1H), 5.71 (s, 2H), 3.53-3.61 (m, 2H), 3.42 (t, J=5.91 Hz, 2H), 3.31 (s, 3H), 2.86 (t, J=7.55 Hz, 2H), 2.07 (t, J=7.33 Hz, 2H), 0.84-0.97 (m, 2H), −0.03 (s, 9H).

Step C: 4-bromo-N-({4-chloro-3-[(3-chloro-5-cyanophenyl)oxy]-2-fluorophenyl}methyl)-2-[3-(methyloxy)propyl]-1H-imidazole-5-carboxamide The procedure and process are similar to that described herein except that 4-bromo-2-[3-(methyloxy)propyl]-1-({[2-(trimethylsilyl)ethyl]oxy}methyl)-1H-imidazole-5-carbaldehyde (0.084 g, 0.22 mmol) was employed to provide the acid as a clear oil which was used without further purification. The above acid and 3-{[3-(aminomethyl)-6-chloro-2-fluorophenyl]oxy}-5-chlorobenzonitrile (0.069 g, 0.22 mmol) were employed in a similar process described herein to prepare the title compound (0.045 g, 36%) as a white solid after deprotection and purification by Reverse-Phase HPLC (water:acetonitrile with 0.1% TFA) followed by neutralization. 1H NMR (400 MHz, METHANOL-$d_4$) δ ppm 7.55 (s, 1H), 7.35-7.43 (m, 2H), 7.26 (s, 1H), 7.23 (s, 1H), 4.64 (s, 2H), 3.41 (t, J=6.11 Hz, 2H), 3.31 (s, 3H), 2.76 (t, J=7.62 Hz, 2H), 1.88-2.00 (m, 2H). ES-LCMS: m/z 555.0, 556.9, 558.6 (M+1).

Example 345

4-bromo-N-({4-chloro-3-[(3-chloro-5-cyanophenyl)oxy]-2-fluorophenyl}methyl)-2-{[(2-hydroxyethyl)amino]methyl}-1H-imidazole-5-carboxamide

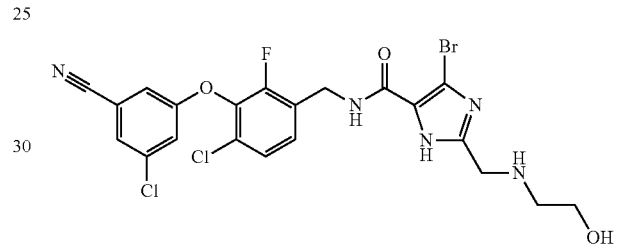

MsCl (0.020 mL, 0.26 mmol) was added to a solution of 4-bromo-N-({4-chloro-3-[(3-chloro-5-cyanophenyl)oxy]-2-fluorophenyl}methyl)-2-(hydroxymethyl)-1H-imidazole-5-carboxamide (0.045 g, 0.09 mmol) and Et$_3$N (0.14 mL, 1.00 mmol) in CH$_2$Cl$_2$ (1 mL). After 1 h, ethanolamine (0.20 mL, 3.31 mmol) was added and the reaction mixture was stirred at RT overnight. Purification was achieved by Reverse-Phase HPLC (water:acetonitrile with 0.1% NH$_4$OH). The title compound (0.010, 21%) was isolated as a white solid. 1H NMR (400 MHz, METHANOL-$d_4$) δ ppm 7.56 (s, 1H), 7.36-7.43 (m, 2H), 7.27 (br. s., 1H), 7.24 (br. s., 1H), 4.64 (s, 2H), 3.86 (s, 2H), 3.66 (t, J=5.36 Hz, 2H), 2.77 (t, J=5.13 Hz, 2H). ES-LCMS: m/z 556.1, 558.4, 560.0 (M+1).

Example 346

4-bromo-N-({4-chloro-3-[(3-chloro-5-cyanophenyl)oxy]-2-fluorophenyl}methyl)-2-({[2-(dimethylamino)ethyl]amino}methyl)-1H-imidazole-5-carboxamide bis(trifluoroacetate)

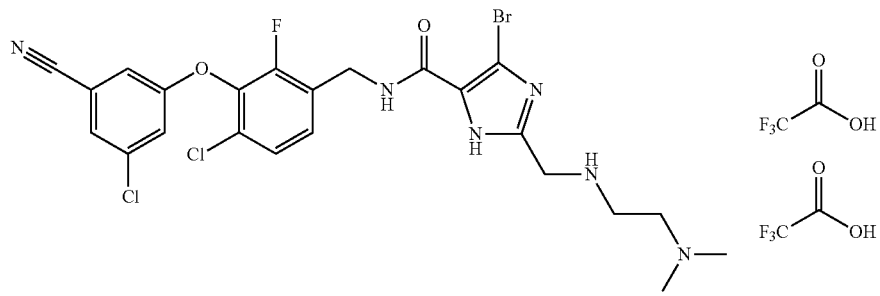

The title compound (0.09 g, 11%) was obtained as a white solid from 4-bromo-N-({4-chloro-3-[(3-chloro-5-cyanophenyl)oxy]-2-fluorophenyl}methyl)-2-(hydroxymethyl)-1H-imidazole-5-carboxamide (0.045 g, 0.09 mmol) (0.052 g, 0.10 mmol) using a procedure and process similar to that described herein. 1H NMR (400 MHz, METHANOL-$d_4$) δ ppm 7.54-7.58 (m, 1H), 7.36-7.43 (m, 2H), 7.29 (t, J=1.92 Hz, 1H), 7.20 (s, 1H), 4.65 (s, 2H), 4.21 (s, 2H), 3.37-3.45 (m, 4H), 2.95 (s, 6H). ES-LCMS: m/z 583.1, 585.1, 587.1 (M+1).

Example 347

4-chloro-N-({4-chloro-3-[(3-cyano-5-fluorophenyl)oxy]-2-fluorophenyl}methyl)-1H-imidazole-5-carboxamide

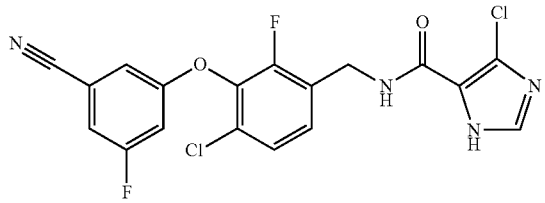

Step A: 3-[(6-chloro-2-fluoro-3-methylphenyl)oxy]-5-fluorobenzonitrile

KOtBu (6.23 ml of a 1M solution in THF, 6.23 mmol) was added to a solution of 6-chloro-2-fluoro-3-methylphenol (1.00 g, 6.23 mmol) and 18-CROWN-6 (0.823 g, 3.11 mmol) in DMSO (12 ml) at RT. After 20 mins, 3,5-difluorobenzonitrile (0.87 g, 6.23 mmol) was added and the solution was heated at 120° C. overnight. The reaction mixture was poured into water (50 mL) and extracted with EtOAc (2×20 mL). The organic layer was dried (Na2SO4), filtered, concentrated, and purified by silica gel chromatography (0-25% EtOAc/hexs) to provide 3-[(6-chloro-2-fluoro-3-methylphenyl)oxy]-5-fluorobenzonitrile (1.15 g, 66%) as an off-white solid. 1H NMR (400 MHz, CHLOROFORM-d) δ ppm 7.21 (dd, J=8.42, 1.46 Hz, 1H), 7.06-7.14 (m, 2H), 6.87-6.95 (m, 2H), 2.33 (d, J=2.11 Hz, 3H).

Step B: 3-{[3-(bromomethyl)-6-chloro-2-fluorophenyl]oxy}-5-fluorobenzonitrile

The title compound (0.95 g, 65%) was obtained as a clear oil from 3-[(6-chloro-2-fluoro-3-methylphenyl)oxy]-5-fluorobenzonitrile (1.15 g, 4.11 mmol) using a procedure and process similar to that described herein. 1H NMR (400 MHz, CHLOROFORM-d) δ ppm 7.22-7.37 (m, 2H), 7.01-7.16 (m, 1H), 6.83-6.97 (m, 2 H), 4.48 (s, 2H).

Step C: 4-chloro-N-({4-chloro-3-[(3-cyano-5-fluorophenyl)oxy]-2-fluorophenyl}methyl)-1H-imidazole-5-carboxamide The procedure and process are similar to that described herein except that 3-{[3-(bromomethyl)-6-chloro-2-fluorophenyl]oxy}-5-fluorobenzonitrile (0.95 g, 2.66 mmol) was employed to provide the amine as an off-white solid (0.71 g, 89%) which was used without further purification. The above amine (0.059 g, 0.20 mmol) and 4-chloro-1-({[2-(trimethylsilyl)ethyl]oxy}methyl)-1H-imidazole-5-carboxylic acid (0.055 g, 0.20 mmol) were employed in a similar process described herein to prepare the title compound (0.030 g, 36%) as a white solid after deprotection and purification by Reverse-Phase HPLC (water:acetonitrile with 0.1% TFA). 1H NMR (400 MHz, METHANOL-d4) δ ppm 8.25 (br. s., 1H) 7.73 (s, 1H) 7.28-7.44 (m, 3H) 7.13 (s, 1H) 7.03-7.10 (m, 1H) 4.66 (s, 2H). ES-LCMS: m/z 422.9, 425.0 (M+1).

Example 348

4-chloro-N-({4-chloro-3-[(3-cyano-5-fluorophenyl)oxy]-2-fluorophenyl}methyl)-2-methyl-1H-imidazole-5-carboxamide

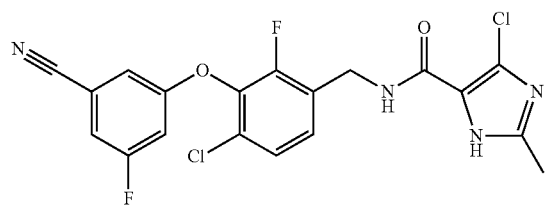

The above amine (0.059 g, 0.20 mmol) and 4-chloro-2-methyl-1H-imidazole-5-carboxylic acid (0.032 g, 0.20 mmol) were employed in a similar process described herein to prepare the title compound (0.043 g, 49%) as a white solid after purification by Reverse-Phase HPLC (water:acetonitrile with 0.1% TFA) followed by neutralization. 1H NMR (400 MHz, METHANOL-d4) δ ppm 7.28-7.44 (m, 3H), 7.12 (s, 1H), 7.04-7.09 (m, 1H), 4.64 (s, 2H), 2.35 (s, 3H). ES-LCMS: m/z 437.0, 439.0 (M+1).

Example 349

4-bromo-$N^5$-({4-chloro-3-[(3-chloro-5-cyanophenyl)oxy]-2-fluorophenyl}methyl)-$N^2$,$N^2$-dimethyl-1H-imidazole-2,5-dicarboxamide

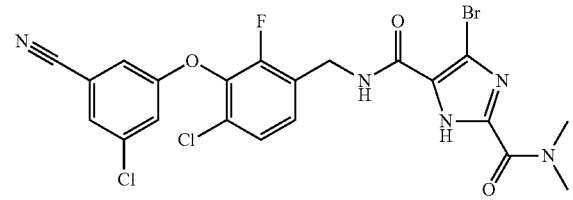

Step A: 4,5-dibromo-N,N-dimethyl-1-({[2-(trimethylsilyl)ethyl]oxy}methyl)-1H-imidazole-2-carboxamide The title compound (0.34 g, 69%) was obtained as a clear oil from 2,4,5-tribromo-1-({[2-(trimethylsilyl)ethyl]oxy}methyl)-1H-imidazole (0.48 g, 1.11 mmol) and dimethylcarbamoyl chloride (0.74 mL, 8.05 mmol) using a procedure and process similar to that described herein. 1H NMR (400 MHz, CHLOROFORM-d) δ ppm 5.68 (s, 2H), 3.55 (t, J=8.15 Hz, 2H), 3.29 (s, 3H), 3.10 (s, 3H), 0.90 (t, J=8.24 Hz, 2H), −0.01 (s, 9H).

Step B: 4-bromo-5-formyl-N,N-dimethyl-1-({[2-(trimethylsilyl)ethyl]oxy}methyl)-1H-imidazole-2-carboxamide The title compound (0.17 g, 58%) was obtained as a light yellow oil from 4,5-dibromo-N,N-dimethyl-1-({[2-(trimethylsilyl)ethyl]oxy}methyl)-1H-imidazole-2-carboxamide (0.34 g, 0.79 mmol) using a procedure and process similar to that described herein. 1H NMR (400 MHz, CHLOROFORM-d) δ ppm 9.83 (s, 1H), 5.89 (s, 2H), 3.55 (m, 2H), 3.14 (s, 3H), 3.10 (s, 3H), 0.88 (m, 2H), −0.04 (s, 9H).

Step C: 4-bromo-N$^5$-({4-chloro-3-[(3-chloro-5-cyanophenyl)oxy]-2-fluorophenyl}methyl)-N$^2$,N$^2$-dimethyl-1H-imidazole-2,5-dicarboxamide The procedure and process are similar to that described herein except that 4-bromo-5-formyl-N,N-dimethyl-1-({[2-(trimethylsilyl)ethyl]oxy}methyl)-1H-imidazole-2-carboxamide (0.17 g, 0.46 mmol) was employed to provide the acid as a clear oil which was used without further purification. The above acid (0.080 g, 0.20 mmol) and 3-{[3-(aminomethyl)-6-chloro-2-fluorophenyl]oxy}-5-chlorobenzonitrile (0.062 g, 0.20 mmol) were employed in a similar process described herein to prepare the title compound (0.004 g, 4%) as a white solid after deprotection and purification by Reverse-Phase HPLC (water:acetonitrile with 0.1% TFA). 1H NMR (400 MHz, CHLOROFORM-d) δ ppm 11.05 (br. s., 1H), 7.30-7.41 (m, 3H), 7.13-7.20 (m, 1H), 7.03 (br. s., 1H), 4.73 (d, J=5.04 Hz, 2H), 3.66 (s, 3H), 3.14 (s, 3H). ES-LCMS: m/z 554.0, 556.0, 558.0 (M+1).

Example 350

2-(aminomethyl)-4-bromo-N-({4-chloro-3-[(3-chloro-5-cyanophenyl)oxy]-2-fluorophenyl}methyl)-1H-imidazole-5-carboxamide

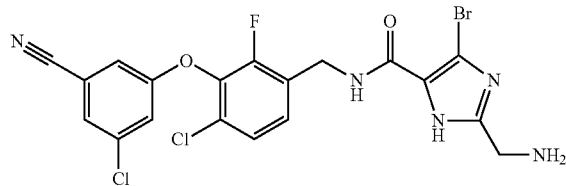

Ms-Cl (0.023 ml, 0.30 mmol) was added to a solution of 4-bromo-N-({4-chloro-3-[(3-chloro-5-cyanophenyl)oxy]-2-fluorophenyl}methyl)-2-(hydroxymethyl)-1-({[2-(trimethylsilyl)ethyl]oxy}methyl)-1H-imidazole-5-carboxamide (0.097 g, 0.15 mmol) and DIEA (0.26 ml, 1.50 mmol) in DMF (1 ml) and the reaction mixture was stirred at room temperature for 1 h. Ammonia (1 ml of a 7M solution in methanol, 7.00 mmol) was added and stirring was continued overnight. Deprotection using similar procedures as that described herein and purification by Reverse-Phase HPLC (water:acetonitrile with 0.1% NH$_4$OH) provided the title compound (0.004 g, 5%) as an off-white solid. 1H NMR (400 MHz, METHANOL-d4) δ ppm 8.32 (br. s., 1H), 7.56 (s, 1H), 7.33-7.45 (m, 2H), 7.28 (br. s., 1H), 7.21 (s, 1H), 4.65 (br. s., 2H), 4.19 (s, 2H). ES-LCMS: m/z 511.9, 513.9, 515.9 (M+1).

Example 351

4-chloro-N-({4-chloro-3-[(3-cyanophenyl)oxy]-2-fluorophenyl}methyl)-2-methyl-1H-imidazole-5-carboxamide

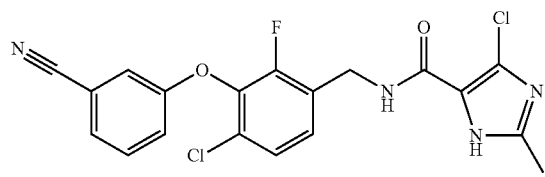

A solution of 3-{[3-(aminomethyl)-6-chloro-2-fluorophenyl]oxy}-5-bromobenzonitrile (0.20 g, 0.56 mmol), sodium formate (0.057 g, 0.84 mmol) and Pd(Ph$_3$P)$_4$ (0.032 g, 0.028 mmol) in DMF (1.13 ml) was heated at 100° C. for 6 h. Water was added and the mixture was extracted with EtOAc. The organic phase was dried (Na$_2$SO$_4$), filtered, and dried to afford 3-{[3-(aminomethyl)-6-chloro-2-fluorophenyl]oxy}benzonitrile, which was used without further purification. The above amine (0.28 mmol) and 4-chloro-2-methyl-1H-imidazole-5-carboxylic acid (0.040 g, 0.25 mmol) were employed in a similar process described herein to prepare the title compound (0.042 g, 40%) as a white solid after purification by Reverse-Phase HPLC (water:acetonitrile with 0.1% TFA) followed by neutralization. 1H NMR (400 MHz, CHLOROFORM-d) δ ppm 11.89 (br. s., 1H), 7.32-7.45 (m, 2H), 7.12-7.31 (m, 4H), 7.08 (s, 1H), 4.70 (d, J=5.91 Hz, 2H), 2.37 (s, 3H). ES-LCMS: m/z 419.0, 421.0 (M+1).

Example 352

4-chloro-N-({4-chloro-3-[(3-cyanophenyl)oxy]-2-fluorophenyl}methyl)-1H-imidazole-5-carboxamide

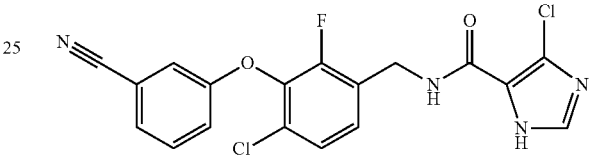

The previously described 3-{[3-(aminomethyl)-6-chloro-2-fluorophenyl]oxy}benzonitrile (0.28 mmol) and 4-chloro-1-({[2-(trimethylsilyl)ethyl]oxy}methyl)-1H-imidazole-5-carboxylic acid (0.055 g, 0.20 mmol) were employed in a similar process described herein to prepare the title compound (0.056 g, 69%) as a white solid after deprotection and purification by Reverse-Phase HPLC (water:acetonitrile with 0.1% TFA). 1H NMR (400 MHz, METHANOL-d4) δ ppm 7.73 (s, 1H) 7.42-7.55 (m, 2H) 7.29-7.42 (m, 2H) 7.17-7.27 (m, 2H) 4.65 (s, 2H). ES-LCMS: m/z 405.0, 407.0 (M+1).

Example 353

4-chloro-N-({4-chloro-3-[(6-chloro-4-cyano-2-pyridinyl)oxy]-2-fluorophenyl}methyl)-2-methyl-1H-imidazole-5-carboxamide

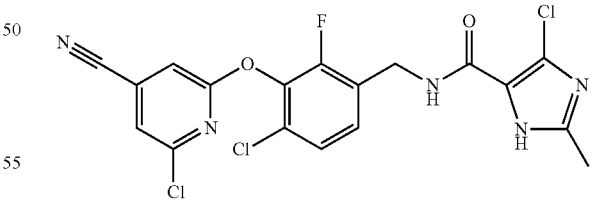

The previously described 2-{[3-(aminomethyl)-6-chloro-2-fluorophenyl]oxy}-6-chloro-4-pyridinecarbonitrile (0.040 g, 0.13 mmol) and 4-chloro-2-methyl-1H-imidazole-5-carboxylic acid (0.023 g, 0.14 mmol) were employed in a similar process described herein to prepare the title compound (0.037 g, 64%) as a white solid after purification by Reverse-Phase HPLC (water:acetonitrile with 0.1% TFA) followed by neutralization. 1H NMR (400 MHz, CHLOROFORM-d) δ ppm 11.92 (br. s., 1H) 7.13-7.34 (m, 5H) 4.72 (d, J=5.91 Hz, 2H) 2.36 (s, 3H). ES-LCMS: m/z 453.9, 456.0 (M+1).

Example 354

4-bromo-N-({4-chloro-3-[(6-chloro-4-cyano-2-pyridinyl)oxy]-2-fluorophenyl}methyl)-2-methyl-1H-imidazole-5-carboxamide

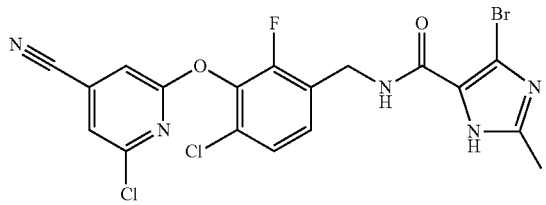

The previously described 2-{[3-(aminomethyl)-6-chloro-2-fluorophenyl]oxy}-6-chloro-4-pyridinecarbonitrile (0.040 g, 0.13 mmol) and 4-bromo-2-methyl-1H-imidazole-5-carboxylic acid (0.064 g, 0.14 mmol) were employed in a similar process described herein to prepare the title compound (0.064 g, quant.) as a white solid after purification by Reverse-Phase HPLC (water:acetonitrile with 0.1% TFA) followed by neutralization. 1H NMR (400 MHz, CHLOROFORM-d) δ ppm 12.11 (br. s., 1H) 7.36 (t, J=5.84 Hz, 1H) 7.18-7.31 (m, 4H) 4.73 (d, J=5.91 Hz, 2H) 2.37 (s, 3H). ES-LCMS: m/z 497.9, 499.9, 501.9 (M+1).

Example 355

4-chloro-N-({4-chloro-3-[(3-chloro-5-cyanophenyl)oxy]-2-fluorophenyl}methyl)-2-(methyloxy)-1H-imidazole-5-carboxamide

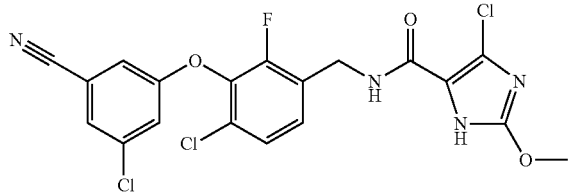

Step A: 4,5-dichloro-2-(methyloxy)-1-({[2-(trimethylsilyl)ethyl]oxy}methyl)-1H-imidazole A solution of 2-bromo-4,5-dichloro-1-({[2-(trimethylsilyl)ethyl]oxy}methyl)-1H-imidazole (0.12 g, 0.35 mmol), sodium methoxide (0.12 mL of a 25% solution in methanol, 0.53 mmol) and CuBr (0.010 g, 0.07 mmol) in methanol (0.5 mL) was heated at 100° C. for 6 h. Dilute aqueous NaCN and CH$_2$Cl$_2$ were added and the solution was stirred for a few minutes. The solution was extracted with EtOAc. The organic phase was dried (Na$_2$SO$_4$), filtered, and purified by silica gel chromatography (0-40% EtOAc/hex) to afford the title compound (0.070 g, 67%) as a clear oil. 1H NMR (400 MHz, CHLOROFORM-d) δ ppm 5.11 (s, 2H) 4.02 (s, 3H) 3.51-3.63 (m, 2H) 0.88-0.97 (m, 2H) −0.01 (s, 9H).

Step B: 4-chloro-2-(methyloxy)-1-({[2-(trimethylsilyl)ethyl]oxy}methyl)-1H-imidazole-5-carbaldehyde The title compound (0.42 g, 80%) was obtained as a clear oil from 4,5-dichloro-2-(methyloxy)-1-({[2-(trimethylsilyl)ethyl]oxy}methyl)-1H-imidazole (0.54 g, 1.82 mmol) using a procedure and process similar to that described herein. 1H NMR (400 MHz, CHLOROFORM-d) δ ppm 9.68 (s, 1H) 5.53 (s, 2H) 4.15 (s, 3H) 3.57-3.65 (m, 2 H) 0.87-0.96 (m, 2H) −0.01 (s, 9H).

Step C: 4-chloro-N-({4-chloro-3-[(3-chloro-5-cyanophenyl)oxy]-2-fluorophenyl}methyl)-2-(methyloxy)-1H-imidazole-5-carboxamide The procedure and process are similar to that described herein except that 4-chloro-2-(methyloxy)-1-({[2-(trimethylsilyl)ethyl]oxy}methyl)-1H-imidazole-5-carbaldehyde (0.42 g, 1.46 mmol) was employed to provide the acid as a clear oil which was used without further purification. The above acid (0.60 mmol) and 3-{[3-(aminomethyl)-6-chloro-2-fluorophenyl]oxy}-5-chlorobenzonitrile (0.19 g, 0.60 mmol) were employed in a similar process described herein to prepare the title compound (0.16 g, 56%) as a white solid after deprotection and purification by Reverse-Phase HPLC (water:acetonitrile with 0.1% TFA). 1H NMR (400 MHz, CHLOROFORM-d) δ ppm 9.67 (br. s., 1H) 7.28-7.40 (m, 3H) 7.17 (s, 1H) 7.03 (s, 1H) 6.99 (t, J=5.77 Hz, 1H) 4.69 (d, J=5.91 Hz, 2H) 4.04 (s, 3H). ES-LCMS: m/z 469.0, 471.0 (M+1).

Example 356

5-chloro-N-({4-chloro-3-[(3-chloro-5-cyanophenyl)oxy]-2-fluorophenyl}methyl)-2-oxo-2,3-dihydro-1H-imidazole-4-carboxamide

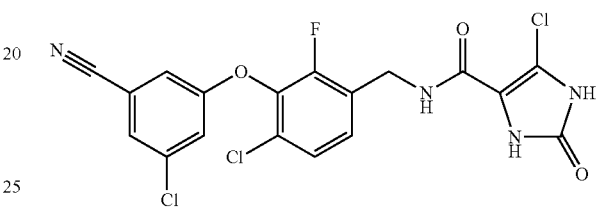

BBr$_3$ (0.28 mL of a 1M solution in CH$_2$Cl$_2$, 0.28 mmol) was added to a solution of 4-chloro-N-({4-chloro-3-[(3-chloro-5-cyanophenyl)oxy]-2-fluorophenyl}methyl)-2-(methyloxy)-1H-imidazole-5-carboxamide (0.044 g, 0.093 mmol) in CH$_2$Cl$_2$ (1 mL). After 2 h, additional BBr$_3$ (0.30 mL of a 1M solution in CH$_2$Cl$_2$, 0.30 mmol) was added and the reaction mixture was stirred for 3 days. The solution was evaporated, additional BBr$_3$ (1 mL of a 1M solution in CH$_2$Cl$_2$, 1 mmol) was added and the reaction mixture was stirred for 5 days. Sat'd NaHCO$_3$ was added and the mixture was extracted with EtOAc and then CH$_2$Cl$_2$. The organic phase was dried (Na$_2$SO$_4$), filtered, and purified by Reverse-Phase HPLC (water:acetonitrile with 0.1% TFA) to provide the title compound (0.006 g, 15%) as a white solid. 1H NMR (400 MHz, DMSO-d6) δ ppm 11.38 (s, 1H) 10.41 (s, 1H) 8.06 (t, J=5.68 Hz, 1H) 7.82 (s, 1H) 7.48-7.54 (m, 2H) 7.46 (t, J=1.97 Hz, 1
H) 7.38 (t, J=8.00 Hz, 1H) 4.46 (d, J=5.57 Hz, 2H). ES-LCMS: m/z 454.9, 456.9, 458.9 (M+1).

Example 357

4-bromo-N-({4-chloro-3-[(3-chloro-5-cyanophenyl)oxy]-2-fluorophenyl}methyl)-2-(methylthio)-1H-imidazole-5-carboxamide

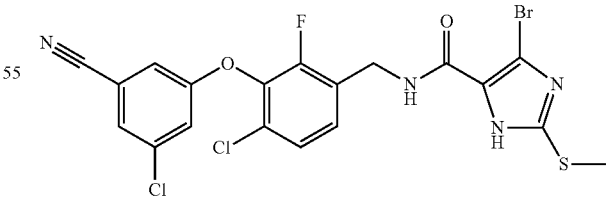

The procedure and process are similar to that described herein except that 2-azido-4-bromo-1-({[2-(trimethylsilyl)ethyl]oxy}methyl)-1H-imidazole-5-carbaldehyde (0.20 g, 0.60 mmol) was employed to provide the acid as a clear oil which was used without further purification. The above acid (0.29 mmol) and 3-{[3-(aminomethyl)-6-chloro-2-fluorophenyl]oxy}-5-chlorobenzonitrile (0.089 g, 0.29 mmol)

were employed in a similar process described herein to prepare the title compound (0.067 g, 44%) as a white solid after deprotection and purification by Reverse-Phase HPLC (water:acetonitrile with 0.1% TFA) followed by neutralization. 1H NMR (400 MHz, CHLOROFORM-d) δ ppm 10.99 (br. s., 1H) 7.28-7.42 (m, 4H) 7.17 (s, 1H) 7.04 (s, 1H) 4.75 (d, J=6.04 Hz, 2H) 2.65 (s, 3H). ES-LCMS: m/z 528.9, 530.9, 532.9 (M+1).

Example 358

4-bromo-N-({4-chloro-3-[(3-chloro-5-cyanophenyl)oxy]-2-fluorophenyl}methyl)-2-(methylsulfonyl)-1H-imidazole-5-carboxamide

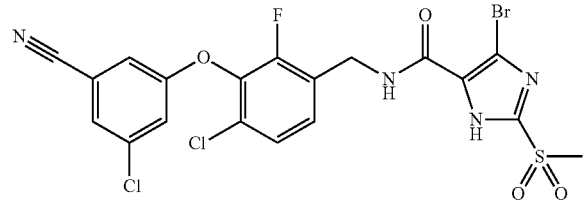

The procedure and process are similar to that described herein except that 4-bromo-2-(methylsulfonyl)-1-({[2-(trimethylsilyl)ethyl]oxy}methyl)-1H-imidazole-5-carbaldehyde (0.043 g, 0.11 mmol) was employed to provide the acid as a clear oil which was used without further purification. The above acid and 3-{[3-(aminomethyl)-6-chloro-2-fluorophenyl]oxy}-5-chlorobenzonitrile (0.035 g, 0.11 mmol) were employed in a similar process described herein to prepare the title compound (0.037 g, 59%) as a white solid after deprotection and purification by Reverse-Phase HPLC (water:acetonitrile with 0.1% TFA). 1H NMR (400 MHz, CHLOROFORM-d) δ ppm 11.45 (br. s., 1H) 7.30-7.43 (m, 3H) 7.18 (s, 1H) 7.02 (s, 1H) 4.77 (br. s., 2H) 3.31 (s, 3H). ES-LCMS: m/z 560.9, 562.9, 564.9 (M+1).

Example 359

2-(acetylamino)-4-chloro-N-({4-chloro-3-[(3-chloro-5-cyanophenyl)oxy]-2-fluorophenyl}methyl)-1H-imidazole-5-carboxamide

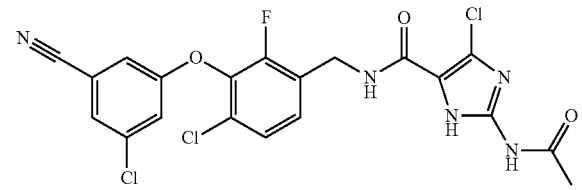

Step A: 4-chloro-N-({4-chloro-3-[(3-chloro-5-cyanophenyl)oxy]-2-fluorophenyl}methyl)-2-[(trimethyl-λ$^5$-phosphanylidene)amino]-1-({[2-(trimethylsilyl)ethyl]oxy}methyl)-1H-imidazole-5-carboxamide To a 0° C. solution of 2-azido-4-chloro-N-({4-chloro-3-[(3-chloro-5-cyanophenyl)oxy]-2-fluorophenyl}methyl)-1-({[2-(trimethylsilyl)ethyl]oxy}methyl)-1H-imidazole-5-carboxamide (1.86 g, 3.05 mmol) in THF (25 ml) was added a 1M solution of trimethylphosphine in THF (6.10 ml, 6.10 mmol). Gas evolution occurred and the reaction mixture was stirred at RT for 1 h. The reaction mixture was evaporated and taken up in EtOAc and water. The organic phase was dried (Na$_2$SO$_4$), filtered and evaporated to provide the title compound (1.96 g, 97%) as an off-white foam.

Step B: 4-chloro-N-({4-chloro-3-[(3-chloro-5-cyanophenyl)oxy]-2-fluorophenyl}methyl)-2-(diacetylamino)-1-({[2-(trimethylsilyl)ethyl]oxy}methyl)-1H-imidazole-5-carboxamide Acetyl chloride (0.10 ml, 1.41 mmol) was added to a solution of 4-chloro-N-({4-chloro-3-[(3-chloro-5-cyanophenyl)oxy]-2-fluorophenyl}methyl)-2-[(trimethyl-λ$^5$-phosphanylidene)amino]-1-({[2-(trimethylsilyl)ethyl]oxy}methyl)-1H-imidazole-5-carboxamide (0.11 g, 0.16 mmol) in CH$_2$Cl$_2$ (1.0 ml) and the reaction mixture was stirred at 45° C. for 1 h. Sat'd aqueous NaHCO3 was added and the aqueous layer was extracted with EtOAc. The organic layers were combined, dried (Na2SO4), filtered, concentrated and purified by silica gel chromatography (0-40% EtOAc/hexanes) to provide the title compound (0.047 g, 44%) as a clear oil. 1H NMR (400 MHz, CHLOROFORM-d) δ ppm 7.32-7.35 (m, 1H) 7.28-7.32 (m, 2H) 7.19 (t, J=6.04 Hz, 1H) 7.13 (t, J=2.01 Hz, 1H) 7.01 (s, 1H) 5.56 (s, 2H) 4.67 (d, J=6.13 Hz, 2H) 3.55-3.63 (m, 2H) 2.30 (s, 6H) 0.80-0.89 (m, 2H)-0.04 (s, 9H).

Step C: 2-(acetylamino)-4-chloro-N-({4-chloro-3-[(3-chloro-5-cyanophenyl)oxy]-2-fluorophenyl}methyl)-1H-imidazole-5-carboxamide A solution of 4-chloro-N-({4-chloro-3-[(3-chloro-5-cyanophenyl)oxy]-2-fluorophenyl}methyl)-2-(diacetylamino)-1-({[2-(trimethylsilyl)ethyl]oxy}methyl)-1H-imidazole-5-carboxamide (0.047 g, 0.071 mmol) and TFA (0.5 mL, 6.5 mmol) in CH$_2$Cl$_2$ (1.0 mL) was stirred at RT overnight. The solution was concentrated and purified by Reverse-Phase HPLC (water:acetonitrile with 0.1% TFA) to provide the title compound (0.007 g, 21%) as a white solid. 1H NMR (400 MHz, DMSO-d6) δ ppm 11.88 (br. s., 1H) 11.52 (br. s., 1H) 8.81 (br. s., 1H) 7.82 (s, 1H) 7.51-7.55 (m, 2H) 7.50 (s, 1H) 7.47 (t, J=2.01 Hz, 1H) 7.39 (t, J=7.87 Hz, 1H) 4.49 (d, J=5.59 Hz, 2H) 2.09 (s, 3H). ES-LCMS: m/z 496.4, 498.4, 500.3 (M+1).

Example 360

2-[bis(methylsulfonyl)amino]-4-chloro-N-({4-chloro-3-[(3-chloro-5-cyanophenyl)oxy]-2-fluorophenyl}methyl)-1H-imidazole-5-carboxamide

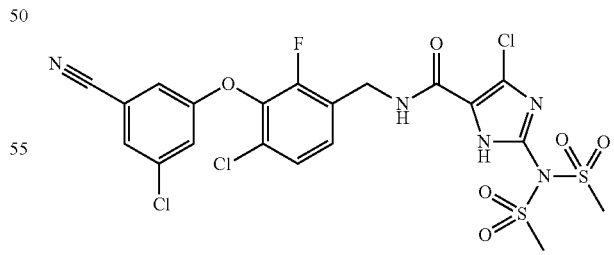

Ms-Cl (0.013 mL, 0.17 mmol) was added to a solution of 2-amino-4-chloro-N-({4-chloro-3-[(3-chloro-5-cyanophenyl)oxy]-2-fluorophenyl}methyl)-1-({[2-(trimethylsilyl)ethyl]oxy}methyl)-1H-imidazole-5-carboxamide (0.097 g, 0.17 mmol) and DIEA (0.032 mL, 0.18 mmol) in CH$_2$Cl$_2$ (1.7 ml) at RT, After 1 h, additional reagents were added: Ms-Cl (0.013 mL, 0.17 mmol) and DIEA (0.032 mL, 0.18 mmol).

Sat'd NaHCO₃ was added and the solution was extracted with CH₂Cl₂. The organic phase was dried (Na₂SO₄), filtered, concentrated and treated with TFA/CH₂Cl₂ (as described herein), and purified by Reverse-Phase HPLC (water:acetonitrile with 0.1% TFA) to provide the title compound (0.033 g, 33%) as a white solid. 1H NMR (400 MHz, DMSO-d6) δ ppm 11.97 (br. s., 1H) 8.47 (t, J=4.99 Hz, 1H) 7.83 (s, 1H) 7.44-7.55 (m, 3H) 7.40 (t, J=7.83 Hz, 1H) 4.40-4.64 (m, 2 H) 3.64 (s, 6H). ES-LCMS: m/z 609.9, 611.9, 613.9 (M+1).

Example 361

4-chloro-N-({4-chloro-3-[(3-chloro-5-cyanophenyl)oxy]-2-fluorophenyl}methyl)-2-[(methylsulfonyl)amino]-1H-imidazole-5-carboxamide

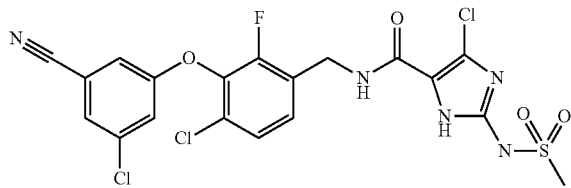

A solution of 2-[bis(methylsulfonyl)amino]-4-chloro-N-({4-chloro-3-[(3-chloro-5-cyanophenyl)oxy]-2-fluorophenyl}methyl)-1H-imidazole-5-carboxamide (0.030 g, 0.049 mmol) and TBAF (0.059 mL of a 1M solution in THF, 0.059 mmol) in THF (0.5 mL) was heated overnight under reflux. Additional TBAF (0.050 mL, 0.050 mmol) was added and stirring was continued at RT for 3 days. The solution was concentrated and purified by Reverse-Phase HPLC (water:acetonitrile with 0.1% TFA) to provide the title compound (0.012 g, 46%) as a white solid. 1H NMR (400 MHz, DMSO-d6) δ ppm 12.79 (br. s., 1H) 10.64 (br. s., 1H) 8.35 (br. s., 1H) 7.83 (s, 1H) 7.44-7.55 (m, 3H) 7.39 (t, J=6.59 Hz, 1H) 4.51 (br. s., 2H) 3.20 (br. s., 3H). ES-LCMS: m/z 532.1, 534.1, 536.0 (M+1).

Example 362

4-chloro-N-({4-chloro-3-[(3-chloro-5-cyanophenyl)oxy]-2-fluorophenyl}methyl)-2-(ethylamino)-1H-imidazole-5-carboxamide trifluoroacetate

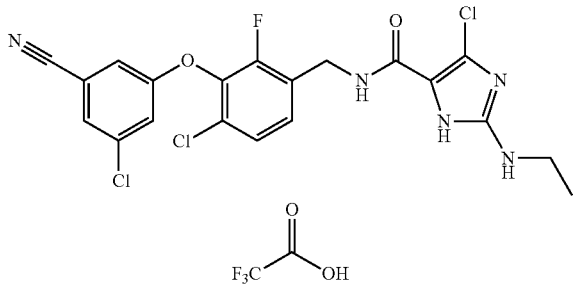

Trimethylphosphine (0.24 mL of a 1M solution in THF, 0.24 mmol) was added to a solution of 2-azido-4-chloro-N-({4-chloro-3-[(3-chloro-5-cyanophenyl)oxy]-2-fluorophenyl}methyl)-1H-imidazole-5-carboxamide (0.058 g, 0.12 mmol) in CH₂Cl₂ (1 mL) After 2 h, acetaldehyde (0.2 mL, 3.54 mmol) was added and the reaction mixture was stirred at RT overnight. The solution was cooled to 0° C. and MeOH (2 mL) and then NaBH₄ (50 mg, 1.32 mmol) were added. After 20 mins, sat'd NaHCO₃ was added and the mixture was extracted with EtOAc. The organic phase was dried (Na₂SO₄), filtered, concentrated and purified by Reverse-Phase HPLC (water:acetonitrile with 0.1% TFA) to provide the title compound (0.028 g, 39%) as a white solid. 1H NMR (400 MHz, METHANOL-d4) δ ppm 7.56 (s, 1H) 7.34-7.45 (m, 2H) 7.27 (t, J=2.01 Hz, 1H) 7.21 (s, 1H) 4.63 (s, 2H) 1.24 (t, J=7.23 Hz, 3H). ES-LCMS: m/z 482.1, 484.1, 486.1 (M+1).

Example 363

4-chloro-N-({4-chloro-3-[(3-chloro-5-cyanophenyl)oxy]-2-fluorophenyl}methyl)-2-(methylamino)-1H-imidazole-5-carboxamide trifluoroacetate

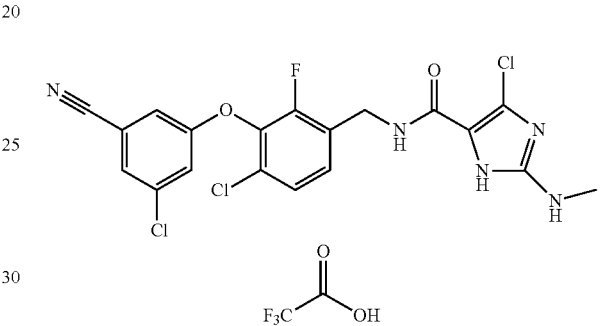

Step A: bis(1,1-dimethylethyl) [4-chloro-5-[(({4-chloro-3-[(3-chloro-5-cyanophenyl)oxy]-2-fluorophenyl}methyl){[(1,1-dimethylethyl)oxy]carbonyl}amino)carbonyl]-1-({[2-(trimethylsilyl)ethyl]oxy}methyl)-1H-imidazol-2-yl]imidodicarbonate A solution of 2-amino-4-chloro-N-({4-chloro-3-[(3-chloro-5-cyanophenyl)oxy]-2-fluorophenyl}methyl)-1-({[2-(trimethylsilyl)ethyl]oxy}methyl)-1H-imidazole-5-carboxamide (0.48 g, 0.82 mmol), Boc₂O (1.44 g, 6.59 mmol), triethylamine (0.34 mL, 2.47 mmol) and DMAP (0.02 g, 0.16 mmol) in CH₂Cl₂ (2.1 mL) and CH₃CN (2.1 mL) was stirred at RT overnight. Sat'd NaHCO₃ was added and the solution was extracted with CH₂Cl₂. The organic phase was dried (Na₂SO₄), filtered, and purified by silica gel chromatography (0-35% EtOAc/hex) to afford the title compound (0.62 g, 85%) as a white foam. 1H NMR (400 MHz, CHLOROFORM-d) δ ppm 7.32-7.38 (m, 2H) 7.28 (br. s., 1H) 7.14 (t, J=1.99 Hz, 1H) 7.04 (br. s., 1H) 5.66 (d, J=10.58 Hz, 1H) 5.05-5.21 (m, 2H) 4.82-4.97 (m, 1H) 3.47-3.67 (m, 2H) 1.56 (s, 9H) 1.47 (s, 18H) 1.38 (s, 9H) 0.80-0.97 (m, 2H) −0.01 (s, 9H).

Step B: 1,1-dimethylethyl[4-chloro-5-[(({4-chloro-3-[(3-chloro-5-cyanophenyl)oxy]-2-fluorophenyl}methyl){[(1,1-dimethylethyl)oxy]carbonyl}amino)carbonyl]-1-({[2-(trimethylsilyl)ethyl]oxy}methyl)-1H-imidazol-2-yl]carbamate A solution of bis(1,1-dimethylethyl) [4-chloro-5-[(({4-chloro-3-[(3-chloro-5-cyanophenyl)oxy]-2-fluorophenyl}methyl){[(1,1-dimethylethyl)oxy]carbonyl}amino)carbonyl]-1-({[2-(trimethylsilyl)ethyl]oxy}methyl)-1H-imidazol-2-yl]imidodicarbonate (0.62 g, 0.70 mmol) and lithium bromide (0.19 g, 2.17 mmol) in CH₃CN (8 mL) was stirred at 65° C. for 5 h. The solution was evaporated and purified by silica gel chromatography (0-50% EtOAc/hex) to afford the title compound (0.27 g, 50%) as a white foam. 1H NMR (400 MHz, CHLOROFORM-d) δ ppm 7.31-7.38 (m, 2H) 7.27-7.29 (m, 1H) 7.14 (t, J=1.92 Hz, 1H) 7.03 (br. s., 1H) 6.99 (s, 1H) 5.60 (d, J=10.44 Hz, 1H) 5.36 (d, J=10.71 Hz, 1H) 5.06-5.20 (m, 1H) 4.76-4.88 (m, 1H) 3.60 (t, J=7.55 Hz, 2H) 1.52 (s, 9H) 1.37 (s, 9H) 0.86-0.98 (m, 2H) 0.00 (s, 9H).

Step C: 4-chloro-N-({4-chloro-3-[(3-chloro-5-cyanophenyl)oxy]-2-fluorophenyl}methyl)-2-(methylamino)-1H-imidazole-5-carboxamide trifluoroacetate NaH (8 mg of a 60% suspension in mineral oil, 0.20 mmol) was added to a solution of 1,1-dimethylethyl[4-chloro-5-[(({4-chloro-3-[(3-chloro-5-cyanophenyl)oxy]-2-fluorophenyl}methyl){[(1,1-dimethylethyl)oxy]carbonyl}amino)carbonyl]-1-({[2-(trimethylsilyl)ethyl]oxy}methyl)-1H-imidazol-2-yl]carbamate (0.103 g, 0.13 mmol) in DMF (1 mL). After 30 mins, iodomethane (0.2 mL, 3.20 mmol) was added and the reaction mixture was stirred for 3 h and evaporated. The residue was treated with TFA (0.5 mL) in $CH_2Cl_2$ (1 mL) and then evaporated and purified by Reverse-Phase HPLC (water:acetonitrile with 0.1% TFA) to provide the title compound (0.015 g, 20%) as a white solid. 1H NMR (400 MHz, METHANOL-d4) δ ppm 7.56 (s, 1H) 7.32-7.43 (m, 2H) 7.27 (t, J=1.97 Hz, 1H) 7.22 (s, 1H) 4.63 (s, 2H) 2.89 (s, 3H). ES-LCMS: m/z 468.1, 470.0, 472.0 (M+1).

Example 364

4-chloro-N-[(4-chloro-3-{[3-cyano-5-(methyloxy)phenyl]oxy}-2-fluorophenyl)methyl]-1H-imidazole-5-carboxamide

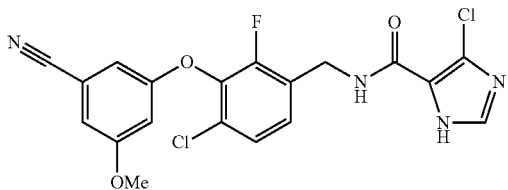

Step A: 3-[(2,3-difluoro-6-nitrophenyl)oxy]-5-(methyloxy)benzonitrile

NaH (2.05 g, 51.2 mmol) was added portionwise to a 0° C. solution of 3-hydroxy-5-(methyloxy)benzonitrile (7.63 g, 51.2 mmol) (prepared following the procedure in Magano et al. J. Org. Chem. 2006, 71, 7103) in THF (205 mL). When addition was complete, the thick suspension was stirred at this temperature for another 30 mins, and trifluoronitrobenzene (9.51 g, 53.7 mmol) was then added. The reaction mixture was stirred at RT for 3 h, dilute HCl was added and the solution was extracted with EtOAc. The organic layer was dried ($Na_2SO_4$), filtered, evaporated and purified by silica gel chromatography (0-30% EtOAc/hexanes) to afford the title compound (14.44 g, 92%) as a light yellow solid. 1H NMR (400 MHz, CHLOROFORM-d) δ ppm 7.96 (ddd, J=9.36, 4.97, 2.24 Hz, 1H) 7.28-7.35 (m, 1H) 6.95 (d, J=0.73 Hz, 1H) 6.78 (t, J=2.15 Hz, 1H) 6.73 (s, 1H) 3.85 (s, 3H).

Step B: bis(1,1-dimethylethyl)(3-{[3-cyano-5-(methyloxy)phenyl]oxy}-2-fluoro-4-nitrophenyl)propanedioate Di-tert-butyl malonate (11.22 g, 51.9 mmol) was added dropwise. to a 0° C. solution of NaH (5.09 g, 127 mmol) in THF (150 ml). The reaction mixture was allowed to warm to RT, stirred for an additional 30 mins, and cooled to 0° C. A solution of 3-[(2,3-difluoro-6-nitrophenyl)oxy]-5-(methyloxy)benzonitrile (14.44 g, 47.2 mmol) in THF (50 mL) was added slowly and the reaction mixture was stirred at RT overnight. Dilute HCl was carefully added and the solution was extracted with EtOAc (3×100 mL). The organic layer was dried ($Na_2SO_4$), filtered, concentrated, and purified by silica gel chromatography (0-35% EtOAc/hexanes) to afford the title compound (22.9 g, 97%) as a light yellow solid. 1H NMR (400 MHz, CHLOROFORM-d) δ ppm 7.88 (dd, J=8.79, 1.46 Hz, 1H) 7.62 (dd, J=8.65, 6.46 Hz, 1H) 6.92 (s, 1H) 6.68-6.79 (m, 2 H) 4.81 (s, 1H) 3.83 (s, 3H) 1.49 (s, 16H).

Step C: 3-[(2-fluoro-3-methyl-6-nitrophenyl)oxy]-5-(methyloxy)benzonitrile

A solution of bis(1,1-dimethylethyl)(3-{[3-cyano-5-(methyloxy)phenyl]oxy}-2-fluoro-4-nitrophenyl)propanedioate (12.79 g, 25.5 mmol) in $CH_2Cl_2$ (25 ml) and TFA (25 ml, 324 mmol) was stirred at RT overnight. The reaction mixture was evaporated and the residue was dissolved in water and EtOAc. The aqueous layer was extracted with EtOAc. The organic layers were dried ($Na_2SO_4$), filtered, evaporated to give (3-{[3-cyano-5-(methyloxy)phenyl]oxy}-2-fluoro-4-nitrophenyl)acetic acid as a brown solid that was used without further purification. A solution of the above acid and $Cu_2O$ (0.74 g, 5.2 mmol) in acetonitrile (50 mL) was heated under reflux overnight. The reaction mixture was brought to RT, filtered through celite, evaporated and purified by silica gel chromatography (0-25% EtOAc/hexanes) to afford the title compound (2.20 g, 29%) as a light brown solid. 1H NMR (400 MHz, CHLOROFORM-d) δ ppm 7.77 (dd, J=8.61, 1.56 Hz, 1H) 6.85-6.90 (m, 1H) 6.73 (t, J=2.06 Hz, 1H) 6.65 (d, J=0.73 Hz, 1H) 3.80 (s, 3H) 2.39 (d, J=2.20 Hz, 3H).

Step D: 3-[(6-amino-2-fluoro-3-methylphenyl)oxy]-5-(methyloxy)benzonitrile

The title compound (1.10 g, 64%) was obtained as a clear oil from 3-[(2-fluoro-3-methyl-6-nitrophenyl)oxy]-5-(methyloxy)benzonitrile (2.20 g, 7.3 mmol) using a procedure and process similar to that described herein. 1H NMR (400 MHz, CHLOROFORM-d) δ ppm 6.84-6.91 (m, 2H) 6.73-6.79 (m, 2H) 6.54 (dd, J=8.24, 1.37 Hz, 1H) 3.82 (s, 3H) 3.70 (br. s., 2H) 2.20 (d, J=1.74 Hz, 3H).

Step E: 3-[(6-chloro-2-fluoro-3-methylphenyl)oxy]-5-(methyloxy)benzonitrile

The title compound (0.84 g, 72%) was obtained from 3-[(6-amino-2-fluoro-3-methylphenyl)oxy]-5-(methyloxy)benzonitrile (1.10 g, 4.04 mmol) using a procedure and process similar to that described herein. 1H NMR (400 MHz, CHLOROFORM-d) δ ppm 7.15 (dd, J=8.4, 1.5 Hz, 1H), 7.04 (t, J=8.0 Hz, 1H), 6.84 (s, 1H), 6.71 (t, J=2.2 Hz, 1H), 6.64 (s, 1H), 3.79 (s, 3H), 2.28 (d, J=2.0 Hz, 3H).

Step F: 3-{[3-(bromomethyl)-6-chloro-2-fluorophenyl]oxy}-5-(methyloxy)benzonitrile The title compound (0.68 g, 64%) was obtained from 3-[(6-chloro-2-fluoro-3-methylphenyl)oxy]-5-(methyloxy)benzonitrile (0.84 g, 2.89 mmol) using a procedure and process similar to that described herein. 1H NMR (400 MHz, CHLOROFORM-d) δ ppm 7.28-7.32 (m, 2H) 6.88-6.92 (m, 1H) 6.73 (t, J=2.24 Hz, 1H) 6.68 (br. s., 1H) 4.50 (s, 2H) 3.83 (s, 3H).

Step G: 3-{[3-(aminomethyl)-6-chloro-2-fluorophenyl]oxy}-5-(methyloxy)benzonitrile The title compound was obtained from 3-{[3-(bromomethyl)-6-chloro-2-fluorophenyl]oxy}-5-(methyloxy)benzonitrile (0.68 g, 1.84 mmol) using a procedure and process similar to that described herein. The product was assumed to be quantitative and used without further purification.

Step H: 4-chloro-N-[(4-chloro-3-{[3-cyano-5-(methyloxy)phenyl]oxy}-2-fluorophenyl)methyl]-1H-imidazole-5-carboxamide 3-{[3-(aminomethyl)-6-chloro-2-fluorophenyl]oxy}-5-(methyloxy)benzonitrile (0.30 mmol) and 4-chloro-1-({[2-(trimethylsilyl)ethyl]oxy}methyl)-1H-imidazole-5-carboxylic acid (0.083 g, 0.30 mmol) were employed in a similar process described herein to prepare the title compound (0.096 g, 74%) as a white solid after deprotection and purification by Reverse-Phase HPLC (water:acetonitrile with 0.1% TFA).

1H NMR (400 MHz, METHANOL-d4) δ ppm 7.74 (s, 1H) 7.29-7.46 (m, 2H) 7.04 (s, 1H) 6.69-6.83 (m, 2H) 4.65 (s, 2H) 3.83 (s, 3H). ES-LCMS: m/z 435.8, 437.7 (M+1).

Example 365

4-chloro-N-[(4-chloro-3-{[3-cyano-5-(methyloxy) phenyl]oxy}-2-fluorophenyl)methyl]-2-methyl-1H-imidazole-5-carboxamide trifluoroacetate

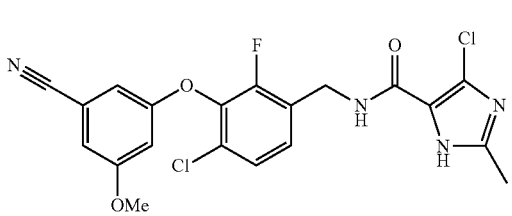

3-{[3-(aminomethyl)-6-chloro-2-fluorophenyl]oxy}-5-(methyloxy)benzonitrile (0.30 mmol) and 4-chloro-2-methyl-1H-imidazole-5-carboxylic acid (0.048 g, 0.30 mmol) were employed in a similar process described herein to prepare the title compound (0.053 g, 32%) as a white solid after purification by Reverse-Phase HPLC (water:acetonitrile with 0.1% TFA). 1H NMR (400 MHz, METHANOL-d4) δ ppm 7.31-7.41 (m, 2H) 7.04 (d, J=1.10 Hz, 1H) 6.77 (t, J=2.20 Hz, 1H) 6.74 (s, 1H) 4.64 (s, 2H) 3.83 (s, 3H) 2.40 (s, 3H). ES-LCMS: m/z 448.8, 450.9 (M+1).

Example 366

2-amino-4-chloro-N-[(4-chloro-3-{[3-cyano-5-(methyloxy)phenyl]oxy}-2-fluorophenyl)methyl]-1H-imidazole-5-carboxamide trifluoroacetate

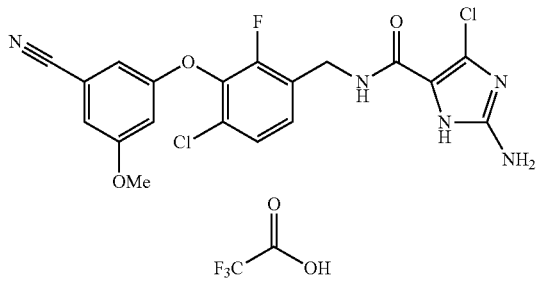

3-{[3-(aminomethyl)-6-chloro-2-fluorophenyl]oxy}-5-(methyloxy)benzonitrile (0.30 mmol) and 2-azido-4-chloro-1H-imidazole-5-carboxylic acid (0.056 g, 0.30 mmol) were employed in a similar process described herein to prepare the title compound (0.14 g, 80%) as a white solid after reduction and purification by Reverse-Phase HPLC (water:acetonitrile with 0.1% TFA). 1H NMR (400 MHz, METHANOL-d4) ppm 7.29-7.43 (m, 2H) 7.04 (s, 1H) 6.77 (t, J=2.01 Hz, 1H) 6.72 (s, 1H) 4.62 (s, 2 H) 3.83 (s, 3H), ES-LCMS: m/z 450.9, 452.8 (M+1).

Example 367

Methyl (4-chloro-5-{[({4-chloro-3-[(3-chloro-5-cyanophenyl)oxy]-2-fluorophenyl}methyl)amino]carbonyl}-1H-imidazol-2-yl)carbamate

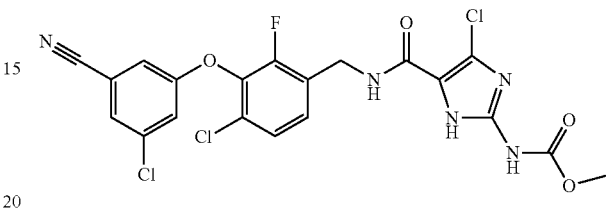

Methyl chloroformate (0.020 mL, 0.26 mmol) was added to a solution of 2-amino-4-chloro-N-({4-chloro-3-[(3-chloro-5-cyanophenyl)oxy]-2-fluorophenyl}methyl)-1-({[2-(trimethylsilyl)ethyl]oxy}methyl)-1H-imidazole-5-carboxamide (0.050 g, 0.086 mmol) and DIEA (0.075 mL, 0.43 mmol) in CH₂Cl₂ (0.5 mL). The reaction mixture was stirred at RT overnight. TFA (0.5 mL) was added and the reaction mixture was stirred at RT for another 1 h. The reaction mixture was then evaporated and taken up in MeOH (1 mL). NaBH₄ (0.030 g, 0.80 mmol) was added and the reaction mixture was stirred overnight. CH₂Cl₂ and sat'd NaHCO₃ were added and the solution was extracted with CH₂Cl₂. The organic layer was dried (Na2SO4), filtered, concentrated and purified by Reverse-Phase HPLC (water:acetonitrile with 0.1% TFA) to afford the title compound (0.008 g, 19%) as a white solid. 1H NMR (400 MHz, METHANOL-d4) δ ppm 7.56 (s, 1H) 7.34-7.44 (m, 2H) 7.25-7.29 (m, 1H) 7.24 (s, 1H) 4.57-4.70 (m, 2H) 3.81 (s, 3H). ES-LCMS: m/z 512.01, 513.97 (M+1).

Example 368

3-chloro-5-({6-chloro-2-fluoro-3-[(6-oxo-6,7-dihydro-1H-purin-1-yl)methyl]phenyl}oxy)benzonitrile trifluoroacetate

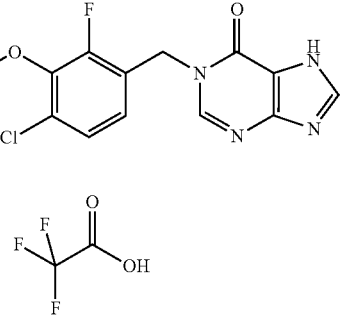

Step A: ethyl 4-{[(1E)-(dimethylamino)methylidene]amino}-1H-imidazole-5-carboxylate A solution of ethyl 4-amino-1H-imidazole-5-carboxylate (0.65 g, 4.19 mmol) and DMF-DMA (11.22 ml, 84 mmol) in DMF (3 mL) was stirred at RT under nitrogen for 3 days. The excess DMF-DMA and DMF were removed under vacuum to give the desired compound as a white solid. 1H NMR (400 MHz, DMSO-$d_6$) δ ppm 10.34-13.68 (m, 1H), 8.09 (s, 1H), 7.36 (s, 1H), 4.12 (q, 2H), 2.96 (d, 6H), 1.22 (t, 3H).

Step B: 3-chloro-5-({6-chloro-2-fluoro-3-[(6-oxo-6,7-dihydro-1H-purin-1-yl)methyl]phenyl}oxy)benzonitrile trifluoroacetate A solution of 3-{[3-(aminomethyl)-6-chloro-2-fluorophenyl]oxy}-5-chlorobenzonitrile (0.1 g, 0.321 mmol), ethyl 4-{[(1E)-(dimethylamino)methylidene]amino}-1H-imidazole-5-carboxylate (0.074 g, 0.354 mmol) and phenol (0.091 g, 0.964 mmol) in DCM (3 mL) was placed into an oil bath at 150° C. under nitrogen for 5 min. The reaction was cooled to RT and MeOH (5 mL) was added. After 15 min a white precipitate formed which was filtered and dried. EtOH (10 mL) was added to the white solid and heated to reflux then cooled to RT. The solid was filtered and dried to give the desired compound in ~90% purity. The material was purified by Reverse Phase HPLC (MeCN/water+0.1% TFA) to give 0.04 g (22%) of the title compound as a white solid. 1H NMR (400 MHz, DMSO-$d_6$) δ ppm 8.45 (s, 1H), 8.18 (s, 1H), 7.82 (s, 1H), 7.54 (s, 1H), 7.41-7.51 (m, 2H), 7.22 (t, 1H), 5.30 (s, 2H), 2.55 (t, 1H). LCMS m/z 430.1 (M+H).

Example 369

3-chloro-5-({6-chloro-2-fluoro-3-[(4-oxo-4,5-dihydro-3H-pyrrolo[3,2-d]pyrimidin-3-yl)methyl]phenyl}oxy)benzonitrile

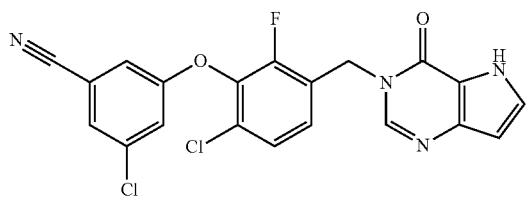

Step A: ethyl 3-{[(1E/Z)-(dimethylamino)methylidene]amino}-1H-pyrrole-2-carboxylate A solution of ethyl 3-amino-1H-pyrrole-2-carboxylate hydrochloride (0.7 g, 3.67 mmol) and DMF-DMA (9.83 ml, 73.4 mmol) in DMF (3 mL) was stirred at RT under nitrogen for 3 days. The excess DMF-DMA and DMF were removed under vacuum to give a yellow oily solid. Ethyl acetate (20 mL) and Et$_2$O (10 mL) were added and the mixture was sonicated. The white solid was filtered off and the filtrate was concentrated to give an oil that was used without further purification.

Step B: 3-chloro-5-({6-chloro-2-fluoro-3-[(4-oxo-4,5-dihydro-3H-pyrrolo[3,2-d]pyrimidin-3-yl)methyl]phenyl}oxy)benzonitrile The title compound was prepared in a manner similar to that described herein using 3-{[3-(aminomethyl)-6-chloro-2-fluorophenyl]oxy}-5-chlorobenzonitrile (0.1 g, 0.321 mmol), ethyl 3-{[(1E/Z)-(dimethylamino)methylidene]amino}-1H-pyrrole-2-carboxylate (0.135 g, 0.643 mmol) and phenol (0.091 g, 0.964 mmol) in DCM (3 mL) to give 0.074 g (53%) of the title compound as a white solid. 1H NMR (400 MHz, DMSO-$d_6$) δ ppm 12.19 (br. s., 1H), 8.22 (s, 1H), 7.83 (s, 1H), 7.34-7.59 (m, 4H), 7.16 (t, 1H), 6.41 (t, 1H), 5.29 (s, 2H). LCMS m/z 427.2 (M−H).

Example 370

3-bromo-5-({6-chloro-2-fluoro-3-[(6-oxo-6,7-dihydro-1H-purin-1-yl)methyl]phenyl}oxy)benzonitrile

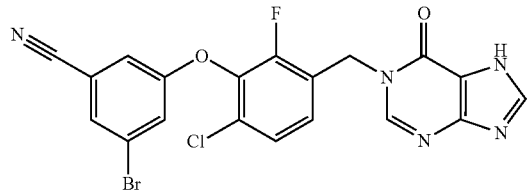

The title compound was prepared in a manner similar to that described herein using 3-{[3-(aminomethyl)-6-chloro-2-fluorophenyl]oxy}-5-bromobenzonitrile (0.61 g, 1.715 mmol), ethyl 4-{[(1E)-(dimethylamino)methylidene]amino}-1H-imidazole-5-carboxylate (0.397 g, 1.887 mmol) and phenol (0.484 g, 5.15 mmol) in DCM (3 mL) to give 0.31 g (38%) of the title compound as a white solid. 1H NMR (400 MHz, DMSO-$d_6$) δ ppm 7.58 (br. s., 1H), 8.45 (s, 1H), 8.17 (br. s., 1H), 7.93 (s, 1H), 7.58 (d, 2H), 7.47 (d, 1H), 7.21 (t, 1H), 5.30 (s, 2H). LCMS m/z 474.1 (M−H).

Example 371

3-({6-bromo-2-fluoro-3-[(6-oxo-6,7-dihydro-1H-purin-1-yl)methyl]phenyl}oxy)-5-chlorobenzonitrile

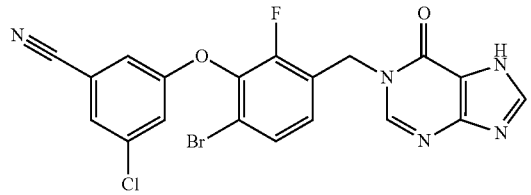

The title compound was prepared in a manner similar to that described herein using 3-{[3-(aminomethyl)-6-bromo-2-fluorophenyl]oxy}-5-chlorobenzonitrile (0.15 g, 0.422 mmol), ethyl 4-{[(1E)-(dimethylamino)methylidene]amino}-1H-imidazole-5-carboxylate (0.098 g, 0.464 mmol) and phenol (0.052 g, 0.548 mmol) in DCM (2 mL) to give 0.070 (34%) of the title compound. 1H NMR (400 MHz, DMSO-$d_6$) δ ppm 8.44 (s, 1H), 8.17 (s, 1H), 7.82 (s, 1H), 7.59 (d, 1H), 7.52 (s, 1H), 7.46 (s, 1H), 7.15 (t, 1H), 5.28 (s, 2H).

Example 372

3-({6-chloro-2-fluoro-3-[(6-oxo-6,7-dihydro-1H-purin-1-yl)methyl]phenyl}oxy)-5-ethenylbenzonitrile trifluoroacetate

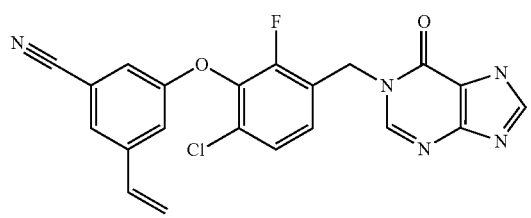

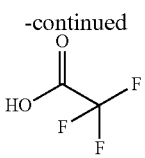

A mixture of 3-bromo-5-({6-chloro-2-fluoro-3-[(6-oxo-6,7-dihydro-1H-purin-1-yl)methyl]phenyl}oxy)benzonitrile (150 mg, 0.316 mmol), Potassium vinyl trifluoroborate (85 mg, 0.632 mmol), PdCl$_2$(dppf)-CH$_2$Cl$_2$Adduct (25.8 mg, 0.032 mmol) and TEA (0.220 ml, 1.580 mmol) in n-propanol (10 ml) was heated at 100° C. for 48 h. The mixture was cooled down to 0° C. and water (30 ml) was added to afford a solid. The solid was further washed 5 times with water and then 3 times with ether. The solid was purified with reverse phase HPLC to give a white solid 3-({6-chloro-2-fluoro-3-[(6-oxo-6,7-dihydro-1H-purin-1-yl)methyl]phenyl}oxy)-5-ethenylbenzonitrile trifluoroacetate (35 mg, 20.67% yield). 1H NMR (400 MHz, DMSO-d$_6$) δ ppm 8.41 (s, 1H) 8.14 (s, 1H) 7.75 (s, 1H) 7.40-7.48 (m, 1H) 7.37 (s, 1H) 7.22-7.30 (m, 1H) 7.16 (t, 1H) 6.70 (dd, 1H) 5.99 (d, 1H) 5.39 (d, 1H) 5.25 (s, 2H). LC-MS (ES$^+$) m/z 421.65, [M+1].

Example 373

3-({6-chloro-2-fluoro-3-[(6-oxo-6,7-dihydro-1H-purin-1-yl)methyl]phenyl}oxy)-5-(2-propen-1-yl)benzonitrile

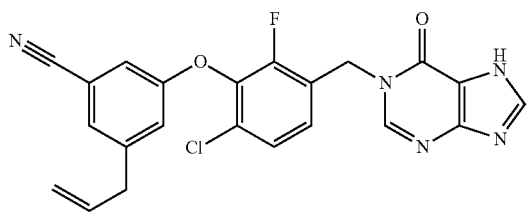

A mixture of 3-bromo-5-({6-chloro-2-fluoro-3-[(6-oxo-6,7-dihydro-1H-purin-1-yl)methyl]phenyl}oxy)benzonitrile (78 mg, 0.164 mmol), allyltri-n-butyltin (0.082 ml, 0.263 mmol) and tetrakis(triphenylphosphine)palladium(0) (18.99 mg, 0.016 mmol) was heated in a personal microwave reactor at 160° C. for 20 min. The mixture was filtrated and was purified with reverse phase HPLC to afford a white solid 3-({6-chloro-2-fluoro-3-[(6-oxo-6,7-dihydro-1H-purin-1-yl)methyl]phenyl}oxy)-5-(2-propen-1-yl)benzonitrile (20 mg, 27.9% yield). 1H NMR (400 MHz, DMSO-d$_6$) δ ppm 8.41 (s, 1H) 8.06-8.20 (m, 1H) 7.35-7.52 (m, 1H) 7.23-7.32 (m, 1H) 7.18 (s, 1H) 7.12 (s, 1H) 5.79-5.98 (m, 1H) 5.27 (s, 2H) 5.02 (s, 1H) 3.38 (d, 2H). LC-MS (ES$^+$) m/z 435.50, [M+1].

Example 374

3-chloro-5-({6-chloro-2-fluoro-3-[(4-oxo-1,4-dihydro-5H-imidazo[4,5-c]pyridin-5-yl)methyl]phenyl}oxy)benzonitrile trifluoroacetate

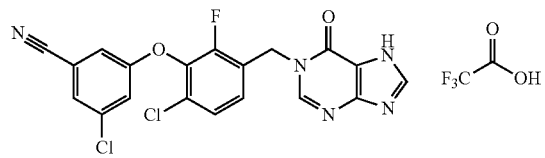

NaH (0.033 g, 0.833 mmol) was added to a 0 C solution of 3-deazahypoxanthine (0.045 g, 0.33 mmol) (prepared according to the literature reference: Kotera et al. *J. Am. Chem. Soc.* 2004, 126, 9532) in DMF (3 mL). The reaction mixture was stirred at RT for 1.5 h. DMSO (2 mL) and 3-{[3-(bromomethyl)-6-chloro-2-fluorophenyl]oxy}-5-chlorobenzonitrile (0.048 g, 0.13 mmol) was added and the solution was continued stirring overnight. Water was added and the reaction mixture was evaporated to dryness. The residue was purified by Reverse-Phase HPLC (water:acetonitrile with 0.1% TFA) to provide the title compound (0.038 g, 21%) as a white solid. 1H NMR (400 MHz, DMSO-d6) δ ppm 8.44 (s, 1H) 7.83 (s, 1H) 7.59 (d, 1H) 7.53 (s, 1H) 7.45-7.50 (m, 2H) 7.10 (t, 1H) 6.72 (d, 1H) 5.30 (s, 2H). ES-LCMS: m/z 429.2, 431.1 (M+1).

Example 375

4-bromo-N-[(4-chloro-3-{[3-cyano-5-(difluoromethyl)phenyl]oxy}-2-fluorophenyl)methyl]-1H-imidazole-5-carboxamide

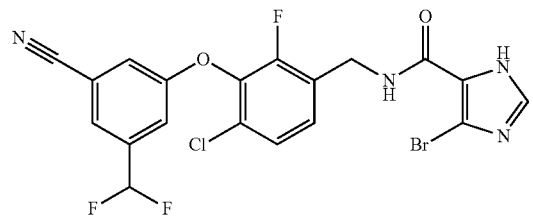

To a solution of 3-{[3-(aminomethyl)-6-chloro-2-fluorophenyl]oxy}-5-(difluoromethyl)benzonitrile trifluoroacetate (90 mg, 0.204 mmol), 4-bromo-1H-imidazole-5-carboxylic acid (39.0 mg, 0.204 mmol) and HOBT (31.3 mg, 0.204 mmol) in DMF (3 ml) was added EDC (39.1 mg, 0.204 mmol) and the reaction mixture was stirred at RT for 30 minutes. The crude material was purified via reverse phase HPLC to give the title compound (56 mg, 55% yield). $^1$H NMR (DMSO-d$_6$) δ ppm 8.42 (br. s., 1H) 7.85 (s, 1H) 7.79 (s, 1H) 7.72 (s, 1H) 7.47-7.58 (m, 2H) 7.38 (t, 1H) 7.07 (t, 1H) 4.51 (d, 2H). LC-MS (ES$^+$) m/z 499.00 [M+H].

Example 376

5-chloro-N-[(4-chloro-3-{[3-cyano-5-(hydroxymethyl)phenyl]oxy}-2-fluorophenyl)methyl]-1-methyl-1H-imidazole-4-carboxamide

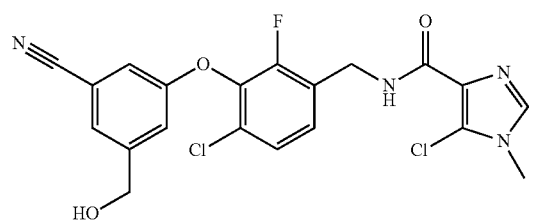

Step A: 1,1-dimethylethyl({4-chloro-3-[(3-cyano-5-formylphenyl)oxy]-2-fluorophenyl}methyl){[4-chloro-1-({[2-(trimethylsilyl)ethyl]oxy}methyl)-1H-imidazol-5-yl]carbonyl}carbamate To a solution of 4-chloro-N-({4-chloro-3-[(3-cyano-5-formylphenyl)oxy]-2-fluorophenyl}methyl)-1-({[2-(trimethylsilyl)ethyl]oxy}methyl)-1H-imidazole-5-carboxamide (117 mg, 0.208 mmol) and DMAP (2.54 mg, 0.021 mmol) in DCM (5 ml) was added BOC-Anhydride (0.145 ml, 0.623 mmol) and the reaction mixture was stirred at RT overnight. The solvent was removed and the crude material was purified via silica gel chromatography to give the title compound (102 mg, 74% yield). $^1$H NMR (DMSO-d$_5$) δ ppm 9.93 (s, 1H) 8.11 (s, 1H) 8.03 (s, 1H) 7.85 (s, 1H) 7.56 (d, 1H) 7.51 (d, 1H) 7.36 (t, 1H) 5.58 (d, 1H) 5.31 (d, 1H) 4.94-5.12 (m, 1H) 4.68-4.90 (m, 1H) 3.33-3.49 (m, 2H) 1.21 (s, 9H) 0.66-0.92 (m, 2H) −0.11 (s, 9H).

Step B: 1,1-dimethylethyl[(4-chloro-3-{[3-cyano-5-(hydroxymethyl)phenyl]oxy}-2-fluorophenyl)methyl]{[4-chloro-1-({[2-(trimethylsilyl)ethyl]oxy}methyl)-1H-imidazol-5-yl]carbonyl}carbamate To a solution of 1,1-dimethylethyl({4-chloro-3-[(3-cyano-5-formylphenyl)oxy]-2-fluorophenyl}methyl){[4-chloro-1-({[2-(trimethylsilyl)ethyl]oxy}methyl)-1H-imidazol-5-yl]carbonyl}carbamate (101 mg, 0.152 mmol) in methanol (10 ml) was added sodium borohydride (5.76 mg, 0.152 mmol) and the reaction mixture was stirred for 15 minutes at RT. The reaction mixture was diluted with EtOAc and washed with water. The solvent was removed and the crude material was purified via silica gel chromatography to give the title compound (82 mg, 81% yield). $^1$H NMR (DMSO-d$_6$) δ ppm 8.06 (s, 1H) 7.43-7.55 (m, 2H) 7.34 (t, 1H) 7.22 (s, 1H) 7.18 (s, 1H) 5.61 (d, 1H) 5.44 (t, 1H) 5.29-5.39 (m, 1H) 4.98-5.09 (m, 1H) 4.78-4.90 (m, 1H) 4.49 (d, 2H) 3.34-3.53 (m, 2H) 1.25 (s, 9H) 0.70-0.96 (m, 2H) −0.08 (s, 9H).

Step C: 5-chloro-N-[(4-chloro-3-{[3-cyano-5-(hydroxymethyl)phenyl]oxy}-2-fluorophenyl)methyl]-1-methyl-1H-imidazole-4-carboxamide To a solution of 1,1-dimethylethyl[(4-chloro-3-{[3-cyano-5-(hydroxymethyl)phenyl]oxy}-2-fluorophenyl)methyl]{[4-chloro-1-({[2-(trimethylsilyl)ethyl]oxy}methyl)-1H-imidazol-5-yl]carbonyl}carbamate (66 mg, 0.099 mmol) in DCM (5 ml) was added Meerwein's reagent (16.13 mg, 0.109 mmol) and the reaction mixture was stirred for 4 hours at RT. TFA (2.0 ml, 26.0 mmol) was added and the reaction mixture was stirred at RT for another 2 hours. The solvent was removed and the crude material was purified via reverse phase HPLC to give the title compound (34 mg, 76% yield). $^1$H NMR (DMSO-d$_6$) δ ppm 8.66 (t, 1H) 7.87 (s, 1H) 7.44-7.57 (m, 2H) 7.25-7.39 (m, 2H) 7.19 (s, 1H) 4.51 (s, 2H) 4.45 (d, 2 H) 2.50 (s, 3H). LC-MS (ES$^+$) m/z 449.11 [M+H].

Example 377

4-bromo-N-({4-bromo-3-[(3-chloro-5-cyanophenyl)oxy]-2-fluorophenyl}methyl)-1H-imidazole-5-carboxamide

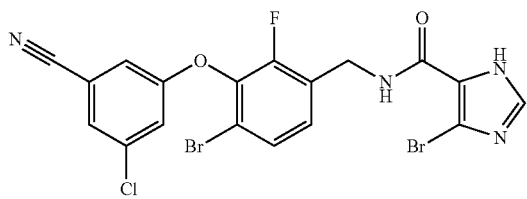

EDC (0.059 g, 0.309 mmol) and HOBT (0.042 g, 0.309 mmol) were added to a solution of 3-{[3-(aminomethyl)-6-bromo-2-fluorophenyl]oxy}-5-chlorobenzonitrile (0.100 g, 0.281 mmol) and 4-bromo-1H-imidazole-5-carboxylic acid (0.054 g, 0.281 mmol) in DMF (2 ml). The mixture was stirred at RT overnight. The reaction mixture was extracted with ethyl acetate and saturated aqueous sodium bicarbonate and the organic layer was dried over sodium sulfate and concentrated. Purification by reverse phase HPLC (acetonitrile:water with 0.1% formic acid) gave 0.068 g (45%) of the title compound as a white solid. $^1$H NMR (400 MHz, DMSO-d$_6$) δ ppm 8.34 (br. s., 1H), 7.77 (s, 2H), 7.58 (d, 1H), 7.45 (s, 1H), 7.40 (t, 1H), 7.27 (t, 1H), 4.45 (d, 2H). ES MS: m/z 527 (M+1).

Example 378

N-({4-bromo-3-[(3-chloro-5-cyanophenyl)oxy]-2-fluorophenyl}methyl)-4-chloro-1H-imidazole-5-carboxamide

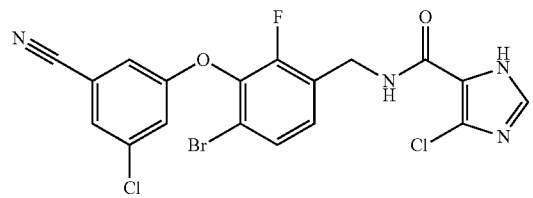

EDC (0.028 g, 0.148 mmol) and HOBT (0.020 g, 0.148 mmol) were added to a solution of 3-{[3-(aminomethyl)-6-bromo-2-fluorophenyl]oxy}-5-chlorobenzonitrile (0.053 g, 0.148 mmol) and 4-chloro-1-({[2-(trimethylsilyl)ethyl]oxy}methyl)-1H-imidazole-5-carboxylic acid (0.041 g, 0.148 mmol) in DMF (2 mL). The mixture was stirred at RT overnight. The reaction mixture was extracted with ethyl acetate and saturated aqueous sodium bicarbonate. The organic layer was dried over sodium sulfate and concentrated to give a yellow oil which was dissolved in dichloromethane (1.5 mL). Trifluoroacetic acid (0.5 ml, 6.49 mmol) was added and the mixture was stirred at RT overnight. Purification by reverse phase HPLC (acetonitrile:water with 0.1% formic acid) gave the title compound 0.002 g, 2.5%) as a white solid. $^1$H NMR (400 MHz, methanol-d$_4$) δ ppm 7.69 (s, 1H), 7.48-7.55 (m, 2H), 7.29 (t, 1H), 7.22 (d, 1H), 7.19 (s, 1H), 4.61 (s, 2H). ES MS m/z 483 (M+1).

Example 379

N-({4-bromo-3-[(3-chloro-5-cyanophenyl)oxy]-2-fluorophenyl}methyl)-4-chloro-2-[(dimethylamino)sulfonyl]-1H-imidazole-5-carboxamide

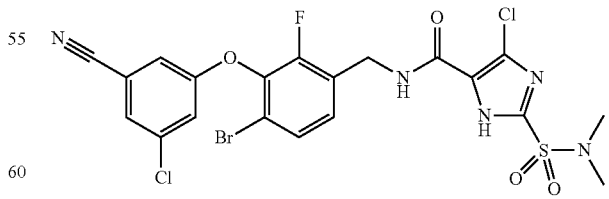

Step A: 4,5-dichloro-1-({[2-(trimethylsilyl)ethyl]oxy}methyl)-1H-imidazole-2-sulfonyl chloride BuLi (0.69 ml of a 2.4M solution in hex, 1.65 mmol) was added dropwise to a −78° C. solution of 2-bromo-4,5-dichloro-1-({[2-(trimethylsilyl)ethyl]oxy}methyl)-1H-imidazole (0.57 g, 1.65 mmol) in THF (3 ml). After 15 mins, SO2 was bubbled through the reaction mixture via a needle for 15 mins. The stirred reaction was allowed to warm to RT slowly overnight. The solution was then cooled to 0° C. and a solution of NCS (0.44 g, 3.30 mmol) in CH$_2$Cl$_2$ (4 mL) was added and stirring was continued at RT. After 2 h, the reaction mixture was filtered through celite and the solvent was evaporated to give the title compound as a light brown residue that was used without purification and assumed to be quantitative.

Step B: 4,5-dichloro-N,N-dimethyl-1-({[2-(trimethylsilyl)ethyl]oxy}methyl)-1H-imidazole-2-sulfonamide A solution of 4,5-dichloro-1-({[2-(trimethylsilyl)ethyl]oxy}methyl)-1H-imidazole-2-sulfonyl chloride (0.826 mmol) in acetone (2.5 mL) and THF (1.5 mL) was added to dimethylamine (2.0 mL of a 2M solution in THF, 4.0 mmol). The reaction mixture was stirred at RT for 1 h and then evaporated to dryness. The residue was taken up in EtOAc and washed with brine. The organic layer was dried (Na$_2$SO$_4$), filtered, evaporated and purified by silica gel chromatography (0-30% EtOAc/hexanes) to provide the title compound (0.18 g, 57%) as a light yellow oil. 1H NMR (400 MHz, CHLOROFORM-d) δ ppm 5.62 (s, 2H), 3.61-3.75 (m, 2H), 3.06 (s, 6H), 0.84-1.00 (m, 3H), 0.00 (s, 9H).

Step C: 4-chloro-5-formyl-N,N-dimethyl-1-({[2-(trimethylsilyl)ethyl]oxy}methyl)-1H-imidazole-2-sulfonamide nBuLi (0.21 ml of a 2.4M solution in hex, 0.51 mmol) was added dropwise to a −78° C. solution of 4,5-dichloro-N,N-dimethyl-1-({[2-(trimethylsilyl)ethyl]oxy}methyl)-1H-imidazole-2-sulfonamide (0.18 g, 0.47 mmol) in THF (3 ml). The reaction mixture was stirred for 30 mins and DMF (0.4 ml, 5.17 mmol) was added. After 10 mins, the cooling bath was removed and the reaction mixture was warmed to RT. Sat'd NaHCO$_3$ was added and the solution was extracted with EtOAc. The organic layer was dried (Na$_2$SO$_4$), filtered, evaporated, and purified by silica gel chromatography (0-20% EtOAc/hexanes) to provide the title compound (0.085 g, 49%) as a clear oil. 1H NMR (400 MHz, CHLOROFORM-d) δ ppm 9.93 (s, 1H), 5.94 (s, 2H), 3.63-3.70 (m, 2H), 3.09 (s, 6H), 0.89-0.98 (m, 2H), −0.02 (s, 9H).

Step D: N-({4-bromo-3-[(3-chloro-5-cyanophenyl)oxy]-2-fluorophenyl}methyl)-4-chloro-2-[(dimethylamino)sulfonyl]-1H-imidazole-5-carboxamide A solution of NaClO$_2$ (0.21 g, 2.31 mmol) and NaH$_2$PO$_4$.H$_2$O (0.19 g, 1.39 mmol) in H$_2$O (0.5 mL) was added to a solution of 4-chloro-5-formyl-N,N-dimethyl-1-({[2-(trimethylsilyl)ethyl]oxy}methyl)-1H-imidazole-2-sulfonamide (0.085 g, 0.23 mmol) and 2-methyl-2-butene (1.39 mL of a 2M solution in THF, 2.77 mmol) in THF (0.70 mL) and t-BuOH (0.16 mL). The reaction mixture was stirred at RT for 1 h and extracted with EtOAc. The organic layer was dried (Na$_2$SO$_4$), filtered and dried to provide 4-chloro-2-[(dimethylamino)sulfonyl]-1-({[2-(trimethylsilyl)ethyl]oxy}methyl)-1H-imidazole-5-carboxylic acid as a clear oil that was assumed to be quantitative and used without further purification.

The above acid (0.12 mmol) and 3-{[3-(aminomethyl)-6-bromo-2-fluorophenyl]oxy}-5-chlorobenzonitrile (0.051 g, 0.14 mmol) were employed using a procedure similar to that described herein to provide the title compound (0.022 g, 32%) as a white solid after deprotection and purification by Reverse-Phase HPLC (water:acetonitrile with 0.1% formic acid). 1H NMR (400 MHz, METHANOL-d4) δ ppm 7.51-7.58 (m, 2H), 7.34 (t, J=7.9 Hz, 1H), 7.25 (t, J=2.0 Hz, 1H), 7.22 (s, 1H), 4.62 (s, 2H), 2.87 (s, 6 H). ES-LCMS: m/z 590.1, 592.0, 594.0 (M+1).

Example 380

4-chloro-N-({4-chloro-3-[(3-chloro-5-cyanophenyl)oxy]-2-fluorophenyl}methyl)-2-[(dimethylamino)sulfonyl]-1H-imidazole-5-carboxamide 4-chloro-2-[(dimethylamino)sulfonyl]-1-({[2-(trimethylsilyl)ethyl]oxy}methyl)-1H-imidazole-5-carboxylic acid (0.12 mmol) and 3-{[3-(aminomethyl)-6-chloro-2-fluorophenyl]oxy}-5-chlorobenzonitrile (0.045 g, 0.14 mmol) were employed using a procedure similar to that described herein to provide the title compound (0.039 g, 59%) as a white solid after deprotection and purification by Reverse-Phase HPLC (water:acetonitrile with 0.1% formic acid). 1H NMR (400 MHz, METHANOL-d4) δ ppm 7.54 (s, 1H), 7.34-7.42 (m, 2H), 7.26 (s, 1H), 7.22 (s, 1H), 4.64 (s, 2H), 2.86 (s, 6H). ES-LCMS: m/z 546.1, 547.9, 550.0 (M+1).

Example 381

N-({4-bromo-3-[(3-chloro-5-cyanophenyl)oxy]-2-fluorophenyl}methyl)-4-chloro-2-[(methylamino)sulfonyl]-1H-imidazole-5-carboxamide Step A: 4-chloro-5-({[(1,1-dimethylethyl)(dimethyl)silyl]oxy}methyl)-1-({[2-(trimethylsilyl)ethyl]oxy}methyl)-1H-imidazole Sodium borohydride (0.37 g, 9.78 mmol) was added to a 0° C. solution of 4-chloro-1-({[2-(trimethylsilyl)ethyl]oxy}methyl)-1H-imidazole-5-carbaldehyde (1.70 g, 6.52 mmol) in methanol (26 ml). Gas evolution was observed and the reaction mixture was stirred at RT for 30 mins and evaporated. Sat'd NaHCO$_3$ and CH$_2$Cl$_2$ were added to the residue and the aqueous layer was extracted with CH$_2$Cl$_2$ (4×20 mL). The combined organic phase was dried (Na$_2$SO$_4$), filtered and evaporated to give [4-chloro-1-({[2-(trimethylsilyl)ethyl]oxy}methyl)-1H-imidazol-5-yl]methanol as a light yellow oil. A solution of this alcohol, imidazole (0.89 g, 13.0 mmol) and TBSCI (1.47 g, 9.78 mmol) in CH$_2$Cl$_2$ (22 mL) was stirred at RT overnight. Sat'd NaHCO$_3$ was added and the aqueous layer was extracted with CH$_2$Cl$_2$ (2×20 mL). The combined organic phase was dried (Na$_2$SO$_4$), filtered, evaporated and purified by silica gel chromatography (0-35% EtOAc/hexanes) to give the title compound (2.19 g, 89%) as a clear oil. 1H NMR (400 MHz, CHLOROFORM-d) δ ppm 7.44 (s, 1H), 5.35 (s, 2H), 4.72 (s, 2H), 3.51 (t, J=8.2 Hz, 2H), 0.90-0.96 (m, 2H), 0.89 (s, 9H), 0.09 (s, 6H), 0.00 (s, 9H).

Step B: 4-chloro-5-({[(1,1-dimethylethyl)(dimethyl)silyl]oxy}methyl)-1-({[2-(trimethylsilyl)ethyl]oxy}methyl)-1H-imidazole-2-sulfonyl chloride BuLi (0.60 ml of a 2.4M solution in hex, 1.43 mmol) was added dropwise to a −78° C. solution of 4-chloro-5-({[(1,1-dimethylethyl)(dimethyl)silyl]oxy}methyl)-1-({[2-(trimethylsilyl)ethyl]oxy}methyl)-1H-imidazole (0.54 g, 1.43 mmol) in THF (7 ml). The reaction mixture was stirred at this temperature for 15 mins and then at −60° C. for 2 h. The solution was cooled to −78° C. and SO2 was bubbled through the reaction mixture via a needle for 15 mins. The stirred reaction was allowed to warm to RT slowly overnight. CH$_2$Cl$_2$ (3 mL) was added and the solution was then cooled to 0° C. and NCS (0.38 g, 2.87 mmol) was added and stirring was continued at RT. After 2 h, the reaction mixture was filtered through celite and the solvent was evaporated to give the title compound as a light brown residue that was used without purification and assumed to be quantitative.

Step C: 4-chloro-5-({[(1,1-dimethylethyl)(dimethyl)silyl]oxy}methyl)-N-methyl-1-({[2-(trimethylsilyl)ethyl]oxy}methyl)-1H-imidazole-2-sulfonamide A solution of 4-chloro-5-({[(1,1-dimethylethyl)(dimethyl)silyl]oxy}methyl)-1-({[2-(trimethylsilyl)ethyl]oxy}methyl)-1H-imidazole-2-sulfonyl chloride (0.341 g, 0.72 mmol) in acetone (4.5 mL) and THF (2.5 mL) was added to a 0° C. solution of methylamine (3.6 mL of a 2M solution in THF, 7.2 mmol) in THF (2 mL). The reaction mixture was stirred at RT for 1 h and evaporated. The residue was taken up in EtOAc and washed with brine. The organic phase was dried (Na$_2$SO$_4$), filtered evaporated, and purified by silica gel chromatography (0-25% EtOA/hexanes) to give the title compound (0.23 g, 68%) as a light yellow oil. 1H NMR (400 MHz, CHLOROFORM-d) δ ppm 5.85 (br. s., 1H), 5.73 (s, 2H), 4.75 (s, 2H), 3.59-3.68 (m, 2H), 2.86 (d, J=5.1 Hz, 3H), 0.93 (d, J=8.4 Hz, 2H), 0.89 (s, 9H), 0.10 (s, 6H), −0.01 (s, 9H).

Step D: 4-chloro-5-formyl-N-methyl-1-({[2-(trimethylsilyl)ethyl]oxy}methyl)-1H-imidazole-2-sulfonamide A 1M solution of TBAF (1.2 mL, 1.2 mmol) was neutralized with a drop of HOAc and added to a solution of 4-chloro-5-({[(1,1-dimethylethyl)(dimethyl)silyl]oxy}methyl)-N-methyl-1-({[2-(trimethylsilyl)ethyl]oxy}methyl)-1H-imidazole-2-sulfonamide in THF (3 mL). The reaction mixture was stirred for 2 h at RT. Sat'd NaHCO$_3$ was added and the aqueous phase was extracted with CH$_2$Cl$_2$. The combined organic phase was dried (Na$_2$SO$_4$), filtered, and evaporated to give 4-chloro-5-(hydroxymethyl)-N-methyl-1-({[2-(trimethylsilyl)ethyl]oxy}methyl)-1H-imidazole-2-sulfonamide as a light yellow oil that was used without purification and assumed to be quantitative.

A solution of the above alcohol, MnO$_2$ (0.42 g, 4.86 mmol) in CH$_2$Cl$_2$ (5 mL) was stirred at RT for 1 h. Additional MnO$_2$ (0.42 g, 4.86 mmol) was added and the reaction mixture was heated at 40° C. overnight and then evaporated and purified by silica gel chromatography (0-35% EtOAc/hex) to afford the title compound (0.083 g, 48%) as a clear oil. 1H NMR (400 MHz, CHLOROFORM-d) δ ppm 9.93 (s, 1H), 6.00 (s, 2H), 5.33 (br. s., 1H), 3.60-3.69 (m, 2H), 2.90 (s, 3H), −0.02 (s, 9H).

Step E: N-({4-bromo-3-[(3-chloro-5-cyanophenyl)oxy]-2-fluorophenyl}methyl)-4-chloro-2-[(methylamino)sulfonyl]-1H-imidazole-5-carboxamide A solution of NaClO$_2$ (0.21 g, 2.34 mmol) and NaH$_2$PO$_4$.H$_2$O (0.19 g, 1.41 mmol) in H$_2$O (0.5 mL) was added to a solution of 4-chloro-5-formyl-N-methyl-1-({[2-(trimethylsilyl)ethyl]oxy}methyl)-1H-imidazole-2-sulfonamide (0.083 g, 0.23 mmol) and 2-methyl-2-butene (1.41 mL of a 2M solution in THF, 2.81 mmol) in THF (0.70 mL) and t-BuOH (0.16 mL). The reaction mixture was stirred at RT for 1 h and extracted with EtOAc. The organic layer was dried (Na$_2$SO$_4$), filtered and dried to provide 4-chloro-2-[(methylamino)sulfonyl]-1-({[2-(trimethylsilyl)ethyl]oxy}methyl)-1H-imidazole-5-carboxylic acid as a clear oil that was assumed to be quantitative and used without further purification.

The above acid (0.12 mmol) and 3-{[3-(aminomethyl)-6-bromo-2-fluorophenyl]oxy}-5-chlorobenzonitrile (0.050 g, 0.13 mmol) were employed using a procedure similar to that described herein to provide the title compound (0.026 g, 38%) as a white solid after deprotection and purification by Reverse-Phase HPLC (water:acetonitrile with 0.1% formic acid). 1H NMR (400 MHz, METHANOL-d4) δ ppm 7.51-7.61 (m, 2H), 7.33 (t, J=7.8 Hz, 1H), 7.25 (s, 1H), 7.22 (s, 1H), 4.62 (s, 2H), 2.72 (s, 3H). ES-LCMS: m/z 575.9, 577.8, 579.8 (M+1).

Example 382

4-chloro-N-({4-chloro-3-[(3-chloro-5-cyanophenyl)oxy]-2-fluorophenyl}methyl)-2-[(methylamino)sulfonyl]-1H-imidazole-5-carboxamide

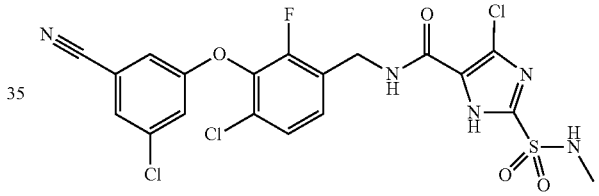

4-chloro-2-[(methylamino)sulfonyl]-1-({[2-(trimethylsilyl)ethyl]oxy}methyl)-1H-imidazole-5-carboxylic acid (0.12 mmol) and 3-{[3-(aminomethyl)-6-chloro-2-fluorophenyl]oxy}-5-chlorobenzonitrile (0.040 g, 0.13 mmol) were employed using a procedure similar to that described herein to provide the title compound (0.034 g, 54%) as a white solid after deprotection and purification by Reverse-Phase HPLC (water:acetonitrile with 0.1% formic acid). 1H NMR (400 MHz, METHANOL-d4) δ ppm 7.55 (s, 1H), 7.40 (s, 2H), 7.27 (s, 1H), 7.24 (s, 1H), 4.63 (s, 2H), 2.70 (s, 3 H). ES-LCMS: m/z 532.1, 534.1, 536.0 (M+1).

Example 383

4-chloro-N-[(4-chloro-3-{[3-cyano-5-(4-morpholinylmethyl)phenyl]oxy}-2-fluorophenyl)methyl]-1H-imidazole-5-carboxamide

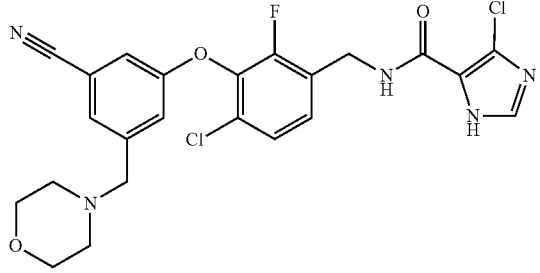

4-chloro-N-({4-chloro-3-[(3-cyano-5-formylphenyl)oxy]-2-fluorophenyl}methyl)-1-({[2-(trimethylsilyl)ethyl]oxy}methyl)-1H-imidazole-5-carboxamide (40 mg, 0.071 mmol) and morpholine (6.18 mg, 0.071 mmol) were mixed in 1,2-dichloroethane (2 mL) and treated with sodium triacetoxyborohydride (21 mg, 0.099 mmol) and acetic acid (4.06 µl, 0.071 mmol). The mixture was stirred at RT for 1 h then TFA (2 ml, 26.0 mmol) was added to the solution and stirred for 30 min. The solvent was removed under vacuum and the crude product was purified by Reverse Phase HPLC (MeCN/water 0.1% formic acid) to give 30 mg (84%) of the title compound as a white solid. $^1$H NMR (400 MHz, methanol-d4) δ ppm 8.08 (s, 1H), 7.61-7.81 (m, 1H), 7.46 (s, 1H), 7.29-7.41 (m, 2H), 7.24 (s, 1H), 7.08-7.19 (m, 1H), 4.63 (s, 2H), 3.52-3.84 (m, 4H), 2.53 (m., 4H). LC-MS (ES$^+$) m/z 502.9 [M+1].

Example 384

4-chloro-N-({4-chloro-3-[(3-cyano-5-{[(1methylethyl)amino]methyl}phenyl) oxy]-2-fluorophenyl}methyl)-1H-imidazole-5-carboxamide

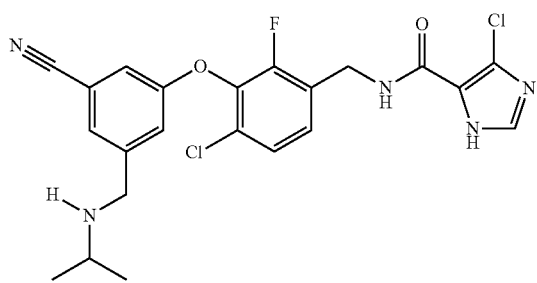

The title compound was prepared in a similar manner as described herein using 4-chloro-N-({4-chloro-3-[(3-cyano-5-formylphenyl)oxy]-2-fluorophenyl}methyl)-1-({[2-(trimethylsilyl)ethyl]oxy}methyl)-1H-imidazole-5-carboxamide (40 mg, 0.071 mmol) and 2-propanamine (4.20 mg, 0.071 mmol) to give 25 mg (74%) of a white solid. $^1$H NMR (400 MHz, methanol-d4) δ ppm 8.29 (s, 2H), 7.72 (s, 1H), 7.60 (s, 1H), 7.26-7.53 (m, 3H), 4.63 (s, 2H), 4.24 (s, 2H), 3.36-3.56 (m, 1H), 1.36 (d, 6H). LC-MS (ES$^+$) m/z 476.2, [M+1].

Example 385

3-{[6-chloro-3-({[(4-chloro-1H-imidazol-5-yl)carbonyl]amino}methyl)-2-fluorophenyl]oxy}-5-cyanobenzoic acid

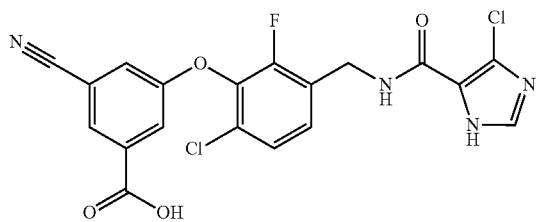

Step A: 3-({6-chloro-3-[({[4-chloro-1-({[2-(trimethylsilyl)ethyl]oxy}methyl)-1H-imidazol-5-yl]carbonyl}amino)methyl]-2-fluorophenyl}oxy)-5-cyanobenzoic acid To a solution of 4-chloro-N-({4-chloro-3-[(3-cyano-5-formylphenyl)oxy]-2-fluorophenyl}methyl)-1-({[2-(trimethylsilyl)ethyl]oxy}methyl)-1H-imidazole-5-carboxamide (200 mg, 0.355 mmol) in 2-methyl-2-butene (4.44 ml, 4.44 mmol) was added a solution of sodium chlorite (401 mg, 3.55 mmol) and sodium dihydrogenphosphate monohydride (302 mg, 2.130 mmol) in water (2 mL). The mixture was stirred for 4 hours and the solvent was removed under vacuum. The residue was diluted with EtOAc and washed with water. The organic layer was dried over sodium sulfate, filtered and concentrated. The crude product was purified by reverse phase HPLC (MeCN/water 0.1% formic acid) to give 130 mg (63%) of the title compound as a white solid. 1H NMR (400 MHz, DMSO-d$_6$) δ ppm 8.78 (t, 1H), 7.88-8.14 (m, 2H), 7.81 (s, 1H), 7.31-7.61 (m, 3H), 5.49 (s, 2H), 4.35-4.59 (m, 2 H), 3.31 (s, 2H), 0.57-0.85 (m, 2H), −0.09 (s, 9H). LC-MS (ES$^+$) m/z 578.25, [M+H].

Step B: 3-{[6-chloro-3-({[(4-chloro-1H-imidazol-5-yl)carbonyl]amino}methyl)-2-fluorophenyl]oxy}-5-cyanobenzoic acid To a solution of 3-({6-chloro-3-[({[4-chloro-1-({[2-(trimethylsilyl)ethyl]oxy}methyl)-1H-imidazol-5-yl]carbonyl}amino)methyl]-2-fluorophenyl}oxy)-5-cyanobenzoic acid (30 mg, 0.052 mmol) in DCM (2 ml) was added TFA (2 ml). The mixture was stirred for 30 min and the solvent was removed under vacuum. The crude product was purified by Reverse Phase HPLC (MeCN/water 0.1% formic acid) to give 20 mg (86%) of the title compound as a white solid. 1H NMR (400 MHz, methanol-d4) δ ppm 8.02 (s, 1H) 7.58-7.79 (m, 2H) 7.49 (d, 1H) 7.23-7.43 (m, 2H) 4.63 (s, 2H). LC-MS (ES$^+$) m/z 448.10, [M+H].

Example 386

2-(aminosulfonyl)-N-({4-bromo-3-[(3-chloro-5-cyanophenyl)oxy]-2-fluorophenyl}methyl)-4-chloro-1H-imidazole-5-carboxamide

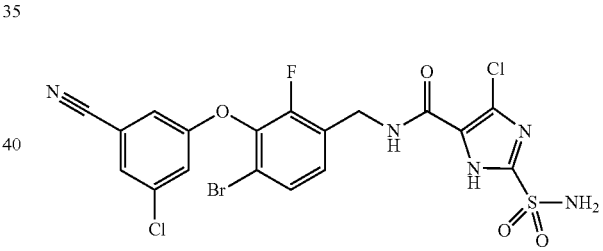

Step A: 4-chloro-5-({[(1,1-dimethylethyl)(dimethyl)silyl]oxy}methyl)-1-({[2-(trimethylsilyl)ethyl]oxy}methyl)-1H-imidazole-2-sulfonamide Ammonium hydroxide (5.0 mL, 128 mmol) was added to a 0° C. solution of 4-chloro-5-({[(1,1-dimethylethyl)(dimethyl)silyl]oxy}methyl)-1-({[2-(trimethylsilyl)ethyl]oxy}methyl)-1H-imidazole-2-sulfonyl chloride (1.33 g, 2.8 mmol) in acetone (4.5 mL) and THF (2.5 mL). The reaction mixture was stirred at RT for 30 min and evaporated. The residue was taken up in EtOAc and washed with brine. The organic phase was dried (Na$_2$SO$_4$), filtered, evaporated, and purified by silica gel chromatography (0-25% EtOA/hexanes) to give the title compound (0.95 g, 74%) as a light yellow oil. 1H NMR (400 MHz, CHLOROFORM-d) δ ppm 5.71 (s, 2H), 5.37 (br. s., 2H), 4.75 (s, 2H), 3.59-3.70 (m, 2H), 0.92-0.97 (m, 2H), 0.91 (s, 9H), 0.11 (s, 6H), 0.02 (s, 9H).

Step B: 4-chloro-5-formyl-1-({[2-(trimethylsilyl)ethyl]oxy}methyl)-1H-imidazole-2-sulfonamide The title compound (0.18 g, 25%) was obtained as a yellow oil from 4-chloro-5-({[(1,1-dimethylethyl)(dimethyl)silyl]oxy}methyl)-1-({[2-(trimethylsilyl)ethyl]oxy}methyl)-1H-imidazole-2-sulfonamide (0.95 g, 2.1 mmol) using a procedure similar to that described herein. 1H NMR (400 MHz, CHLOROFORM-d) δ ppm 9.96 (s, 1H), 6.07 (s, 2H), 3.62-3.73 (m, 2H), 2.58 (br. s., 2H), 0.94-0.98 (m, 2H), 0.01 (s, 9H).

Step C: 2-(aminosulfonyl)-N-({4-bromo-3-[(3-chloro-5-cyanophenyl)oxy]-2-fluorophenyl}methyl)-4-chloro-1H-imidazole-5-carboxamide A procedure and process similar to that described herein was used to obtain 2-(aminosulfonyl)-4-chloro-1-({[2-(trimethylsilyl)ethyl]oxy}methyl)-1H-imidazole-5-carboxylic acid from 4-chloro-5-formyl-1-({[2-(trimethylsilyl)ethyl]oxy}methyl)-1H-imidazole-2-sulfonamide (0.18 g, 0.52 mmol). The acid was a clear oil that was assumed to be quantitative and used without further purification. The above acid (0.26 mmol) and 3-{[3-(aminomethyl)-6-bromo-2-fluorophenyl]oxy}-5-chlorobenzonitrile (0.102 g, 0.29 mmol) were employed using a procedure similar to that described herein to provide the title compound (0.059 g, 40%) as a white solid after deprotection and purification by Reverse-Phase HPLC (water:acetonitrile with 0.1% formic acid). 1H NMR (400 MHz, METHANOL-d4) δ ppm 7.52-7.58 (m, 2H), 7.34 (t, J=7.8 Hz, 1H), 7.26 (t, J=2.0 Hz, 1H), 7.23 (s, 1H), 4.62 (s, 2H). ES-LCMS: m/z 561.9, 563.9, 565.9 (M+1).

Example 387

2-(aminosulfonyl)-4-chloro-N-({4-chloro-3-[(3-chloro-5-cyanophenyl)oxy]-2-fluorophenyl}methyl)-1H-imidazole-5-carboxamide

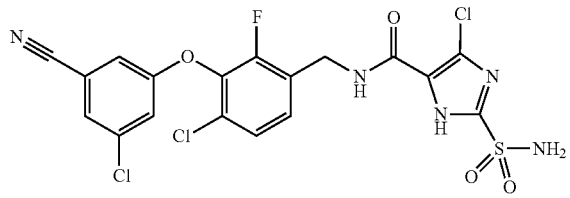

2-(aminosulfonyl)-4-chloro-1-({[2-(trimethylsilyl)ethyl]oxy}methyl)-1H-imidazole-5-carboxylic acid (0.26 mmol) and 3-{[3-(aminomethyl)-6-chloro-2-fluorophenyl]oxy}-5-chlorobenzonitrile (0.089 g, 0.29 mmol) were employed using a procedure similar to that described herein to provide the title compound (0.055 g, 41%) as a white solid after deprotection and purification by Reverse-Phase HPLC (water:acetonitrile with 0.1% formic acid). 1H NMR (400 MHz, METHANOL-d4) δ ppm 7.55 (t, 1H), 7.35-7.43 (m, 2H), 7.27 (t, J=2.0 Hz, 1H), 7.24 (s, 1H), 4.63 (s, 2H). ES-LCMS: m/z 516.0, 518.0, 519.9 (M−1).

BIOLOGICAL SECTION

Inhibition of Viral Replication

I. HeLa Cell Assay

The HeLa cell assay described herein is a modified version of Kimpton J. and Emerman M., Detection of replication-competent and pseudotyped human immunodeficiency virus with a sensitive cell line on the basis of activation of an integrated β-galactosidase gene, *J. Virol.* 66:2232-2239 (1992), in which HIV-1 infection is detected by the activation of an HIV-LTR driven β-galactosidase reporter that is integrated into the genome of a CD4+ HeLa cell line. Quantitation of β-galactosidase is achieved by measuring the activation of a chemiluminescent substrate (Applied Biosystems). The concentration of each compound required to inhibit 50% ($IC_{50}$) of the HIV-1 induced β-galactosidase signal, relative to untreated controls, is determined for each isogenic, recombinant virus.

A. Materials
  HeLa-CD4-LTR-β-gal cell line (AIDS Research and Reference Reagent
  Program, Division of AIDS, NIAID)
  DMEM (GibcoBRL #12430-047)
  Trypsin-EDTA (GibcoBRL #25300-054)
  Heat inactivated Fetal Bovine Serum (FBS) (Hyclone # SH30070.03)
  Geneticin (GibcoBRL #10131-035)
  Hygromycin B (GibcoBRL #1687-010)
  96-well, black, clear-bottom, tissue culture-treated plates (Costar #3904)
  0.45 micron cellulose acetate filtration unit (Corning #430768)
  DEAE-dextran (Sigma # D-9885)
  Phosphate Buffered Saline (PBS) (GibcoBRL #14190-144)
  Dimethyl Sulfoxide (DMSO) (ATCC #741625)
  Gal-Screen Reporter Gene Assay System (Applied Biosystems # T1031)

B. Growth and Maintenance of the CD4-HIV LTR-β-gal HeLa Cell Line.
  HeLa-CD4-LTR-β-gal cells are propagated in DMEM containing 10% fetal bovine serum+0.2 mg/ml geneticin+0.1 mg/ml hygromycin B. Cells are split by standard trypsinization when confluency reaches 80% (roughly every 2 to 3 days).

C. Construction of HIV-1 Reverse Transcriptase (RT) Mutants
  DNA encoding the HIV-1 reverse transcriptase is subcloned from a M13 phage into a general shuttle vector, pBCSK+, as a ~1.65 kbp EcoRI/HindIII ended DNA fragment. The HIV DNA insert of the resulting plasmid, is completely sequenced on both strands prior to use in site directed mutagenesis experiments. Specific amino acid replacements are made using Stratagene Quick Change reagents and mutagenic oligonucleotides. The mutations that are made include K103N, V106A, Y181C, and Y188L. Following mutagenesis, the entire mutant RT coding sequence is verified by sequencing both DNA strands.

D. Construction of Isogenic HIV-1 RT Mutant Virus
  K103N, V106A, Y181C, and Y188L mutant HIV-1 strains and wild type strains are isolated by a modified Recombinant Virus Assay (Kellam P. and Larder B., Recombinant virus assay: a rapid, phenotypic assay for assessment of drug susceptibility of human immunodeficiency virus type 1 isolates, *Antimicrobial Agents and Chemotherapy,* 38:23-30, 1994). Ten million MT4 T-cells (maintained in RPMI containing 10% fetal bovine serum, split 1:5 every 5 to 6 days) are co-transfected with EcoRI/HindIII digested mutant RT plasmid and Bst EII-digested HIV-1$_{HXB2\Delta RT}$ DNA in the presence of DMRIE-C transfection reagent (Gibco) according to supplier's recommended protocol. Each mutant RT coding sequence is crossed into the RT-deleted HIV-1 viral DNA backbone by in vivo homologous recombination. Transfected cell cultures are expanded and monitored until syncitia formation and CPE are extensive. Virus is harvested by clear spin of the culture supernatants, filtration of the supernatants through a 0.45 micron membrane and frozen at −80° C. as primary stocks. Recombinant progeny virus is sequenced in the RT region to confirm the mutant genotype. Some virus stocks require further expansion by infection of MT4 cells, harvested as above and stored as frozen aliquots. All stocks are titered in HeLa MAGI cells for assay.

E. Titering of Virus Stocks.

HIV-1 virus stocks are titered in the HeLa-CD4-LTR-β-gal assay system to establish the appropriate infecting dose. The endpoint for this assay is relative light units (RLUs), and titer is recorded as RLUs/ml. Virus stocks are diluted (serial 1:2) into DMEM containing 10% FBS plus 25 ug/ml DEAE-dextran and assayed as described in the "Experimental Protocol" section below without test compound.

A "multiplicity of infection" (MOI) defined as infectious units per cell is usually not calculated but is typically $\ll 1.0$. Relationship of RLUs/ml to other measures of infectivity such as HeLa PFU/ml or MT4 TCID50/ml may not be consistent from lot to lot or strain to strain and should be determined for each lot.

F. Experimental Protocol

Day 1
1. Seed 96-well plate(s) (Costar #3904) with HeLa-CD4-LTR-β-gal @ 3×10³ cells per well in 100 ul DMEM containing 10% FBS. Incubate @ 37° C., 5% $CO_2$ overnight.

Day 2
1. Thaw virus stock in a water bath (room temperature) and dilute into DMEM+10% FBS+25 ug/ml DEAE-dextran to an infectious dose of approximately 10 million RLU/ml. The dilution of virus will vary depending on the titer of the stock (see "Titering of virus stocks" above).
2. Remove all of the media from every well with an 8 or 12-channel manifold aspirator. Work with one plate at a time to prevent drying of the HeLa-CD4-LTR-β-gal monolayer. Add 35 ul (approximately 350,000 total RLUs) of diluted virus to each well. Incubate @ 37° C., 5% $CO_2$ for 2 hours.
3. During the virus adsorption period prepare compound titration plates at 1.35× final concentration. In general, test compounds are titrated robotically on a Beckman 2000 laboratory automation workstation (Beckman Coulter) in a four-fold stepwise manner from 2.7 uM (2 uM final) down to 0.01 nM (0.008 nM final). This scheme will allow for 8 test compounds per 96-well plate with 10 dilution points and 2 controls per compound (n=1). Test compounds are titrated into DMEM+10% FBS+0.135% DMSO (0.1% final). The final volume of titrated compound in each well should be at least 150 ul and DMSO should be at 0.135% (0.1% final) including the no compound controls.
4. With a RapidPlate 96/384 liquid handling system (Zymark) remove 100 ul of titrated compound from every well of the titration plate prepared in step 3 above and add to the virus adsorption plate (step 2 above).
5. Incubate @ 37° C., 5% $CO_2$ for 72 hours.

Day 5
1. With a RapidPlate 96/384 liquid handling system (Zymark) reduce supernatants to 50 uL and add 50 uL of reconstituted Gal-Screen according to manufacturer's recommended protocol.
2. Mix plate(s) vigorously on a platform shaker.
3. Read plate(s) in a Topcount luminometer (Packard) at 1 s/well.

G. Data Analysis

Raw data are transformed into percent of control by the following formula: (raw signal in each well/average raw signal for the two no compound controls in the same row)*100. Percent of control is plotted vs. compound concentration using either Robsage or Robofit programs (GSK). The default model is $Y=Vmax*1-(x^n/(K^n+x^n))$, however, any other model giving a reasonable estimation of the $IC_{50}$ ("K" in formula) may be used.

Table 1 provides data regarding activity of certain compounds of the present invention against HIV wild type (WTRVA) and several resistant mutants, including K103N, V106A, and Y181C.

TABLE 1

| Ex. | Structure | K103N | V106A | WTRVA | Y181C |
|---|---|---|---|---|---|
| 2 | (structure) | C | C | C | C |
| 3 | (structure) | C | C | C | C |
| 4 | (structure) | B | C | B | C |

TABLE 1-continued

| Ex. | Structure | K103N | V106A | WTRVA | Y181C |
|---|---|---|---|---|---|
| 5 | 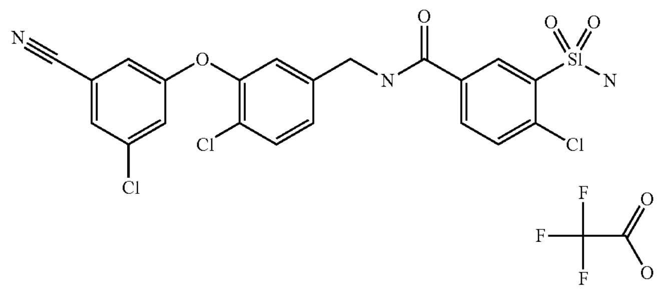 | C | C | B | C |
| 6 | 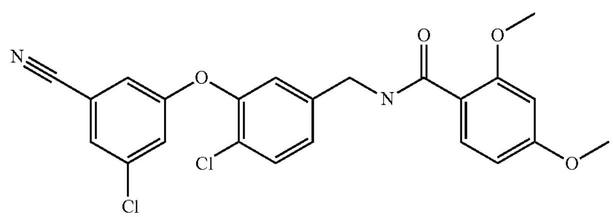 | C | C | B | C |
| 7 | 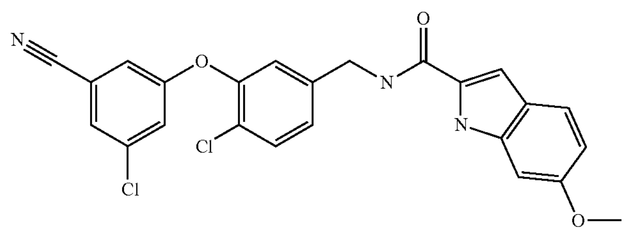 | C | C | B | C |
| 8 | 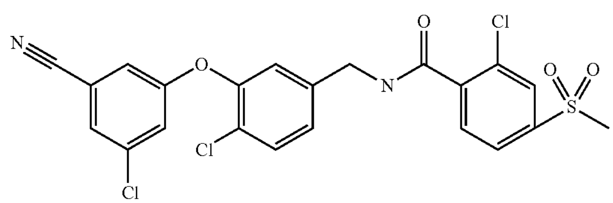 | C | C | B | C |
| 9 | 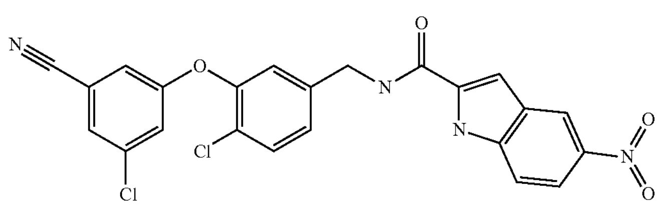 | C | C | C | C |
| 10 | 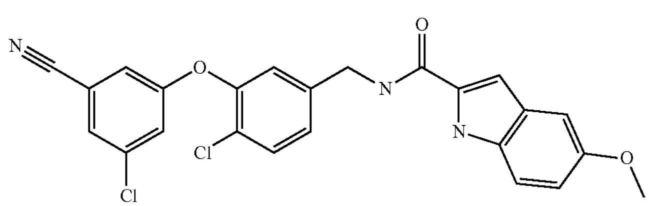 | C | C | B | C |
| 11 | 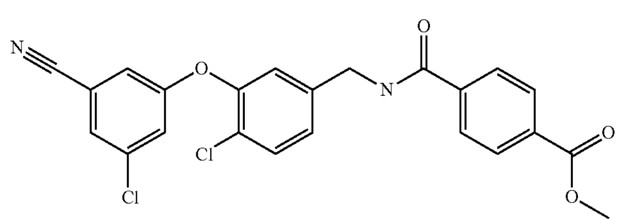 | C | C | C | C |

TABLE 1-continued

| Ex. | Structure | K103N | V106A | WTRVA | Y181C |
|---|---|---|---|---|---|
| 14 | 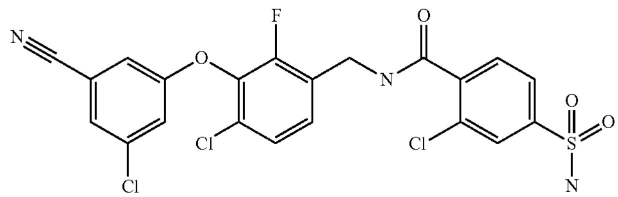 | B | B | B | B |
| 15 | 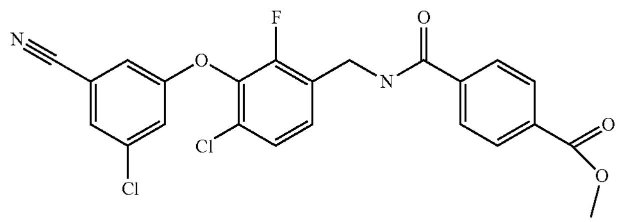 | B | C | B | C |
| 16 | 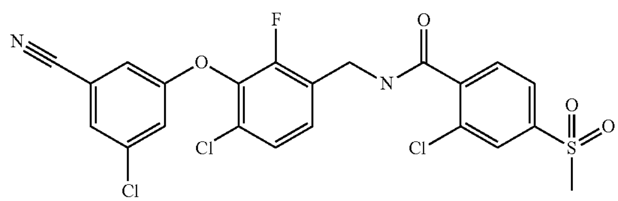 | B | B | B | B |
| 17 | 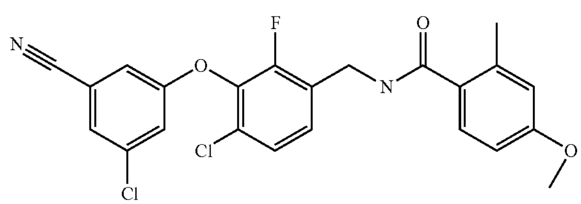 | B | B | B | B |
| 18 | 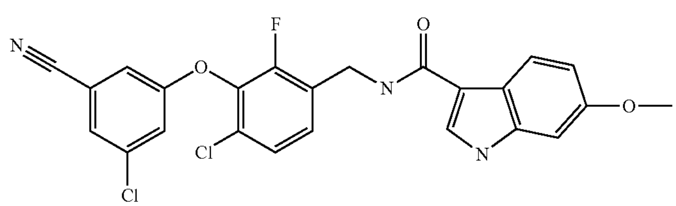 | C | C | B | C |
| 19 | 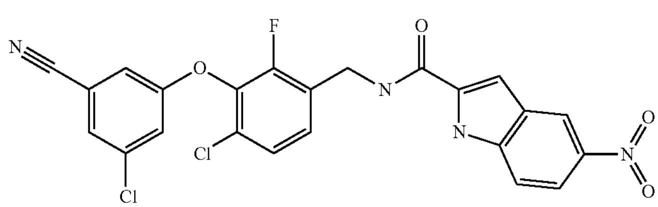 | B | B | A | B |
| 20 | 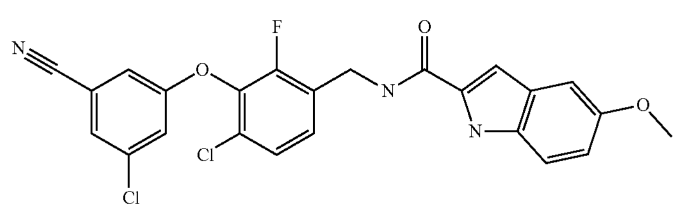 | B | B | B | B |

TABLE 1-continued

| Ex. | Structure | K103N | V106A | WTRVA | Y181C |
|---|---|---|---|---|---|
| 21 | (structure) | B | B | B | B |
| 22 | (structure) | A | B | A | A |
| 23 | (structure) | B | B | B | B |
| 24 | (structure) | A | B | A | B |
| 25 | (structure) | A | B | A | A |
| 26 | (structure) | A | B | A | A |
| 27 | (structure) | B | B | B | B |

TABLE 1-continued

| Ex. | Structure | K103N | V106A | WTRVA | Y181C |
|---|---|---|---|---|---|
| 28 | 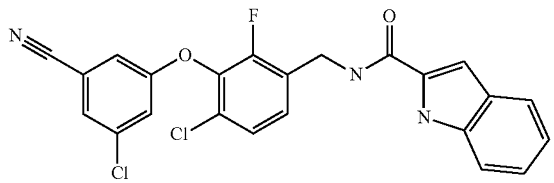 | B | B | A | B |
| 29 | 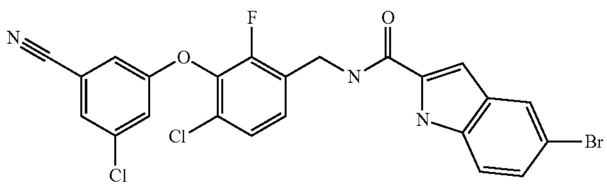 | B | B | B | B |
| 30 | 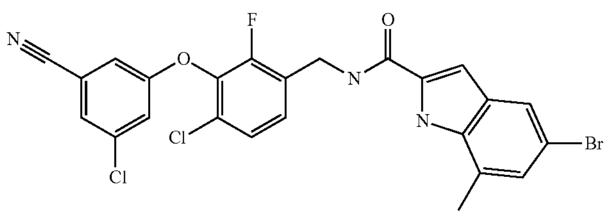 | B | C | B | C |
| 31 | 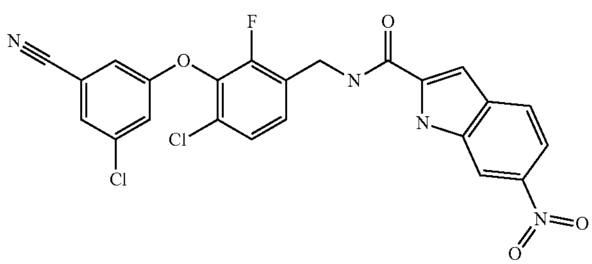 | B | B | B | B |
| 32 | 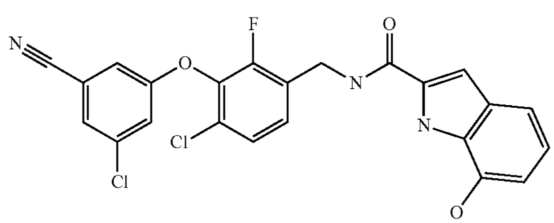 | B | C | B | B |
| 33 | 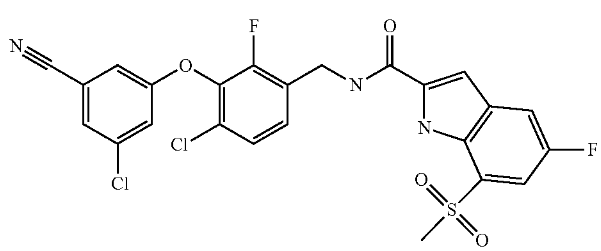 | B | C | B | B |
| 34 | 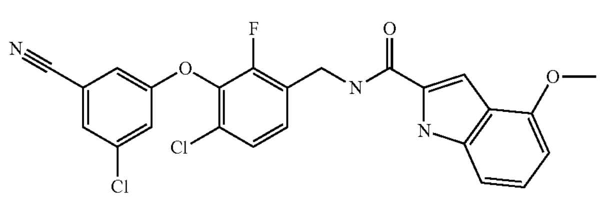 | B | B | A | B |

TABLE 1-continued

| Ex. | Structure | K103N | V106A | WTRVA | Y181C |
|---|---|---|---|---|---|
| 35 | [structure] | B | B | A | B |
| 36 | [structure] | A | A | A | A |
| 37 | [structure] | B | C | B | C |
| 38 | [structure] | B | B | B | B |
| 39 | [structure] | B | B | A | B |
| 40 | [structure] | B | B | B | B |
| 41 | [structure] | B | C | B | B |

TABLE 1-continued

| Ex. | Structure | K103N | V106A | WTRVA | Y181C |
|---|---|---|---|---|---|
| 42 | 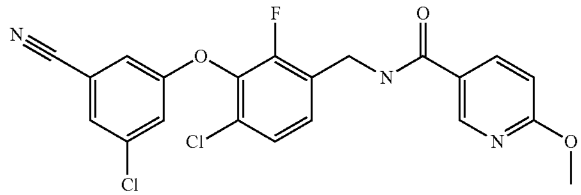 | C | C | B | C |
| 43 | 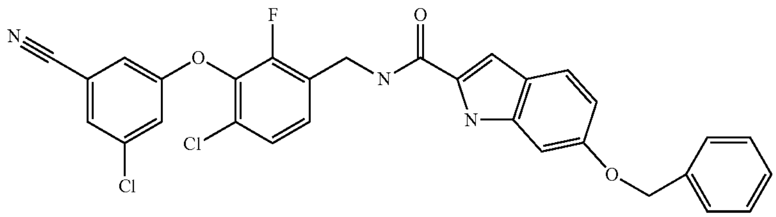 | B | C | B | C |
| 44 | 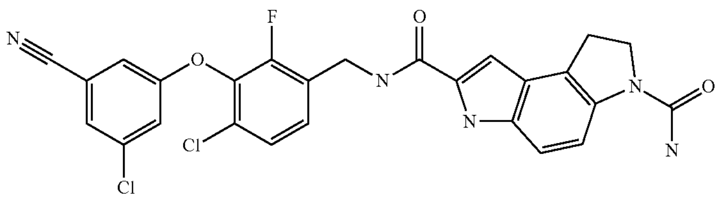 | A | B | A | B |
| 45 | 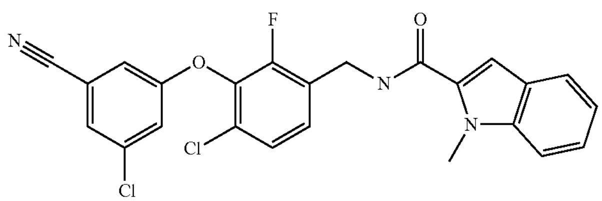 | C | C | B | C |
| 46 | | B | B | A | B |
| 47 | | B | C | B | B |

TABLE 1-continued
| Ex. | Structure | K103N | V106A | WTRVA | Y181C |
|---|---|---|---|---|---|
| 48 | 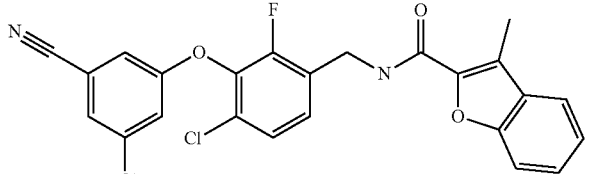 | B | B | B | B |
| 49 | 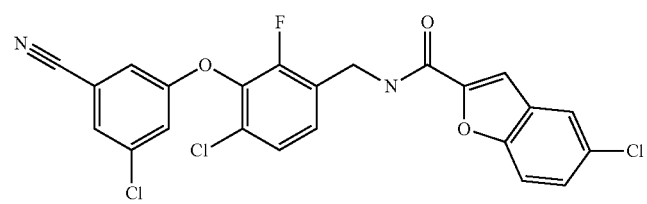 | C | C | C | C |
| 50 | 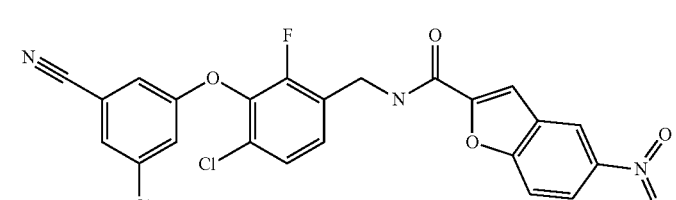 | B | C | B | C |
| 51 | 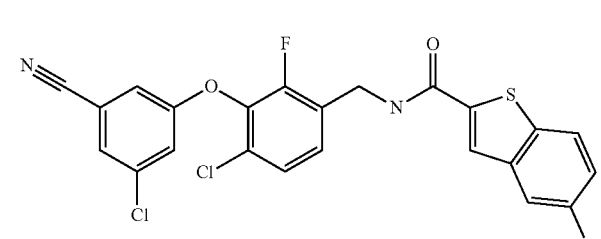 | C | C | C | C |

TABLE 1-continued
| Ex. | Structure | K103N | V106A | WTRVA | Y181C |
|---|---|---|---|---|---|
| 52 | 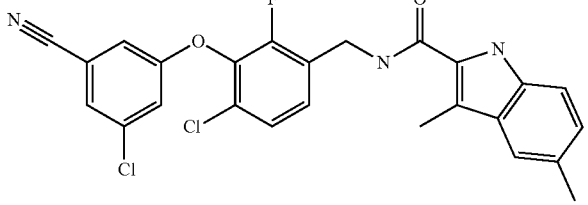 | B | B | B | B |
| 53 | 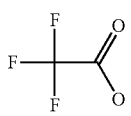 | B | B | B | B |
| 54 | 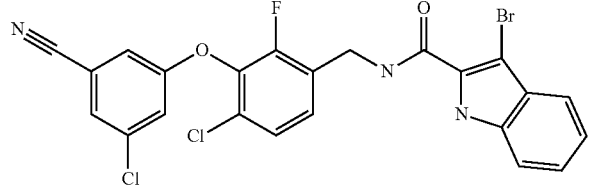 | A | A | A | A |
| 55 | 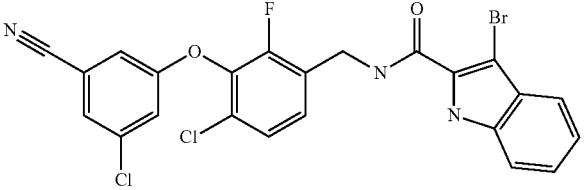 | B | B | B | B |

TABLE 1-continued

| Ex. | Structure | K103N | V106A | WTRVA | Y181C |
|---|---|---|---|---|---|
| 56 | 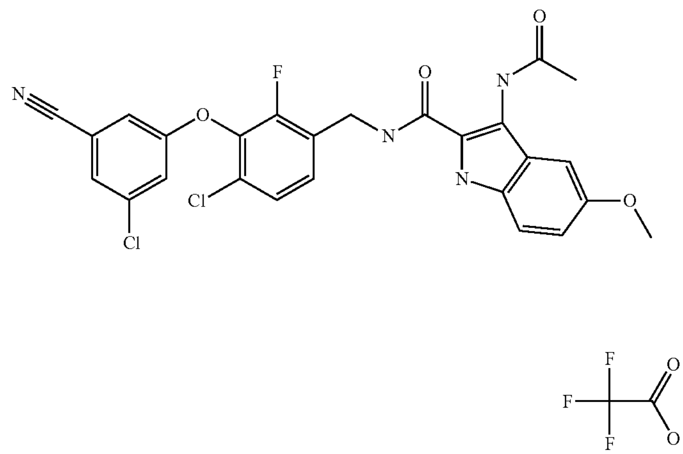 | C | C | B | C |
| 57 | 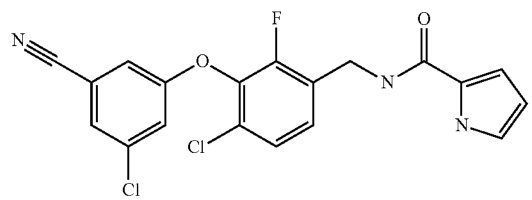 | A | B | A | A |
| 58 | 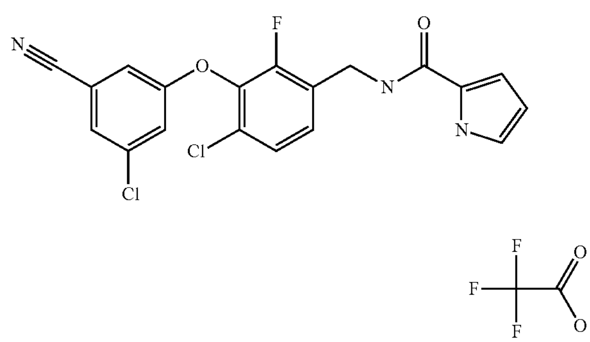 | A | A | A | A |
| 59 | 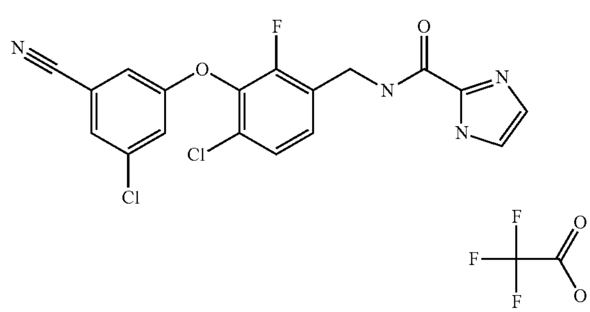 | A | A | A | A |
| 60 | 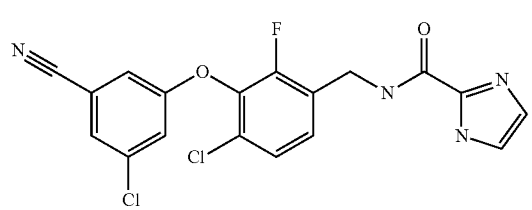 | A | B | A | A |

TABLE 1-continued
| Ex. | Structure | K103N | V106A | WTRVA | Y181C |
|---|---|---|---|---|---|
| 61 | 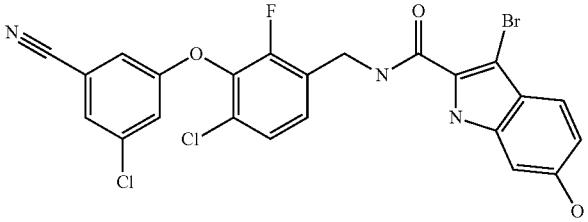 | A | A | A | A |
| 62 | 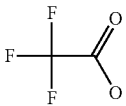 | A | A | A | A |
| 63 | 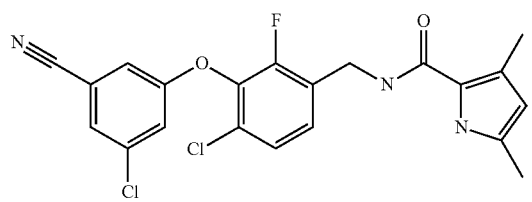 | A | A | A | A |
| 64 | 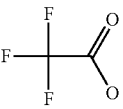 | B | B | B | B |

TABLE 1-continued
| Ex. | Structure | K103N | V106A | WTRVA | Y181C |
|---|---|---|---|---|---|
| 65 | 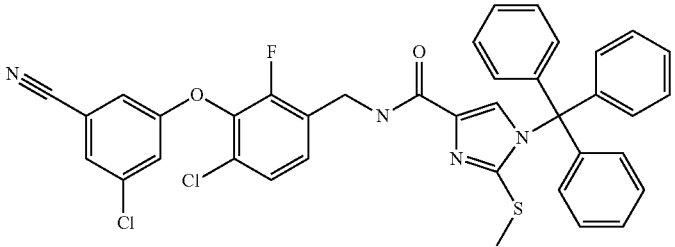 | B | B | B | B |
| 66 | 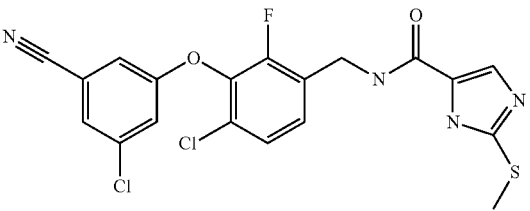 | B | B | B | B |
| 67 | 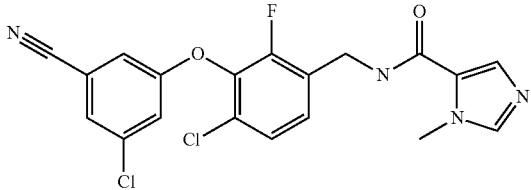 | B | C | B | C |
| 68 | 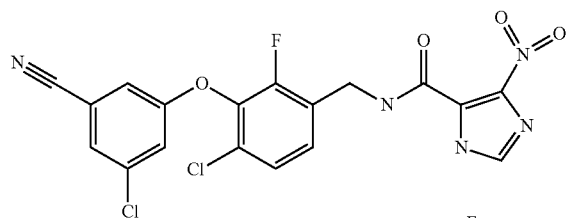 | A | A | A | A |

TABLE 1-continued
| Ex. | Structure | K103N | V106A | WTRVA | Y181C |
|---|---|---|---|---|---|
| 69 | 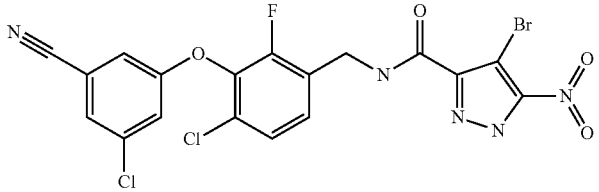 | B | B | B | B |
| 70 | 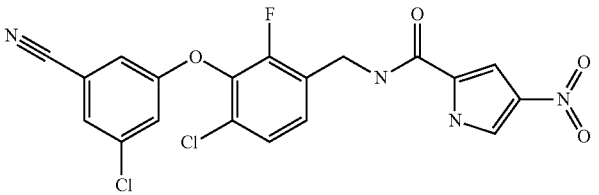 | A | B | A | A |
| 71 | 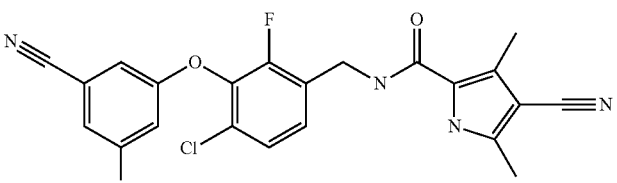 | A | A | A | A |
| 72 | 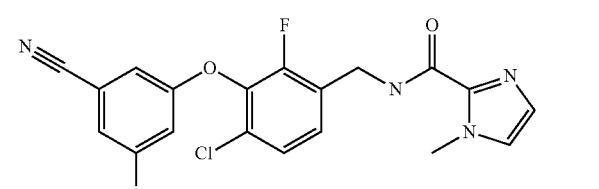 | B | C | B | B |
| 73 | 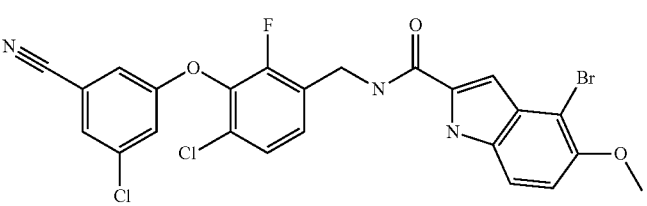 | B | B | B | B |

TABLE 1-continued

| Ex. | Structure | K103N | V106A | WTRVA | Y181C |
|---|---|---|---|---|---|
| 74 | 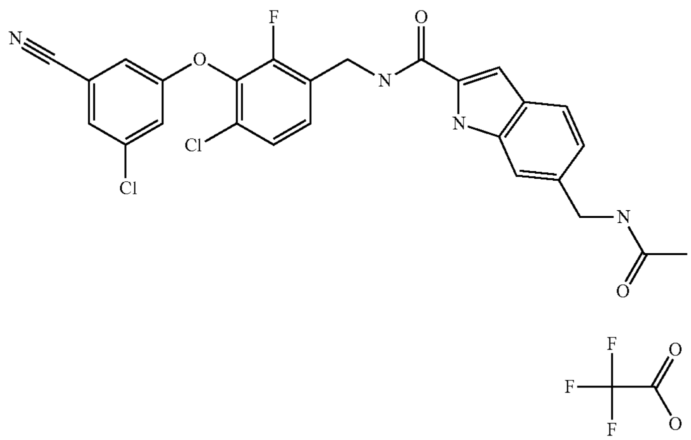 | A | A | A | A |
| 75 | 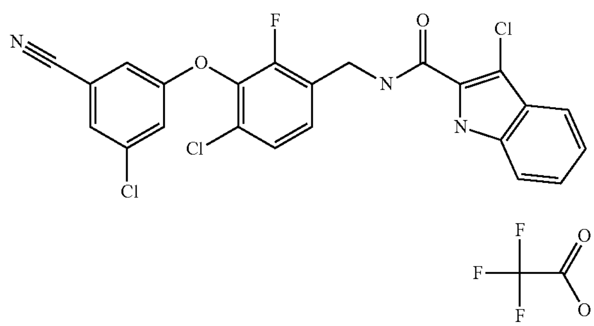 | A | A | A | B |
| 76 | 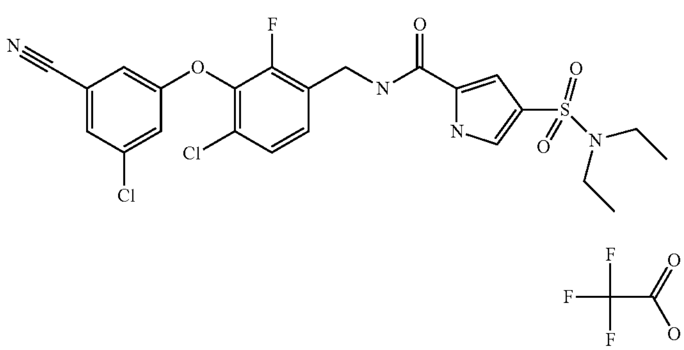 | B | C | B | B |
| 77 | 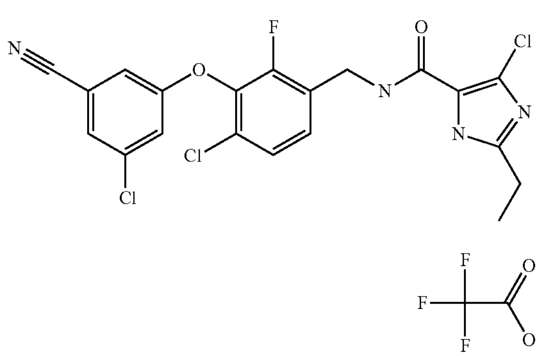 | A | A | A | A |

TABLE 1-continued
| Ex. | Structure | K103N | V106A | WTRVA | Y181C |
|---|---|---|---|---|---|
| 78 | 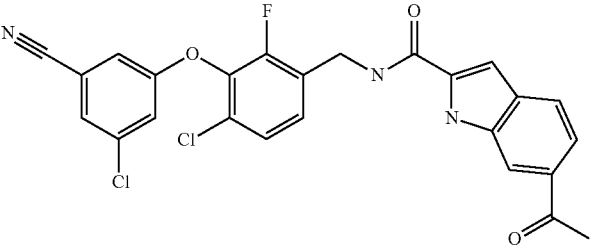 | A | B | A | B |
| 79 | 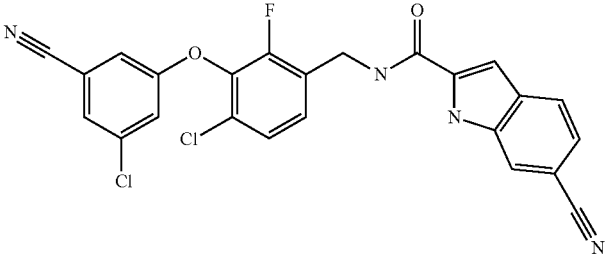 | A | B | A | A |
| 80 | 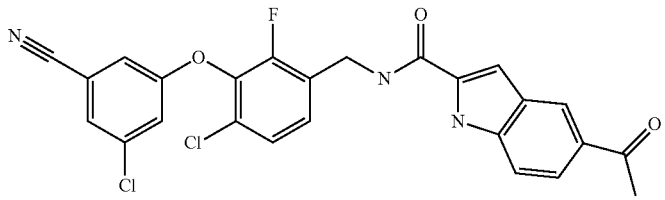 | A | B | A | A |
| 81 | 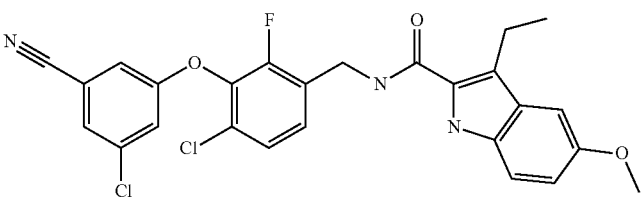 | A | B | B | B |

TABLE 1-continued

| Ex. | Structure | K103N | V106A | WTRVA | Y181C |
|---|---|---|---|---|---|
| 82 | 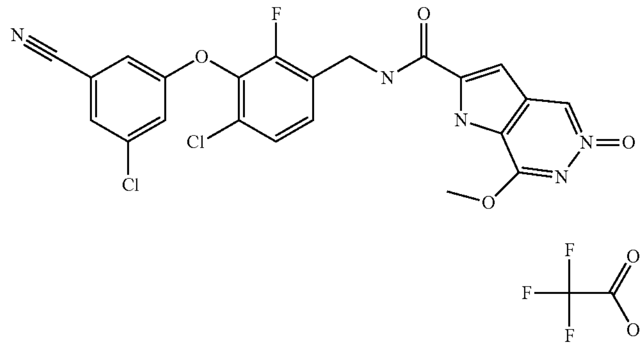 | C | C | B | C |
| 83 | 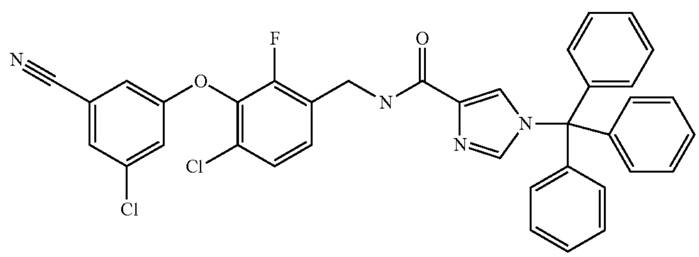 | C | C | C | C |
| 84 | 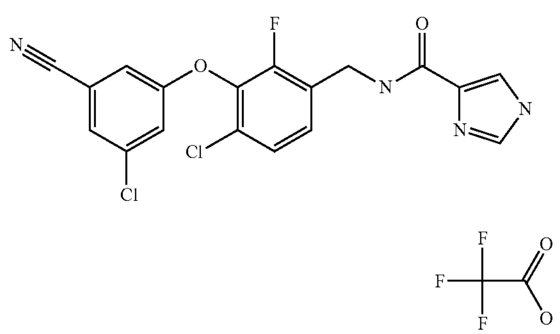 | B | B | A | B |
| 85 | 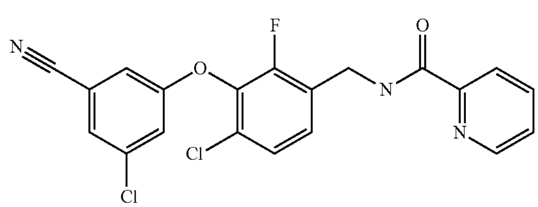 | B | B | A | B |
| 86 | 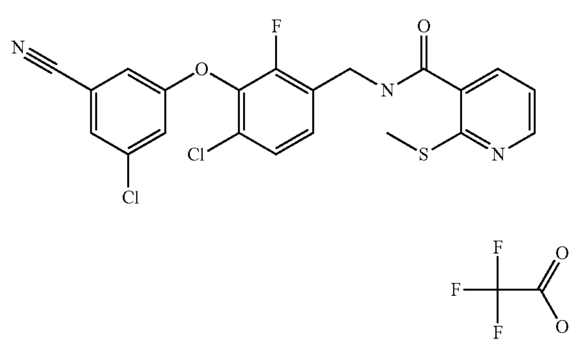 | B | C | B | B |

TABLE 1-continued

| Ex. | Structure | K103N | V106A | WTRVA | Y181C |
|---|---|---|---|---|---|
| 87 | 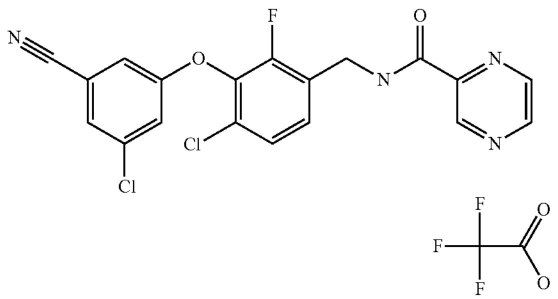 | B | C | A | B |
| 88 | 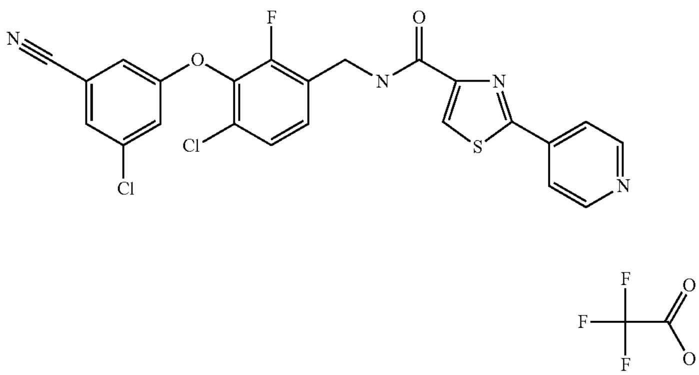 | B | B | B | B |
| 89 | 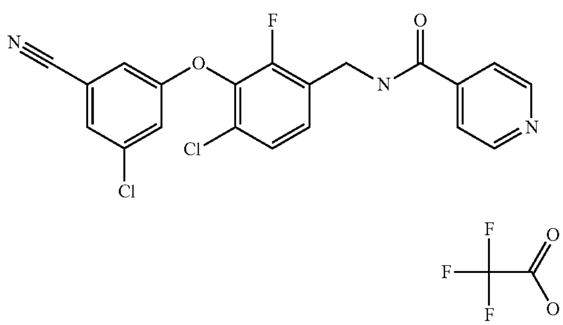 | B | B | B | B |
| 90 | 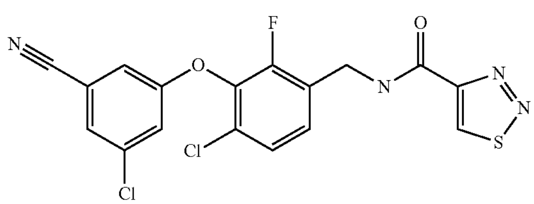 | B | C | A | B |
| 91 | 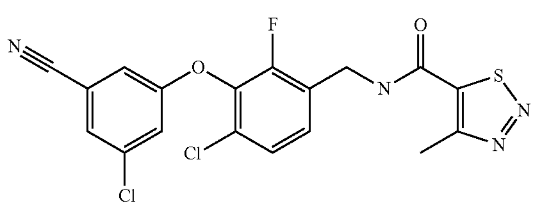 | B | B | A | B |
| 92 | 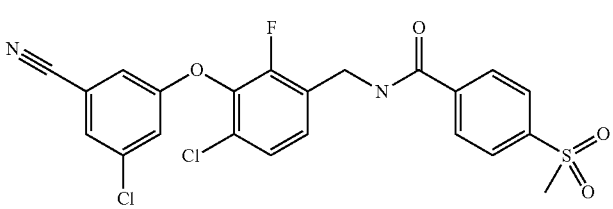 | B | B | B | B |

TABLE 1-continued

| Ex. | Structure | K103N | V106A | WTRVA | Y181C |
|---|---|---|---|---|---|
| 93 | 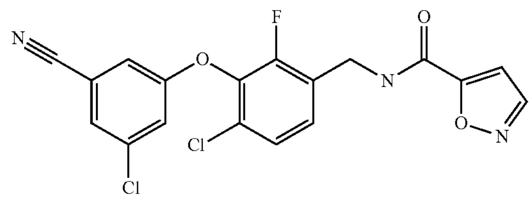 | B | B | B | B |
| 94 | | B | C | B | B |
| 95 | 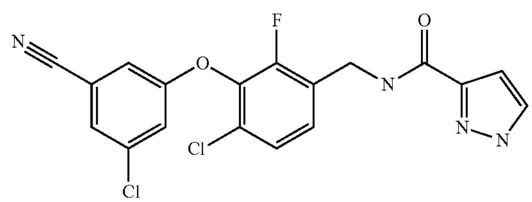 | B | C | B | B |
| 96 | | C | C | B | C |
| 97 | | B | C | A | B |

TABLE 1-continued

| Ex. | Structure | K103N | V106A | WTRVA | Y181C |
|---|---|---|---|---|---|
| 98 | 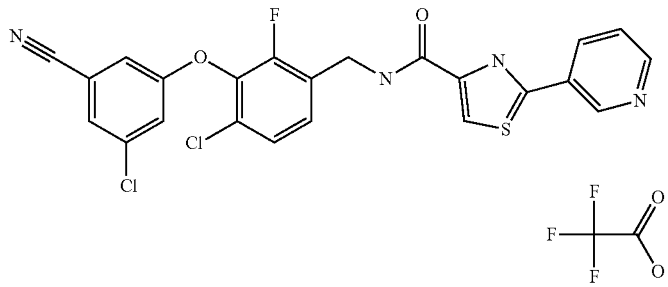 | B | B | A | B |
| 99 | 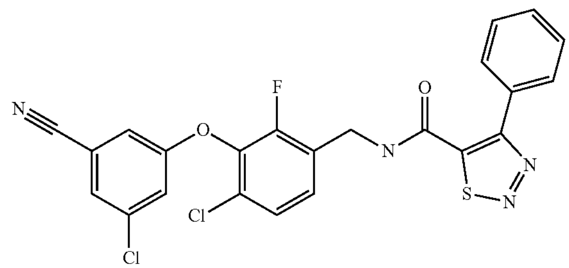 | C | C | C | C |
| 100 | 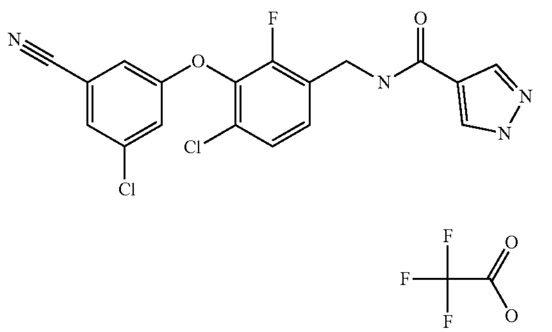 | B | B | A | B |
| 101 | 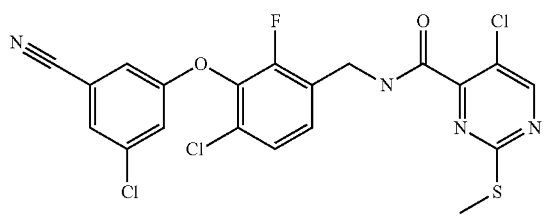 | C | C | B | C |
| 102 | 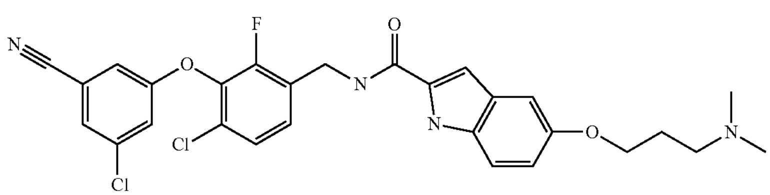 | A | B | A | A |
| 103 | 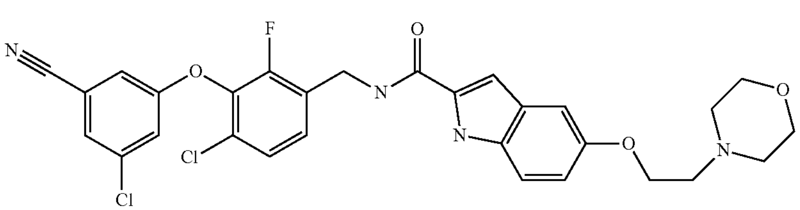 | A | B | A | A |

TABLE 1-continued

| Ex. | Structure | K103N | V106A | WTRVA | Y181C |
|---|---|---|---|---|---|
| 104 | 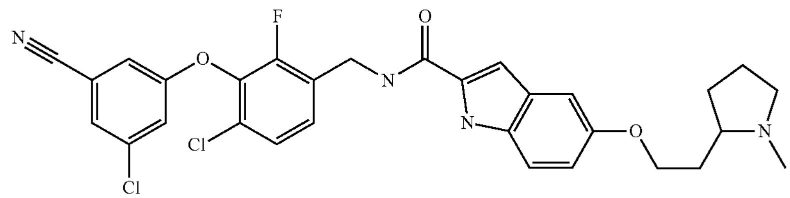 | A | B | A | A |
| 105 | 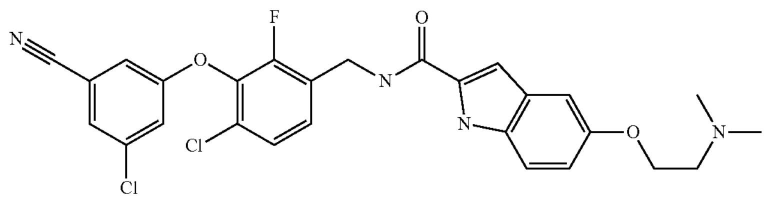 | A | B | A | A |
| 106 | 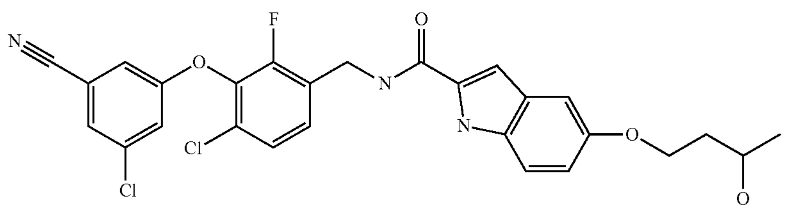 | A | B | A | A |
| 107 | 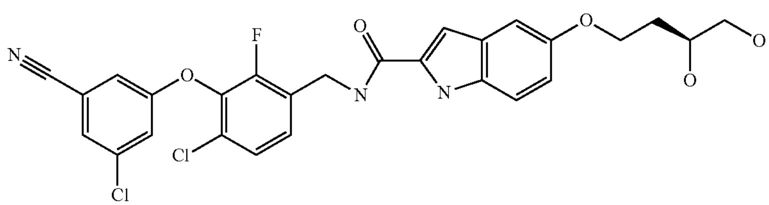 | A | A | A | A |
| 108 | 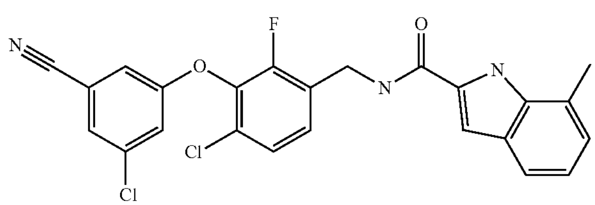 | B | B | B | B |
| 109 | 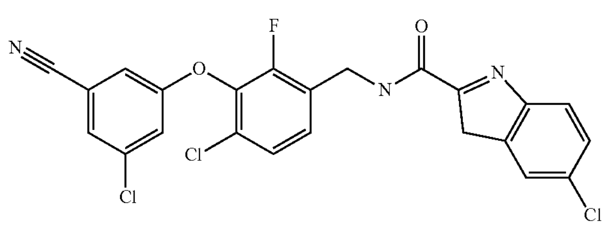 | B | B | B | B |
| 110 | 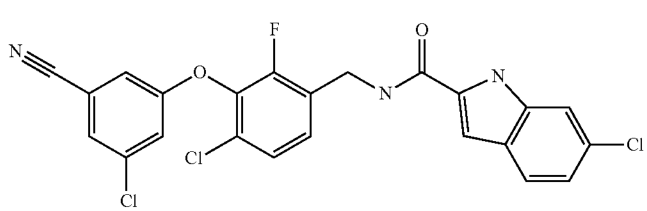 | B | B | B | B |

TABLE 1-continued

| Ex. | Structure | K103N | V106A | WTRVA | Y181C |
|---|---|---|---|---|---|
| 111 | 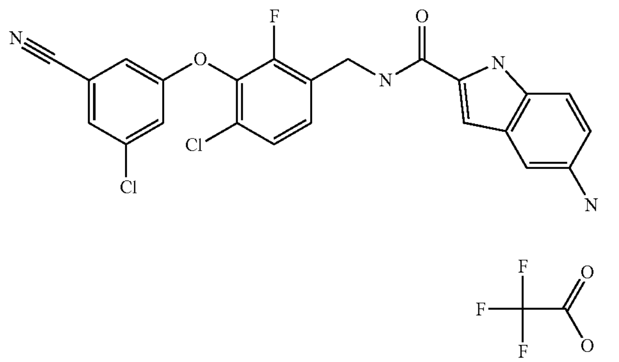 | A | B | A | A |
| 112 | 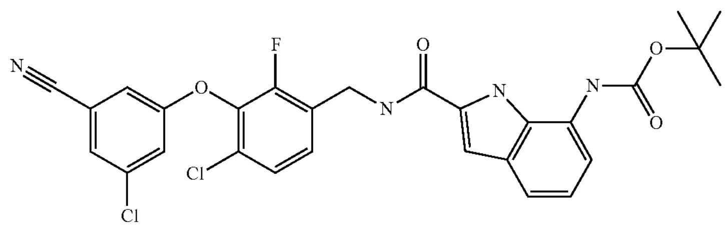 | B | C | B | C |
| 113 | 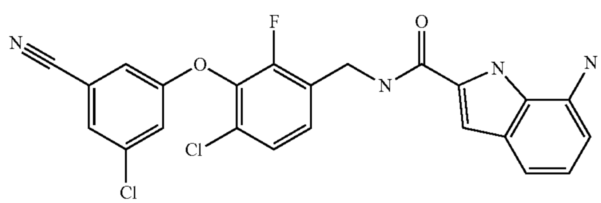 | A | B | A | B |
| 114 | 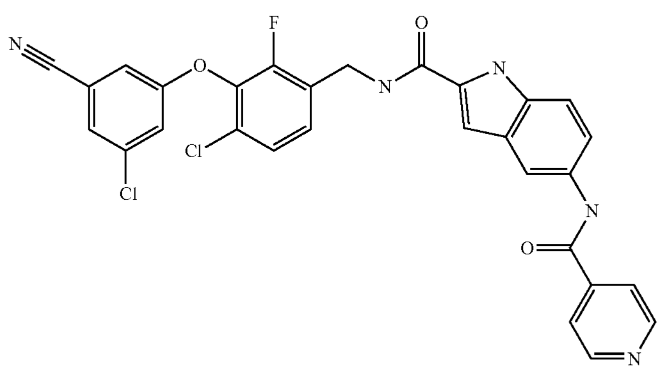 | A | B | A | A |
| 115 | 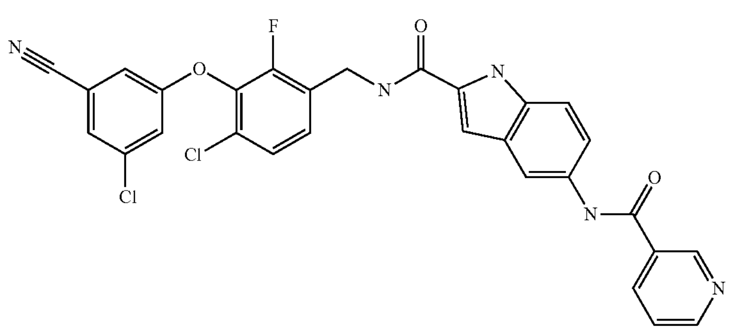 | A | B | A | A |

TABLE 1-continued

| Ex. | Structure | K103N | V106A | WTRVA | Y181C |
|---|---|---|---|---|---|
| 116 | 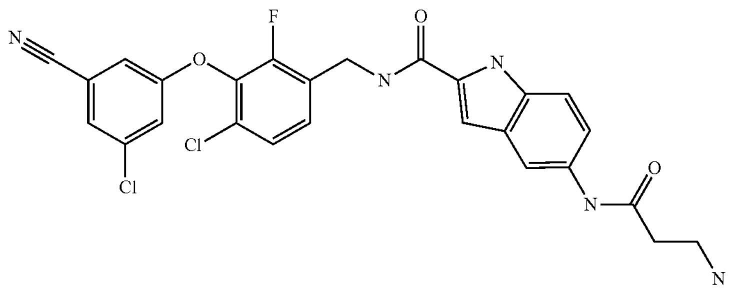 | A | B | A | B |
| 117 | 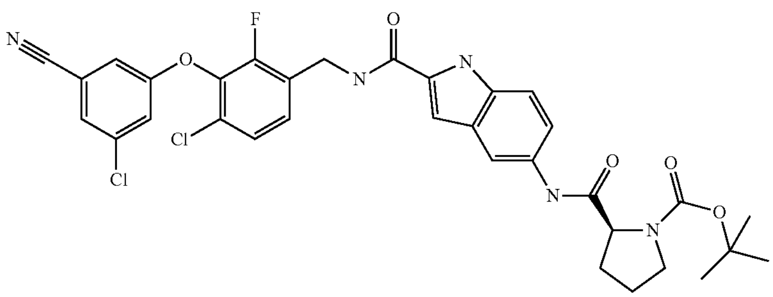 | B | B | A | B |
| 118 | 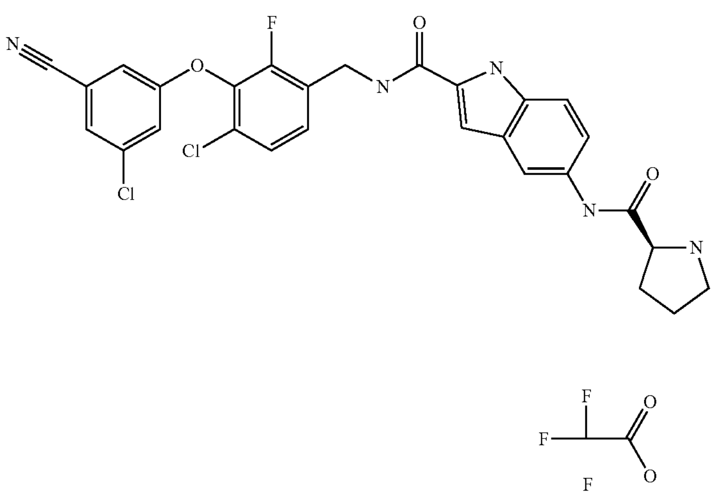 | A | B | A | B |
| 119 | 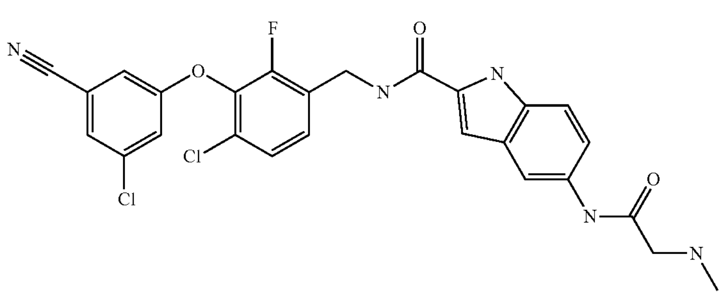 | A | B | A | B |

TABLE 1-continued

| Ex. | Structure | K103N | V106A | WTRVA | Y181C |
|---|---|---|---|---|---|
| 120 | | A | B | A | B |
| 121 | 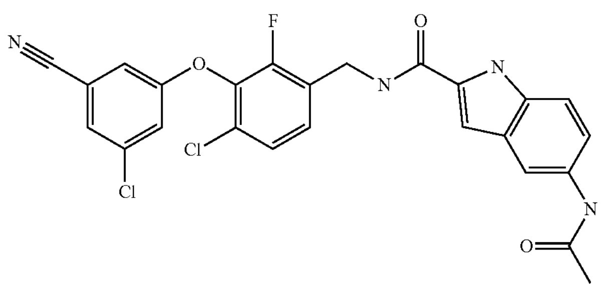 | A | B | A | A |
| 122 | 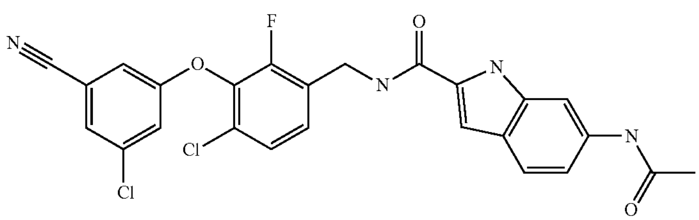 | A | A | A | A |
| 123 | | A | B | A | A |
| 124 | 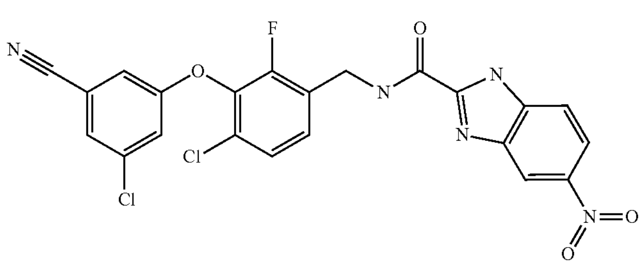 | B | B | B | B |

TABLE 1-continued

| Ex. | Structure | K103N | V106A | WTRVA | Y181C |
|---|---|---|---|---|---|
| 125 | 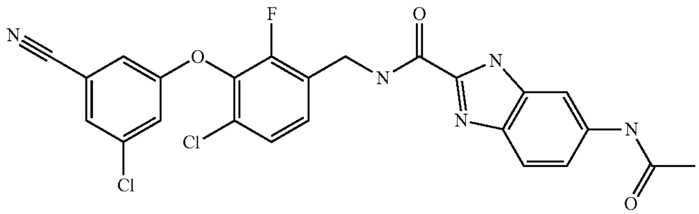 | A | B | A | A |
| 126 | 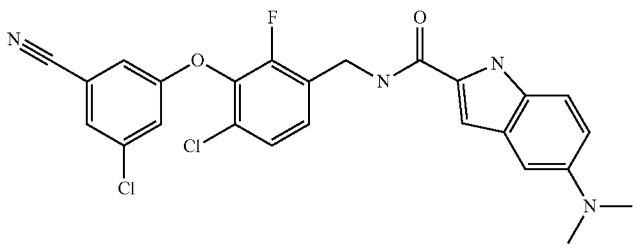 | B | B | A | B |
| 127 | 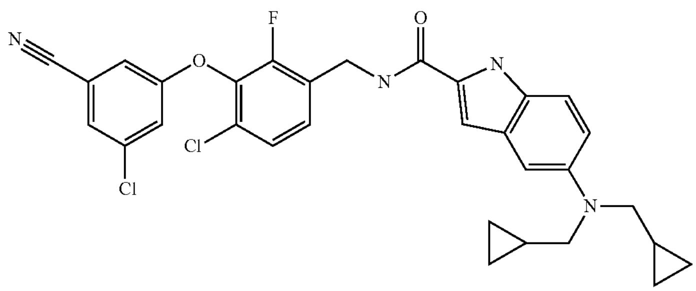 | B | B | B | B |
| 128 | 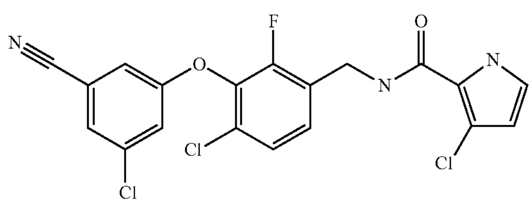 | A | A | A | A |
| 129 | 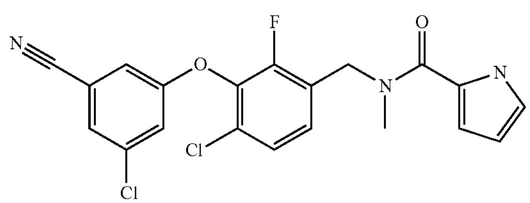 | A | A | A | A |
| 130 | 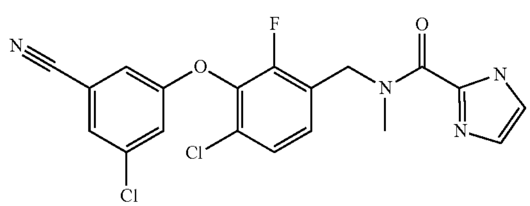 | A | B | A | A |
| 131 | 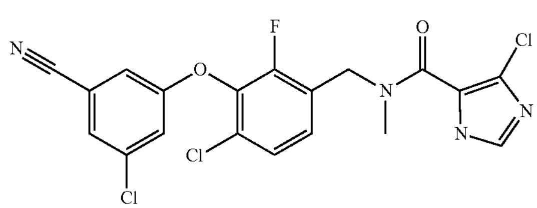 | A | A | A | A |

TABLE 1-continued

| Ex. | Structure | K103N | V106A | WTRVA | Y181C |
|---|---|---|---|---|---|
| 132 | 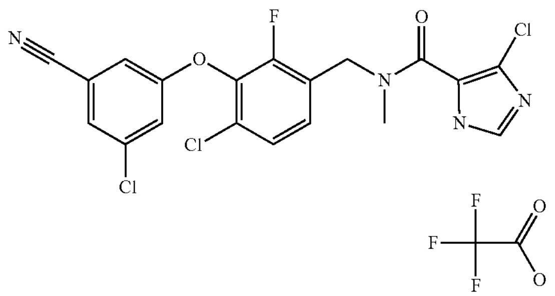 | A | B | A | A |
| 133 | 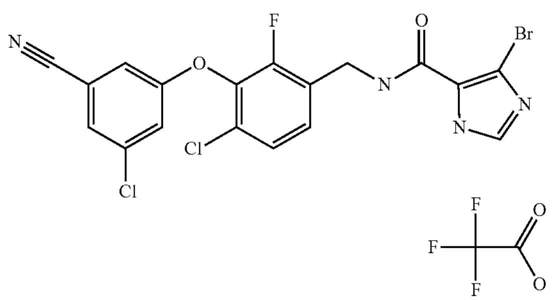 | A | A | A | A |
| 134 | 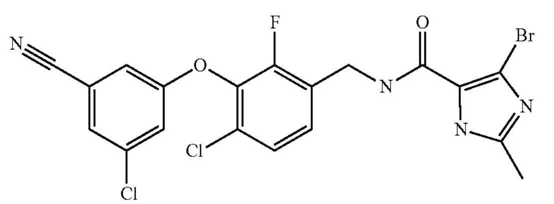 | A | A | A | A |
| 135 | 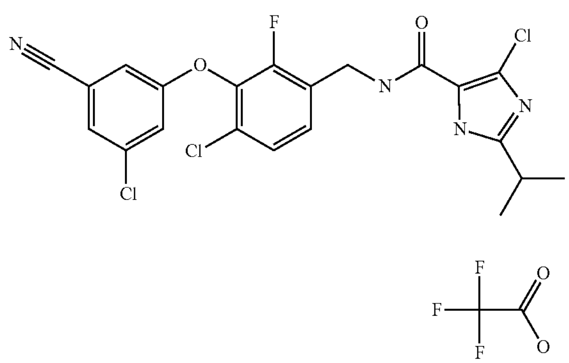 | A | A | A | A |
| 136 | 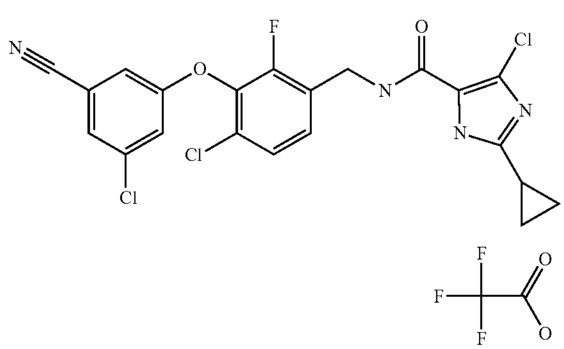 | A | A | A | A |

TABLE 1-continued

| Ex. | Structure | K103N | V106A | WTRVA | Y181C |
|---|---|---|---|---|---|
| 137 | 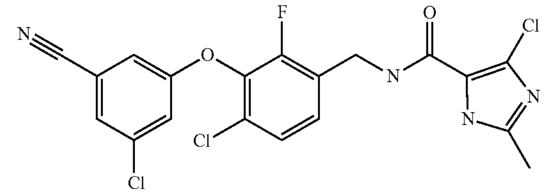 | A | A | A | A |
| 138 | 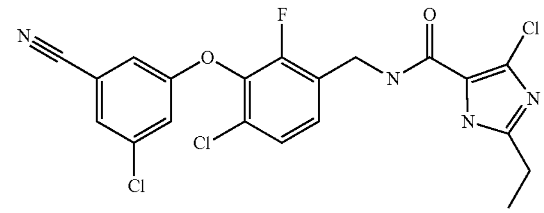 | A | A | A | A |
| 139 | 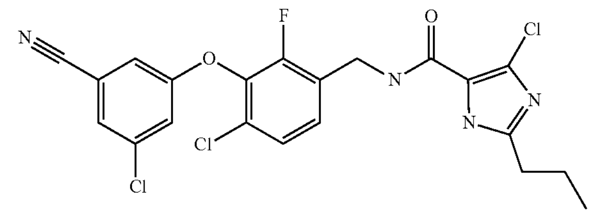 | A | A | A | A |
| 140 | | A | B | A | A |
| 141 | 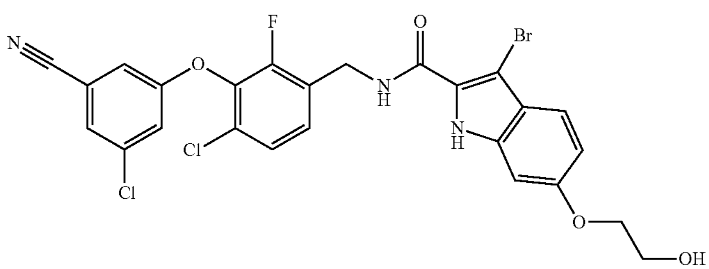 | A | A | A | A |
| 142 | 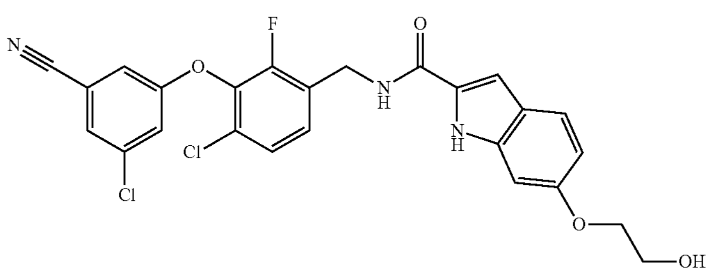 | A | A | A | A |

*"A" indicates an activity level of less than 10 nM.
"B" indicates an activity level of between 10 nM and 1 μM.
"C" indicates an activity level of greater than 1 μM.

Compounds of the present invention demonstrate anti-HIV activity in the range of $IC_{50}$ of about 1 nM to about 50 µM. In one aspect of the invention, compounds of the present invention have anti-HIV activity in the range of up to about 10 nM. In another aspect of the invention, compounds of the present invention have anti-HIV activity in the range of from about 10 nM to about 1 µM. In another aspect of the invention, compounds of the present invention have anti-HIV activity in the range of greater than 1 µM.

The compounds of Example number 128, 131, 133, 143, 144, 145, 146, 148, 149, 150, 151, 152, 156, 157, 158, 159, 204, 230A, 230B, 231, 232, 233, 234, 235, 236, 237, 239, 240, 241, 248, 249, 250, 251, 252, 253, 269, 270, 271, 272, 273, 274, 286, 290, 291, 293, 299, 300, 304, 305, 306, 307, 308, 309, 310, 311, 317, 319, 327, 329, 362, 363, 366, 373, 375, 377, 378 and 383 demonstrated $IC_{50}$ values of less than 10 nM against K103N, V106A, WTRVA, Y181C, and Y188L in the HeLa cell assay.

The compounds of Example number 254, 368, and 369 demonstrated $IC_{50}$ values of less than 10 nM against K103N, V106A, WTRVA, Y181C and $IC_{50}$ values in the range of 10 nM-1 µM against Y188L in the HeLa cell assay.

Test compounds were employed in free, salt or solvated form.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A compound of formula (I):

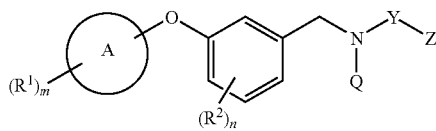

(I)

wherein m is 1, 2, 3 or 4;
n is 2;
each $R^1$ independently is halogen, —CN, $C_1$-$C_5$ alkyl, $C_2$-$C_5$ alkenyl, $C_2$-$C_6$ alkynyl, $C_3$-$C_7$ cycloalkyl, hydroxyl, $C_1$-$C_8$ alkoxy, —C(O)OR$^5$, —C(O)N(R$^5$)$_2$, —OR$^5$, —R$^3$CN, or —N(R$^5$)$_2$;
each $R^2$ independently is halogen;
A is $C_5$-$C_{12}$ aryl or $C_5$-$C_{12}$ heterocycle;
Q is hydrogen or $C_1$-$C_4$ alkyl;
Y is —C(O)—, —S(O)$_2$—, or —S(O)—;
Z is $C_4$-$C_{12}$ aryl, $C_3$-$C_{14}$ heterocycle, R$^3$Het, or R$^3$Ar, each optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N(R$^5$)C(O)R$^5$, —N(R$^5$)$_2$, —OR$^5$, —C$_3$-C$_{12}$ Het, —C(O)N(R$^5$)$_2$, C$_4$-C$_{12}$ Ar, —SR$^5$, —S(O)$_2$N(R$^5$)$_2$, —OR$^3$HetC(O)R$^5$, —OCF$_3$, —S(O)$_2$R$^5$, —OR$^3$R$^5$, —N(R$^5$)C(O)R$^3$OR$^5$; —N(R$^5$)C(O)R$^3$N(R$^5$)$_2$, —N(R$^5$)C(O)R$^3$R$^5$, —OR$^3$N(R$^5$)$_2$, —R$^3$Het, —R$^3$N(R$^5$)$_2$, —R$^3$N(R$^5$)C(O)R$^5$, —OR$^3$SR$^5$, —C(O)R$^5$, —C(R$^5$)$_3$, —R$^3$C(O)OR$^5$, —R$^3$C(O)N(R$^5$)$_2$, or —N(R$^5$)S(O)$_2$R$^5$; or Z is linked to Q to form a $C_4$-$C_{14}$ heterocycle together with the nitrogen atom and Y group to which they are attached and are optionally substituted with —C(O)OR$^5$ or $C_1$-$C_6$ alkoxy;
each $R^5$ independently is hydrogen, $C_1$-$C_8$ alkyl, $C_3$-$C_7$ cycloalkyl, oxo, $C_3$-$C_{12}$ heterocycle, $C_4$-$C_{12}$ aryl or $C_1$-$C_8$ alkoxy, each optionally substituted with hydroxyl, $C_1$-$C_4$ alkoxy or $C_3$-$C_7$ cycloalkyl;
$R^3$ is $C_2$-$C_6$ alkenylene or $C_1$-$C_4$ alkylene, each optionally substituted with hydroxyl or $C_1$-$C_8$ alkoxy;
Het is $C_3$-$C_{12}$ heterocycle and is optionally substituted with one or more of $C_1$-$C_6$ alkyl, —C(O)N(R$^5$)$_2$, —R$^3$S(O)$_2$R$^5$, or halogen; and
Ar is $C_4$-$C_{12}$ aryl and is optionally substituted with one or more of $C_1$-$C_6$ alkyl or halogen; or a pharmaceutically acceptable salt thereof.

2. A compound of formula (I) according to claim 1 wherein m is 2.

3. A compound of formula (I) according to claim 1 wherein Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N(R$^5$)C(O)R$^5$, —N(R$^5$)$_2$, —OR$^5$, —C$_3$-C$_{12}$ Het, —C(O)N(R$^5$)$_2$, C$_4$-C$_{12}$ Ar, —SR$^5$, —S(O)$_2$N(R$^5$)$_2$, —OR$^3$HetC(O)R$^5$, —OCF$_3$, —S(O)$_2$R$^5$, —OR$^3$R$^5$, —N(R$^5$)C(O)R$^3$OR$^5$; —N(R$^5$)C(O)R$^3$N(R$^5$)$_2$, —N(R$^5$)C(O)R$^3$R$^5$, —OR$^3$N(R$^5$)$_2$, —R$^3$Het, —R$^3$N(R$^5$)$_2$, —R$^3$N(R$^5$)C(O)R$^5$, —OR$^3$SR$^5$, —C(O)R$^5$, —C(R$^5$)$_3$, —R$^3$C(O)OR$^5$, —R$^3$C(O)N(R$^5$)$_2$, or —N(R$^5$)S(O)$_2$R$^5$.

4. A compound of formula (I) according to claim 1 wherein Y is —C(O)—, Q is hydrogen, and Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N(R$^5$)C(O)R$^5$, —N(R$^5$)$_2$, —OR$^5$, —C$_3$-C$_{12}$ Het, —C(O)N(R$^5$)$_2$, C$_4$-C$_{12}$ Ar, —SR$^5$, —S(O)$_2$N(R$^5$)$_2$, —OR$^3$HetC(O)R$^5$, —OCF$_3$, —S(O)$_2$R$^5$, —OR$^3$R$^5$, —N(R$^5$)C(O)R$^3$OR$^5$; —N(R$^5$)C(O)R$^3$N(R$^5$)$_2$, —N(R$^5$)C(O)R$^3$R$^5$, —OR$^3$N(R$^5$)$_2$, —R$^3$Het, —R$^3$N(R$^5$)$_2$, —R$^3$N(R$^5$)C(O)R$^5$, —OR$^3$SR$^5$, —C(O)R$^5$, —C(R$^5$)$_3$, —R$^3$C(O)OR$^5$, —R$^3$C(O)N(R$^5$)$_2$, or —N(R$^5$)S(O)$_2$R$^5$.

5. A compound of formula (I) according to claim 1 wherein Y is —C(O)—, Q is $C_1$-$C_8$ alkyl, and Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N(R$^5$)C(O)R$^5$, —N(R$^5$)$_2$, —OR$^5$, —C$_3$-C$_{12}$ Het, —C(O)N(R$^5$)$_2$, C$_4$-C$_{12}$ Ar, —SR$^5$, —S(O)$_2$N(R$^5$)$_2$, —OR$^3$HetC(O)R$^5$, —OCF$_3$, —S(O)$_2$R$^5$, —OR$^3$R$^5$, —N(R$^5$)C(O)R$^3$OR$^5$; —N(R$^5$)C(O)R$^3$N(R$^5$)$_2$, —N(R$^5$)C(O)R$^3$R$^5$, —OR$^3$N(R$^5$)$_2$, —R$^3$Het, —R$^3$N(R$^5$)$_2$, —R$^3$N(R$^5$)C(O)R$^5$, —OR$^3$SR$^5$, —C(O)R$^5$, —C(R$^5$)$_3$, —R$^3$C(O)OR$^5$, —R$^3$C(O)N(R$^5$)$_2$, or —N(R$^5$)S(O)$_2$R$^5$.

6. A compound of formula (I) according to claim 1 wherein m is 2 and one $R^1$ is halogen and one $R^1$ is —CN.

7. A compound of formula (I) according to claim 1 wherein m is 2, n is 2, and Z is $C_3$-$C_{14}$ heterocycle optionally substituted with one or more of $C_1$-$C_8$ alkyl, $C_3$-$C_7$ cycloalkyl, $C_1$-$C_8$ alkoxy, halogen, oxo, hydroxyl, —CN, —NO$_2$, —N(R$^5$)C(O)R$^5$, —N(R$^5$)$_2$, —OR$^5$, —C$_3$-C$_{12}$ Het, —C(O)N(R$^5$)$_2$, C$_4$-C$_{12}$ Ar, —SR$^5$, S(O)$_2$N(R$^5$)$_2$, —OR$^3$HetC(O)R$^5$, —OCF$_3$, —S(O)$_2$R$^5$, —OR$^3$R$^5$, —N(R$^5$)C(O)R$^3$OR$^5$; —N(R$^5$)C(O)R$^3$N(R$^5$)$_2$, —N(R$^5$)C(O)R$^3$R$^5$, —OR$^3$N(R$^5$)$_2$, —R$^3$Het, —R$^3$N(R$^5$)$_2$, —R$^3$N(R$^5$)C(O)R$^5$, —OR$^3$SR$^5$, —C(O)R$^5$, —C(R$^5$)$_3$, —R$^3$C(O)OR$^5$, —R$^3$C(O)N(R$^5$)$_2$, or —N(R$^5$)S(O)$_2$R$^5$.

8. A compound of formula (I) according to claim 1 wherein Z is selected from the group consisting of

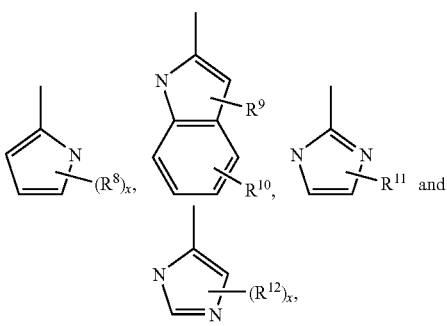

wherein x is 1, 2 or 3;
each $R^8$ is independently hydrogen, halogen, $N(R^{15})_2$, $OR^{15}$, $SR^{15}$, $C(O)N(R^{15})_2$, $C(O)OR^{15}$, $CF_3$, $C_1$-$C_8$ alkyl, $C_1$-$C_8$ alkoxy, or —CN, wherein each $C_1$-$C_8$ alkyl or $C_1$-$C_8$ alkoxy is optionally substituted with hydroxyl, $C_1$-$C_4$ alkoxy or $C_3$-$C_7$ cycloalkyl;
$R^9$ is hydrogen or halogen;
$R^{10}$ is hydrogen, hydroxyl, $C_1$-$C_8$ alkoxy, —$N(R^{15})C(O)R^{15}$, —$N(R^{15})C(O)R^{13}N(R^{15})_2$, —$N(R^{15})_2$, or —$R^{13}N(R^{15})C(O)R^{15}$;
$R^{13}$ is $C_1$-$C_6$ alkylene;
each $R^{15}$ is independently hydrogen, $C_1$-$C_8$ alkyl, $C_3$-$C_7$ cycloalkyl, $C_3$-$C_{12}$ heterocycle, $C_4$-$C_{12}$ aryl or $C_1$-$C_8$ alkoxy, each optionally substituted with hydroxyl, $C_1$-$C_4$ alkoxy or $C_3$-$C_7$ cycloalkyl;
$R^{11}$ is hydrogen or $C_1$-$C_6$ alkoxy; and
each $R^{12}$ is independently hydrogen, halogen, $C_1$-$C_8$ alkyl, $C_1$-$C_8$ alkoxy, $C_3$-$C_6$ cycloalkyl, $N(R^{15})_2$, $OR^{15}$, $SR^{15}$, $C(O)N(R^{15})_2$, $C(O)OR^{15}$, or —$N(O)_2$, wherein each $C_1$-$C_8$ alkyl or $C_1$-$C_8$ alkoxy is optionally substituted with hydroxyl, $C_1$-$C_4$ alkoxy or $C_3$-$C_7$ cycloalkyl.

9. A compound of formula (I) according to claim 1 wherein Y is —C(O)— and Z is selected from the group consisting of

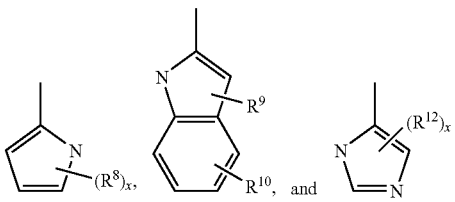

wherein x is 1 or 2;
each $R^8$ is independently hydrogen, halogen, —$N(R^{15})_2$, —$OR^{15}$, —$SR^{15}$, —$C(O)N(R^{15})_2$, —$C(O)OR^{15}$, $C_1$-$C_4$ alkyl, or —CN;
$R^9$ is hydrogen or halogen;
$R^{10}$ is hydrogen, hydroxyl, or $C_1$-$C_6$ alkoxy;
each $R^{12}$ is independently hydrogen, halogen, $C_1$-$C_4$ alkyl, $C_3$-$C_6$ cycloalkyl, —$N(R^{15})_2$, —$OR^{15}$, —$SR^{15}$, —$C(O)N(R^{15})_2$, $C(O)OR^{15}$, or —$N(O)_2$; and
each $R^{15}$ is independently hydrogen, $C_1$-$C_8$ alkyl, $C_3$-$C_7$ cycloalkyl, $C_3$-$C_{12}$ heterocycle, $C_4$-$C_{12}$ aryl or $C_1$-$C_8$ alkyl, each optionally substituted with hydroxyl, $C_1$-$C_4$ alkoxy or $C_3$-$C_7$ cycloalkyl.

10. A compound selected from the group consisting of:
3-chloro-N-({4-chloro-3-[(3-chloro-5-cyanophenyl)oxy]-2-fluorophenyl}methyl)-1H-pyrrole-2-carboxamide;
4-chloro-N-({4-chloro-3-[(3-chloro-5-cyanophenyl)oxy]-2-fluorophenyl}methyl)-1H-imidazole-5-carboxamide;
4-bromo-N-({4-chloro-3-[(3-chloro-5-cyanophenyl)oxy]-2-fluorophenyl}methyl)-1H-imidazole-5-carboxamide;
4-chloro-N-({4-chloro-3-[(3-cyano-5-ethenylphenyl)oxy]-2-fluorophenyl}methyl)-1H-imidazole-5-carboxamide;
4-chloro-N-({4-chloro-3-[(2,5-dichloro-3-cyanophenyl)oxy]-2-fluorophenyl}methyl)-1H-imidazole-5-carboxamide;
4-chloro-N-({4-chloro-3-[(3-cyano-5-methylphenyl)oxy]-2-fluorophenyl}methyl)-1H-imidazole-5-carboxamide;
4-bromo-N-({4-chloro-3-[(3-cyano-5-methylphenyl)oxy]-2-fluorophenyl}methyl)-2-methyl-1H-imidazole-5-carboxamide;
4-chloro-N-({4-chloro-3-[(3-cyano-5-ethylphenyl)oxy]-2-fluorophenyl}methyl)-1H-imidazole-5-carboxamide;
4-bromo-N-({4-chloro-3-[(3-cyano-5-ethylphenyl)oxy]-2-fluorophenyl}methyl)-2-methyl-1H-imidazole-5-carboxamide;
N-({3-[(3-bromo-5-cyanophenyl)oxy]-4-chloro-2-fluorophenyl}methyl)-4-chloro-1H-imidazole-5-carboxamide;
4-chloro-N-({4-chloro-3-[(3-cyano-5-propylphenyl)oxy]-2-fluorophenyl}methyl)-1H-imidazole-5-carboxamide;
4-chloro-N-({4-chloro-3-[(3-cyano-5-cyclopropylphenyl)oxy]-2-fluorophenyl}methyl)-1H-imidazole-5-carboxamide;
4-chloro-N-[(4-chloro-3-{[3-cyano-5-(2-propen-1-yl)phenyl]oxy}-2-fluorophenyl)methyl]-1H-imidazole-5-carboxamide;
4-chloro-N-[(4-chloro-3-{[3-cyano-5-(cyclopropylmethyl)phenyl]oxy}-2-fluorophenyl)methyl]-1H-imidazole-5-carboxamide;
4-chloro-N-[(4-chloro-3-{[3-cyano-5-(1-methylethenyl)phenyl]oxy}-2-fluorophenyl)methyl]-1H-imidazole-5-carboxamide;
4-chloro-N-[(4-chloro-3-{[3-cyano-5-(1-methylethyl)phenyl]oxy}-2-fluorophenyl)methyl]-1H-imidazole-5-carboxamide;
3-bromo-N-({4-chloro-3-[(3-chloro-5-cyanophenyl)oxy]-2-fluorophenyl}methyl)-1H-pyrrole-2-carboxamide;
2-amino-4-chloro-N-({4-chloro-3-[(3-chloro-5-cyanophenyl)oxy]-2-fluorophenyl}methyl)-1H-imidazole-5-carboxamide;
N-({4-bromo-3-[(3-chloro-5-cyanophenyl)oxy]-2-fluorophenyl}methyl)-4-chloro-2-methyl-1H-imidazole-5-carboxamide;
N-({4-bromo-3-[(3-chloro-5-cyanophenyl)oxy]-2-fluorophenyl}methyl)-4-chloro-2-methyl-1H-imidazole-5-carboxamide;
4-bromo-N-({4-bromo-3-[(3-chloro-5-cyanophenyl)oxy]-2-fluorophenyl}methyl)-2-methyl-1H-imidazole-5-carboxamide;
4-bromo-N-({4,5-dibromo-3-[(3-chloro-5-cyanophenyl)oxy]-2-fluorophenyl}methyl)-2-methyl-1H-imidazole-5-carboxamide;
2-amino-4-bromo-N-({4-chloro-3-[(3-chloro-5-cyanophenyl)oxy]-2-fluorophenyl}methyl)-1H-imidazole-5-carboxamide;
2-amino-4-bromo-N-({4-bromo-3-[(3-chloro-5-cyanophenyl)oxy]-2-fluorophenyl}methyl)-1H-imidazole-5-carboxamide;
2-amino-N-({4-bromo-3-[(3-chloro-5-cyanophenyl)oxy]-2-fluorophenyl}methyl)-4-chloro-1H-imidazole-5-carboxamide;

2-amino-N-({4-bromo-3-[(3-cyano-5-methylphenyl)
oxy]-2-fluorophenyl}methyl)-4-chloro-1H-imidazole-
5-carboxamide;
N-({4-bromo-3-[(3-chloro-5-cyanophenyl)oxy]-2-
fluorophenyl}methyl)-4-chloro-2-(hydroxymethyl)-
1H-imidazole-5-carboxamide;
4-chloro-N-[(4-chloro-3-{[3-cyano-5-(2-propen-1-yl)
phenyl]oxy}-2-fluorophenyl)methyl]-2-methyl-1H-
imidazole-5-carboxamide;
4-chloro-N-({3-[(3-chloro-5-cyanophenyl)oxy]-4-ethyl-
2-fluorophenyl}methyl)-2-methyl-1H-imidazole-5-
carboxamide;
4-chloro-N-({3-[(3-chloro-5-cyanophenyl)oxy]-4-ethyl-
2-fluorophenyl}methyl)-1H-imidazole-5-carboxamide;
2-amino-4-chloro-N-({3-[(3-chloro-5-cyanophenyl)oxy]-
4-ethyl-2-fluorophenyl}methyl)-1H-imidazole-5-car-
boxamide;
4-chloro-N-{[3-[(3-chloro-5-cyanophenyl)oxy]-4-(dif-
luoromethyl)-2-fluorophenyl]methyl}-1H-imidazole-
5-carboxamide;
2-amino-4-chloro-N-{[3-[(3-chloro-5-cyanophenyl)oxy]-
4-(difluoromethyl)-2-fluorophenyl]methyl}-1H-imida-
zole-5-carboxamide;
4-Chloro-N-({3-[(3-chloro-5-cyanophenyl)oxy]-4-ethe-
nyl-2-fluorophenyl}methyl)-2-methyl-1H-imidazole-
5-carboxamide;
4-Chloro-N-({3-[(3-chloro-5-cyanophenyl)oxy]-4-cyclo-
propyl-2-fluorophenyl}methyl)-2-methyl-1H-imida-
zole-5-carboxamide;
4-Chloro-N-({4-chloro-3-[(4-cyano-6-methyl-2-pyridi-
nyl)oxy]-2-fluorophenyl}methyl)-2-methyl-1H-imida-
zole-5-carboxamide;
4-Chloro-N-({4-chloro-3-[(4-cyano-6-ethenyl-2-pyridi-
nyl)oxy]-2-fluorophenyl}methyl)-2-methyl-1H-imida-
zole-5-carboxamide;
4-Chloro-N-({4-chloro-3-[(4-cyano-6-cyclopropyl-2-py-
ridinyl)oxy]-2-fluorophenyl}methyl)-2-methyl-1H-
imidazole-5-carboxamide;
4-Chloro-N-({4-chloro-3-[(4-cyano-6-ethyl-2-pyridinyl)
oxy]-2-fluorophenyl}methyl)-2-methyl-1H-imidazole-
5-carboxamide;
4-bromo-N-[(4-chloro-3-{[3-cyano-5-(trifluoromethyl)
phenyl]oxy}-2-fluorophenyl)methyl]-1H-imidazole-5-
carboxamide;
4-chloro-N-({4-chloro-3-[(3-chloro-5-ethylphenyl)oxy]-
2-fluorophenyl}methyl)-1H-imidazole-5-carboxamide;
4-chloro-N-{[4-chloro-3-({3-chloro-5-[(E)-2-cyanoethe-
nyl]phenyl}oxy)-2-fluorophenyl]methyl}-1H-imida-
zole-5-carboxamide;
4-chloro-N-({4-chloro-3-[(3-chloro-5-ethynylphenyl)
oxy]-2-fluorophenyl}methyl)-1H-imidazole-5-car-
boxamide;
N-({3-[(3-bromo-5-cyanophenyl)oxy]-4-chloro-2-
fluorophenyl}methyl)-4-chloro-2-methyl-1H-imida-
zole-5-carboxamide;
4-chloro-N-[(4-chloro-3-{[3-cyano-5-(difluoromethyl)
phenyl]oxy}-2-fluorophenyl)methyl]-2-methyl-1H-
imidazole-5-carboxamide;
4-chloro-N-({4-chloro-3-[(3-chloro-5-cyanophenyl)oxy]-
5-cyano-2-fluorophenyl}methyl)-2-methyl-1H-imida-
zole-5-carboxamide;
4-chloro-N-({4-chloro-3-[(3-cyano-5-methylphenyl)
oxy]-2-fluorophenyl}methyl)-2-methyl-1H-imidazole-
5-carboxamide;
4-chloro-N-({4-chloro-3-[(2,5-dichloro-3-cyanophenyl)
oxy]-2-fluorophenyl}methyl)-2-methyl-1H-imidazole-
5-carboxamide;

2-amino-4-chloro-N-({4-chloro-3-[(3-cyano-5-cyclopro-
pylphenyl)oxy]-2-fluorophenyl}methyl)-1H-imida-
zole-5-carboxamide;
4-chloro-N-({4-chloro-3-[(3-cyano-5-cyclopropyl phe-
nyl)oxy]-2-fluorophenyl}methyl)-2-methyl-1H-imida-
zole-5-carboxamide;
4-chloro-N-[(4-chloro-3-{[3-cyano-5-(difluoromethyl)
phenyl]oxy}-2-fluorophenyl)methyl]-1H-imidazole-5-
carboxamide;
4-chloro-N-({4-chloro-3-[(3-cyano-5-ethynylphenyl)
oxy]-2-fluorophenyl}methyl)-1H-imidazole-5-car-
boxamide;
4-chloro-N-{[4-chloro-3-({3-cyano-5-[(dimethylamino)
methyl]phenyl}oxy)-2-fluorophenyl]methyl}-1H-imi-
dazole-5-carboxamide;
4-chloro-N-[(4-chloro-3-{[3-cyano-5-(1-propyn-1-yl)
phenyl]oxy}-2-fluorophenyl)methyl]-1H-imidazole-5-
carboxamide;
4-chloro-N-{[4-chloro-3-({3-chloro-5-[(3R)-3-hydroxy-
1-butyn-1-yl]phenyl}oxy)-2-fluorophenyl]methyl}-
1H-imidazole-5-carboxamide;
2-amino-4-chloro-N-[(4-chloro-3-{[3-cyano-5-(difluo-
romethyl)phenyl]oxy}-2-fluorophenyl)methyl]-1H-
imidazole-5-carboxamide;
4-bromo-N-({4-chloro-3-[(3-chloro-5-cyanophenyl)oxy]-
2-fluorophenyl}methyl)-1H-imidazole-5-carboxamide;
4-chloro-N-({4-chloro-3-[(3-chloro-5-cyanophenyl)oxy]-
2-fluorophenyl}methyl)-2-(ethylamino)-1H-imida-
zole-5-carboxamide;
4-chloro-N-({4-chloro-3-[(3-chloro-5-cyanophenyl)oxy]-
2-fluorophenyl}methyl)-2-(methylamino)-1H-imida-
zole-5-carboxamide;
2-amino-4-chloro-N-[(4-chloro-3-{[3-cyano-5-(methy-
loxy)phenyl]oxy}-2-fluorophenyl)methyl]-1H-imida-
zole-5-carboxamide;
3-({6-chloro-2-fluoro-3-[(6-oxo-6,7-dihydro-1H-purin-1-
yl)methyl]phenyl}oxy)-5-(2-propen-1-yl)benzonitrile;
4-bromo-N-[(4-chloro-3-{[3-cyano-5-(difluoromethyl)
phenyl]oxy}-2-fluorophenyl)methyl]-1H-imidazole-5-
carboxamide; and
4-bromo-N-({4-bromo-3-[(3-chloro-5-cyanophenyl)
oxy]-2-fluorophenyl}methyl)-1H-imidazole-5-car-
boxamide;
and pharmaceutically acceptable salts thereof.

11. A pharmaceutically acceptable salt of a compound according to claim 10.

12. A pharmaceutical composition comprising a compound according to claim 1, and a pharmaceutically acceptable carrier.

13. A pharmaceutical composition according to claim 12 in the form of a tablet, capsule, liquid or suspension.

14. A method for inhibiting the replication of a human immunodeficiency virus in a cell infected with said virus comprising contacting the cell infected with the virus with an antiviral effective amount of a compound according to claim 1.

15. A method for inhibiting the replication of a human immunodeficiency virus in a cell infected with said virus, comprising contacting the cell infected with the virus with an antiviral effective amount of a first therapeutic agent that is a compound according to claim 1 and at least one additional therapeutic agent selected from the group consisting of zidovudine, didanosine, lamivudine, zalcitabine, abacavir, stavidine, adefovir, adefovir dipivoxil, nevirapine, delavirdine, efavirenz, TMC-278, TMC-125, saquinavir, ritonavir, indinavir, nelfinavir, amprenavir, fosamprenavir, brecanavir, palinavir, lasinavir, atazanavir, tipranavir, enfuvirtide, T-1249, L-870,810, raltegravir, vicriviroc, and maraviroc.

16. A method for inhibiting a human immunodeficiency virus in a cell infected with said virus, comprising contacting the cell infected with the virus with an antiviral effective amount of a compound according to claim 10.

17. A method for inhibiting a human immunodeficiency virus in a cell infected with said virus, comprising contacting the cell infected with the virus with an antiviral effective amount of a first therapeutic agent that is a compound according to claim 10 and at least one additional therapeutic agent selected from the group consisting of zidovudine, didanosine, lamivudine, zalcitabine, abacavir, stavidine, adefovir, adefovir dipivoxil, nevirapine, delavirdine, efavirenz, TMC-278, TMC-125, saquinavir, ritonavir, indinavir, nelfinavir, amprenavir, fosamprenavir, brecanavir, palinavir, lasinavir, atazanavir, tipranavir, enfuvirtide, T-1249, L-870,810, raltegravir, vicriviroc, and maraviroc.

* * * * *